United States Patent [19]

Taylor

[11] Patent Number: 4,946,494

[45] Date of Patent: Aug. 7, 1990

[54] HERBICIDAL PYRIDINE SULFONYLUREAS

[75] Inventor: Eric D. Taylor, Wilmington, Del.

[73] Assignee: E. I. Du Pont de Nemours and Company, Wilmington, Del.

[21] Appl. No.: 243,865

[22] Filed: Sep. 15, 1988

Related U.S. Application Data

[63] Continuation-in-part of Ser. No. 115,502, Oct. 30, 1987, abandoned.

[51] Int. Cl.$^5$ .................. C07D 401/12; A01N 43/66; A01N 43/68; A01N 43/70

[52] U.S. Cl. .......................................... 71/93; 71/90; 544/219; 544/207; 544/209; 544/212; 544/113; 544/198

[58] Field of Search ...................... 71/93, 90; 544/219, 544/207, 209, 212, 113, 198

[56] References Cited

U.S. PATENT DOCUMENTS

| | | | |
|---|---|---|---|
| 4,518,776 | 5/1985 | Meyer et al. | 544/206 |
| 4,544,401 | 10/1985 | Levitt | 71/92 |
| 4,579,583 | 4/1986 | Föry et al. | 71/92 |
| 4,639,264 | 1/1987 | Töpfl | 71/87 |
| 4,690,707 | 9/1987 | Föry et al. | 71/93 |

FOREIGN PATENT DOCUMENTS 101670 2/1984 European Pat. Off. .

Primary Examiner—John M. Ford

[57] ABSTRACT

The invention relates to certain 6-amino-substituted 2-pyridinesulfonylureas, intermediates thereof, and compositions and methods of their use.

15 Claims, No Drawings

HERBICIDAL PYRIDINE SULFONYLUREAS

RELATED APPLICATION

This application is a continuation-in-part of Ser. No. 115,502 filed on Oct. 30, 1987, now abandoned.

BACKGROUND OF THE INVENTION

This invention relates to novel pyridine sulfonylurea herbicidal compounds, agriculturally suitable compositions thereof and a method of using them to control the growth of undesired vegetation.

New compounds effective for controlling the growth of undesired vegetation are in constant demand. In the most common situation, such compounds are sought to selectively control the growth of weeds in useful crops such as cotton, rice, corn, wheat and soybeans, to name a few. Unchecked weed growth in such crops can cause significant losses, reducing profit to the farmer and increasing costs to the consumer. In other situations, herbicides are desired which will control all plant growth. Examples of areas in which complete control of all vegetation is desired are areas around railroad tracks and industrial storage areas. There are many products commercially available for these purposes, but the search continues for products which are more effective, less costly and environmentally safe.

The "sulfonylurea" herbicides are an extremely potent class of herbicides discovered within the last few years. A multitude of structural variations exist within this class of herbicides, but they generally consist of a sulfonylurea bridge, —SO$_2$NHCONH—, linking two aromatic or heteroaromatic rings.

U.S. Pat. Nos. 4,579,583 and 4,690,707 disclose herbicidal pyridinesulfonylureas of the formula

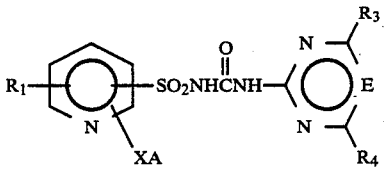

wherein

XA is NR$_6$R$_7$; and

R$_6$ and R$_7$ are independently H, C$_1$-C$_4$ alkyl, C$_3$-C$_6$ alkenyl, C$_3$-C$_6$ alkynyl, C$_3$-C$_6$ alkoxyalkyl, C$_1$-C$_4$ cyanoalkyl, or taken together form a 5- or 6-membered heterocyclic ring which may also contain O, S, SO or NR$_8$.

U.S. Pat. No. 4,544,401 discloses herbicidal pyridine sulfonylureas of the formula

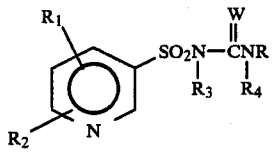

wherein

R$_1$ is NR$_6$R$_7$; and

R$_2$ is H, Cl, Br or CH$_3$.

EP-A-101,670 discloses a process for the preparation of herbicidal sulfonylureas of the formula

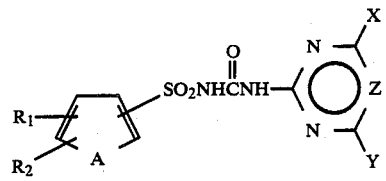

wherein

A is —C=N—; and

R$_1$ is NH(C$_1$-C$_4$)alkyl or N(C$_1$-C$_4$ alkyl)$_2$.

U.S. Pat. No. 4,518,776 discloses a process for the preparation of herbicidal sulfonylureas of the formula

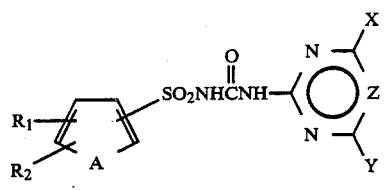

wherein

A is —C=N—; and

R$_1$ is NH$_2$, NH(C$_1$-C$_4$)alkyl or N(C$_1$-C$_4$ alkyl)$_2$.

SUMMARY OF THE INVENTION

This invention relates to novel agriculturally suitable herbicidal compounds of the Formula

wherein

W is O or S;

R is H or CH$_3$;

R$_1$ is H, F, Cl, Br, I, CN, C$_1$-C$_2$ alkyl, C$_1$-C$_2$ haloalkyl, OCH$_3$, OCH$_2$CH$_3$, OCH$_2$CF$_3$, OCF$_2$H, SCH$_3$, SCF$_2$H, C$_1$-C$_3$ alkylsulfonyl or SO$_2$CF$_2$H;

R$_2$ is H, C$_1$-C$_4$ alkyl, C$_1$-C$_2$ haloalkyl, CN, OH, C$_1$-C$_2$ alkoxy, NH$_2$, NHCH$_3$, N(CH$_3$)$_2$, C$_1$-C$_2$ alkyl substituted by CN, C$_1$-C$_2$ alkoxy or C$_1$-C$_2$ alkylthio, C$_3$-C$_4$ cycloalkyl, C$_3$-C$_4$ alkenyl, C$_3$-C$_4$ alkynyl or C(O)R$_5$;

R$_3$ is H, C$_1$-C$_4$ alkyl or C$_1$-C$_2$ haloalkyl; or

R$_2$ and R$_3$ may be taken together as —(CH$_2$)$_n$— or

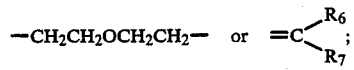

R$_4$ is H, F, Cl or CH$_3$;

R$_5$ is H, C$_1$-C$_3$ alkyl, C$_1$-C$_2$ alkoxy, NH$_2$, NHCH$_3$ or N(CH$_3$)$_2$;

R$_6$ is H, C$_1$-C$_2$ alkyl or phenyl;

R$_7$ is H or CH$_3$;

n is 2, 3, 4 or 5;

p is 0 or 1;

A is

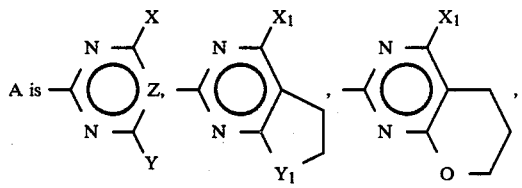

A-1  A-2  A-3

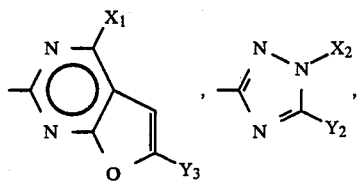

A-4  A-5

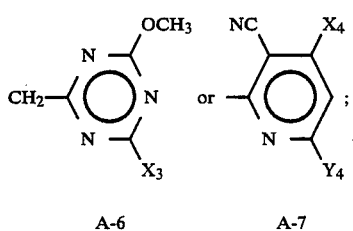

A-6  A-7

X is H, $C_1$–$C_4$ alkyl, $C_1$–$C_4$ alkoxy, $C_1$–$C_4$ haloalkoxy, $C_1$–$C_4$ haloalkyl, $C_1$–$C_4$ haloalkylthio, $C_1$–$C_4$ alkylthio, halogen, $C_2$–$C_5$ alkoxyalkyl, $C_2$–$C_5$ alkoxyalkoxy, amino, $C_1$–$C_3$ alkylamino or di($C_1$–$C_3$ alkyl)amino;

Y is H, $C_1$–$C_4$ alkyl, $C_1$–$C_4$ alkoxy, $C_1$–$C_4$ haloalkoxy, $C_1$–$C_4$ haloalkylthio, $C_1$–$C_4$ alkylthio, $C_2$–$C_5$ alkoxyalkyl, $C_2$–$C_5$ alkoxyalkoxy, amino, $C_1$–$C_3$ alkylamino, di($C_1$–$C_3$ alkyl)amino, $C_3$–$C_4$ alkenyloxy, $C_3$–$C_4$ alkynyloxy, $C_2$–$C_5$ alkylthioalkyl, $C_2$–$C_5$ alkylsulfinylalkyl, $C_2$–$C_5$ alkylsulfonylalkyl, $C_1$–$C_4$ haloalkyl, $C_2$–$C_4$ alkynyl, $C_3$–$C_5$ cycloalkyl, azido, cyano,

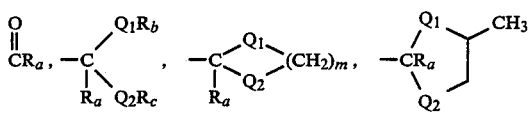

or $N(OCH_3)CH_3$;
m is 2 or 3;
$Q_1$ and $Q_2$ are independently O or S;
$R_a$ is H or $C_1$–$C_3$ alkyl;
$R_b$ and $R_c$ are independently $C_1$–$C_3$ alkyl;
Z is CH, N, $CCH_3$, $CC_2H_5$, CCl or CBr;
$Y_1$ is O or $CH_2$;
$X_1$ is $CH_3$, $OCH_3$, $OC_2H_5$ or $OCF_2H$;
$X_2$ is $CH_3$, $C_2H_5$ or $CH_2CF_3$;
$Y_2$ is $OCH_3$, $OC_2H_5$, $SCH_3$, $SC_2H_5$, $CH_3$ or $CH_2CH_3$;
$X_3$ is $CH_3$ or $OCH_3$;
$Y_3$ is H or $CH_3$;
$X_4$ is $CH_3$, $OCH_3$, $OC_2H_5$, $CH_2OCH_3$ or Cl; and
$Y_4$ is $CH_3$, $OCH_3$, $OC_2H_5$ or Cl;
and their agriculturally suitable salts; provided that
(1) when X is halogen, then Z is CH and Y is $OCH_3$, $OC_2H_5$, $NH_2$, $NHCH_3$, $N(CH_3)_2$, $OCF_2H$, $OCF_2Br$ or $N(OCH_3)CH_3$;
(2) when X and/or Y is $C_1$ haloalkoxy, then Z is CH;

(3) when W is S, then R is H, A is A-1, Z is CH or N, and Y is $CH_3$, $OCH_3$, $OC_2H_5$, $CH_2OCH_3$, $C_2H_5$, $CF_3$, $SCH_3$, $OCH_2CH=CH_2$, $OCH_2C\equiv CH$, $OCH_2CH_2OCH_3$, $CH(OCH_3)_2$ or

(4) when the total number of carbon atoms of X and Y is greater than four, then the combined number of carbons of $R_2$ and $R_3$ is less than or equal to six; and
(5) $X_4$ and $Y_4$ L are not simultaneously Cl.

In the above definitions, the term "alkyl," used either alone or in compound words such as "alkylthio" or "haloalkyl," denotes straight chain or branched alkyl, e.g., methyl, ethyl, n-propyl, isopropyl or the different butyl isomers.

Alkoxy denotes methoxy, ethoxy, n-propoxy, isopropoxy and the different butoxy isomers.

Alkenyl denotes straight chain or branched alkenes, e.g., vinyl, 1-propenyl, 2-propenyl, 3-propenyl and the different butenyl isomers.

Alkynyl denotes straight chain or branched alkynes, e.g., ethynyl, 1-propynyl, 2-propynyl and the different butynyl isomers.

The term "halogen," either alone or in compound words such as "haloalkyl," denotes fluorine, chlorine, bromine or iodine. Further, when used in compound words such as "haloalkyl" said alkyl may be monohalogenated or fully substituted with halogen atoms, which may be the same or different. Examples of haloalkyl include $CH_2CH_2F$, $CF_2CF_3$ and $CH_2CHFCl$.

The total number of carbon atoms in a substituent group is indicated byy the $C_i$–$C_j$ prefix where i and j are numbers from 1 to 4. For example, $C_3$–$C_4$ alkenyl would designate propenyl through butenyl.

Compounds of the invention preferred for reasons of increased ease of synthesis and/or greater herbicidal efficacy are:

1. Compounds of Formula I wherein $R_4$ is H;
2. Compounds of Preferred 1 wherein $R_2$ is $C_1$–$C_2$ haloalkyl, OH, $C_1$–$C_2$ alkoxy, $NH_2$, $NHCH_3$, $N(CH_3)_2$, $C_1$–$C_2$ alkyl substituted by $C_1$–$C_2$ alkylthio, $C_3$–$C_4$ cycloalkyl or $C(O)R_5$;
   $R_3$ is H, $C_1$–$C_4$ alkyl or $C_1$–$C_2$ haloalkyl; or
   $R_2$ and $R_3$ are taken together as —$(CH_2)_n$— or

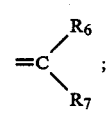

and
n is 2 or 3.
3. Compounds of Preferred 2 wherein
   W is O;
   X is $C_1$–$C_2$ alkyl, $C_1$–$C_2$ alkoxy, F, Cl, Br, I, $OCF_2H$, $CH_2F$, $CF_3$, $OCH_2CH_2F$, $OCH_2CHF_2$, $OCH_2CF_3$, $CH_2Cl$ or $CH_2Br$;
   Y is H, $C_1$–$C_2$ alkyl, $C_1$–$C_2$ alkoxy, $CH_2OCH_3$, $CH_2OCH_2CH_3$, $NHCH_3$, $N(OCH_3)CH_3$, $N(CH_3)_2$, $CF_3$, $SCH_3$, $OCH_2CH=CH_2$, $OCH_2C\equiv CH$, $OCH_2CH_2OCH_3$, $CH_2SCH_3$, $C(O)R_a$,

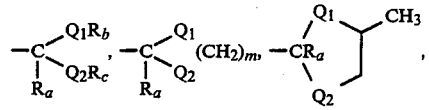

OCF$_2$H, SCF$_2$H, OCF$_2$Br, cyclopropyl, C≡CH or C≡CCH$_3$; and

Z is CH or N.

4. Compounds of Preferred 3 wherein
   R$_2$ is NH$_2$, NHCH$_3$, N(CH$_3$)$_2$, CF$_3$, CF$_2$H, OH, OCH$_3$, CH$_2$SCH$_3$, cyclopropyl or C(O)R$_5$;
   R$_3$ is H, CH$_3$ or CH$_2$CH$_3$; or
   R$_2$ and R$_3$ are taken together as —(CH$_2$)$_n$— or

R$_5$ is H, CH$_3$, OCH$_3$, NH$_2$, NHCH$_3$ or N(CH$_3$)$_2$; and
R$_6$ is H or C$_1$–C$_2$ alkyl.

5. Compounds of Preferred 4 wherein
   A is A-1;
   X is CH$_3$, OCH$_3$, OCH$_2$CH$_3$, Cl, OCF$_2$H or OCH$_2$CF$_3$; and
   Y is CH$_3$, OCH$_3$, CH$_2$CH$_3$, CH$_2$OCH$_3$, NHCH$_3$ or CH(OCH$_3$)$_2$.

6. Compounds of Preferred 5 wherein
   R is H;
   R$_1$ is H; and
   p is O.

7. Compounds of Preferred 1 wherein
   R$_2$ is H, C$_1$–C$_4$ alkyl, CN, C$_1$–C$_2$ alkyl substituted by CN or C$_1$–C$_2$ alkoxy, C$_3$–C$_4$ alkenyl or C$_3$–C$_4$ alkynyl;
   R$_3$ is H, C$_1$–C$_4$ alkyl or C$_1$–C$_2$ haloalkyl; or
   R$_2$ and R$_3$ are taken together as —(CH$_2$)$_n$— or —CH$_2$CH$_2$OCH$_2$CH$_2$—; and
   n is 4 or 5.

8. Compounds of Preferred 7 wherein
   W is O;
   X is C$_1$–C$_2$ alkyl, C$_1$–C$_2$ alkoxy, F, Cl, Br, I, OCF$_2$H, CH$_2$F, CF$_3$, OCH$_2$CH$_2$F, OCH$_2$CHF$_2$, OCH$_2$CF$_3$, CH$_2$Cl or CH$_2$Br;
   Y is H, C$_1$–C$_2$ alkyl, C$_1$–C$_2$ alkoxy, CH$_2$OCH$_3$, CH$_2$OCH$_2$CH$_3$, NHCH$_3$, N(OCH$_3$)CH$_3$, N(CH$_3$)$_2$, CF$_3$, SCH$_3$, OCH$_2$CH=CH$_2$, OCH$_2$C≡CH, OCH$_2$CH$_2$OCH$_3$, CH$_2$SCH$_3$, C(O)R$_a$,

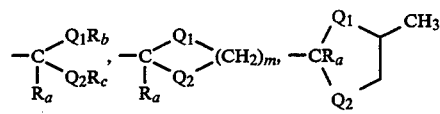

OCF$_2$H, SCF$_2$H, OCF$_2$Br, cyclopropyl, C≡CH or C≡CCH$_3$; and

Z is CH or N.

9. Compounds of Preferred 8 wherein
   R$_2$ is H, C$_1$–C$_4$ alkyl, CN, CH$_2$CN, CH$_2$OCH$_3$, allyl or propargyl; and
   R$_3$ is H, CH$_3$ or CH$_2$CH$_3$.

10. Compounds of Preferred 9 wherein
    A is A-1;
    X is CH$_3$, OCH$_3$, OCH$_2$CH$_3$, Cl, OCF$_2$H or OCH$_2$CF$_3$; and
    Y is CH$_3$, OCH$_3$, CH$_2$CH$_3$, CH$_2$OCH$_3$, NHCH$_3$ or CH(OCH$_3$)$_2$.

11. Compounds of Preferred 10 wherein
    R is H;
    R$_1$ is H; and
    p is O.

12. Compounds of Formula I wherein
    R$_4$ is F, Cl or CH$_3$.

13. Compounds of Preferred 12 wherein
    R$_2$ is C$_1$–C$_2$ haloalkyl, OH, C$_1$–C$_2$ alkoxy, NH$_2$, NHCH$_3$, N(CH$_3$)$_2$, C$_1$–C$_2$ alkyl substituted by C$_1$–C$_2$ alkylthio, C$_3$–C$_4$ cycloalkyl or C(O)R$_5$;
    R$_3$ is H, C$_1$–C$_4$ alkyl or C$_1$–C$_2$ haloalkyl; or
    R$_2$ and R$_3$ are taken together as —(CH$_2$)$_n$—, or

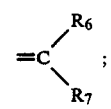

and
n is 2 or 3.

14. Compounds of Preferred 13 wherein
    W is O;
    X is C$_1$–C$_2$ alkyl, C$_1$–C$_2$ alkoxy, F, Cl, Br, I, OCF$_2$H, CH$_2$F, CF$_3$, OCH$_2$CH$_2$F, OCH$_2$CHF$_2$, OCH$_2$CF$_3$, CH$_2$Cl or CH$_2$Br;
    Y is H, C$_1$–C$_2$ alkyl, C$_1$–C$_2$ alkoxy, CH$_2$OCH$_3$, CH$_2$OCH$_2$CH$_3$, NHCH$_3$, N(OCH$_3$)CH$_3$, N(CH$_3$)$_2$, CF$_3$, SCH$_3$, OCH$_2$CH=CH$_2$, OCH$_2$C≡CH, OCH$_2$CH$_2$OCH$_3$, CH$_2$SCH$_3$, C(O)R$_a$,

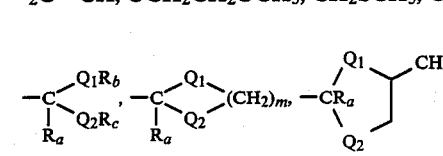

OCF$_2$H, SCF$_2$H, OCF$_2$Br, cyclopropyl, C≡CH or C≡CCH$_3$; and

Z is CH or N.

15. Compounds of Preferred 14 wherein
    R$_2$ is NH$_2$, NHCH$_3$, N(CH$_3$)$_2$, CF$_3$, CF$_2$H, OH, OCH$_3$, CH$_2$SCH$_3$, cyclopropyl or C(O)R$_5$;
    R$_3$ is H, CH$_3$ or CH$_2$CH$_3$; or
    R$_2$ and R$_3$ are taken together as —(CH$_2$)$_n$—, or

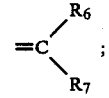

R$_5$ is H, CH$_3$, OCH$_3$, NH$_2$, NHCH$_3$ or N(CH$_3$)$_2$; and
R$_6$ is H or C$_1$–C$_2$ alkyl.

16. Compounds of Preferred 15 wherein
    A is A-1;
    X is CH$_3$, OCH$_3$, OCH$_2$CH$_3$, Cl, OCF$_2$H or OCH$_2$CF$_3$; and
    Y is CH$_3$, OCH$_3$, CH$_2$CH$_3$, CH$_2$OCH$_3$, MHCH$_3$ or CH(OCH$_3$)$_2$.

17. Compounds of Preferred 16 wherein
    R is H;
    R$_1$ is H; and
    p is O.

18. Compounds of Preferred 12 wherein
   $R_2$ is H, $C_1$–$C_4$ alkyl, CN, $C_1$–$C_2$ alkyl substituted by CN or $C_1$–$C_2$ alkoxy, $C_3$–$C_4$ alkenyl or $C_3$–$C_4$ alkynyl;
   $R_3$ is H, $C_1$–$C_4$ alkyl or $C_1$–$C_2$ haloalkyl; or
   $R_2$ and $R_3$ are taken together as —$(CH_2)_n$— or —$CH_2CH_2OCH_2CH_2$—; and
   n is 4 or 5.
19. Compounds of Preferred 18 wherein
   W is O;
   X is $C_1$–$C_2$ alkyl, $C_1$–$C_2$ alkoxy, F, Cl, Br, I, $OCF_2H$, $CH_2F$, $CF_3$, $OCH_2CH_2F$, $OCH_2CHF_2$, $OCH_2CF_3$, $CH_2Cl$ or $CH_2Br$;
   Y is H, $C_1$–$C_2$ alkyl, $C_1$–$C_2$ alkoxy, $CH_2OCH_3$, $CH_2OCH_2CH_3$, $NHCH_3$, $N(OCH_3)CH_3$, $N(CH_3)_2$, $CF_3$, $SCH_3$, $OCH_2CH=CH_2$, $OCH_2C\equiv CH$, $OCH_2CH_2OCH_3$, $CH_2SCH_3$, $C(O)R_a$,

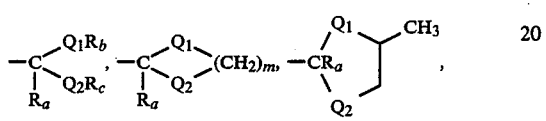

$OCF_2H$, $SCF_2H$, $OCF_2Br$, cyclopropyl, $C\equiv CH$ or $C\equiv OCH_3$; and
   Z is CH or N.
20. Compounds of Preferred 19 wherein
   $R_2$ is H, $C_1$–$C_4$ alkyl, CN, $CH_2CN$, $CH_2OCH_3$, allyl or propargyl; and
   $R_3$ is H, $CH_3$ or $CH_2CH_3$.
21. Compounds of Preferred 20 wherein
   A is A-1;
   X is $CH_3$, $OCH_3$, $OCH_2CH_3$, Cl, $OCF_2H$ or $OCH_2CF_3$; and
   Y is $CH_3$, $OCH_3$, $CH_2CH_3$, $CH_2OCH_3$, $NHCH_3$ or $CH(OCH_3)_2$.
22. Compounds of Preferred 21 wherein
   R is H;
   $R_1$ is H; and
   p is O.

Compounds of the invention specifically preferred for reasons of greatest ease of synthesis and/or greatest herbicidal efficacy are N-[[(4,6-dimethoxy-2-pyrimidinyl)amino]carbonyl]-6-(dimethylamino)-2-pyridinesulfonamide, m.p. 141°–143° C.; 6-(dimethylamino)-N-[[[4-ethoxy-6-(methylamino)-1,3,5-triazin-2-yl]amino]carbonyl]-2-pyridinesulfonamide, m.p. 186°–188° C.; and N-[[[(4-ethoxy-6-(dimethylamino)-1,3,5-triazin-2-yl]amino]carbonyl]-6-(methylamino)-2-pyridinesulfonamide, m.p. 116°–117° C.

This invention also comprises intermediates of Formula II utilized in the preparation of the compounds of Formula I.

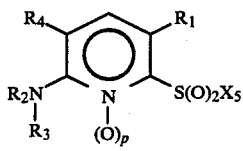

wherein
$R_1$, $R_2$, $R_3$, $R_4$ and p are as previously defined; and
$X_5$ is Cl, $NH_2$ or $NHC(CH_3)_3$;
provided that when
$R_1$ is H, $R_3$ is H, $R_4$ is H, p is O and $X_5$ is $NH_2$, then $R_2$ is other than H.

The compounds of this invention are highly active as preemergent and/or postemergent herbicides or plant growth regulants. Some of the compounds demonstrate selective safety toward cereal crops, maize (corn), cotton and oilseed rape. The invention comprises in addition to the novel compounds agriculturally suitable compositions containing said novel compounds and a method of using said compounds and/or compositions as preemergent and/or postemergent herbicides or plant growth regulants.

DETAILED DESCRIPTION OF THE INVENTION

Compounds of Formula I can be prepared by the methods described in Equations 1 and 2.

Equation 1

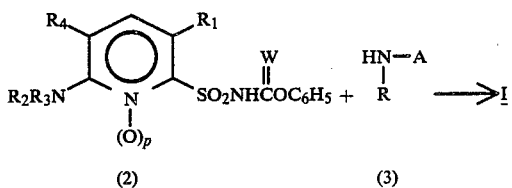

The reaction shown in Equation 1 is carried out by contacting a phenyl carbamate or phenyl thiocarbamate of Formula (2) with an aminoheterocycle of Formula (3) in an inert organic solvent such as dioxane or tetrahydrofuran at temperatures of about 20° C. to 100° C. for a period of about one-half to twenty-four hours. The product can be isolated by evaporation of the reaction solvent and purified by triturating the residue with solvents such as 1-chlorobutane or ethyl ether and filtering, by recrystallizing from mixtures of solvents such as 1,2-dichloroethane, 1-chlorobutane and heptane or by chromatography on silica gel.

Equation 2

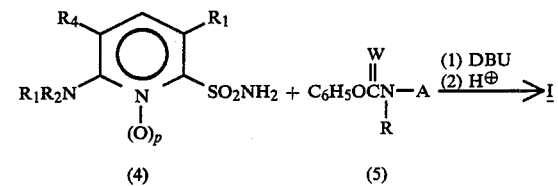

The reaction of Equation 2 can be carried out by contacting a sulfonamide of Formula (4) with a heterocycle phenyl carbamate of Formula (5) in the presence of 1,8-diazabicyclo[5,4,0]undec-7-ene (DBU), by methods analogous to those described in South African Patent Application 830441. The phenyl carbamates of Formula (5) can be prepared by methods (or modifications thereof) described in South African Patent Application 825671 and South African Patent Application 825045.

Phenylcarbamates and phenylthiocarbamates of Formula (2) (Equation 1) can be prepared from sulfonamides of Formula (4) (Equation 2) by methods described (or modifications thereof) in U.S. Pat. No. 4,443,243. The sulfonamides (4) can be prepared via the routes shown in Equations 3–7, or by modifications thereof.

Equation 3

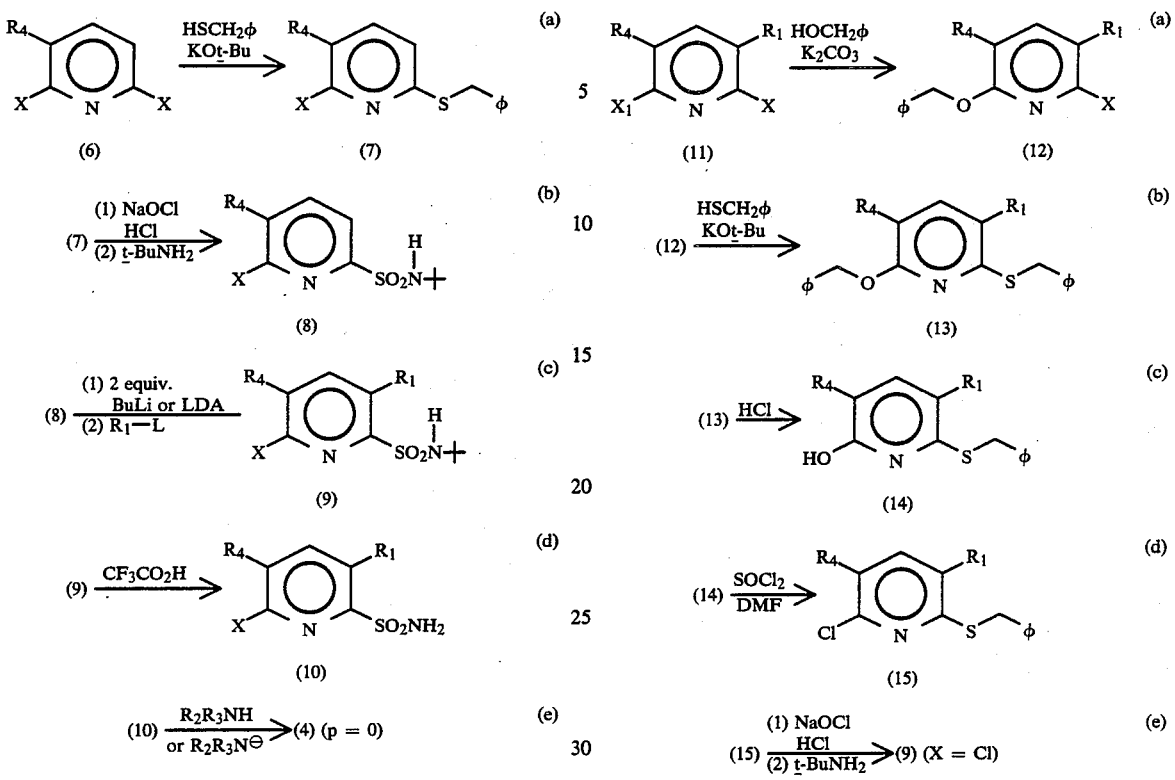

wherein:

X is F or Cl, and

L is a leaving group such as Cl, Br, I, alkyl sulfide, etc.;

and with the provision that when $R_1=H$, then Step (3c) is omitted.

Dihalopyridine (6) (The Chemistry of Heterocyclic Compounds, Vol. 14, Wiley-Interscience, New York (1964)) is contacted with benzyl mercaptan in the presence of potassium tert-butoxide in a solvent such as dimethylformamide to produce the sulfide (7). The product is isolated by partitioning the reaction mixture between water and ether (Equation 3a).

The sulfide (7) is converted to tert-butyl sulfonamide (8) by treatment with hypochlorite solution followed by tert-butylamine using the methods described in South African Patent Application 848845 (Equation 3b).

Metallation of compound (8) by treatment with two equivalents of a strong base such as n-butyllithium or lithium diisopropylamide (LDA) followed by treatment with an appropriate electrophile ($R_1$-L) produces compound (9). An appropriate choice of electrophile $R_1$-L would be evident to one skilled in the art (Equation 3c).

Contacting tert-butylsulfonamide (9) with trifluoroacetic acid affords sulfonamide (10). The product may be isolated by evaporation of the volatiles followed by trituration of the residue with an organic solvent such as ether (Equation 3d).

Treatment of (10) with at least two equivalents of ammonia or of a primary or secondary amine or with the anion of a primary or secondary amide or of a cyanamide produces sulfonamide (4) (p=0). The product may be isolated by evaporating the volatiles in vacuo and triturating the residue with water or by partitioning the mixture between water and an organic solvent (Equation 3e).

Equation 4 wherein:

X and $X_1$ may be independently F, Cl or Br.

The dihalopyridine (11)(*The Chemistry of Heterocyclic Compounds*, Vol. 14, Wiley-Interscience, New York (1964)) is contacted with benzyl alcohol in the presence of an acid acceptor such as potassium carbonate in an inert solvent such as dimethyl sulfoxide to produce the ether (12). The product is isolated by partitioning the reaction mixture between water and ether (Equation 4a).

The compound (12) is converted to sulfide (13) as described previously for Equation 3a (Equation 4b).

Treatment of (13) with concentrated hydrochloric acid produces the pyridinol (14). The product is isolated by partitioning the reaction mixture between water and an organic solvent (Equation 4c).

The pyridinol (14) is converted to chloride (15) by refluxing with thionyl chloride in the presence of dimethylformamide (DMF). The product is isolated by evaporation of the volatiles in vacuo and partitioning the residue between water and an organic solvent (Equation 4d).

The chloride (15) is converted to sulfonamide (9) (X=Cl) as described previously for Equation 3b (Equation 4e).

Equation 5

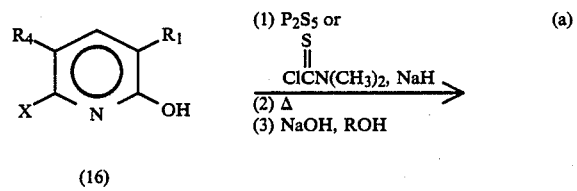

-continued $$\text{(17)} \quad R_4\text{-pyridine-}R_1 \text{ with } X \text{ and } SH$$

$$(17) \xrightarrow[(2) \underline{t}\text{-BuNH}_2]{(1) \text{ NaOCl, HCl}} (9) \quad (b)$$

wherein:

X is F, Cl or Br.

The hydroxypyridine (16) (*The Chemistry of Heterocyclic Compounds*, Vol. 14, Wiley-Interscience, New York (1964)) is converted to mercaptopyridine (17) by treatment with phosphorous pentasulfide or via the thiocarbamate according to the procedure of Newman, et al. in *J. Org. Chem.* 31 3980 (1966) (Equation 5a).

Mercaptopyridine (17) is converted to sulfonamide (9) as described previously for Equation 3b (Equation 5b).

Equation 6

$$(9) \xrightarrow{[O]} \text{(18)} \quad (a)$$

$$(18) \xrightarrow{CF_3CO_2H} \text{(19)} \quad (b)$$

$$(19) \xrightarrow{R_2R_3NH} (4) \ (p=1) \quad (c)$$

wherein:

X is f, Cl or Br.

Sulfonamide (9) may be converted to the N-oxide (18) by methods such as those described (or modifications thereof) in Evans, et al., *Rec. Trav.* 78 408 (1959). Some of the oxidants of choice for this transformation are m-chloroperoxybezoic acid, peracetic acid, etc. (Equation 6a).

Compound (18) may be converted to sulfonamide (19) as described previously for Equation 3d (Equation 6b).

Sulfonamide (19) may be converted to sulfonamide (4) (p=1) as described previously for Equation 3e (Equation 6c).

Equation 7

$$(8) \xrightarrow{[O]} \text{(20)} \quad (a)$$

$$(20) \xrightarrow[(2) R_1\text{-L}]{(1) \text{ 2 equiv. BuLi or LDA}} (18) \quad (b)$$

wherein:

X is F or Cl, and

L is as previously defined.

In cases where the substituent $R_1$ is sensitive to oxidation, this substituent may be introduced subsequent to the N-oxidation reaction. Thus, the sulfonamide (8) is converted to the N-oxide (20) by methods described for Equation 6a (Equation 7a).

The N-oxide (20) is metallated and reacted with an electrophile ($R_1$-L) to produce sulfonamide (18) as described previously for Equation 3c (Equation 7b).

For further details pertaining to lithiations of pyridine ring systems see, Epsztajn et al., *Tetrahedron Lett.*, 4739 (1980); snieckus et al., *J. Am. Chem. Soc.*, 102, 1457 (1980); Kuraishi et al., *Tet. Lett.*, 2049 (1983); Meyers et al., *J. Org. Chem.*, 47, 2633 (1982); Taylor et al., *J. Org. Chem.*, 48, 4156 (1983) and Breant et al., *Synthesis*, 822 (1983).

For a general treatment of pyridines and pyridine N-oxides see, Katritzky, A. R., and Rees, C.W., "Comprehensive Heterocyclic Chemistry", Vol. 2, Pergamon Press, Oxford, New York, Part 2A, 1984.

Phenyl carbamates and phenyl thiocarbamates (5) of Equation 2 can be prepared from heterocyclic amines (3) by methods, or modifications thereof known to those skilled in the art, described in South African Patent Application 82/5671 and South African Patent Application 82/5045.

The synthesis of heterocyclic amines such as those represented by Formula 3 (Equation 1) has been reviewed in "The Chemistry of Heterocyclic Compounds," a series published by Interscience Publ., New York and London. Aminopyrimidines are described by D. J. Brown in "The Pyrimidines," Vol. XVI of the series mentioned above which is herein incorporated by reference. The 2-amino-1,3,5-triazines of Formula 3, where A is A-1 and Z is N, can be prepared according to the methods described by E. M. Smolin and L. Rapaport in "s-Triazines and Derivatives," Vol. XIII.

Pyrimidines of Formula 3, where A is A-1 and Y is an acetal or thioacetal substituent, can be prepared by methods taught in European Patent Application No. 84,224 (published July 27, 1983).

Pyrimidines of Formula 3, where A is A-1 and Y is cyclopropyl or $OCF_2H$ can be synthesized according to the methods taught in U.S. Pat. No. 4,515,626 and U.S. Pat. No. 4,540,782, respectively.

Compounds of Formula 3, where A is A-2 or A-3, can be prepared by procedures disclosed in U.S. Pat. No. 4,339,267.

Compounds of Formula 3, where A is A-4, can be prepared by methods taught in U.S. Pat. No. 4,487,626.

Additional references dealing with the synthesis of bicyclic pyrimidines of Formula 3, where A is A-2, A-3, or A-4 are Braker, Sheehan, Spitzmiller and Lott, *J. Am. Chem. Soc.*, 69, 3072 (1947); Mitler and Bhattachanya, *Quart. J. Indian Chem. Soc.*, 4, 152 (1927); Shrage and Hitchings, *J. Org. Chem.*, 16, 1153 (1951); Caldwell, Kornfeld and Donnell, *J. Am. Chem., Soc.*, 63, 2188 (1941); and Fissekis, Myles and Brown, *J. Org. Chem.*, 29, 2670 (1964).

Compounds of Formula 3, where a is A-5, can be prepared by methods taught in U.S. Pat. No. 4,421,550.

Compounds of Formula 3, where A is A-6, can be prepared by methods taught in U.S. Pat. No. 4,496,392.

Compounds of Formula 3, where A is A-7, can be prepared by methods taught in EP-A-125,864.

Agriculturally suitable salts of compounds of Formula I are also useful herbicides and can be prepared by well-known methods including those described in U.S. Pat. No. 4,127,405.

The following Example illustrates the synthesis of the compounds of this invention. Temperatures are reported in degrees Celsius. Abbreviations for nuclear magnetic resonance (NMR) are s=singlet, d=doublet, dd=doublet of doublets, br=broad, and peak positions are reported as parts per million downfield from internal tetramethylsilane. The NMR spectra were measured at 200 MHz.

EXAMPLE 1

Step A

N-(1,1-dimethylethyl)-6-fluoro-2-pyridinesulfonamide

To 13.46 g (120 mmol) potassium tert-butoxide dissolved in 200 ml dry DMF was added dropwise 11.8 ml (12.5 g, 200 mmol) benzyl mercaptan while maintaining a temperature of 0° C. to 5° C. This mixture was warmed to room temperature for 15 min, then cooled to −30° C., when 9.1 ml (11.5 g, 100 mmol) 2,6-difluoropyridine was added all at once. The reaction mixture was stirred 2 hr at 0° C., then at room temperature overnight. The mixture was then poured into 800 ml ice-water and extracted into 800 ml of ether. The ether layer was washed with three 200-ml portions of water, dried over magnesium sulfate, filtered and concentrated in vacuo to leave 21.97 g of a yellow oil.

This crude sulfide was dissolved in 400 ml of methylene chloride, 200 ml of water was added and the mixture cooled to 0° C. Then 28.4 ml (341 mmol) of concentrated hydrochloric acid was added, followed by dropwise addition with vigorous stirring of 484 ml (341 mmol) of 5.25% sodium hypochlorite (Clorox ®) while maintaining a temperature of 0° C. to 5° C. After stirring another 20 min at 0° C., the mixture was separated and the organic phase was dried over magnesium sulfate, filtered and concentrated in vacuo, maintaining a temperature of no higher than 25° C.

The residue was dissolved in 100 ml of methylene chloride and added dropwise to 25 ml (17.4 g, 238 mmol) tert-butylamine in 200 ml of methylene chloride, maintaining a temperature of 20° C. to 25° C. The mixture was stirred 3 days at room temperature, then washed with 100 ml of water, dried over magnesium sulfate, filtered and concentrated in vacuo to leave a dark oil, which was triturated with hexanes to afford 15.90 g of olive-green solid, m.p. 88° C. to 90° C.

NMR (CDCl$_3$): δ 1.25 (s, 9H), 4.96 (br s, 1H), 7.13 (dd, 1H), 7.95 (m, 1H), 8.02 (dd, 1H).

Step B

6-Fluoropyridine-2-sulfonamide

To 100 ml trifluoroacetic acid was added 11.6 g (50 mmol) of N-(1,1-dimethylethyl)-6-fluoro-2-pyridinesulfonamide and the mixture was refluxed for two days. The volatiles were then removed in vacuo and the residue triturated with ether to afford 7.23 g of tan solid, m.p. 110° C. to 111° C.

NMR (CDCl$_3$): δ 7.30 (d, 1H), 8.00 (d, 1H), 8.17 (dd, 1H).

Step C 6-(Methylamino)pyridine-2-sulfonamide

To 10 ml of condensed methylamine was added 1.86 g (10 mmol) of 6-fluoropyridine-2-sulfonamide. The mixture was allowed to reflux under a dry-ice condenser for 4 hr, then excess amine was allowed to evaporate overnight. The residue was crystallized with water to yield 1.64 g of tan solid, m.p. 124° C. to 126° C. NMR (CDCl$_3$): δ 2.64 (s, 3H), 6.12 (br s, 2H), 6.30 (d, 1H), 6.86 (d, 1H), 7.23 (dd, 1H).

Step D

2-[[(4,6-dimethoxypyrimidin-2-yl)aminocarbonyl]aminosulfonyl]-6-(methylamino)pyridine To a suspension of 0.20 g (1.0 mmol) of 6-(methylamino)pyridine-2-sulfonamide and 0.28 g (1.0 mmol) of 4,6-dimethoxypyrimidin-2-yl phenyl carbamate in 1.0 ml of acetonitrile waa added 0.20 ml (0.20 g, 1.3 mmol) of 1,8-diazabicyclo[5,4,0]undec-7-ene. The mixture was stirred at room temperature for 1 hr, then 3 ml of water was added. Dropwise addition of 1N hydrochloric acid precipitated a solid which was filtered and washed with water to afford 0.21 g of the title compound as a white powder, m.p. 166° C. to 168° C. NMR(CDCl$_3$+CF$_3$CO$_2$D): δ 3.09 (s, 3H), 4.01 (s, 6H), 5.88 (s, 1H), 7.10 (d, 1H), 7.51 (d, 1H), 7.94 (dd, 1H).

By applying the procedures of Example 1 and those described in Equations 1 through 7, the compounds in Tables I through IV can be prepared by one skilled in the art (melting points are in ° C.).

GENERAL STRUCTURES FOR TABLES

General Structure 1

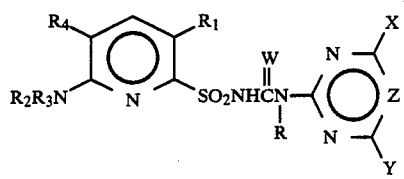

General Structure 2

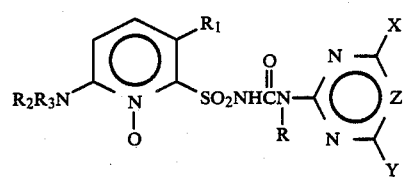

General Structure 3

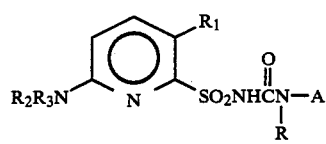

General Structure 4

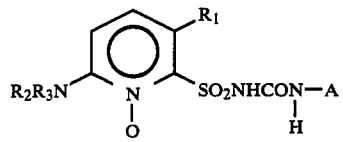

TABLE I

General Structure 1

| R¹ | R² | R³ | R⁴ | W | R | X | Y | Z |
|---|---|---|---|---|---|---|---|---|
| H | H | H | H | O | H | OCH₃ | OCH₃ | CH |
| H | H | H | H | O | H | Cl | OCH₃ | CH |
| H | H | H | H | O | H | CH₃ | OCH₃ | CH |
| H | H | H | H | O | H | CH₃ | CH₃ | CH |
| H | H | H | H | O | H | OCH₃ | OCH₃ | N |
| H | H | H | H | O | H | CH₃ | OCH₃ | N |
| H | H | H | H | O | H | CH₃ | CH₃ | N |
| H | H | H | H | O | H | OCH₂CH₃ | OCH₂CH₃ | N |
| H | H | H | H | O | H | NHCH₃ | OCH₂CH₃ | N |
| H | H | H | H | O | H | N(CH₃)₂ | OCH₂CH₃ | N |
| H | H | H | H | O | H | N(CH₃)₂ | OCH₃ | N |
| H | H | H | H | O | H | N(CH₃)₂ | OCH₂CF₃ | N |
| H | H | H | H | O | CH₃ | CH₃ | OCH₃ | N |
| H | H | H | H | S | H | OCH₃ | OCH₃ | CH |
| H | H | H | H | S | H | Cl | OCH₃ | CH |
| H | H | H | H | S | H | CH₃ | OCH₃ | CH |
| H | H | H | H | S | H | CH₃ | CH₃ | CH |
| H | H | H | H | S | H | OCH₃ | OCH₃ | N |
| H | H | H | H | S | H | CH₃ | OCH₃ | N |
| H | H | CH₃ | H | O | H | OCH₃ | OCH₃ | CH |
| H | H | CH₃ | H | O | H | Cl | OCH₃ | CH |
| H | H | CH₃ | H | O | H | CH₃ | OCH₃ | CH |
| H | H | CH₃ | H | O | H | CH₃ | CH₃ | CH |
| H | H | CH₃ | H | O | H | OCH₃ | OCH₃ | N |
| H | H | CH₃ | H | O | H | CH₃ | OCH₃ | N |
| H | H | CH₃ | H | O | H | CH₃ | CH₃ | N |
| H | H | CH₃ | H | O | H | OCH₂CH₃ | OCH₂CH₃ | N |
| H | H | CH₃ | H | O | H | NHCH₃ | OCH₂CH₃ | N |
| H | H | CH₃ | H | O | H | N(CH₃)₂ | OCH₂CH₃ | N |
| H | H | CH₃ | H | O | H | N(CH₃)₂ | OCH₃ | N |
| H | H | CH₃ | H | O | H | N(CH₃)₂ | OCH₂CF₃ | N |
| H | H | CH₃ | H | O | CH₃ | CH₃ | OCH₃ | N |
| H | H | CH₃ | H | S | H | OCH₃ | OCH₃ | CH |
| H | H | CH₃ | H | S | H | Cl | OCH₃ | CH |
| H | H | CH₃ | H | S | H | CH₃ | OCH₃ | CH |
| H | H | CH₃ | H | S | H | CH₃ | CH₃ | CH |
| H | H | CH₃ | H | S | H | OCH₃ | OCH₃ | N |
| H | H | CH₃ | H | S | H | CH₃ | OCH₃ | N |
| H | H | CH₂CH₃ | H | O | H | OCH₃ | OCH₃ | CH |
| H | H | CH₂CH₃ | H | O | H | Cl | OCH₃ | CH |
| H | H | CH₂CH₃ | H | O | H | CH₃ | OCH₃ | CH |
| H | H | CH₂CH₃ | H | O | H | CH₃ | CH₃ | CH |
| H | H | CH₂CH₃ | H | O | H | OCH₃ | OCH₃ | N |
| H | H | CH₂CH₃ | H | O | H | CH₃ | OCH₃ | N |
| H | H | CH₂CH₃ | H | O | H | CH₃ | CH₃ | N |
| H | H | CH₂CH₃ | H | O | H | OCH₂CH₃ | OCH₂CH₃ | N |
| H | H | CH₂CH₃ | H | O | H | NHCH₃ | OCH₂CH₃ | N |
| H | H | CH₂CH₃ | H | O | H | N(CH₃)₂ | OCH₂CH₃ | N |
| H | H | CH₂CH₃ | H | O | H | N(CH₃)₂ | OCH₃ | N |
| H | H | CH₂CH₃ | H | O | H | N(CH₃)₂ | OCH₂CF₃ | N |
| H | H | CH₂CH₃ | H | O | CH₃ | CH₃ | OCH₃ | N |
| H | H | CH₂CH₃ | H | S | H | OCH₃ | OCH₃ | CH |
| H | H | CH₂CH₃ | H | S | H | Cl | OCH₃ | CH |
| H | H | CH₂CH₃ | H | S | H | CH₃ | OCH₃ | CH |
| H | H | CH₂CH₃ | H | S | H | CH₃ | CH₃ | CH |
| H | H | CH₂CH₃ | H | S | H | OCH₃ | OCH₃ | N |
| H | H | CH₂CH₃ | H | S | H | CH₃ | OCH₃ | N |
| H | H | CH₂CF₃ | H | O | H | OCH₃ | OCH₃ | CH |
| H | H | CH₂CF₃ | H | O | H | Cl | OCH₃ | CH |
| H | H | CH₂CF₃ | H | O | H | CH₃ | OCH₃ | CH |
| H | H | CH₂CF₃ | H | O | H | CH₃ | CH₃ | CH |
| H | H | CH₂CF₃ | H | O | H | OCH₃ | OCH₃ | N |
| H | H | CH₂CF₃ | H | O | H | CH₃ | OCH₃ | N |
| H | H | CH₂CF₃ | H | O | H | CH₃ | CH₃ | N |
| H | H | CH₂CF₃ | H | O | H | OCH₂CH₃ | OCH₂CH₃ | N |
| H | H | CH₂CF₃ | H | O | H | NHCH₃ | OCH₂CH₃ | N |
| H | H | CH₂CF₃ | H | O | H | N(CH₃)₂ | OCH₂CH₃ | N |
| H | H | CH₂CF₃ | H | O | H | N(CH₃)₂ | OCH₃ | N |
| H | H | CH₂CF₃ | H | O | H | N(CH₃)₂ | OCH₂CF₃ | N |
| H | H | CH₂CF₃ | H | O | CH₃ | CH₃ | OCH₃ | N |
| H | H | CH₂CF₃ | H | S | H | OCH₃ | OCH₃ | CH |
| H | H | CH₂CF₃ | H | S | H | Cl | OCH₃ | CH |
| H | H | CH₂CF₃ | H | S | H | CH₃ | OCH₃ | CH |
| H | H | CH₂CF₃ | H | S | H | CH₃ | CH₃ | CH |
| H | H | CH₂CF₃ | H | S | H | OCH₃ | OCH₃ | N |
| H | H | CH₂CF₃ | H | S | H | CH₃ | OCH₃ | N |
| H | CH₂CH₂Cl | H | H | O | H | OCH₃ | OCH₃ | CH |
| H | CH₂CH₂Cl | H | H | O | H | Cl | OCH₃ | CH |
| H | CH₂CH₂Cl | H | H | O | H | CH₃ | OCH₃ | CH |
| H | CH₂CH₂Cl | H | H | O | H | CH₃ | CH₃ | CH |

TABLE I-continued

| | | | | | | | | |
|---|---|---|---|---|---|---|---|---|
| H | CH₂CH₂Cl | H | H | O | H | OCH₃ | OCH₃ | N |
| H | CH₂CH₂Cl | H | H | O | H | CH₃ | OCH₃ | N |
| H | CH₂CH₂Cl | H | H | O | H | CH₃ | CH₃ | N |
| H | CH₂CH₂Cl | H | H | O | H | OCH₂CH₃ | OCH₂CH₃ | N |
| H | CH₂CH₂Cl | H | H | O | H | NHCH₃ | OCH₂CH₃ | N |
| H | CH₂CH₂Cl | H | H | O | H | N(CH₃)₂ | OCH₂CH₃ | N |
| H | CH₂CH₂Cl | H | H | O | H | N(CH₃)₂ | OCH₂CF₃ | N |
| H | CH₂CH₂Cl | H | H | O | CH₃ | CH₃ | OCH₃ | N |
| H | CH₂CH₂Cl | H | H | S | H | OCH₃ | OCH₃ | CH |
| H | CH₂CH₂Cl | H | H | S | H | Cl | OCH₃ | CH |
| H | CH₂CH₂Cl | H | H | S | H | CH₃ | OCH₃ | CH |
| H | CH₂CH₂Cl | H | H | S | H | CH₃ | CH₃ | CH |
| H | CH₂CH₂Cl | H | H | S | H | OCH₃ | OCH₃ | N |
| H | CH₂CH₂Cl | H | H | S | H | CH₃ | OCH₃ | N |
| H | CH₂CN | H | H | O | H | OCH₃ | OCH₃ | CH |
| H | CH₂CN | H | H | O | H | CL | OCH₃ | CH |
| H | CH₂CN | H | H | O | H | CH₃ | OCH₃ | CH |
| H | CH₂CN | H | H | O | H | CH₃ | CH₃ | CH |
| H | CH₂CN | H | H | O | H | OCH₃ | OCH₃ | N |
| H | CH₂CN | H | H | O | H | CH₃ | OCH₃ | N |
| H | CH₂CN | H | H | O | H | CH₃ | CH₃ | N |
| H | CH₂CN | H | H | O | H | OCH₂CH₃ | OCH₂CH₃ | N |
| H | CH₂CN | H | H | O | H | NHCH₃ | OCH₂CH₃ | N |
| H | CH₂CN | H | H | O | H | N(CH₃)₂ | OCH₂CH₃ | N |
| H | CH₂CN | H | H | O | H | N(CH₃)₂ | OCH₃ | N |
| H | CH₂CN | H | H | O | H | N(CH₃)₂ | OCH₂CF₃ | N |
| H | CH₂CN | H | H | O | CH₃ | CH₃ | OCH₃ | N |
| H | CH₂CN | H | H | S | H | OCH₃ | OCH₃ | CH |
| H | CH₂CN | H | H | S | H | Cl | OCH₃ | CH |
| H | CH₂CN | H | H | S | H | CH₃ | OCH₃ | CH |
| H | CH₂CN | H | H | S | H | CH₃ | CH₃ | CH |
| H | CH₂CN | H | H | S | H | OCH₃ | OCH₃ | N |
| H | CH₂CN | H | H | S | H | CH₃ | OCH₃ | N |
| H | CH₂CH=CH₂ | H | H | O | H | OCH₃ | OCH₃ | CH |
| H | CH₂CH=CH₂ | H | H | O | H | Cl | OCH₃ | CH |
| H | CH₂CH=CH₂ | H | H | O | H | CH₃ | OCH₃ | CH |
| H | CH₂CH=CH₂ | H | H | O | H | CH₃ | CH₃ | CH |
| H | CH₂CH=CH₂ | H | H | O | H | OCH₃ | OCH₃ | N |
| H | CH₂CH=CH₂ | H | H | O | H | CH₃ | OCH₃ | N |
| H | CH₂CH=CH₂ | H | H | O | H | CH₃ | CH₃ | N |
| H | CH₂CH=CH₂ | H | H | O | H | OCH₂CH₃ | OCH₂CH₃ | N |
| H | CH₂CH=CH₂ | H | H | O | H | NHCH₃ | OCH₂CH₃ | N |
| H | CH₂CH=CH₂ | H | H | O | H | N(CH₃)₂ | OCH₂CH₃ | N |
| H | CH₂CH=CH₂ | H | H | O | H | N(CH₃)₂ | OCH₃ | N |
| H | CH₂CH=CH₂ | H | H | O | H | N(CH₃)₂ | OCH₂CF₃ | N |
| H | CH₂CH=CH₂ | H | H | O | CH₃ | CH₃ | OCH₃ | N |
| H | CH₂CH=CH₂ | H | H | S | H | OCH₃ | OCH₃ | CH |
| H | CH₂CH=CH₂ | H | H | S | H | Cl | OCH₃ | CH |
| H | CH₂CH=CH₂ | H | H | S | H | CH₃ | OCH₃ | CH |
| H | CH₂CH=CH₂ | H | H | S | H | CH₃ | CH₃ | CH |
| H | CH₂CH=CH₂ | H | H | S | H | OCH₃ | OCH₃ | N |
| H | CH₂CH=CH₂ | H | H | S | H | CH₃ | OCH₃ | N |
| H | CH₂C≡CH | H | H | O | H | OCH₃ | OCH₃ | CH |
| H | CH₂C≡CH | H | H | O | H | Cl | OCH₃ | CH |
| H | CH₂C≡CH | H | H | O | H | CH₃ | OCH₃ | CH |
| H | CH₂C≡CH | H | H | O | H | CH₃ | CH₃ | CH |
| H | CH₂C≡CH | H | H | O | H | OCH₃ | OCH₃ | N |
| H | CH₂C≡CH | H | H | O | H | CH₃ | OCH₃ | N |
| H | CH₂C≡CH | H | H | O | H | CH₃ | CH₃ | N |
| H | CH₂C≡CH | H | H | O | H | OCH₂CH₃ | OCH₂CH₃ | N |
| H | CH₂C≡CH | H | H | O | H | NHCH₃ | OCH₂CH₃ | N |
| H | CH₂C≡CH | H | H | O | H | N(CH₃)₂ | OCH₂CH₃ | N |
| H | CH₂C≡CH | H | H | O | H | N(CH₃)₂ | OCH₃ | N |
| H | CH₂C≡CH | H | H | O | H | N(CH₃)₂ | OCH₂CF₃ | N |
| H | CH₂C≡CH | H | H | O | CH₃ | CH₃ | OCH₃ | N |
| H | CH₂C≡CH | H | H | S | H | OCH₃ | OCH₃ | CH |
| H | CH₂C≡CH | H | H | S | H | CH₃ | OCH₃ | CH |
| H | CH₂C≡CH | H | H | S | H | CH₃ | CH₃ | CH |
| H | CH₂C≡CH | H | H | S | H | OCH₃ | OCH₃ | N |
| H | CH₂C≡CH | H | H | S | H | CH₃ | OCH₃ | N |
| H | CH₂CH₂OCH₃ | H | H | O | H | OCH₃ | OCH₃ | CH |
| H | CH₂CH₂OCH₃ | H | H | O | H | Cl | OCH₃ | CH |
| H | CH₂CH₂OCH₃ | H | H | O | H | CH₃ | OCH₃ | CH |
| H | CH₂CH₂OCH₃ | H | H | O | H | CH₃ | CH₃ | CH |
| H | CH₂CH₂OCH₃ | H | H | O | H | OCH₃ | OCH₃ | N |
| H | CH₂CH₂OCH₃ | H | H | O | H | CH₃ | OCH₃ | N |
| H | CH₂CH₂OCH₃ | H | H | O | H | CH₃ | CH₃ | N |
| H | CH₂CH₂OCH₃ | H | H | O | H | OCH₂CH₃ | OCH₂CH₃ | N |
| H | CH₂CH₂OCH₃ | H | H | O | H | NHCH₃ | OCH₂CH₃ | N |
| H | CH₂CH₂OCH₃ | H | H | O | H | N(CH₃)₂ | OCH₂CH₃ | N |
| H | CH₂CH₂OCH₃ | H | H | O | H | N(CH₃)₂ | OCH₃ | N |
| H | CH₂CH₂OCH₃ | H | H | O | H | N(CH₃)₂ | OCH₂CF₃ | N |

TABLE I-continued

| | | | | | | | | |
|---|---|---|---|---|---|---|---|---|
| H | CH₂CH₂OCH₃ | H | H | O | CH₃ | CH₃ | OCH₃ | N |
| H | CH₂CH₂OCH₃ | H | H | S | H | OCH₃ | OCH₃ | CH |
| H | CH₂CH₂OCH₃ | H | H | S | H | Cl | OCH₃ | CH |
| H | CH₂CH₂OCH₃ | H | H | S | H | CH₃ | OCH₃ | CH |
| H | CH₂CH₂OCH₃ | H | H | S | H | CH₃ | CH₃ | CH |
| H | CH₂CH₂OCH₃ | H | H | S | H | OCH₃ | OCH₃ | N |
| H | CH₂CH₂OCH₃ | H | H | S | H | CH₃ | OCH₃ | N |
| H | cyclo-C₃H₇ | H | H | O | H | OCH₃ | OCH₃ | CH |
| H | cyclo-C₃H₇ | H | H | O | H | Cl | OCH₃ | CH |
| H | cyclo-C₃H₇ | H | H | O | H | CH₃ | OCH₃ | CH |
| H | cyclo-C₃H₇ | H | H | O | H | CH₃ | CH₃ | CH |
| H | cyclo-C₃H₇ | H | H | O | H | OCH₃ | OCH₃ | N |
| H | cyclo-C₃H₇ | H | H | O | H | CH₃ | OCH₃ | N |
| H | cyclo-C₃H₇ | H | H | O | H | N(CH₃)₂ | OCH₃ | N |
| H | cyclo-C₃H₇ | H | H | O | H | OCH₂CH₃ | OCH₂CH₃ | N |
| H | cyclo-C₃H₇ | H | H | O | H | NHCH₃ | OCH₂CH₃ | N |
| H | cyclo-C₃H₇ | H | H | O | H | N(CH₃)₂ | OCH₂CH₃ | N |
| H | cyclo-C₃H₇ | H | H | O | H | N(CH₃)₂ | OCH₃ | N |
| H | cyclo-C₃H₇ | H | H | O | H | N(CH₃)₂ | OCH₂CF₃ | N |
| H | cyclo-C₃H₇ | H | H | O | CH₃ | CH₃ | OCH₃ | N |
| H | cyclo-C₃H₇ | H | H | S | H | OCH₃ | OCH₃ | CH |
| H | cyclo-C₃H₇ | H | H | S | H | Cl | OCH₃ | CH |
| H | cyclo-C₃H₇ | H | H | S | H | CH₃ | OCH₃ | CH |
| H | cyclo-C₃H₇ | H | H | S | H | CH₃ | CH₃ | CH |
| H | cyclo-C₃H₇ | H | H | S | H | OCH₃ | OCH₃ | N |
| H | cyclo-C₃H₇ | H | H | S | H | CH₃ | OCH₃ | N |
| H | CH₃ | CH₃ | H | O | H | OCH₃ | OCH₃ | CH |
| H | CH₃ | CH₃ | H | O | H | Cl | OCH₃ | CH |
| H | CH₃ | CH₃ | H | O | H | CH₃ | OCH₃ | CH |
| H | CH₃ | CH₃ | H | O | H | CH₃ | CH₃ | CH |
| H | CH₃ | CH₃ | H | O | H | OCH₃ | OCH₃ | N |
| H | CH₃ | CH₃ | H | O | H | CH₃ | OCH₃ | N |
| H | CH₃ | CH₃ | H | O | H | CH₃ | CH₃ | N |
| H | CH₃ | CH₃ | H | O | H | OCH₂CH₃ | OCH₂CH₃ | N |
| H | CH₃ | CH₃ | H | O | H | NHCH₃ | OCH₂CH₃ | N |
| H | CH₃ | CH₃ | H | O | H | N(CH₃)₂ | OCH₂CH₃ | N |
| H | CH₃ | CH₃ | H | O | H | N(CH₃)₂ | OCH₃ | N |
| H | CH₃ | CH₃ | H | O | H | N(CH₃)₂ | OCH₂CF₃ | N |
| H | CH₃ | CH₃ | H | O | CH₃ | CH₃ | OCH₃ | N |
| H | CH₃ | CH₃ | H | S | H | OCH₃ | OCH₃ | CH |
| H | CH₃ | CH₃ | H | S | H | Cl | OCH₃ | CH |
| H | CH₃ | CH₃ | H | S | H | CH₃ | OCH₃ | CH |
| H | CH₃ | CH₃ | H | S | H | CH₃ | CH₃ | CH |
| H | CH₃ | CH₃ | H | S | H | OCH₃ | OCH₃ | N |
| H | CH₃ | CH₃ | H | S | H | CH₃ | OCH₃ | N |
| H | CH₃ | CH₃ | H | O | H | OCH₃ | OCH₃ | CH |
| H | CH₃ | CH₃ | H | O | H | Cl | OCH₃ | CH |
| H | CH₃ | CH₃ | H | O | H | CH₃ | OCH₃ | CH |
| H | CH₃ | CH₃ | H | O | H | CH₃ | CH₃ | CH |
| H | CH₃ | CH₃ | H | O | H | OCH₃ | OCH₃ | N |
| H | CH₃ | CH₃ | H | O | H | CH₃ | OCH₃ | N |
| H | CH₃ | CH₃ | H | O | H | CH₃ | CH₃ | N |
| H | CH₃ | CH₃ | H | O | H | OCH₂CH₃ | OCH₂CH₃ | N |
| H | CH₃ | CH₃ | H | O | H | NHCH₃ | OCH₂CH₃ | N |
| H | CH₃ | CH₃ | H | O | H | N(CH₃)₂ | OCH₂CH₃ | N |
| H | CH₃ | CH₃ | H | O | H | N(CH₃)₂ | OCH₃ | N |
| H | CH₃ | CH₃ | H | O | H | N(CH₃)₂ | OCH₂CF₃ | N |
| H | CH₃ | CH₃ | H | O | CH₃ | CH₃ | OCH₃ | N |
| H | CH₃ | CH₃ | H | S | H | OCH₃ | OCH₃ | CH |
| H | CH₃ | CH₃ | H | S | H | Cl | OCH₃ | CH |
| H | CH₃ | CH₃ | H | S | H | CH₃ | OCH₃ | CH |
| H | CH₃ | CH₃ | H | S | H | CH₃ | CH₃ | CH |
| H | CH₃ | CH₃ | H | S | H | OCH₃ | OCH₃ | N |
| H | CH₃ | CH₃ | H | S | H | CH₃ | OCH₃ | N |
| H | CH₃ | CH₃ | Cl | O | H | OCH₃ | OCH₃ | CH |
| H | CH₃ | CH₃ | Cl | O | H | Cl | OCH₃ | CH |
| H | CH₃ | CH₃ | Cl | O | H | CH₃ | OCH₃ | CH |
| H | CH₃ | CH₃ | Cl | O | H | CH₃ | CH₃ | CH |
| H | CH₃ | CH₃ | Cl | O | H | OCH₃ | OCH₃ | N |
| H | CH₃ | CH₃ | Cl | O | H | CH₃ | OCH₃ | N |
| H | CH₃ | CH₃ | Cl | O | H | CH₃ | CH₃ | N |
| H | CH₃ | CH₃ | Cl | O | H | OCH₂CH₃ | OCH₂CH₃ | N |
| H | CH₃ | CH₃ | Cl | O | H | NHCH₃ | OCH₂CH₃ | N |
| H | CH₃ | CH₃ | Cl | O | H | N(CH₃)₂ | OCH₂CH₃ | N |
| H | CH₃ | CH₃ | Cl | O | H | N(CH₃)₂ | OCH₃ | N |
| H | CH₃ | CH₃ | Cl | O | H | N(CH₃)₂ | OCH₂CF₃ | N |
| H | CH₃ | CH₃ | Cl | O | CH₃ | CH₃ | OCH₃ | N |
| H | CH₃ | CH₃ | Cl | S | H | OCH₃ | OCH₃ | CH |
| H | CH₃ | CH₃ | Cl | S | H | OCH₃ | CH | |
| H | CH₃ | CH₃ | Cl | S | H | CH₃ | OCH₃ | CH |
| H | CH₃ | CH₃ | Cl | S | H | CH₃ | CH₃ | CH |
| H | CH₃ | CH₃ | Cl | S | H | OCH₃ | OCH₃ | N |

TABLE I-continued

| | | | | | | | | |
|---|---|---|---|---|---|---|---|---|
| H | CH₃ | CH₃ | Cl | S | H | CH₃ | OCH₃ | N |
| H | CH₃ | CH₃ | Cl | O | H | OCH₃ | OCH₃ | CH |
| H | CH₃ | CH₃ | Cl | O | H | Cl | OCH₃ | CH |
| H | CH₃ | CH₃ | Cl | O | H | CH₃ | OCH₃ | CH |
| H | CH₃ | CH₃ | Cl | O | H | CH₃ | CH₃ | CH |
| H | CH₃ | CH₃ | Cl | O | H | OCH₃ | OCH₃ | N |
| H | CH₃ | CH₃ | Cl | O | H | CH₃ | OCH₃ | N |
| H | CH₃ | CH₃ | Cl | O | H | CH₃ | CH₃ | N |
| H | CH₃ | CH₃ | Cl | O | H | OCH₂CH₃ | OCH₂CH₃ | N |
| H | CH₃ | CH₃ | Cl | O | H | NHCH₃ | OCH₂CH₃ | N |
| H | CH₃ | CH₃ | Cl | O | H | N(CH₃)₂ | OCH₂CH₃ | N |
| H | CH₃ | CH₃ | Cl | O | H | N(CH₃)₂ | OCH₃ | N |
| H | CH₃ | CH₃ | Cl | O | H | N(CH₃)₂ | OCH₂CF₃ | N |
| H | CH₃ | CH₃ | Cl | O | CH₃ | CH₃ | OCH₃ | N |
| H | CH₃ | CH₃ | Cl | S | H | OCH₃ | OCH₃ | CH |
| H | CH₃ | CH₃ | Cl | S | H | Cl | OCH₃ | CH |
| H | CH₃ | CH₃ | Cl | S | H | CH₃ | OCH₃ | CH |
| H | CH₃ | CH₃ | Cl | S | H | CH₃ | CH₃ | CH |
| H | CH₃ | CH₃ | Cl | S | H | OCH₃ | OCH₃ | N |
| H | CH₃ | CH₃ | Cl | S | H | CH₃ | OCH₃ | N |
| H | CH₃ | CH₃ | CH₃ | O | H | OCH₃ | OCH₃ | CH |
| H | CH₃ | CH₃ | CH₃ | O | H | Cl | OCH₃ | CH |
| H | CH₃ | CH₃ | CH₃ | O | H | CH₃ | OCH₃ | CH |
| H | CH₃ | CH₃ | CH₃ | O | H | CH₃ | CH₃ | CH |
| H | CH₃ | CH₃ | CH₃ | O | H | OCH₃ | OCH₃ | N |
| H | CH₃ | CH₃ | CH₃ | O | H | CH₃ | OCH₃ | N |
| H | CH₃ | CH₃ | CH₃ | O | H | CH₃ | CH₃ | N |
| H | CH₃ | CH₃ | CH₃ | O | H | OCH₂CH₃ | OCH₂CH₃ | N |
| H | CH₃ | CH₃ | CH₃ | O | H | NHCH₃ | OCH₂CH₃ | N |
| H | CH₃ | CH₃ | CH₃ | O | H | N(CH₃)₂ | OCH₂CH₃ | N |
| H | CH₃ | CH₃ | CH₃ | O | H | N(CH₃)₂ | OCH₃ | N |
| H | CH₃ | CH₃ | CH₃ | O | H | N(CH₃)₂ | OCH₂CF₃ | N |
| H | CH₃ | CH₃ | CH₃ | O | CH₃ | CH₃ | OCH₃ | N |
| H | CH₃ | CH₃ | CH₃ | S | H | OCH₃ | OCH₃ | CH |
| H | CH₃ | CH₃ | CH₃ | S | H | Cl | OCH₃ | CH |
| H | CH₃ | CH₃ | CH₃ | S | H | CH₃ | OCH₃ | CH |
| H | CH₃ | CH₃ | CH₃ | S | H | CH₃ | OCH₃ | CH |
| H | CH₃ | CH₃ | CH₃ | S | H | OCH₃ | OCH₃ | N |
| H | CH₃ | CH₃ | CH₃ | S | H | CH₃ | OCH₃ | N |
| H | CH₃ | CH₃ | CH₃ | O | H | OCH₃ | OCH₃ | CH |
| H | CH₃ | CH₃ | CH₃ | O | H | Cl | OCH₃ | CH |
| H | CH₃ | CH₃ | CH₃ | O | H | CH₃ | OCH₃ | CH |
| H | CH₃ | CH₃ | CH₃ | O | H | CH₃ | CH₃ | CH |
| H | CH₃ | CH₃ | CH₃ | O | H | OCH₃ | OCH₃ | N |
| H | CH₃ | CH₃ | CH₃ | O | H | CH₃ | OCH₃ | N |
| H | CH₃ | CH₃ | CH₃ | O | H | CH₃ | CH₃ | N |
| H | CH₃ | CH₃ | CH₃ | O | H | OCH₂CH₃ | OCH₂CH₃ | N |
| H | CH₃ | CH₃ | CH₃ | O | H | NHCH₃ | OCH₂CH₃ | N |
| H | CH₃ | CH₃ | CH₃ | O | H | N(CH₃)₂ | OCH₂CH₃ | N |
| H | CH₃ | CH₃ | CH₃ | O | H | N(CH₃)₂ | OCH₃ | N |
| H | CH₃ | CH₃ | CH₃ | O | H | N(CH₃)₂ | OCH₂CF₃ | N |
| H | CH₃ | CH₃ | CH₃ | O | CH₃ | CH₃ | OCH₃ | N |
| H | CH₃ | CH₃ | CH₃ | S | H | OCH₃ | OCH₃ | CH |
| H | CH₃ | CH₃ | CH₃ | S | H | Cl | OCH₃ | CH |
| H | CH₃ | CH₃ | CH₃ | S | H | CH₃ | OCH₃ | CH |
| H | CH₃ | CH₃ | CH₃ | S | H | CH₃ | CH₃ | CH |
| H | CH₃ | CH₃ | CH₃ | S | H | OCH₃ | OCH₃ | N |
| H | CH₃ | CH₃ | CH₃ | S | H | CH₃ | OCH₃ | N |
| H | CH₂CH=CH₂ | CH₃ | H | O | H | OCH₃ | OCH₃ | CH |
| H | CH₂CH=CH₂ | CH₃ | H | O | H | Cl | OCH₃ | CH |
| H | CH₂CH=CH₂ | CH₃ | H | O | H | CH₃ | OCH₃ | CH |
| H | CH₂CH=CH₂ | CH₃ | H | O | H | CH₃ | CH₃ | CH |
| H | CH₂CH=CH₂ | CH₃ | H | O | H | OCH₃ | OCH₃ | N |
| H | CH₂CH=CH₂ | CH₃ | H | O | H | CH₃ | OCH₃ | N |
| H | CH₂CH=CH₂ | CH₃ | H | O | H | CH₃ | CH₃ | N |
| H | CH₂CH=CH₂ | CH₃ | H | O | H | OCH₂CH₃ | OCH₂CH₃ | N |
| H | CH₂CH=CH₂ | CH₃ | H | O | H | NHCH₃ | OCH₂CH₃ | N |
| H | CH₂CH=CH₂ | CH₃ | H | O | H | N(CH₃)₂ | OCH₂CH₃ | N |
| H | CH₂CH=CH₂ | CH₃ | H | O | H | N(CH₃)₂ | OCH₃ | N |
| H | CH₂CH=CH₂ | CH₃ | H | O | H | N(CH₃)₂ | OCH₂CF₃ | N |
| H | CH₂CH=CH₂ | CH₃ | H | O | CH₃ | CH₃ | OCH₃ | N |
| H | CH₂CH=CH₂ | CH₃ | H | S | H | OCH₃ | OCH₃ | CH |
| H | CH₂CH=CH₂ | CH₃ | H | S | H | Cl | OCH₃ | CH |
| H | CH₂CH=CH₂ | CH₃ | H | S | H | CH₃ | OCH₃ | CH |
| H | CH₂CH=CH₂ | CH₃ | H | S | H | CH₃ | CH₃ | CH |
| H | CH₂CH=CH₂ | CH₃ | H | S | H | OCH₃ | OCH₃ | N |
| H | CH₂CH=CH₂ | CH₃ | H | S | H | CH₃ | OCH₃ | N |
| H | CH₂C≡CH | CH₃ | H | O | H | OCH₃ | OCH₃ | CH |
| H | CH₂C≡CH | CH₃ | H | O | H | Cl | OCH₃ | CH |
| H | CH₂C≡CH | CH₃ | H | O | H | CH₃ | OCH₃ | CH |
| H | CH₂C≡CH | CH₃ | H | O | H | CH₃ | CH₃ | CH |
| H | CH₂C≡CH | CH₃ | H | O | H | OCH₃ | OCH₃ | N |

TABLE I-continued

| | | | | | | | | |
|---|---|---|---|---|---|---|---|---|
| H | CH₂C≡CH | CH₃ | H | O | H | CH₃ | OCH₃ | N |
| H | CH₂C≡CH | CH₃ | H | O | H | CH₃ | CH₃ | N |
| H | CH₂C≡CH | CH₃ | H | O | H | OCH₂CH₃ | OCH₂CH₃ | N |
| H | CH₂C≡CH | CH₃ | H | O | H | NHCH₃ | OCH₂CH₃ | N |
| H | CH₂C≡CH | CH₃ | H | O | H | N(CH₃)₂ | OCH₂CH₃ | N |
| H | CH₂C≡CH | CH₃ | H | O | H | N(CH₃)₂ | OCH₃ | N |
| H | CH₂C≡CH | CH₃ | H | O | H | N(CH₃)₂ | OCH₂CF₃ | N |
| H | CH₂C≡CH | CH₃ | H | O | CH₃ | CH₃ | OCH₃ | N |
| H | CH₂C≡CH | CH₃ | H | S | H | OCH₃ | OCH₃ | CH |
| H | CH₂C≡CH | CH₃ | H | S | H | Cl | OCH₃ | CH |
| H | CH₂C≡CH | CH₃ | H | S | H | CH₃ | OCH₃ | CH |
| H | CH₂C≡CH | CH₃ | H | S | H | CH₃ | CH₃ | CH |
| H | CH₂C≡CH | CH₃ | H | S | H | OCH₃ | OCH₃ | N |
| H | CH₂C≡CH | CH₃ | H | S | H | CH₃ | OCH₃ | N |
| H | CH₂CH₃ | CH₂CH₃ | H | O | H | OCH₃ | OCH₃ | CH |
| H | CH₂CH₃ | CH₂CH₃ | H | O | H | Cl | OCH₃ | CH |
| H | CH₂CH₃ | CH₂CH₃ | H | O | H | CH₃ | OCH₃ | CH |
| H | CH₂CH₃ | CH₂CH₃ | H | O | H | CH₃ | CH₃ | CH |
| H | CH₂CH₃ | CH₂CH₃ | H | O | H | OCH₃ | OCH₃ | N |
| H | CH₂CH₃ | CH₂CH₃ | H | O | H | CH₃ | OCH₃ | N |
| H | CH₂CH₃ | CH₂CH₃ | H | O | H | CH₃ | CH₃ | N |
| H | CH₂CH₃ | CH₂CH₃ | H | O | H | OCH₂CH₃ | OCH₂CH₃ | N |
| H | CH₂CH₃ | CH₂CH₃ | H | O | H | NHCH₃ | OCH₂CH₃ | N |
| H | CH₂CH₃ | CH₂CH₃ | H | O | H | N(CH₃)₂ | OCH₂CH₃ | N |
| H | CH₂CH₂ | CH₂CH₃ | H | O | H | N(CH₃)₂ | OCH₃ | N |
| H | CH₂CH₃ | CH₂CH₃ | H | O | H | N(CH₃)₂ | OCH₂CF₃ | N |
| H | CH₂CH₃ | CH₂CH₃ | H | O | CH₃ | CH₃ | OCH₃ | N |
| H | CH₂CH₃ | CH₂CH₃ | H | S | H | OCH₃ | OCH₃ | CH |
| H | CH₂CH₃ | CH₂CH₃ | H | S | H | Cl | OCH₃ | CH |
| H | CH₂CH₃ | CH₂CH₃ | H | S | H | CH₃ | OCH₃ | CH |
| H | CH₂CH₃ | CH₂CH₃ | H | S | H | CH₃ | CH₃ | CH |
| H | CH₂CH₃ | CH₂CH₃ | H | S | H | OCH₃ | OCH₃ | N |
| H | CH₂CH₃ | CH₂CH₃ | H | S | H | CH₃ | OCH₃ | N |
| H | OCH₃ | CH₃ | H | O | H | OCH₃ | OCH₃ | CH |
| H | OCH₃ | CH₃ | H | O | H | Cl | OCH₃ | CH |
| H | OCH₃ | CH₃ | H | O | H | CH₃ | OCH₃ | CH |
| H | OCH₃ | CH₃ | H | O | H | CH₃ | CH₃ | CH |
| H | OCH₃ | CH₃ | H | O | H | OCH₃ | OCH₃ | NO |
| H | OCH₃ | CH₃ | H | O | H | CH₃ | OCH₃ | N |
| H | OCH₃ | CH₃ | H | O | H | CH₃ | CH₃ | N |
| H | OCH₃ | CH₃ | H | O | H | OCH₂CH₃ | OCH₂CH₃ | N |
| H | OCH₃ | CH₃ | H | O | H | NHCH₃ | OCH₂CH₃ | N |
| H | OCH₃ | CH₃ | H | O | H | N(CH₃)₂ | OCH₂CH₃ | N |
| H | OCH₃ | CH₃ | H | O | H | N(CH₃)₂ | OCH₃ | N |
| H | OCH₃ | CH₃ | H | O | H | N(CH₃)₂ | OCH₂CF₃ | N |
| H | OCH₃ | CH₃ | H | O | CH₃ | CH₃ | OCH₃ | N |
| H | OCH₃ | CH₃ | H | S | H | OCH₃ | OCH₃ | CH |
| H | OCH₃ | CH₃ | H | S | H | Cl | OCH₃ | CH |
| H | OCH₃ | CH₃ | H | S | H | CH₃ | OCH₃ | CH |
| H | OCH₃ | CH₃ | H | S | H | CH₃ | CH₃ | CH |
| H | OCH₃ | CH₃ | H | S | H | OCH₃ | OCH₃ | N |
| H | OCH₃ | CH₃ | H | S | H | CH₃ | OCH₃ | N |
| H | NHCH₃ | CH₃ | H | O | H | OCH₃ | OCH₃ | CH |
| H | NHCH₃ | CH₃ | H | O | H | Cl | OCH₃ | CH |
| H | NHCH₃ | CH₃ | H | O | H | CH₃ | OCH₃ | CH |
| H | NHCH₃ | CH₃ | H | O | H | CH₃ | CH₃ | CH |
| H | NHCH₃ | CH₃ | H | O | H | OCH₃ | OCH₃ | N |
| H | NHCH₃ | CH₃ | H | O | H | CH₃ | OCH₃ | N |
| H | NHCH₃ | CH₃ | H | O | H | CH₃ | OCH₃ | N |
| H | NHCH₃ | CH₃ | H | O | H | CH₃ | CH₃ | N |
| H | NHCH₃ | CH₃ | H | O | H | OCH₂CH₃ | OCH₂CH₃ | N |
| H | NHCH₃ | CH₃ | H | O | H | NHCH₃ | OCH₂CH₃ | N |
| H | NHCH₃ | CH₃ | H | O | H | N(CH₃)₂ | OCH₂CH₃ | N |
| H | NHCH₃ | CH₃ | H | O | H | N(CH₃)₂ | OCH₃ | N |
| H | NHCH₃ | CH₃ | H | O | H | N(CH₃)₃ | OCH₂CF₃ | N |
| H | NHCH₃ | CH₃ | H | O | CH₃ | CH₃ | OCH₃ | N |
| H | NHCH₃ | CH₃ | H | S | H | OCH₃ | OCH₃ | CH |
| H | NHCH₃ | CH₃ | H | S | H | Cl | OCH₃ | CH |
| H | NHCH₃ | CH₃ | H | S | H | CH₃ | OCH₃ | CH |
| H | NHCH₃ | CH₃ | H | S | H | CH₃ | CH₃ | CH |
| H | NHCH₃ | CH₃ | H | S | H | OCH₃ | OCH₃ | N |
| H | NHCH₃ | CH₃ | H | S | H | CH₃ | OCH₃ | N |
| H | N(CH₃)₂ | CH₃ | H | O | H | OCH₃ | OCH₃ | CH |
| H | N(CH₃)₂ | CH₃ | H | O | H | Cl | OCH₃ | CH |
| H | N(CH₃)₂ | CH₃ | H | O | H | CH₃ | OCH₃ | CH |
| H | N(CH₃)₂ | CH₃ | H | O | H | CH₃ | CH₃ | CH |
| H | N(CH₃)₂ | CH₃ | H | O | H | OCH₃ | OCH₃ | N |
| H | N(CH₃)₂ | CH₃ | H | O | H | CH₃ | OCH₃ | N |
| H | N(CH₃)₂ | CH₃ | H | O | H | CH₃ | CH₃ | N |
| H | N(CH₃)₂ | CH₃ | H | O | H | OCH₂CH₃ | OCH₂CH₃ | N |
| H | N(CH₃)₂ | CH₃ | H | O | H | NHCH₃ | OCH₂CH₃ | N |
| H | N(CH₃)₂ | CH₃ | H | O | H | N(CH₃)₂ | OCH₂CH₃ | N |

TABLE I-continued

| | | | | | | | | |
|---|---|---|---|---|---|---|---|---|
| H | N(CH₃)₂ | CH₃ | H | O | H | N(CH₃)₂ | OCH₃ | N |
| H | N(CH₃)₂ | CH₃ | H | O | H | N(CH₃)₂ | OCH₂CF₃ | N |
| H | N(CH₃)₂ | CH₃ | H | O | CH₃ | CH₃ | OCH₃ | N |
| H | N(CH₃)₂ | CH₃ | H | S | H | OCH₃ | OCH₃ | CH |
| H | N(CH₃)₂ | CH₃ | H | S | H | Cl | OCH₃ | CH |
| H | N(CH₃)₂ | CH₃ | H | S | H | CH₃ | OCH₃ | CH |
| H | N(CH₃)₂ | CH₃ | H | S | H | CH₃ | CH₃ | CH |
| H | N(CH₃)₂ | CH₃ | H | S | H | CH₃ | OCH₃ | N |
| H | OH | CH₃ | H | O | H | OCH₃ | OCH₃ | CH |
| H | OH | CH₃ | H | O | H | Cl | OCH₃ | CH |
| H | OH | CH₃ | H | O | H | CH₃ | OCH₃ | CH |
| H | OH | CH₃ | H | O | H | CH₃ | CH₃ | CH |
| H | OH | CH₃ | H | O | H | OCH₃ | OCH₃ | N |
| H | OH | CH₃ | H | O | H | CH₃ | OCH₃ | N |
| H | OH | CH₃ | H | O | H | CH₃ | CH₃ | N |
| H | OH | CH₃ | H | O | H | OCH₂CH₃ | OCH₂CH₃ | N |
| H | OH | CH₃ | H | O | H | NHCH₃ | OCH₂CH₃ | N |
| H | OH | CH₃ | H | O | H | N(CH₃)₂ | OCH₂CH₃ | N |
| H | OH | CH₃ | H | O | H | N(CH₃)₂ | OCH₃ | N |
| H | OH | CH₃ | H | O | H | N(CH₃)₂ | OCH₂CF₃ | N |
| H | OH | CH₃ | H | O | CH₃ | CH₃ | OCH₃ | N |
| H | OH | CH₃ | H | S | H | OCH₃ | OCH₃ | CH |
| H | OH | CH₃ | H | S | H | Cl | OCH₃ | CH |
| H | OH | CH₃ | H | S | H | CH₃ | OCH₃ | CH |
| H | OH | CH₃ | H | S | H | CH₃ | CH₃ | CH |
| H | OH | CH₃ | H | S | H | OCH₃ | OCH₃ | N |
| H | OH | CH₃ | H | S | H | CH₃ | OCH₃ | N |
| H | NH₂ | CH₃ | H | O | H | OCH₃ | OCH₃ | CH |
| H | NH₂ | CH₃ | H | O | H | Cl | OCH₃ | CH |
| H | NH₂ | CH₃ | H | O | H | CH₃ | OCH₃ | CH |
| H | NH₂ | CH₃ | H | O | H | CH₃ | CH₃ | CH |
| H | NH₂ | CH₃ | H | O | H | OCH₃ | OCH₃ | N |
| H | NH₂ | CH₃ | H | O | H | CH₃ | OCH₃ | N |
| H | NH₂ | CH₃ | H | O | H | CH₃ | CH₃ | N |
| H | NH₂ | CH₃ | H | O | H | OCH₂CH₃ | OCH₂CH₃ | N |
| H | NH₂ | CH₃ | H | O | H | NHCH₃ | OCH₂CH₃ | N |
| H | NH₂ | CH₃ | H | O | H | N(CH₃)₂ | OCH₂CH₃ | N |
| H | NH₂ | CH₃ | H | O | H | N(CH₃)₂ | OCH₃ | N |
| H | NH₂ | CH₃ | H | O | H | N(CH₃)₂ | OCH₂CF₃ | N |
| H | NH₂ | CH₃ | H | O | CH₃ | CH₃ | OCH₃ | N |
| H | NH₂ | CH₃ | H | S | H | OCH₃ | OCH₃ | CH |
| H | NH₂ | CH₃ | H | S | H | Cl | OCH₃ | CH |
| H | NH₂ | CH₃ | H | S | H | CH₃ | OCH₃ | CH |
| H | NH₂ | CH₃ | H | S | H | CH₃ | CH₃ | CH |
| H | NH₂ | CH₃ | H | S | H | OCH₃ | OCH₃ | N |
| H | NH₂ | CH₃ | H | S | H | CH₃ | OCH₃ | N |
| H | CN | CH₃ | H | O | H | OCH₃ | OCH₃ | CH |
| H | CN | CH₃ | H | O | H | Cl | OCH₃ | CH |
| H | CN | CH₃ | H | O | H | CH₃ | OCH₃ | CH |
| H | CN | CH₃ | H | O | H | CH₃ | CH₃ | CH |
| H | CN | CH₃ | H | O | H | OCH₃ | OCH₃ | N |
| H | CN | CH₃ | H | O | H | CH₃ | OCH₃ | N |
| H | CN | CH₃ | H | O | H | CH₃ | CH₃ | N |
| H | CN | CH₃ | H | O | H | OCH₂CH₃ | OCH₂CH₃ | N |
| H | CN | CH₃ | H | O | H | NHCH₃ | OCH₂CH₃ | N |
| H | CN | CH₃ | H | O | H | N(CH₃)₂ | OCH₂CH₃ | N |
| H | CN | CH₃ | H | O | H | N(CH₃)₂ | OCH₃ | N |
| H | CN | CH₃ | H | O | H | N(CH₃)₂ | OCH₂CF₃ | N |
| H | CN | CH₃ | H | O | CH₃ | CH₃ | OCH₃ | N |
| H | CN | CH₃ | H | S | H | OCH₃ | OCH₃ | CH |
| H | CN | CH₃ | H | S | H | Cl | OCH₃ | CH |
| H | CN | CH₃ | H | S | H | CH₃ | OCH₃ | CH |
| H | CN | CH₃ | H | S | H | CH₃ | CH₃ | CH |
| H | CN | CH₃ | H | S | H | OCH₃ | OCH₃ | N |
| H | CN | CH₃ | H | S | H | CH₃ | OCH₃ | N |
| H | COCH₃ | CH₃ | H | O | H | Cl | OCH₃ | CH |
| H | COCH₃ | CH₃ | H | O | H | CH₃ | OCH₃ | CH |
| H | COCH₃ | CH₃ | H | O | H | CH₃ | CH₃ | CH |
| H | COCH₃ | CH₃ | H | O | H | OCH₃ | OCH₃ | N |
| H | COCH₃ | CH₃ | H | O | H | CH₃ | OCH₃ | N |
| H | COCH₃ | CH₃ | H | O | H | CH₃ | CH₃ | N |
| H | COCH₃ | CH₃ | H | O | H | OCH₂CH₃ | OCH₂CH₃ | N |
| H | COCH₃ | CH₃ | H | O | H | NHCH₃ | OCH₂CH₃ | N |
| H | COCH₃ | CH₃ | H | O | H | N(CH₃)₂ | OCH₂CH₃ | N |
| H | COCH₃ | CH₃ | H | O | H | N(CH₃)₂ | OCH₃ | N |
| H | COCH₃ | CH₃ | H | O | H | N(CH₃)₂ | OCH₂CF₃ | N |
| H | COCH₃ | CH₃ | H | O | CH₃ | CH₃ | OCH₃ | N |
| H | COCH₃ | CH₃ | H | S | H | OCH₃ | OCH₃ | CH |
| H | COCH₃ | CH₃ | H | S | H | Cl | OCH₃ | CH |
| H | COCH₃ | CH₃ | H | S | H | CH₃ | OCH₃ | CH |
| H | COCH₃ | CH₃ | H | S | H | CH₃ | CH₃ | CH |
| H | COCH₃ | CH₃ | H | S | H | OCH₃ | OCH₃ | N |

TABLE I-continued

| | | | | | | | | |
|---|---|---|---|---|---|---|---|---|
| H | COCH$_3$ | CH$_3$ | H | S | H | CH$_3$ | OCH$_3$ | N |
| H | CO$_2$CH$_3$ | CH$_3$ | H | O | H | OCH$_3$ | OCH$_3$ | CH |
| H | CO$_2$CH$_3$ | CH$_3$ | H | O | H | Cl | OCH$_3$ | CH |
| H | CO$_2$CH$_3$ | CH$_3$ | H | O | H | CH$_3$ | OCH$_3$ | CH |
| H | CO$_2$CH$_3$ | CH$_3$ | H | O | H | CH$_3$ | CH$_3$ | CH |
| H | CO$_2$CH$_3$ | CH$_3$ | H | O | H | OCH$_3$ | OCH$_3$ | N |
| H | CO$_2$CH$_3$ | CH$_3$ | H | O | H | CH$_3$ | OCH$_3$ | N |
| H | CO$_2$CH$_3$ | CH$_3$ | H | O | H | CH$_3$ | CH$_3$ | N |
| H | CO$_2$CH$_3$ | CH$_3$ | H | O | H | OCH$_2$CH$_3$ | OCH$_2$CH$_3$ | N |
| H | CO$_2$CH$_3$ | CH$_3$ | H | O | H | NHCH$_3$ | OCH$_2$CH$_3$ | N |
| H | CO$_2$CH$_3$ | CH$_3$ | H | O | H | N(CH$_3$)$_2$ | OCH$_2$CH$_3$ | N |
| H | CO$_2$CH$_3$ | CH$_3$ | H | O | H | N(CH$_3$)$_2$ | OCH$_3$ | N |
| H | CO$_2$CH$_3$ | CH$_3$ | H | O | H | N(CH$_3$)$_2$ | OCH$_2$CF$_3$ | N |
| H | CO$_2$CH$_3$ | CH$_3$ | H | O | CH$_3$ | CH$_3$ | OCH$_3$ | N |
| H | CO$_2$CH$_3$ | CH$_3$ | H | S | H | OCH$_3$ | OCH$_3$ | CH |
| H | CO$_2$CH$_3$ | CH$_3$ | H | S | H | Cl | OCH$_3$ | CH |
| H | CO$_2$CH$_3$ | CH$_3$ | H | S | H | CH$_3$ | OCH$_3$ | CH |
| H | CO$_2$CH$_3$ | CH$_3$ | H | S | H | CH$_3$ | CH$_3$ | CH |
| H | CO$_2$CH$_3$ | CH$_3$ | H | S | H | OCH$_3$ | OCH$_3$ | N |
| H | CO$_2$CH$_3$ | CH$_3$ | H | S | H | CH$_3$ | OCH$_3$ | N |
| H | CON(CH$_3$)$_2$ | CH$_3$ | H | O | H | OCH$_3$ | OCH$_3$ | CH |
| H | CON(CH$_3$)$_2$ | CH$_3$ | H | O | H | Cl | OCH$_3$ | H |
| H | CON(CH$_3$)$_2$ | CH$_3$ | H | O | H | CH$_3$ | OCH$_3$ | CH |
| H | CON(CH$_3$)$_2$ | CH$_3$ | H | O | H | CH$_3$ | CH$_3$ | CH |
| H | CON(CH$_3$)$_2$ | CH$_3$ | H | O | H | OCH$_3$ | OCH$_3$ | N |
| H | CON(CH$_3$)$_2$ | CH$_3$ | H | O | H | CH$_3$ | OCH$_3$ | N |
| H | CON(CH$_3$)$_2$ | CH$_3$ | H | O | H | CH$_3$ | CH$_3$ | N |
| H | CON(CH$_3$)$_2$ | CH$_3$ | H | O | H | OCH$_2$CH$_3$ | OCH$_2$CH$_3$ | N |
| H | CON(CH$_3$)$_2$ | CH$_3$ | H | O | H | NHCH$_3$ | OCH$_2$CH$_3$ | N |
| H | CON(CH$_3$)$_2$ | CH$_3$ | H | O | H | N(CH$_3$)$_2$ | OCH$_2$CH$_3$ | N |
| H | CON(CH$_3$)$_2$ | CH$_3$ | H | O | H | N(CH$_3$)$_2$ | OCH$_3$ | N |
| H | CON(CH$_3$)$_2$ | CH$_3$ | H | O | H | N(CH$_3$)$_2$ | OCH$_2$CF$_3$ | N |
| H | CON(CH$_3$)$_2$ | CH$_3$ | H | O | CH$_3$ | CH$_3$ | OCH$_3$ | CH |
| H | CON(CH$_3$)$_2$ | CH$_3$ | H | S | H | OCH$_3$ | OCH$_3$ | CH |
| H | CON(CH$_3$)$_2$ | CH$_3$ | H | S | H | Cl | OCH$_3$ | CH |
| H | CON(CH$_3$)$_2$ | CH$_3$ | H | S | H | CH$_3$ | OCH$_3$ | CH |
| H | CON(CH$_3$)$_2$ | CH$_3$ | H | S | H | CH$_3$ | CH$_3$ | CH |
| H | CON(CH$_3$)$_2$ | CH$_3$ | H | S | H | OCH$_3$ | CH$_3$ | N |
| H | CON(CH$_3$)$_2$ | CH$_3$ | H | S | H | CH$_3$ | OCH$_3$ | N |
| H | —CH$_2$CH$_2$CH$_2$— | | H | O | H | OCH$_3$ | OCH$_3$ | CH |
| H | —CH$_2$CH$_2$CH$_2$— | | H | O | H | Cl | OCH$_3$ | CH |
| H | —CH$_2$CH$_2$CH$_2$— | | H | O | H | CH$_3$ | OCH$_3$ | CH |
| H | —CH$_2$CH$_2$CH$_2$— | | H | O | H | CH$_3$ | OCH$_3$ | CH |
| H | —CH$_2$CH$_2$CH$_2$— | | H | O | H | CH$_3$ | CH$_3$ | N |
| H | —CH$_2$CH$_2$CH$_2$— | | H | O | H | OCH$_2$CH$_3$ | OCH$_2$CH$_3$ | N |
| H | —CH$_2$CH$_2$CH$_2$— | | H | O | H | NHCH$_3$ | OCH$_2$CH$_3$ | N |
| H | —CH$_2$CH$_2$CH$_2$— | | H | O | H | N(CH$_3$)$_2$ | OCH$_2$CH$_3$ | N |
| H | —CH$_2$CH$_2$CH$_2$— | | H | O | H | N(CH$_3$)$_2$ | OCH$_2$CF$_3$ | N |
| H | —CH$_2$CH$_2$CH$_2$— | | H | O | CH$_3$ | CH$_3$ | OCH$_3$ | N |
| H | —CH$_2$CH$_2$CH$_2$— | | H | S | H | OCH$_3$ | OCH$_3$ | CH |
| H | —CH$_2$CH$_2$CH$_2$— | | H | S | H | Cl | OCH$_3$ | CH |
| H | —CH$_2$CH$_2$CH$_2$— | | H | S | H | CH$_3$ | OCH$_3$ | CH |
| H | —CH$_2$CH$_2$CH$_2$— | | H | S | H | CH$_3$ | CH$_3$ | CH |
| H | —CH$_2$CH$_2$OCH$_2$— | | H | S | H | OCH$_3$ | OCH$_3$ | N |
| H | —CH$_2$CH$_2$OCH$_2$— | | H | S | H | CH$_3$ | OCH$_3$ | N |
| H | —CH$_2$CH$_2$OCH$_2$CH$_2$— | | H | O | H | OCH$_3$ | OCH$_3$ | H |
| H | —CH$_2$CH$_2$OCH$_2$CH$_2$— | | H | O | H | Cl | OCH$_3$ | CH |
| H | —CH$_2$CH$_2$OCH$_2$CH$_2$— | | H | O | H | CH$_3$ | OCH$_3$ | CH |
| H | —CH$_2$CH$_2$OCH$_2$CH$_2$— | | H | O | H | CH$_3$ | CH$_3$ | CH |
| H | —CH$_2$CH$_2$OCH$_2$CH$_2$— | | H | O | H | OCH$_3$ | OCH$_3$ | N |
| H | —CH$_2$CH$_2$OCH$_2$CH$_2$— | | H | O | H | CH$_3$ | OCH$_3$ | N |
| H | —CH$_2$CH$_2$OCH$_2$CH$_2$— | | H | O | H | CH$_3$ | CH$_3$ | N |
| H | —CH$_2$CH$_2$OCH$_2$CH$_2$— | | H | O | H | OCH$_2$CH$_3$ | OCH$_2$CH$_3$ | N |
| H | —CH$_2$CH$_2$OCH$_2$CH$_2$— | | H | O | H | NHCH$_3$ | OCH$_2$CH$_3$ | N |
| H | —CH$_2$CH$_2$OCH$_2$CH$_2$— | | H | O | H | N(CH$_3$)$_2$ | OCH$_2$CH$_3$ | N |
| H | —CH$_2$CH$_2$OCH$_2$CH$_2$— | | H | O | H | N(CH$_3$)$_2$ | OCH$_3$ | N |
| H | —CH$_2$CH$_2$OCH$_2$CH$_2$— | | H | O | H | N(CH$_3$)$_2$ | OCH$_2$CF$_3$ | N |
| H | —CH$_2$CH$_2$OCH$_2$CH$_2$— | | H | O | CH$_3$ | CH$_3$ | OCH$_3$ | N |
| H | —CH$_2$CH$_2$OCH$_2$CH$_2$— | | H | S | H | OCH$_3$ | OCH$_3$ | CH |
| H | —CH$_2$CH$_2$OCH$_2$CH$_2$— | | H | S | H | CH$_3$ | OCH$_3$ | CH |
| H | —CH$_2$CH$_2$OCH$_2$CH$_2$— | | H | S | H | CH$_3$ | CH$_3$ | CH |
| H | —CH$_2$CH$_2$OCH$_2$CH$_2$— | | H | S | H | OCH$_3$ | OCH$_3$ | N |
| H | —CH$_2$CH$_2$OCH$_2$CH$_2$— | | H | S | H | CH$_3$ | OCH$_3$ | N |
| Cl | H | H | H | O | H | OCH$_3$ | OCH$_3$ | CH |
| Cl | H | H | H | O | H | Cl | OCH$_3$ | CH |
| Cl | H | H | H | O | H | CH$_3$ | OCH$_3$ | CH |
| Cl | H | H | H | O | H | CH$_3$ | CH$_3$ | CH |
| Cl | H | H | H | O | H | OCH$_3$ | OCH$_3$ | N |
| Cl | H | H | H | O | H | CH$_3$ | OCH$_3$ | N |
| Cl | H | H | H | O | H | CH$_3$ | CH$_3$ | N |
| Cl | H | H | H | O | H | OCH$_2$CH$_3$ | OCH$_2$CH$_3$ | N |

TABLE I-continued

| | | | | | | | | |
|---|---|---|---|---|---|---|---|---|
| Cl | H | H | H | O | H | NHCH$_3$ | OCH$_2$CH$_3$ | N |
| Cl | H | H | H | O | H | N(CH$_3$)$_2$ | OCH$_2$CH$_3$ | N |
| Cl | H | H | H | O | H | N(CH$_3$)$_2$ | OCH$_3$ | N |
| Cl | H | H | H | O | H | N(CH$_3$)$_2$ | OCH$_2$CF$_3$ | N |
| Cl | H | H | H | O | CH$_3$ | CH$_3$ | OCH$_3$ | N |
| Cl | H | H | H | S | H | OCH$_3$ | OCH$_3$ | CH |
| Cl | H | H | H | S | H | Cl | OCH$_3$ | CH |
| Cl | H | H | H | S | H | CH$_3$ | OCH$_3$ | CH |
| Cl | H | H | H | S | H | CH$_3$ | CH$_3$ | CH |
| Cl | H | H | H | S | H | OCH$_3$ | OCH$_3$ | N |
| Cl | H | H | H | S | H | CH$_3$ | OCH$_3$ | N |
| Cl | H | CH$_3$ | H | O | H | OCH$_3$ | OCH$_3$ | CH |
| Cl | H | CH$_3$ | H | O | H | Cl | OCH$_3$ | CH |
| Cl | H | CH$_3$ | H | O | H | CH$_3$ | OCH$_3$ | CH |
| Cl | H | CH$_3$ | H | O | H | CH$_3$ | CH$_3$ | CH |
| Cl | H | CH$_3$ | H | O | H | OCH$_3$ | OCH$_3$ | N |
| Cl | H | CH$_3$ | H | O | H | CH$_3$ | OCH$_3$ | N |
| Cl | H | CH$_3$ | H | O | H | CH$_3$ | CH$_3$ | N |
| Cl | H | CH$_3$ | H | O | H | OCH$_2$CH | OCH$_2$CH$_3$ | N |
| Cl | H | CH$_3$ | H | O | H | NHCH$_3$ | OCH$_2$CH$_3$ | N |
| Cl | H | CH$_3$ | H | O | H | N(CH$_3$)$_2$ | OCH$_2$CH$_3$ | N |
| Cl | H | CH$_3$ | H | O | H | N(CH$_3$)$_2$ | OCH$_3$ | N |
| Cl | H | CH$_3$ | H | O | H | N(CH$_3$)$_2$ | OCH$_2$CF$_3$ | N |
| Cl | H | CH$_3$ | H | O | CH$_3$ | CH$_3$ | OCH$_3$ | N |
| Cl | H | CH$_3$ | H | S | H | OCH$_3$ | OCH$_3$ | CH |
| Cl | H | CH$_3$ | H | S | H | Cl | OCH$_3$ | CH |
| Cl | H | CH$_3$ | H | S | H | CH$_3$ | OCH$_3$ | CH |
| Cl | H | CH$_3$ | H | S | H | CH$_3$ | CH$_3$ | CH |
| Cl | H | CH$_3$ | H | S | H | OCH$_3$ | OCH$_3$ | N |
| Cl | H | CH$_3$ | H | S | H | CH$_3$ | OCH$_3$ | N |
| Cl | H | H | CH$_3$ | O | H | OCH$_3$ | OCH$_3$ | CH |
| Cl | H | H | CH$_3$ | O | H | Cl | OCH$_3$ | CH |
| Cl | H | H | CH$_3$ | O | H | CH$_3$ | OCH$_3$ | CH |
| Cl | H | H | CH$_3$ | O | H | CH$_3$ | CH$_3$ | CH |
| Cl | H | H | CH$_3$ | O | H | OCH$_3$ | OCH$_3$ | N |
| Cl | H | H | CH$_3$ | O | H | CH$_3$ | CH$_3$ | N |
| Cl | H | H | CH$_3$ | O | H | OCH$_2$CH$_3$ | OCH$_2$CH$_3$ | N |
| Cl | H | H | CH$_3$ | O | H | NHCH$_3$ | OCH$_2$CH$_3$ | N |
| Cl | H | H | CH$_3$ | O | H | N(CH$_3$)$_2$ | OCH$_2$CH$_3$ | N |
| Cl | H | H | CH$_3$ | O | H | N(CH$_3$)$_2$ | OCH$_3$ | N |
| Cl | H | H | CH$_3$ | O | H | N(CH$_3$)$_2$ | OCH$_2$CF$_3$ | N |
| Cl | H | H | CH$_3$ | O | CH$_3$ | CH$_3$ | OCH$_3$ | N |
| Cl | H | H | CH$_3$ | S | H | OCH$_3$ | OCH$_3$ | CH |
| Cl | H | H | CH$_3$ | S | H | Cl | OCH$_3$ | CH |
| Cl | H | H | CH$_3$ | S | H | CH$_3$ | OCH$_3$ | CH |
| Cl | H | H | CH$_3$ | S | H | CH$_3$ | CH$_3$ | CH |
| Cl | H | H | CH$_3$ | S | H | OCH$_3$ | OCH$_3$ | N |
| Cl | H | H | CH$_3$ | S | H | CH$_3$ | OCH$_3$ | N |
| Cl | H | CH$_3$ | CH$_3$ | O | H | OCH$_3$ | OCH$_3$ | CH |
| Cl | H | CH$_3$ | CH$_3$ | O | H | Cl | OCH$_3$ | CH |
| Cl | H | CH$_3$ | CH$_3$ | O | H | CH$_3$ | OCH$_3$ | CH |
| Cl | H | CH$_3$ | CH$_3$ | O | H | CH$_3$ | CH$_3$ | CH |
| Cl | H | CH$_3$ | CH$_3$ | O | H | OCH$_3$ | OCH$_3$ | N |
| Cl | H | CH$_3$ | CH$_3$ | O | H | CH$_3$ | OCH$_3$ | N |
| Cl | H | CH$_3$ | CH$_3$ | O | H | CH$_3$ | CH$_3$ | N |
| Cl | H | CH$_3$ | CH$_3$ | O | H | OCH$_2$CH$_3$ | OCH$_2$CH$_3$ | N |
| Cl | H | CH$_3$ | CH$_3$ | O | H | NHCH$_3$ | OCH$_2$CH$_3$ | N |
| Cl | H | CH$_3$ | CH$_3$ | O | H | N(CH$_3$)$_2$ | OCH$_2$CH$_3$ | N |
| Cl | H | CH$_3$ | CH$_3$ | O | H | N(CH$_3$)$_2$ | OCH$_3$ | N |
| Cl | H | CH$_3$ | CH$_3$ | O | H | N(CH$_3$)$_2$ | OCH$_2$CF$_3$ | N |
| Cl | H | CH$_3$ | CH$_3$ | O | CH$_3$ | CH$_3$ | OCH$_3$ | N |
| Cl | H | CH$_3$ | CH$_3$ | S | H | OCH$_3$ | OCH$_3$ | CH |
| Cl | H | CH$_3$ | CH$_3$ | S | H | Cl | OCH$_3$ | CH |
| Cl | H | CH$_3$ | CH$_3$ | S | H | CH$_3$ | OCH$_3$ | CH |
| Cl | H | CH$_3$ | CH$_3$ | S | H | CH$_3$ | CH$_3$ | CH |
| Cl | H | CH$_3$ | CH$_3$ | S | H | OCH$_3$ | OCH$_3$ | N |
| Cl | H | CH$_3$ | CH$_3$ | S | H | CH$_3$ | OCH$_3$ | N |
| Cl | H | H | Cl | O | H | OCH$_3$ | OCH$_3$ | CH |
| Cl | H | H | Cl | O | H | Cl | OCH$_3$ | CH |
| Cl | H | H | Cl | O | H | CH$_3$ | OCH$_3$ | CH |
| Cl | H | H | Cl | O | H | CH$_3$ | CH$_3$ | CH |
| Cl | H | H | Cl | O | H | OCH$_3$ | OCH$_3$ | N |
| Cl | H | H | Cl | O | H | CH$_3$ | OCH$_3$ | N |
| Cl | H | H | Cl | O | H | CH$_3$ | CH$_3$ | N |
| Cl | H | H | Cl | O | H | OCH$_2$CH$_3$ | OCH$_2$CH$_3$ | N |
| Cl | H | H | Cl | O | H | NHCH$_3$ | OCH$_2$CH$_3$ | N |
| Cl | H | H | Cl | O | H | N(CH$_3$)$_2$ | OCH$_2$CH$_3$ | N |
| Cl | H | H | Cl | O | H | N(CH$_3$)$_2$ | OCH$_3$ | N |
| Cl | H | H | Cl | O | H | N(CH$_3$)$_2$ | OCH$_2$CF$_3$ | N |
| Cl | H | H | Cl | O | CH$_3$ | CH$_3$ | OCH$_3$ | N |
| Cl | H | H | Cl | S | H | OCH$_3$ | OCH$_3$ | CH |

TABLE I-continued

| | | | | | | | | |
|---|---|---|---|---|---|---|---|---|
| Cl | H | H | Cl | S | H | Cl | OCH$_3$ | CH |
| Cl | H | H | Cl | S | H | CH$_3$ | OCH$_3$ | CH |
| Cl | H | H | Cl | S | H | CH$_3$ | CH$_3$ | CH |
| Cl | H | H | Cl | S | H | OCH$_3$ | OCH$_3$ | N |
| Cl | H | H | Cl | S | H | CH$_3$ | OCH$_3$ | N |
| Cl | H | CH$_3$ | Cl | O | H | OCH$_3$ | OCH$_3$ | CH |
| Cl | H | CH$_3$ | Cl | O | H | Cl | OCH$_3$ | CH |
| Cl | H | CH$_3$ | Cl | O | H | CH$_3$ | OCH$_3$ | CH |
| Cl | H | CH$_3$ | Cl | O | H | CH$_3$ | CH$_3$ | CH |
| Cl | H | CH$_3$ | Cl | O | H | OCH$_3$ | OCH$_3$ | N |
| Cl | H | CH$_3$ | Cl | O | H | CH$_3$ | OCH$_3$ | N |
| Cl | H | CH$_3$ | Cl | O | H | CH$_3$ | CH$_3$ | N |
| Cl | H | CH$_3$ | Cl | O | H | OCH$_2$CH$_3$ | OCH$_2$CH$_3$ | N |
| Cl | H | CH$_3$ | Cl | O | H | NHCH$_3$ | OCH$_2$CH$_3$ | N |
| Cl | H | CH$_3$ | Cl | O | H | N(CH$_3$)$_2$ | OCH$_2$CH$_3$ | N |
| Cl | H | CH$_3$ | Cl | O | H | N(CH$_3$)$_2$ | OCH$_3$ | N |
| Cl | H | CH$_3$ | Cl | O | H | N(CH$_3$)$_2$ | OCH$_2$CF$_3$ | N |
| Cl | H | CH$_3$ | Cl | O | CH$_3$ | CH$_3$ | OCH$_3$ | N |
| Cl | H | CH$_3$ | Cl | S | H | OCH$_3$ | OCH$_3$ | CH |
| Cl | H | CH$_3$ | Cl | S | H | Cl | OCH$_3$ | CH |
| Cl | H | CH$_3$ | Cl | S | H | CH$_3$ | OCH$_3$ | CH |
| Cl | H | CH$_3$ | Cl | S | H | CH$_3$ | CH$_3$ | CH |
| Cl | H | CH$_3$ | Cl | S | H | OCH$_3$ | OCH$_3$ | N |
| Cl | H | CH$_3$ | Cl | S | H | CH$_3$ | OCH$_3$ | N |
| Cl | H | CH$_2$CH$_3$ | Cl | O | H | OCH$_3$ | OCH$_3$ | CH |
| Cl | H | CH$_2$CH$_3$ | H | O | H | Cl | OCH$_3$ | CH |
| Cl | H | CH$_2$CH$_3$ | H | O | H | CH$_3$ | OCH$_3$ | CH |
| Cl | H | CH$_2$CH$_3$ | H | O | H | OCH$_3$ | CH$_3$ | CH |
| Cl | H | CH$_2$CH$_3$ | H | O | H | OCH$_3$ | OCH$_3$ | N |
| Cl | H | CH$_2$CH$_3$ | H | O | H | CH$_3$ | OCH$_3$ | N |
| Cl | H | CH$_2$CH$_3$ | H | O | H | CH$_3$ | CH$_3$ | N |
| Cl | H | CH$_2$CH$_3$ | H | O | H | OCH$_2$CH$_3$ | OCH$_2$CH$_3$ | N |
| Cl | H | CH$_2$CH$_3$ | H | O | H | NHCH$_3$ | CH$_2$CH$_3$ | N |
| Cl | H | CH$_2$CH$_3$ | H | O | H | (CH$_3$)$_2$ | OCH$_2$CH$_3$ | N |
| Cl | H | CH$_2$CH$_3$ | H | O | H | N(CH$_3$)$_2$ | OCH$_3$ | N |
| Cl | H | CH$_2$CH$_3$ | H | O | H | N(CH$_3$)$_2$ | OCH$_2$CF$_3$ | N |
| Cl | H | CH$_2$CH$_3$ | H | O | CH$_3$ | CH$_3$ | OCH$_3$ | N |
| Cl | H | CH$_2$CH$_3$ | H | S | H | OCH$_3$ | CH$_3$ | CH |
| Cl | H | CH$_2$CH$_3$ | H | S | H | Cl | OCH$_3$ | CH |
| Cl | H | CH$_2$CH$_3$ | H | S | H | CH$_3$ | OCH$_3$ | CH |
| Cl | H | CH$_2$CH$_3$ | H | S | H | CH$_3$ | CH$_3$ | CH |
| Cl | H | CH$_2$CH$_3$ | H | S | H | OCH$_3$ | OCH$_3$ | N |
| Cl | H | CH$_2$CH$_3$ | H | S | H | CH$_3$ | OCH$_3$ | N |
| Cl | H | CH$_2$CF$_3$ | H | O | H | OCH$_3$ | OCH$_3$ | CH |
| Cl | H | CH$_2$CF$_3$ | H | O | H | Cl | OCH$_3$ | CH |
| Cl | H | CH$_2$CF$_3$ | H | O | H | CH$_3$ | OCH$_3$ | CH |
| Cl | H | CH$_2$CF$_3$ | H | O | H | CH$_3$ | CH$_3$ | CH |
| Cl | H | CH$_2$CF$_3$ | H | O | H | OCH$_2$CH$_3$ | OCH$_2$CH$_3$ | N |
| Cl | H | CH$_2$CF$_3$ | H | O | H | CH$_3$ | OCH$_3$ | N |
| Cl | H | CH$_2$CF$_3$ | H | O | H | CH$_3$ | CH$_3$ | N |
| Cl | H | CH$_2$CF$_3$ | H | O | H | OCH$_2$CH$_3$ | OCH$_2$CH$_3$ | N |
| Cl | H | CH$_2$CF$_3$ | H | O | H | NHCH$_3$ | OCH$_2$CH$_3$ | N |
| Cl | H | CH$_2$CF$_3$ | H | O | H | N(CH$_3$)$_2$ | OCH$_2$CH$_3$ | N |
| Cl | H | CH$_2$CF$_3$ | H | O | H | N(CH$_3$)$_2$ | OCH$_3$ | N |
| Cl | H | CH$_2$CF$_3$ | H | O | H | N(CH$_3$)$_2$ | OCH$_2$CF$_3$ | N |
| Cl | H | CH$_2$CF$_3$ | H | O | CH$_3$ | CH$_3$ | OCH$_3$ | N |
| Cl | H | CH$_2$CF$_3$ | H | S | H | OCH$_3$ | OCH$_3$ | CH |
| Cl | H | CH$_2$CF$_3$ | H | S | H | Cl | OCH$_3$ | CH |
| Cl | H | CH$_2$CF$_3$ | H | S | H | CH$_3$ | OCH$_3$ | CH |
| Cl | H | CH$_2$CF$_3$ | H | S | H | CH$_3$ | CH$_3$ | CH |
| Cl | H | CH$_2$CF$_3$ | H | S | H | OCH$_3$ | OCH$_3$ | N |
| Cl | H | CH$_2$CF$_3$ | H | S | H | CH$_3$ | OCH$_3$ | N |
| Cl | CH$_2$CH$_2$Cl | H | H | O | H | OCH$_3$ | OCH$_3$ | CH |
| Cl | CH$_2$CH$_2$Cl | H | H | O | H | Cl | OCH$_3$ | CH |
| Cl | CH$_2$CH$_2$Cl | H | H | O | H | CH$_3$ | OCH$_3$ | CH |
| Cl | CH$_2$CH$_2$Cl | H | H | O | H | CH$_3$ | CH$_3$ | CH |
| Cl | CH$_2$CH$_2$Cl | H | H | O | H | OCH$_3$ | OCH$_3$ | N |
| Cl | CH$_2$CH$_2$Cl | H | H | O | H | CH$_3$ | OCH$_3$ | N |
| Cl | CH$_2$CH$_2$Cl | H | H | O | H | CH$_3$ | CH$_3$ | N |
| Cl | CH$_2$CH$_2$Cl | H | H | O | H | OCH$_2$CH$_3$ | OCH$_2$CH$_3$ | N |
| Cl | CH$_2$CH$_2$Cl | H | H | O | H | NHCH$_3$ | OCH$_2$CH$_3$ | N |
| Cl | CH$_2$CH$_2$Cl | H | H | O | H | N(CH$_3$)$_2$ | OCH$_2$CH$_3$ | N |
| Cl | CH$_2$CH$_2$Cl | H | H | O | H | N(CH$_3$)$_2$ | OCH$_3$ | N |
| Cl | CH$_2$CH$_2$Cl | H | H | O | H | N(CH$_3$)$_2$ | OCH$_2$CF$_3$ | N |
| Cl | CH$_2$CH$_2$Cl | H | H | O | CH$_3$ | CH$_3$ | OCH$_3$ | N |
| Cl | CH$_2$CH$_2$Cl | H | H | S | H | OCH$_3$ | OCH$_3$ | CH |
| Cl | CH$_2$CH$_2$Cl | H | H | S | H | Cl | OCH$_3$ | CH |
| Cl | CH$_2$CH$_2$Cl | H | H | S | H | CH$_3$ | OCH$_3$ | CH |
| Cl | CH$_2$CH$_2$Cl | H | H | S | H | CH$_3$ | CH$_3$ | CH |
| Cl | CH$_2$CH$_2$Cl | H | H | S | H | OCH$_3$ | OCH$_3$ | N |
| Cl | CH$_2$CH$_2$Cl | H | H | S | H | CH$_3$ | OCH$_3$ | N |
| Cl | CH$_2$CN | H | H | O | H | OCH$_3$ | OCH$_3$ | CH |

TABLE I-continued

| | | | | | | | | |
|---|---|---|---|---|---|---|---|---|
| Cl | CH$_2$CN | H | H | O | H | Cl | OCH$_3$ | CH |
| Cl | CH$_2$CN | H | H | O | H | CH$_3$ | OCH$_3$ | CH |
| Cl | CH$_2$CN | H | H | O | H | CH$_3$ | CH$_3$ | CH |
| Cl | CH$_2$CN | H | H | O | H | OCH$_3$ | OCH$_3$ | N |
| Cl | CH$_2$CN | H | H | O | H | CH$_3$ | OCH$_3$ | N |
| Cl | CH$_2$CN | H | H | O | H | CH$_3$ | CH$_3$ | N |
| Cl | CH$_2$CN | H | H | O | H | OCH$_2$CH$_3$ | OCH$_2$CH$_3$ | N |
| Cl | CH$_2$CN | H | H | O | H | NHCH$_3$ | OCH$_2$CH$_3$ | N |
| Cl | CH$_2$CN | H | H | O | H | N(CH$_3$)$_2$ | OCH$_2$CH$_3$ | N |
| Cl | CH$_2$CN | H | H | O | H | N(CH$_3$)$_2$ | OCH$_3$ | N |
| Cl | CH$_2$CN | H | H | O | H | N(CH$_3$)$_2$ | OCH$_2$CF$_3$ | N |
| Cl | CH$_2$CN | H | H | O | CH$_3$ | CH$_3$ | OCH$_3$ | N |
| Cl | CH$_2$CN | H | H | S | H | OCH$_3$ | OCH$_3$ | CH |
| Cl | CH$_2$CN | H | H | S | H | Cl | OCH$_3$ | CH |
| Cl | CH$_2$CN | H | H | S | H | CH$_3$ | OCH$_3$ | CH |
| Cl | CH$_2$CN | H | H | S | H | CH$_3$ | CH$_3$ | CH |
| Cl | CH$_2$CN | H | H | S | H | OCH$_3$ | OCH$_3$ | N |
| Cl | CH$_2$CN | H | H | S | H | CH$_3$ | OCH$_3$ | N |
| Cl | CH$_2$CH=CH$_2$ | H | H | O | H | OCH$_3$ | OCH$_3$ | CH |
| Cl | CH$_2$CH=CH$_2$ | H | H | O | H | Cl | OCH$_3$ | CH |
| Cl | CH$_2$CH=CH$_2$ | H | H | O | H | CH$_3$ | OCH$_3$ | CH |
| Cl | CH$_2$CH=CH$_2$ | H | H | O | H | CH$_3$ | CH$_3$ | CH |
| Cl | CH$_2$CH=CH$_2$ | H | H | O | H | OCH$_3$ | OCH$_3$ | N |
| Cl | CH$_2$CH=CH$_2$ | H | H | O | H | CH$_3$ | OCH$_3$ | N |
| Cl | CH$_2$CH=CH$_2$ | H | H | O | H | CH$_3$ | CH$_3$ | N |
| Cl | CH$_2$CH=CH$_2$ | H | H | O | H | OCH$_2$CH$_3$ | OCH$_2$CH$_3$ | N |
| Cl | CH$_2$CH=CH$_2$ | H | H | O | H | NHCH$_3$ | OCH$_2$CH$_3$ | N |
| Cl | CH$_2$CH=CH$_2$ | H | H | O | H | N(CH$_3$)$_2$ | OCH$_2$CH$_3$ | N |
| Cl | CH$_2$CH=CH$_2$ | H | H | O | H | N(CH$_3$)$_2$ | OCH$_3$ | N |
| Cl | CH$_2$CH=CH$_2$ | H | H | O | H | N(CH$_3$)$_2$ | OCH$_2$CF$_3$ | N |
| Cl | CH$_2$CH=CH$_2$ | H | H | O | CH$_3$ | CH$_3$ | OCH$_3$ | N |
| Cl | CH$_2$CH=CH$_2$ | H | H | S | H | OCH$_3$ | OCH$_3$ | CH |
| Cl | CH$_2$CH=CH$_2$ | H | H | S | H | Cl | OCH$_3$ | CH |
| Cl | CH$_2$CH=CH$_2$ | H | H | S | H | CH$_3$ | OCH$_3$ | CH |
| Cl | CH$_2$CH=CH$_2$ | H | H | S | H | CH$_3$ | CH$_3$ | CH |
| Cl | CH$_2$CH=CH$_2$ | H | H | S | H | OCH$_3$ | OCH$_3$ | N |
| Cl | CH$_2$CH=CH$_2$ | H | H | S | H | CH$_3$ | OCH$_3$ | N |
| Cl | CH$_2$C≡CH | H | H | O | H | OCH$_3$ | OCH$_3$ | CH |
| Cl | CH$_2$C≡CH | H | H | O | H | Cl | OCH$_3$ | CH |
| Cl | CH$_2$C≡CH | H | H | O | H | CH$_3$ | OCH$_3$ | CH |
| Cl | CH$_2$C≡CH | H | H | O | H | CH$_3$ | CH$_3$ | CH |
| Cl | CH$_2$C≡CH | H | H | O | H | OCH$_3$ | OCH$_3$ | N |
| Cl | CH$_2$C≡CH | H | H | O | H | CH$_3$ | OCH$_3$ | N |
| Cl | CH$_2$C≡CH | H | H | O | H | CH$_3$ | CH$_3$ | N |
| Cl | CH$_2$C≡CH | H | H | O | H | OCH$_2$CH$_3$ | OCH$_2$CH$_3$ | N |
| Cl | CH$_2$C≡CH | H | H | O | H | NHCH$_3$ | OCH$_2$CH$_3$ | N |
| Cl | CH$_2$C≡CH | H | H | O | H | N(CH$_3$)$_2$ | OCH$_2$CH$_3$ | N |
| Cl | CH$_2$C≡CH | H | H | O | H | N(CH$_3$)$_2$ | OCH$_3$ | N |
| Cl | CH$_2$C≡CH | H | H | O | H | N(CH$_3$)$_2$ | OCH$_2$CF$_3$ | N |
| Cl | CH$_2$C≡CH | H | H | O | CH$_3$ | CH$_3$ | OCH$_3$ | N |
| Cl | CH$_2$C≡CH | H | H | S | H | OCH$_3$ | OCH$_3$ | CH |
| Cl | CH$_2$C≡CH | H | H | S | H | Cl | OCH$_3$ | CH |
| Cl | CH$_2$C≡CH | H | H | S | H | CH$_3$ | OCH$_3$ | CH |
| Cl | CH$_2$C≡CH | H | H | S | H | CH$_3$ | CH$_3$ | CH |
| Cl | CH$_2$C≡CH | H | H | S | H | OCH$_3$ | OCH$_3$ | N |
| Cl | CH$_2$C≡CH | H | H | S | H | CH$_3$ | OCH$_3$ | N |
| Cl | CH$_2$CH$_2$OCH$_3$ | H | H | O | H | OCH$_3$ | OCH$_3$ | CH |
| Cl | CH$_2$CH$_2$OCH$_3$ | H | H | O | H | Cl | OCH$_3$ | CH |
| Cl | CH$_2$CH$_2$OCH$_3$ | H | H | O | H | CH$_3$ | OCH$_3$ | CH |
| Cl | CH$_2$CH$_2$OCH$_3$ | H | H | O | H | OCH$_3$ | OCH$_3$ | N |
| Cl | CH$_2$CH$_2$OCH$_3$ | H | H | O | H | CH$_3$ | OCH$_3$ | N |
| Cl | CH$_2$CH$_2$OCH$_3$ | H | H | O | H | CH$_3$ | CH$_3$ | N |
| Cl | CH$_2$CH$_2$OCH$_3$ | H | H | O | H | OCH$_2$CH$_3$ | OCH$_2$CH$_3$ | N |
| Cl | CH$_2$CH$_2$OCH$_3$ | H | H | O | H | NHCH$_3$ | OCH$_2$CH$_3$ | N |
| Cl | CH$_2$CH$_2$OCH$_3$ | H | H | O | H | N(CH$_3$)$_2$ | OCH$_2$CH$_3$ | N |
| Cl | CH$_2$CH$_2$OCH$_3$ | H | H | O | H | N(CH$_3$)$_2$ | OCH$_3$ | N |
| Cl | CH$_2$CH$_2$OCH$_3$ | H | H | O | H | N(CH$_3$)$_2$ | OCH$_2$CF$_3$ | N |
| Cl | CH$_2$CH$_2$OCH$_3$ | H | H | O | CH$_3$ | CH$_3$ | OCH$_3$ | N |
| Cl | CH$_2$CH$_2$OCH$_3$ | H | H | S | H | OCH$_3$ | OCH$_3$ | CH |
| Cl | CH$_2$CH$_2$OCH$_3$ | H | H | S | H | Cl | OCH$_3$ | CH |
| Cl | CH$_2$CH$_2$OCH$_3$ | H | H | S | H | CH$_3$ | OCH$_3$ | CH |
| Cl | CH$_2$CH$_2$OCH$_3$ | H | H | S | H | CH$_3$ | CH$_3$ | CH |
| Cl | CH$_2$CH$_2$OCH$_3$ | H | H | S | H | OCH$_3$ | OCH$_3$ | N |
| Cl | CH$_2$CH$_2$OCH$_3$ | H | H | S | H | CH$_3$ | OCH$_3$ | N |
| Cl | cyclo-C$_3$H$_7$ | H | H | O | H | OCH$_3$ | OCH$_3$ | CH |
| Cl | cyclo-C$_3$H$_7$ | H | H | O | H | Cl | OCH$_3$ | CH |
| Cl | cyclo-C$_3$H$_7$ | H | H | O | H | CH$_3$ | OCH$_3$ | CH |
| Cl | cyclo-C$_3$H$_7$ | H | H | O | CH$_3$ | CH$_3$ | OCH$_3$ | CH |
| Cl | cyclo-C$_3$H$_7$ | H | H | O | H | OCH$_3$ | OCH$_3$ | N |
| Cl | cyclo-C$_3$H$_7$ | H | H | O | H | CH$_3$ | OCH$_3$ | N |
| Cl | cyclo-C$_3$H$_7$ | H | H | O | H | CH$_3$ | CH$_3$ | N |

TABLE I-continued

| | | | | | | | | |
|---|---|---|---|---|---|---|---|---|
| Cl | cyclo-C₃H₇ | H | H | O | H | OCH₂CH₃ | OCH₂CH₃ | N |
| Cl | cyclo-C₃H₇ | H | H | O | H | NHCH₃ | OCH₂CH₃ | N |
| Cl | cyclo-C₃H₇ | H | H | O | H | N(CH₃)₂ | OCH₂CH₃ | N |
| Cl | cyclo-C₃H₇ | H | H | O | H | N(CH₃)₂ | OCH₃ | N |
| Cl | cyclo-C₃H₇ | H | H | O | H | N(CH₃)₂ | OCH₂CF₃ | N |
| Cl | cyclo-C₃H₇ | H | H | O | CH₃ | CH₃ | OCH₃ | N |
| Cl | cyclo-C₃H₇ | H | H | S | H | Cl | OCH₃ | CH |
| Cl | cyclo-C₃H₇ | H | H | S | H | CH₃ | OCH₃ | CH |
| Cl | cyclo-C₃H₇ | H | H | S | H | CH₃ | CH₃ | CH |
| Cl | cyclo-C₃H₇ | H | H | S | H | OCH₃ | OCH₃ | N |
| Cl | cyclo-C₃H₇ | H | H | S | H | CH₃ | OCH₃ | N |
| Cl | CH₃ | CH₃ | H | O | H | OCH₃ | OCH₃ | CH |
| Cl | CH₃ | CH₃ | H | O | H | Cl | OCH₃ | CH |
| Cl | CH₃ | CH₃ | H | O | H | CH₃ | OCH₃ | CH |
| Cl | CH₃ | CH₃ | H | O | H | CH₃ | CH₃ | CH |
| Cl | CH₃ | CH₃ | H | O | H | OCH₃ | OCH₃ | N |
| Cl | CH₃ | CH₃ | H | O | H | CH₃ | OCH₃ | N |
| Cl | CH₃ | CH₃ | H | O | H | CH₃ | CH₃ | N |
| Cl | CH₃ | CH₃ | H | O | H | OCH₂CH₃ | OCH₂CH₃ | N |
| Cl | CH₃ | CH₃ | H | O | H | NHCH₃ | OCH₂CH₃ | N |
| Cl | CH₃ | CH₃ | H | O | H | N(CH₃)₂ | OCH₂CH₃ | N |
| Cl | CH₃ | CH₃ | H | O | H | N(CH₃)₂ | OCH₃ | N |
| Cl | CH₃ | CH₃ | H | O | H | N(CH₃)₂ | OCH₂CF₃ | N |
| Cl | CH₃ | CH₃ | H | O | CH₃ | CH₃ | OCH₃ | N |
| Cl | CH₃ | CH₃ | H | S | H | OCH₃ | OCH₃ | CH |
| Cl | CH₃ | CH₃ | H | S | H | Cl | OCH₃ | CH |
| Cl | CH₃ | CH₃ | H | S | H | CH₃ | OCH₃ | CH |
| Cl | CH₃ | CH₃ | H | S | H | CH₃ | CH₃ | CH |
| Cl | CH₃ | CH₃ | H | S | H | OCH₃ | OCH₃ | N |
| Cl | CH₃ | CH₃ | H | S | H | CH₃ | OCH₃ | N |
| Cl | CH₃ | CH₂CH₃ | H | O | H | OCH₃ | OCH₃ | CH |
| Cl | CH₃ | CH₂CH₃ | H | O | H | Cl | OCH₃ | CH |
| Cl | CH₃ | CH₂CH₃ | H | O | H | CH₃ | OCH₃ | CH |
| Cl | CH₃ | CH₂CH₃ | H | O | H | CH₃ | CH₃ | CH |
| Cl | CH₃ | CH₂CH₃ | H | O | H | OCH₃ | OCH₃ | N |
| Cl | CH₃ | CH₂CH₃ | H | O | H | CH₃ | OCH₃ | N |
| Cl | CH₃ | CH₂CH₃ | H | O | H | CH₃ | CH₃ | N |
| Cl | CH₃ | CH₂CH₃ | H | O | H | OCH₂CH₃ | OCH₂CH₃ | N |
| Cl | CH₃ | CH₂CH₃ | H | O | H | NHCH₃ | OCH₂CH₃ | N |
| Cl | CH₃ | CH₂CH₃ | H | O | H | N(CH₃)₂ | OCH₂CH₃ | N |
| Cl | CH₃ | CH₂CH₃ | H | O | H | N(CH₃)₂ | OCH₃ | N |
| Cl | CH₃ | CH₂CH₃ | H | O | H | N(CH₃)₂ | OCH₂CF₃ | N |
| Cl | CH₃ | CH₂CH₃ | H | O | CH₃ | CH₃ | OCH₃ | N |
| Cl | CH₃ | CH₂CH₃ | H | S | H | OCH₃ | OCH₃ | CH |
| Cl | CH₃ | CH₂CH₃ | H | S | H | Cl | OCH₃ | CH |
| Cl | CH₃ | CH₂CH₃ | H | S | H | CH₃ | OCH₃ | CH |
| Cl | CH₃ | CH₂CH₃ | H | S | H | CH₃ | CH₃ | CH |
| Cl | CH₃ | CH₂CH₃ | H | S | H | OCH₃ | OCH₃ | N |
| Cl | CH₃ | CH₂CH₃ | H | S | H | CH₃ | OCH₃ | N |
| Cl | CH₃ | CH₃ | CH₃ | O | H | OCH₃ | OCH₃ | CH |
| Cl | CH₃ | CH₃ | CH₃ | O | H | Cl | OCH₃ | CH |
| Cl | CH₃ | CH₃ | CH₃ | O | H | CH₃ | OCH₃ | CH |
| Cl | CH₃ | CH₃ | CH₃ | O | H | CH₃ | CH₃ | CH |
| Cl | CH₃ | CH₃ | CH₃ | O | H | OCH₃ | OCH₃ | N |
| Cl | CH₃ | CH₃ | CH₃ | O | H | CH₃ | OCH₃ | N |
| Cl | CH₃ | CH₃ | CH₃ | O | H | CH₃ | CH₃ | N |
| Cl | CH₃ | CH₃ | CH₃ | O | H | OCH₂CH₃ | OCH₂CH₃ | N |
| Cl | CH₃ | CH₃ | CH₃ | O | H | NHCH₃ | OCH₂CH₃ | N |
| Cl | CH₃ | CH₃ | CH₃ | O | H | N(CH₃)₂ | OCH₂CH₃ | N |
| Cl | CH₃ | CH₃ | CH₃ | O | H | N(CH₃)₂ | OCH₃ | N |
| Cl | CH₃ | CH₃ | CH₃ | O | H | N(CH₃)₂ | OCH₂CF₃ | N |
| Cl | CH₃ | CH₃ | CH₃ | O | CH₃ | CH₃ | OCH₃ | N |
| Cl | CH₃ | CH₃ | CH₃ | S | H | OCH₃ | OCH₃ | CH |
| Cl | CH₃ | CH₃ | CH₃ | S | H | Cl | OCH₃ | CH |
| Cl | CH₃ | CH₃ | CH₃ | S | H | CH₃ | OCH₃ | CH |
| Cl | CH₃ | CH₃ | CH₃ | S | H | CH₃ | CH₃ | CH |
| Cl | CH₃ | CH₃ | CH₃ | S | H | OCH₃ | OCH₃ | N |
| Cl | CH₃ | CH₃ | CH₃ | S | H | CH₃ | CH₃ | N |
| Cl | CH₃ | CH₃ | Cl | O | H | OCH₃ | OCH₃ | CH |
| Cl | CH₃ | CH₃ | Cl | O | H | Cl | OCH₃ | CH |
| Cl | CH₃ | CH₃ | Cl | O | H | CH₃ | OCH₃ | CH |
| Cl | CH₃ | CH₃ | Cl | O | H | CH₃ | CH₃ | CH |
| Cl | CH₃ | CH₃ | Cl | O | H | OCH₃ | OCH₃ | N |
| Cl | CH₃ | CH₃ | Cl | O | H | CH₃ | OCH₃ | N |
| Cl | CH₃ | CH₃ | Cl | O | H | NHCH₃ | OCH₂CF₃ | N |
| Cl | CH₃ | CH₃ | Cl | O | H | OCH₂CH₃ | OCH₂CH₃ | N |
| Cl | CH₃ | CH₃ | Cl | O | H | NHCH₃ | OCH₂CH₃ | N |
| Cl | CH₃ | CH₃ | Cl | O | H | N(CH₃)₂ | OCH₂CH₃ | N |
| Cl | CH₃ | CH₃ | Cl | O | H | N(CH₃)₂ | OCH₃ | N |
| Cl | CH₃ | CH₃ | Cl | O | H | N(CH₃)₂ | OCH₂CF₃ | N |
| Cl | CH₃ | CH₃ | Cl | O | CH | CH₃ | OCH₃ | N |

TABLE I-continued

| | | | | | | | | |
|---|---|---|---|---|---|---|---|---|
| Cl | CH₃ | CH₃ | Cl | S | H | OCH₃ | OCH₃ | CH |
| Cl | CH₃ | CH₃ | Cl | S | H | Cl | OCH₃ | CH |
| Cl | CH₃ | CH₃ | Cl | S | H | CH₃ | OCH₃ | CH |
| Cl | CH₃ | CH₃ | Cl | S | H | CH₃ | CH₃ | CH |
| Cl | CH₃ | CH₃ | Cl | S | OCH₃ | OCH₃ | N | |
| Cl | CH₃ | CH₃ | Cl | CH₃OCH₃ | N | | | |
| Cl | CH₂CH₃ | CH₂CH₃ | H | O | H | OCH₃ | OCH₃ | CH |
| Cl | CH₂CH₃ | CH₂CH₃ | H | O | H | Cl | OCH₃ | CH |
| Cl | CH₂CH₃ | CH₂CH₃ | H | O | H | CH₃ | OCH₃ | CH |
| Cl | CH₂CH₃ | CH₂CH₃ | H | O | H | CH₃ | CH₃ | CH |
| Cl | CH₂CH₃ | CH₂CH₃ | H | O | H | OCH₃ | OCH₃ | N |
| Cl | CH₂CH₃ | CH₂CH₃ | H | O | H | CH₃ | OCH₃ | N |
| Cl | CH₂CH₃ | CH₂CH₃ | H | O | H | CH₃ | CH₃ | N |
| Cl | CH₂CH₃ | CH₂CH₃ | H | O | H | OCH₂CH₃ | OCH₂CH₃ | N |
| Cl | CH₂CH₃ | CH₂CH₃ | H | O | H | NHCH₃ | OCH₂CH₃ | N |
| Cl | CH₂CH₃ | CH₂CH₃ | H | O | H | N(CH₃)₂ | OCH₂CH₃ | N |
| Cl | CH₂CH₃ | CH₂CH₃ | H | O | H | N(CH₃)₂ | OCH₃ | N |
| Cl | CH₂CH₃ | CH₂CH₃ | H | O | CH₃ | CH₃ | OCH₃ | N |
| Cl | CH₂CH₃ | CH₂CH₃ | H | S | H | OCH₃ | OCH₃ | CH |
| Cl | CH CH₃ | CH₂CH₃ | H | S | H | Cl | OCH₃ | CH |
| Cl | CH₂CH₃ | CH₂CH₃ | H | S | H | CH₃ | OCH₃ | CH |
| Cl | CH₂CH₃ | CH₂CH₃ | H | S | H | CH₃ | CH₃ | CH |
| Cl | CH₂CH₃ | CH₂CH₃ | H | S | H | OCH₃ | OCH₃ | N |
| Cl | CH₂CH₃ | CH₂CH₃ | H | S | H | CH₃ | OCH₃ | N |
| Cl | OCH₃ | CH₃ | H | O | H | OCH₃ | OCH₃ | CH |
| Cl | OCH₃ | CH₃ | H | O | H | Cl | OCH₃ | CH |
| Cl | OCH₃ | CH₃ | H | O | H | CH₃ | OCH₃ | CH |
| Cl | OCH₃ | CH₃ | H | O | H | CH₃ | CH₃ | CH |
| Cl | OCH₃ | CH₃ | H | O | H | OCH₃ | OCH₃ | N |
| Cl | OCH₃ | CH₃ | H | O | H | CH₃ | OCH₃ | N |
| Cl | OCH₃ | CH₃ | H | O | H | CH₃ | CH₃ | N |
| Cl | OCH₃ | CH₃ | H | O | H | OCH₂CH₃ | OCH₂CH₃ | N |
| Cl | OCH₃ | CH₃ | H | O | H | NHCH₃ | OCH₂CH₃ | N |
| Cl | OCH₃ | CH₃ | H | O | H | N(CH₃)₂ | OCH₂CH₃ | N |
| Cl | OCH₃ | CH₃ | H | O | H | N(CH₃)₂ | OCH₃ | N |
| Cl | OCH₃ | CH₃ | H | O | H | N(CH₃)₂ | OCH₂CF₃ | N |
| Cl | OCH₃ | CH₃ | H | O | CH₃ | CH₃ | OCH₃ | N |
| Cl | OCH₃ | CH₃ | H | S | H | OCH₃ | OCH₃ | CH |
| Cl | OCH₃ | CH₃ | H | S | H | Cl | OCH₃ | CH |
| Cl | OCH₃ | CH₃ | H | S | H | CH₃ | OCH₃ | CH |
| Cl | OCH₃ | CH₃ | H | S | H | CH₃ | CH₃ | CH |
| Cl | OCH₃ | CH₃ | H | S | H | OCH₃ | OCH₃ | N |
| Cl | OCH₃ | CH₃ | H | S | H | CH₃ | OCH₃ | N |
| Cl | NHCH₃ | CH₃ | H | O | H | OCH₃ | OCH₃ | CH |
| Cl | NHCH₃ | CH₃ | H | O | H | Cl | OCH₃ | CH |
| Cl | NHCH₃ | CH₃ | H | O | H | CH₃ | OCH₃ | CH |
| Cl | NHCH₃ | CH₃ | H | O | H | CH₃ | CH₃ | CH |
| Cl | NHCH₃ | CH₃ | H | O | H | OCH₃ | OCH₃ | N |
| Cl | NHCH₃ | CH₃ | H | O | H | CH₃ | OCH₃ | N |
| Cl | NHCH₃ | CH₃ | H | O | H | CH₃ | CH | N |
| Cl | NHCH₃ | CH₃ | H | O | H | OCH₂CH₃ | OCH₃ | N |
| Cl | NHCH₃ | CH₃ | H | O | H | NHCH₃ | OCH₂CH₃ | N |
| Cl | NHCH₃ | CH₃ | H | O | H | N(CH₃)₂ | OCH₂CH₃ | N |
| Cl | NHCH₃ | CH₃ | H | O | H | N(CH₃)₂ | OCH₃ | N |
| Cl | NHCH₃ | CH₃ | H | O | H | N(CH₃)₂ | OCH₂CF₃ | N |
| Cl | NHCH₃ | CH₃ | H | O | CH₃ | CH₃ | OCH₃ | N |
| Cl | NHCH₃ | CH₃ | H | S | H | OCH₃ | OCH₃ | CH |
| Cl | NHCH₃ | CH₃ | H | S | H | Cl | OCH₃ | CH |
| Cl | NHCH₃ | CH₃ | H | S | H | CH₃ | OCH₃ | CH |
| Cl | NHCH₃ | CH₃ | H | S | H | CH₃ | CH₃ | CH |
| Cl | NHCH₃ | CH₃ | H | S | H | OCH₃ | OCH₃ | N |
| Cl | NHCH₃ | CH₃ | H | S | H | CH₃ | OCH₃ | N |
| Cl | N(CH₃)₂ | CH₃ | H | O | H | OCH₃ | OCH₃ | CH |
| Cl | N(CH₃)₂ | CH₃ | H | O | H | Cl | OCH₃ | CH |
| Cl | N(CH₃)₂ | CH₃ | H | O | H | CH₃ | OCH₃ | CH |
| Cl | N(CH₃)₂ | CH₃ | H | O | H | CH₃ | CH₃ | CH |
| Cl | N(CH₃)₂ | CH₃ | H | O | H | OCH₃ | OCH₃ | N |
| Cl | N(CH₃)₂ | CH₃ | H | O | H | CH₃ | OCH₃ | N |
| Cl | N(CH₃)₂ | CH₃ | H | O | H | CH₃ | CH₃ | N |
| Cl | N(CH₃)₂ | CH₃ | H | O | H | OCH₂CH₃ | OCH₂CH₃ | N |
| Cl | N(CH₃)₂ | CH₃ | H | O | H | NHCH₃ | OCH₂CH₃ | N |
| Cl | N(CH₃)₂ | CH₃ | H | O | H | N(CH₃)₂ | OCH₂CH₃ | N |
| Cl | N(CH₃)₂ | CH₃ | H | O | H | N(CH₃)₂ | OCH₃ | N |
| Cl | N(CH₃)₂ | CH₃ | H | O | H | N(CH₃)₂ | OCH₂CF₃ | N |
| Cl | N(CH₃)₂ | CH₃ | H | O | CH₃ | CH₃ | OCH₃ | N |
| Cl | N(CH₃)₂ | CH₃ | H | S | H | OCH₃ | OCH₃ | CH |
| Cl | N(CH₃)₂ | CH₃ | H | S | H | Cl | OCH₃ | CH |
| Cl | N(CH₃)₂ | CH₃ | H | S | H | CH₃ | OCH₃ | CH |
| Cl | N(CH₃)₂ | CH₃ | H | S | H | CH₃ | CH₃ | CH |
| Cl | N(CH₃)₂ | CH₃ | H | S | H | OCH₃ | OCH₃ | N |
| Cl | N(CH₃)₂ | CH₃ | H | S | H | CH₃ | OCH₃ | N |
| Cl | —CH₂CH₂CH₂— | | H | O | H | OCH₃ | OCH₃ | CH |

TABLE I-continued

| | | | | | | | | |
|---|---|---|---|---|---|---|---|---|
| Cl | —CH₂CH₂CH₂— | | H | O | H | Cl | OCH₃ | CH |
| Cl | —CH₂CH₂CH₂— | | H | O | H | CH₃ | OCH₃ | CH |
| Cl | —CH₂CH₂CH₂— | | H | O | H | CH₃ | CH₃ | CH |
| Cl | —CH₂CH₂CH₂— | | H | O | H | OCH₃ | OCH₃ | N |
| Cl | —CH₂CH₂CH₂— | | H | O | H | CH₃ | OCH₃ | N |
| Cl | —CH₂CH₂CH₂— | | H | O | H | CH₃ | CH₃ | N |
| Cl | —CH₂CH₂CH₂— | | H | O | H | OCH₂CH₃ | OCH₂CH₃ | N |
| Cl | —CH₂CH₂CH₂— | | H | O | H | NHCH₃ | OCH₂CH₃ | N |
| Cl | —CH₂CH₂CH₂— | | H | O | H | N(CH₃)₂ | OCH₂CH₃ | N |
| Cl | —CH₂CH₂CH₂— | | H | O | H | N(CH₃)₂ | OCH₃ | N |
| Cl | —CH₂CH₂CH₂— | | H | O | H | N(CH₃)₂ | OCH₂CF₃ | N |
| Cl | —CH₂CH₂CH₂— | | H | O | CH₃ | CH₃ | OCH₃ | N |
| Cl | —CH₂CH₂CH₂— | | H | S | H | OCH₃ | OCH₃ | CH |
| Cl | —CH₂CH₂CH₂— | | H | S | H | Cl | OCH₃ | CH |
| Cl | —CH₂CH₂CH₂— | | H | S | H | CH₃ | OCH₃ | CH |
| Cl | —CH₂CH₂CH₂— | | H | S | H | CH₃ | CH₃ | CH |
| Cl | —CH₂CH₂CH₂— | | H | S | H | OCH₃ | OCH₃ | N |
| Cl | —CH₂CH₂CH₂— | | H | S | H | CH₃ | OCH₃ | N |
| Cl | —CH₂CH₂CH₂— | | H | O | H | OCH₃ | OCH₃ | CH |
| Cl | —CH₂CH₂OCH₂CH₂— | | H | O | H | Cl | OCH₃ | CH |
| Cl | —CH₂CH₂OCH₂CH₂— | | H | O | H | CH₃ | OCH₃ | CH |
| Cl | —CH₂CH₂OCH₂CH₂— | | H | O | H | CH₃ | CH₃ | CH |
| Cl | —CH₂CH₂OCH₂CH₂— | | H | O | H | OCH₃ | OCH₃ | N |
| Cl | —CH₂CH₂OCH₂CH₂— | | H | O | H | CH₃ | OCH₃ | N |
| Cl | —CH₂CH₂OCH₂CH₂— | | H | O | H | CH₃ | CH₃ | N |
| Cl | —CH₂CH₂OCH₂CH₂— | | H | O | H | OCH₂CH₃ | OCH₂CH₃ | N |
| Cl | —CH₂CH₂OCH₂CH₂— | | H | O | H | NHCH₃ | OCH₂CH₃ | N |
| Cl | —CH₂CH₂OCH₂CH₂— | | H | O | H | N(CH₃)₂ | OCH₂CH₃ | N |
| Cl | —CH₂CH₂OCH₂CH₂— | | H | O | H | N(CH₃)₂ | OCH₃ | N |
| Cl | —CH₂CH₂OCH₂CH₂— | | H | O | H | N(CH₃)₂ | OCH₂CF₃ | N |
| Cl | —CH₂CH₂OCH₂CH₂— | | H | O | CH₃ | CH₃ | OCH₃ | N |
| Cl | —CH₂CH₂OCH₂CH₂— | | H | S | H | OCH₃ | OCH₃ | CH |
| Cl | —CH₂CH₂OCH₂CH₂— | | H | S | H | Cl | OCH₃ | CH |
| Cl | —CH₂CH₂OCH₂CH₂— | | H | S | H | CH₃ | OCH₃ | CH |
| Cl | —CH₂CH₂OCH₂CH₂— | | H | S | H | CH₃ | CH₃ | CH |
| Cl | —CH₂CH₂OCH₂CH₂— | | H | S | H | OCH₃ | OCH₃ | N |
| Cl | —CH₂CH₂OCH₂CH₂— | | H | S | H | CH₃ | OCH₃ | N |
| CH₃ | H | H | H | O | H | OCH₃ | OCH₃ | CH |
| CH₃ | H | H | H | O | H | Cl | OCH₃ | CH |
| CH₃ | H | H | H | O | H | CH₃ | OCH₃ | CH |
| CH₃ | H | H | H | O | H | CH₃ | CH₃ | CH |
| CH₃ | H | H | H | O | H | OCH₃ | OCH₃ | N |
| CH₃ | H | H | H | O | H | CH₃ | OCH₃ | N |
| CH₃ | H | H | H | O | H | CH₃ | CH₃ | N |
| CH₃ | H | H | H | O | H | OCH₂CH₃ | OCH₂CH₃ | N |
| CH₃ | H | H | H | O | H | NHCH₃ | OCH₂CH₃ | N |
| CH₃ | H | H | H | O | H | N(CH₃)₂ | OCH₂CH₃ | N |
| CH₃ | H | H | H | O | H | N(CH₃)₂ | OCH₃ | N |
| CH₃ | H | H | H | O | H | N(CH₃)₂ | OCH₂CF₃ | N |
| CH₃ | H | H | H | O | CH₃ | CH₃ | OCH₃ | N |
| CH₃ | H | H | H | S | H | OCH₃ | OCH₃ | CH |
| CH₃ | H | H | H | S | H | Cl | OCH₃ | CH |
| CH₃ | H | H | H | S | H | CH₃ | OCH₃ | CH |
| CH₃ | H | H | H | S | H | CH₃ | CH₃ | CH |
| CH₃ | H | H | H | S | H | OCH₃ | OCH₃ | N |
| CH₃ | H | H | H | S | H | CH₃ | OCH₃ | N |
| CH₃ | H | CH₃ | H | O | H | OCH₃ | OCH₃ | CH |
| CH₃ | H | CH₃ | H | O | H | Cl | OCH₃ | CH |
| CH₃ | H | CH₃ | H | O | H | CH₃ | OCH₃ | CH |
| CH₃ | H | CH₃ | H | O | H | CH₃ | CH₃ | CH |
| CH₃ | H | CH₃ | H | O | H | OCH₃ | OCH₃ | N |
| CH₃ | H | CH₃ | H | O | H | CH₃ | OCH₃ | N |
| CH₃ | H | CH₃ | H | O | H | CH₃ | CH₃ | N |
| CH₃ | H | CH₃ | H | O | H | OCH₂CH₃ | OCH₂CH₃ | N |
| CH₃ | H | CH₃ | H | O | H | NHCH₃ | OCH₂CH₃ | N |
| CH₃ | H | CH₃ | H | O | H | N(CH₃)₂ | OCH₂CH₃ | N |
| CH₃ | H | CH₃ | H | O | H | N(CH₃)₂ | OCH₃ | N |
| CH₃ | H | CH₃ | H | O | H | N(CH₃)₂ | OCH₂CF₃ | N |
| CH₃ | H | CH₃ | H | O | CH₃ | CH₃ | OCH₃ | N |
| CH₃ | H | CH₃ | H | S | H | OCH₃ | OCH₃ | CH |
| CH₃ | H | CH₃ | H | S | H | Cl | OCH₃ | CH |
| CH₃ | H | CH₃ | H | S | H | CH₃ | OCH₃ | CH |
| CH₃ | H | CH₃ | H | S | H | CH₃ | CH₃ | CH |
| CH₃ | H | CH₃ | H | S | H | OCH₃ | OCH₃ | N |
| CH₃ | H | CH₃ | H | S | H | CH₃ | OCH₃ | N |
| CH₃ | H | CH₂CH₃ | H | O | H | OCH₃ | OCH₃ | CH |
| CH₃ | H | CH₂CH₃ | H | O | H | Cl | OCH₃ | CH |
| CH₃ | H | CH₂CH₃ | H | O | H | CH₃ | OCH₃ | CH |
| CH₃ | H | CH₂CH₃ | H | O | H | CH₃ | CH₃ | CH |
| CH₃ | H | CH₂CH₃ | H | O | H | OCH₃ | OCH₃ | N |
| CH₃ | H | CH₂CH₃ | H | O | H | CH₃ | OCH₃ | N |
| CH₃ | H | CH₂CH₃ | H | O | H | CH₃ | CH₃ | N |

TABLE I-continued

| | | | | | | | | |
|---|---|---|---|---|---|---|---|---|
| CH₃ | H | | CH₂CH₃ | H | O | H | OCH₂CH₃ | OCH₂CH₃ | N |
| CH₃ | H | | CH₂CH₃ | H | O | H | NHCH₃ | OCH₂CH₃ | N |
| CH₃ | H | | CH₂CH₃ | H | O | H | N(CH₃)₂ | OCH₂CH₃ | N |
| CH₃ | H | | CH₂CH₃ | H | O | H | N(CH₃)₂ | OCH₃ | N |
| CH₃ | H | | CH₂CH₃ | H | O | H | N(CH₃)₂ | OCH₂CF₃ | N |
| CH₃ | H | | CH₂CH₃ | H | O | CH₃ | CH₃ | OCH₃ | N |
| CH₃ | H | | CH₂CH₃ | H | S | H | OCH₃ | OCH₃ | CH |
| CH₃ | H | | CH₂CH₃ | H | S | H | Cl | OCH₃ | CH |
| CH₃ | H | | CH₂CH₃ | H | S | H | CH₃ | OCH₃ | CH |
| CH₃ | H | | CH₂CH₃ | H | S | H | CH₃ | CH₃ | CH |
| CH₃ | H | | CH₂CH₃ | H | S | H | OCH₃ | OCH₃ | N |
| CH₃ | H | | CH₂CH₃ | H | S | H | CH₃ | OCH₃ | N |
| CH₃ | H | | CH₂CF₃ | H | O | H | OCH₃ | OCH₃ | CH |
| CH₃ | H | | CH₂CF₃ | H | O | H | Cl | OCH₃ | CH |
| CH₃ | H | | CH₂CF₃ | H | O | H | CH₃ | OCH₃ | CH |
| CH₃ | H | | CH₂CF₃ | H | O | H | CH₃ | CH₃ | CH |
| CH₃ | H | | CH₂CF₃ | H | O | H | OCH₃ | OCH₃ | N |
| CH₃ | H | | CH₂CF₃ | H | O | H | CH₃ | OCH₃ | N |
| CH₃ | H | | CH₂CF₃ | H | O | H | CH₃ | CH₃ | N |
| CH₃ | H | | CH₂CF₃ | H | O | H | OCH₂CH₃ | OCH₂CH₃ | N |
| CH₃ | H | | CH₂CF₃ | H | O | H | NHCH₃ | OCH₂CH₃ | N |
| CH₃ | H | | CH₂CF₃ | H | O | H | N(CH₃)₂ | OCH₂CH₃ | N |
| CH₃ | H | | CH₂CF₃ | H | O | H | N(CH₃)₂ | OCH₃ | N |
| CH₃ | H | | CH₂CF₃ | H | O | H | N(CH₃)₂ | OCH₂CF₃ | N |
| CH₃ | H | | CH₂CF₃ | H | O | CH₃ | CH₃ | OCH₃ | N |
| CH₃ | H | | CH₂CF₃ | H | S | H | OCH₃ | OCH₃ | CH |
| CH₃ | H | | CH₂CF₃ | H | S | H | Cl | OCH₃ | CH |
| CH₃ | H | | CH₂CF₃ | H | S | H | CH₃ | OCH₃ | CH |
| CH₃ | H | | CH₂CF₃ | H | S | H | CH₃ | CH₃ | CH |
| CH₃ | H | | CH₂CF₃ | H | S | H | OCH₃ | OCH₃ | N |
| CH₃ | H | | CH₂CF₃ | H | S | H | CH₃ | OCH₃ | N |
| CH₃ | CH₂CH₂Cl | | H | H | O | H | OCH₃ | OCH₃ | CH |
| CH₃ | CH₂CH₂Cl | | H | H | O | H | Cl | OCH₃ | CH |
| CH₃ | CH₂CH₂Cl | | H | H | O | H | CH₃ | OCH₃ | CH |
| CH₃ | CH₂CH₂Cl | | H | H | O | H | CH₃ | CH₃ | CH |
| CH₃ | CH₂CH₂Cl | | H | H | O | H | OCH₃ | OCH₃ | N |
| CH₃ | CH₂CH₂Cl | | H | H | O | H | CH₃ | OCH₃ | N |
| CH₃ | CH₂CH₂Cl | | H | H | O | H | CH₃ | OCH₃ | N |
| CH₃ | CH₂CH₂Cl | | H | H | O | H | OCH₂CH₃ | OCH₂CH₃ | N |
| CH₃ | CH₂CH₂Cl | | H | H | O | H | NHCH₃ | OCH₂CH₃ | N |
| CH₃ | CH₂CH₂Cl | | H | H | O | H | N(CH₃)₂ | OCH₂CH₃ | N |
| CH₃ | CH₂CH₂Cl | | H | H | O | H | N(CH₃)₂ | OCH₃ | N |
| CH₃ | CH₂CH₂Cl | | H | H | O | H | N(CH₃)₂ | OCH₂CF₃ | N |
| CH₃ | CH₂CH₂Cl | | H | H | O | CH₃ | CH₃ | OCH₃ | N |
| CH₃ | CH₂CH₂Cl | | H | H | S | H | OCH₃ | OCH₃ | CH |
| CH₃ | CH₂CH₂Cl | | H | H | S | H | Cl | OCH₃ | CH |
| CH₃ | CH₂CH₂Cl | | H | H | S | H | CH₃ | OCH₃ | CH |
| CH₃ | CH₂CH₂Cl | | H | H | S | H | CH₃ | CH₃ | CH |
| CH₃ | CH₂CH₂Cl | | H | H | S | H | OCH₃ | OCH₃ | CH |
| CH₃ | CH₂CH₂Cl | | H | H | S | H | CH₃ | OCH₃ | N |
| CH₃ | CH₂CN | | H | H | O | H | OCH₃ | CH₃ | CH |
| CH₃ | CH₂CN | | H | H | O | H | Cl | OCH₃ | CH |
| CH₃ | CH₂CN | | H | H | O | H | CH₃ | OCH₃ | CH |
| CH₃ | CH₂CN | | H | H | O | H | CH₃ | CH₃ | CH |
| CH₃ | CH₂CN | | H | H | O | H | OCH₃ | OCH₃ | CH |
| CH₃ | CH₂CN | | H | H | O | H | CH₃ | OCH₃ | N |
| CH₃ | CH₂CN | | H | H | O | H | CH₃ | OCH₃ | N |
| CH₃ | CH₂CN | | H | H | O | H | CH₃ | CH₃ | N |
| CH₃ | CH₂CN | | H | H | O | H | OCH₂CH₃ | OCH₂CH₃ | N |
| CH₃ | CH₂CN | | H | H | O | H | NHCH₃ | OCH₂CH₃ | N |
| CH₃ | CH₂CN | | H | H | O | H | N(CH₃)₂ | OCH₂CH₃ | N |
| CH₃ | CH₂CN | | H | H | O | H | N(CH₃)₂ | OCH₃ | N |
| CH₃ | CH₂CN | | H | H | O | H | N(CH₃)₂ | OCH₂CF₃ | N |
| CH₃ | CH₂CN | | H | H | O | CH₃ | CH₃ | OCH₃ | N |
| CH₃ | CH₂CN | | H | H | S | H | OCH₃ | OCH₃ | CH |
| CH₃ | CH₂CN | | H | H | S | H | Cl | OCH₃ | CH |
| CH₃ | CH₂CN | | H | H | S | H | CH₃ | OCH₃ | CH |
| CH₃ | CH₂CN | | H | H | S | H | CH₃ | CH₃ | CH |
| CH₃ | CH₂CN | | H | H | S | H | OCH₃ | OCH₃ | N |
| CH₃ | CH₂CN | | H | H | S | H | CH₃ | OCH₃ | N |
| CH₃ | CH₂CH=CH₂ | | H | H | O | H | OCH₃ | CH₃ | CH |
| CH₃ | CH₂CH=CH₂ | | H | H | O | H | Cl | OCH₃ | CH |
| CH₃ | CH₂CH=CH₂ | | H | H | O | H | CH₃ | OCH₃ | CH |
| CH₃ | CH₂CH=CH₂ | | H | H | O | H | CH₃ | CH₃ | CH |
| CH₃ | CH₂CH=CH₂ | | H | H | O | H | OCH₃ | OCH₃ | N |
| CH₃ | CH₂CH=CH₂ | | H | H | O | H | CH₃ | OCH₃ | N |
| CH₃ | CH₂CH=CH₂ | | H | H | O | H | CH₃ | CH₃ | N |
| CH₃ | CH₂CH=CH₂ | | H | H | O | H | OCH₂CH₃ | OCH₂CH₃ | N |
| CH₃ | CH₂CH=CH₂ | | H | H | O | H | NHCH₃ | OCH₂CH₃ | N |
| CH₃ | CH₂CH=CH₂ | | H | H | O | H | N(CH₃)₂ | OCH₂CH₃ | N |
| CH₃ | CH₂CH=CH₂ | | H | H | O | H | N(CH₃)₂ | OCH₃ | N |
| CH₃ | CH₂CH=CH₂ | | H | H | O | H | N(CH₃)₂ | OCH₂CF₃ | N |

TABLE I-continued

| | | | | | | | | | |
|---|---|---|---|---|---|---|---|---|---|
| CH₃ | CH₂CH=CH₂ | H | H | O | CH₃ | CH₃ | OCH₃ | N |
| CH₃ | CH₂CH=CH₂ | H | H | S | H | OCH₃ | OCH₃ | CH |
| CH₃ | CH₂CH=CH₂ | H | H | S | H | Cl | OCH₃ | CH |
| CH₃ | CH₂CH=CH₂ | H | H | S | H | CH₃ | OCH₃ | CH |
| CH₃ | CH₂CH=CH₂ | H | H | S | H | CH₃ | CH₃ | CH |
| CH₃ | CH₂CH=CH₂ | H | H | S | H | OCH₃ | OCH₃ | N |
| CH₃ | CH₂CH=CH₂ | H | H | S | H | CH₃ | OCH₃ | N |
| CH₃ | CH₂CH=CH₂ | H | H | O | H | OCH₃ | OCH₃ | CH |
| CH₃ | CH₂C≡CH | H | H | O | H | Cl₃ | OCH | CH |
| CH₃ | CH₂C≡CH | H | H | O | H | CH₃ | OCH₃ | CH |
| CH₃ | CH₂C≡CH | H | H | O | H | CH₃ | CH₃ | CH |
| CH₃ | CH₂C≡CH | H | H | O | H | OCH₃ | OCH₃ | N |
| CH₃ | CH₂C≡CH | H | H | O | H | CH₃ | OCH₃ | N |
| CH₃ | CH₂C≡CH | H | H | O | H | CH₃ | CH₃ | N |
| CH₃ | CH₂C≡CH | H | H | O | H | OCH₂CH₃ | OCH₂CH₃ | N |
| CH₃ | CH₂C≡CH | H | H | O | H | NHCH₃ | OCH₂CH₃ | N |
| CH₃ | CH₂C≡CH | H | H | O | H | N(CH₃)₂ | OCH₂CH₃ | N |
| CH₃ | CH₂C≡CH | H | H | O | H | N(CH₃)₂ | OCH₃ | N |
| CH₃ | CH₂C≡CH | H | H | O | H | N(CH₃)₂ | OCH₂CF₃ | N |
| CH₃ | CH₂C≡CH | H | H | O | CH₃ | CH₃ | OCH₃ | N |
| CH₃ | CH₂C≡CH | H | H | S | H | OCH₃ | OCH₃ | CH |
| CH₃ | CH₂C≡CH | H | H | S | H | Cl | OCH₃ | CH |
| CH₃ | CH₂C≡CH | H | H | S | H | CH₃ | OCH₃ | CH |
| CH₃ | CH₂C≡CH | H | H | S | H | CH₃ | CH₃ | CH |
| CH₃ | CH₂C≡CH | H | H | S | H | OCH₃ | OCH₃ | N |
| CH₃ | CH₂C≡CH | H | H | S | H | CH₃ | OCH₃ | N |
| CH₃ | CH₂CH₂OCH₃ | H | H | O | H | OCH₃ | OCH₃ | CH |
| CH₃ | CH₂CH₂OCH₃ | H | H | O | H | Cl | OCH₃ | CH |
| CH₃ | CH₂CH₂OCH₃ | H | H | O | H | CH₃ | OCH₃ | CH |
| CH₃ | CH₂CH₂OCH₃ | H | H | O | H | CH₃ | CH₃ | CH |
| CH₃ | CH₂CH₂OCH₃ | H | H | O | H | OCH₃ | OCH₃ | N |
| CH₃ | CH₂CH₂OCH₃ | H | H | O | H | CH₃ | OCH₃ | N |
| CH₃ | CH₂CH₂OCH₃ | H | H | O | H | CH₃ | CH₃ | N |
| CH₃ | CH₂CH₂OCH₃ | H | H | O | H | OCH₂CH₃ | OCH₂CH₃ | N |
| CH₃ | CH₂CH₂OCH₃ | H | H | O | H | NHCH₃ | OCH₂CH₃ | N |
| CH₃ | CH₂CH₂OCH₃ | H | H | O | H | N(CH₃)₂ | OCH₂CH₃ | N |
| CH₃ | CH₂CH₂OCH₃ | H | H | O | H | N(CH₃)₂ | OCH₃ | N |
| CH₃ | CH₂CH₂OCH₃ | H | H | O | H | N(CH₃)₂ | OCH₂CF₃ | N |
| CH₃ | CH₂CH₂OCH₃ | H | H | O | CH₃ | CH₃ | OCH₃ | N |
| CH₃ | CH₂CH₂OCH₃ | H | H | S | H | OCH₃ | OCH₃ | CH |
| CH₃ | CH₂CH₂OCH₃ | H | H | S | H | Cl | OCH₃ | CH |
| CH₃ | CH₂CH₂OCH₃ | H | H | S | H | CH₃ | OCH₃ | CH |
| CH₃ | CH₂CH₂OCH₃ | H | H | S | H | CH₃ | CH₃ | CH |
| CH₃ | CH₂CH₂OCH₃ | H | H | S | H | OCH₃ | OCH₃ | N |
| CH₃ | CH₂CH₂OCH₃ | H | H | S | H | CH₃ | OCH₃ | N |
| CH₃ | cyclo-C₃H₇ | H | H | O | H | OCH₃ | OCH₃ | CH |
| CH₃ | cyclo-C₃H₇ | H | H | O | H | Cl₃ | OCH | CH |
| CH₃ | cylco-C₃H₇ | H | H | O | H | CH₃ | OCH₃ | CH |
| CH₃ | cyclo-C₃H₇ | H | H | O | H | CH₃ | CH₃ | CH |
| CH₃ | cyclo-C₃H₇ | H | H | O | H | OCH₃ | OCH₃ | N |
| CH₃ | cyclo-C₃H₇ | H | H | O | H | CH₃ | OCH₃ | N |
| CH₃ | cyclo-C₃H₇ | H | H | O | H | CH₃ | CH₃ | N |
| CH₃ | cyclo-C₃H₇ | H | H | O | H | OCH₂CH₃ | OCH₂CH₃ | N |
| CH₃ | cyclo-C₃H₇ | H | H | O | H | NHCH₃ | OCH₂CH₃ | N |
| CH₃ | cyclo-C₃H₇ | H | H | O | H | N(CH₃)₂ | OCH₂CH₃ | N |
| CH₃ | cyclo-C₃H₇ | H | H | O | H | N(CH₃)₂ | OCH₃ | N |
| CH₃ | cyclo-C₃H₇ | H | H | O | H | N(CH₃)₂ | OCH₂CF₃ | N |
| CH₃ | cyclo-C₃H₇ | H | H | O | CH₃ | CH₃ | OCH₃ | N |
| CH₃ | cyclo-C₃H₇ | H | H | S | H | OCH₃ | OCH₃ | CH |
| CH₃ | cyclo-C₃H₇ | H | H | S | H | Cl | OCH₃ | CH |
| CH₃ | cyclo-C₃H₇ | H | H | S | H | CH₃ | OCH₃ | CH |
| CH₃ | cyclo-C₃H₇ | H | H | S | H | CH₃ | CH₃ | CH |
| CH₃ | cyclo-C₃H₇ | H | H | S | H | OCH₃ | OCH₃ | N |
| CH₃ | cyclo-C₃H₇ | H | H | S | H | CH₃ | OCH₃ | N |
| CH₃ | CH₃ | CH₃ | H | O | H | OCH₃ | OCH₃ | CH |
| CH₃ | CH₃ | CH₃ | H | O | H | Cl | OCH₃ | CH |
| CH₃ | CH₃ | CH₃ | H | O | H | CH₃ | OCH₃ | CH |
| CH₃ | CH₃ | CH₃ | H | O | H | CH₃ | CH₃ | CH |
| CH₃ | CH₃ | CH₃ | H | O | H | OCH₃ | OCH₃ | N |
| CH₃ | CH₃ | CH₃ | H | O | H | CH₃ | OCH₃ | N |
| CH₃ | CH₃ | CH₃ | H | O | H | CH₃ | CH₃ | N |
| CH₃ | CH₃ | CH₃ | H | O | H | OCH₂CH₃ | OCH₂CH₃ | N |
| CH₃ | CH₃ | CH₃ | H | O | H | NHCH₃ | OCH₂CH₃ | N |
| CH₃ | CH₃ | CH₃ | H | O | H | N(CH₃)₂ | OCH₂CH₃ | N |
| CH₃ | CH₃ | CH₃ | H | O | H | N(CH₃)₂ | OCH₃ | N |
| CH₃ | CH₃ | CH₃ | H | O | H | N(CH₃)₂ | OCH₂CF₃ | N |
| CH₃ | CH₃ | CH₃ | H | O | CH₃ | CH₃ | OCH₃ | N |
| CH₃ | CH₃ | CH₃ | H | S | H | OCH₃ | OCH₃ | CH |
| CH₃ | CH₃ | CH₃ | H | S | H | Cl | OCH₃ | CH |
| CH₃ | CH₃ | CH₃ | H | S | H | CH₃ | OCH₃ | CH |
| CH₃ | CH₃ | CH₃ | H | S | H | CH₃ | CH₃ | CH |
| CH₃ | CH₃ | CH₃ | H | S | H | OCH₃ | OCH₃ | N |

TABLE I-continued

| | | | | | | | | |
|---|---|---|---|---|---|---|---|---|
| CH$_3$ | CH$_3$ | CH$_3$ | H | S | H | CH$_3$ | OCH$_3$ | N |
| CH$_3$ | CH$_3$ | CH$_2$CH$_3$ | H | O | H | OCH$_3$ | OCH$_3$ | CH |
| CH$_3$ | CH$_3$ | CH$_2$CH$_3$ | H | O | H | Cl | OCH$_3$ | CH |
| CH$_3$ | CH$_3$ | CH$_2$CH$_3$ | H | O | H | CH$_3$ | OCH$_3$ | CH |
| CH$_3$ | CH$_3$ | CH$_2$CH$_3$ | H | O | H | CH$_3$ | CH$_3$ | CH |
| CH$_3$ | CH$_3$ | CH$_2$CH$_3$ | H | O | H | OCH$_3$ | OCH$_3$ | N |
| CH$_3$ | CH$_3$ | CH$_2$CH$_3$ | H | O | H | CH$_3$ | OCH$_3$ | N |
| CH$_3$ | CH$_3$ | CH$_2$CH$_3$ | H | O | H | CH$_3$ | CH$_3$ | N |
| CH$_3$ | CH$_3$ | CH$_2$CH$_3$ | H | O | H | OCH$_2$CH$_3$ | OCH$_2$CH$_3$ | N |
| CH$_3$ | CH$_3$ | CH$_2$CH$_3$ | H | O | H | NHCH$_3$ | OCH$_2$CH$_3$ | N |
| CH$_3$ | CH$_3$ | CH$_2$CH$_3$ | H | O | H | N(CH$_3$)$_2$ | OCH$_2$CH$_3$ | N |
| CH$_3$ | CH$_3$ | CH$_2$CH$_3$ | H | O | H | N(CH$_3$)$_2$ | OCH$_3$ | N |
| CH$_3$ | CH$_3$ | CH$_2$CH$_3$ | H | O | H | N(CH$_3$)$_2$ | OCH$_2$CF$_3$ | N |
| CH$_3$ | CH$_3$ | CH$_2$CH$_3$ | H | O | CH$_3$ | CH$_3$ | OCH$_3$ | N |
| CH$_3$ | CH$_3$ | CH$_2$CH$_3$ | H | S | H | OCH$_3$ | OCH$_3$ | CH |
| CH$_3$ | CH$_3$ | CH$_2$CH$_3$ | H | S | H | Cl | OCH$_3$ | CH |
| CH$_3$ | CH$_3$ | CH$_2$CH$_3$ | H | S | H | CH$_3$ | OCH$_3$ | CH |
| CH$_3$ | CH$_3$ | CH$_2$CH$_3$ | H | S | H | CH$_3$ | CH$_3$ | CH |
| CH$_3$ | CH$_3$ | CH$_2$CH$_3$ | H | S | H | OCH$_3$ | OCH$_3$ | N |
| CH$_3$ | CH$_3$ | CH$_2$CH$_3$ | H | S | H | CH$_3$ | OCH$_3$ | N |
| CH$_3$ | CH$_2$CH$_3$ | CH$_2$CH$_3$ | H | O | H | OCH$_3$ | OCH$_3$ | CH |
| CH$_3$ | CH$_2$CH$_3$ | CH$_2$CH$_3$ | H | O | H | Cl | OCH$_3$ | CH |
| CH$_3$ | CH$_2$CH$_3$ | CH$_2$CH$_3$ | H | O | H | CH$_3$ | OCH$_3$ | CH |
| CH$_3$ | CH$_2$CH$_3$ | CH$_2$CH$_3$ | H | O | H | CH$_3$ | CH$_3$ | CH |
| CH$_3$ | CH$_2$CH$_3$ | CH$_2$CH$_3$ | H | O | H | OCH$_3$ | OCH$_3$ | N |
| CH$_3$ | CH$_2$CH$_3$ | CH$_2$CH$_3$ | H | O | H | CH$_3$ | OCH$_3$ | N |
| CH$_3$ | CH$_2$CH$_3$ | CH$_2$CH$_3$ | H | O | H | CH$_3$ | CH$_3$ | N |
| CH$_3$ | CH$_2$CH$_3$ | CH$_2$CH$_3$ | H | O | H | OCH$_2$CH$_3$ | OCH$_2$CH$_3$ | N |
| CH$_3$ | CH$_2$CH$_3$ | CH$_2$CH$_3$ | H | O | H | NHCH$_3$ | OCH$_2$CH$_3$ | N |
| CH$_3$ | CH$_2$CH$_3$ | CH$_2$CH$_3$ | H | O | H | N(CH$_3$)$_2$ | OCH$_2$CH$_3$ | N |
| CH$_3$ | CH$_2$CH$_3$ | CH$_2$CH$_3$ | H | O | H | N(CH$_3$)$_2$ | OCH$_3$ | N |
| CH$_3$ | CH$_2$CH$_3$ | CH$_2$CH$_3$ | H | O | H | N(CH$_3$)$_2$ | OCH$_2$CF$_3$ | N |
| CH$_3$ | CH$_2$CH$_3$ | CH$_2$CH$_3$ | H | O | CH$_3$ | CH$_3$ | OCH$_3$ | N |
| CH$_3$ | CH$_2$CH$_3$ | CH$_2$CH$_3$ | H | S | H | OCH$_3$ | OCH$_3$ | CH |
| CH$_3$ | CH$_2$CH$_3$ | CH$_2$CH$_3$ | H | S | H | Cl | OCH$_3$ | CH |
| CH$_3$ | CH$_2$CH$_3$ | CH$_2$CH$_3$ | H | S | H | CH$_3$ | OCH$_3$ | CH |
| CH$_3$ | CH$_2$CH$_3$ | CH$_2$CH$_3$ | H | S | H | CH$_3$ | CH$_3$ | CH |
| CH$_3$ | CH$_2$CH$_3$ | CH$_2$CH$_3$ | H | S | H | OCH$_3$ | OCH$_3$ | N |
| CH$_3$ | CH$_2$CH$_3$ | CH$_2$CH$_3$ | H | S | H | CH$_3$ | OCH$_3$ | N |
| CH$_3$ | OCH$_3$ | CH$_3$ | H | O | H | OCH$_3$ | OCH$_3$ | CH |
| CH$_3$ | OCH$_3$ | CH$_3$ | H | O | H | Cl$_3$ | OCH | CH |
| CH$_3$ | OCH$_3$ | CH$_3$ | H | O | H | CH$_3$ | OCH$_3$ | CH |
| CH$_3$ | OCH$_3$ | CH$_3$ | H | O | H | CH$_3$ | CH$_3$ | CH |
| CH$_3$ | OCH$_3$ | CH$_3$ | H | O | H | OCH$_3$ | OCH$_3$ | N |
| CH$_3$ | OCH$_3$ | CH$_3$ | H | O | H | CH$_3$ | OCH$_3$ | N |
| CH$_3$ | OCH$_3$ | CH$_3$ | H | O | H$_3$ | CH | CH$_3$ | N |
| CH$_3$ | OCH$_3$ | CH$_3$ | H | O | H | OCH$_2$CH$_3$ | OCH$_2$CH$_3$ | N |
| CH$_3$ | OCH$_3$ | CH$_3$ | H | O | H | NHCH$_3$ | OCH$_2$CH$_3$ | N |
| CH$_3$ | OCH$_3$ | CH$_3$ | H | O | H | N(CH$_3$)$_2$ | OCH$_2$CH$_3$ | N |
| CH$_3$ | OCH$_3$ | CH$_3$ | H | O | H | N(CH$_3$)$_2$ | OCH$_3$ | N |
| CH$_3$ | OCH$_3$ | CH$_3$ | H | O | H | N(CH$_3$)$_2$ | OCH$_2$CF$_3$ | N |
| CH$_3$ | OCH$_3$ | CH$_3$ | H | O | CH$_3$ | CH$_3$ | OCH$_3$ | N |
| CH$_3$ | OCH$_3$ | CH$_3$ | H | S | H | OCH$_3$ | OCH$_3$ | CH |
| CH$_3$ | OCH$_3$ | CH$_3$ | H | S | H | Cl | OCH$_3$ | CH |
| CH$_3$ | OCH$_3$ | CH$_3$ | H | S | H | CH$_3$ | OCH$_3$ | CH |
| CH$_3$ | OCH$_3$ | CH$_3$ | H | S | H | CH$_3$ | CH$_3$ | CH |
| CH$_3$ | OCH$_3$ | CH$_3$ | H | S | H | OCH$_3$ | OCH$_3$ | N |
| CH$_3$ | OCH$_3$ | CH$_3$ | H | S | H | CH$_3$ | OCH$_3$ | N |
| CH$_3$ | NHCH$_3$ | CH$_3$ | H | O | H | OCH$_3$ | OCH$_3$ | CH |
| CH$_3$ | NHCH$_3$ | CH$_3$ | H | O | H | Cl | OCH$_3$ | CH |
| CH$_3$ | NHCH$_3$ | CH$_3$ | H | O | H | CH$_3$ | OCH$_3$ | CH |
| CH$_3$ | NHCH$_3$ | CH$_3$ | H | O | H | CH$_3$ | CH$_3$ | CH |
| CH$_3$ | NHCH$_3$ | CH$_3$ | H | O | H | OCH$_3$ | OCH$_3$ | N |
| CH$_3$ | NHCH$_3$ | CH$_3$ | H | O | H | CH$_3$ | OCH$_3$ | N |
| CH$_3$ | NHCH$_3$ | CH$_3$ | H | O | H | CH$_3$ | CH$_3$ | N |
| CH$_3$ | NHCH$_3$ | CH$_3$ | H | O | H | OCH$_2$CH$_3$ | OCH$_2$CH$_3$ | N |
| CH$_3$ | NHCH$_3$ | CH$_3$ | H | O | H | NHCH$_3$ | OCH$_2$CH$_3$ | N |
| CH$_3$ | NHCH$_3$ | CH$_3$ | H | O | H | N(CH$_3$)$_2$ | OCH$_2$CH$_3$ | N |
| CH$_3$ | NHCH$_3$ | CH$_3$ | H | O | H | N(CH$_3$)$_2$ | OCH$_3$ | N |
| CH$_3$ | NHCH$_3$ | CH$_3$ | H | O | H | N(CH$_3$)$_2$ | OCH$_2$CF$_3$ | N |
| CH$_3$ | NHCH$_3$ | CH$_3$ | H | O | CH$_3$ | CH$_3$ | OCH$_3$ | N |
| CH$_3$ | NHCH$_3$ | CH$_3$ | H | S | H | OCH$_3$ | OCH$_3$ | CH |
| CH$_3$ | NHCH$_3$ | CH$_3$ | H | S | H | Cl | OCH$_3$ | CH |
| CH$_3$ | NHCH$_3$ | CH$_3$ | H | S | H | CH$_3$ | OCH$_3$ | CH |
| CH$_3$ | NHCH$_3$ | CH$_3$ | H | S | H | CH$_3$ | CH$_3$ | CH |
| CH$_3$ | NHCH$_3$ | CH$_3$ | H | S | H | OCH$_3$ | OCH$_3$ | N |
| CH$_3$ | NHCH$_3$ | CH$_3$ | H | S | H | CH$_3$ | OCH$_3$ | N |
| CH$_3$ | N(CH$_3$)$_2$ | CH$_3$ | H | O | H | OCH$_3$ | OCH$_3$ | CH |
| CH$_3$ | N(CH$_3$)$_2$ | CH$_3$ | H | O | H | Cl | OCH$_3$ | CH |
| CH$_3$ | N(CH$_3$)$_2$ | CH$_3$ | H | O | H | CH$_3$ | OCH$_3$ | CH |
| CH$_3$ | N(CH$_3$)$_2$ | CH$_3$ | H | O | H | CH$_3$ | CH$_3$ | CH |

TABLE I-continued

| | | | | | | | | | |
|---|---|---|---|---|---|---|---|---|---|
| CH₃ | N(CH₃)₂ | CH₃ | H | O | H | OCH₃ | OCH₃ | N | |
| CH₃ | N(CH₃)₂ | CH₃ | H | O | H | CH₃ | OCH₃ | N | |
| CH₃ | N(CH₃)₂ | CH₃ | H | O | H | CH₃ | CH₃ | N | |
| CH₃ | N(CH₃)₂ | CH₃ | H | O | H | OCH₂CH₃ | OCH₂CH₃ | N | |
| CH₃ | N(CH₃)₂ | CH₃ | H | O | H | NHCH₃ | OCH₂CH₃ | N | |
| CH₃ | N(CH₃)₂ | CH₃ | H | O | H | N(CH₃)₂ | OCH₂CH₃ | N | |
| CH₃ | N(CH₃)₂ | CH₃ | H | O | H | N(CH₃)₂ | OCH₃ | N | |
| CH₃ | N(CH₃)₂ | CH₃ | H | O | H | N(CH₃)₂ | OCH₂CF₃ | N | |
| CH₃ | N(CH₃)₂ | CH₃ | H | O | CH₃ | CH₃ | OCH₃ | N | |
| CH₃ | N(CH₃)₂ | CH₃ | H | S | H | OCH₃ | OCH₃ | CH | |
| CH₃ | N(CH₃)₂ | CH₃ | H | S | H | Cl | OCH₃ | CH | |
| CH₃ | N(CH₃)₂ | CH₃ | H | S | H | CH₃ | OCH₃ | CH | |
| CH₃ | N(CH₃)₂ | CH₃ | H | S | H | CH₃ | CH₃ | CH | |
| CH₃ | N(CH₃)₂ | CH₃ | H | S | H | OCH₃ | OCH₃ | N | |
| CH₃ | N(CH₃)₂ | CH₃ | H | S | H | CH₃ | OCH₃ | N | |
| CH₃ | —CH₂CH₂CH₂— | | H | O | H | OCH₃ | OCH₃ | CH | |
| CH₃ | —CH₂CH₂CH₂— | | H | O | H | Cl | OCH₃ | CH | |
| CH₃ | —CH₂CH₂CH₂— | | H | O | H | CH₃ | OCH₃ | CH | |
| CH₃ | —CH₂CH₂CH₂— | | H | O | H | CH₃ | CH₃ | CH | |
| CH₃ | —CH₂CH₂CH₂— | | H | O | H | OCH₃ | OCH₃ | N | |
| CH₃ | —CH₂CH₂CH₂— | H | O | H | CH₃ | OCH₃ | N | | |
| CH₃ | —CH₂CH₂CH₂— | | H | O | H | CH₃ | CH₃ | N | |
| CH₃ | —CH₂CH₂CH₂— | | H | O | H | OCH₂CH₃ | OCH₂CH₃ | N | |
| CH₃ | —CH₂CH₂CH₂— | | H | O | H | NHCH₃ | OCH₂CH₃ | N | |
| CH₃ | —CH₂CH₂CH₂— | | H | O | H | N(CH₃)₂ | OCH₂CH₃ | N | |
| CH₃ | —CH₂CH₂CH₂— | | H | O | H | N(CH₃)₂ | OCH₃ | N | |
| CH₃ | —CH₂CH₂CH₂— | | H | O | H | N(CH₃)₂ | OCH₂CF₃ | N | |
| CH₃ | —CH₂CH₂CH₂— | | H | O | CH₃ | CH₃ | OCH₃ | N | |
| CH₃ | —CH₂CH₂CH₂— | | H | S | H | OCH₃ | OCH₃ | CH | |
| CH₃ | —CH₂CH₂CH₂— | | H | S | H | Cl | OCH₃ | CH | |
| CH₃ | —CH₂CH₂CH₂— | | H | S | H | CH₃ | OCH₃ | CH | |
| CH₃ | —CH₂CH₂CH₂— | | H | S | H | CH₃ | CH₃ | CH | |
| CH₃ | —CH₂CH₂CH₂— | | H | S | H | OCH₃ | OCH₃ | N | |
| CH₃ | —CH₂CH₂CH₂— | | H | S | H | CH₃ | OCH₃ | N | |
| CH₃ | —CH₂CH₂OCH₂CH₂— | | H | O | H | OCH₃ | OCH₃ | CH | |
| CH₃ | —CH₂CH₂OCH₂CH₂— | | H | O | H | Cl | OCH₃ | CH | |
| CH₃ | —CH₂OCH₂CH₂— | | H | O | H | CH₃ | OCH₃ | CH | |
| CH₃ | —CH₂CH₂OCH₂CH₂— | | H | O | H | CH₃ | CH₃ | CH | |
| CH₃ | —CH₂CH₂OCH₂CH₂— | | H | O | H | OCH₃ | OCH₃ | N | |
| CH₃ | —CH₂CH₂OCH₂CH₂— | | H | O | H | CH₃ | OCH₃ | N | |
| CH₃ | —CH₂CH₂OCH₂CH₂— | | H | O | H | CH₃ | CH₃ | N | |
| CH₃ | —CH₂CH₂OCH₂CH₂— | | H | O | H | OCH₂CH₃ | OCH₂CH₃ | N | |
| CH₃ | —CH₂CH₂OCH₂CH₂— | | H | O | H | NHCH₃ | OCH₂CH₃ | N | |
| CH₃ | —CH₂CH₂OCH₂CH₂— | | H | O | H | N(CH₃)₂ | OCH₂CH₃ | N | |
| CH₃ | —CH₂CH₂OCH₂CH₂— | | H | O | H | N(CH₃)₂ | OCH₃ | N | |
| CH₃ | —CH₂CH₂OCH₂CH₂— | | H | O | H | N(CH₃)₂ | OCH₂CF₃ | N | |
| CH₃ | —CH₂CH₂OCH₂CH₂— | | H | O | CH₃ | CH₃ | OCH₃ | N | |
| CH₃ | —CH₂CH₂OCH₂CH₂— | | H | S | H | OCH₃ | OCH₃ | CH | |
| CH₃ | —CH₂CH₂OCH₂CH₂— | | H | S | H | Cl | OCH₃ | CH | |
| CH₃ | —CH₂CH₂OCH₂CH₂— | | H | S | H | CH₃ | OCH₃ | CH | |
| CH₃ | —CH₂CH₂OCH₂CH₂— | | H | S | H | CH₃ | CH₃ | CH | |
| CH₃ | —CH₂CH₂OCH₂CH₂— | | H | S | H | OCH₃ | OCH₃ | N | |
| CH₃ | —CH₂CH₂OCH₂CH₂— | | H | S | H | CH₃ | OCH₃ | N | |
| SCH₃ | H | H | H | O | H | OCH₃ | OCH₃ | CH | |
| SCH₃ | H | H | H | O | H | Cl | OCH₃ | CH | |
| SCH₃ | H | H | H | O | H | CH₃ | OCH₃ | CH | |
| SCH₃ | H | H | H | O | H | CH₃ | CH₃ | CH | |
| SCH₃ | H | H | H | O | H | OCH₃ | OCH₃ | N | |
| SCH₃ | H | H | H | O | H | CH₃ | OCH₃ | N | |
| SCH₃ | H | H | H | O | H | CH₃ | CH₃ | N | |
| SCH₃ | H | H | H | O | H | OCH₂CH₃ | OCH₂CH₃ | N | |
| SCH₃ | H | H | H | O | H | NHCH₃ | OCH₂CH₃ | N | |
| SCH₃ | H | H | H | O | H | N(CH₃)₂ | OCH₂CH₃ | N | |
| SCH₃ | H | H | H | O | H | N(CH₃)₂ | OCH₃ | N | |
| SCH₃ | H | H | H | O | H | N(CH₃)₂ | OCH₂CF₃ | N | |
| SCH₃ | H | H | H | O | CH₃ | CH₃ | OCH₃ | N | |
| SCH₃ | H | H | H | S | H | OCH₃ | OCH₃ | CH | |
| SCH₃ | H | H | H | S | H | Cl | OCH₃ | CH | |
| SCH₃ | H | H | H | S | H | CH₃ | OCH₃ | CH | |
| SCH₃ | H | H | H | S | H | CH₃ | CH₃ | CH | |
| SCH₃ | H | H | H | S | H | CH₃ | OCH₃ | N | |
| SCH₃ | H | H | H | S | H | OCH₃ | OCH₃ | N | |
| SCH₃ | H | CH₃ | H | O | H | OCH₃ | OCH₃ | CH | |
| SCH₃ | H | CH₃ | H | O | H | Cl | OCH₃ | CH | |
| SCH₃ | H | CH₃ | H | O | H | CH₃ | OCH₃ | CH | |
| SCH₃ | H | CH₃ | H | O | H | CH₃ | CH₃ | CH | |
| SCH₃ | H | CH₃ | H | O | H | OCH₃ | OCH₃ | N | |
| SCH₃ | H | CH₃ | H | O | H | CH₃ | OCH₃ | N | |
| SCH₃ | H | CH₃ | H | O | H | CH₃ | CH₃ | N | |
| SCH₃ | H | CH₃ | H | O | H | OCH₂CH₃ | OCH₂CH₃ | N | |
| SCH₃ | H | CH₃ | H | O | H | NHCH₃ | OCH₂CH₃ | N | |
| SCH₃ | H | CH₃ | H | O | H | N(CH₃)₂ | OCH₂CH₃ | N | |

TABLE I-continued

| | | | | | | | | |
|---|---|---|---|---|---|---|---|---|
| SCH₃ | H | CH₃ | H | O | H | N(CH₃)₂ | OCH₃ | N |
| SCH₃ | H | CH₃ | H | O | H | N(CH₃)₂ | OCH₂CF₃ | N |
| SCH₃ | H | CH₃ | H | O | CH₃ | CH₃ | OCH₃ | N |
| SCH₃ | H | CH₃ | H | S | H | OCH₃ | OCH₃ | CH |
| SCH₃ | H | CH₃ | H | S | H | Cl | OCH₃ | CH |
| SCH₃ | H | CH₃ | H | S | H | CH₃ | OCH₃ | CH |
| SCH₃ | H | CH₃ | H | S | H | CH₃ | CH₃ | CH |
| SCH₃ | H | CH₃ | H | S | H | OCH₃ | OCH₃ | N |
| SCH₃ | H | CH₃ | H | S | H | CH₃ | OCH₃ | N |
| SCH₃ | H | CH₂CH₃ | H | O | H | OCH₃ | OCH₃ | CH |
| SCH₃ | H | CH₂CH₃ | H | O | H | Cl | OCH₃ | CH |
| SCH₃ | H | CH₂CH₃ | H | O | H | CH₃ | OCH₃ | CH |
| SCH₃ | H | CH₂CH₃ | H | O | H | CH₃ | CH₃ | CH |
| SCH₃ | H | CH₂CH₃ | H | O | H | OCH₃ | OCH₃ | N |
| SCH₃ | H | CH₂CH₃ | H | O | H | CH₃ | OCH₃ | N |
| SCH₃ | H | CH₂CH₃ | H | O | H | CH₃ | CH₃ | N |
| SCH₃ | H | CH₂CH₃ | H | O | H | OCH₂CH₃ | OCH₂CH₃ | N |
| SCH₃ | H | CH₂CH₃ | H | O | H | NHCH₃ | OCH₂CH₃ | N |
| SCH₃ | H | CH₂CH₃ | H | O | H | N(CH₃)₂ | OCH₂CH₃ | N |
| SCH₃ | H | CH₂CH₃ | H | O | H | N(CH₃)₂ | OCH₃ | N |
| SCH₃ | H | CH₂CH₃ | H | O | H | N(CH₃)₂ | OCH₂CF₃ | N |
| SCH₃ | H | CH₂CH₃ | H | O | CH₃ | CH₃ | OCH₃ | N |
| SCH₃ | H | CH₂CH₃ | H | S | H | OCH₃ | OCH₃ | CH |
| SCH₃ | H | CH₂CH₃ | H | S | H | Cl | OCH₃ | CH |
| SCH₃ | H | CH₂CH₃ | H | S | H | CH₃ | OCH₃ | CH |
| SCH₃ | H | CH₂CH₃ | H | S | H | CH₃ | CH₃ | CH |
| SCH₃ | H | CH₂CH₃ | H | S | H | OCH₃ | OCH | N |
| SCH₃ | H | CH₂CH₃ | H | S | H | CH₃ | OCH₃ | N |
| SCH₃ | H | CH₂CF₃ | H | O | H | OCH₃ | OCH₃ | CH |
| SCH₃ | H | CH₂CF₃ | H | O | H | Cl | OCH₃ | CH |
| SCH₃ | H | CH₂CF₃ | H | O | H | CH₃ | OCH₃ | CH |
| SCH₃ | H | CH₂CF₃ | H | O | H | CH₃ | CH₃ | CH |
| SCH₃ | H | CH₂CF₃ | H | O | H | OCH₃ | OCH₃ | N |
| SCH₃ | H | CH₂CF₃ | H | O | H | CH₃ | OCH₃ | N |
| SCH₃ | H | CH₂CF₃ | H | O | H | CH₃ | CH₃ | N |
| SCH₃ | H | CH₂CF₃ | H | O | H | OCH₂CH₃ | OCH₂CH₃ | N |
| SCH₃ | H | CH₂CF₃ | H | O | H | NHCH₃ | OCH₂CH₃ | N |
| SCH₃ | H | CH₂CF₃ | H | O | H | N(CH₃)₂ | OCH₂CH₃ | N |
| SCH₃ | H | CH₂CF₃ | H | O | H | N(CH₃)₂ | OCH₃ | N |
| SCH₃ | H | CH₂CF₃ | H | O | H | N(CH₃)₂ | OCH₂CF₃ | N |
| SCH₃ | H | CH₂CF₃ | H | O | CH₃ | CH₃ | OCH₃ | N |
| SCH₃ | H | CH₂CF₃ | H | S | H | OCH₃ | OCH | CH |
| SCH₃ | H | CH₂CF₃ | H | S | H | Cl | OCH₃ | CH |
| SCH₃ | H | CH₂CF₃ | H | S | H | CH₃ | OCH₃ | CH |
| SCH₃ | H | CH₂CF₃ | H | S | H | CH₃ | CH₃ | CH |
| SCH₃ | H | CH₂CF₃ | H | S | H | OCH₃ | OCH₃ | N |
| SCH₃ | H | CH₂CF₃ | H | S | H | CH₃ | OCH₃ | N |
| SCH₃ | CH₂CH₂Cl | H | H | O | H | OCH₃ | OCH₃ | CH |
| SCH₃ | CH₂CH₂Cl | H | H | O | H | CH₃ | OCH₃ | CH |
| SCH₃ | CH₂CH₂Cl | H | H | O | H | CH₃ | CH₃ | CH |
| SCH₃ | CH₂CH₂Cl | H | H | O | H | OCH₃ | OCH₃ | N |
| SCH₃ | CH₂CH₂Cl | H | H | O | H | CH₃ | OCH₃ | N |
| SCH₃ | CH₂CH₂Cl | H | H | O | H | CH₃ | CH₃ | N |
| SCH₃ | CH₂CH₂Cl | H | H | O | H | OCH₂CH₃ | OCH₂CH₃ | N |
| SCH₃ | CH₂CH₂Cl | H | H | O | H | NHCH₃ | OCH₂CH₃ | N |
| SCH₃ | CH₂CH₂Cl | H | H | O | H | N(CH₃)₂ | OCH₂CH₃ | N |
| SCH₃ | CH₂CH₂Cl | H | H | O | H | N(CH₃)₂ | OCH₃ | N |
| SCH₃ | CH₂CH₂Cl | H | H | O | H | N(CH₃)₂ | OCH₂CF₃ | N |
| SCH₃ | CH₂CH₂Cl | H | H | O | CH₃ | CH₃ | OCH₃ | N |
| SCH₃ | CH₂CH₂Cl | H | H | S | H | OCH₃ | OCH₃ | CH |
| SCH₃ | CH₂CH₂Cl | H | H | S | H | Cl | OCH₃ | CH |
| SCH₃ | CH₂CH₂Cl | H | H | S | H | CH₃ | OCH₃ | CH |
| SCH₃ | CH₂CH₂Cl | H | H | S | H | CH₃ | CH₃ | CH |
| SCH₃ | CH₂CH₂Cl | H | H | S | H | OCH₃ | OCH₃ | N |
| SCH₃ | CH₂CH₂Cl | H | H | S | H | CH₃ | OCH₃ | N |
| SCH₃ | CH₂CN | H | H | O | H | OCH₃ | OCH₃ | CH |
| SCH₃ | CH₂CN | H | H | O | H | Cl | OCH₃ | CH |
| SCH₃ | CH₂CN | H | H | O | H | CH₃ | OCH₃ | CH |
| SCH₃ | CH₂CN | H | H | O | H | CH₃ | CH₃ | CH |
| SCH₃ | CH₂CN | H | H | O | H | OCH₃ | OCH₃ | N |
| SCH₃ | CH₂CN | H | H | O | H | CH₃ | OCH₃ | N |
| SCH₃ | CH₂CN | H | H | O | H | CH₃ | CH₃ | N |
| SCH₃ | CH₂CN | H | H | O | H | OCH₂CH₃ | OCH₂CH₃ | N |
| SCH₃ | CH₂CN | H | H | O | H | NHCH₃ | OCH₂CH₃ | N |
| SCH₃ | CH₂CN | H | H | O | H | N(CH₃)₂ | OCH₂CH₃ | N |
| SCH₃ | CH₂CN | H | H | O | H | N(CH₃)₂ | OCH₃ | N |
| SCH₃ | CH₂CN | H | H | O | H | N(CH₃)₂ | OCH₂CF₃ | N |
| SCH₃ | CH₂CN | H | H | O | CH₃ | CH₃ | OCH₃ | N |
| SCH₃ | CH₂CN | H | H | S | H | OCH₃ | OCH₃ | CH |
| SCH₃ | CH₂CN | H | H | S | H | Cl | OCH₃ | CH |
| SCH₃ | CH₂CN | H | H | S | H | CH₃ | OCH₃ | CH |
| SCH₃ | CH₂CN | H | H | S | H | CH₃ | CH₃ | CH |

TABLE I-continued

| | | | | | | | | |
|---|---|---|---|---|---|---|---|---|
| SCH$_3$ | CH$_2$CN | H | H | S | H | OCH$_3$ | OCH$_3$ | N |
| SCH$_3$ | CH$_2$CN | H | H | S | H | CH$_3$ | OCH$_3$ | N |
| SCH$_3$ | CH$_2$CH=CH$_2$ | H | H | O | H | OCH$_3$ | OCH$_3$ | CH |
| SCH$_3$ | CH$_2$CH=CH$_2$ | H | H | O | H | Cl | OCH$_3$ | CH |
| SCH$_3$ | CH$_2$CH=CH$_2$ | H | H | O | H | CH$_3$ | OCH$_3$ | CH |
| SCH$_3$ | CH$_2$CH=CH$_2$ | H | H | O | H | CH$_3$ | CH$_3$ | CH |
| SCH$_3$ | CH$_2$CH=CH$_2$ | H | H | O | H | OCH$_3$ | OCH$_3$ | N |
| SCH$_3$ | CH$_2$CH=CH$_2$ | H | H | O | H | CH$_3$ | OCH$_3$ | N |
| SCH$_3$ | CH$_2$CH=CH$_2$ | H | H | O | H | CH$_3$ | CH$_3$ | N |
| SCH$_3$ | CH$_2$CH=CH$_2$ | H | H | O | H | OCH$_2$CH$_3$ | OCH$_2$CH$_3$ | N |
| SCH$_3$ | CH$_2$CH=CH$_2$ | H | H | O | H | NHCH$_3$ | OCH$_2$CH$_3$ | N |
| SCH$_3$ | CH$_2$CH=CH$_2$ | H | H | O | H | N(CH$_3$)$_2$ | OCH$_2$CH$_3$ | N |
| SCH$_3$ | CH$_2$CH=CH$_2$ | H | H | O | H | N(CH$_3$)$_2$ | OCH$_3$ | N |
| SCH$_3$ | CH$_2$CH=CH$_2$ | H | H | O | H | N(CH$_3$)$_2$ | OCH$_2$CF$_3$ | N |
| SCH$_3$ | CH$_2$CH=CH$_2$ | H | H | O | CH$_3$ | CH$_3$ | OCH$_3$ | N |
| SCH$_3$ | CH$_2$CH=CH$_2$ | H | H | S | H | OCH$_3$ | OCH$_3$ | CH |
| SCH$_3$ | CH$_2$CH=CH$_2$ | H | H | S | H | Cl | OCH$_3$ | CH |
| SCH$_3$ | CH$_2$CH=CH$_2$ | H | H | S | H | CH$_3$ | OCH$_3$ | CH |
| SCH$_3$ | CH$_2$CH=CH$_2$ | H | H | S | H | CH$_3$ | CH$_3$ | CH |
| SCH$_3$ | CH$_2$CH=CH$_2$ | H | H | S | H | OCH$_3$ | OCH$_3$ | N |
| SCH$_3$ | CH$_2$CH=CH$_2$ | H | H | S | H | CH$_3$ | OCH$_3$ | N |
| SCH$_3$ | CH$_2$C≡CH | H | H | O | H | OCH$_3$ | OCH$_3$ | CH |
| SCH$_3$ | CH$_2$C≡CH | H | H | O | H | Cl | OCH$_3$ | CH |
| SCH$_3$ | CH$_2$C≡CH | H | H | O | H | CH$_3$ | OCH$_3$ | CH |
| SCH$_3$ | CH$_2$C≡CH | H | H | O | H | CH$_3$ | CH$_3$ | CH |
| SCH$_3$ | CH$_2$C≡CH | H | H | O | H | OCH$_3$ | OCH$_3$ | N |
| SCH$_3$ | CH$_2$C≡CH | H | H | O | H | CH$_3$ | OCH$_3$ | N |
| SCH$_3$ | CH$_2$C≡CH | H | H | O | H | CH$_3$ | CH$_3$ | N |
| SCH$_3$ | CH$_2$C≡CH | H | H | O | H | OCH$_2$CH$_3$ | OCH$_2$CH$_3$ | N |
| SCH$_3$ | CH$_2$C≡CH | H | H | O | H | NHCH$_3$ | OCH$_2$CH$_3$ | N |
| SCH$_3$ | CH$_2$C≡CH | H | H | O | H | N(CH$_3$)$_2$ | OCH$_2$CH$_3$ | N |
| SCH$_3$ | CH$_2$C≡CH | H | H | O | H | N(CH$_3$)$_2$ | OCH$_3$ | N |
| SCH$_3$ | CH$_2$C≡CH | H | H | O | H | N(CH$_3$)$_2$ | OCH$_2$CF$_3$ | N |
| SCH$_3$ | CH$_2$C≡CH | H | H | O | CH$_3$ | CH$_3$ | OCH$_3$ | N |
| SCH$_3$ | CH$_2$C≡CH | H | H | S | H | OCH$_3$ | OCH$_3$ | CH |
| SCH$_3$ | CH$_2$C≡CH | H | H | S | H | Cl | OCH$_3$ | CH |
| SCH$_3$ | CH$_2$C≡CH | H | H | S | H | CH$_3$ | OCH$_3$ | CH |
| SCH$_3$ | CH$_2$C≡CH | H | H | S | H | CH$_3$ | CH$_3$ | CH |
| SCH$_3$ | CH$_2$C≡CH | H | H | S | H | OCH$_3$ | OCH$_3$ | N |
| SCH$_3$ | CH$_2$C≡CH | H | H | S | H | CH$_3$ | OCH$_3$ | N |
| SCH$_3$ | CH$_2$CH$_2$OCH$_3$ | H | H | O | H | OCH$_3$ | OCH$_3$ | CH |
| SCH$_3$ | CH$_2$CH$_2$OCH$_3$ | H | H | O | H | Cl | OCH$_3$ | CH |
| SCH$_3$ | CH$_2$CH$_2$OCH$_3$ | H | H | O | H | CH$_3$ | OCH$_3$ | CH |
| SCH$_3$ | CH$_2$CH$_2$OCH$_3$ | H | H | O | H | CH$_3$ | CH$_3$ | CH |
| SCH$_3$ | CH$_2$CH$_2$OCH$_3$ | H | H | O | H | OCH$_3$ | OCH$_3$ | N |
| SCH$_3$ | CH$_2$CH$_2$OCH$_3$ | H | H | O | H | CH$_3$ | OCH$_3$ | N |
| SCH$_3$ | CH$_2$CH$_2$OCH$_3$ | H | H | O | H | CH$_3$ | CH$_3$ | N |
| SCH$_3$ | CH$_2$CH$_2$OCH$_3$ | H | H | O | H | OCH$_2$CH$_3$ | OCH$_2$CH$_3$ | N |
| SCH$_3$ | CH$_2$CH$_2$OCH$_3$ | H | H | O | H | NHCH$_3$ | OCH$_2$CH$_3$ | N |
| SCH$_3$ | CH$_2$CH$_2$OCH$_3$ | H | H | O | H | N(CH$_3$)$_2$ | OCH$_2$CH$_3$ | N |
| SCH$_3$ | CH$_2$CH$_2$OCH$_3$ | H | H | O | H | N(CH$_3$)$_2$ | OCH$_3$ | N |
| SCH$_3$ | CH$_2$CH$_2$OCH$_3$ | H | H | O | H | N(CH$_3$)$_2$ | OCH$_2$CF$_3$ | N |
| SCH$_3$ | CH$_2$CH$_2$OCH$_3$ | H | H | O | CH$_3$ | CH$_3$ | OCH$_3$ | N |
| SCH$_3$ | CH$_2$CH$_2$OCH$_3$ | H | H | S | H | OCH$_3$ | OCH$_3$ | CH |
| SCH$_3$ | CH$_2$CH$_2$OCH$_3$ | H | H | S | H | Cl | OCH$_3$ | CH |
| SCH$_3$ | CH$_2$CH$_2$OCH$_3$ | H | H | S | H | CH$_3$ | OCH$_3$ | CH |
| SCH$_3$ | CH$_2$CH$_2$OCH$_3$ | H | H | S | H | CH$_3$ | CH$_3$ | CH |
| SCH$_3$ | CH$_2$CH$_2$OCH$_3$ | H | H | S | H | OCH$_3$ | OCH$_3$ | N |
| SCH$_3$ | CH$_2$CH$_2$OCH$_3$ | H | H | S | H | CH$_3$ | OCH$_3$ | N |
| SCH$_3$ | cyclo-C$_3$H$_7$ | H | H | O | H | OCH$_3$ | OCH$_3$ | CH |
| SCH$_3$ | cyclo-C$_3$H$_7$ | H | H | O | H | Cl | OCH$_3$ | CH |
| SCH$_3$ | cyclo-C$_3$H$_7$ | H | H | O | H | CH$_3$ | OCH$_3$ | CH |
| SCH$_3$ | cyclo-C$_3$H$_7$ | H | H | O | H | CH$_3$ | CH$_3$ | CH |
| SCH$_3$ | cyclo-C$_3$H$_7$ | H | H | O | H | OCH$_3$ | OCH$_3$ | N |
| SCH$_3$ | cyclo-C$_3$H$_7$ | H | H | O | H | CH$_3$ | OCH$_3$ | N |
| SCH$_3$ | cyclo-C$_3$H$_7$ | H | H | O | H | CH$_3$ | CH$_3$ | N |
| SCH$_3$ | cyclo-C$_3$H$_7$ | H | H | O | H | OCH$_2$CH$_3$ | OCH$_2$CH$_3$ | N |
| SCH$_3$ | cyclo-C$_3$H$_7$ | H | H | O | H | NHCH$_3$ | OCH$_2$CH$_3$ | N |
| SCH$_3$ | cyclo-C$_3$H$_7$ | H | H | O | H | N(CH$_3$)$_2$ | OCH$_2$CH$_3$ | N |
| SCH$_3$ | cyclo-C$_3$H$_7$ | H | H | O | H | N(CH$_3$)$_2$ | OCH$_3$ | N |
| SCH$_3$ | cyclo-C$_3$H$_7$ | H | H | O | H | N(CH$_3$)$_2$ | OCH$_2$CF$_3$ | N |
| SCH$_3$ | cyclo-C$_3$H$_7$ | H | H | O | CH$_3$ | CH$_3$ | OCH$_3$ | N |
| SCH$_3$ | cyclo-C$_3$H$_7$ | H | H | S | H | OCH$_3$ | OCH$_3$ | CH |
| SCH$_3$ | cyclo-C$_3$H$_7$ | H | H | S | H | Cl | OCH$_3$ | CH |
| SCH$_3$ | cyclo-C$_3$H$_7$ | H | H | S | H | CH$_3$ | OCH$_3$ | CH |
| SCH$_3$ | cyclo-C$_3$H$_7$ | H | H | S | H | CH$_3$ | CH$_3$ | CH |
| SCH$_3$ | cyclo-C$_3$H$_7$ | H | H | S | H | OCH$_3$ | OCH$_3$ | N |
| SCH$_3$ | cyclo-C$_3$H$_7$ | H | H | S | H | CH$_3$ | OCH$_3$ | N |
| SCH$_3$ | CH$_3$ | CH$_3$ | H | O | H | OCH$_3$ | OCH$_3$ | CH |
| SCH$_3$ | CH$_3$ | CH$_3$ | H | O | H | Cl | OCH$_3$ | CH |
| SCH$_3$ | CH$_3$ | CH$_3$ | H | O | H | CH$_3$ | OCH$_3$ | CH |
| SCH$_3$ | CH$_3$ | CH$_3$ | H | O | H | CH$_3$ | CH$_3$ | CH |

TABLE I-continued

| | | | | | | | | |
|---|---|---|---|---|---|---|---|---|
| SCH₃ | CH₃ | CH₃ | H | O | H | OCH₃ | OCH₃ | N |
| SCH₃ | CH₃ | CH₃ | H | O | H | CH₃ | OCH₃ | N |
| SCH₃ | CH₃ | CH₃ | H | O | H | CH₃ | CH₃ | N |
| SCH₃ | CH₃ | CH₃ | H | O | H | OCH₂CH₃ | OCH₂CH₃ | N |
| SCH₃ | CH₃ | CH₃ | H | O | H | NHCH₃ | OCH₂CH₃ | N |
| SCH₃ | CH₃ | CH₃ | H | O | H | N(CH₃)₂ | OCH₂CH₃ | N |
| SCH₃ | CH₃ | CH₃ | H | O | H | N(CH₃)₂ | OCH₃ | N |
| SCH₃ | CH₃ | CH₃ | H | O | H | N(CH₃)₂ | OCH₂CF₃ | N |
| SCH₃ | CH₃ | CH₃ | H | O | CH₃ | CH₃ | OCH₃ | N |
| SCH₃ | CH₃ | CH₃ | H | S | H | OCH₃ | OCH₃ | CH |
| SCH₃ | CH₃ | CH₃ | H | S | H | Cl | OCH₃ | CH |
| SCH₃ | CH₃ | CH₃ | H | S | H | CH₃ | OCH₃ | CH |
| SCH₃ | CH₃ | CH₃ | H | S | H | CH₃ | CH₃ | CH |
| SCH₃ | CH₃ | CH₃ | H | S | H | OCH₃ | OCH₃ | N |
| SCH₃ | CH₃ | CH₃ | H | S | H | CH₃ | OCH₃ | N |
| SCH₃ | CH₃ | CH₂CH₃ | H | O | H | OCH₃ | OCH₃ | CH |
| SCH₃ | CH₃ | CH₂CH₃ | H | O | H | Cl | OCH₃ | CH |
| SCH₃ | CH₃ | CH₂CH₃ | H | O | H | CH₃ | OCH₃ | CH |
| SCH₃ | CH₃ | CH₂CH₃ | H | O | H | CH₃ | CH₃ | CH |
| SCH₃ | CH₃ | CH₂CH₃ | H | O | H | OCH₃ | OCH₃ | N |
| SCH₃ | CH₃ | CH₂CH₃ | H | O | H | CH₃ | OCH₃ | N |
| SCH₃ | CH₃ | CH₂CH₃ | H | O | H | CH₃ | CH₃ | N |
| SCH₃ | CH₃ | CH₂CH₃ | H | O | H | OCH₂CH₃ | OCH₂CH₃ | N |
| SCH₃ | CH₃ | CH₃ | H | O | H | NHCH₃ | OCH₂CH₃ | N |
| SCH₃ | CH₃ | CH₂CH₃ | H | O | H | N(CH₃)₂ | OCH₂CH₃ | N |
| SCH₃ | CH₃ | CH₂CH₃ | H | O | H | N(CH₃)₂ | OCH₃ | N |
| SCH₃ | CH₃ | CH₂CH₃ | H | O | H | N(CH₃)₂ | OCH₂CF₃ | N |
| SCH₃ | CH₃ | CH₂CH₃ | H | O | CH₃ | CH₃ | OCH₃ | N |
| SCH₃ | CH₃ | CH₂CH₃ | H | S | H | OCH₃ | OCH₃ | CH |
| SCH₃ | CH₃ | CH₂CH₃ | H | S | H | Cl | OCH₃ | CH |
| SCH₃ | CH₃ | CH₂CH₃ | H | S | H | CH₃ | OCH₃ | CH |
| SCH₃ | CH₃ | CH₂CH₃ | H | S | H | CH₃ | CH₃ | CH |
| SCH₃ | CH₃ | CH₂CH₃ | H | S | H | OCH₃ | OCH₃ | N |
| SCH₃ | CH₃ | CH₃ | H | S | H | CH₃ | OCH₃ | N |
| SCH₃ | CH₂CH₃ | CH₂CH₃ | H | O | H | OCH₃ | OCH₃ | CH |
| SCH₃ | CH₂CH₃ | CH₂CH₃ | H | O | H | Cl | OCH₃ | CH |
| SCH₃ | CH₂CH₃ | CH₂CH₃ | H | O | H | CH₃ | OCH₃ | CH |
| SCH₃ | CH₂CH₃ | CH₂CH₃ | H | O | H | CH₃ | CH₃ | CH |
| SCH₃ | CH₂CH₃ | CH₂CH₃ | H | O | H | OCH₃ | OCH₃ | N |
| SCH₃ | CH₂CH₃ | CH₂CH₃ | H | O | H | CH₃ | OCH₃ | N |
| SCH₃ | CH₂CH₃ | CH₂CH₃ | H | O | H | CH₃ | CH | N |
| SCH₃ | CH₂CH₃ | CH₂CH₃ | H | O | H | OCH₂CH₃ | OCH₂CH₃ | N |
| SCH₃ | CH₂CH₃ | CH₂CH₃ | H | O | H | NHCH₃ | OCH₂CH₃ | N |
| SCH₃ | CH₂CH₃ | CH₂CH₃ | H | O | H | N(CH₃)₂ | OCH₂CH₃ | N |
| SCH₃ | CH₂CH₃ | CH₂CH₃ | H | O | H | N(CH₃)₂ | OCH₃ | N |
| SCH₃ | CH₂CH₃ | CH₂CH₃ | H | O | H | N(CH₃)₂ | OCH₂CF₃ | N |
| SCH₃ | CH₂CH₃ | CH₂CH₃ | H | O | CH₃ | CH₃ | OCH₃ | N |
| SCH₃ | CH₂CH₃ | CH₂CH₃ | H | S | H | OCH₃ | OCH₃ | CH |
| SCH₃ | CH₂CH₃ | CH₂CH₃ | H | S | H | Cl | OCH₃ | CH |
| SCH₃ | CH₂CH₃ | CH₂CH₃ | H | S | H | CH₃ | OCH₃ | CH |
| SCH₃ | CH₂CH₃ | CH₂CH₃ | H | S | H | CH₃ | CH₃ | CH |
| SCH₃ | CH₂CH₃ | CH₂CH₃ | H | S | H | OCH₃ | OCH₃ | N |
| SCH₃ | CH₂CH₃ | CH₂CH₃ | H | S | H | CH₃ | OCH₃ | N |
| SCH₃ | OCH₃ | CH₃ | H | O | H | OCH₃ | OCH₃ | CH |
| SCH₃ | OCH₃ | CH₃ | H | O | H | Cl | OCH₃ | CH |
| SCH₃ | OCH₃ | CH₃ | H | O | H | CH₃ | OCH₃ | CH |
| SCH₃ | OCH₃ | CH₃ | H | O | H | CH₃ | CH₃ | CH |
| SCH₃ | OCH₃ | CH₃ | H | O | H | OCH₃ | OCH₃ | N |
| SCH₃ | OCH₃ | CH₃ | H | O | H | CH₃ | OCH₃ | N |
| SCH₃ | OCH₃ | CH₃ | H | O | H | CH₃ | CH₃ | N |
| SCH₃ | OCH₃ | CH₃ | H | O | H | OCH₂CH₃ | OCH₂CH₃ | N |
| SCH₃ | OCH₃ | CH₃ | H | O | H | NHCH₃ | OCH₂CH₃ | N |
| SCH₃ | OCH₃ | CH₃ | H | O | H | N(CH₃)₂ | OCH₂CH₃ | N |
| SCH₃ | OCH₃ | CH₃ | H | O | H | N(CH₃)₂ | OCH₃ | N |
| SCH₃ | OCH₃ | CH₃ | H | O | H | N(CH₃)₂ | OCH₂CF₃ | N |
| SCH₃ | OCH₃ | CH₃ | H | O | CH₃ | CH₃ | OCH₃ | N |
| SCH₃ | OCH₃ | CH₃ | H | S | H | OCH₃ | OCH₃ | CH |
| SCH₃ | OCH₃ | CH₃ | H | S | H | Cl | OCH₃ | CH |
| SCH₃ | OCH₃ | CH₃ | H | S | H | CH₃ | OCH₃ | CH |
| SCH₃ | OCH₃ | CH₃ | H | S | H | CH₃ | CH₃ | CH |
| SCH₃ | OCH₃ | CH₃ | H | S | H | OCH₃ | OCH₃ | N |
| SCH₃ | OCH₃ | CH₃ | H | S | H | OCH₃ | OCH₃ | N |
| SCH₃ | NHCH₃ | CH₃ | H | O | H | OCH₃ | OCH₃ | CH |
| SCH₃ | NHCH₃ | CH₃ | H | O | H | Cl | OCH₃ | CH |
| SCH₃ | NHCH₃ | CH₃ | H | O | H | CH₃ | OCH₃ | CH |
| SCH₃ | NHCH₃ | CH₃ | H | O | H | CH₃ | CH₃ | CH |
| SCH₃ | NHCH₃ | H | H | O | H | OCH₃ | OCH₃ | N |
| SCH₃ | NHCH₃ | CH₃ | H | O | H | CH₃ | OCH₃ | N |
| SCH₃ | NHCH₃ | CH₃ | H | O | H | CH₃ | CH₃ | N |
| SCH₃ | NHCH₃ | CH₃ | H | O | H | OCH₂CH₃ | OCH₂CH₃ | N |
| SCH₃ | NHCH₃ | CH₃ | H | O | H | NHCH₃ | OCH₂CH₃ | N |
| SCH₃ | NHCH₃ | CH₃ | H | O | H | N(CH₃)₂ | OCH₂CH₃ | N |

TABLE I-continued

| | | | | | | | | |
|---|---|---|---|---|---|---|---|---|
| SCH$_3$ | NHCH$_3$ | CH$_3$ | H | O | H | N(CH$_3$)$_2$ | OCH$_3$ | N |
| SCH$_3$ | NHCH$_3$ | CH$_3$ | H | O | H | N(CH$_3$)$_2$ | OCH$_2$CF$_3$ | N |
| SCH$_3$ | NHCH$_3$ | CH$_3$ | H | O | CH$_3$ | CH$_3$ | OCH$_3$ | N |
| SCH$_3$ | NHCH$_3$ | CH$_3$ | H | S | H | OCH$_3$ | OCH$_3$ | CH |
| SCH$_3$ | NHCH$_3$ | CH$_3$ | H | S | H | Cl | OCH$_3$ | CH |
| SCH$_3$ | NHCH$_3$ | CH$_3$ | H | S | H | CH$_3$ | OCH$_3$ | CH |
| SCH$_3$ | NHCH$_3$ | CH$_3$ | H | S | H | CH$_3$ | CH$_3$ | CH |
| SCH$_3$ | NHCH$_3$ | CH$_3$ | H | S | H | OCH$_3$ | OCH$_3$ | N |
| SCH$_3$ | NHCH$_3$ | CH$_3$ | H | S | H | CH$_3$ | OCH$_3$ | N |
| SCH$_3$ | N(CH$_3$)$_2$ | CH$_3$ | H | O | H | OCH$_3$ | OCH$_3$ | CH |
| SCH$_3$ | N(CH$_3$)$_2$ | CH$_3$ | H | O | H | Cl | OCH$_3$ | CH |
| SCH$_3$ | N(CH$_3$)$_2$ | CH$_3$ | H | O | H | CH$_3$ | OCH$_3$ | CH |
| SCH$_3$ | N(CH$_3$)$_2$ | CH$_3$ | H | O | H | CH$_3$ | CH$_3$ | CH |
| SCH$_3$ | N(CH$_3$)$_2$ | CH$_3$ | H | O | H | OCH$_3$ | OCH$_3$ | N |
| SCH$_3$ | N(CH$_3$)$_2$ | CH$_3$ | H | O | H | CH$_3$ | OCH$_3$ | N |
| SCH$_3$ | N(CH$_3$)$_2$ | CH$_3$ | H | O | H | CH$_3$ | CH$_3$ | N |
| SCH$_3$ | N(CH$_3$)$_2$ | CH$_3$ | H | O | H | OCH$_2$CH$_3$ | OCH$_2$CH$_3$ | N |
| SCH$_3$ | N(CH$_3$)$_2$ | CH$_3$ | H | O | H | NHCH$_3$ | OCH$_2$CH$_3$ | N |
| SCH$_3$ | N(CH$_3$)$_2$ | CH$_3$ | H | O | H | N(CH$_3$)$_2$ | OCH$_2$CH$_3$ | N |
| SCH$_3$ | N(CH$_3$)$_2$ | CH$_3$ | H | O | H | N(CH$_3$)$_2$ | OCH$_3$ | N |
| SCH$_3$ | N(CH$_3$)$_2$ | CH$_3$ | H | O | H | N(CH$_3$)$_2$ | OCH$_2$CF$_3$ | N |
| SCH$_3$ | N(CH$_3$)$_2$ | CH$_3$ | H | O | CH$_3$ | CH$_3$ | OCH$_3$ | N |
| SCH$_3$ | N(CH$_3$)$_2$ | CH$_3$ | H | S | H | OCH$_3$ | OCH$_3$ | CH |
| SCH$_3$ | N(CH$_3$)$_2$ | CH$_3$ | H | S | H | Cl | OCH$_3$ | CH |
| SCH$_3$ | N(CH$_3$)$_2$ | CH$_3$ | H | S | H | CH$_3$ | OCH$_3$ | CH |
| SCH$_3$ | N(CH$_3$)$_2$ | CH$_3$ | H | S | H | CH$_3$ | CH$_3$ | CH |
| SCH$_3$ | N(CH$_3$)$_2$ | CH$_3$ | H | S | H | OCH$_3$ | OCH$_3$ | N |
| SCH$_3$ | N(CH$_3$)$_2$ | CH$_3$ | H | S | H | CH$_3$ | OCH$_3$ | N |
| SCH$_3$ | —CH$_2$CH$_2$CH$_2$— | | H | O | H | OCH$_3$ | OCH$_3$ | CH |
| SCH$_3$ | —CH$_2$CH$_2$CH$_2$— | | H | O | H | Cl | OCH$_3$ | CH |
| SCH$_3$ | —CH$_2$CH$_2$CH$_2$— | | H | O | H | CH$_3$ | OCH$_3$ | CH |
| SCH$_3$ | —CH$_2$CH$_2$CH$_2$— | | H | O | H | CH$_3$ | CH$_3$ | CH |
| SCH$_3$ | —CH$_2$CH$_2$CH$_2$— | | H | O | H | OCH$_3$ | OCH$_3$ | N |
| SCH$_3$ | —CH$_2$CH$_2$CH$_2$— | | H | O | H | CH$_3$ | OCH$_3$ | N |
| SCH$_3$ | —CH$_2$CH$_2$CH$_2$— | | H | O | H | OCH$_2$CH$_3$ | OCH$_2$CH$_3$ | N |
| SCH$_3$ | —CH$_2$CH$_2$CH$_2$— | | H | O | H | NHCH$_3$ | OCH$_2$CH$_3$ | N |
| SCH$_3$ | —CH$_2$CH$_2$CH$_2$— | | H | O | H | N(CH$_3$)$_2$ | OCH$_2$CH$_3$ | N |
| SCH$_3$ | —CH$_2$CH$_2$CH$_2$— | | H | O | H | N(CH$_3$)$_2$ | OCH$_3$ | N |
| SCH$_3$ | —CH$_2$CH$_2$CH$_2$— | | H | O | H | N(CH$_3$)$_2$ | OCH$_2$CF$_3$ | N |
| SCH$_3$ | —CH$_2$CH$_2$CH$_2$— | | H | O | CH$_3$ | CH$_3$ | OCH$_3$ | N |
| SCH$_3$ | —CH$_2$CH$_2$CH$_2$— | | H | S | H | OCH$_3$ | OCH$_3$ | CH |
| SCH$_3$ | —CH$_2$CH$_2$CH$_2$— | | H | S | H | Cl | OCH$_3$ | CH |
| SCH$_3$ | —CH$_2$CH$_2$CH$_2$— | | H | S | H | CH$_3$ | OCH$_3$ | CH |
| SCH$_3$ | —CH$_2$CH$_2$CH$_2$— | | H | S | H | CH$_3$ | CH$_3$ | CH |
| SCH$_3$ | —CH$_2$CH$_2$CH$_2$— | | H | S | H | OCH$_3$ | OCH$_3$ | N |
| SCH$_3$ | —CH$_2$CH$_2$CH$_2$— | | H | S | H | CH$_3$ | OCH$_3$ | N |
| SCH$_3$ | —CH$_2$CH$_2$OCH$_2$CH$_2$— | | H | O | H | OCH$_3$ | OCH$_3$ | CH |
| SCH$_3$ | —CH$_2$CH$_2$OCH$_2$CH$_2$— | | H | O | H | Cl | OCH$_3$ | CH |
| SCH$_3$ | —CH$_2$CH$_2$OCH$_2$CH$_2$— | | H | O | H | CH$_3$ | OCH$_3$ | CH |
| SCH$_3$ | —CH$_2$CH$_2$OCH$_2$CH$_2$— | | H | O | H | CH$_3$ | CH$_3$ | CH |
| SCH$_3$ | —CH$_2$CH$_2$OCH$_2$CH$_2$— | | H | O | H | OCH$_3$ | OCH$_3$ | N |
| SCH$_3$ | —CH$_2$CH$_2$OCH$_2$CH$_2$— | | H | O | H | CH$_3$ | OCH$_3$ | N |
| SCH$_3$ | —CH$_2$CH$_2$OCH$_2$CH$_2$— | | H | O | H | CH$_3$ | CH$_3$ | N |
| SCH$_3$ | —CH$_2$CH$_2$OCH$_2$CH$_2$— | | H | O | H | OCH$_2$CH$_3$ | OCH$_2$CH$_3$ | N |
| SCH$_3$ | —CH$_2$CH$_2$OCH$_2$CH$_2$— | | H | O | H | NHCH$_3$ | OCH$_2$CH$_3$ | N |
| SCH$_3$ | —CH$_2$CH$_2$OCH$_2$CH$_2$— | | H | O | H | N(CH$_3$)$_2$ | OCH$_2$CH$_3$ | N |
| SCH$_3$ | —CH$_2$CH$_2$OCH$_2$CH$_2$— | | H | O | H | N(CH$_3$)$_2$ | OCH$_3$ | N |
| SCH$_3$ | —CH$_2$CH$_2$OCH$_2$CH$_2$— | | H | O | H | N(CH$_3$)$_2$ | OCH$_2$CF$_3$ | N |
| SCH$_3$ | —CH$_2$CH$_2$OCH$_2$CH$_2$— | | H | O | CH$_3$ | CH$_3$ | OCH$_3$ | N |
| SCH$_3$ | —CH$_2$CH$_2$OCH$_2$CH$_2$— | | H | S | H | OCH$_3$ | OCH$_3$ | CH |
| SCH$_3$ | —CH$_2$CH$_2$OCH$_2$CH$_2$— | | H | S | H | Cl | OCH$_3$ | CH |
| SCH$_3$ | —CH$_2$CH$_2$OCH$_2$CH$_2$— | | H | S | H | CH$_3$ | OCH$_3$ | CH |
| SCH$_3$ | —CH$_2$CH$_2$OCH$_2$CH$_2$— | | H | S | H | CH$_3$ | CH$_3$ | CH |
| SCH$_3$ | —CH$_2$CH$_2$OCH$_2$CH$_2$— | | H | S | H | OCH$_3$ | OCH$_3$ | N |
| SCH$_3$ | —CH$_2$CH$_2$OCH$_2$CH$_2$— | | H | S | H | CH$_3$ | OCH$_3$ | N |
| SO$_2$CH$_3$ | CH$_3$ | CH$_3$ | H | O | H | OCH$_3$ | OCH$_3$ | CH |
| SO$_2$CH$_2$CH$_3$ | H | | H | O | H | OCH$_3$ | OCH$_3$ | CH |
| SO$_2$CH$_2$CH$_3$ | H | | H | O | H | Cl | OCH$_3$ | CH |
| SO$_2$CH$_2$CH$_3$ | H | | H | O | H | CH$_3$ | OCH$_3$ | CH |
| SO$_2$CH$_2$CH$_3$ | H | | H | O | H | CH$_3$ | CH$_3$ | CH |
| SO$_2$CH$_2$CH$_3$ | H | | H | O | H | OCH$_3$ | OCH$_3$ | N |
| SO$_2$CH$_2$CH$_3$ | H | | H | O | H | CH$_3$ | OCH$_3$ | N |
| SO$_2$CH$_2$CH$_3$ | H | | H | O | H | CH$_3$ | CH$_3$ | N |
| SO$_2$CH$_2$CH$_3$ | H | | H | O | H | OCH$_2$CH$_3$ | OCH$_2$CH$_3$ | N |
| SO$_2$CH$_2$CH$_3$ | H | | H | O | H | NHCH$_3$ | OCH$_2$CH$_3$ | N |
| SO$_2$CH$_2$CH$_3$ | H | | H | O | H | N(CH$_3$)$_2$ | OCH$_2$CH$_3$ | N |
| SO$_2$CH$_2$CH$_3$ | H | | H | O | H | N(CH$_3$)$_2$ | OCH$_3$ | N |
| SO$_2$CH$_2$CH$_3$ | H | | H | O | H | N(CH$_3$)$_2$ | OCH$_2$CF$_3$ | N |
| SO$_2$CH$_2$CH$_3$ | H | | H | O | CH$_3$ | CH$_3$ | OCH$_3$ | N |
| SO$_2$CH$_2$CH$_3$ | H | | H | S | H | OCH$_3$ | OCH$_3$ | CH |
| SO$_2$CH$_2$CH$_3$ | H | | H | S | H | Cl | OCH$_3$ | CH |
| SO$_2$CH$_2$CH$_3$ | H | | H | S | H | CH$_3$ | OCH$_3$ | CH |

TABLE I-continued

| | | | | | | | | |
|---|---|---|---|---|---|---|---|---|
| SO₂CH₂CH₃ | H | H | H | S | H | CH₃ | CH₃ | CH |
| SO₂CH₂CH₃ | H | H | H | S | H | OCH₃ | OCH₃ | N |
| SO₂CH₂CH₃ | H | H | H | S | H | CH₃ | OCH₃ | N |
| SO₂CH₂CH₃ | H | CH₃ | H | O | H | OCH₃ | OCH₃ | CH |
| SO₂CH₂CH₃ | H | CH₃ | H | O | H | Cl | OCH₃ | CH |
| SO₂CH₂CH₃ | H | CH₃ | H | O | H | CH₃ | OCH₃ | CH |
| SO₂CH₂CH₃ | H | CH₃ | H | O | H | CH₃ | CH₃ | CH |
| SO₂CH₂CH₃ | H | CH₃ | H | O | H | OCH₃ | OCH₃ | N |
| SO₂CH₂CH₃ | H | CH₃ | H | O | H | CH₃ | OCH₃ | N |
| SO₂CH₃CH₃ | H | CH₃ | H | O | H | CH₃ | CH₃ | N |
| SO₂CH₂CH₃ | H | CH₃ | H | O | H | OCH₂CH₃ | OCH₂CH₃ | N |
| SO₂CH₂CH₃ | H | CH₃ | H | O | H | NHCH₃ | OCH₂CH₃ | N |
| SO₂CH₂CH₃ | H | CH₃ | H | O | H | N(CH₃)₂ | OCH₂CH₃ | N |
| SO₂CH₂CH₃ | H | CH₃ | H | O | H | N(CH₃)₂ | OCH₃ | N |
| SO₂CH₃CH₃ | H | CH₃ | H | O | H | N(CH₃)₂ | OCH₂CF₃ | N |
| SO₂CH₂CH₃ | H | CH₃ | H | O | CH₃ | CH₃ | OCH₃ | N |
| SO₂CH₂CH₃ | H | CH₃ | H | S | H | OCH₃ | OCH₃ | CH |
| SO₂CH₂CH₃ | H | CH₃ | H | S | H | Cl | OCH₃ | CH |
| SO₂CH₂CH₃ | H | CH₃ | H | S | H | CH₃ | OCH₃ | CH |
| SO₂CH₂CH₃ | H | CH₃ | H | S | H | CH₃ | CH₃ | CH |
| SO₂CH₂CH₃ | H | CH₃ | H | S | H | OCH₃ | OCH₃ | N |
| SO₂CH₂CH₃ | H | CH₃ | H | S | H | CH₃ | OCH₃ | N |
| SO₂CH₂CH₃ | H | CH₂CH₃ | H | O | H | OCH₃ | OCH₃ | CH |
| SO₂CH₂CH₃ | H | CH₂CH₃ | H | O | H | Cl | OCH₃ | CH |
| SO₂CH₂CH₃ | H | CH₂CH₃ | H | O | H | CH₃ | OCH₃ | CH |
| SO₂CH₂CH₃ | H | CH₂CH₃ | H | O | H | CH₃ | CH₃ | CH |
| SO₂CH₂CH₃ | H | CH₂CH₃ | H | O | H | OCH₃ | OCH₃ | N |
| SO₂CH₂CH₃ | H | CH₂CH₃ | H | O | H | CH₃ | OCH₃ | N |
| SO₂CH₂CH₃ | H | CH₂CH₃ | H | O | H | CH₃ | CH₃ | N |
| SO₂CH₂CH₃ | H | CH₂CH₃ | H | O | H | OCH₂CH₃ | OCH₂CH₃ | N |
| SO₂CH₂CH₃ | H | CH₂CH₃ | H | O | H | NHCH₃ | OCH₂CH₃ | N |
| SO₂CH₂CH₃ | H | CH₂CH₃ | H | O | H | N(CH₃)₂ | OCH₂CH₃ | N |
| SO₂CH₂CH₃ | H | CH₂CH₃ | H | O | H | N(CH₃)₂ | OCH₃ | N |
| SO₂CH₂CH₃ | H | CH₂CH₃ | H | O | H | N(CH₃)₂ | OCH₂CF₃ | N |
| SO₂CH₂CH₃ | H | CH₂CH₃ | H | O | CH₃ | CH₃ | OCH₃ | N |
| SO₂CH₂CH₃ | H | CH₂CH₃ | H | S | H | OCH₃ | OCH₃ | CH |
| SO₂CH₂CH₃ | H | CH₂CH₃ | H | S | H | Cl | OCH₃ | CH |
| SO₂CH₂CH₃ | H | CH₂CH₃ | H | S | H | CH₃ | OCH₃ | CH |
| SO₂CH₂CH₃ | H | CH₂CH₃ | H | S | H | CH₃ | CH₃ | CH |
| SO₂CH₂CH₃ | H | CH₂CH₃ | H | S | H | OCH₃ | OCH₃ | N |
| SO₂CH₂CH₃ | H | CH₂CH₃ | H | S | H | CH₃ | OCH₃ | N |
| SO₂CH₂CH₃ | H | CH₂CF₃ | H | O | H | OCH₃ | OCH₃ | CH |
| SO₂CH₂CH₃ | H | CH₂CF₃ | H | O | H | Cl | OCH₃ | CH |
| SO₂CH₂CH₃ | H | CH₂CF₃ | H | O | H | CH₃ | OCH₃ | CH |
| SO₂CH₂CH₃ | H | CH₂CF₃ | H | O | H | CH₃ | CH₃ | CH |
| SO₂CH₂CH₃ | H | CH₂CF₃ | H | O | H | OCH₃ | OCH₃ | N |
| SO₂CH₂CH₃ | H | CH₂CF₃ | H | O | H | CH₃ | OCH₃ | N |
| SO₂CH₂CH₃ | H | CH₂CF₃ | H | O | H | CH₃ | CH₃ | N |
| SO₂CH₂CH₃ | H | CH₂CF₃ | H | O | H | OCH₂CH₃ | OCH₂CH₃ | N |
| SO₂CH₂CH₃ | H | CH₂CF₃ | H | O | H | NHCH₃ | OCH₂CH₃ | N |
| SO₂CH₂CH₃ | H | CH₂CF₃ | H | O | H | N(CH₃)₂ | OCH₂CH₃ | N |
| SO₂CH₂CH₃ | H | CH₂CF₃ | H | O | H | N(CH₃)₂ | OCH₃ | N |
| SO₂CH₂CH₃ | H | CH₂CF₃ | H | O | H | N(CH₃)₂ | OCH₂CF₃ | N |
| SO₂CH₂CH₃ | H | CH₂CF₃ | H | O | CH₃ | CH₃ | OCH₃ | N |
| SO₂CH₂CH₃ | H | CH₂CF₃ | H | S | H | OCH₃ | OCH₃ | CH |
| SO₂CH₂CH₃ | H | CH₂CF₃ | H | S | H | Cl | OCH₃ | CH |
| SO₂CH₂CH₃ | H | CH₂CF₃ | H | S | H | CH₃ | OCH₃ | CH |
| SO₂CH₂CH₃ | H | CH₂CF₃ | H | S | H | CH₃ | CH₃ | CH |
| SO₂CH₂CH₃ | H | CH₂CF₃ | H | S | H | OCH₃ | OCH₃ | N |
| SO₂CH₂CH₃ | H | CH₂CF₃ | H | S | H | CH₃ | OCH₃ | N |
| SO₂CH₂CH₃ | CH₂CH₂Cl | H | H | O | H | OCH₃ | OCH₃ | CH |
| SO₂CH₂CH₃ | CH₂CH₂Cl | H | H | O | H | Cl | OCH₃ | CH |
| SO₂CH₂CH₃ | CH₂CH₂Cl | H | H | O | H | CH₃ | OCH₃ | CH |
| SO₂CH₂CH₃ | CH₂CH₂Cl | H | H | O | H | CH₃ | CH₃ | CH |
| SO₂CH₂CH₃ | CH₂CH₂Cl | H | H | O | H | OCH₃ | OCH₃ | N |
| SO₂CH₂CH₃ | CH₂CH₂Cl | H | H | O | H | CH₃ | OCH₃ | N |
| SO₂CH₂CH₃ | CH₂CH₂Cl | H | H | O | H | CH₃ | CH₃ | N |
| SO₂CH₂CH₃ | CH₂CH₂Cl | H | H | O | H | OCH₂CH₃ | OCH₂CH₃ | N |
| SO₂CH₂CH₃ | CH₂CH₂Cl | H | H | O | H | NHCH₃ | OCH₂CH₃ | N |
| SO₂CH₂CH₃ | CH₂CH₂Cl | H | H | O | H | N(CH₃)₂ | OCH₂CH₃ | N |
| SO₂CH₂CH₃ | CH₂CH₂Cl | H | H | O | H | N(CH₃)₂ | OCH₂CF₃ | N |
| SO₂CH₂CH₃ | CH₂CH₂Cl | H | H | O | CH₃ | CH₃ | OCH₃ | N |
| SO₂CH₂CH₃ | CH₂CH₂Cl | H | H | S | H | OCH₃ | OCH₃ | CH |
| SO₂CH₂CH₃ | CH₂CH₂Cl | H | H | S | H | Cl | OCH₃ | CH |
| SO₂CH₂CH₃ | CH CH₂Cl | H | H | S | H | CH₃ | OCH₃ | CH |
| SO₂CH₂CH₃ | CH₂CH₂Cl | H | H | S | H | CH₃ | CH₃ | CH |
| SO₂CH₂CH₃ | CH₂CH₂Cl | H | H | S | H | OCH₃ | OCH₃ | N |
| SO₂CH₂CH₃ | CH₂CH₂Cl | H | H | S | H | CH₃ | OCH₃ | N |
| SO₂CH₂CH₃ | CH₂CN | H | H | O | H | OCH₃ | OCH₃ | CH |
| SO₂CH₂CH₃ | CH₂CN | H | H | O | H | Cl | OCH₃ | CH |
| SO₂CH₂CH₃ | CH₂CN | H | H | O | H | CH₃ | OCH₃ | CH |
| SO₂CH₂CH₃ | CH₂CN | H | H | O | H | CH₃ | CH₃ | CH |

TABLE I-continued

| | | | | | | | | |
|---|---|---|---|---|---|---|---|---|
| SO₂CH₂CH₃ | CH₂CN | H | H | O | H | OCH₃ | OCH₃ | N |
| SO₂CH₂CH₃ | CH₂CN | H | H | O | H | CH₃ | OCH₃ | N |
| SO₂CH₂CH₃ | CH₂CN | H | H | O | H | CH₃ | CH₃ | N |
| SO₂CH₂CH₃ | CH₂CN | H | H | O | H | OCH₂CH₃ | OCH₂CH₃ | N |
| SO₂CH₂CH₃ | CH₂CN | H | H | O | H | NHCH₃ | OCH₂CH₃ | N |
| SO₂CH₂CH₃ | CH₂CN | H | H | O | H | N(CH₃)₂ | OCH₂CH₃ | N |
| SO₂CH₂CH₃ | CH₂CN | H | H | O | H | N(CH₃)₂ | OCH₃ | N |
| SO₂CH₂CH₃ | CH₂CN | H | H | O | H | N(CH₃)₂ | OCH₂CF₃ | N |
| SO₂CH₂CH₃ | CH₂CN | H | H | O | CH₃ | CH₃ | OCH₃ | N |
| SO₂CH₂CH₃ | CH₂CN | H | H | S | H | OCH₃ | OCH₃ | CH |
| SO₂CH₂CH₃ | CH₂CN | H | H | S | H | Cl | OCH₃ | CH |
| SO₂CH₂CH₃ | CH₂CN | H | H | S | H | CH₃ | OCH₃ | CH |
| SO₂CH₂CH₃ | CH₂CN | H | H | S | H | CH₃ | CH₃ | CH |
| SO₂CH₂CH₃ | CH₂CN | H | H | S | H | OCH₃ | OCH₃ | N |
| SO₂CH₂CH₃ | CH₂CN | H | H | S | H | CH₃ | OCH₃ | N |
| SO₂CH₂CH₃ | CH₂CH=CH₂ | H | H | O | H | Cl | OCH₃ | CH |
| SO₂CH₂CH₃ | CH₂CH=CH₂ | H | H | O | H | CH₃ | OCH₃ | CH |
| SO₂CH₂CH₃ | CH₂CH=CH₂ | H | H | O | H | CH₃ | CH₃ | CH |
| SO₂CH₂CH₃ | CH₂CH=CH₂ | H | H | O | H | OCH₃ | OCH₃ | N |
| SO₂CH₂CH₃ | CH₂CH=CH₂ | H | H | O | H | Cl | OCH₃ | CH |
| SO₂CH₂CH₃ | CH₂CH=CH₂ | H | H | O | H | CH₃ | CH₃ | N |
| SO₂CH₂CH₃ | CH₂CH=CH₂ | H | H | O | H | OCH₂CH₃ | OCH₂CH₃ | N |
| SO₂CH₂CH₃ | CH₂CH=CH₂ | H | H | O | H | NHCH₃ | OCH₂CH₃ | N |
| SO₂CH₂CH₃ | CH₂CH=CH₂ | H | H | O | H | N(CH₃)₂ | OCH₂CH₃ | N |
| SO₂CH₂CH₃ | CH₂CH=CH₂ | H | H | O | H | N(CH₃)₂ | OCH₃ | N |
| SO₂CH₂CH₃ | CH₂CH=CH₂ | H | H | O | H | N(CH₃)₂ | OCH₂CF₃ | N |
| SO₂CH₂CH₃ | CH₂CH=CH₂ | H | H | O | CH₃ | OCH₃ | OCH₃ | N |
| SO₂CH₂CH₃ | CH₂CH=CH₂ | H | H | S | H | OCH₃ | OCH₃ | CH |
| SO₂CH₂CH₃ | CH₂CH=CH₂ | H | H | S | H | Cl | OCH₃ | CH |
| SO₂CH₂CH₃ | CH₂CH=CH₂ | H | H | S | H | CH₃ | OCH₃ | CH |
| SO₂CH₂CH₃ | CH₂CH=CH₂ | H | H | S | H | CH₃ | CH₃ | CH |
| SO₂CH₂CH₃ | CH₂CH=CH₂ | H | H | S | H | OCH₃ | OCH₃ | N |
| SO₂CH₂CH₃ | CH₂CH=CH₂ | H | H | S | H | CH₃ | OCH₃ | N |
| SO₂CH₂CH₃ | CH₂C≡CH | H | H | O | H | OCH | OCH₃ | CH |
| SO₂CH₂CH₃ | CH₂C≡CH | H | H | O | H | Cl | OCH₃ | CH |
| SO₂CH₂CH₃ | CH₂C≡CH | H | H | O | H | CH₃ | OCH₃ | CH |
| SO₂CH₂CH₃ | CH₂C≡CH | H | H | O | H | CH₃ | CH₃ | CH |
| SO₂CH₂CH₃ | CH₂C≡CH | H | H | O | H | OCH₃ | OCH₃ | N |
| SO₂CH₂CH₃ | CH₂C≡CH | H | H | O | H | CH₃ | OCH₃ | N |
| SO₂CH₂CH₃ | CH₂C≡CH | H | H | O | H | CH₃ | CH₃ | N |
| SO₂CH₂CH₃ | CH₂C≡CH | H | H | O | H | OCH₂CH₃ | OCH₂CH₃ | N |
| SO₂CH₂CH₃ | CH₂C≡CH | H | H | O | H | NHCH₃ | OCH₂CH₃ | N |
| SO₂CH₂CH₃ | CH₂C≡CH | H | H | O | H | N(CH₃)₂ | OCH₂CH₃ | N |
| SO₂CH₂CH₃ | CH₂C≡CH | H | H | O | H | N(CH₃)₂ | OCH₃ | N |
| SO₂CH₂CH₃ | CH₂C≡CH | H | H | O | H | N(CH₃)₂ | OCH₂CF₃ | N |
| SO₂CH₂CH₃ | CH₂C≡CH | H | H | O | CH₃ | CH₃ | OCH₃ | N |
| SO₂CH₂CH₃ | CH₂C≡CH | H | H | S | H | OCH₃ | OCH₃ | CH |
| SO₂CH₂CH₃ | CH₂C≡CH | H | H | S | H | Cl | OCH₃ | CH |
| SO₂CH₂CH₃ | CH₂C≡CH | H | H | S | H | CH₃ | OCH₃ | CH |
| SO₂CH₂CH₃ | CH₂C≡CH | H | H | S | H | CH₃ | CH₃ | CH |
| SO₂CH₂CH₃ | CH₂C≡CH | H | H | S | H | OCH₃ | OCH₃ | N |
| SO₂CH₂CH₃ | CH₂C≡CH | H | H | S | H | CH₃ | OCH₃ | N |
| SO₂CH₂CH₃ | CH₂CH₂OCH₃ | H | H | O | H | OCH₃ | OCH₃ | CH |
| SO₂CH₂CH₃ | CH₂CH₂OCH₃ | H | H | O | H | Cl | OCH₃ | CH |
| SO₂CH₂CH₃ | CH₂CH₂OCH₃ | H | H | O | H | CH₃ | OCH₃ | CH |
| SO₂CH₂CH₃ | CH₂CH₂OCH₃ | H | H | O | H | CH₃ | CH₃ | CH |
| SO₂CH₂CH₃ | CH₂CH₂OCH₃ | H | H | O | H | OCH₃ | OCH₃ | N |
| SO₂CH₂CH₃ | CH₂CH₂OCH₃ | H | H | O | H | CH₃ | OCH₃ | N |
| SO₂CH₂CH₃ | CH₂CH₂OCH₃ | H | H | O | H | CH₃ | CH₃ | N |
| SO₂CH₂CH₃ | CH₂CH₂OCH₃ | H | H | O | H | OCH₂CH₃ | OCH₂CH₃ | N |
| SO₂CH₂CH₃ | CH₂CH₂OCH₃ | H | H | O | H | NHCH₃ | OCH₂CH₃ | N |
| SO₂CH₂CH₃ | CH₂CH₂OCH₃ | H | H | O | H | N(CH₃)₂ | OCH₂CH₃ | N |
| SO₂CH₂CH₃ | CH₂CH₂OCH₃ | H | H | O | H | N(CH₃)₂ | OCH₃ | N |
| SO₂CH₂CH₃ | CH₂CH₂OCH₃ | H | H | O | H | N(CH₃)₂ | OCH₂CF₃ | N |
| SO₂CH₂CH₃ | CH₂CH₂OCH₃ | H | H | O | CH₃ | CH₃ | OCH₃ | N |
| SO₂CH₂CH₃ | CH₂CH₂OCH₃ | H | H | S | H | OCH₃ | OCH₃ | CH |
| SO₂CH₂CH₃ | CH₂CH₂OCH₃ | H | H | S | H | Cl | OCH₃ | CH |
| SO₂CH₂CH₃ | CH₂CH₂OCH₃ | H | H | S | H | CH₃ | OCH₃ | CH |
| SO₂CH₂CH₃ | CH₂CH₂OCH₃ | H | H | S | H | CH₃ | CH₃ | CH |
| SO₂CH₂CH₃ | CH₂CH₂OCH₃ | H | H | S | H | OCH₃ | OCH₃ | N |
| SO₂CH₂CH₃ | CH₂CH₂OCH₃ | H | H | S | H | CH₃ | OCH₃ | N |
| SO₂CH₂CH₃ | cyclo-C₃H₇ | H | H | O | H | OCH₃ | OCH₃ | CH |
| SO₂CH₂CH₃ | cyclo-C₃H₇ | H | H | O | H | Cl | OCH₃ | CH |
| SO₂CH₂CH₃ | cyclo-C₃H₇ | H | H | O | H | CH₃ | OCH₃ | CH |
| SO₂CH₂CH₃ | cyclo-C₃H₇ | H | H | O | H | CH₃ | CH₃ | CH |
| SO₂CH₂CH₃ | cyclo-C₃H₇ | H | H | O | H | OCH₃ | OCH₃ | N |
| SO₂CH₂CH₃ | cyclo-C₃H₇ | H | H | O | H | CH₃ | OCH₃ | N |
| SO₂CH₂CH₃ | cyclo-C₃H₇ | H | H | O | H | CH₃ | CH₃ | N |

-continued

| | | | | | | | | |
|---|---|---|---|---|---|---|---|---|
| SO$_2$CH$_2$CH$_3$ | cyclo-C$_3$H$_7$ | H | H | O | H | OCH$_2$CH$_3$ | OCH$_2$CH$_3$ | N |
| SO$_2$CH$_2$CH$_3$ | cyclo-C$_3$H$_7$ | H | H | O | H | NHCH$_3$ | OCH$_2$CH$_3$ | N |
| SO$_2$CH$_2$CH$_3$ | cyclo-C$_3$H$_7$ | H | H | O | H | N(CH$_3$)$_2$ | OCH$_2$CH$_3$ | N |
| SO$_2$CH$_2$CH$_3$ | cyclo-C$_3$H$_7$ | H | H | O | H | N(CH$_3$)$_2$ | OCH$_3$ | N |
| SO$_2$CH$_2$CH$_3$ | cyclo-C$_3$H$_7$ | H | H | O | H | N(CH$_3$)$_2$ | OCH$_2$CF$_3$ | N |
| SO$_2$CH$_2$CH$_3$ | cyclo-C$_3$H$_7$ | H | H | O | CH$_3$ | CH$_3$ | OCH$_3$ | N |
| SO$_2$CH$_2$CH$_3$ | cyclo-C$_3$H$_7$ | H | H | S | H | OCH$_3$ | OCH$_3$ | CH |
| SO$_2$CH$_2$CH$_3$ | cyclo-C$_3$H$_7$ | H | H | S | H | Cl | OCH$_3$ | CH |
| SO$_2$CH$_2$CH$_3$ | cyclo-C$_3$H$_7$ | H | H | S | H | CH$_3$ | OCH$_3$ | CH |
| SO$_2$CH$_2$CH$_3$ | cyclo-C$_3$H$_7$ | H | H | S | H | CH$_3$ | CH$_3$ | CH |
| SO$_2$CH$_2$CH$_3$ | cyclo-C$_3$H$_7$ | H | H | S | H | OCH$_3$ | OCH$_3$ | N |
| SO$_2$CH$_2$CH$_3$ | cyclo-C$_3$H$_7$ | H | H | S | H | CH$_3$ | OCH$_3$ | N |
| SO$_2$CH$_2$CH$_3$ | CH$_3$ | CH$_3$ | H | O | H | OCH$_3$ | OCH$_3$ | CH |
| SO$_2$CH$_2$CH$_3$ | CH$_3$ | CH$_3$ | H | O | H | Cl | OCH$_3$ | CH |
| SO$_2$CH$_2$CH$_3$ | CH$_3$ | CH$_3$ | H | O | H | CH$_3$ | OCH$_3$ | CH |
| SO$_2$CH$_2$CH$_3$ | CH$_3$ | CH$_3$ | H | O | H | CH$_3$ | CH$_3$ | CH |
| SO$_2$CH$_2$CH$_3$ | CH$_3$ | CH$_3$ | H | O | H | OCH$_3$ | OCH$_3$ | N |
| SO$_2$CH$_2$CH$_3$ | CH$_3$ | CH$_3$ | H | O | H | CH$_3$ | OCH$_3$ | N |
| SO$_2$CH$_2$CH$_3$ | CH$_3$ | CH$_3$ | H | O | H | CH$_3$ | CH$_3$ | N |
| SO$_2$CH$_2$CH$_3$ | CH$_3$ | CH$_3$ | H | O | H | OCH$_2$CH$_3$ | OCH$_2$CH$_3$ | N |
| SO$_2$CH$_2$CH$_3$ | CH$_3$ | CH$_3$ | H | O | H | NHCH$_3$ | OCH$_2$CH$_3$ | N |
| SO$_2$CH$_2$CH$_3$ | CH$_3$ | CH$_3$ | H | O | H | N(CH$_3$)$_2$ | OCH$_2$CH$_3$ | N |
| SO$_2$CH$_2$CH$_3$ | CH$_3$ | CH$_3$ | H | O | H | N(CH$_3$)$_2$ | OCH$_3$ | N |
| SO$_2$CH$_2$CH$_3$ | CH$_3$ | CH$_3$ | H | O | H | N(CH$_3$)$_2$ | OCH$_2$CF$_3$ | N |
| SO$_2$CH$_2$CH$_3$ | CH$_3$ | CH$_3$ | H | O | CH$_3$ | CH$_3$ | OCH$_3$ | N |
| SO$_2$CH$_2$CH$_3$ | CH$_3$ | CH$_3$ | H | S | H | OCH$_3$ | OCH$_3$ | CH |
| SO$_2$CH$_2$CH$_3$ | CH$_3$ | CH$_3$ | H | S | H | Cl | OCH$_3$ | CH |
| SO$_2$CH$_2$CH$_3$ | CH$_3$ | CH$_3$ | H | S | H | CH$_3$ | OCH$_3$ | CH |
| SO$_2$CH$_2$CH$_3$ | CH$_3$ | CH$_3$ | H | S | H | CH$_3$ | CH$_3$ | CH |
| SO$_2$CH$_2$CH$_3$ | CH$_3$ | CH$_3$ | H | S | H | OCH$_3$ | OCH$_3$ | N |
| SO$_2$CH$_2$CH$_3$ | CH$_3$ | CH$_3$ | H | S | H | CH$_3$ | OCH$_3$ | N |
| SO$_2$CH$_2$CH$_3$ | CH$_3$ | CH$_2$CH$_3$ | H | O | H | OCH$_3$ | OCH$_3$ | CH |
| SO$_2$CH$_2$CH$_3$ | CH$_3$ | CH$_2$CH$_3$ | H | O | H | Cl | OCH$_3$ | CH |
| SO$_2$CH$_2$CH$_3$ | CH$_3$ | CH$_2$CH$_3$ | H | O | H | CH$_3$ | OCH$_3$ | CH |
| SO$_2$CH$_2$CH$_3$ | CH$_3$ | CH$_2$CH$_3$ | H | O | H | CH$_3$ | CH$_3$ | CH |
| SO$_2$CH$_2$CH$_3$ | CH$_3$ | CH$_2$CH$_3$ | H | O | H | OCH$_3$ | OCH$_3$ | N |
| SO$_2$CH$_2$CH$_3$ | CH$_3$ | CH$_2$CH$_3$ | H | O | H | CH$_3$ | OCH$_3$ | N |
| SO$_2$CH$_2$CH$_3$ | CH$_3$ | CH$_2$CH$_3$ | H | O | H | CH$_3$ | CH$_3$ | N |
| SO$_2$CH$_2$CH$_3$ | CH$_3$ | CH$_2$CH$_3$ | H | O | H | OCH$_2$CH$_3$ | OCH$_2$CH$_3$ | N |
| SO$_2$CH$_2$CH$_3$ | CH$_3$ | CH$_2$CH$_3$ | H | O | H | NHCH$_3$ | OCH$_2$CH$_3$ | N |
| SO$_2$CH$_2$CH$_3$ | CH$_3$ | CH$_2$CH$_3$ | H | O | H | N(CH$_3$)$_2$ | OCH$_2$CH$_3$ | N |
| SO$_2$CH$_2$CH$_3$ | CH$_3$ | CH$_2$CH$_3$ | H | O | H | N(CH$_3$)$_2$ | OCH$_3$ | N |
| SO$_2$CH$_2$CH$_3$ | CH$_3$ | CH$_2$CH$_3$ | H | O | H | N(CH$_3$)$_2$ | OCH$_2$CF$_3$ | N |
| SO$_2$CH$_2$CH$_3$ | CH$_3$ | CH$_2$CH$_3$ | H | O | CH$_3$ | CH$_3$ | OCH$_3$ | N |
| SO$_2$CH$_2$CH$_3$ | CH$_3$ | CH$_2$CH$_3$ | H | S | H | OCH$_3$ | OCH$_3$ | CH |
| SO$_2$CH$_2$CH$_3$ | CH$_3$ | CH$_2$CH$_3$ | H | S | H | Cl | OCH$_3$ | CH |
| SO$_2$CH$_2$CH$_3$ | CH$_3$ | CH$_2$CH$_3$ | H | S | H | CH$_3$ | OCH$_3$ | CH |
| SO$_2$CH$_2$CH$_3$ | CH$_3$ | CH$_2$CH$_3$ | H | S | H | CH$_3$ | CH$_3$ | CH |
| SO$_2$CH$_2$CH$_3$ | CH$_3$ | CH$_2$CH$_3$ | H | S | H | OCH$_3$ | OCH$_3$ | N |
| SO$_2$CH$_2$CH$_3$ | CH$_3$ | CH$_2$CH$_3$ | H | S | H | CH$_3$ | OCH$_3$ | N |
| SO$_2$CH$_2$CH$_3$ | CH$_2$CH$_3$ | CH$_2$CH$_3$ | H | O | H | OCH$_3$ | OCH$_3$ | CH |
| SO$_2$CH$_2$CH$_3$ | CH$_2$CH$_3$ | CH$_2$CH$_3$ | H | O | H | Cl | OCH$_3$ | CH |
| SO$_2$CH$_2$CH$_3$ | CH$_2$CH$_3$ | CH$_2$CH$_3$ | H | O | H | CH$_3$ | OCH$_3$ | CH |
| SO$_2$CH$_2$CH$_3$ | CH$_2$CH$_3$ | CH$_2$CH$_3$ | H | O | H | CH$_3$ | CH$_3$ | CH |
| SO$_2$CH$_2$CH$_3$ | CH$_2$CH$_3$ | CH$_2$CH$_3$ | H | O | H | OCH$_3$ | OCH$_3$ | N |
| SO$_2$CH$_2$CH$_3$ | CH$_2$CH$_3$ | CH$_2$CH$_3$ | H | O | H | CH$_3$ | OCH$_3$ | N |
| SO$_2$CH$_2$CH$_3$ | CH$_2$CH$_3$ | CH$_2$CH$_3$ | H | O | H | CH$_3$ | CH$_3$ | N |
| SO$_2$CH$_2$CH$_3$ | CH$_2$CH$_3$ | CH$_2$CH$_3$ | H | O | H | OCH$_2$CH$_3$ | OCH$_2$CH$_3$ | N |
| SO$_2$CH$_2$CH$_3$ | CH$_2$CH$_3$ | CH$_2$CH$_3$ | H | O | H | NHCH$_3$ | OCH$_2$CH$_3$ | N |
| SO$_2$CH$_2$CH$_3$ | CH$_2$CH$_3$ | CH$_2$CH$_3$ | H | O | H | N(CH$_3$)$_2$ | OCH$_2$CH$_3$ | N |
| SO$_2$CH$_2$CH$_3$ | CH$_2$CH$_3$ | CH$_2$CH$_3$ | H | O | H | N(CH$_3$)$_2$ | OCH$_3$ | N |
| SO$_2$CH$_2$CH$_3$ | CH$_2$CH$_3$ | CH$_2$CH$_3$ | H | O | H | N(CH$_3$)$_2$ | OCH$_2$CF$_3$ | N |
| SO$_2$CH$_2$CH$_3$ | CH$_2$CH$_3$ | CH$_2$CH$_3$ | H | O | CH$_3$ | CH$_3$ | OCH$_3$ | N |
| SO$_2$CH$_2$CH$_3$ | CH$_2$CH$_3$ | CH$_2$CH$_3$ | H | S | H | OCH$_3$ | OCH$_3$ | CH |
| SO$_2$CH$_2$CH$_3$ | CH$_2$CH$_3$ | CH$_2$CH$_3$ | H | S | H | Cl | OCH$_3$ | CH |
| SO$_2$CH$_2$CH$_3$ | CH$_2$CH$_3$ | CH$_2$CH$_3$ | H | S | H | CH$_3$ | OCH$_3$ | CH |
| SO$_2$CH$_2$CH$_3$ | CH$_2$CH$_3$ | CH$_2$CH$_3$ | H | S | H | CH$_3$ | CH$_3$ | CH |
| SO$_2$CH$_2$CH$_3$ | CH$_2$CH$_3$ | CH$_2$CH$_3$ | H | S | H | OCH$_3$ | OCH$_3$ | N |
| SO$_2$CH$_2$CH$_3$ | CH$_2$CH$_3$ | CH$_2$CH$_3$ | H | S | H | CH$_3$ | OCH$_3$ | N |
| SO$_2$CH$_2$CH$_3$ | OCH$_3$ | CH$_3$ | H | O | H | OCH$_3$ | OCH$_3$ | CH |
| SO$_2$CH$_2$CH$_3$ | OCH$_3$ | CH$_3$ | H | O | H | Cl | OCH$_3$ | CH |
| SO$_2$CH$_2$CH$_3$ | OCH$_3$ | CH$_3$ | H | O | H | CH$_3$ | OCH$_3$ | CH |
| SO$_2$CH$_2$CH$_3$ | OCH$_3$ | CH$_3$ | H | O | H | CH$_3$ | CH$_3$ | CH |
| SO$_2$CH$_2$CH$_3$ | OCH$_3$ | CH$_3$ | H | O | H | OCH$_3$ | OCH$_3$ | N |
| SO$_2$CH$_2$CH$_3$ | OCH$_3$ | CH$_3$ | H | O | H | CH$_3$ | OCH$_3$ | N |
| SO$_2$CH$_2$CH$_3$ | OCH$_3$ | CH$_3$ | H | O | H | CH$_3$ | CH$_3$ | N |
| SO$_2$CH$_2$CH$_3$ | OCH$_3$ | CH$_3$ | H | O | H | OCH$_2$CH$_3$ | OCH$_2$CH$_3$ | N |
| SO$_2$CH$_2$CH$_3$ | OCH$_3$ | CH$_3$ | H | O | H | NHCH$_3$ | OCH$_2$CH$_3$ | N |
| SO$_2$CH$_2$CH$_3$ | OCH$_3$ | CH$_3$ | H | O | H | N(CH$_3$)$_2$ | OCH$_2$CH$_3$ | N |
| SO$_2$CH$_2$CH$_3$ | OCH$_3$ | CH$_3$ | H | O | H | N(CH$_3$)$_2$ | OCH$_3$ | N |
| SO$_2$CH$_2$CH$_3$ | OCH$_3$ | CH$_3$ | H | O | H | N(CH$_3$)$_2$ | OCH$_2$CF$_3$ | N |
| SO$_2$CH$_2$CH$_3$ | OCH$_3$ | CH$_3$ | H | O | CH$_3$ | CH$_3$ | OCH$_3$ | N |

-continued

| | | | | | | | | |
|---|---|---|---|---|---|---|---|---|
| SO₂CH₂CH₃ | OCH₃ | CH₃ | S | O | H | OCH₃ | OCH₃ | CH |
| SO₂CH₂CH₃ | OCH₃ | CH₃ | H | S | H | Cl | OCH₃ | CH |
| SO₂CH₂CH₃ | OCH₃ | CH₃ | H | S | H | CH₃ | OCH₃ | CH |
| SO₂CH₂CH₃ | OCH₃ | CH₃ | H | S | H | CH₃ | CH₃ | CH |
| SO₂CH₂CH₃ | OCH₃ | CH₃ | H | S | H | OCH₃ | OCH₃ | N |
| SO₂CH₂CH₃ | OCH₃ | CH₃ | H | S | H | CH₃ | OCH₃ | N |
| SO₂CH₂CH₃ | NHCH₃ | CH₃ | H | O | H | OCH₃ | OCH₃ | CH |
| SO₂CH₂CH₃ | NHCH₃ | CH₃ | H | O | H | Cl | OCH₃ | CH |
| SO₂CH₂CH₃ | NHCH₃ | CH₃ | H | O | H | CH₃ | OCH₃ | CH |
| SO₂CH₂CH₃ | NHCH₃ | CH₃ | H | O | H | CH₃ | CH₃ | CH |
| SO₂CH₂CH₃ | NHCH₃ | CH₃ | H | O | H | OCH₃ | OCH₃ | N |
| SO₂CH₂CH₃ | NHCH₃ | CH₃ | H | O | H | CH₃ | OCH₃ | N |
| SO₂CH₂CH₃ | NHCH₃ | CH₃ | H | O | H | CH₃ | CH₃ | N |
| SO₂CH₂CH₃ | NHCH₃ | CH₃ | H | O | H | OCH₂CH₃ | OCH₂CH₃ | N |
| SO₂CH₂CH₃ | NHCH₃ | CH₃ | H | O | H | NHCH₃ | OCH₂CH₃ | N |
| SO₂CH₂CH₃ | NHCH₃ | CH₃ | H | O | H | N(CH₃)₂ | OCH₂CH₃ | N |
| SO₂CH₂CH₃ | NHCH₃ | CH₃ | H | O | H | N(CH₃)₂ | OCH₃ | N |
| SO₂CH₂CH₃ | NHCH₃ | CH₃ | H | O | H | N(CH₃)₂ | OCH₂CF₃ | N |
| SO₂CH₂CH₃ | NHCH₃ | CH₃ | H | O | CH₃ | CH₃ | OCH₃ | N |
| SO₂CH₂CH₃ | NHCH₃ | CH₃ | H | S | H | OCH₃ | OCH₃ | CH |
| SO₂CH₂CH₃ | NHCH₃ | CH₃ | H | S | H | Cl | OCH₃ | CH |
| SO₂CH₂CH₃ | NHCH₃ | CH₃ | H | S | H | CH₃ | OCH₃ | CH |
| SO₂CH₂CH₃ | NHCH₃ | CH₃ | H | S | H | CH₃ | CH₃ | CH |
| SO₂CH₂CH₃ | NHCH₃ | CH₃ | H | S | H | OCH₃ | OCH₃ | N |
| SO₂CH₂CH₃ | NHCH₃ | CH₃ | H | S | H | CH₃ | OCH₃ | N |
| SO₂CH₂CH₃ | N(CH₃)₂ | CH | H | O | H | OCH₃ | OCH₃ | CH |
| SO₂CH₂CH₃ | N(CH₃)₂ | CH | H | O | H | Cl | OCH₃ | CH |
| SO₂CH₂CH₃ | N(CH₃)₂ | CH₃ | H | O | H | CH₃ | OCH₃ | CH |
| SO₂CH₂CH₃ | N(CH₃)₂ | CH₃ | H | O | H | CH₃ | CH₃ | CH |
| SO₂CH₂CH₃ | N(CH₃)₂ | CH₃ | H | O | H | OCH₃ | OCH₃ | N |
| SO₂CH₂CH₃ | N(CH₃)₂ | CH₃ | H | O | H | CH₃ | OCH₃ | N |
| SO₂CH₂CH₃ | N(CH₃)₂ | CH₃ | H | O | H | CH₃ | CH₃ | N |
| SO₂CH₂CH₃ | N(CH₃)₂ | CH₃ | H | O | H | OCH₂CH₃ | OCH₂CH₃ | N |
| SO₂CH₂CH₃ | N(CH₃)₂ | CH₃ | H | O | H | NHCH₃ | OCH₂CH₃ | N |
| SO CH₂CH₃ | N(CH₃)₂ | CH₃ | H | O | H | N(CH₃)₂ | OCH₂CH₃ | N |
| SO₂CH₂CH₃ | N(CH₃)₂ | CH₃ | H | O | H | N(CH₃)₂ | OCH₃ | N |
| SO₂CH₂CH₃ | N(CH₃)₂ | CH₃ | H | O | H | N(CH₃)₂ | OCH₂CF₃ | N |
| SO₂CH₂CH₃ | N(CH₃)₂ | CH₃ | H | O | CH₃ | CH₃ | OCH₃ | N |
| SO₂CH₂CH₃ | N(CH₃)₂ | CH₃ | H | S | H | OCH₃ | OCH₃ | CH |
| SO₂CH₂CH₃ | N(CH₃)₂ | CH₃ | H | S | H | Cl | OCH₃ | CH |
| SO₂CH₂CH₃ | N(CH₃)₂ | CH₃ | H | S | H | CH₃ | OCH₃ | CH |
| SO₂CH₂CH₃ | N(CH₃)₂ | CH₃ | H | S | H | CH₃ | CH₃ | CH |
| SO₂CH₂CH₃ | N(CH₃)₂ | CH₃ | H | S | H | OCH₃ | OCH₃ | N |
| SO₂CH₂CH₃ | N(CH₃)₂ | CH₃ | H | S | H | CH₃ | OCH₃ | N |
| SO₂CH₂CH₃ | —CH₂CH₂CH₂— | | H | O | H | OCH₃ | CCH₃ | CH |
| SO₂CH₂CH₃ | —CH₂CH₂CH₂— | | H | O | H | Cl | OCH₃ | CH |
| SO₂CH₂CH₃ | —CH₂CH₂CH₂— | | H | O | H | CH₃ | OCH₃ | CH |
| SO₂CH₂CH₃ | —CH₂CH₂CH₂— | | H | O | H | CH₃ | CH₃ | CH |
| SO₂CH₂CH₃ | —CH₂CH₂CH₂— | | H | O | H | OCH₃ | OCH₃ | N |
| SO₂CH₂CH₃ | —CH₂CH₂CH₂— | | H | O | H | CH₃ | OCH₃ | N |
| SO₂CH₂CH₃ | —CH₂CH₂CH₂— | | H | O | H | CH₃ | CH₃ | N |
| SO₂CH₂CH₃ | —CH₂CH₂CH₂— | | H | O | H | OCH₂CH₃ | OCH₂CH₃ | N |
| SO₂CH₂CH₃ | —CH₂CH₂CH₂— | | H | O | H | NHCH₃ | OCH₂CH₃ | N |
| SO₂CH₂CH₃ | —CH₂CH₂CH₂— | | H | O | H | N(CH₃)₂ | OCH₂CH₃ | N |
| SO₂CH₂CH₃ | —CH₂CH₂CH₂— | | H | O | H | N(CH₃)₂ | OCH₃ | N |
| SO₂CH₂CH₃ | —CH₂CH₂CH₂— | | H | O | H | N(CH₃)₂ | OCH₂CF₃ | N |
| SO₂CH₂CH₃ | —CH₂CH₂CH₂— | | H | O | CH₃ | CH₃ | OCH₃ | N |
| SO₂CH₂CH₃ | —CH₂CH₂CH₂— | | H | S | H | OCH₃ | OCH₃ | CH |
| SO₂CH₂CH₃ | —CH₂CH₂CH₂— | | H | S | H | Cl | OCH₃ | CH |
| SO₂CH₂CH₃ | —CH₂CH₂CH₂— | | H | S | H | CH₃ | OCH₃ | CH |
| SO₂CH₂CH₃ | —CH₂CH₂CH₂— | | H | S | H | CH₃ | CH₃ | CH |
| SO₂CH₂CH₃ | —CH₂CH₂CH₂— | | H | S | H | OCH₃ | OCH₃ | N |
| SO₂CH₂CH₃ | —CH₂CH₂CH₂— | | H | S | H | CH₃ | OCH₃ | N |
| SO₂CH₂CH₃ | —CH₂CH₂OCH₂CH₂— | | H | O | H | OCH₃ | OCH₃ | CH |
| SO₂CH₂CH₃ | —CH₂CH₂OCH₂CH₂— | | H | O | H | Cl | OCH₃ | CH |
| SO₂CH₂CH₃ | —CH₂CH₂OCH₂CH₂— | | H | O | H | CH₃ | OCH₃ | CH |
| SO₂CH₂CH₃ | —CH₂CH₂OCH₂CH₂— | | H | O | H | CH₃ | CH₃ | CH |
| SO₂CH₂CH₃ | —CH₂CH₂OCH₂CH₂— | | H | O | H | OCH₃ | OCH₃ | N |
| SO₂CH₂CH₃ | —CH₂CH₂OCH₂CH₂— | | H | O | H | CH₃ | OCH₃ | N |
| SO₂CH₂CH₃ | —CH₂CH₂OCH₂CH₂— | | H | O | H | CH₃ | CH₃ | N |
| SO₂CH₂CH₃ | —CH₂CH₂OCH₂CH₂— | | H | O | H | OCH₂CH₃ | OCH₂CH₃ | N |
| SO₂CH₂CH₃ | —CH₂CH₂OCH₂CH₂— | | H | O | H | NHCH₃ | OCH₂CH₃ | N |
| SO₂CH₂CH₃ | —CH₂CH₂OCH₂CH₂— | | H | O | H | N(CH₃)₂ | OCH₂CH₃ | N |
| SO₂CH₂CH₃ | —CH₂CH₂OCH₂CH₂— | | H | O | H | N(CH₃)₂ | OCH₃ | N |
| SO₂CH₂CH₃ | —CH₂CH₂OCH₂CH₂— | | H | O | H | N(CH₃)₂ | OCH₂CF₃ | N |
| SO₂CH₂CH₃ | —CH₂CH₂OCH₂CH₂— | | H | O | CH₃ | CH₃ | OCH₃ | N |
| SO₂CH₂CH₃ | —CH₂CH₂OCH₂CH₂— | | H | S | H | OCH₃ | OCH₃ | CH |
| SO₂CH₂CH₃ | —CH₂CH₂OCH₂CH₂— | | H | S | H | Cl | OCH₃ | CH |
| SO₂CH₂CH₃ | —CH₂CH₂OCH₂CH₂— | | H | S | H | CH₃ | OCH₃ | CH |
| SO₂CH₂CH₃ | —CH₂CH₂OCH₂CH₂— | | H | S | H | OCH₃ | OCH₃ | N |
| SO₂CH₂CH₃ | —CH₂CH₂OCH₂CH₂— | | H | S | H | CH₃ | OCH₃ | N |

-continued

| | | | | | | | | |
|---|---|---|---|---|---|---|---|---|
| Br | CH₃ | H | H | O | H | OCH₃ | OCH₃ | CH |
| Br | CH₃ | H | H | O | H | Cl | OCH₃ | CH |
| Br | CH₃ | H | H | O | H | CH₃ | OCH₃ | CH |
| Br | CH | H | H | O | H | CH₃ | CH₃ | CH |
| Br | CH₃ | H | H | O | H | OCH₃ | OCH₃ | N |
| Br | CH₃ | H | H | O | H | CH₃ | OCH₃ | N |
| Br | CH₃ | H | H | O | H | CH₃ | CH₃ | N |
| Br | CH₃ | H | H | O | H | OCH₂CH₃ | OCH₂CH₃ | N |
| Br | CH₃ | H | H | O | H | NHCH₃ | OCH₂CH₃ | N |
| Br | CH₃ | H | H | O | H | N(CH₃)₂ | OCH₂CH₃ | N |
| Br | CH₃ | H | H | O | H | N(CH₃)₂ | OCH₃ | N |
| Br | CH₃ | H | H | O | H | N(CH₃)₂ | OCH₂CF₃ | N |
| Br | CH₃ | H | H | O | CH₃ | CH₃ | OCH₃ | N |
| Br | CH₃ | H | H | S | H | OCH₃ | OCH₃ | CH |
| Br | CH₃ | H | H | S | H | Cl | OCH₃ | CH |
| Br | CH₃ | H | H | S | H | CH₃ | OCH₃ | CH |
| Br | CH₃ | H | H | S | H | CH₃ | CH₃ | CH |
| Br | CH₃ | H | H | S | H | OCH₃ | OCH₃ | N |
| Br | CH₃ | H | H | S | H | CH₃ | OCH₃ | N |
| Br | CH₂CH=CH₂ | H | H | O | H | OCH₃ | OCH₃ | CH |
| Br | CH₂CH=CH₂ | H | H | O | H | Cl | OCH₃ | CH |
| Br | CH₂CH=CH₂ | H | H | O | H | CH₃ | OCH₃ | CH |
| Br | CH₂CH=CH₂ | H | H | O | H | CH₃ | CH₃ | CH |
| Br | CH₂CH=CH₂ | H | H | O | H | OCH₃ | OCH₃ | N |
| Br | CH₂CH=CH₂ | H | H | O | H | CH₃ | OCH₃ | N |
| Br | CH₂CH=CH₂ | H | H | O | H | CH₃ | CH₃ | N |
| Br | CH₂CH=CH₂ | H | H | O | H | OCH₂CH₃ | OCH₂CH₃ | N |
| Br | CH₂CH=CH₂ | H | H | O | H | NHCH₃ | OCH₂CH₃ | N |
| Br | CH₂CH=CH₂ | H | H | O | H | N(CH₃)₂ | OCH₂CH₃ | N |
| Br | CH₂CH=CH₂ | H | H | O | H | N(CH₃)₂ | OCH₃ | N |
| Br | CH₂CH=CH₂ | H | H | O | H | N(CH₃)₂ | OCH₂CF₃ | N |
| Br | CH₂CH=CH₂ | H | H | O | CH₃ | CH₃ | OCH₃ | N |
| Br | CH₂CH=CH₂ | H | H | S | H | OCH₃ | OCH₃ | CH |
| Br | CH₂CH=CH₂ | H | H | S | H | Cl | OCH₃ | CH |
| Br | CH₂CH=CH₂ | H | H | S | H | CH₃ | OCH₃ | CH |
| Br | CH₂CH=CH₂ | H | H | S | H | CH₃ | CH₃ | CH |
| Br | CH₂CH=CH₂ | H | H | S | H | OCH₃ | OCH₃ | N |
| Br | CH₂CH=CH₂ | H | H | S | H | CH₃ | OCH₃ | N |
| Br | CH₃ | CH₃ | H | O | H | OCH₃ | OCH₃ | CH |
| Br | CH₃ | CH₃ | H | O | H | Cl | OCH₃ | CH |
| Br | CH₃ | CH₃ | H | O | H | CH₃ | OCH₃ | CH |
| Br | CH₃ | CH₃ | H | O | H | CH₃ | CH₃ | CH |
| Br | CH₃ | CH₃ | H | O | H | OCH₃ | OCH₃ | N |
| Br | CH₃ | CH₃ | H | O | H | CH₃ | OCH₃ | N |
| Br | CH₃ | CH₃ | H | O | H | CH₃ | CH₃ | N |
| Br | CH₃ | CH₃ | H | O | H | OCH₂CH₃ | OCH₂CH₃ | N |
| Br | CH₃ | CH₃ | H | O | H | NHCH₃ | OCH₂CH₃ | N |
| Br | CH₃ | CH₃ | H | O | H | N(CH₃)₂ | OCH₂CH₃ | N |
| Br | CH₃ | CH₃ | H | O | H | N(CH₃)₂ | OCH₃ | N |
| Br | CH₃ | CH₃ | H | O | H | N(CH₃)₂ | OCH₂CF₃ | N |
| Br | CH₃ | CH₃ | H | O | CH₃ | CH₃ | OCH₃ | N |
| Br | CH₃ | CH₃ | H | S | H | OCH₃ | OCH₃ | CH |
| Br | CH₃ | CH₃ | H | S | H | Cl | OCH₃ | CH |
| Br | CH₃ | CH₃ | H | S | H | CH₃ | OCH₃ | CH |
| Br | CH₃ | CH₃ | H | S | H | CH₃ | CH₃ | CH |
| Br | CH₃ | CH₃ | H | S | H | OCH₃ | OCH₃ | N |
| Br | CH₃ | CH₃ | H | S | H | CH₃ | OCH₃ | N |
| Br | —CH₂CH₂CH₂— | | H | O | H | OCH₃ | OCH₃ | CH |
| Br | —CH₂CH₂CH₂— | | H | O | H | Cl | OCH₃ | CH |
| Br | —CH₂CH₂CH₂— | | H | O | H | CH₃ | OCH₃ | CH |
| Br | —CH₂CH₂CH₂— | | H | O | H | CH₃ | CH₃ | CH |
| Br | —CH₂CH₂CH₂— | | H | O | H | OCH₃ | OCH₃ | N |
| Br | —CH₂CH₂CH₂— | | H | O | H | CH₃ | OCH₃ | N |
| Br | —CH₂CH₂CH₂— | | H | O | H | CH₃ | CH₃ | N |
| Br | —CH₂CH₂CH₂— | | H | O | H | OCH₂CH₃ | OCH₂CH₃ | N |
| Br | —CH₂CH₂CH₂— | | H | O | H | NHCH₃ | OCH₂CH₃ | N |
| Br | —CH₂CH₂CH₂— | | H | O | H | N(CH₃)₂ | OCH₂CH₃ | N |
| Br | —CH₂CH₂CH₂— | | H | O | H | N(CH₃)₂ | OCH₃ | N |
| Br | —CH₂CH₂CH₂— | | H | O | H | N(CH₃)₂ | OCH₂CF₃ | N |
| Br | —CH₂CH₂CH₂— | | H | O | CH₃ | CH₃ | OCH₃ | N |
| Br | —CH₂CH₂CH₂— | | H | S | H | OCH₃ | OCH₃ | CH |
| Br | —CH₂CH₂CH₂— | | H | S | H | Cl | OCH₃ | CH |
| Br | —CH₂CH₂CH₂— | | H | S | H | CH₃ | OCH₃ | CH |
| Br | —CH₂CH₂CH₂— | | H | S | H | CH₃ | CH₃ | CH |
| Br | —CH₂CH₂CH₂— | | H | S | H | OCH₃ | OCH₃ | N |
| Br | —CH₂CH₂CH₂— | | H | S | H | CH₃ | OCH₃ | N |
| CH₂CH₃ | CH₃ | H | H | O | H | OCH₃ | OCH₃ | CH |
| CH₂CH₃ | CH₃ | H | H | O | H | Cl | OCH₃ | CH |
| CH₂CH₃ | CH₃ | H | H | O | H | CH₃ | OCH₃ | CH |
| CH₂CH₃ | CH₃ | H | H | O | H | CH₃ | CH₃ | CH |
| CH₂CH₃ | CH₃ | H | H | O | H | OCH₃ | OCH₃ | N |
| CH₂CH₃ | CH₃ | H | H | O | H | CH₃ | OCH₃ | N |

-continued

| | | | | | | | | |
|---|---|---|---|---|---|---|---|---|
| CH$_2$CH$_3$ | CH$_3$ | H | H | O | H | CH$_3$ | CH$_3$ | N |
| CH$_2$CH$_3$ | CH$_3$ | H | H | O | H | OCH$_2$CH$_3$ | OCH$_2$CH$_3$ | N |
| CH$_2$CH$_3$ | CH$_3$ | H | H | O | H | NHCH$_3$ | OCH$_2$CH$_3$ | N |
| CH$_2$CH$_3$ | CH$_3$ | H | H | O | H | N(CH$_3$)$_2$ | OCH$_2$CH$_3$ | N |
| CH$_2$CH$_3$ | CH$_3$ | H | H | O | H | N(CH$_3$)$_2$ | OCH$_3$ | N |
| CH$_2$CH$_3$ | CH$_3$ | H | H | O | H | N(CH$_3$)$_2$ | OCH$_2$CF$_3$ | N |
| CH$_2$CH$_3$ | CH$_3$ | H | H | O | CH$_3$ | CH$_3$ | OCH$_3$ | N |
| CH$_2$CH$_3$ | CH$_3$ | H | H | S | H | OCH$_3$ | OCH$_3$ | CH |
| CH$_2$CH$_3$ | CH$_3$ | H | H | S | H | Cl | OCH$_3$ | CH |
| CH$_2$CH$_3$ | CH$_3$ | H | H | S | H | CH$_3$ | OCH$_3$ | CH |
| CH$_2$CH$_3$ | CH$_3$ | H | H | S | H | CH$_3$ | CH$_3$ | CH |
| CH$_2$CH$_3$ | CH$_3$ | H | H | S | H | OCH$_3$ | OCH$_3$ | N |
| CH$_2$CH$_3$ | CH$_3$ | H | H | S | H | CH$_3$ | OCH$_3$ | N |
| CH$_2$CH$_3$ | CH$_2$CH=CH$_2$ | H | H | O | H | OCH$_3$ | OCH$_3$ | CH |
| CH$_2$CH$_3$ | CH$_2$CH=CH$_2$ | H | H | O | H | Cl | OCH$_3$ | CH |
| CH$_2$CH$_3$ | CH$_2$CH=CH$_2$ | H | H | O | H | CH$_3$ | OCH$_3$ | CH |
| CH$_2$CH$_3$ | CH$_2$CH=CH$_2$ | H | H | O | H | CH$_3$ | CH$_3$ | CH |
| CH$_2$CH$_3$ | CH$_2$CH=CH$_2$ | H | H | O | H | OCH$_3$ | OCH$_3$ | N |
| CH$_2$CH$_3$ | CH$_2$CH=CH$_2$ | H | H | O | H | CH$_3$ | OCH$_3$ | N |
| CH$_2$CH$_3$ | CH$_2$CH=CH$_2$ | H | H | O | H | CH$_3$ | CH$_3$ | N |
| CH$_2$CH$_3$ | CH$_2$CH=CH$_2$ | H | H | O | H | OCH$_2$CH$_3$ | OCH$_2$CH$_3$ | N |
| CH$_2$CH$_3$ | CH$_2$CH=CH$_2$ | H | H | O | H | NHCH$_3$ | OCH$_2$CH$_3$ | N |
| CH$_2$CH$_3$ | CH$_2$CH=CH$_2$ | H | H | O | H | N(CH$_3$)$_2$ | OCH$_2$CH$_3$ | N |
| CH$_2$CH$_3$ | CH$_2$CH=CH$_2$ | H | H | O | H | N(CH$_3$)$_2$ | OCH$_3$ | N |
| CH$_2$CH$_3$ | CH$_2$CH=CH$_2$ | H | H | O | H | N(CH$_3$)$_2$ | OCH$_2$CF$_3$ | N |
| CH$_2$CH$_3$ | CH$_2$CH=CH$_2$ | H | H | O | CH$_3$ | CH$_3$ | OCH$_3$ | N |
| CH$_2$CH$_3$ | CH$_2$CH=CH$_2$ | H | H | S | H | OCH$_3$ | OCH$_3$ | CH |
| CH$_2$CH$_3$ | CH$_2$CH=CH$_2$ | H | H | S | H | Cl | OCH$_3$ | CH |
| CH$_2$CH$_3$ | CH$_2$CH=CH$_2$ | H | H | S | H | CH$_3$ | OCH$_3$ | CH |
| CH$_2$CH$_3$ | CH$_2$CH=CH$_2$ | H | H | S | H | CH$_3$ | CH$_3$ | CH |
| CH$_2$CH$_3$ | CH$_2$CH=CH$_2$ | H | H | S | H | OCH$_3$ | OCH$_3$ | N |
| CH$_2$CH$_3$ | CH$_2$CH=CH$_2$ | H | H | S | H | CH$_3$ | OCH$_3$ | N |
| CH$_2$CH$_3$ | CH$_3$ | CH$_3$ | H | O | H | OCH$_3$ | OCH$_3$ | CH |
| CH$_2$CH$_3$ | CH$_3$ | CH$_3$ | H | O | H | Cl | OCH$_3$ | CH |
| CH$_2$CH$_3$ | CH$_3$ | CH$_3$ | H | O | H | CH$_3$ | OCH$_3$ | CH |
| CH$_2$CH$_3$ | CH$_3$ | CH$_3$ | H | O | H | CH$_3$ | CH$_3$ | CH |
| CH$_2$CH$_3$ | CH$_3$ | CH$_3$ | H | O | H | OCH$_3$ | OCH$_3$ | N |
| CH$_2$CH$_3$ | CH$_3$ | CH$_3$ | H | O | H | CH$_3$ | OCH$_3$ | N |
| CH$_2$CH$_3$ | CH$_3$ | CH$_3$ | H | O | H | CH$_3$ | CH$_3$ | N |
| CH$_2$CH$_3$ | CH$_3$ | CH$_3$ | H | O | H | OCH$_2$CH$_3$ | OCH$_2$CH$_3$ | N |
| CH$_2$CH$_3$ | CH$_3$ | CH$_3$ | H | O | H | NHCH$_3$ | OCH$_2$CH$_3$ | N |
| CH$_2$CH$_3$ | CH$_3$ | CH$_3$ | H | O | H | N(CH$_3$)$_2$ | OCH$_2$CH$_3$ | N |
| CH$_2$CH$_3$ | CH$_3$ | CH$_3$ | H | O | H | N(CH$_3$)$_2$ | OCH$_3$ | N |
| CH$_2$CH$_3$ | CH$_3$ | CH$_3$ | H | O | H | N(CH$_3$)$_2$ | OCH$_2$CF$_3$ | N |
| CH$_2$CH$_3$ | CH$_3$ | CH$_3$ | H | O | CH$_3$ | CH$_3$ | OCH$_3$ | N |
| CH$_2$CH$_3$ | CH$_3$ | CH$_3$ | H | S | H | OCH$_3$ | OCH$_3$ | CH |
| CH$_2$CH$_3$ | CH$_3$ | CH$_3$ | H | S | H | Cl | OCH$_3$ | CH |
| CH$_2$CH$_3$ | CH$_3$ | CH$_3$ | H | S | H | CH$_3$ | OCH$_3$ | CH |
| CH$_2$CH$_3$ | CH$_3$ | CH$_3$ | H | S | H | CH$_3$ | CH$_3$ | CH |
| CH$_2$CH$_3$ | CH$_3$ | CH$_3$ | H | S | H | OCH$_3$ | OCH$_3$ | N |
| CH$_2$CH$_3$ | CH$_3$ | CH$_3$ | H | S | H | CH$_3$ | OCH$_3$ | N |
| CH$_2$CH$_3$ | —CH$_2$CH$_2$CH$_2$— | | H | O | H | OCH$_3$ | OCH$_3$ | CH |
| CH$_2$CH$_3$ | —CH$_2$CH$_2$CH$_2$— | | H | O | H | Cl | OCH$_3$ | CH |
| CH$_2$CH$_3$ | —CH$_2$CH$_2$CH$_2$— | | H | O | H | CH$_3$ | OCH$_3$ | CH |
| CH$_2$CH$_3$ | —CH$_2$CH$_2$CH$_2$— | | H | O | H | CH$_3$ | CH$_3$ | CH |
| CH$_2$CH$_3$ | —CH$_2$CH$_2$CH$_2$— | | H | O | H | OCH$_3$ | OCH$_3$ | N |
| CH$_2$CH$_3$ | —CH$_2$CH$_2$CH$_2$— | | H | O | H | CH$_3$ | OCH$_3$ | N |
| CH$_2$CH$_3$ | —CH$_2$CH$_2$CH$_2$— | | H | O | H | CH$_3$ | CH$_3$ | N |
| CH$_2$CH$_3$ | —CH$_2$CH$_2$CH$_2$— | | H | O | H | OCH$_2$CH$_3$ | OCH$_2$CH$_3$ | N |
| CH$_2$CH$_3$ | —CH$_2$CH$_2$CH$_2$— | | H | O | H | NHCH$_3$ | OCH$_2$CH$_3$ | N |
| CH$_2$CH$_3$ | —CH$_2$CH$_2$CH$_2$— | | H | O | H | N(CH$_3$)$_2$ | OCH$_2$CH$_3$ | N |
| CH$_2$CH$_3$ | —CH$_2$CH$_2$CH$_2$— | | H | O | H | N(CH$_3$)$_2$ | OCH$_3$ | N |
| CH$_2$CH$_3$ | —CH$_2$CH$_2$CH$_2$— | | H | O | H | N(CH$_3$)$_2$ | OCH$_2$CF$_3$ | N |
| CH$_2$CH$_3$ | —CH$_2$CH$_2$CH$_2$— | | H | O | CH$_3$ | CH$_3$ | OCH$_3$ | N |
| CH$_2$CH$_3$ | —CH$_2$CH$_2$CH$_2$— | | H | S | H | OCH$_3$ | OCH$_3$ | CH |
| CH$_2$CH$_3$ | —CH$_2$CH$_2$CH$_2$— | | H | S | H | Cl | OCH$_3$ | CH |
| CH$_2$CH$_3$ | —CH$_2$CH$_2$CH$_2$— | | H | S | H | CH$_3$ | OCH$_3$ | CH |
| CH$_2$CH$_3$ | —CH$_2$CH$_2$CH$_2$— | | H | S | H | CH$_3$ | CH$_3$ | CH |
| CH$_2$CH$_3$ | —CH$_2$CH$_2$CH$_2$— | | H | S | H | OCH$_3$ | OCH$_3$ | N |
| CH$_2$CH$_3$ | —CH$_2$CH$_2$CH$_2$— | | H | S | H | CH$_3$ | OCH$_3$ | N |
| CF$_3$ | CH$_3$ | CH$_3$ | H | O | H | OCH$_3$ | OCH$_3$ | CH |
| CF$_3$ | CH$_3$ | CH$_3$ | H | O | H | Cl | OCH$_3$ | CH |
| CF$_3$ | CH$_3$ | CH$_3$ | H | O | H | CH$_3$ | OCH$_3$ | CH |
| CF$_3$ | CH$_3$ | CH$_3$ | H | O | H | CH$_3$ | CH$_3$ | CH |
| CF$_3$ | CH$_3$ | CH$_3$ | H | O | H | OCH$_3$ | OCH$_3$ | N |
| CF$_3$ | CH$_3$ | CH$_3$ | H | O | H | CH$_3$ | OCH$_3$ | N |
| CF$_3$ | CH$_3$ | CH$_3$ | H | O | H | CH$_3$ | CH$_3$ | N |
| CF$_3$ | CH$_3$ | CH$_3$ | H | O | H | OCH$_2$CH$_3$ | OCH$_2$CH$_3$ | N |
| CF$_3$ | CH$_3$ | CH$_3$ | H | O | H | NHCH$_3$ | OCH$_2$CH$_3$ | N |
| CF$_3$ | CH$_3$ | CH$_3$ | H | O | H | N(CH$_3$)$_2$ | OCH$_2$CH$_3$ | N |
| CF$_3$ | CH$_3$ | CH$_3$ | H | O | H | N(CH$_3$)$_2$ | OCH$_3$ | N |
| CF$_3$ | CH$_3$ | CH$_3$ | H | O | H | N(CH$_3$)$_2$ | OCH$_2$CF$_3$ | N |

-continued

| | | | | | | | | |
|---|---|---|---|---|---|---|---|---|
| CF₃ | CH₃ | CH₃ | H | O | CH₃ | CH₃ | OCH₃ | N |
| CF₃ | CH₃ | CH₃ | H | S | H | OCH₃ | OCH₃ | CH |
| CF₃ | CH₃ | CH₃ | H | S | H | Cl | OCH₃ | CH |
| CF₃ | CH₃ | CH₃ | H | S | H | CH₃ | OCH₃ | CH |
| CF₃ | CH₃ | CH₃ | H | S | H | CH₃ | CH₃ | CH |
| CF₃ | CH₃ | CH₃ | H | S | H | OCH₃ | OCH₃ | N |
| CF₃ | CH₃ | CH₃ | H | S | H | CH₃ | OCH₃ | N |
| CF₃ | —CH₂CH₂CH₂— | | H | O | H | OCH₃ | OCH₃ | CH |
| CF₃ | —CH₂CH₂CH₂— | | H | O | H | Cl | OCH₃ | CH |
| CF₃ | —CH₂CH₂CH₂— | | H | O | H | CH₃ | OCH₃ | CH |
| CF₃ | —CH₂CH₂CH₂— | | H | O | H | CH₃ | CH₃ | CH |
| CF₃ | —CH₂CH₂CH₂— | | H | O | H | OCH₃ | OCH₃ | N |
| CF₃ | —CH₂CH₂CH₂— | | H | O | H | CH₃ | OCH₃ | N |
| CF₃ | —CH₂CH₂CH₂— | | H | O | H | CH₃ | CH₃ | N |
| CF₃ | —CH₂CH₂CH₂— | | H | O | H | OCH₂CH₃ | OCH₂CH₃ | N |
| CF₃ | —CH₂CH₂CH₂— | | H | O | H | NHCH₃ | OCH₂CH₃ | N |
| CF₃ | —CH₂CH₂CH₂— | | H | O | H | N(CH₃)₂ | OCH₂CH₃ | N |
| CF₃ | —CH₂CH₂CH₂— | | H | O | H | N(CH₃)₂ | OCH₃ | N |
| CF₃ | —CH₂CH₂CH₂— | | H | O | H | N(CH₃)₂ | OCH₂CF₃ | N |
| CF₃ | —CH₂CH₂CH₂— | | H | O | CH₃ | CH₃ | OCH₃ | N |
| CF₃ | —CH₂CH₂CH₂— | | H | S | H | OCH₃ | OCH₃ | CH |
| CF₃ | —CH₂CH₂CH₂— | | H | S | H | Cl | OCH₃ | CH |
| CF₃ | —CH₂CH₂CH₂— | | H | S | H | CH₃ | OCH₃ | CH |
| CF₃ | —CH₂CH₂CH₂— | | H | S | H | CH₃ | CH₃ | CH |
| CF₃ | —CH₂CH₂CH₂— | | H | S | H | OCH₃ | OCH₃ | N |
| CF₃ | —CH₂CH₂CH₂— | | H | S | H | CH₃ | OCH₃ | N |
| CF₃ | CH₃ | CH₃ | H | O | H | OCH₃ | OCH₃ | CH |
| CF₃ | CH₃ | CH₃ | H | O | H | Cl | OCH₃ | CH |
| CF₃ | CH₃ | CH₃ | H | O | H | CH₃ | OCH₃ | CH |
| CF₃ | CH₃ | CH₃ | H | O | H | CH₃ | CH₃ | CH |
| CF₃ | CH₃ | CH₃ | H | O | H | OCH₃ | OCH₃ | N |
| CF₃ | CH₃ | CH₃ | H | O | H | CH₃ | OCH₃ | N |
| CF₃ | CH₃ | CH₃ | H | O | H | CH₃ | CH₃ | N |
| CF₃ | CH₃ | CH₃ | H | O | H | OCH₂CH₃ | OCH₂CH₃ | N |
| CF₃ | CH₃ | CH₃ | H | O | H | NHCH₃ | OCH₂CH₃ | N |
| CF₃ | CH₃ | CH₃ | H | O | H | N(CH₃)₂ | OCH₂CH₃ | N |
| CF₃ | CH₃ | CH₃ | H | O | H | N(CH₃)₂ | OCH₃ | N |
| CF₃ | CH₃ | CH₃ | H | O | H | N(CH₃)₂ | OCH₂CF₃ | N |
| CF₃ | CH₃ | CH₃ | H | O | CH₃ | CH₃ | OCH₃ | N |
| CF₃ | CH₃ | CH₃ | H | S | H | OCH₃ | OCH₃ | CH |
| CF₃ | CH₃ | CH₃ | H | S | H | Cl | OCH₃ | CH |
| CF₃ | CH₃ | CH₃ | H | S | H | CH₃ | OCH₃ | CH |
| CF₃ | CH₃ | CH₃ | H | S | H | CH₃ | CH₃ | CH |
| CF₃ | CH₃ | CH₃ | H | S | H | OCH₃ | OCH₃ | N |
| CF₃ | CH₃ | CH₃ | H | S | H | CH₃ | OCH₃ | N |
| CF₃ | —CH₂CH₂CH₂— | | H | O | H | OCH₃ | OCH₃ | CH |
| CF₃ | —CH₂CH₂CH₂— | | H | O | H | Cl | OCH₃ | CH |
| CF₃ | —CH₂CH₂CH₂— | | H | O | H | CH₃ | OCH₃ | CH |
| CF₃ | —CH₂CH₂CH₂— | | H | O | H | CH₃ | CH₃ | CH |
| CF₃ | —CH₂CH₂CH₂— | | H | O | H | OCH₃ | OCH₃ | N |
| CF₃ | —CH₂CH₂CH₂— | | H | O | H | CH₃ | OCH₃ | N |
| CF₃ | —CH₂CH₂CH₂— | | H | O | H | CH₃ | CH₃ | N |
| CF₃ | —CH₂CH₂CH₂— | | H | O | H | OCH₂CH₃ | OCH₂CH₃ | N |
| CF₃ | —CH₂CH₂CH₂— | | H | O | H | NHCH₃ | OCH₂CH₃ | N |
| CF₃ | —CH₂CH₂CH₂— | | H | O | H | N(CH₃)₂ | OCH₂CH₃ | N |
| CF₃ | —CH₂CH₂CH₂— | | H | O | H | N(CH₃)₂ | OCH₃ | N |
| CF₃ | —CH₂CH₂CH₂— | | H | O | H | N(CH₃)₂ | OCH₂CF₃ | N |
| CF₃ | —CH₂CH₂CH₂— | | H | O | CH₃ | CH₃ | OCH₃ | N |
| CF₃ | —CH₂CH₂CH₂— | | H | S | H | OCH₃ | OCH₃ | CH |
| CF₃ | —CH₂CH₂CH₂— | | H | S | H | Cl | OCH₃ | CH |
| CF₃ | —CH₂CH₂CH₂— | | H | S | H | CH₃ | OCH₃ | CH |
| CF₃ | —CH₂CH₂CH₂— | | H | S | H | CH₃ | CH₃ | CH |
| CF₃ | —CH₂CH₂CH₂— | | H | S | H | OCH₃ | OCH₃ | N |
| CF₃ | —CH₂CH₂CH₂— | | H | S | H | CH₃ | OCH₃ | N |
| CH₂CH₂Cl | CH₃ | H | H | O | H | OCH₃ | OCH₃ | CH |
| CH₂CH₂Cl | CH₃ | H | H | O | H | Cl | OCH₃ | CH |
| CH₂CH₂Cl | CH₃ | H | H | O | H | CH₃ | OCH₃ | CH |
| CH₂CH₂Cl | CH₃ | H | H | O | H | CH₃ | CH₃ | CH |
| CH₂CH₂Cl | CH₃ | H | H | O | H | OCH₃ | OCH₃ | N |
| CH₂CH₂Cl | CH₃ | H | H | O | H | CH₃ | OCH₃ | N |
| CH₂CH₂Cl | CH₃ | H | H | O | H | CH₃ | CH₃ | N |
| CH₂CH₂Cl | CH₃ | H | H | O | H | OCH₂CH₃ | OCH₂CH₃ | N |
| CH₂CH₂Cl | CH₃ | H | H | O | H | NHCH₃ | OCH₂CH₃ | N |
| CH₂CH₂Cl | CH₃ | H | H | O | H | N(CH₃)₂ | OCH₂CH₃ | N |
| CH₂CH₂Cl | CH₃ | H | H | O | H | N(CH )2 | OCH₃ | N |
| CH₂CH₂Cl | CH₃ | H | H | O | H | N(CH₃)₂ | OCH₂CF₃ | N |
| CH₂CH₂Cl | CH₃ | H | H | O | CH | CH₃ | OCH₃ | N |
| CH₂CH₂Cl | CH₃ | H | H | S | H | OCH₃ | OCH₃ | CH |
| CH₂CH₂Cl | CH₃ | H | H | S | H | Cl | OCH₃ | CH |
| CH₂CH₂Cl | CH₃ | H | H | S | H | CH₃ | OCH₃ | CH |
| CH₂CH₂Cl | CH₃ | H | H | S | H | CH₃ | CH₃ | CH |
| CH₂CH₂Cl | CH₃ | H | H | S | H | OCH₃ | OCH₃ | N |

-continued

| | | | | | | | | |
|---|---|---|---|---|---|---|---|---|
| CH₂CH₂Cl | CH₃ | H | H | S | H | CH₃ | OCH₃ | N |
| CH₂CH₂Cl | CH₂CH=CH₂ | H | H | O | H | OCH₃ | OCH₃ | CH |
| CH₂CH₂Cl | CH₂CH=CH₂ | H | H | O | H | Cl | OCH₃ | CH |
| CH₂CH₂Cl | CH₂CH=CH₂ | H | H | O | H | CH₃ | OCH₃ | CH |
| CH₂CH₂Cl | CH₂CH=CH₂ | H | H | O | H | CH₃ | CH₃ | CH |
| CH₂CH₂Cl | CH₂CH=CH₂ | H | H | O | H | OCH₃ | OCH₃ | N |
| CH₂CH₂Cl | CH₂CH=CH₂ | H | H | O | H | CH₃ | OCH₃ | N |
| CH₂CH₂Cl | CH₂CH=CH₂ | H | H | O | H | CH₃ | CH₃ | N |
| CH₂CH₂Cl | CH₂CH=CH₂ | H | H | O | H | OCH₂CH₃ | OCH₂CH₃ | N |
| CH₂CH₂Cl | CH₂CH=CH₂ | H | H | O | H | NHCH₃ | OCH₂CH₃ | N |
| CH₂CH₂Cl | CH₂CH=CH₂ | H | H | O | H | N(CH₃)₂ | OCH₂CH₃ | N |
| CH₂CH₂Cl | CH₂CH=CH₂ | H | H | O | H | N(CH₃)₂ | OCH₃ | N |
| CH₂CH₂Cl | CH₂CH=CH₂ | H | H | O | H | N(CH₃)₂ | OCH₂CF₃ | N |
| CH₂CH₂Cl | CH₂CH=CH₂ | H | H | O | CH₃ | CH₃ | OCH₃ | N |
| CH₂CH₂Cl | CH₂CH=CH₂ | H | H | S | H | OCH₃ | OCH₃ | CH |
| CH₂CH₂Cl | CH₂CH=CH₂ | H | H | S | H | Cl | OCH₃ | CH |
| CH₂CH₂Cl | CH₂CH=CH₂ | H | H | S | H | CH₃ | OCH₃ | CH |
| CH₂CH₂Cl | CH₂CH=CH₂ | H | H | S | H | CH₃ | CH₃ | CH |
| CH₂CH₂Cl | CH₂CH=CH₂ | H | H | S | H | OCH₃ | OCH₂ | N |
| CH₂CH₂Cl | CH₂CH=CH₂ | H | H | S | H | CH₃ | OCH₃ | N |
| CH₂CH₂Cl | CH₃ | CH₃ | H | O | H | OCH₃ | OCH₃ | CH |
| CH₂CH₂Cl | CH₃ | CH₃ | H | O | H | Cl | OCH₃ | CH |
| CH₂CH₂Cl | CH₃ | CH₃ | H | O | H | CH₃ | OCH₃ | CH |
| CH₂CH₂Cl | CH₃ | CH₃ | H | O | H | CH₃ | CH₃ | CH |
| CH₂CH₂Cl | CH₃ | CH₃ | H | O | H | OCH₃ | OCH₃ | N |
| CH₂CH₂Cl | CH₃ | CH₃ | H | O | H | CH₃ | OCH₃ | N |
| CH₂CH₂Cl | CH₃ | CH₃ | H | O | H | CH₃ | CH₃ | N |
| CH₂CH₂Cl | CH₃ | CH₃ | H | O | H | OCH₂CH₃ | OCH₂CH₃ | N |
| CH₂CH₂Cl | CH₃ | CH₃ | H | O | H | NHCH₃ | OCH₂CH₃ | N |
| CH₂CH₂Cl | CH₃ | CH₃ | H | O | H | N(CH₃)₂ | OCH₂CH₃ | N |
| CH₂CH₂Cl | CH₃ | CH₃ | H | O | H | N(CH₃)₂ | OCH₃ | N |
| CH₂CH₂Cl | CH₃ | CH₃ | H | O | H | N(CH₃)₂ | OCH₂CF₃ | N |
| CH₂CH₂Cl | CH₃ | CH₃ | H | O | CH₃ | CH₃ | OCH₃ | N |
| CH₂CH₂Cl | CH₃ | CH₃ | H | S | H | OCH₃ | OCH₃ | CH |
| CH₂CH₂Cl | CH₃ | CH₃ | H | S | H | Cl | OCH₃ | CH |
| CH₂CH₂Cl | CH₃ | CH₃ | H | S | H | CH₃ | OCH₃ | CH |
| CH₂CH₂Cl | CH₃ | CH₃ | H | S | H | CH₃ | CH₃ | CH |
| CH₂CH₂Cl | CH₃ | CH₃ | H | S | H | OCH₃ | OCH₃ | N |
| CH₂CH₂Cl | CH₃ | CH₃ | H | S | H | CH₃ | OCH₃ | N |
| CH₂CH₂Cl | —CH₂CH₂CH₂— | | H | O | H | OCH₃ | OCH₃ | CH |
| CH₂CH₂Cl | —CH₂CH₂CH₂— | | H | O | H | Cl | OCH₃ | CH |
| CH₂CH₂Cl | —CH₂CH₂CH₂— | | H | O | H | CH₃ | OCH₃ | CH |
| CH₂CH₂Cl | —CH₂CH₂CH₂— | | H | O | H | CH₃ | CH₃ | CH |
| CH₂CH₂Cl | —CH₂CH₂CH₂— | | H | O | H | OCH₃ | OCH₃ | N |
| CH₂CH₂Cl | —CH$_{CH2}$CH₂— | | H | O | H | CH₃ | CH₃ | N |
| CH₂CH₂Cl | —CH₂CH₂CH₂— | | H | O | H | OCH₂CH₃ | OCH₂CH₃ | N |
| CH₂CH₂Cl | —CH₂CH₂CH₂— | | H | O | H | NHCH₃ | OCH₂CH₃ | N |
| CH₂CH₂Cl | —CH₂CH₂CH₂— | | H | O | H | N(CH₃)₂ | OCH₂CH₃ | N |
| CH₂CH₂Cl | —CH₂CH₂CH₂— | | H | O | H | N(CH₃)₂ | OCH₃ | N |
| CH₂CH₂Cl | —CH₂CH₂CH₂— | | H | O | H | N(CH₃)₂ | OCH₂CF₃ | N |
| CH₂CH₂Cl | —CH₂CH₂CH₂— | | H | O | CH₃ | CH₃ | OCH₃ | N |
| CH₂CH₂Cl | —CH₂CH₂CH₂— | | H | S | H | OCH₃ | OCH₃ | CH |
| CH₂CH₂Cl | —CH₂CH₂CH₂— | | H | S | H | Cl | OCH₃ | CH |
| CH₂CH₂Cl | —CH₂CH₂CH₂— | | H | S | H | CH₃ | OCH₃ | CH |
| CH₂CH₂Cl | —CH₂CH₂CH₂— | | H | S | H | CH₃ | CH₃ | CH |
| CH₂CH₂Cl | —CH₂CH₂CH₂— | | H | S | H | OCH₃ | OCH₃ | N |
| CH₂CH₂Cl | —CH₂CH₂CH₂— | | H | S | H | CH₃ | OCH₃ | N |
| OCH₃ | CH₃ | H | H | O | H | OCH₃ | OCH₃ | CH |
| OCH₃ | CH₃ | H | H | O | H | Cl | OCH₃ | CH |
| OCH₃ | CH₃ | H | H | O | H | CH₃ | OCH₃ | CH |
| OCH₃ | CH₃ | H | H | O | H | CH₃ | CH₃ | CH |
| OCH₃ | CH₃ | H | H | O | H | OCH₃ | OCH₃ | N |
| OCH₃ | CH₃ | H | H | O | H | CH₃ | OCH₃ | N |
| OCH₃ | CH₃ | H | H | O | H | CH₃ | CH₃ | N |
| OCH₃ | CH₃ | H | H | O | H | OCH₂CH₃ | OCH₂CH₃ | N |
| OCH₃ | CH₃ | H | H | O | H | NHCH₃ | OCH₂CH₃ | N |
| OCH₃ | CH₃ | H | H | O | H | N(CH₃)₂ | OCH₂CH₃ | N |
| OCH₃ | CH₃ | H | H | O | H | N(CH₃)₂ | OCH₃ | N |
| OCH₃ | CH₃ | H | H | O | H | N(CH₃)₂ | OCH₂CF₃ | N |
| OCH₃ | CH₃ | H | H | O | CH₃ | CH₃ | OCH₃ | N |
| OCH₃ | CH₃ | H | H | S | H | OCH₃ | OCH₃ | CH |
| OCH₃ | CH₃ | H | H | S | H | Cl | OCH₃ | CH |
| OCH₃ | CH₃ | H | H | S | H | CH₃ | OCH₃ | CH |
| OCH₃ | CH₃ | H | H | S | H | CH₃ | CH₃ | CH |
| OCH₃ | CH₃ | H | H | S | H | OCH₃ | OCH₃ | N |
| OCH₃ | CH₃ | H | H | S | H | CH₃ | OCH₃ | N |
| OCH₃ | CH₂CH=CH₂ | H | H | O | H | OCH₃ | OCH₃ | CH |
| OCH₃ | CH₂CH=CH₂ | H | H | O | H | Cl | OCH₃ | CH |
| OCH₃ | CH₂CH=CH₂ | H | H | O | H | CH₃ | OCH₃ | CH |
| OCH₃ | CH₂CH=CH₂ | H | H | O | H | CH₃ | CH₃ | CH |
| OCH₃ | CH₂CH=CH₂ | H | H | O | H | OCH₃ | OCH₃ | N |

-continued

| | | | | | | | | |
|---|---|---|---|---|---|---|---|---|
| OCH₃ | CH₂CH=CH₂ | H | H | O | H | CH₃ | OCH₃ | N |
| OCH₃ | CH₂CH=CH₂ | H | H | O | H | CH₃ | CH₃ | N |
| OCH₃ | CH₂CH=CH₂ | H | H | O | H | OCH₂CH₃ | OCH₂CH₃ | N |
| OCH₃ | CH₂CH=CH₂ | H | H | O | H | NHCH₃ | OCH₂CH₃ | N |
| OCH₃ | CH₂CH=CH₂ | H | H | O | H | N(CH₃)₂ | OCH₂CH₃ | N |
| OCH₃ | CH₂CH=CH₂ | H | H | O | H | N(CH₃)₂ | OCH₃ | N |
| OCH₃ | CH₂CH=CH₂ | H | H | O | H | N(CH₃)₂ | OCH₂CF₃ | N |
| OCH₃ | CH₂CH=CH₂ | H | H | O | CH₃ | CH₃ | OCH₃ | N |
| OCH₃ | CH₂CH=CH₂ | H | H | S | H | OCH₃ | OCH₃ | CH |
| OCH₃ | CH₂CH=CH₂ | H | H | S | H | Cl | OCH₃ | CH |
| OCH₃ | CH₂CH=CH₂ | H | H | S | H | CH₃ | OCH₃ | CH |
| OCH₃ | CH₂CH=CH₂ | H | H | S | H | CH₃ | CH₃ | CH |
| OCH₃ | CH₂CH=CH₂ | H | H | S | H | OCH₃ | OCH₃ | N |
| OCH₃ | CH₂CH=CH₂ | H | H | S | H | CH₃ | OCH₃ | N |
| OCH₃ | CH₃ | CH₃ | H | O | H | OCH₃ | OCH₃ | CH |
| OCH₃ | CH₃ | CH₃ | H | O | H | Cl | OCH₃ | CH |
| OCH₃ | CH₃ | CH₃ | H | O | H | CH₃ | OCH₃ | CH |
| OCH₃ | CH₃ | CH₃ | H | O | H | CH₃ | CH₃ | CH |
| OCH₃ | CH₃ | CH₃ | H | O | H | OCH₃ | OCH₃ | N |
| OCH₃ | CH₃ | CH₃ | H | O | H | CH₃ | OCH₃ | N |
| OCH₃ | CH₃ | CH₃ | H | O | H | CH₃ | CH₃ | N |
| OCH₃ | CH₃ | CH₃ | H | O | H | OCH₂CH₃ | OCH₂CH₃ | N |
| OCH₃ | CH₃ | CH₃ | H | O | H | NHCH₃ | OCH₂CH₃ | N |
| OCH₃ | CH₃ | CH₃ | H | O | H | N(CH₃)₂ | OCH₂CH₃ | N |
| OCH₃ | CH₃ | CH₃ | H | O | H | N(CH₃)₂ | OCH₃ | N |
| OCH₃ | CH₃ | CH₃ | H | O | H | N(CH₃)₂ | OCH₂CF₃ | N |
| OCH₃ | CH₃ | CH₃ | H | O | CH | CH₃ | OCH₃ | N |
| OCH₃ | CH₃ | CH₃ | H | S | H | OCH₃ | OCH₃ | CH |
| OCH₃ | CH₃ | CH₃ | H | S | H | Cl | OCH₃ | CH |
| OCH₃ | CH₃ | CH₃ | H | S | H | CH₃ | OCH₃ | CH |
| OCH₃ | CH₃ | CH₃ | H | S | H | CH₃ | CH₃ | CH |
| OCH₃ | CH₃ | CH₃ | H | S | H | OCH₃ | OCH₃ | N |
| OCH₃ | CH₃ | CH₃ | H | S | H | CH₃ | OCH₃ | N |
| OCH₃ | —CH₂CH₂CH₂— | | H | O | H | OCH₃ | OCH₃ | CH |
| OCH₃ | —CH₂CH₂CH₂— | | H | O | H | Cl | OCH₃ | CH |
| OCH₃ | —CH₂CH₂CH₂— | | H | O | H | CH₃ | OCH₃ | CH |
| OCH₃ | —CH₂CH₂CH₂— | | H | O | H | CH₃ | CH₃ | CH |
| OCH₃ | —CH₂CH₂CH₂— | | H | O | H | OCH₃ | OCH₃ | N |
| OCH₃ | —CH₂CH₂CH₂— | | H | O | H | CH₃ | OCH₃ | N |
| OCH₃ | —CH₂CH₂CH₂— | | H | O | H | CH₃ | CH₃ | N |
| OCH₃ | —CH₂CH₂CH₂— | | H | O | H | OCH₂CH₃ | OCH₂CH₃ | N |
| OCH₃ | —CH₂CH₂CH₂— | | H | O | H | NHCH₃ | OCH₂CH₃ | N |
| OCH₃ | —CH₂CH₂CH₂— | | H | O | H | N(CH₃)₂ | OCH₂CH₃ | N |
| OCH₃ | —CH₂CH₂CH₂— | | H | O | H | N(CH₃)₂ | OCH₃ | N |
| OCH₃ | —CH₂CH₂CH₂— | | H | O | H | N(CH₃)₂ | OCH₂CF₃ | N |
| OCH₃ | —CH₂CH₂CH₂— | | H | O | CH₃ | CH₃ | OCH₃ | N |
| OCH₃ | —CH₂CH₂CH₂— | | H | S | H | OCH₃ | OCH₃ | CH |
| OCH₃ | —CH₂CH₂CH₂— | | H | S | H | Cl | OCH₃ | CH |
| OCH₃ | —CH₂CH₂CH₂— | | H | S | H | CH₃ | OCH₃ | CH |
| OCH₃ | —CH₂CH₂CH₂— | | H | S | H | CH₃ | CH₃ | CH |
| OCH₃ | —CH₂CH₂CH₂— | | H | S | H | OCH₃ | OCH₃ | N |
| OCH₃ | —CH₂CH₂CH₂— | | H | S | H | CH₃ | OCH₃ | N |
| OCF₂H | CH₃ | H | H | O | H | OCH₃ | OCH₃ | CH |
| OCF₂H | CH₃ | H | H | O | H | Cl | OCH₃ | CH |
| OCF₂H | CH₃ | H | H | O | H | CH₃ | OCH₃ | CH |
| OCF₂H | CH₃ | H | H | O | H | CH₃ | CH₃ | CH |
| OCF₂H | CH₃ | H | H | O | H | OCH₃ | OCH₃ | N |
| OCF₂H | CH₃ | H | H | O | H | CH₃ | OCH₃ | N |
| OCF₂H | CH₃ | H | H | O | H | CH₃ | CH₃ | N |
| OCF₂H | CH₃ | H | H | O | H | OCH₂CH₃ | OCH₂CH₃ | N |
| OCF₂H | CH₃ | H | H | O | H | NHCH₃ | OCH₂CH₃ | N |
| OCF₂H | CH₃ | H | H | O | H | N(CH₃)₂ | OCH₂CH₃ | N |
| OCF₂H | CH₃ | H | H | O | H | N(CH₃)₂ | OCH₃ | N |
| OCF₂H | CH₃ | H | H | O | H | N(CH₃)₂ | OCH₂CF₃ | N |
| OCF₂H | CH₃ | H | H | O | CH₃ | CH₃ | OCH₃ | N |
| OCF₂H | CH₃ | H | H | S | H | OCH₃ | OCH₃ | CH |
| OCF₂H | CH₃ | H | H | S | H | Cl | OCH₃ | CH |
| OCF₂H | CH₃ | H | H | S | H | CH₃ | OCH₃ | CH |
| OCF₂H | CH₃ | H | H | S | H | CH₃ | CH₃ | CH |
| OCF₂H | CH₃ | H | H | S | H | OCH₃ | OCH₃ | N |
| OCF₂H | CH₃ | H | H | S | H | CH₃ | OCH₃ | N |
| OCF₂H | CH₂CH=CH₂ | H | H | O | H | OCH₃ | OCH₃ | CH |
| OCF₂H | CH₂CH=CH₂ | H | H | O | H | Cl | OCH₃ | CH |
| OCF₂H | CH₂CH=CH₂ | H | H | O | H | CH₃ | OCH₃ | CH |
| OCF₂H | CH₂CH=CH₂ | H | H | O | H | CH₃ | CH₃ | CH |
| OCF₂H | CH₂CH=CH₂ | H | H | O | H | OCH₃ | OCH₃ | N |
| OCF₂H | CH₂CH=CH₂ | H | H | O | H | CH₃ | OCH₃ | N |
| OCF₂H | CH₂CH=CH₂ | H | H | O | H | CH₃ | CH₃ | N |
| OCF₂H | CH₂CH=CH₂ | H | H | O | H | OCH₂CH₃ | OCH₂CH₃ | N |
| OCF₂H | CH₂CH=CH₂ | H | H | O | H | NHCH₃ | OCH₂CH₃ | N |
| OCF₂H | CH₂CH=CH₂ | H | H | O | H | N(CH₃)₂ | OCH₂CH₃ | N |
| OCF₂H | CH₂CH=CH₂ | H | H | O | H | N(CH₃)₂ | OCH₃ | N |

| | | | | | | | | |
|---|---|---|---|---|---|---|---|---|
| OCF$_2$H | CH$_2$CH=CH$_2$ | | H | H | O | H | N(CH$_3$)$_2$ | OCH CF$_3$ | N |
| OCF$_2$H | CH$_2$CH=CH$_2$ | | H | H | O | CH | CH$_3$ | OCH$_3$ | N |
| OCF$_2$H | CH$_2$CH=CH$_2$ | | H | H | S | H | OCH$_3$ | OCH$_3$ | CH |
| OCF$_2$H | CH$_2$CH=CH$_2$ | | H | H | S | H | Cl | OCH$_3$ | CH |
| OCF$_2$H | CH$_2$CH=CH$_2$ | | H | H | S | H | CH$_3$ | OCH$_3$ | CH |
| OCF$_2$H | CH$_2$CH=CH$_2$ | | H | H | S | H | CH$_3$ | CH$_3$ | CH |
| OCF$_2$H | CH$_2$CH=CH$_2$ | | H | H | S | H | OCH$_3$ | OCH$_3$ | N |
| OCF$_2$H | CH$_2$CH=CH$_2$ | | H | H | S | H | CH$_3$ | OCH$_3$ | N |
| OCF$_2$H | CH$_3$ | CH$_3$ | H | O | H | OCH$_3$ | OCH$_3$ | CH |
| OCF$_2$H | CH$_3$ | CH$_3$ | H | O | H | Cl | OCH$_3$ | CH |
| OCF$_2$H | CH$_3$ | CH$_3$ | H | O | H | CH$_3$ | OCH$_3$ | CH |
| OCF$_2$H | CH$_3$ | CH$_3$ | H | O | H | CH$_3$ | CH$_3$ | CH |
| OCF$_2$H | CH$_3$ | CH$_3$ | H | O | H | OCH$_3$ | OCH$_3$ | N |
| OCF$_2$H | CH$_3$ | CH$_3$ | H | O | H | CH$_3$ | OCH$_3$ | N |
| OCF$_2$H | CH$_3$ | CH$_3$ | H | O | H | CH$_3$ | CH$_3$ | N |
| OCF$_2$H | CH$_3$ | CH$_3$ | H | O | H | OCH$_2$CH$_3$ | OCH$_2$CH$_3$ | N |
| OCF$_2$H | CH$_3$ | CH$_3$ | H | O | H | NHCH$_3$ | OCH$_2$CH$_3$ | N |
| OCF$_2$H | CH$_3$ | CH$_3$ | H | O | H | N(CH$_3$)$_2$ | OCH$_2$CH$_3$ | N |
| OCF$_2$H | CH$_3$ | CH$_3$ | H | O | H | N(CH$_3$)$_2$ | OCH$_3$ | N |
| OCF$_2$H | CH$_3$ | CH$_3$ | H | O | H | N(CH$_3$)$_2$ | OCH$_2$CF$_3$ | N |
| OCF$_2$H | CH$_3$ | CH$_3$ | H | O | CH$_3$ | CH$_3$ | OCH$_3$ | N |
| OCF$_2$H | CH$_3$ | CH$_3$ | H | S | H | OCH$_3$ | OCH$_3$ | CH |
| OCF$_2$H | CH$_3$ | CH$_3$ | H | S | H | Cl | OCH$_3$ | CH |
| OCF$_2$H | CH$_3$ | CH$_3$ | H | S | H | CH$_3$ | OCH$_3$ | CH |
| OCF$_2$H | CH$_3$ | CH$_3$ | H | S | H | CH$_3$ | CH$_3$ | CH |
| OCF$_2$H | CH$_3$ | CH$_3$ | H | S | H | OCH$_3$ | OCH$_3$ | N |
| OCF$_2$H | CH$_3$ | CH$_3$ | H | S | H | CH$_3$ | OCH$_3$ | N |
| OCF$_2$H | —CH$_2$CH$_2$CH$_2$— | | H | O | H | OCH$_3$ | OCH$_3$ | CH |
| OCF$_2$H | —CH$_2$CH$_2$CH$_2$— | | H | O | H | Cl | OCH$_3$ | CH |
| OCF$_2$H | —CH$_2$CH$_2$CH$_2$— | | H | O | H | CH$_3$ | OCH$_3$ | CH |
| OCF$_2$H | —CH$_2$CH$_2$CH$_2$— | | H | O | H | CH$_3$ | CH$_3$ | CH |
| OCF$_2$H | —CH$_2$CH$_2$CH$_2$— | | H | O | H | OCH$_3$ | OCH$_3$ | N |
| OCF$_2$H | —CH$_2$CH$_2$CH$_2$— | | H | O | H | CH$_3$ | OCH$_3$ | N |
| OCF$_2$H | —CH$_2$CH$_2$CH$_2$— | | H | O | H | CH$_3$ | CH$_3$ | N |
| OCF$_2$H | —CH$_2$CH$_2$CH$_2$— | | H | O | H | OCH$_2$CH$_3$ | OCH$_2$CH$_3$ | N |
| OCF$_2$H | —CH$_2$CH$_2$CH$_2$— | | H | O | H | NHCH$_3$ | OCH$_2$CH$_3$ | N |
| OCF$_2$H | —CH$_2$CH$_2$CH$_2$— | | H | O | H | N(CH$_3$)$_2$ | OCH$_2$CH$_3$ | N |
| OCF$_2$H | —CH$_2$CH$_2$CH$_2$— | | H | O | H | N(CH$_3$)$_2$ | OCH$_3$ | N |
| OCF$_2$H | —CH$_2$CH$_2$CH$_2$— | | H | O | H | N(CH$_3$)$_2$ | OCH$_2$CF$_3$ | N |
| OCF$_2$H | —CH$_2$CH$_2$CH$_2$— | | H | O | CH | CH$_3$ | OCH$_3$ | N |
| OCF$_2$H | —CH$_2$CH$_2$CH$_2$— | | H | S | H | OCH$_3$ | OCH$_3$ | CH |
| OCF$_2$H | —CH$_2$CH$_2$CH$_2$— | | H | S | H | Cl | OCH$_3$ | CH |
| OCF$_2$H | —CH$_2$CH$_2$CH$_2$— | | H | S | H | CH$_3$ | OCH$_3$ | CH |
| OCF$_2$H | —CH$_2$CH$_2$CH$_2$— | | H | S | H | OCH$_3$ | OCH$_3$ | N |
| OCF$_2$H | —CH$_2$CH$_2$CH$_2$— | | H | S | H | CH$_3$ | OCH$_3$ | N |
| SCF$_2$H | CH$_3$ | H | H | O | H | OCH$_3$ | OCH$_3$ | CH |
| SCF$_2$H | CH$_3$ | H | H | O | H | Cl | OCH$_3$ | CH |
| SCF$_2$H | CH$_3$ | H | H | O | H | CH$_3$ | OCH$_3$ | CH |
| SCF$_2$H | CH$_3$ | H | H | O | H | CH$_3$ | CH$_3$ | CH |
| SCF$_2$H | CH$_3$ | H | H | O | H | OCH$_3$ | OCH$_3$ | N |
| SCF$_2$H | CH$_3$ | H | H | O | H | CH$_3$ | OCH$_3$ | N |
| SCF$_2$H | CH$_3$ | H | H | O | H | CH$_3$ | CH$_3$ | N |
| SCF$_2$H | CH$_3$ | H | H | O | H | OCH$_2$CH$_3$ | OCH$_2$CH$_3$ | N |
| SCF$_2$H | CH$_3$ | H | H | O | H | NHCH$_3$ | OCH$_2$CH$_3$ | N |
| SCF$_2$H | CH$_3$ | H | H | O | H | N(CH$_3$)$_2$ | OCH$_2$CH$_3$ | N |
| SCF$_2$H | CH$_3$ | H | H | O | H | N(CH$_3$)$_2$ | OCH$_3$ | N |
| SCF$_2$H | CH$_3$ | H | H | O | H | N(CH$_3$)$_2$ | OCH$_2$CF$_3$ | N |
| SCF$_2$H | CH$_3$ | H | H | O | CH$_3$ | CH$_3$ | OCH$_3$ | N |
| SCF$_2$H | CH$_3$ | H | H | S | H | OCH$_3$ | OCH$_3$ | CH |
| SCF$_2$H | CH$_3$ | H | H | S | H | Cl | OCH$_3$ | CH |
| SCF$_2$H | CH$_3$ | H | H | S | H | CH$_3$ | OCH$_3$ | CH |
| SCF$_2$H | CH$_3$ | H | H | S | H | CH$_3$ | CH$_3$ | CH |
| SCF$_2$H | CH$_3$ | H | H | S | H | OCH$_3$ | OCH$_3$ | N |
| SCF$_2$H | CH$_3$ | H | H | S | H | CH$_3$ | OCH$_3$ | N |
| SCF$_2$H | CH$_2$CH=CH$_2$ | H | H | O | H | OCH$_3$ | OCH$_3$ | CH |
| SCF$_2$H | CH$_2$CH=CH$_2$ | H | H | O | H | Cl | OCH$_3$ | CH |
| SCF$_2$H | CH$_2$CH=CH$_2$ | H | H | O | H | CH$_3$ | OCH$_3$ | CH |
| SCF$_2$H | CH$_2$CH=CH$_2$ | H | H | O | H | CH$_3$ | CH$_3$ | CH |
| SCF$_2$H | CH$_2$CH=CH$_2$ | H | H | O | H | OCH$_3$ | OCH$_3$ | N |
| SCF$_2$H | CH$_2$CH=CH$_2$ | H | H | O | H | CH$_3$ | OCH$_3$ | N |
| SCF$_2$H | CH$_2$CH=CH$_2$ | H | H | O | H | CH$_3$ | CH$_3$ | N |
| SCF$_2$H | CH$_2$CH=CH$_2$ | H | H | O | H | OCH$_2$CH$_3$ | OCH$_2$CH$_3$ | N |
| SCF$_2$H | CH$_2$CH=CH$_2$ | H | H | O | H | NHCH$_3$ | OCH$_2$CH$_3$ | N |
| SCF$_2$H | CH$_2$CH=CH$_2$ | H | H | O | H | N(CH$_3$)$_2$ | OCH$_2$CH$_3$ | N |
| SCF$_2$H | CH$_2$CH=CH$_2$ | H | H | O | H | N(CH$_3$)$_2$ | OCH$_3$ | N |
| SCF$_2$H | CH$_2$CH=CH$_2$ | H | H | O | H | N(CH$_3$)$_2$ | OCH$_2$CF$_3$ | N |
| SCF$_2$H | CH$_2$CH=CH$_2$ | H | H | O | CH$_3$ | CH$_3$ | OCH$_3$ | N |
| SCF$_2$H | CH$_2$CH=CH$_2$ | H | H | S | H | OCH$_3$ | OCH$_3$ | CH |
| SCF$_2$H | CH$_2$CH=CH$_2$ | H | H | S | H | Cl | OCH$_3$ | CH |
| SCF$_2$H | CH$_2$CH=CH$_2$ | H | H | S | H | CH$_3$ | OCH$_3$ | CH |
| SCF$_2$H | CH$_2$CH=CH$_2$ | H | H | S | H | CH$_3$ | CH$_3$ | CH |

-continued

| | | | | | | | | |
|---|---|---|---|---|---|---|---|---|
| SCF₂H | CH₂CH=CH₂ | | H | H | S | H | OCH₃ | OCH₃ | N |
| SCF₂H | CH₂CH=CH₂ | | H | H | S | H | CH₃ | OCH₃ | N |
| SCF₂H | CH₃ | CH₃ | H | O | H | OCH₃ | OCH₃ | CH |
| SCF₂H | CH₃ | CH₃ | H | O | H | Cl | OCH₃ | CH |
| SCF₂H | CH₃ | CH₃ | H | O | H | CH₃ | OCH₃ | CH |
| SCF₂H | CH₃ | CH₃ | H | O | H | CH₃ | CH₃ | CH |
| SCF₂H | CH₃ | CH₃ | H | O | H | OCH₃ | OCH₃ | N |
| SCF₂H | CH₃ | CH₃ | H | O | H | CH₃ | OCH₃ | N |
| SCF₂H | CH₃ | CH₃ | H | O | H | CH₃ | CH₃ | N |
| SCF₂H | CH₃ | CH₃ | H | O | H | OCH₂CH₃ | OCH₂CH₃ | N |
| SCF₂H | CH₃ | CH₃ | H | O | H | NHCH₃ | OCH₂CH₃ | N |
| SCF₂H | CH₃ | CH₃ | H | O | H | N(CH₃)₂ | OCH₂CH₃ | N |
| SCF₂H | CH₃ | CH₃ | H | O | H | N(CH₃)₂ | OCH₃ | N |
| SCF₂H | CH₃ | CH₃ | H | O | H | N(CH₃)₂ | OCH₂CF₃ | N |
| SCF₂H | CH₃ | CH₃ | H | O | CH₃ | CH₃ | OCH₃ | N |
| SCF₂H | CH₃ | CH₃ | H | S | H | OCH₃ | OCH₃ | CH |
| SCF₂H | CH₃ | CH₃ | H | S | H | Cl | OCH₃ | CH |
| SCF₂H | CH₃ | CH₃ | H | S | H | CH₃ | OCH₃ | CH |
| SCF₂H | CH₃ | CH₃ | H | S | H | CH₃ | CH₃ | CH |
| SCF₂H | CH₃ | CH₃ | H | S | H | OCH₃ | OCH₃ | N |
| SCF₂H | CH₃ | CH₃ | H | S | H | CH₃ | OCH₃ | N |
| SCF₂H | —CH₂CH₂CH₂— | | H | O | H | OCH₃ | OCH₃ | CH |
| SCF₂H | —CH₂CH₂CH₂— | | H | O | H | Cl | OCH₃ | CH |
| SCF₂H | —CH₂CH₂CH₂— | | H | O | H | CH₃ | OCH₃ | CH |
| SCF₂H | —CH₂CH₂CH₂— | | H | O | H | CH₃ | CH₃ | CH |
| SCF₂H | —CH₂CH₂CH₂— | | H | O | H | OCH₃ | OCH₃ | N |
| SCF₂H | —CH₂CH₂CH₂— | | H | O | H | CH₃ | OCH₃ | N |
| SCF₂H | —CH₂CH₂CH₂— | | H | O | H | CH₃ | CH₃ | N |
| SCF₂H | —CH₂CH₂CH₂— | | H | O | H | OCH₂CH₃ | OCH₂CH₃ | N |
| SCF₂H | —CH₂CH₂CH₂— | | H | O | H | NHCH₃ | OCH₂CH₃ | N |
| SCF₂H | —CH₂CH₂CH₂— | | H | O | H | N(CH₃)₂ | OCH₂CH₃ | N |
| SCF₂H | —CH₂CH₂CH₂— | | H | O | H | N(CH₃)₂ | OCH₃ | N |
| SCF₂H | —CH₂CH₂CH₂— | | H | O | H | N(CH₃)₂ | OCH₂CF₃ | N |
| SCF₂H | —CH₂CH₂CH₂— | | H | O | H | CH₃ | OCH₃ | CH |
| SCF₂H | —CH₂CH₂CH₂— | | H | S | H | OCH₃ | OCH₃ | CH |
| SCF₂H | —CH₂CH₂CH₂— | | H | S | H | Cl | OCH₃ | CH |
| SCF₂H | —CH₂CH₂CH₂— | | H | S | H | CH₃ | OCH₃ | CH |
| SCF₂H | —CH₂CH₂CH₂— | | H | S | H | CH₃ | CH₃ | CH |
| SCF₂H | —CH₂CH₂CH₂— | | H | S | H | OCH₃ | OCH₃ | N |
| SCF₂H | —CH₂CH₂CH₂— | | H | S | H | CH₃ | OCH₃ | N |
| NO₂ | CH₃ | | H | H | O | H | OCH₃ | OCH₃ | CH |
| NO₂ | CH₃ | | H | H | O | H | Cl | OCH₃ | CH |
| NO₂ | CH₃ | | H | H | O | H | CH₃ | OCH₃ | CH |
| NO₂ | CH₃ | | H | H | O | H | CH₃ | CH₃ | CH |
| NO₂ | CH₂ | | H | H | O | H | OCH₃ | OCH₃ | N |
| NO₂ | CH₃ | | H | H | O | H | CH₃ | OCH₃ | N |
| NO₂ | CH₃ | | H | H | O | H | CH₃ | CH₃ | N |
| NO₂ | CH₃ | | H | H | O | H | OCH₂CH₃ | OCH₂CH₃ | N |
| NO₂ | CH₃ | | H | H | O | H | NHCH₃ | OCH₂CH₃ | N |
| NO₂ | CH₃ | | H | H | O | H | N(CH₃)₂ | OCH₂CH₃ | N |
| NO₂ | CH₃ | | H | H | O | H | N(CH₃)₂ | OCH₃ | N |
| NO₂ | CH₃ | | H | H | O | H | N(CH₃)₂ | OCH₃CF₃ | N |
| NO₂ | CH₃ | | H | H | O | CH₃ | CH₃ | OCH₃ | N |
| NO₂ | CH₃ | | H | H | S | H | OCH₃ | OCH₃ | CH |
| NO₂ | CH₃ | | H | H | S | H | Cl | OCH₃ | CH |
| NO₂ | CH₃ | | H | H | S | H | CH₃ | OCH₃ | CH |
| NO₂ | CH₃ | | H | H | S | H | CH₃ | CH₃ | CH |
| NO₂ | CH₃ | | H | H | S | H | OCH₃ | OCH₃ | N |
| NO₂ | CH₃ | | H | H | S | H | CH₃ | OCH₃ | N |
| NO₂ | CH₂CH=CH₂ | | H | H | O | H | OCH₃ | OCH₃ | CH |
| NO₂ | CH₂CH=CH₂ | | H | H | O | H | Cl | OCH₃ | CH |
| NO₂ | CH₂CH=CH₂ | | H | H | O | H | CH₃ | OCH₃ | CH |
| NO₂ | CH₂CH=CH₂ | | H | H | O | H | CH₃ | CH₃ | CH |
| NO₂ | CH₂CH=CH₂ | | H | H | O | H | OCH₃ | OCH₃ | N |
| NO₂ | CH₂CH=CH₂ | | H | H | O | H | CH₃ | OCH₃ | N |
| NO₂ | CH₂CH=CH₂ | | H | H | O | H | CH₃ | CH₃ | N |
| NO₂ | CH₂CH=CH₂ | | H | H | O | H | OCH₂CH₃ | OCH₂CH₃ | N |
| NO₂ | CH₂CH=CH₂ | | H | H | O | H | NHCH₃ | CH₂CH₃ | N |
| NO₂ | CH₂CH=CH₂ | | H | H | O | H | N(CH₃)₂ | OCH₂CH₃ | N |
| NO₂ | CH₂CH=CH₂ | | H | H | O | H | N(CH₃)₂ | OCH₃ | N |
| NO₂ | CH₂CH=CH₂ | | H | H | O | H | N(CH₃)₂ | OCH₂CF₃ | N |
| NO₂ | CH₂CH=CH₂ | | H | H | O | CH₃ | CH₃ | OCH₃ | N |
| NO₂ | CH₂CH=CH₂ | | H | H | S | H | OCH₃ | OCH₃ | CH |
| NO₂ | CH₂CH=CH₂ | | H | H | S | H | Cl | OCH₃ | CH |
| NO₂ | CH₂CH=CH₂ | | H | H | S | H | CH₃ | OCH₃ | CH |
| NO₂ | CH₂CH=CH₂ | | H | H | S | H | CH₃ | CH₃ | CH |
| NO₂ | CH₂CH=CH₂ | | H | H | S | H | OCH₃ | OCH₃ | N |
| NO₂ | CH₂CH=CH₂ | | H | H | S | H | CH₃ | OCH₃ | N |
| NO₂ | CH₃ | CH₃ | H | O | H | OCH₃ | OCH₃ | CH |
| NO₂ | CH₃ | CH₃ | H | O | H | Cl | OCH₃ | CH |
| NO₂ | CH₃ | CH₃ | H | O | H | CH₃ | OCH₃ | CH |
| NO₂ | CH₃ | CH₃ | H | O | H | CH₃ | CH₃ | CH |

-continued

| | | | | | | | | |
|---|---|---|---|---|---|---|---|---|
| NO₂ | CH₃ | CH₃ | H | O | H | OCH₃ | OCH₃ | N |
| NO₂ | CH₃ | CH₃ | H | O | H | CH₃ | OCH₃ | N |
| NO₂ | CH₃ | CH₃ | H | O | H | CH₃ | CH₃ | N |
| NO₂ | CH₃ | CH₃ | H | O | H | OCH₂CH₃ | OCH₂CH₃ | N |
| NO₂ | CH₃ | CH₃ | H | O | H | NHCH₃ | OCH₂CH₃ | N |
| NO₂ | CH₃ | CH₃ | H | O | H | N(CH₃)₂ | OCH₂CH₃ | N |
| NO₂ | CH₃ | CH₃ | H | O | H | N(CH₃)₂ | OCH₃ | N |
| NO₂ | CH₃ | CH₃ | H | O | H | N(CH₃)₂ | OCH₂CF₃ | N |
| NO₂ | CH₃ | CH₃ | H | O | CH₃ | CH₃ | OCH₃ | N |
| NO₂ | CH₃ | CH₃ | H | S | H | OCH₃ | OCH₃ | CH |
| NO₂ | CH₃ | CH₃ | H | S | H | Cl | OCH₃ | CH |
| NO₂ | CH₃ | CH₃ | H | S | H | CH₃ | OCH₃ | CH |
| NO₂ | CH₃ | CH₃ | H | S | H | CH₃ | CH₃ | CH |
| NO₂ | CH₃ | CH₃ | H | S | H | OCH₃ | OCH₃ | N |
| NO₂ | CH₃ | CH₃ | H | S | H | CH₃ | OCH₃ | N |
| NO₂ | —CH₂CH₂CH₂— | | H | O | H | OCH₃ | OCH₃ | CH |
| NO₂ | —CH₂CH₂CH₂— | | H | O | H | Cl | OCH₃ | CH |
| NO₂ | —CH₂CH₂CH₂— | | H | O | H | CH₃ | OCH₃ | CH |
| NO₂ | —CH₂CH₂CH₂— | | H | O | H | CH₃ | CH₃ | CH |
| NO₂ | —CH₂CH₂CH₂— | | H | O | H | OCH₃ | OCH₃ | N |
| NO₂ | —CH₂CH₂CH₂— | | H | O | H | CH₃ | OCH₃ | N |
| NO₂ | —CH₂CH₂CH₂— | | H | O | H | CH₃ | CH₃ | N |
| NO₂ | —CH₂CH₂CH₂— | | H | O | H | OCH₂CH₃ | OCH₂CH₃ | N |
| NO₂ | —CH₂CH₂CH₂— | | H | O | H | NHCH₃ | OCH₂CH₃ | N |
| NO₂ | —CH₂CH₂CH₂— | | H | O | H | N(CH₃)₂ | OCH₂CH₃ | N |
| NO₂ | —CH₂CH₂CH₂— | | H | O | H | N(CH₃)₂ | OCH₃ | N |
| NO₂ | —CH₂CH₂CH₂— | | H | O | H | N(CH₃)₂ | OCH₂CF₃ | N |
| NO₂ | —CH₂CH₂CH₂— | | H | O | CH₃ | CH₃ | OCH₃ | N |
| NO₂ | —CH₂CH₂CH₂— | | H | S | H | OCH₃ | OCH₃ | CH |
| NO₂ | —CH₂CH₂CH₂— | | H | S | H | Cl | OCH₃ | CH |
| NO₂ | —CH₂CH₂CH₂— | | H | S | H | CH₃ | OCH₃ | CH |
| NO₂ | —CH₂CH₂CH₂— | | H | S | H | CH₃ | CH₃ | CH |
| NO₂ | —CH₂CH₂CH₂— | | H | S | H | OCH₃ | OCH₃ | N |
| NO₂ | —CH₂CH₂CH₂— | | H | S | H | CH₃ | OCH₃ | N |
| SO₂CF₂H | CH₃ | | H | H | O | H | OCH₃ | CH₃ | CH |
| SO₂CF₂H | CH₃ | | H | H | O | H | Cl | OCH₃ | CH |
| SO₂CF₂H | CH₃ | | H | H | O | H | CH₃ | OCH₃ | CH |
| SO₂CF₂H | CH₃ | | H | H | O | H | CH₃ | CH₃ | CH |
| SO₂CF₂H | CH₃ | | H | H | O | H | OCH₃ | OCH₃ | N |
| SO₂CF₂H | CH₃ | | H | H | O | H | CH₃ | OCH₃ | N |
| SO₂CF₂H | CH₃ | | H | H | O | H | CH₃ | CH₃ | N |
| SO₂CF₂H | CH₃ | | H | H | O | H | OCH₂CH₃ | OCH₂CH₃ | N |
| SO₂CF₂H | CH₃ | | H | H | O | H | NHCH₃ | OCH₃CH₃ | N |
| SO₂CF₂H | CH₃ | | H | H | O | H | N(CH₃)₂ | OCH₂CH₃ | N |
| SO₂CF₂H | CH₃ | | H | H | O | H | N(CH₃)₂ | OCH₃ | N |
| SO₂CF₂H | CH₃ | | H | H | O | H | N(CH₃)₂ | OCH₂CF₃ | N |
| SO₂CF₂H | CH₃ | | H | H | O | CH₃ | CH₃ | OCH₃ | N |
| SO₂CF₂H | CH₃ | | H | H | S | H | OCH₃ | OCH₃ | CH |
| SO₂CF₂H | CH₃ | | H | H | S | H | Cl | OCH₃ | CH |
| SO₂CF₂H | CH₃ | | H | H | S | H | CH₃ | OCH₃ | CH |
| SO₂CF₂H | CH₃ | | H | H | S | H | CH₃ | CH₃ | CH |
| SO₂CF₂H | CH₃ | | H | H | S | H | OCH₃ | OCH₃ | N |
| SO₂CF₂H | CH₃ | | H | H | S | H | CH₃ | OCH₃ | N |
| SO₂CF₂H | CH₂CH=CH₂ | | H | H | O | H | OCH₃ | OCH₃ | CH |
| SO₂CF₂H | CH₂CH=CH₂ | | H | H | O | H | Cl | OCH₃ | CH |
| SO₂CF₂H | CH₂CH=CH₂ | | H | H | O | H | CH₃ | OCH₃ | CH |
| SO₂CF₂H | CH₂CH=CH₂ | | H | H | O | H | CH₃ | CH₃ | CH |
| SO₂CF₂H | CH₂CH=CH₂ | | H | H | O | H | OCH₃ | OCH₃ | N |
| SO₂CF₂H | CH₂CH=CH₂ | | H | H | O | H | CH₃ | OCH₃ | N |
| SO₂CF₂H | CH₂CH=CH₂ | | H | H | O | H | CH₃ | CH₃ | N |
| SO₂CF₂H | CH₂CH=CH₂ | | H | H | O | H | OCH₂CH₃ | OCH₂CH₃ | N |
| SO₂CF₂H | CH₂CH=CH₂ | | H | H | O | H | NHCH₃ | OCH₂CH₃ | N |
| SO₂CF₂H | CH₂CH=CH₂ | | H | H | O | H | N(CH₃)₂ | OCH₂CH₃ | N |
| SO₂CF₂H | CH₂CH=CH₂ | | H | H | O | H | N(CH₃)₂ | OCH₃ | N |
| SO₂CF₂H | CH₂CH=CH₂ | | H | H | O | H | N(CH₃)₂ | OCH₂CF₃ | N |
| SO₂CF₂H | CH₂CH=CH₂ | | H | H | O | CH₃ | CH₃ | OCH₃ | N |
| SO₂CF₂H | CH₂CH=CH₂ | | H | H | S | H | OCH₃ | OCH₃ | CH |
| SO₂CF₂H | CH₂CH=CH₂ | | H | H | S | H | Cl | OCH₃ | CH |
| SO₂CF₂H | CH₂CH=CH₂ | | H | H | S | H | CH₃ | OCH₃ | CH |
| SO₂CF₂H | CH₂CH=CH₂ | | H | H | S | H | CH₃ | CH₃ | CH |
| SO₂CF₂H | CH₂CH=CH₂ | | H | H | S | H | OCH₃ | OCH₃ | N |
| SO₂CF₂H | CH₂CH=CH₂ | | H | H | S | H | CH₃ | OCH₃ | N |
| SO₂CF₂H | CH₃ | CH₃ | H | O | H | OCH₃ | OCH₃ | CH |
| SO₂CF₂H | CH₃ | CH₃ | H | O | H | Cl | OCH₃ | CH |
| SO₂CF₂H | CH₃ | CH₃ | H | O | H | CH₃ | OCH₃ | CH |
| SO₂CF₂H | CH₃ | CH₃ | H | O | H | CH₃ | CH₃ | CH |
| SO₂CF₂H | CH₃ | CH₃ | H | O | H | OCH₃ | OCH₃ | N |
| SO₂CF₂H | CH₃ | CH₃ | H | O | H | CH₃ | OCH₃ | N |
| SO₂CF₂H | CH₃ | CH₃ | H | O | H | CH₃ | CH₃ | N |
| SO₂CF₂H | CH₃ | CH₃ | H | O | H | OCH₂CH₃ | OCH₂CH₃ | N |
| SO₂CF₂H | CH₃ | CH₃ | H | O | H | NHCH₃ | OCH₂CH₃ | N |
| SO₂CF₂H | CH₃ | CH₃ | H | O | H | N(CH₃)₂ | OCH₂CH₃ | N |

| | | | | | | | |
|---|---|---|---|---|---|---|---|
| SO₂CF₂H | CH₃ | CH₃ | H | O | H | N(CH₃)₂ | OCH₃ | N |
| SO₂CF₂H | CH₃ | CH₃ | H | O | H | N(CH₃)₂ | OCH₂CF₃ | N |
| SO₂CF₂H | CH₃ | CH₃ | H | O | CH₃ | CH₃ | OCH₃ | N |
| SO₂CF₂H | CH₃ | CH₃ | H | S | H | OCH₃ | OCH₃ | CH |
| SO₂CF₂H | CH₃ | CH₃ | H | S | H | Cl | OCH₃ | CH |
| SO₂CF₂H | CH₃ | CH₃ | H | S | H | CH₃ | OCH₃ | CH |
| SO₂CF₂H | CH₃ | CH₃ | H | S | H | CH₃ | CH₃ | CH |
| SO₂CF₂H | CH₃ | CH₃ | H | S | H | OCH₃ | OCH₃ | N |
| SO₂CF₂H | CH₃ | CH₃ | H | S | H | CH₃ | OCH₃ | N |
| SO₂CF₂H | —CH₂CH₂CH₂— | | H | O | H | OCH₃ | OCH₃ | CH |
| SO₂CF₂H | —CH₂CH₂CH₂— | | H | O | H | Cl | OCH₃ | CH |
| SO₂CF₂H | —CH₂CH₂CH₂— | | H | O | H | CH₃ | OCH₃ | CH |
| SO₂CF₂H | —CH₂CH₂CH₂— | | H | O | H | CH₃ | CH₃ | CH |
| SO₂CF₂H | —CH₂CH₂CH₂— | | H | O | H | OCH₃ | OCH₃ | N |
| SO₂CF₂H | —CH₂CH₂CH₂— | | H | O | H | CH₃ | OCH₃ | N |
| SO₂CF₂H | —CH₂CH₂CH₂— | | H | O | H | CH₃ | CH₃ | N |
| SO₂CF₂H | —CH₂CH₂CH₂— | | H | O | H | OCH₂CH₃ | OCH₂CH₃ | N |
| SO₂CF₂H | —CH₂CH₂CH₂— | | H | O | H | NHCH₃ | OCH₂CH₃ | N |
| SO₂CF₂H | —CH₂CH₂CH₂— | | H | O | H | N(CH₃)₂ | OCH₂CH₃ | N |
| SO₂CF₂H | —CH₂CH₂CH₂— | | H | O | H | N(CH₃)₂ | OCH₃ | N |
| SO₂CF₂H | —CH₂CH₂CH₂— | | H | O | H | N(CH₃)₂ | OCH₂CF₃ | N |
| SO₂CF₂H | —CH₂CH₂CH₂— | | H | O | CH₃ | CH₃ | OCH₃ | N |
| SO₂CF₂H | —CH₂CH₂CH₂— | | H | S | H | OCH₃ | OCH₃ | CH |
| SO₂CF₂H | —CH₂CH₂CH₂— | | H | S | H | Cl | OCH₃ | CH |
| SO₂CF₂H | —CH₂CH₂CH₂— | | H | S | H | CH₃ | OCH₃ | CH |
| SO₂CF₂H | —CH₂CH₂CH₂— | | H | S | H | CH₃ | CH₃ | CH |
| SO₂CF₂H | —CH₂CH₂CH₂— | | H | S | H | OCH₃ | OCH₃ | N |
| SO₂CF₂H | —CH₂CH₂CH₂— | | H | S | H | CH₃ | OCH₃ | N |

TABLE II

GENERAL STRUCTURE 2

| R₁ | R₂ | R₃ | R | X | Y | Z |
|---|---|---|---|---|---|---|
| H | H | H | H | OCH₃ | OCH₃ | CH |
| H | H | H | H | Cl | OCH₃ | CH |
| H | H | H | H | CH₃ | OCH₃ | CH |
| H | H | H | H | CH₃ | CH₃ | CH |
| H | H | H | H | OCH₃ | OCH₃ | N |
| H | H | H | H | CH₃ | OCH₃ | N |
| H | H | H | H | NHCH₃ | OCH₂CH₃ | N |
| H | H | H | CH₃ | CH₃ | OCH₃ | N |
| H | CH₃ | H | H | OCH₃ | OCH₃ | CH |
| H | CH₃ | H | H | Cl | OCH₃ | CH |
| H | CH₃ | H | H | CH₃ | OCH₃ | CH |
| H | CH₃ | H | H | CH₃ | CH₃ | CH |
| H | CH₃ | H | H | OCH₃ | OCH₃ | N |
| H | CH₃ | H | H | CH₃ | OCH₃ | N |
| H | CH₃ | H | H | NHCH₃ | OCH₂CH₃ | N |
| H | CH₃ | H | CH₃ | CH₃ | OCH₃ | N |
| H | CH₂CH₃ | H | H | OCH₃ | OCH₃ | CH |
| H | CH₂CH₃ | H | H | Cl | OCH₃ | CH |
| H | CH₂CH₃ | H | H | CH₃ | OCH₃ | CH |
| H | CH₂CH₃ | H | H | CH₃ | CH₃ | CH |
| H | CH₂CH₃ | H | H | OCH₃ | OCH₃ | N |
| H | CH₂CH₃ | H | H | CH₃ | OCH₃ | N |
| H | CH₂CH₃ | H | H | NHCH₃ | OCH₂CH₃ | N |
| H | CH₂CH₃ | H | CH₃ | CH₃ | OCH₃ | N |
| H | CH₂CF₃ | H | H | OCH₃ | OCH₃ | CH |
| H | CH₂CF₃ | H | H | Cl | OCH₃ | CH |
| H | CH₂CF₃ | H | H | CH₃ | OCH₃ | CH |
| H | CH₂CF₃ | H | H | CH₃ | CH₃ | CH |
| H | CH₂CF₃ | H | H | OCH₃ | OCH₃ | N |
| H | CH₂CF₃ | H | H | CH₃ | OCH₃ | N |
| H | CH₂CF₃ | H | H | NHCH₃ | OCH₂CH₃ | N |
| H | CH₂CF₃ | H | CH₃ | CH₃ | OCH₃ | N |
| H | CH₂CH=CH₂ | H | H | OCH₃ | OCH₃ | CH |
| H | CH₂CH=CH₂ | H | H | Cl | OCH₃ | CH |
| H | CH₂CH=CH₂ | H | H | CH₃ | OCH₃ | CH |
| H | CH₂CH=CH₂ | H | H | CH₃ | CH₃ | CH |
| H | CH₂CH=CH₂ | H | H | OCH₃ | OCH₃ | N |
| H | CH₂CH=CH₂ | H | H | CH₃ | OCH₃ | N |
| H | CH₂CH=CH₂ | H | H | NHCH₃ | OCH₂CH₃ | N |
| H | CH₂CH=CH₂ | H | CH₃ | CH₃ | OCH₃ | N |
| H | CH₂C≡CH | H | H | OCH₃ | OCH₃ | CH |
| H | CH₂C≡CH | H | H | Cl | OCH₃ | CH |
| H | CH₂C≡CH | H | H | CH₃ | OCH₃ | CH |
| H | CH₂C≡CH | H | H | CH₃ | CH₃ | CH |
| H | CH₂C≡CH | H | H | OCH₃ | OCH₃ | N |
| H | CH₂C≡CH | H | H | CH₃ | OCH₃ | N |
| H | CH₂C≡CH | H | H | NHCH₃ | OCH₂CH₃ | N |
| H | CH₂C≡CH | H | CH₃ | CH₃ | OCH₃ | N |

TABLE II-continued

GENERAL STRUCTURE 2

| R₁ | R₂ | R₃ | R | X | Y | Z |
|---|---|---|---|---|---|---|
| H | CH₂CH₂Cl | H | H | OCH₃ | OCH₃ | CH |
| H | CH₂CH₂Cl | H | H | Cl | OCH₃ | CH |
| H | CH₂CH₂Cl | H | H | CH₃ | OCH₃ | CH |
| H | CH₂CH₂Cl | H | H | CH₃ | CH₃ | CH |
| H | CH₂CH₂Cl | H | H | OCH₃ | OCH₃ | N |
| H | CH₂CH₂Cl | H | H | CH₃ | OCH₃ | N |
| H | CH₂CH₂Cl | H | H | NHCH₃ | OCH₂CH₃ | N |
| H | CH₂CH₂Cl | H | CH₃ | CH₃ | OCH₃ | N |
| H | CH₂CN | H | H | OCH₃ | OCH₃ | CH |
| H | CH₂CN | H | H | Cl | OCH₃ | CH |
| H | CH₂CN | H | H | CH₃ | OCH₃ | CH |
| H | CH₂CN | H | H | CH₃ | CH₃ | CH |
| H | CH₂CN | H | H | OCH₃ | OCH₃ | N |
| H | CH₂CN | H | H | CH₃ | OCH₃ | N |
| H | CH₂CN | H | H | NHCH₃ | OCH₂CH | N |
| H | CH₂CN | H | CH₃ | CH₃ | OCH₃ | N |
| H | CH₂CH₂OCH₃ | H | H | OCH₃ | OCH₃ | CH |
| H | CH₂CH₂OCH₃ | H | H | Cl | OCH₃ | CH |
| H | CH₂CH₂OCH₃ | H | H | CH₃ | OCH₃ | CH |
| H | CH₂CH₂OCH₃ | H | H | CH₃ | CH₃ | CH |
| H | CH₂CH₂OCH₃ | H | H | OCH₃ | OCH₃ | N |
| H | CH₂CH₂OCH₃ | H | H | CH₃ | OCH₃ | N |
| H | CH₂CH₂OCH₃ | H | H | NHCH₃ | OCH₂CH₃ | N |
| H | CH₂CH₂OCH₃ | H | CH₃ | CH₃ | OCH₃ | N |
| H | cyclo-C₃H₇ | H | H | OCH₃ | OCH₃ | CH |
| H | cyclo-C₃H₇ | H | H | Cl | OCH₃ | CH |
| H | cyclo-C₃H₇ | H | H | CH₃ | OCH₃ | CH |
| H | cyclo-C₃H₇ | H | H | CH₃ | CH₃ | CH |
| H | cyclo-C₃H₇ | H | H | OCH₃ | OCH₃ | N |
| H | cyclo-C₃H₇ | H | H | CH₃ | OCH₃ | N |
| H | cyclo-C₃H₇ | H | H | NHCH₃ | OCH₂CH₃ | N |
| H | cyclo-C₃H₇ | H | CH₃ | CH₃ | OCH₃ | N |
| H | CH₃ | CH₃ | H | OCH₃ | OCH₃ | CH |
| H | CH₃ | CH₃ | H | Cl | OCH₃ | CH |
| H | CH₃ | CH₃ | H | CH₃ | OCH₃ | CH |
| H | CH₃ | CH₃ | H | CH₃ | CH₃ | CH |
| H | CH₃ | CH₃ | H | OCH₃ | OCH₃ | N |
| H | CH₃ | CH₃ | H | CH₃ | OCH₃ | N |
| H | CH₃ | CH₃ | H | NHCH₃ | OCH₂CH₃ | N |
| H | CH₃ | CH₃ | CH₃ | CH₃ | OCH₃ | N |
| H | CH₂CH₃ | CH₃ | H | OCH₃ | OCH₃ | CH |
| H | CH₂CH₃ | CH₃ | H | Cl | OCH₃ | CH |
| H | CH₂CH₃ | CH₃ | H | CH₃ | OCH₃ | CH |
| H | CH₂CH₃ | CH₃ | H | CH₃ | CH₃ | CH |
| H | CH₂CH₃ | CH₃ | H | OCH₃ | OCH₃ | N |
| H | CH₂CH₃ | CH₃ | H | CH₃ | OCH₃ | N |
| H | CH₂CH₃ | CH₃ | H | NHCH₃ | OCH₂CH₃ | N |
| H | CH₂CH₃ | CH₃ | CH₃ | CH₃ | OCH₃ | N |
| H | CH₂CH₃ | CH₂CH₃ | H | OCH₃ | OCH₃ | CH |
| H | CH₂CH₃ | CH₂CH₃ | H | Cl | OCH₃ | CH |
| H | CH₂CH₃ | CH₂CH₃ | H | CH₃ | OCH₃ | CH |
| H | CH₂CH₃ | CH₂CH₃ | H | CH₃ | CH₃ | CH |
| H | CH₂CH₃ | CH₂CH₃ | H | OCH₃ | OCH₃ | N |
| H | CH₂CH₃ | CH₂CH₃ | H | CH₃ | OCH₃ | N |
| H | CH₂CH₃ | CH₂CH₃ | H | NHCH₃ | OCH₂CH₃ | N |
| H | CH₂CH₃ | CH₂CH₃ | CH₃ | CH₃ | OCH₃ | N |
| H | OCH₃ | CH₃ | H | OCH₃ | OCH₃ | CH |
| H | OCH₃ | CH₃ | H | Cl | OCH₃ | CH |
| H | OCH₃ | CH₃ | H | CH₃ | OCH₃ | CH |
| H | OCH₃ | CH₃ | H | CH₃ | CH₃ | CH |
| H | OCH₃ | CH₃ | H | OCH₃ | OCH₃ | N |
| H | OCH₃ | CH₃ | H | CH₃ | OCH₃ | N |
| H | OCH₃ | CH₃ | H | NHCH₃ | OCH₂CH₃ | N |
| H | OCH₃ | CH₃ | CH₃ | CH₃ | OCH₃ | N |
| H | N(CH₃)₂ | CH₃ | H | OCH₃ | OCH₃ | CH |
| H | N(CH₃)₂ | CH₃ | H | Cl | OCH₃ | CH |
| H | N(CH₃)₂ | CH₃ | H | CH₃ | OCH₃ | CH |
| H | N(CH₃)₂ | CH₃ | H | CH₃ | CH₃ | CH |
| H | N(CH₃)₂ | CH₃ | H | OCH₃ | OCH₃ | N |
| H | N(CH₃)₂ | CH₃ | H | CH₃ | OCH₃ | N |
| H | N(CH₃)₂ | CH₃ | H | NHCH₃ | OCH₂CH₃ | N |
| H | N(CH₃)₂ | CH₃ | CH₃ | CH₃ | OCH₃ | N |
| H | —CH₂CH₂CH₂— |  | H | OCH₃ | OCH₃ | CH |
| H | —CH₂CH₂CH₂— |  | H | OCH₃ | OCH₃ | CH |
| H | —CH₂CH₂CH₂— |  | H | CH₃ | OCH₃ | CH |
| H | —CH₂CH₂CH₂— |  | H | CH₃ | CH₃ | CH |
| H | —CH₂CH₂CH₂— |  | H | OCH₃ | OCH₃ | N |
| H | —CH₂CH₂CH₂— |  | H | CH₃ | OCH₃ | N |
| H | —CH₂CH₂CH₂— |  | H | NHCH₃ | OCH₂CH₃ | N |
| H | —CH₂CH₂CH₂— |  | CH₃ | CH₃ | OCH₃ | N |

TABLE II-continued

GENERAL STRUCTURE 2

| R₁ | R₂ | R₃ | R | X | Y | Z |
|---|---|---|---|---|---|---|
| Cl | H | H | H | OCH₃ | OCH₃ | CH |
| Cl | H | H | H | Cl | OCH₃ | CH |
| Cl | H | H | H | CH₃ | OCH₃ | CH |
| Cl | H | H | H | CH₃ | CH₃ | CH |
| Cl | H | H | H | OCH₃ | OCH₃ | N |
| Cl | H | H | H | CH₃ | OCH₃ | N |
| Cl | H | H | H | NHCH₃ | OCH₂CH₃ | N |
| Cl | H | H | CH₃ | CH₃ | OCH₃ | N |
| Cl | H | CH₃ | H | OCH₃ | OCH₃ | CH |
| Cl | H | CH₃ | H | Cl | OCH₃ | CH |
| Cl | H | CH₃ | H | CH₃ | OCH₃ | CH |
| Cl | H | CH₃ | H | CH₃ | CH₃ | CH |
| Cl | H | CH₃ | H | OCH₃ | OCH₃ | N |
| Cl | H | CH₃ | H | CH₃ | OCH₃ | N |
| Cl | H | CH₃ | H | NHCH₃ | OCH₂CH₃ | N |
| Cl | H | CH₃ | CH₃ | CH₃ | OCH₃ | N |
| Cl | H | CH₂CH₃ | H | OCH₃ | OCH₃ | CH |
| Cl | H | CH₂CH₃ | H | Cl | OCH₃ | CH |
| Cl | H | CH₂CH₃ | H | CH₃ | OCH₃ | CH |
| Cl | H | CH₂CH₃ | H | CH₃ | CH₃ | CH |
| Cl | H | CH₂CH₃ | H | OCH₃ | OCH₃ | N |
| Cl | H | CH₂CH₃ | H | CH₃ | OCH₃ | N |
| Cl | H | CH₂CH₃ | H | NHCH₃ | OCH₂CH₃ | N |
| Cl | H | CH₂CH₃ | CH₃ | CH₃ | OCH₃ | N |
| Cl | H | CH₂CF₃ | H | OCH₃ | OCH₃ | CH |
| Cl | H | CH₂CF₃ | H | Cl | OCH₃ | CH |
| Cl | H | CH₂CF₃ | H | CH₃ | OCH₃ | CH |
| Cl | H | CH₂CF₃ | H | CH₃ | CH₃ | CH |
| Cl | H | CH₂CF₃ | H | OCH₃ | OCH₃ | N |
| Cl | H | CH₂CF₃ | H | CH₃ | OCH₃ | N |
| Cl | H | CH₂CF₃ | H | NHCH₃ | OCH₂CH₃ | N |
| Cl | H | CH₂CF₃ | CH₃ | CH₃ | OCH₃ | N |
| Cl | CH₂CH=CH₂ | H | H | OCH₃ | OCH₃ | CH |
| Cl | CH₂CH=CH₂ | H | H | Cl | OCH₃ | CH |
| Cl | CH₂CH=CH₂ | H | H | CH₃ | OCH₃ | CH |
| Cl | CH₂CH=CH₂ | H | H | CH₃ | CH₃ | CH |
| Cl | CH₂CH=CH₂ | H | H | OCH₃ | OCH₃ | N |
| Cl | CH₂CH=CH₂ | H | H | CH₃ | OCH₃ | N |
| Cl | CH₂CH=CH₂ | H | H | NHCH₃ | OCH₂CH₃ | N |
| Cl | CH₂CH=CH₂ | H | CH₃ | CH₃ | OCH₃ | N |
| Cl | CH₂C≡CH | H | H | OCH₃ | OCH₃ | CH |
| Cl | CH₂C≡CH | H | H | Cl | OCH₃ | CH |
| Cl | CH₂C≡CH | H | H | CH₃ | OCH₃ | CH |
| Cl | CH₂C≡CH | H | H | CH₃ | CH₃ | CH |
| Cl | CH₂C≡CH | H | H | OCH₃ | OCH₃ | N |
| Cl | CH₂C≡CH | H | H | CH₃ | OCH₃ | N |
| Cl | CH₂C≡CH | H | H | NHCH₃ | OCH₂CH₃ | N |
| Cl | CH₂C≡CH | H | CH₃ | CH₃ | OCH₃ | N |
| Cl | CH₂CH₂Cl | H | H | OCH₃ | OCH₃ | CH |
| Cl | CH₂CH₂Cl | H | H | Cl | OCH₃ | CH |
| Cl | CH₂CH₂Cl | H | H | CH₃ | OCH₃ | CH |
| Cl | CH₂CH₂Cl | H | H | CH₃ | CH₃ | CH |
| Cl | CH₂CH₂Cl | H | H | OCH₃ | OCH₃ | N |
| Cl | CH₂CH₂Cl | H | H | CH₃ | OCH₃ | N |
| Cl | CH₂CH₂Cl | H | H | NHCH₃ | OCH₂CH₃ | N |
| Cl | CH₂CH₂Cl | H | CH₃ | CH₃ | OCH₃ | N |
| Cl | CH₂CN | H | H | OCH₃ | OCH₃ | CH |
| Cl | CH₂CN | H | H | Cl | OCH₃ | CH |
| Cl | CH₂CN | H | H | CH₃ | OCH₃ | CH |
| Cl | CH₂CN | H | H | CH₃ | CH₃ | CH |
| Cl | CH₂CN | H | H | OCH₃ | OCH₃ | N |
| Cl | CH₂CN | H | H | CH₃ | OCH₃ | N |
| Cl | CH₂CN | H | H | NHCH₃ | OCH₂CH₃ | N |
| Cl | CH₂CN | H | CH₃ | CH₃ | OCH₃ | N |
| Cl | CH₂CH₂OCH₃ | H | H | OCH₃ | OCH₃ | CH |
| Cl | CH₂CH₂OCH₃ | H | H | Cl | OCH₃ | CH |
| Cl | CH₂CH₂OCH₃ | H | H | CH₃ | OCH₃ | CH |
| Cl | CH₂CH₂OCH₃ | H | H | CH₃ | CH₃ | CH |
| Cl | CH₂CH₂OCH₃ | H | H | OCH₃ | OCH₃ | N |
| Cl | CH₂CH₂OCH₃ | H | H | CH₃ | OCH₃ | N |
| Cl | CH₂CH₂OCH₃ | H | H | NHCH₃ | OCH₂CH₃ | N |
| Cl | CH₂CH₂OCH₃ | H | CH₃ | CH₃ | OCH₃ | N |
| Cl | cyclo-C₃H₇ | H | H | OCH₃ | OCH₃ | CH |
| Cl | cyclo-C₃H₇ | H | H | Cl | OCH₃ | CH |
| Cl | cyclo-C₃H₇ | H | H | CH₃ | OCH₃ | CH |
| Cl | cyclo-C₃H₇ | H | H | CH₃ | CH₃ | CH |
| Cl | cyclo-C₃H₇ | H | H | OCH₃ | OCH₃ | N |
| Cl | cyclo-C₃H₇ | H | H | CH₃ | OCH₃ | N |
| Cl | cyclo-C₃H₇ | H | H | NHCH₃ | OCH₂CH₃ | N |
| Cl | cyclo-C₃H₇ | H | CH₃ | CH₃ | OCH₃ | N |

TABLE II-continued
GENERAL STRUCTURE 2

| R₁ | R₂ | R₃ | R | X | Y | Z |
|---|---|---|---|---|---|---|
| Cl | CH₃ | CH₃ | H | OCH₃ | OCH₃ | CH |
| Cl | CH₃ | CH₃ | H | Cl | OCH₃ | CH |
| Cl | CH₃ | CH₃ | H | CH₃ | OCH₃ | CH |
| Cl | CH₃ | CH₃ | H | CH₃ | CH₃ | CH |
| Cl | CH₃ | CH₃ | H | OCH₃ | OCH₃ | N |
| Cl | CH₃ | CH₃ | H | CH₃ | OCH₃ | N |
| Cl | CH₃ | CH₃ | H | NHCH₃ | OCH₂CH₃ | N |
| Cl | CH₃ | CH₃ | CH₃ | CH₃ | OCH₃ | N |
| Cl | CH₂CH₃ | CH₃ | H | OCH₃ | OCH₃ | CH |
| Cl | CH₂CH₃ | CH₃ | H | Cl | OCH₃ | CH |
| Cl | CH₂CH₃ | CH₃ | H | CH₃ | OCH₃ | CH |
| Cl | CH₂CH₃ | CH₃ | H | CH₃ | CH₃ | CH |
| Cl | CH₂CH₃ | CH₃ | H | OCH₃ | OCH₃ | N |
| Cl | CH₂CH₃ | CH₃ | H | CH₃ | OCH₃ | N |
| Cl | CH₂CH₃ | CH₃ | H | NHCH₃ | OCH₂CH₃ | N |
| Cl | CH₂CH₃ | CH₃ | H | CH₃ | OCH₃ | N |
| Cl | CH₂CH₃ | CH₂CH₃ | H | OCH₃ | OCH₃ | CH |
| Cl | CH₂CH₃ | CH₂CH₃ | H | Cl | OCH₃ | CH |
| Cl | CH₂CH₃ | CH₂CH₃ | H | CH₃ | OCH₃ | CH |
| Cl | CH₂CH₃ | CH₂CH₃ | H | CH₃ | CH₃ | CH |
| Cl | CH₂CH₃ | CH₂CH₃ | H | OCH₃ | OCH₃ | N |
| Cl | CH₂CH₃ | CH₂CH₃ | H | CH₃ | OCH₃ | N |
| Cl | CH₂CH₃ | CH₂CH₃ | H | NHCH₃ | OCH₂CH₃ | N |
| Cl | CH₂CH₃ | CH₂CH₃ | CH₃ | CH₃ | OCH₃ | N |
| Cl | OCH₃ | CH₃ | H | OCH₃ | OCH₃ | CH |
| Cl | OCH₃ | CH₃ | H | Cl | OCH₃ | CH |
| Cl | OCH₃ | CH₃ | h | CH₃ | OCH₃ | CH |
| Cl | OCH₃ | CH₃ | H | CH₃ | CH₃ | CH |
| Cl | OCH₃ | CH₃ | H | OCH₃ | OCH₃ | N |
| Cl | OCH₃ | CH₃ | H | CH₃ | OCH₃ | N |
| Cl | OCH₃ | CH₃ | H | NHCH₃ | OCH₂CH₃ | N |
| Cl | OCH₃ | CH₃ | CH₃ | CH₃ | OCH₃ | N |
| Cl | N(CH₃)₂ | CH₃ | H | OCH₃ | OCH₃ | CH |
| Cl | N(CH₃)₂ | CH₃ | H | Cl | OCH₃ | CH |
| Cl | N(CH₃)₂ | CH₃ | H | CH₃ | OCH₃ | CH |
| Cl | N(CH₃)₂ | CH₃ | H | CH₃ | CH₃ | CH |
| Cl | N(CH₃)₂ | CH₃ | H | OCH₃ | OCH₃ | N |
| Cl | N(CH₃)₂ | CH₃ | H | CH₃ | OCH₃ | N |
| Cl | N(CH₃)₂ | CH₃ | H | NHCH₃ | OCH₂CH₃ | N |
| Cl | N(CH₃)₂ | CH₃ | CH₃ | CH₃ | OCH₃ | N |
| Cl | —CH₂CH₂CH₂— | | H | OCH₃ | OCH₃ | CH |
| Cl | —CH₂CH₂CH₂— | | H | Cl | OCH₃ | CH |
| Cl | —CH₂CH₂CH₂— | | H | CH₃ | OCH₃ | CH |
| Cl | —CH₂CH₂CH₂— | | H | CH₃ | CH₃ | CH |
| Cl | —CH₂CH₂CH₂— | | H | OCH₃ | OCH₃ | N |
| Cl | —CH₂CH₂CH₂— | | H | CH₃ | OCH₃ | N |
| Cl | —CH₂CH₂CH₂— | | H | NHCH₃ | OCH₂CH₃ | N |
| Cl | —CH₂CH₂CH₂— | | CH₃ | CH₃ | OCH₃ | N |
| CH₃ | H | H | H | OCH₃ | OCH₃ | CH |
| CH₃ | H | H | H | Cl | OCH₃ | CH |
| CH₃ | H | H | H | CH₃ | OCH₃ | CH |
| CH₃ | H | H | H | CH₃ | CH₃ | CH |
| CH₃ | H | H | H | OCH₃ | OCH₃ | N |
| CH₃ | H | H | H | CH₃ | OCH₃ | N |
| CH₃ | H | H | H | NHCH₃ | OCH₂CH₃ | N |
| CH₃ | H | H | CH₃ | CH₃ | OCH₃ | N |
| CH₃ | H | CH₃ | H | OCH₃ | OCH₃ | CH |
| CH₃ | H | CH₃ | H | Cl | OCH₃ | CH |
| CH₃ | H | CH₃ | H | CH₃ | OCH₃ | CH |
| CH₃ | H | CH₃ | H | CH₃ | CH₃ | CH |
| CH₃ | H | CH₃ | H | OCH₃ | OCH₃ | N |
| CH₃ | H | CH₃ | H | CH₃ | OCH₃ | N |
| CH₃ | H | CH₃ | H | NHCH₃ | OCH₂CH₃ | N |
| CH₃ | H | CH₃ | CH₃ | CH₃ | OCH₃ | N |
| CH₃ | H | CH₂CH₃ | H | OCH₃ | OCH₃ | CH |
| CH₃ | H | CH₂CH₃ | H | Cl | OCH₃ | CH |
| CH₃ | H | CH₂CH₃ | H | CH₃ | OCH₃ | CH |
| CH₃ | H | CH₂CH₃ | H | CH₃ | CH₃ | CH |
| CH₃ | H | CH₂CH₃ | H | OCH₃ | OCH₃ | N |
| CH₃ | H | CH₂CH₃ | H | CH₃ | OCH₃ | N |
| CH₃ | H | CH₂CH₃ | H | NHCH₃ | OCH₂CH₃ | N |
| CH₃ | H | CH₂CH₃ | CH₃ | CH₃ | OCH₃ | N |
| CH₃ | H | CH₂CF₃ | H | OCH₃ | OCH₃ | CH |
| CH₃ | H | CH₂CF₃ | H | Cl | OCH₃ | CH |
| CH₃ | H | CH₂CF₃ | H | CH₃ | OCH₃ | CH |
| CH₃ | H | CH₂CF₃ | H | CH₃ | CH₃ | CH |
| CH₃ | H | CH₂CF₃ | H | OCH₃ | OCH₃ | N |
| CH₃ | H | CH₂CF₃ | H | CH₃ | OCH₃ | N |
| CH₃ | H | CH₂CF₃ | H | NHCH₃ | OCH₂CH₃ | N |
| CH₃ | H | CH₂CF₃ | CH₃ | CH₃ | OCH₃ | N |

TABLE II-continued
GENERAL STRUCTURE 2

| R₁ | R₂ | R₃ | R | X | Y | Z |
|---|---|---|---|---|---|---|
| CH₃ | CH₂CH=CH₂ | H | H | OCH₃ | OCH₃ | CH |
| CH₃ | CH₂CH=CH₂ | H | H | Cl | OCH₃ | CH |
| CH₃ | CH₂CH=CH₂ | H | H | CH₃ | OCH₃ | CH |
| CH₃ | CH₂CH=CH₂ | H | H | CH₃ | CH₃ | CH |
| CH₃ | CH₂CH=CH₂ | H | H | OCH₃ | OCH₃ | N |
| CH₃ | CH₂CH=CH₂ | H | H | CH₃ | OCH₃ | N |
| CH₃ | CH₂CH=CH₂ | H | H | NHCH₃ | OCH₂CH₃ | N |
| CH₃ | CH₂CH=CH₂ | H | CH₃ | CH₃ | OCH₃ | N |
| CH₃ | CH₂C≡CH | H | H | OCH₃ | OCH₃ | CH |
| CH₃ | CH₂C≡CH | H | H | Cl | OCH₃ | CH |
| CH₃ | CH₂C≡CH | H | H | CH₃ | OCH₃ | CH |
| CH₃ | CH₂C≡CH | H | H | CH₃ | CH₃ | CH |
| CH₃ | CH₂C≡CH | H | H | OCH₃ | OCH₃ | N |
| CH₃ | CH₂C≡CH | H | H | CH₃ | OCH₃ | N |
| CH₃ | CH₂C≡CH | H | H | NHCH₃ | OCH₂CH₃ | N |
| CH₃ | CH₂C≡CH | H | CH₃ | CH₃ | OCH₃ | N |
| CH₃ | CH₂CH₂Cl | H | H | OCH₃ | OCH₃ | CH |
| CH₃ | CH₂CH₂Cl | H | H | Cl | OCH₃ | CH |
| CH₃ | CH₂CH₂Cl | H | H | CH₃ | OCH₃ | CH |
| CH₃ | CH₂CH₂Cl | H | H | CH₃ | CH₃ | CH |
| CH₃ | CH₂CH₂Cl | H | H | OCH₃ | OCH₃ | N |
| CH₃ | CH₂CH₂Cl | H | H | CH₃ | OCH₃ | N |
| CH₃ | CH₂CH₂Cl | H | H | NHCH₃ | OCH₂CH₃ | N |
| CH₃ | CH₂CH₂Cl | H | CH₃ | CH₃ | OCH₃ | N |
| CH₃ | CH₂CN | H | H | OCH₃ | OCH₃ | CH |
| CH₃ | CH₂CN | H | H | Cl | OCH₃ | CH |
| CH₃ | CH₂CN | H | H | CH₃ | OCH₃ | CH |
| CH₃ | CH₂CN | H | H | CH₃ | CH₃ | CH |
| CH₃ | CH₂CN | H | H | OCH₃ | OCH₃ | N |
| CH₃ | CH₂CN | H | H | CH₃ | OCH₃ | N |
| CH₃ | CH₂CN | H | H | NHCH₃ | OCH₂CH₃ | N |
| CH₃ | CH₂CN | H | CH₃ | CH₃ | OCH₃ | N |
| CH₃ | CH₂CH₂OCH₃ | H | H | OCH₃ | OCH₃ | CH |
| CH₃ | CH₂CH₂OCH₃ | H | H | Cl | OCH₃ | CH |
| CH₃ | CH₂CH₂OCH₃ | H | H | CH₃ | OCH₃ | CH |
| CH₃ | CH₂CH₂OCH₃ | H | H | CH₃ | CH₃ | CH |
| CH₃ | CH₂CH₂OCH₃ | H | H | OCH₃ | OCH₃ | N |
| CH₃ | CH₂CH₂OCH₃ | H | H | CH₃ | OCH₃ | N |
| CH₃ | CH₂CH₂OCH₃ | H | H | NHCH₃ | OCH₂CH₃ | N |
| CH₃ | CH₂CH₂OCH₃ | H | CH₃ | CH₃ | OCH₃ | N |
| CH₃ | cyclo-C₃H₇ | H | H | OCH₃ | OCH₃ | CH |
| CH₃ | cyclo-C₃H₇ | H | H | Cl | OCH₃ | CH |
| CH₃ | cyclo-C₃H₇ | H | H | CH₃ | OCH₃ | CH |
| CH₃ | cyclo-C₃H₇ | H | H | CH₃ | CH₃ | CH |
| CH₃ | cyclo-C₃H₇ | H | H | OCH₃ | OCH₃ | N |
| CH₃ | cyclo-C₃H₇ | H | H | CH₃ | OCH₃ | N |
| CH₃ | cyclo-C₃H₇ | H | H | NHCH₃ | OCH₂CH₃ | N |
| CH₃ | cyclo-C₃H₇ | H | CH₃ | CH₃ | OCH₃ | N |
| CH₃ | CH₃ | CH₃ | H | OCH₃ | OCH₃ | CH |
| CH₃ | CH₃ | CH₃ | H | Cl | OCH₃ | CH |
| CH₃ | CH₃ | CH₃ | H | CH₃ | OCH₃ | CH |
| CH₃ | CH₃ | CH₃ | H | CH₃ | CH₃ | CH |
| CH₃ | CH₃ | CH₃ | H | OCH₃ | OCH₃ | N |
| CH₃ | CH₃ | CH₃ | H | CH₃ | OCH₃ | N |
| CH₃ | CH₃ | CH₃ | H | NHCH₃ | OCH₂CH₃ | N |
| CH₃ | CH₃ | CH₃ | CH₃ | CH₃ | OCH₃ | N |
| CH₃ | CH₂CH₃ | CH₃ | H | OCH₃ | OCH₃ | CH |
| CH₃ | CH₂CH₃ | CH₃ | H | Cl | OCH₃ | CH |
| CH₃ | CH₂CH₃ | CH₃ | H | CH₃ | OCH₃ | CH |
| CH₃ | CH₂CH₃ | CH₃ | H | CH₃ | CH₃ | CH |
| CH₃ | CH₂CH₃ | CH₃ | H | OCH₃ | OCH₃ | N |
| CH₃ | CH₂CH₃ | CH₃ | H | CH₃ | OCH₃ | N |
| CH₃ | CH₂CH₃ | CH₃ | H | NHCH₃ | OCH₂CH₃ | N |
| CH₃ | CH₂CH₃ | CH₃ | CH₃ | CH₃ | OCH₃ | N |
| CH₃ | CH₂CH₃ | CH₂CH₃ | H | OCH₃ | OCH₃ | CH |
| CH₃ | CH₂CH₃ | CH₂CH₃ | H | Cl | OCH₃ | CH |
| CH₃ | CH₂CH₃ | CH₂CH₃ | H | CH₃ | OCH₃ | CH |
| CH₃ | CH₂CH₃ | CH₂CH₃ | H | CH₃ | CH₃ | CH |
| CH₃ | CH₂CH₃ | CH₂CH₃ | H | OCH₃ | OCH₃ | N |
| CH₃ | CH₂CH₃ | CH₂CH₃ | H | CH₃ | OCH₃ | N |
| CH₃ | CH₂CH₃ | CH₂CH₃ | H | NHCH₃ | OCH₂CH₃ | N |
| CH₃ | CH₂CH₃ | CH₂CH₃ | CH₃ | CH₃ | OCH₃ | N |
| CH₃ | OCH₃ | CH₃ | H | OCH₃ | OCH₃ | CH |
| CH₃ | OCH₃ | CH₃ | H | Cl | OCH₃ | CH |
| CH₃ | OCH₃ | CH₃ | H | CH₃ | OCH₃ | CH |
| CH₃ | OCH₃ | CH₃ | H | CH₃ | CH₃ | CH |
| CH₃ | OCH₃ | CH₃ | H | OCH₃ | OCH₃ | N |
| CH₃ | OCH₃ | CH₃ | H | CH₃ | OCH₃ | N |
| CH₃ | OCH₃ | CH₃ | H | NHCH₃ | OCH₂CH₃ | N |
| CH₃ | OCH₃ | CH₃ | CH₃ | CH₃ | OCH₃ | N |

TABLE II-continued

GENERAL STRUCTURE 2

| R₁ | R₂ | R₃ | R | X | Y | Z |
|---|---|---|---|---|---|---|
| CH₃ | N(CH₃)₂ | CH₃ | H | OCH₃ | OCH₃ | CH |
| CH₃ | N(CH₃)₂ | CH₃ | H | Cl | OCH₃ | CH |
| CH₃ | N(CH₃)₂ | CH₃ | H | CH₃ | OCH₃ | CH |
| CH₃ | N(CH₃)₂ | CH₃ | H | CH₃ | CH₃ | CH |
| CH₃ | N(CH₃)₂ | CH₃ | H | OCH₃ | OCH₃ | N |
| CH₃ | N(CH₃)₂ | CH₃ | H | CH₃ | OCH₃ | N |
| CH₃ | N(CH₃)₂ | CH₃ | H | NHCH₃ | OCH₂CH₃ | N |
| CH₃ | N(CH₃)₂ | CH₃ | CH₃ | CH₃ | OCH₃ | N |
| CH₃ | —CH₂CH₂CH₂— | | H | OCH₃ | OCH₃ | CH |
| CH₃ | —CH₂CH₂CH₂— | | H | Cl | OCH₃ | CH |
| CH₃ | —CH₂CH₂CH₂— | | H | CH₃ | OCH₃ | CH |
| CH₃ | —CH₂CH₂CH₂— | | H | CH₃ | CH₃ | CH |
| CH₃ | —CH₂CH₂CH₂— | | H | OCH₃ | OCH₃ | N |
| CH₃ | —CH₂CH₂CH₂— | | H | CH₃ | OCH₃ | N |
| CH₃ | —CH₂CH₂CH₂— | | H | NHCH₃ | OCH₂CH₃ | N |
| CH₃ | —CH₂CH₂CH₂— | | CH₃ | CH₃ | OCH₃ | N |
| SCH₃ | H | H | H | OCH₃ | OCH₃ | CH |
| SCH₃ | H | H | H | Cl | OCH₃ | CH |
| SCH₃ | H | H | H | CH₃ | OCH₃ | CH |
| SCH₃ | H | H | H | CH₃ | CH₃ | CH |
| SCH₃ | H | H | H | OCH₃ | OCH₃ | N |
| SCH₃ | H | H | H | CH₃ | OCH₃ | N |
| SCH₃ | H | H | H | NHCH₃ | OCH₂CH₃ | N |
| SCH₃ | H | H | CH₃ | CH₃ | OCH₃ | N |
| SCH₃ | H | CH₃ | H | OCH₃ | OCH₃ | CH |
| SCH₃ | H | CH₃ | H | Cl | OCH₃ | CH |
| SCH₃ | H | CH₃ | H | CH₃ | OCH₃ | CH |
| SCH₃ | H | CH₃ | H | CH₃ | CH₃ | CH |
| SCH₃ | H | CH₃ | H | OCH₃ | OCH₃ | N |
| SCH₃ | H | CH₃ | H | CH₃ | OCH₃ | N |
| SCH₃ | H | CH₃ | H | NHCH₃ | OCH₂CH₃ | N |
| SCH₃ | H | CH₃ | CH₃ | CH₃ | OCH₃ | N |
| SCH₃ | H | CH₂CH₃ | H | OCH₃ | OCH₃ | CH |
| SCH₃ | H | CH₂CH₃ | H | Cl | OCH₃ | CH |
| SCH₃ | H | CH₂CH₃ | H | CH₃ | OCH₃ | CH |
| SCH₃ | H | CH₂CH₃ | H | CH₃ | CH₃ | CH |
| SCH₃ | H | CH₂CH₃ | H | OCH₃ | OCH₃ | N |
| SCH₃ | H | CH₂CH₃ | H | CH₃ | OCH₃ | N |
| SCH₃ | H | CH₂CH₃ | H | NHCH₃ | OCH₂CH₃ | N |
| SCH₃ | H | CH₂CH₃ | CH₃ | CH₃ | OCH₃ | N |
| SCH₃ | H | CH₂CF₃ | H | OCH₃ | OCH₃ | CH |
| SCH₃ | H | CH₂CF₃ | H | Cl | OCH₃ | CH |
| SCH₃ | H | CH₂CF₃ | H | CH₃ | OCH₃ | CH |
| SCH₃ | H | CH₂CF₃ | H | CH₃ | CH₃ | CH |
| SCH₃ | H | CH₂CF₃ | H | OCH₃ | OCH₃ | N |
| SCH₃ | H | CH₂CF₃ | H | CH₃ | OCH₃ | N |
| SCH₃ | H | CH₂CF₃ | H | NHCH₃ | OCH₂CH₃ | N |
| SCH₃ | H | CH₂CF₃ | CH₃ | CH₃ | OCH₃ | N |
| SCH₃ | CH₂CH=CH₂ | H | H | OCH₃ | OCH₃ | CH |
| SCH₃ | CH₂CH=CH₂ | H | H | Cl | OCH₃ | CH |
| SCH₃ | CH₂CH=CH₂ | H | H | CH₃ | OCH₃ | CH |
| SCH₃ | CH₂CH=CH₂ | H | H | CH₃ | CH₃ | CH |
| SCH₃ | CH₂CH=CH₂ | H | H | OCH₃ | OCH₃ | N |
| SCH₃ | CH₂CH=CH₂ | H | H | CH₃ | OCH₃ | N |
| SCH₃ | CH₂CH=CH₂ | H | H | NHCH₃ | OCH₂CH₃ | N |
| SCH₃ | CH₂CH=CH₂ | H | CH₃ | CH₃ | OCH₃ | N |
| SCH₃ | CH₂C≡CH | H | H | OCH₃ | OCH₃ | CH |
| SCH₃ | CH₂C≡CH | H | H | Cl | OCH₃ | CH |
| SCH₃ | CH₂C≡CH | H | H | CH₃ | OCH₃ | CH |
| SCH₃ | CH₂C≡CH | H | H | CH₃ | CH₃ | CH |
| SCH₃ | CH₂C≡CH | H | H | OCH₃ | OCH₃ | N |
| SCH₃ | CH₂C≡CH | H | H | CH₃ | OCH₃ | N |
| SCH₃ | CH₂C≡CH | H | H | NHCH₃ | OCH₂CH₃ | N |
| SCH₃ | CH₂C≡CH | H | CH₃ | CH₃ | OCH₃ | N |
| SCH₃ | CH₂CH₂Cl | H | H | OCH₃ | OCH₃ | CH |
| SCH₃ | CH₂CH₂Cl | H | H | Cl | OCH₃ | CH |
| SCH₃ | CH₂CH₂Cl | H | H | CH₃ | OCH₃ | CH |
| SCH₃ | CH₂CH₂Cl | H | H | CH₃ | CH₃ | CH |
| SCH₃ | CH₂CH₂Cl | H | H | OCH₃ | OCH₃ | N |
| SCH₃ | CH₂CH₂Cl | H | H | CH₃ | OCH₃ | N |
| SCH₃ | CH₂CH₂Cl | H | H | NHCH₃ | OCH₂CH₃ | N |
| SCH₃ | CH₂CH₂Cl | H | CH₃ | CH₃ | OCH₃ | N |
| SCH₃ | CH₂CN | H | H | OCH₃ | OCH₃ | CH |
| SCH₃ | CH₂CN | H | H | Cl | OCH₃ | CH |
| SCH₃ | CH₂CN | H | H | CH₃ | OCH₃ | CH |
| SCH₃ | CH₂CN | H | H | CH₃ | CH₃ | CH |
| SCH₃ | CH₂CN | H | H | OCH₃ | OCH₃ | N |
| SCH₃ | CH₂CN | H | H | CH₃ | OCH₃ | N |
| SCH₃ | CH₂CN | H | H | NHCH₃ | OCH₂CH₃ | N |
| SCH₃ | CH₂CN | H | CH₃ | CH₃ | OCH₃ | N |

TABLE II-continued

GENERAL STRUCTURE 2

| R₁ | R₂ | R₃ | R | X | Y | Z |
|---|---|---|---|---|---|---|
| SCH₃ | CH₂CH₂OCH₃ | H | H | OCH₃ | OCH₃ | CH |
| SCH₃ | CH₂CH₂OCH₃ | H | H | Cl | OCH₃ | CH |
| SCH₃ | CH₂CH₂OCH₃ | H | H | CH₃ | OCH₃ | CH |
| SCH₃ | CH₂CH₂OCH₃ | H | H | CH₃ | CH₃ | CH |
| SCH₃ | CH₂CH₂OCH₃ | H | H | OCH₃ | OCH₃ | N |
| SCH₃ | CH₂CH₂OCH₃ | H | H | CH₃ | OCH₃ | N |
| SCH₃ | CH₂CH₂OCH₃ | H | H | NHCH₃ | OCH₂CH₃ | N |
| SCH₃ | CH₂CH₂OCH₃ | H | CH₃ | CH₃ | OCH₃ | N |
| SCH₃ | cyclo-C₃H₇ | H | H | OCH₃ | OCH₃ | CH |
| SCH₃ | cyclo-C₃H₇ | H | H | Cl | OCH₃ | CH |
| SCH₃ | cyclo-C₃H₇ | H | H | CH₃ | OCH₃ | CH |
| SCH₃ | cyclo-C₃H₇ | H | H | CH₃ | CH₃ | CH |
| SCH₃ | cyclo-C₃H₇ | H | H | OCH₃ | OCH₃ | N |
| SCH₃ | cyclo-C₃H₇ | H | H | CH₃ | OCH₃ | N |
| SCH₃ | cyclo-C₃H₇ | H | H | NHCH₃ | OCH₂CH₃ | N |
| SCH₃ | cyclo-C₃H₇ | H | CH₃ | CH₃ | OCH₃ | N |
| SCH₃ | CH₃ | CH₃ | H | OCH₃ | OCH₃ | CH |
| SCH₃ | CH₃ | CH₃ | H | Cl | OCH₃ | CH |
| SCH₃ | CH₃ | CH₃ | H | CH₃ | OCH₃ | CH |
| SCH₃ | CH₃ | CH₃ | H | CH₃ | CH₃ | CH |
| SCH₃ | CH₃ | CH₃ | H | OCH₃ | OCH₃ | N |
| SCH₃ | CH₃ | CH₃ | H | CH₃ | OCH₃ | N |
| SCH₃ | CH₃ | CH₃ | H | NHCH₃ | OCH₂CH₃ | N |
| SCH₃ | CH₃ | CH₃ | CH₃ | CH₃ | OCH₃ | N |
| SCH₃ | CH₂CH₃ | CH₃ | H | OCH₃ | OCH₃ | CH |
| SCH₃ | CH₂CH₃ | CH₃ | H | Cl | OCH₃ | CH |
| SCH₃ | CH₂CH₃ | CH₃ | H | CH₃ | OCH₃ | CH |
| SCH₃ | CH₂CH₃ | CH₃ | H | CH₃ | CH₃ | CH |
| SCH₃ | CH₂CH₃ | CH₃ | H | OCH₃ | OCH₃ | N |
| SCH₃ | CH₂CH₃ | CH₃ | H | CH₃ | OCH₃ | N |
| SCH₃ | CH₂CH₃ | CH₃ | H | NHCH₃ | OCH₂CH₃ | N |
| SCH₃ | CH₂CH₃ | CH₃ | CH₃ | CH₃ | OCH₃ | N |
| SCH₃ | CH₂CH₃ | CH₂CH₃ | H | OCH₃ | OCH₃ | CH |
| SCH₃ | CH₂CH₃ | CH₂CH₃ | H | Cl | OCH₃ | CH |
| SCH₃ | CH₂CH₃ | CH₂CH₃ | H | CH₃ | OCH₃ | CH |
| SCH₃ | CH₂CH₃ | CH₂CH₃ | H | CH₃ | CH₃ | CH |
| SCH₃ | CH₂CH₃ | CH₂CH₃ | H | OCH₃ | OCH₃ | N |
| SCH₃ | CH₂CH₃ | CH₂CH₃ | H | CH₃ | OCH₃ | N |
| SCH₃ | CH₂CH₃ | CH₂CH₃ | H | NHCH₃ | OCH₂CH₃ | N |
| SCH₃ | CH₂CH₃ | CH₂CH₃ | CH₃ | CH₃ | OCH₃ | N |
| SCH₃ | OCH₃ | CH₃ | H | OCH₃ | OCH₃ | CH |
| SCH₃ | OCH₃ | CH₃ | H | Cl | OCH₃ | CH |
| SCH₃ | OCH₃ | CH₃ | H | CH₃ | OCH₃ | CH |
| SCH₃ | OCH₃ | CH₃ | H | CH₃ | CH₃ | CH |
| SCH₃ | OCH₃ | CH₃ | H | OCH₃ | OCH₃ | N |
| SCH₃ | OCH₃ | CH₃ | H | CH₃ | OCH₃ | N |
| SCH₃ | OCH₃ | CH₃ | H | NHCH₃ | OCH₂CH₃ | N |
| SCH₃ | OCH₃ | CH₃ | CH₃ | CH₃ | OCH₃ | N |
| SCH₃ | N(CH₃)₂ | CH₃ | H | OCH₃ | OCH₃ | CH |
| SCH₃ | N(CH₃)₂ | CH₃ | H | Cl | OCH₃ | CH |
| SCH₃ | N(CH₃)₂ | CH₃ | H | CH₃ | OCH₃ | CH |
| SCH₃ | N(CH₃)₂ | CH₃ | H | CH₃ | CH₃ | CH |
| SCH₃ | N(CH₃)₂ | CH₃ | H | OCH₃ | OCH₃ | N |
| SCH₃ | N(CH₃)₂ | CH₃ | H | CH₃ | OCH₃ | N |
| SCH₃ | N(CH₃)₂ | CH₃ | H | NHCH₃ | OCH₂CH₃ | N |
| SCH₃ | N(CH₃)₂ | CH₃ | CH₃ | CH₃ | OCH₃ | N |
| SCH₃ | —CH₂CH₂CH₂— | | H | OCH₃ | OCH₃ | CH |
| SCH₃ | —CH₂CH₂CH₂— | | H | Cl | OCH₃ | CH |
| SCH₃ | —CH₂CH₂CH₂— | | H | CH₃ | OCH₃ | CH |
| SCH₃ | —CH₂CH₂CH₂— | | H | CH₃ | CH₃ | CH |
| SCH₃ | —CH₂CH₂CH₂— | | H | OCH₃ | OCH₃ | N |
| SCH₃ | —CH₂CH₂CH₂— | | H | CH₃ | OCH₃ | N |
| SCH₃ | —CH₂CH₂CH₂— | | H | NHCH₃ | OCH₂CH₃ | N |
| SCH₃ | —CH₂CH₂CH₂— | | CH₃ | CH₃ | OCH₃ | N |
| SO₂CH₂CH₃ | H | H | H | OCH₃ | OCH₃ | CH |
| SO₂CH₂CH₃ | H | H | H | Cl | OCH₃ | CH |
| SO₂CH₂CH₃ | H | H | H | CH₃ | OCH₃ | CH |
| SO₂CH₂CH₃ | H | H | H | CH₃ | CH₃ | CH |
| SO₂CH₂CH₃ | H | H | H | OCH₃ | OCH₃ | N |
| SO₂CH₂CH₃ | H | H | H | CH₃ | OCH₃ | N |
| SO₂CH₂CH₃ | H | H | H | NHCH₃ | OCH₂CH₃ | N |
| SO₂CH₂CH₃ | H | H | CH₃ | CH₃ | OCH₃ | N |
| SO₂CH₂CH₃ | H | CH₃ | H | OCH₃ | OCH₃ | CH |
| SO₂CH₂CH₃ | H | CH₃ | H | Cl | OCH₃ | CH |
| SO₂CH₂CH₃ | H | CH₃ | H | CH₃ | OCH₃ | CH |
| SO₂CH₂CH₃ | H | CH₃ | H | CH₃ | CH₃ | CH |
| SO₂CH₂CH₃ | H | CH₃ | H | OCH₃ | OCH₃ | N |
| SO₂CH₂CH₃ | H | CH₃ | H | CH₃ | OCH₃ | N |
| SO₂CH₂CH₃ | H | CH₃ | H | NHCH₃ | OCH₂CH₃ | N |
| SO₂CH₂CH₃ | H | CH₃ | CH₃ | CH₃ | OCH₃ | N |

TABLE II-continued
GENERAL STRUCTURE 2

| R₁ | R₂ | R₃ | R | X | Y | Z |
|---|---|---|---|---|---|---|
| SO₂CH₂CH₃ | H | CH₂CH₃ | H | OCH₃ | OCH₃ | CH |
| SO₂CH₂CH₃ | H | CH₂CH₃ | H | Cl | OCH₃ | CH |
| SO₂CH₂CH₃ | H | CH₂CH₃ | H | CH₃ | OCH₃ | CH |
| SO₂CH₂CH₃ | H | CH₂CH₃ | H | CH₃ | CH₃ | CH |
| SO₂CH₂CH₃ | H | CH₂CH₃ | H | OCH₃ | OCH₃ | N |
| SO₂CH₂CH₃ | H | CH₂CH₃ | H | CH₃ | OCH₃ | N |
| SO₂CH₂CH₃ | H | CH₂CH₃ | H | NHCH₃ | OCH₂CH₃ | N |
| SO₂CH₂CH₃ | H | CH₂CH₃ | CH₃ | CH₃ | OCH₃ | N |
| SO₂CH₂CH₃ | H | CH₂CF₃ | H | OCH₃ | OCH₃ | CH |
| SO₂CH₂CH₃ | H | CH₂CF₃ | H | Cl | OCH₃ | CH |
| SO₂CH₂CH₃ | H | CH₂CF₃ | H | CH₃ | OCH₃ | CH |
| SO₂CH₂CH₃ | H | CH₂CF₃ | H | CH₃ | CH₃ | CH |
| SO₂CH₂CH₃ | H | CH₂CF₃ | H | OCH₃ | OCH₃ | N |
| SO₂CH₂CH₃ | H | CH₂CF₃ | H | CH₃ | OCH₃ | N |
| SO₂CH₂CH₃ | H | CH₂CF₃ | H | NHCH₃ | OCH₂CH₃ | N |
| SO₂CH₂CH₃ | H | CH₂CF₃ | CH₃ | CH₃ | OCH₃ | N |
| SO₂CH₂CH₃ | CH₂CH=CH₂ | H | H | OCH₃ | OCH₃ | CH |
| SO₂CH₂CH₃ | CH₂CH=CH₂ | H | H | Cl | OCH₃ | CH |
| SO₂CH₂CH₃ | CH₂CH=CH₂ | H | H | CH₃ | OCH₃ | CH |
| SO₂CH₂CH₃ | CH₂CH=CH₂ | H | H | CH₃ | CH₃ | CH |
| SO₂CH₂CH₃ | CH₂CH=CH₂ | H | H | OCH₃ | OCH₃ | N |
| SO₂CH₂CH₃ | CH₂CH=CH₂ | H | H | CH₃ | OCH₃ | N |
| SO₂CH₂CH₃ | CH₂CH=CH₂ | H | H | NHCH₃ | OCH₂CH₃ | N |
| SO₂CH₂CH₃ | CH₂CH=CH₂ | H | CH₃ | CH₃ | OCH₃ | N |
| SO₂CH₂CH₃ | CH₂C≡CH | H | H | OCH₃ | OCH₃ | CH |
| SO₂CH₂CH₃ | CH₂C≡CH | H | H | Cl | OCH₃ | CH |
| SO₂CH₂CH₃ | CH₂C≡CH | H | H | CH₃ | OCH₃ | CH |
| SO₂CH₂CH₃ | CH₂C≡CH | H | H | CH₃ | CH₃ | CH |
| SO₂CH₂CH₃ | CH₂C≡CH | H | H | OCH₃ | OCH₃ | N |
| SO₂CH₂CH₃ | CH₂C≡CH | H | H | CH₃ | OCH₃ | N |
| SO₂CH₂CH₃ | CH₂C≡CH | H | H | NHCH₃ | OCH₂CH₃ | N |
| SO₂CH₂CH₃ | CH₂C≡CH | H | CH₃ | CH₃ | OCH₃ | N |
| SO₂CH₂CH₃ | CH₂CH₂Cl | H | H | OCH₃ | OCH₃ | CH |
| SO₂CH₂CH₃ | CH₂CH₂Cl | H | H | Cl | OCH₃ | CH |
| SO₂CH₂CH₃ | CH₂CH₂Cl | H | H | CH₃ | OCH₃ | CH |
| SO₂CH₂CH₃ | CH₂CH₂Cl | H | H | CH₃ | CH₃ | CH |
| SO₂CH₂CH₃ | CH₂CH₂Cl | H | H | OCH₃ | OCH₃ | N |
| SO₂CH₂CH₃ | CH₂CH₂Cl | H | H | CH₃ | OCH₃ | N |
| SO₂CH₂CH₃ | CH₂CH₂Cl | H | H | NHCH₃ | OCH₂CH₃ | N |
| SO₂CH₂CH₃ | CH₂CH₂Cl | H | CH₃ | CH₃ | OCH₃ | N |
| SO₂CH₂CH₃ | CH₂CN | H | H | OCH₃ | OCH₃ | CH |
| SO₂CH₂CH₃ | CH₂CN | H | H | Cl | OCH₃ | CH |
| SO₂CH₂CH₃ | CH₂CN | H | H | CH₃ | OCH₃ | CH |
| SO₂CH₂CH₃ | CH₂CN | H | H | CH₃ | CH₃ | CH |
| SO₂CH₂CH₃ | CH₂CN | H | H | OCH₃ | OCH₃ | N |
| SO₂CH₂CH₃ | CH₂CN | H | H | CH₃ | OCH₃ | N |
| SO₂CH₂CH₃ | CH₂CN | H | H | NHCH₃ | OCH₂CH₃ | N |
| SO₂CH₂CH₃ | CH₂CN | H | CH₃ | CH₃ | OCH₃ | N |
| SO₂CH₂CH₃ | CH₂CH₂OCH₃ | H | H | OCH₃ | OCH₃ | CH |
| SO₂CH₂CH₃ | CH₂CH₂OCH₃ | H | H | Cl | OCH₃ | CH |
| SO₂CH₂CH₃ | CH₂CH₂OCH₃ | H | H | CH₃ | OCH₃ | CH |
| SO₂CH₂CH₃ | CH₂CH₂OCH₃ | H | H | CH₃ | CH₃ | CH |
| SO₂CH₂CH₃ | CH₂CH₂OCH₃ | H | H | OCH₃ | OCH₃ | N |
| SO₂CH₂CH₃ | CH₂CH₂OCH₃ | H | H | CH₃ | OCH₃ | N |
| SO₂CH₂CH₃ | CH₂CH₂OCH₃ | H | H | NHCH₃ | OCH₂CH₃ | N |
| SO₂CH₂CH₃ | CH₂CH₂OCH₃ | H | CH₃ | CH₃ | OCH₃ | N |
| SO₂CH₂CH₃ | cyclo-C₃H₇ | H | H | OCH₃ | OCH₃ | CH |
| SO₂CH₂CH₃ | cyclo-C₃H₇ | H | H | Cl | OCH₃ | CH |
| SO₂CH₂CH₃ | cyclo-C₃H₇ | H | H | CH₃ | OCH₃ | CH |
| SO₂CH₂CH₃ | cyclo-C₃H₇ | H | H | CH₃ | CH₃ | CH |
| SO₂CH₂CH₃ | cyclo-C₃H₇ | H | H | OCH₃ | OCH₃ | N |
| SO₂CH₂CH₃ | cyclo-C₃H₇ | H | H | CH₃ | OCH₃ | N |
| SO₂CH₂CH₃ | cyclo-C₃H₇ | H | H | NHCH₃ | OCH₂CH₃ | N |
| SO₂CH₂CH₃ | cyclo-C₃H₇ | H | CH₃ | CH₃ | OCH₃ | N |
| SO₂CH₂CH₃ | CH₃ | CH₃ | H | OCH₃ | OCH₃ | CH |
| SO₂CH₂CH₃ | CH₃ | CH₃ | H | Cl | OCH₃ | CH |
| SO₂CH₂CH₃ | CH₃ | CH₃ | H | CH₃ | OCH₃ | CH |
| SO₂CH₂CH₃ | CH₃ | CH₃ | H | CH₃ | CH₃ | CH |
| SO₂CH₂CH₃ | CH₃ | CH₃ | H | OCH₃ | OCH₃ | N |
| SO₂CH₂CH₃ | CH₃ | CH₃ | H | CH₃ | OCH₃ | N |
| SO₂CH₂CH₃ | CH₃ | CH₃ | H | NHCH₃ | OCH₂CH₃ | N |
| SO₂CH₂CH₃ | CH₃ | CH₃ | CH₃ | CH₃ | OCH₃ | N |
| SO₂CH₂CH₃ | CH₂CH₃ | CH₃ | H | OCH₃ | OCH₃ | CH |
| SO₂CH₂CH₃ | CH₂CH₃ | CH₃ | H | Cl | OCH₃ | CH |
| SO₂CH₂CH₃ | CH₂CH₃ | CH₃ | H | CH₃ | OCH₃ | CH |
| SO₂CH₂CH₃ | CH₂CH₃ | CH₃ | H | CH₃ | CH₃ | CH |
| SO₂CH₂CH₃ | CH₂CH₃ | CH₃ | H | OCH₃ | OCH₃ | N |
| SO₂CH₂CH₃ | CH₂CH₃ | CH₃ | H | CH₃ | OCH₃ | N |
| SO₂CH₂CH₃ | CH₂CH₃ | CH₃ | H | NHCH₃ | OCH₂CH₃ | N |
| SO₂CH₂CH₃ | CH₂CH₃ | CH₃ | CH₃ | CH₃ | OCH₃ | N |

TABLE II-continued

GENERAL STRUCTURE 2

| R₁ | R₂ | R₃ | R | X | Y | Z |
|---|---|---|---|---|---|---|
| SO₂CH₂CH₃ | CH₂CH₃ | CH₂CH₃ | H | OCH₃ | OCH₃ | CH |
| SO₂CH₂CH₃ | CH₂CH₃ | CH₂CH₃ | H | Cl | OCH₃ | CH |
| SO₂CH₂CH₃ | CH₂CH₃ | CH₂CH₃ | H | CH₃ | OCH₃ | CH |
| SO₂CH₂CH₃ | CH₂CH₃ | CH₂CH₃ | H | CH₃ | CH₃ | CH |
| SO₂CH₂CH₃ | CH₂CH₃ | CH₂CH₃ | H | OCH₃ | OCH₃ | N |
| SO₂CH₂CH₃ | CH₂CH₃ | CH₂CH₃ | H | CH₃ | OCH₃ | N |
| SO₂CH₂CH₃ | CH₂CH₃ | CH₂CH₃ | H | NHCH₃ | OCH₂CH₃ | N |
| SO₂CH₂CH₃ | CH₂CH₃ | CH₂CH₃ | CH₃ | CH₃ | OCH₃ | N |
| SO₂CH₂CH₃ | OCH₃ | CH₃ | H | OCH₃ | OCH₃ | CH |
| SO₂CH₂CH₃ | OCH₃ | CH₃ | H | Cl | OCH₃ | CH |
| SO₂CH₂CH₃ | OCH₃ | CH₃ | H | CH₃ | OCH₃ | CH |
| SO₂CH₂CH₃ | OCH₃ | CH₃ | H | CH₃ | CH₃ | CH |
| SO₂CH₂CH₃ | OCH₃ | CH₃ | H | OCH₃ | OCH₃ | N |
| SO₂CH₂CH₃ | OCH₃ | CH₃ | H | CH₃ | OCH₃ | N |
| SO₂CH₂CH₃ | OCH₃ | CH₃ | H | NHCH₃ | OCH₂CH₃ | N |
| SO₂CH₂CH₃ | OCH₃ | CH₃ | CH₃ | CH₃ | OCH₃ | N |
| SO₂CH₂CH₃ | N(CH₃)₂ | CH₃ | H | OCH₃ | OCH₃ | CH |
| SO₂CH₂CH₃ | N(CH₃)₂ | CH₃ | H | Cl | OCH₃ | CH |
| SO₂CH₂CH₃ | N(CH₃)₂ | CH₃ | H | CH₃ | OCH₃ | CH |
| SO₂CH₂CH₃ | N(CH₃)₂ | CH₃ | H | CH₃ | CH₃ | CH |
| SO₂CH₂CH₃ | N(CH₃)₂ | CH₃ | H | OCH₃ | OCH₃ | N |
| SO₂CH₂CH₃ | N(CH₃)₂ | CH₃ | H | CH₃ | OCH₃ | N |
| SO₂CH₂CH₃ | N(CH₃)₂ | CH₃ | H | NHCH₃ | OCH₂CH₃ | N |
| SO₂CH₂CH₃ | N(CH₃)₂ | CH₃ | CH₃ | CH₃ | OCH₃ | N |
| SO₂CH₂CH₃ | —CH₂CH₂CH₂— | | H | OCH₃ | OCH₃ | CH |
| SO₂CH₂CH₃ | —CH₂CH₂CH₂— | | H | Cl | OCH₃ | CH |
| SO₂CH₂CH₃ | —CH₂CH₂CH₂— | | H | CH₃ | OCH₃ | CH |
| SO₂CH₂CH₃ | —CH₂CH₂CH₂— | | H | CH₃ | CH₃ | CH |
| SO₂CH₂CH₃ | —CH₂CH₂CH₂— | | H | OCH₃ | OCH₃ | N |
| SO₂CH₂CH₃ | —CH₂CH₂CH₂— | | H | CH₃ | OCH₃ | N |
| SO₂CH₂CH₃ | —CH₂CH₂CH₂— | | H | NHCH₃ | OCH₂CH₃ | N |
| SO₂CH₂CH₃ | —CH₂CH₂CH₂— | | CH₃ | CH₃ | OCH₃ | N |
| Br | CH₃ | H | H | OCH₃ | OCH₃ | CH |
| Br | CH₃ | H | H | Cl | OCH₃ | CH |
| Br | CH₃ | H | H | CH₃ | OCH₃ | CH |
| Br | CH₃ | H | H | CH₃ | CH₃ | CH |
| Br | CH₃ | H | H | OCH₃ | OCH₃ | N |
| Br | CH₃ | H | H | CH₃ | OCH₃ | N |
| Br | CH₃ | H | H | NHCH₃ | OCH₂CH₃ | N |
| Br | CH₃ | H | CH₃ | CH₃ | OCH₃ | N |
| Br | CH₂CH=CH₂ | H | H | OCH₃ | OCH₃ | CH |
| Br | CH₂CH=CH₂ | H | H | Cl | OCH₃ | CH |
| Br | CH₂CH=CH₂ | H | H | CH₃ | OCH₃ | CH |
| Br | CH₂CH=CH₂ | H | H | CH₃ | CH₃ | CH |
| Br | CH₂CH=CH₂ | H | H | OCH₃ | OCH₃ | N |
| Br | CH₂CH=CH₂ | H | H | CH₃ | OCH₃ | N |
| Br | CH₂CH=CH₂ | H | H | NHCH₃ | OCH₂CH₃ | N |
| Br | CH₂CH=CH₂ | H | CH₃ | CH₃ | OCH₃ | N |
| Br | CH₃ | CH₃ | H | OCH₃ | OCH₃ | CH |
| Br | CH₃ | CH₃ | H | Cl | OCH₃ | CH |
| Br | CH₃ | CH₃ | H | CH₃ | OCH₃ | CH |
| Br | CH₃ | CH₃ | H | CH₃ | CH₃ | CH |
| Br | CH₃ | CH₃ | H | OCH₃ | OCH₃ | N |
| Br | CH₃ | CH₃ | H | CH₃ | OCH₃ | N |
| Br | CH₃ | CH₃ | H | NHCH₃ | OCH₂CH₃ | N |
| Br | CH₃ | CH₃ | CH₃ | CH₃ | OCH₃ | N |
| Br | —CH₂CH₂CH₂— | | H | OCH₃ | OCH₃ | CH |
| Br | —CH₂CH₂CH₂— | | H | Cl | OCH₃ | CH |
| Br | —CH₂CH₂CH₂— | | H | CH₃ | OCH₃ | CH |
| Br | —CH₂CH₂CH₂— | | H | CH₃ | CH₃ | CH |
| Br | —CH₂CH₂CH₂— | | H | OCH₃ | OCH₃ | N |
| Br | —CH₂CH₂CH₂— | | H | CH₃ | OCH₃ | N |
| Br | —CH₂CH₂CH₂— | | H | NHCH₃ | OCH₂CH₃ | N |
| Br | —CH₂CH₂CH₂— | | CH₃ | CH₃ | OCH₃ | N |
| CH₂CH₃ | CH₃ | H | H | OCH₃ | OCH₃ | CH |
| CH₂CH₃ | CH₃ | H | H | Cl | OCH₃ | CH |
| CH₂CH₃ | CH₃ | H | H | CH₃ | OCH₃ | CH |
| CH₂CH₃ | CH₃ | H | H | CH₃ | CH₃ | CH |
| CH₂CH₃ | CH₃ | H | H | OCH₃ | OCH₃ | N |
| CH₂CH₃ | CH₃ | H | H | CH₃ | OCH₃ | N |
| CH₂CH₃ | CH₃ | H | H | NHCH₃ | OCH₂CH₃ | N |
| CH₂CH₃ | CH₃ | H | CH₃ | CH₃ | OCH₃ | N |
| CH₂CH₃ | CH₂CH=CH₂ | H | H | OCH₃ | OCH₃ | CH |
| CH₂CH₃ | CH₂CH=CH₂ | H | H | Cl | OCH₃ | CH |
| CH₂CH₃ | CH₂CH=CH₂ | H | H | CH₃ | OCH₃ | CH |
| CH₂CH₃ | CH₂CH=CH₂ | H | H | CH₃ | CH₃ | CH |
| CH₂CH₃ | CH₂CH=CH₂ | H | H | OCH₃ | OCH₃ | N |
| CH₂CH₃ | CH₂CH=CH₂ | H | H | CH₃ | OCH₃ | N |
| CH₂CH₃ | CH₂CH=CH₂ | H | H | NHCH₃ | OCH₂CH₃ | N |
| CH₂CH₃ | CH₂CH=CH₂ | H | CH₃ | CH₃ | OCH₃ | N |

TABLE II-continued
GENERAL STRUCTURE 2

| R₁ | R₂ | R₃ | R | X | Y | Z |
|---|---|---|---|---|---|---|
| CH₂CH₃ | CH₃ | CH₃ | H | OCH₃ | OCH₃ | CH |
| CH₂CH₃ | CH₃ | CH₃ | H | Cl | OCH₃ | CH |
| CH₂CH₃ | CH₃ | CH₃ | H | CH₃ | OCH₃ | CH |
| CH₂CH₃ | CH₃ | CH₃ | H | CH₃ | CH₃ | CH |
| CH₂CH₃ | CH₃ | CH₃ | H | OCH₃ | OCH₃ | N |
| CH₂CH₃ | CH₃ | CH₃ | H | CH₃ | OCH₃ | N |
| CH₂CH₃ | CH₃ | CH₃ | H | NHCH₃ | OCH₂CH₃ | N |
| CH₂CH₃ | CH₃ | CH₃ | CH₃ | CH₃ | OCH₃ | N |
| CH₂CH₃ | —CH₂CH₂CH₂— | | H | OCH₃ | OCH₃ | CH |
| CH₂CH₃ | —CH₂CH₂CH₂— | | H | Cl | OCH₃ | CH |
| CH₂CH₃ | —CH₂CH₂CH₂— | | H | CH₃ | OCH₃ | CH |
| CH₂CH₃ | —CH₂CH₂CH₂— | | H | CH₃ | CH₃ | CH |
| CH₂CH₃ | —CH₂CH₂CH₂— | | H | OCH₃ | OCH₃ | N |
| CH₂CH₃ | —CH₂CH₂CH₂— | | H | CH₃ | OCH₃ | N |
| CH₂CH₃ | —CH₂CH₂CH₂— | | H | NHCH₃ | OCH₂CH₃ | N |
| CH₂CH₃ | —CH₂CH₂CH₂— | | CH₃ | CH₃ | OCH₃ | N |
| CF₃ | CH₃ | H | H | OCH₃ | OCH₃ | CH |
| CF₃ | CH₃ | H | H | Cl | OCH₃ | CH |
| CF₃ | CH₃ | H | H | CH₃ | OCH₃ | CH |
| CF₃ | CH₃ | H | H | CH₃ | CH₃ | CH |
| CF₃ | CH₃ | H | H | OCH₃ | OCH₃ | N |
| CF₃ | CH₃ | H | H | CH₃ | OCH₃ | N |
| CF₃ | CH₃ | H | H | NHCH₃ | OCH₂CH₃ | N |
| CF₃ | CH₃ | H | CH₃ | CH₃ | OCH₃ | N |
| CF₃ | CH₂CH=CH₂ | H | H | OCH₃ | OCH₃ | CH |
| CF₃ | CH₂CH=CH₂ | H | H | Cl | OCH₃ | CH |
| CF₃ | CH₂CH=CH₂ | H | H | CH₃ | OCH₃ | CH |
| CF₃ | CH₂CH=CH₂ | H | H | CH₃ | CH₃ | CH |
| CF₃ | CH₂CH=CH₂ | H | H | OCH₃ | OCH₃ | N |
| CF₃ | CH₂CH=CH₂ | H | H | CH₃ | OCH₃ | N |
| CF₃ | CH₂CH=CH₂ | H | H | NHCH₃ | OCH₂CH₃ | N |
| CF₃ | CH₂CH=CH₂ | H | CH₃ | CH₃ | OCH₃ | N |
| CF₃ | CH₃ | CH₃ | H | OCH₃ | OCH₃ | CH |
| CF₃ | CH₃ | CH₃ | H | Cl | OCH₃ | CH |
| CF₃ | CH₃ | CH₃ | H | CH₃ | OCH₃ | CH |
| CF₃ | CH₃ | CH₃ | H | CH₃ | CH₃ | CH |
| CF₃ | CH₃ | CH₃ | H | OCH₃ | OCH₃ | N |
| CF₃ | CH₃ | CH₃ | H | CH₃ | OCH₃ | N |
| CF₃ | CH₃ | CH₃ | H | NHCH₃ | OCH₂CH₃ | N |
| CF₃ | CH₃ | CH₃ | CH₃ | CH₃ | OCH₃ | N |
| CF₃ | —CH₂CH₂CH₂— | | H | OCH₃ | OCH₃ | CH |
| CF₃ | —CH₂CH₂CH₂— | | H | Cl | OCH₃ | CH |
| CF₃ | —CH₂CH₂CH₂— | | H | CH₃ | OCH₃ | CH |
| CF₃ | —CH₂CH₂CH₂— | | H | CH₃ | CH₃ | CH |
| CF₃ | —CH₂CH₂CH₂— | | H | OCH₃ | OCH₃ | N |
| CF₃ | —CH₂CH₂CH₂— | | H | CH₃ | OCH₃ | N |
| CF₃ | —CH₂CH₂CH₂— | | H | NHCH₃ | OCH₂CH₃ | N |
| CF₃ | —CH₂CH₂CH₂— | | CH₃ | CH₃ | OCH₃ | N |
| OCH₃ | CH₃ | H | H | OCH₃ | OCH₃ | CH |
| OCH₃ | CH₃ | H | H | Cl | OCH₃ | CH |
| OCH₃ | CH₃ | H | H | CH₃ | OCH₃ | CH |
| OCH₃ | CH₃ | H | H | CH₃ | CH₃ | CH |
| OCH₃ | CH₃ | H | H | OCH₃ | OCH₃ | N |
| OCH₃ | CH₃ | H | H | CH₃ | OCH₃ | N |
| OCH₃ | CH₃ | H | H | NHCH₃ | OCH₂CH₃ | N |
| OCH₃ | CH₃ | H | CH₃ | CH₃ | OCH₃ | N |
| OCH₃ | CH₂CH=CH₂ | H | H | OCH₃ | OCH₃ | CH |
| OCH₃ | CH₂CH=CH₂ | H | H | Cl | OCH₃ | CH |
| OCH₃ | CH₂CH=CH₂ | H | H | CH₃ | OCH₃ | CH |
| OCH₃ | CH₂CH=CH₂ | H | H | CH₃ | CH₃ | CH |
| OCH₃ | CH₂CH=CH₂ | H | H | OCH₃ | OCH₃ | N |
| OCH₃ | CH₂CH=CH₂ | H | H | CH₃ | OCH₃ | N |
| OCH₃ | CH₂CH=CH₂ | H | H | NHCH₃ | OCH₂CH₃ | N |
| OCH₃ | CH₂CH=CH₂ | H | CH₃ | CH₃ | OCH₃ | N |
| OCH₃ | CH₃ | CH₃ | H | OCH₃ | OCH₃ | CH |
| OCH₃ | CH₃ | CH₃ | H | Cl | OCH₃ | CH |
| OCH₃ | CH₃ | CH₃ | H | CH₃ | OCH₃ | CH |
| OCH₃ | CH₃ | CH₃ | H | CH₃ | CH₃ | CH |
| OCH₃ | CH₃ | CH₃ | H | OCH₃ | OCH₃ | N |
| OCH₃ | CH₃ | CH₃ | H | CH₃ | OCH₃ | N |
| OCH₃ | CH₃ | CH₃ | H | NHCH₃ | OCH₂CH₃ | N |
| OCH₃ | CH₃ | CH₃ | CH₃ | CH₃ | OCH₃ | N |
| OCH₃ | —CH₂CH₂CH₂— | | H | OCH₃ | OCH₃ | CH |
| OCH₃ | —CH₂CH₂CH₂— | | H | Cl | OCH₃ | CH |
| OCH₃ | —CH₂CH₂CH₂— | | H | CH₃ | OCH₃ | CH |
| OCH₃ | —CH₂CH₂CH₂— | | H | CH₃ | CH₃ | CH |
| OCH₃ | —CH₂CH₂CH₂— | | H | OCH₃ | OCH₃ | N |
| OCH₃ | —CH₂CH₂CH₂— | | H | CH₃ | OCH₃ | N |
| OCH₃ | —CH₂CH₂CH₂— | | H | NHCH₃ | OCH₂CH₃ | N |
| OCH₃ | —CH₂CH₂CH₂— | | CH₃ | CH₃ | OCH₃ | N |

TABLE II-continued
GENERAL STRUCTURE 2

| R₁ | R₂ | R₃ | R | X | Y | Z |
|---|---|---|---|---|---|---|
| OCF₂H | CH₃ | H | H | OCH₃ | OCH₃ | CH |
| OCF₂H | CH₃ | H | H | Cl | OCH₃ | CH |
| OCF₂H | CH₃ | H | H | CH₃ | OCH₃ | CH |
| OCF₂H | CH₃ | H | H | CH₃ | CH₃ | CH |
| OCF₂H | CH₃ | H | H | OCH₃ | OCH₃ | N |
| OCF₂H | CH₃ | H | H | CH₃ | OCH₃ | N |
| OCF₂H | CH₃ | H | H | NHCH₃ | OCH₂CH₃ | N |
| OCF₂H | CH₃ | H | CH₃ | CH₃ | OCH₃ | N |
| OCF₂H | CH₂CH=CH₂ | H | H | OCH₃ | OCH₃ | CH |
| OCF₂H | CH₂CH=CH₂ | H | H | Cl | OCH₃ | CH |
| OCF₂H | CH₂CH=CH₂ | H | H | CH₃ | OCH₃ | CH |
| OCF₂H | CH₂CH=CH₂ | H | H | CH₃ | CH₃ | CH |
| OCF₂H | CH₂CH=CH₂ | H | H | OCH₃ | OCH₃ | N |
| OCF₂H | CH₂CH=CH₂ | H | H | CH₃ | OCH₃ | N |
| OCF₂H | CH₂CH=CH₂ | H | H | NHCH₃ | OCH₂CH₃ | N |
| OCF₂H | CH₂CH=CH₂ | H | CH₃ | CH₃ | OCH₃ | N |
| OCF₂H | CH₃ | CH₃ | H | OCH₃ | OCH₃ | CH |
| OCF₂H | CH₃ | CH₃ | H | Cl | OCH₃ | CH |
| OCF₂H | CH₃ | CH₃ | H | CH₃ | OCH₃ | CH |
| OCF₂H | CH₃ | CH₃ | H | CH₃ | CH₃ | CH |
| OCF₂H | CH₃ | CH₃ | H | OCH₃ | OCH₃ | N |
| OCF₂H | CH₃ | CH₃ | H | CH₃ | OCH₃ | N |
| OCF₂H | CH₃ | CH₃ | H | NHCH₃ | OCH₂CH₃ | N |
| OCF₂H | CH₃ | CH₃ | CH₃ | CH₃ | OCH₃ | N |
| OCF₂H | —CH₂CH₂CH₂— | | H | OCH₃ | OCH₃ | CH |
| OCF₂H | —CH₂CH₂CH₂— | | H | Cl | OCH₃ | CH |
| OCF₂H | —CH₂CH₂CH₂— | | H | CH₃ | OCH₃ | CH |
| OCF₂H | —CH₂CH₂CH₂— | | H | CH₃ | CH₃ | CH |
| OCF₂H | —CH₂CH₂CH₂— | | H | OCH₃ | OCH₃ | N |
| OCF₂H | —CH₂CH₂CH₂— | | H | CH₃ | OCH₃ | N |
| OCF₂H | —CH₂CH₂CH₂— | | H | NHCH₃ | OCH₂CH₃ | N |
| OCF₂H | —CH₂CH₂CH₂— | | CH₃ | CH₃ | OCH₃ | N |
| SCF₂H | CH₃ | H | H | OCH₃ | OCH₃ | CH |
| SCF₂H | CH₃ | H | H | Cl | OCH₃ | CH |
| SCF₂H | CH₃ | H | H | CH₃ | OCH₃ | CH |
| SCF₂H | CH₃ | H | H | CH₃ | CH₃ | CH |
| SCF₂H | CH₃ | H | H | OCH₃ | OCH₃ | N |
| SCF₂H | CH₃ | H | H | CH₃ | OCH₃ | N |
| SCF₂H | CH₃ | H | H | NHCH₃ | OCH₂CH₃ | N |
| SCF₂H | CH₃ | H | CH₃ | CH₃ | OCH₃ | N |
| SCF₂H | CH₂CH=CH₂ | H | H | OCH₃ | OCH₃ | CH |
| SCF₂H | CH₂CH=CH₂ | H | H | Cl | OCH₃ | CH |
| SCF₂H | CH₂CH=CH₂ | H | H | CH₃ | OCH₃ | CH |
| SCF₂H | CH₂CH=CH₂ | H | H | CH₃ | CH₃ | CH |
| SCF₂H | CH₂CH=CH₂ | H | H | OCH₃ | OCH₃ | N |
| SCF₂H | CH₂CH=CH₂ | H | H | CH₃ | OCH₃ | N |
| SCF₂H | CH₂CH=CH₂ | H | H | NHCH₃ | OCH₂CH₃ | N |
| SCF₂H | CH₂CH=CH₂ | H | CH₃ | CH₃ | OCH₃ | N |
| SCF₂H | CH₃ | CH₃ | H | OCH₃ | OCH₃ | CH |
| SCF₂H | CH₃ | CH₃ | H | Cl | OCH₃ | CH |
| SCF₂H | CH₃ | CH₃ | H | CH₃ | OCH₃ | CH |
| SCF₂H | CH₃ | CH₃ | H | CH₃ | CH₃ | CH |
| SCF₂H | CH₃ | CH₃ | H | OCH₃ | OCH₃ | N |
| SCF₂H | CH₃ | CH₃ | H | CH₃ | OCH₃ | N |
| SCF₂H | CH₃ | CH₃ | H | NHCH₃ | OCH₂CH₃ | N |
| SCF₂H | CH₃ | CH₃ | CH₃ | CH₃ | OCH₃ | N |
| SCF₂H | —CH₂CH₂CH₂— | | H | OCH₃ | OCH₃ | CH |
| SCF₂H | —CH₂CH₂CH₂— | | H | Cl | OCH₃ | CH |
| SCF₂H | —CH₂CH₂CH₂— | | H | CH₃ | OCH₃ | CH |
| SCF₂H | —CH₂CH₂CH₂— | | H | CH₃ | CH₃ | CH |
| SCF₂H | —CH₂CH₂CH₂— | | H | OCH₃ | OCH₃ | N |
| SCF₂H | —CH₂CH₂CH₂— | | H | CH₃ | OCH₃ | N |
| SCF₂H | —CH₂CH₂CH₂— | | H | NHCH₃ | OCH₂CH₃ | N |
| SCF₂H | —CH₂CH₂CH₂— | | CH₃ | CH₃ | OCH₃ | N |
| SO₂CF₂H | CH₃ | H | H | OCH₃ | OCH₃ | CH |
| SO₂CF₂H | CH₃ | H | H | Cl | OCH₃ | CH |
| SO₂CF₂H | CH₃ | H | H | CH₃ | OCH₃ | CH |
| SO₂CF₂H | CH₃ | H | H | CH₃ | CH₃ | CH |
| SO₂CF₂H | CH₃ | H | H | OCH₃ | OCH₃ | N |
| SO₂CF₂H | CH₃ | H | H | CH₃ | OCH₃ | N |
| SO₂CF₂H | CH₃ | H | H | NHCH₃ | OCH₂CH₃ | N |
| SO₂CF₂H | CH₃ | H | CH₃ | CH₃ | OCH₃ | N |
| SO₂CF₂H | CH₂CH=CH₂ | H | H | OCH₃ | OCH₃ | CH |
| SO₂CF₂H | CH₂CH=CH₂ | H | H | Cl | OCH₃ | CH |
| SO₂CF₂H | CH₂CH=CH₂ | H | H | CH₃ | OCH₃ | CH |
| SO₂CF₂H | CH₂CH=CH₂ | H | H | CH₃ | CH₃ | CH |
| SO₂CF₂H | CH₂CH=CH₂ | H | H | OCH₃ | OCH₃ | N |
| SO₂CF₂H | CH₂CH=CH₂ | H | H | CH₃ | OCH₃ | N |
| SO₂CF₂H | CH₂CH=CH₂ | H | H | NHCH₃ | OCH₂CH₃ | N |
| SO₂CF₂H | CH₂CH=CH₂ | H | CH₃ | CH₃ | OCH₃ | N |

TABLE II-continued

GENERAL STRUCTURE 2

| R₁ | R₂ | R₃ | R | X | Y | Z |
|---|---|---|---|---|---|---|
| SO$_2$CF$_2$H | CH$_3$ | CH$_3$ | H | OCH$_3$ | OCH$_3$ | CH |
| SO$_2$CF$_2$H | CH$_3$ | CH$_3$ | H | Cl | OCH$_3$ | CH |
| SO$_2$CF$_2$H | CH$_3$ | CH$_3$ | H | CH$_3$ | OCH$_3$ | CH |
| SO$_2$CF$_2$H | CH$_3$ | CH$_3$ | H | CH$_3$ | CH$_3$ | CH |
| SO$_2$CF$_2$H | CH$_3$ | CH$_3$ | H | OCH$_3$ | OCH$_3$ | N |
| SO$_2$CF$_2$H | CH$_3$ | CH$_3$ | H | CH$_3$ | OCH$_3$ | N |
| SO$_2$CF$_2$H | CH$_3$ | CH$_3$ | H | NHCH$_3$ | OCH$_2$CH$_3$ | N |
| SO$_2$CF$_2$H | CH$_3$ | CH$_3$ | CH$_3$ | CH$_3$ | OCH$_3$ | N |
| SO$_2$CF$_2$H | —CH$_2$CH$_2$CH$_2$— |  | H | OCH$_3$ | OCH$_3$ | CH |
| SO$_2$CF$_2$H | —CH$_2$CH$_2$CH$_2$— |  | H | Cl | OCH$_3$ | CH |
| SO$_2$CF$_2$H | —CH$_2$CH$_2$CH$_2$— |  | H | CH$_3$ | OCH$_3$ | CH |
| SO$_2$CF$_2$H | —CH$_2$CH$_2$CH$_2$— |  | H | CH$_3$ | CH$_3$ | CH |
| SO$_2$CF$_2$H | —CH$_2$CH$_2$CH$_2$— |  | H | OCH$_3$ | OCH$_3$ | N |
| SO$_2$CF$_2$H | —CH$_2$CH$_2$CH$_2$— |  | H | CH$_3$ | OCH$_3$ | N |
| SO$_2$CF$_2$H | —CH$_2$CH$_2$CH$_2$— |  | H | NHCH$_3$ | OCH$_2$CH$_3$ | N |
| SO$_2$CF$_2$H | —CH$_2$CH$_2$CH$_2$— |  | CH$_3$ | CH$_3$ | OCH$_3$ | N |

TABLE II

GENERAL STRUCTURE 3

| R₁ | R₂ | R₃ | A |
|---|---|---|---|
| H | H | H | A-2 (X$_1$=CH$_3$, Y$_1$=CH$_2$) |
| H | H | H | A-3 (X$_1$=CH$_3$) |
| H | H | H | A-3 (X$_1$=OCH$_3$) |
| H | H | H | A-4 (X$_1$=CH$_3$, Y$_3$=CH$_3$) |
| H | H | H | A-4 (X$_1$=CH$_3$, Y$_3$=OCH$_3$) |
| H | H | H | A-4 (X$_1$=OCH$_3$, Y$_3$=CH$_3$) |
| H | H | H | A-5 (X$_2$=CH$_3$, Y$_2$=OCH$_3$) |
| H | H | H | A-5 (X$_2$=CH$_3$, Y$_2$=SCH$_3$) |
| H | H | H | A-6 (X$_3$=OCH$_3$) |
| H | H | H | A-7 (X$_4$=OCH$_3$, Y$_4$=OCH$_3$) |
| H | H | H | A-7 (X$_4$=CH$_3$, Y$_4$=OCH$_3$) |
| H | H | H | A-7 (X$_4$=OCH$_3$, Y$_4$=CH$_3$) |
| H | H | CH$_3$ | A-2 (X$_1$=CH$_3$, Y$_1$=CH$_2$) |
| H | H | CH$_3$ | A-3 (X$_1$=CH$_3$) |
| H | H | CH$_3$ | A-3 (X$_1$=OCH$_3$) |
| H | H | CH$_3$ | A-4 (X$_1$=CH$_3$, Y$_3$=CH$_3$) |
| H | H | CH$_3$ | A-4 (X$_1$=CH$_3$, Y$_3$=OCH$_3$) |
| H | H | CH$_3$ | A-4 (X$_1$=OCH$_3$, Y$_3$=CH$_3$) |
| H | H | CH$_3$ | A-5 (X$_2$=CH$_3$, Y$_2$=OCH$_3$) |
| H | H | CH$_3$ | A-5 (X$_2$=CH$_3$, Y$_2$=SCH$_3$) |
| H | H | CH$_3$ | A-6 (X$_3$=OCH$_3$) |
| H | H | CH$_3$ | A-7 (X$_4$=OCH$_3$, Y$_4$=OCH$_3$) |
| H | H | CH$_3$ | A-7 (X$_4$=CH$_3$, Y$_4$=OCH$_3$) |
| H | H | CH$_3$ | A-7 (X$_4$=OCH$_3$, Y$_4$=CH$_3$) |
| H | H | CH$_2$CH$_3$ | A-2 (X$_1$=CH$_3$, Y$_1$=CH$_2$) |
| H | H | CH$_2$CH | A-3 (X$_1$=CH$_3$) |
| H | H | CH$_2$CH$_3$ | A-3 (X$_1$=OCH$_3$) |
| H | H | CH$_2$CH$_3$ | A-4 (X$_1$=CH$_3$, Y$_3$=CH$_3$) |
| H | H | CH$_2$CH$_3$ | A-4 (X$_1$=CH$_3$, Y$_3$=OCH$_3$) |
| H | H | CH$_2$CH$_3$ | A-4 (X$_1$=OCH$_3$, Y$_3$=CH$_3$) |
| H | H | CH$_2$CH$_3$ | A-5 (X$_2$=CH$_3$, Y$_2$=OCH$_3$) |
| H | H | CH$_2$CH$_3$ | A-5 (X$_2$=CH$_3$, Y$_2$=SCH$_3$) |
| H | H | CH$_2$CH$_3$ | A-6 (X$_3$=OCH$_3$) |
| H | H | CH$_2$CH$_3$ | A-7 (X$_4$=OCH$_3$, Y$_4$=OCH$_3$) |
| H | H | CH$_2$CH$_3$ | A-7 (X$_4$=CH$_3$, Y$_4$=OCH$_3$) |
| H | H | CH$_2$CH$_3$ | A-7 (X$_4$=OCH$_3$, Y$_4$=CH$_3$) |
| H | CH$_2$CF$_3$ | H | A-2 (X$_1$=CH$_3$, Y$_1$=CH$_2$) |
| H | CH$_2$CF$_3$ | H | A-3 (X$_1$=CH$_3$) |
| H | CH$_2$CF$_3$ | H | A-3 (X$_1$=OCH$_3$) |
| H | CH$_2$CF$_3$ | H | A-4 (X$_1$=CH$_3$, Y$_3$=CH$_3$) |
| H | CH$_2$CF$_3$ | H | A-4 (X$_1$=CH$_3$, Y$_3$=OCH$_3$) |
| H | CH$_2$CF$_3$ | H | A-4 (X$_1$=OCH$_3$, Y$_3$=CH$_3$) |
| H | CH$_2$CF$_3$ | H | A-5 (X$_2$=CH$_3$, Y$_2$=OCH$_3$) |
| H | CH$_2$CF$_3$ | H | A-5 (X$_2$=CH$_3$, Y$_2$=SCH$_3$) |
| H | CH$_2$CF$_3$ | H | A-6 (X$_3$=OCH$_3$) |
| H | CH$_2$CF$_3$ | H | A-7 (X$_4$=OCH$_3$, Y$_4$=OCH$_3$) |
| H | CH$_2$CF$_3$ | H | A-7 (X$_4$=CH$_3$, Y$_4$=OCH$_3$) |
| H | CH$_2$CF$_3$ | H | A-7 (X$_4$=OCH$_3$, Y$_4$=CH$_3$) |
| H | CH$_2$CH$_2$Cl | H | A-2 (X$_1$=CH$_3$, Y$_1$=CH$_2$) |
| H | CH$_2$CH$_2$Cl | H | A-3 (X$_1$=CH$_3$) |
| H | CH$_2$CH$_2$Cl | H | A-3 (X$_1$=OCH$_3$) |
| H | CH$_2$CH$_2$Cl | H | A-4 (X$_1$=CH$_3$, Y$_3$=CH$_3$) |
| H | CH$_2$CH$_2$Cl | H | A-4 (X$_1$=CH$_3$, Y$_3$=OCH$_3$) |
| H | CH$_2$CH$_2$Cl | H | A-4 (X$_1$=OCH$_3$, Y$_3$=CH$_3$) |
| H | CH$_2$CH$_2$Cl | H | A-5 (X$_2$=CH$_3$, Y$_2$=OCH$_3$) |
| H | CH$_2$CH$_2$Cl | H | A-5 (X$_2$=CH$_3$, Y$_2$=SCH$_3$) |
| H | CH$_2$CH$_2$Cl | H | A-6 (X$_3$=OCH$_3$) |

TABLE II-continued
GENERAL STRUCTURE 3

| R₁ | R₂ | R₃ | A |
|---|---|---|---|
| H | $CH_2CH_2Cl$ | H | A-7 ($X_4$=$OCH_3$, $Y_4$=$OCH_3$) |
| H | $CH_2CH_2Cl$ | H | A-7 ($X_4$=$CH_3$, $Y_4$=$OCH_3$) |
| H | $CH_2CH_2Cl$ | H | A-7 ($X_4$=$OCH_3$, $Y_4$=$CH_3$) |
| H | $CH_2CN$ | H | A-2 ($X_1$=$CH_3$, $Y_1$=$CH_2$) |
| H | $CH_2CN$ | H | A-3 ($X_1$=$CH_3$) |
| H | $CH_2CN$ | H | A-3 ($X_1$=$OCH_3$) |
| H | $CH_2CN$ | H | A-4 ($X_1$=$CH_3$, $Y_3$=$CH_3$) |
| H | $CH_2CN$ | H | A-4 ($X_1$=$CH_3$, $Y_3$=$OCH_3$) |
| H | $CH_2CN$ | H | A-4 ($X_1$=$OCH_3$, $Y_3$=$CH_3$) |
| H | $CH_2CN$ | H | A-5 ($X_2$=$CH_3$, $Y_2$=$OCH_3$) |
| H | $CH_2CN$ | H | A-5 ($X_2$=$CH_3$, $Y_2$=$SCH_3$) |
| H | $CH_2CN$ | H | A-6 ($X_3$=$OCH_3$) |
| H | $CH_2CN$ | H | A-7 ($X_4$=$OCH_3$, $Y_4$=$OCH_3$) |
| H | $CH_2CN$ | H | A-7 ($X_4$=$CH_3$, $Y_4$=$OCH_3$) |
| H | $CH_2CN$ | H | A-7 ($X_4$=$OCH_3$, $Y_4$=$CH_3$) |
| H | $CH_2CH_2OCH_3$ | H | A-2 ($X_1$=$CH_3$, $Y_1$=$CH_2$) |
| H | $CH_2CH_2OCH_3$ | H | A-3 ($X_1$=$CH_3$) |
| H | $CH_2CH_2OCH_3$ | H | A-3 ($X_1$=$OCH_3$) |
| H | $CH_2CH_2OCH_3$ | H | A-4 ($X_1$=$CH_3$, $Y_3$=$CH_3$) |
| H | $CH_2CH_2OCH_3$ | H | A-4 ($X_1$=$CH_3$, $Y_3$=$OCH_3$) |
| H | $CH_2CH_2OCH_3$ | H | A-4 ($X_1$=$OCH_3$, $Y_3$=$CH_3$) |
| H | $CH_2CH_2OCH_3$ | H | A-5 ($X_2$=$CH_3$, $Y_2$=$OCH_3$) |
| H | $CH_2CH_2OCH_3$ | H | A-5 ($X_2$=$CH_3$, $Y_2$=$SCH_3$) |
| H | $CH_2CH_2OCH_3$ | H | A-6 ($X_3$=$OCH_3$) |
| H | $CH_2CH_2OCH_3$ | H | A-7 ($X_4$=$OCH_3$, $Y_4$=$OCH_3$) |
| H | $CH_2CH_2OCH_3$ | H | A-7 ($X_4$=$CH_3$, $Y_4$=$OCH_3$) |
| H | $CH_2CH_2OCH_3$ | H | A-7 ($X_4$=$OCH_3$, $Y_4$=$CH_3$) |
| H | $CH_2CH$=$CH_2$ | H | A-2 ($X_1$=$CH_3$, $Y_1$=$CH_2$) |
| H | $CH_2CH$=$CH_2$ | H | A-3 ($X_1$=$CH_3$) |
| H | $CH_2CH$=$CH_2$ | H | A-3 ($X_1$=$OCH_3$) |
| H | $CH_2CH$=$CH_2$ | H | A-4 ($X_1$=$CH_3$, $Y_3$=$CH_3$) |
| H | $CH_2CH$=$CH_2$ | H | A-4 ($X_1$=$CH_3$, $Y_3$=$OCH_3$) |
| H | $CH_2CH$=$CH_2$ | H | A-4 ($X_1$=$OCH_3$, $Y_3$=$CH_3$) |
| H | $CH_2CH$=$CH_2$ | H | A-5 ($X_2$=$CH_3$, $Y_2$=$OCH_3$) |
| H | $CH_2CH$=$CH_2$ | H | A-5 ($X_2$=$CH_3$, $Y_2$=$SCH_3$) |
| H | $CH_2CH$=$CH_2$ | H | A-6 ($X_3$=$OCH_3$) |
| H | $CH_2CH$=$CH_2$ | H | A-7 ($X_4$=$OCH_3$, $Y_4$=$OCH_3$) |
| H | $CH_2CH$=$CH_2$ | H | A-7 ($X_4$=$CH_3$, $Y_4$=$OCH_3$) |
| H | $CH_2CH$=$CH_2$ | H | A-7 ($X_4$=$OCH_3$, $Y_4$=$CH_3$) |
| H | $CH_2C$≡$CH$ | H | A-2 ($X_1$=$CH_3$, $Y_1$=$CH_2$) |
| H | $CH_2C$≡$CH$ | H | A-3 ($X_1$=$CH_3$) |
| H | $CH_2C$≡$CH$ | H | A-3 ($X_1$=$OCH_3$) |
| H | $CH_2C$≡$CH$ | H | A-4 ($X_1$=$CH_3$, $Y_3$=$CH_3$) |
| H | $CH_2C$≡$CH$ | H | A-4 ($X_1$=$CH_3$, $Y_3$=$OCH_3$) |
| H | $CH_2C$≡$CH$ | H | A-4 ($X_1$=$OCH_3$, $Y_3$=$CH_3$) |
| H | $CH_2C$≡$CH$ | H | A-5 ($X_2$=$CH_3$, $Y_2$=$OCH_3$) |
| H | $CH_2C$≡$CH$ | H | A-5 ($X_2$=$CH_3$, $Y_2$=$SCH_3$) |
| H | $CH_2C$≡$CH$ | H | A-6 ($X_3$=$OCH_3$) |
| H | $CH_2C$≡$CH$ | H | A-7 ($X_4$=$OCH_3$, $Y_4$=$OCH_3$) |
| H | $CH_2C$≡$CH$ | H | A-7 ($X_4$=$CH_3$, $Y_4$=$OCH_3$) |
| H | $CH_2C$≡$CH$ | H | A-7 ($X_4$=$OCH_3$, $Y_4$=$CH_3$) |
| H | cyclo-$C_3H_7$ | H | A-2 ($X_1$=$CH_3$, $Y_1$=$CH_2$) |
| H | cyclo-$C_3H_7$ | H | A-3 ($X_1$=$CH_3$) |
| H | cyclo-$C_3H_7$ | H | A-3 ($X_1$=$OCH_3$) |
| H | cyclo-$C_3H_7$ | H | A-4 ($X_1$=$CH_3$, $Y_3$=$CH_3$) |
| H | cyclo-$C_3H_7$ | H | A-4 ($X_1$=$CH_3$, $Y_3$=$OCH_3$) |
| H | cyclo-$C_3H_7$ | H | A-4 ($X_1$=$OCH_3$, $Y_3$=$CH_3$) |
| H | cyclo-$C_3H_7$ | H | A-5 ($X_2$=$CH_3$, $Y_2$=$OCH_3$) |
| H | cyclo-$C_3H_7$ | H | A-5 ($X_2$=$CH_3$, $Y_2$=$SCH_3$) |
| H | cyclo-$C_3H_7$ | H | A-6 ($X_3$=$OCH_3$) |
| H | cyclo-$C_3H_7$ | H | A-7 ($X_4$=$OCH_3$, $Y_4$=$OCH_3$) |
| H | cyclo-$C_3H_7$ | H | A-7 ($X_4$=$CH_3$, $Y_4$=$OCH_3$) |
| H | cyclo-$C_3H_7$ | H | A-7 ($X_4$=$OCH_3$, $Y_4$=$CH_3$) |
| H | $CH_3$ | $CH_3$ | A-2 ($X_1$=$CH_3$, $Y_1$=$CH_2$) |
| H | $CH_3$ | $CH_3$ | A-3 ($X_1$=$CH_3$) |
| H | $CH_3$ | $CH_3$ | A-3 ($X_1$=$OCH_3$) |
| H | $CH_3$ | $CH_3$ | A-4 ($X_1$=$CH_3$, $Y_3$=$CH_3$) |
| H | $CH_3$ | $CH_3$ | A-4 ($X_1$=$CH_3$, $Y_3$=$OCH_3$) |
| H | $CH_3$ | $CH_3$ | A-4 ($X_1$=$OCH_3$, $Y_3$=$CH_3$) |
| H | $CH_3$ | $CH_3$ | A-5 ($X_2$=$CH_3$, $Y_2$=$OCH_3$) |
| H | $CH_3$ | $CH_3$ | A-5 ($X_2$=$CH_3$, $Y_2$=$SCH_3$) |
| H | $CH_3$ | $CH_3$ | A-6 ($X_3$=$OCH_3$) |
| H | $CH_3$ | $CH_3$ | A-7 ($X_4$=$OCH_3$, $Y_4$=$OCH_3$) |
| H | $CH_3$ | $CH_3$ | A-7 ($X_4$=$CH_3$, $Y_4$=$OCH_3$) |
| H | $CH_3$ | $CH_3$ | A-7 ($X_4$=$OCH_3$, $Y_4$=$CH_3$) |
| H | $CH_2CH_3$ | $CH_3$ | A-2 ($X_1$=$CH_3$, $Y_1$=$CH_2$) |
| H | $CH_2CH_3$ | $CH_3$ | A-3 ($X_1$=$CH_3$) |
| H | $CH_2CH_3$ | $CH_3$ | A-3 ($X_1$=$OCH_3$) |
| H | $CH_2CH_3$ | $CH_3$ | A-4 ($X_1$=$CH_3$, $Y_3$=$CH_3$) |
| H | $CH_2CH_3$ | $CH_3$ | A-4 ($X_1$=$CH_3$, $Y_3$=$OCH_3$) |

TABLE II-continued

GENERAL STRUCTURE 3

| R₁ | R₂ | R₃ | A |
|---|---|---|---|
| H | CH$_2$CH$_3$ | CH$_3$ | A-4 (X$_1$=OCH$_3$, Y$_3$=CH$_3$) |
| H | CH$_2$CH$_3$ | CH$_3$ | A-5 (X$_2$=CH$_3$, Y$_2$=OCH$_3$) |
| H | CH$_2$CH$_3$ | CH$_3$ | A-5 (X$_2$=CH$_3$, Y$_2$=SCH$_3$) |
| H | CH$_2$CH$_3$ | CH$_3$ | A-6 (X$_3$=OCH$_3$) |
| H | CH$_2$CH$_3$ | CH$_3$ | A-7 (X$_4$=OCH$_3$, Y$_4$=OCH$_3$) |
| H | CH$_2$CH$_3$ | CH$_3$ | A-7 (X$_4$=CH$_3$, Y$_4$=OCH$_3$) |
| H | CH$_2$CH$_3$ | CH$_3$ | A-7 (X$_4$=OCH$_3$, Y$_4$=CH$_3$) |
| H | CH$_2$CH$_3$ | CH$_2$CH$_3$ | A-2 (X$_1$=CH$_3$, Y$_1$=CH$_2$) |
| H | CH$_2$CH$_3$ | CH$_2$CH$_3$ | A-3 (X$_1$=CH$_3$) |
| H | CH$_2$CH$_3$ | CH$_2$CH$_3$ | A-3 (X$_1$=OCH$_3$) |
| H | CH$_2$CH$_3$ | CH$_2$CH$_3$ | A-4 (X$_1$=CH$_3$, Y$_3$=CH$_3$) |
| H | CH$_2$CH$_3$ | CH$_2$CH$_3$ | A-4 (X$_1$=CH$_3$, Y$_3$=OCH$_3$) |
| H | CH$_2$CH$_3$ | CH$_2$CH$_3$ | A-4 (X$_1$=OCH$_3$, Y$_3$=CH$_3$) |
| H | CH$_2$CH$_3$ | CH$_2$CH$_3$ | A-5 (X$_2$=CH$_3$, Y$_2$=OCH$_3$) |
| H | CH$_2$CH$_3$ | CH$_2$CH$_3$ | A-5 (X$_2$=CH$_3$, Y$_2$=SCH$_3$) |
| H | CH$_2$CH$_3$ | CH$_2$CH$_3$ | A-6 (X$_3$=OCH$_3$) |
| H | CH$_2$CH$_3$ | CH$_2$CH$_3$ | A-7 (X$_4$=OCH$_3$, Y$_4$=OCH$_3$) |
| H | CH$_2$CH$_3$ | CH$_2$CH$_3$ | A-7 (X$_4$=CH$_3$, Y$_4$=OCH$_3$) |
| H | CH$_2$CH$_3$ | CH$_2$CH$_3$ | A-7 (X$_4$=OCH$_3$, Y$_4$=CH$_3$) |
| H | OCH$_3$ | CH$_3$ | A-2 (X$_1$=CH$_3$, Y$_1$=CH$_2$) |
| H | OCH$_3$ | CH$_3$ | A-3 (X$_1$=CH$_3$) |
| H | OCH$_3$ | CH$_3$ | A-3 (X$_1$=OCH$_3$) |
| H | OCH$_3$ | CH$_3$ | A-4 (X$_1$=CH$_3$, Y$_3$=CH$_3$) |
| H | OCH$_3$ | CH$_3$ | A-4 (X$_1$=CH$_3$, Y$_3$=OCH$_3$) |
| H | OCH$_3$ | CH$_3$ | A-4 (X$_1$=OCH$_3$, Y$_3$=CH$_3$) |
| H | OCH$_3$ | CH$_3$ | A-5 (X$_2$=CH$_3$, Y$_2$=OCH$_3$) |
| H | OCH$_3$ | CH$_3$ | A-5 (X$_2$=CH$_3$, Y$_2$=SCH$_3$) |
| H | OCH$_3$ | CH$_3$ | A-6 (X$_3$=OCH$_3$) |
| H | OCH$_3$ | CH$_3$ | A-7 (X$_4$=OCH$_3$, Y$_4$=OCH$_3$) |
| H | OCH$_3$ | CH$_3$ | A-7 (X$_4$=CH$_3$, Y$_4$=OCH$_3$) |
| H | OCH$_3$ | CH$_3$ | A-7 (X$_4$=OCH$_3$, Y$_4$=CH$_3$) |
| H | NHCH$_3$ | CH$_3$ | A-2 (X$_1$=CH$_3$, Y$_1$=CH$_2$) |
| H | NHCH$_3$ | CH$_3$ | A-3 (X$_1$=CH$_3$) |
| H | NHCH$_3$ | CH$_3$ | A-3 (X$_1$=OCH$_3$) |
| H | NHCH$_3$ | CH$_3$ | A-4 (X$_1$=CH$_3$, Y$_3$=CH$_3$) |
| H | NHCH$_3$ | CH$_3$ | A-4 (X$_1$=CH$_3$, Y$_3$=OCH$_3$) |
| H | NHCH$_3$ | CH$_3$ | A-4 (X$_1$=OCH$_3$, Y$_3$=CH$_3$) |
| H | NHCH$_3$ | CH$_3$ | A-5 (X$_2$=CH$_3$, Y$_2$=OCH$_3$) |
| H | NHCH$_3$ | CH$_3$ | A-5 (X$_2$=CH$_3$, Y$_2$=SCH$_3$) |
| H | NHCH$_3$ | CH$_3$ | A-6 (X$_3$=OCH$_3$) |
| H | NHCH$_3$ | CH$_3$ | A-7 (X$_4$=OCH$_3$, Y$_4$=OCH$_3$) |
| H | NHCH$_3$ | CH$_3$ | A-7 (X$_4$=CH$_3$, Y$_4$=OCH$_3$) |
| H | NHCH$_3$ | CH$_3$ | A-7 (X$_4$=OCH$_3$, Y$_4$=CH$_3$) |
| H | N(CH$_3$)2 | CH$_3$ | A-2 (X$_1$=CH$_3$, Y$_1$=CH$_2$) |
| H | N(CH$_3$)2 | CH$_3$ | A-3 (X$_1$=CH$_3$) |
| H | N(CH$_3$)2 | CH$_3$ | A-3 (X$_1$=OCH$_3$) |
| H | N(CH$_3$)2 | CH$_3$ | A-4 (X$_1$=CH$_3$, Y$_3$=CH$_3$) |
| H | N(CH$_3$)2 | CH$_3$ | A-4 (X$_1$=CH$_3$, Y$_3$=OCH$_3$) |
| H | N(CH$_3$)2 | CH$_3$ | A-4 (X$_1$=OCH$_3$, Y$_3$=CH$_3$) |
| H | N(CH$_3$)2 | CH$_3$ | A-5 (X$_2$=CH$_3$, Y$_2$=OCH$_3$) |
| H | N(CH$_3$)2 | CH$_3$ | A-5 (X$_2$=CH$_3$, Y$_2$=SCH$_3$) |
| H | N(CH$_3$)2 | CH$_3$ | A-6 (X$_3$=OCH$_3$) |
| H | N(CH$_3$)2 | CH$_3$ | A-7 (X$_4$=OCH$_3$, Y$_4$=OCH$_3$) |
| H | N(CH$_3$)2 | CH$_3$ | A-7 (X$_4$=CH$_3$, Y$_4$=OCH$_3$) |
| H | N(CH$_3$)2 | CH$_3$ | A-7 (X$_4$=OCH$_3$, Y$_4$=CH$_3$) |
| H | —CH$_2$CH$_2$CH$_2$— | | A-2 (X$_1$=CH$_3$, Y$_1$=CH$_2$) |
| H | —CH$_2$CH$_2$CH$_2$— | | A-3 (X$_1$=CH$_3$) |
| H | —CH$_2$CH$_2$CH$_2$— | | A-3 (X$_1$=OCH$_3$) |
| H | —CH$_2$CH$_2$CH$_2$— | | A-4 (X$_1$=CH$_3$, Y$_3$=CH$_3$) |
| H | —CH$_2$CH$_2$CH$_2$— | | A-4 (X$_1$=CH$_3$, Y$_3$=OCH$_3$) |
| H | —CH$_2$CH$_2$CH$_2$— | | A-4 (X$_1$=OCH$_3$, Y$_3$=CH$_3$) |
| H | —CH$_2$CH$_2$CH$_2$— | | A-5 (X$_2$=CH$_3$, Y$_2$=OCH$_3$) |
| H | —CH$_2$CH$_2$CH$_2$— | | A-5 (X$_2$=CH$_3$, Y$_2$=SCH$_3$) |
| H | —CH$_2$CH$_2$CH$_2$— | | A-6 (X$_3$=OCH$_3$) |
| H | —CH$_2$CH$_2$CH$_2$— | | A-7 (X$_4$=OCH$_3$, Y$_4$=OCH$_3$) |
| H | —CH$_2$CH$_2$CH$_2$— | | A-7 (X$_4$=CH$_3$, Y$_4$=OCH$_3$) |
| H | —CH$_2$CH$_2$CH$_2$— | | A-7 (X$_4$=OCH$_3$, Y$_4$=CH$_3$) |
| H | —CH$_2$CH$_2$OCH$_2$CH$_2$— | | A-2 (X$_1$=CH$_3$, Y$_1$=CH$_2$) |
| H | —CH$_2$CH$_2$OCH$_2$CH$_2$— | | A-3 (X$_1$=CH$_3$) |
| H | —CH$_2$CH$_2$OCH$_2$CH$_2$— | | A-3 (X$_1$=OCH$_3$) |
| H | —CH$_2$CH$_2$OCH$_2$CH$_2$— | | A-4 (X$_1$=CH$_3$, Y$_3$=CH$_3$) |
| H | —CH$_2$CH$_2$OCH$_2$CH$_2$— | | A-4 (X$_1$=CH$_3$, Y$_3$=OCH$_3$) |
| H | —CH$_2$CH$_2$OCH$_2$CH$_2$— | | A-4 (X$_1$=OCH$_3$, Y$_3$=CH$_3$) |
| H | —CH$_2$CH$_2$OCH$_2$CH$_2$— | | A-5 (X$_2$=CH$_3$, Y$_2$=OCH$_3$) |
| H | —CH$_2$CH$_2$OCH$_2$CH$_2$— | | A-5 (X$_2$=CH$_3$, Y$_2$=SCH$_3$) |
| H | —CH$_2$CH$_2$OCH$_2$CH$_2$— | | A-6 (X$_3$=OCH$_3$) |
| H | —CH$_2$CH$_2$OCH$_2$CH$_2$— | | A-7 (X$_4$=OCH$_3$, Y$_4$=OCH$_3$) |
| H | —CH$_2$CH$_2$OCH$_2$CH$_2$— | | A-7 (X$_4$=CH$_3$, Y$_4$=OCH$_3$) |
| H | —CH$_2$CH$_2$OCH$_2$CH$_2$— | | A-7 (X$_4$=OCH$_3$, Y$_4$=CH$_3$) |
| Cl | H | H | A-2 (X$_1$=CH$_3$, Y$_1$=CH$_2$) |

TABLE II-continued
GENERAL STRUCTURE 3

| R₁ | R₂ | R₃ | A |
|---|---|---|---|
| Cl | H | H | A-3 ($X_1$=CH$_3$) |
| Cl | H | H | A-3 ($X_1$=OCH$_3$) |
| Cl | H | H | A-4 ($X_1$=CH$_3$, $Y_3$=CH$_3$) |
| Cl | H | H | A-4 ($X_1$=CH$_3$, $Y_3$=OCH$_3$) |
| Cl | H | H | A-4 ($X_1$=OCH$_3$, $Y_3$=CH$_3$) |
| Cl | H | H | A-5 ($X_2$=CH$_3$, $Y_2$=OCH$_3$) |
| Cl | H | H | A-5 ($X_2$=CH$_3$, $Y_2$=SCH$_3$) |
| Cl | H | H | A-6 ($X_3$=OCH$_3$) |
| Cl | H | H | A-7 ($X_4$=OCH$_3$, $Y_4$=OCH$_3$) |
| Cl | H | H | A-7 ($X_4$=CH$_3$, $Y_4$=OCH$_3$) |
| Cl | H | H | A-7 ($X_4$=OCH$_3$, $Y_4$=CH$_3$) |
| Cl | H | CH$_3$ | A-2 ($X_1$=CH$_3$, $Y_1$=CH$_2$) |
| Cl | H | CH$_3$ | A-3 ($X_1$=CH$_3$) |
| Cl | H | CH$_3$ | A-3 ($X_1$=OCH$_3$) |
| Cl | H | CH$_3$ | A-4 ($X_1$=CH$_3$, $Y_3$=CH$_3$) |
| Cl | H | CH$_3$ | A-4 ($X_1$=CH$_3$, $Y_3$=OCH$_3$) |
| Cl | H | CH$_3$ | A-4 ($X_1$=OCH$_3$, $Y_3$=CH$_3$) |
| Cl | H | CH$_3$ | A-5 ($X_2$=CH$_3$, $Y_2$=OCH$_3$) |
| Cl | H | CH$_3$ | A-5 ($X_2$=CH$_3$, $Y_2$=SCH$_3$) |
| Cl | H | CH$_3$ | A-6 ($X_3$=OCH$_3$) |
| Cl | H | CH$_3$ | A-7 ($X_4$=OCH$_3$, $Y_4$=OCH$_3$) |
| Cl | H | CH$_3$ | A-7 ($X_4$=CH$_3$, $Y_4$=OCH$_3$) |
| Cl | H | CH$_3$ | A-7 ($X_4$=OCH$_3$, $Y_4$=CH$_3$) |
| Cl | H | CH$_2$CH$_3$ | A-2 ($X_1$=CH$_3$, $Y_1$=CH$_2$) |
| Cl | H | CH$_2$CH$_3$ | A-3 ($X_1$=CH$_3$) |
| Cl | H | CH$_2$CH$_3$ | A-3 ($X_1$=OCH$_3$) |
| Cl | H | CH$_2$CH$_3$ | A-4 ($X_1$=CH$_3$, $Y_3$=CH$_3$) |
| Cl | H | CH$_2$CH$_3$ | A-4 ($X_1$=CH$_3$, $Y_3$=OCH$_3$) |
| Cl | H | CH$_2$CH$_3$ | A-4 ($X_1$=OCH$_3$, $Y_3$=CH$_3$) |
| Cl | H | CH$_2$CH$_3$ | A-5 ($X_2$=CH$_3$, $Y_2$=OCH$_3$) |
| Cl | H | CH$_2$CH$_3$ | A-5 ($X_2$=CH$_3$, $Y_2$=SCH$_3$) |
| Cl | H | CH$_2$CH$_3$ | A-6 ($X_3$=OCH$_3$) |
| Cl | H | CH$_2$CH$_3$ | A-7 ($X_4$=OCH$_3$, $Y_4$=OCH$_3$) |
| Cl | H | CH$_2$CH$_3$ | A-7 ($X_4$=CH$_3$, $Y_4$=OCH$_3$) |
| Cl | H | CH$_2$CH$_3$ | A-7 ($X_4$=OCH$_3$, $Y_4$=CH$_3$) |
| Cl | CH$_2$CF$_3$ | H | A-2 ($X_1$=CH$_3$, $Y_1$=CH$_2$) |
| Cl | CH$_2$CF$_3$ | H | A-3 ($X_1$=CH$_3$) |
| Cl | CH$_2$CF$_3$ | H | A-3 ($X_1$=OCH$_3$) |
| Cl | CH$_2$CF$_3$ | H | A-4 ($X_1$=CH$_3$, $Y_3$=CH$_3$) |
| Cl | CH$_2$CF$_3$ | H | A-4 ($X_1$=CH$_3$, $Y_3$=OCH$_3$) |
| Cl | CH$_2$CF$_3$ | H | A-4 ($X_1$=OCH$_3$, $Y_3$=CH$_3$) |
| Cl | CH$_2$CF$_3$ | H | A-5 ($X_2$=CH$_3$, $Y_2$=OCH$_3$) |
| Cl | CH$_2$CF$_3$ | H | A-5 ($X_2$=CH$_3$, $Y_2$=SCH$_3$) |
| Cl | CH$_2$CF$_3$ | H | A-6 ($X_3$=OCH$_3$) |
| Cl | CH$_2$CF$_3$ | H | A-7 ($X_4$=OCH$_3$, $Y_4$=OCH$_3$) |
| Cl | CH$_2$CF$_3$ | H | A-7 ($X_4$=CH$_3$, $Y_4$=OCH$_3$) |
| Cl | CH$_2$CF$_3$ | H | A-7 ($X_4$=OCH$_3$, $Y_4$=CH$_3$) |
| Cl | CH$_2$CH$_2$Cl | H | A-2 ($X_1$=CH$_3$, $Y_1$=CH$_2$) |
| Cl | CH$_2$CH$_2$Cl | H | A-3 ($X_2$=CH$_3$) |
| Cl | CH$_2$CH$_2$Cl | H | A-3 ($X_1$=OCH$_3$) |
| Cl | CH$_2$CH$_2$Cl | H | A-4 ($X_1$=CH$_3$, $Y_3$=CH$_3$) |
| Cl | CH$_2$CH$_2$Cl | H | A-4 ($X_1$=CH$_3$, $Y_3$=OCH$_3$) |
| Cl | CH$_2$CH$_2$Cl | H | A-4 ($X_1$=OCH$_3$, $Y_3$=CH$_3$) |
| Cl | CH$_2$CH$_2$Cl | H | A-5 ($X_2$=CH$_3$, $Y_2$=OCH$_3$) |
| Cl | CH$_2$CH$_2$Cl | H | A-5 ($X_2$=CH$_3$, $Y_2$=SCH$_3$) |
| Cl | CH$_2$CH$_2$Cl | H | A-6 ($X_3$=OCH$_3$) |
| Cl | CH$_2$CH$_2$Cl | H | A-7 ($X_4$=OCH$_3$, $Y_4$=OCH$_3$) |
| Cl | CH$_2$CH$_2$Cl | H | A-7 ($X_4$=CH$_3$, $Y_4$=OCH$_3$) |
| Cl | CH$_2$CH$_2$Cl | H | A-7 ($X_4$=OCH$_3$, $Y_4$=CH$_3$) |
| Cl | CH$_2$CN | H | A-2 ($X_1$=CH$_3$, $Y_1$=CH$_2$) |
| Cl | CH$_2$CN | H | A-3 ($X_1$=CH$_3$) |
| Cl | CH$_2$CN | H | A-3 ($X_1$=OCH$_3$) |
| Cl | CH$_2$CN | H | A-4 ($X_1$=CH$_3$, $Y_3$=CH$_3$) |
| Cl | CH$_2$CN | H | A-4 ($X_1$=CH$_3$, $Y_3$=OCH$_3$) |
| Cl | CH$_2$CN | H | A-4 ($X_1$=OCH$_3$, $Y_3$=CH$_3$) |
| Cl | CH$_2$CN | H | A-5 ($X_2$=CH$_3$, $Y_2$=OCH$_3$) |
| Cl | CH$_2$CN | H | A-5 ($X_2$=CH$_3$, $Y_2$=SCH$_3$) |
| Cl | CH$_2$CN | H | A-6 ($X_3$=OCH$_3$) |
| Cl | CH$_2$CN | H | A-7 ($X_4$=OCH$_3$, $Y_4$=OCH$_3$) |
| Cl | CH$_2$CN | H | A-7 ($X_4$=CH$_3$, $Y_4$=OCH$_3$) |
| Cl | CH$_2$CN | H | A-7 ($X_4$=OCH$_3$, $Y_4$=CH$_3$) |
| Cl | CH$_2$CH$_2$OCH$_3$ | H | A-2 ($X_1$=CH$_3$, $Y_1$=CH$_2$) |
| Cl | CH$_2$CH$_2$OCH$_3$ | H | A-3 ($X_2$CH$_3$) |
| Cl | CH$_2$CH$_2$OCH$_3$ | H | A-3 ($X_1$=OCH$_3$) |
| Cl | CH$_2$CH$_2$OCH$_3$ | H | A-4 ($X_1$=CH$_3$, $Y_3$=CH$_3$) |
| Cl | CH$_2$CH$_2$OCH$_3$ | H | A-4 ($X_1$=CH$_3$, $Y_3$=OCH$_3$) |
| Cl | CH$_2$CH$_2$OCH$_3$ | H | A-4 ($X_1$=OCH$_3$, $Y_3$=CH$_3$) |
| Cl | CH$_2$CH$_2$OCH$_3$ | H | A-5 ($X_2$=CH$_3$, $Y_2$=OCH$_3$) |
| Cl | CH$_2$CH$_2$OCH$_3$ | H | A-5 ($X_2$=CH$_3$, $Y_2$=SCH$_3$) |
| Cl | CH$_2$CH$_2$OCH$_3$ | H | A-6 ($X_3$=OCH$_3$) |

TABLE II-continued

GENERAL STRUCTURE 3

| R₁ | R₂ | R₃ | A |
|---|---|---|---|
| Cl | CH₂CH₂OCH₃ | H | A-7 (X₄=OCH₃, Y₄=OCH₃) |
| Cl | CH₂CH₂OCH₃ | H | A-7 (X₄=CH₃, Y₄=OCH₃) |
| Cl | CH₂CH₂OCH₃ | H | A-7 (X₄=OCH₃, Y₄=CH₃) |
| Cl | CH₂CH=CH₂ | H | A-2 (X₁=CH₃, Y₁=CH₂) |
| Cl | CH₂CH=CH₂ | H | A-3 (X₁=CH₃) |
| Cl | CH₂CH=CH₂ | H | A-3 (X₁=OCH₃) |
| Cl | CH₂CH=CH₂ | H | A-4 (X₁=CH₃, Y₃=CH₃) |
| Cl | CH₂CH=CH₂ | H | A-4 (X₁=CH₃, Y₃=OCH₃) |
| Cl | CH₂CH=CH₂ | H | A-4 (X₁=OCH₃, Y₃=CH₃) |
| Cl | CH₂CH=CH₂ | H | A-5 (X₃=CH₃, Y₂=OCH₃) |
| Cl | CH₂CH=CH₂ | H | A-5 (X₂=CH₃, Y₂=SCH₃) |
| Cl | CH₂CH=CH₂ | H | A-6 (X₃=OCH₃) |
| Cl | CH₂CH=CH₂ | H | A-7 (X₄=OCH₃, Y₄=OCH₃) |
| Cl | CH₂CH=CH₂ | H | A-7 (X₄=CH₃, Y₄=OCH₃) |
| Cl | CH₂CH=CH₂ | H | A-7 (X₄=OCH₃, Y₄=CH₃) |
| Cl | CH₂C≡CH | H | A-2 (X₁=CH₃, Y₁=CH₂) |
| Cl | CH₂C≡CH | H | A-3 (X₁=CH₃) |
| Cl | CH₂C≡CH | H | A-3 (X₁=OCH₃) |
| Cl | CH₂C≡CH | H | A-4 (X₁=CH₃, Y₃=CH₃) |
| Cl | CH₂C≡CH | H | A-4 (X₁=CH₃, Y₃=CH₃) |
| Cl | CH₂C≡CH | H | A-4 (X₁=OCH₃, Y₃=CH₃) |
| Cl | CH₂C≡CH | H | A-5 (X₂=CH₃, Y₂=OCH₃) |
| Cl | CH₂C≡CH | H | A-5 (X₂=CH₃, Y₂=SCH₃) |
| Cl | CH₂C≡CH | H | A-6 (X₃=OCH₃) |
| Cl | CH₂C≡CH | H | A-7 (X₄=OCH₃, Y₄=OCH₃) |
| Cl | CH₂C≡CH | H | A-7 (X₄=CH₃, Y₄=OCH₃) |
| Cl | CH₂C≡CH | H | A-7 (X₄=OCH₃, Y₄=CH₃) |
| Cl | cyclo-C₃H₇ | H | A-2 (X₁=CH₃, Y₁=CH₂) |
| Cl | cyclo-C₃H₇ | H | A-3 (X₁=CH₃) |
| Cl | cyclo-C₃H₇ | H | A-3 (X₁=OCH₃) |
| Cl | cyclo-C₃H₇ | H | A-4 (X₁=CH₃, Y₃=CH₃) |
| Cl | cyclo-C₃H₇ | H | A-4 (X₁=CH₃, Y₃=OCH₃) |
| Cl | cyclo-C₃H₇ | H | A-4 (X₁=OCH₃, Y₃=CH₃) |
| Cl | cyclo-C₃H₇ | H | A-5 (X₂=CH₃, Y₂=OCH₃) |
| Cl | cyclo-C₃H₇ | H | A-5 (X₂=CH₃, Y₂=SCH₃) |
| Cl | cyclo-C₃H₇ | H | A-6 (X₃=OCH₃) |
| Cl | cyclo-C₃H₇ | H | A-7 (X₄=OCH₃, Y₄=OCH₃) |
| Cl | cyclo-C₃H₇ | H | A-7 (X₄=CH₃, Y₄=OCH₃) |
| Cl | cyclo-C₃H₇ | H | A-7 (X₄=OCH₃, Y₄=CH₃) |
| Cl | CH₃ | CH₃ | A-2 (X₁=CH₃, Y₁=CH₂) |
| Cl | CH₃ | CH₃ | A-3 (X₁=CH₃) |
| Cl | CH₃ | CH₃ | A-3 (X₁=OCH₃) |
| Cl | CH₃ | CH₃ | A-4 (X₁=CH₃, Y₃=CH₃) |
| Cl | CH₃ | CH₃ | A-4 (X₁=CH₃, Y=OCH₃) |
| Cl | CH₃ | CH₃ | A-4 (X₁=OCH₃, Y₃=CH₃) |
| Cl | CH₃ | CH₃ | A-5 (X₂=CH₃, Y₂=OCH₃) |
| Cl | CH₃ | CH₃ | A-5 (X₂=CH₃, Y₂=SCH₃) |
| Cl | CH₃ | CH₃ | A-6 (X₃=OCH₃) |
| Cl | CH₃ | CH₃ | A-7 (X₄=OCH₃, Y₄=OCH₃) |
| Cl | CH₃ | CH₃ | A-7 (X₄=CH₃, Y₄=OCH₃) |
| Cl | CH₃ | CH₃ | A-7 (X₄=OCH₃, Y₄=CH₃) |
| Cl | CH₂CH₃ | CH₃ | A-2 (X₁=CH₃, Y₁=CH₂) |
| Cl | CH₂CH₃ | CH₃ | A-3 (X₁=CH₃) |
| Cl | CH₂CH₃ | CH₃ | A-3 (X₁=OCH₃) |
| Cl | CH₂CH₃ | CH₃ | A-4 (X₁=CH₃, Y₃=CH₃) |
| Cl | CH₂CH₃ | CH₃ | A-4 (X₁=CH₃, Y₃=OCH₃) |
| Cl | CH₂CH₃ | CH₃ | A-4 (X₁=OCH₃, Y₃=CH₃) |
| Cl | CH₂CH₃ | CH₃ | A-5 (X₂=CH₃, Y₂=OCH₃) |
| Cl | CH₂CH₃ | CH₃ | A-5 (X₂=CH₃, Y₂=SCH₃) |
| Cl | CH₂CH₃ | CH₃ | A-6 (X₃=OCH₃) |
| Cl | CH₂CH₃ | CH₃ | A-7 (X₄=OCH₃, Y₄=OCH₃) |
| Cl | CH₂CH₃ | CH₃ | A-7 (X₄=CH₃, Y₄=OCH₃) |
| Cl | CH₂CH₃ | CH₃ | A-7 (X₄=OCH₃, Y₄=CH₃) |
| Cl | CH₂CH₃ | CH₂CH₃ | A-2 (X₁=CH₃, Y₁=CH₂) |
| Cl | CH₂CH₃ | CH₂CH₃ | A-3 (X₁=CH₃) |
| Cl | CH₂CH₃ | CH₂CH₃ | A-3 (X₁=OCH₃) |
| Cl | CH₂CH₃ | CH₂CH₃ | A-4 (X₁=CH₃, Y₃=CH₃) |
| Cl | CH₂CH₃ | CH₂CH₃ | A-4 (X₁=CH₃, Y₃=OCH₃) |
| Cl | CH₂CH₃ | CH₂CH₃ | A-4 (X₁=OCH₃, Y₃=CH₃) |
| Cl | CH₂CH₃ | CH₂CH₃ | A-5 (X₂=CH₃, Y₂=OCH₃) |
| Cl | CH₂CH₃ | CH₂CH₃ | A-5 (X₂=CH₃, Y₂=SCH₃) |
| Cl | CH₂CH₃ | CH₂CH₃ | A-6 (X₃=OCH₃) |
| Cl | CH₂CH₃ | CH₂CH₃ | A-7 (X₄=OCH₃, Y₄=OCH₃) |
| Cl | CH₂CH₃ | CH₂CH₃ | A-7 (X₄=CH₃, Y₄=OCH₃) |
| Cl | CH₂CH₃ | CH₂CH₃ | A-7 (X₄=OCH₃, Y₄=CH₃) |
| Cl | OCH₃ | CH₃ | A-2 (X₁=CH₃, Y₁=CH₂) |
| Cl | OCH₃ | CH₃ | A-3 (X₁=CH₃) |
| Cl | OCH₃ | CH₃ | A-3 (X₁=OCH₃) |
| Cl | OCH₃ | CH₃ | A-4 (X₁=CH₃, Y₃=CH₃) |
| Cl | OCH₃ | CH₃ | A-4 (X₁=CH₃, Y₃=OCH₃) |

TABLE II-continued
GENERAL STRUCTURE 3

| $R_1$ | $R_2$ | $R_3$ | A |
|---|---|---|---|
| Cl | OCH$_3$ | CH$_3$ | A-4 (X$_1$=OCH$_3$, Y$_3$=CH$_3$) |
| Cl | OCH$_3$ | CH$_3$ | A-5 (X$_2$=CH$_3$, Y$_2$=OCH$_3$) |
| Cl | OCH$_3$ | CH$_3$ | A-5 (X$_2$=CH$_3$, Y$_2$=SCH$_3$) |
| Cl | OCH$_3$ | CH$_3$ | A-6 (X$_3$=OCH$_3$) |
| Cl | OCH$_3$ | CH$_3$ | A-7 (X$_4$=OCH$_3$, Y$_4$=OCH$_3$) |
| Cl | OCH$_3$ | CH$_3$ | A-7 (X$_4$=CH$_3$, Y$_4$=OCH$_3$) |
| Cl | OCH$_3$ | CH$_3$ | A-7 (X$_4$=OCH$_3$, Y$_4$=CH$_3$) |
| Cl | NHCH$_3$ | CH$_3$ | A-2 (X$_1$=CH$_3$, Y$_1$=CH$_2$) |
| Cl | NHCH$_3$ | CH$_3$ | A-3 (X$_1$=CH$_3$) |
| Cl | NHCH$_3$ | CH$_3$ | A-3 (X$_1$=OCH$_3$) |
| Cl | NHCH$_3$ | CH$_3$ | A-4 (X$_1$=CH$_3$, Y$_3$=CH$_3$) |
| Cl | NHCH$_3$ | CH$_3$ | A-4 (X$_1$=CH$_3$, Y$_3$=OCH$_3$) |
| Cl | NHCH$_3$ | CH$_3$ | A-4 (X$_1$=OCH$_3$, Y$_3$=CH$_3$) |
| Cl | NHCH$_3$ | CH$_3$ | A-5 (X$_2$=CH$_3$, Y$_2$=OCH$_3$) |
| Cl | NHCH$_3$ | CH$_3$ | A-5 (X$_2$=CH$_3$, Y$_2$=SCH$_3$) |
| Cl | NHCH$_3$ | CH$_3$ | A-6 (X$_3$=OCH$_3$) |
| Cl | NHCH$_3$ | CH$_3$ | A-7 (X$_4$=OCH$_3$, Y =OCH$_3$) |
| Cl | NHCH$_3$ | CH$_3$ | A-7 (X$_4$=CH$_3$, Y$_4$=OCH$_3$) |
| Cl | NHCH$_3$ | CH$_3$ | A-7 (X$_4$=OCH$_3$, Y$_4$=CH$_3$) |
| Cl | N(CH$_3$)$_2$ | CH$_3$ | A-2 (X$_1$=CH$_3$, Y$_1$=CH$_2$) |
| Cl | N(CH$_3$)$_2$ | CH$_3$ | A-3 (X$_1$=CH$_3$) |
| Cl | N(CH$_3$)$_2$ | CH$_3$ | A-3 (X$_1$=OCH$_3$) |
| Cl | N(CH$_3$)$_2$ | CH$_3$ | A-4 (X$_1$=CH$_3$, Y$_3$=CH$_3$) |
| Cl | N(CH$_3$)$_2$ | CH$_3$ | A-4 (X$_1$=CH$_3$, Y$_3$=OCH$_3$) |
| Cl | N(CH$_3$)$_2$ | CH$_3$ | A-4 (X$_1$=OCH , Y$_3$=CH$_3$) |
| Cl | N(CH$_3$)$_2$ | CH$_3$ | A-5 (X$_2$=CH$_3$, Y$_2$=OCH$_3$) |
| Cl | N(CH$_3$)$_2$ | CH$_3$ | A-5 (X$_2$=CH$_3$, Y$_2$=SCH$_3$) |
| Cl | N(CH$_3$)$_2$ | CH$_3$ | A-6 (X$_3$=OCH$_3$) |
| Cl | N(CH$_3$)$_2$ | CH$_3$ | A-7 (X$_4$=OCH$_3$, Y$_4$=OCH$_3$) |
| Cl | N(CH$_3$)$_2$ | CH$_3$ | A-7 (X$_4$=CH$_3$, Y$_4$=OCH$_3$) |
| Cl | N(CH$_3$)$_2$ | CH$_3$ | A-7 (X$_4$=OCH$_3$, Y$_4$=CH$_3$) |
| Cl | —CH$_2$CH$_2$CH$_2$— | | A-2 (X$_1$=CH$_3$, Y$_1$=CH$_2$) |
| Cl | —CH$_2$CH$_2$CH$_2$— | | A-3 (X$_1$=CH$_3$) |
| Cl | —CH$_2$CH$_2$CH$_2$— | | A-3 (X$_1$=OCH$_3$) |
| Cl | —CH$_2$CH$_2$CH$_2$— | | A-4 (X$_1$=CH$_3$, Y$_3$=CH$_3$) |
| Cl | —CH$_2$CH$_2$CH$_2$— | | A-4 (X$_1$=CH$_3$, Y$_3$=OCH$_3$) |
| Cl | —CH$_2$CH$_2$CH$_2$— | | A-4 (X$_1$=OCH$_3$, Y$_3$=CH$_3$) |
| Cl | —CH$_2$CH$_2$CH$_2$— | | A-5 (X$_2$=CH$_3$, Y$_2$=OCH$_3$) |
| Cl | —CH$_2$CH$_2$CH$_2$— | | A-5 (X$_2$=CH$_3$, Y$_2$SCH$_3$) |
| Cl | —CH$_2$CH$_2$CH$_2$— | | A-6 (X$_3$=OCH$_3$) |
| Cl | —CH$_2$CH$_2$CH$_2$— | | A-7 (X$_4$=OCH$_3$, Y$_4$=OCH$_3$) |
| Cl | —CH$_2$CH$_2$CH$_2$— | | A-7 (X$_4$=CH$_3$, Y$_4$=OCH$_3$) |
| Cl | —CH$_2$CH$_2$CH$_2$— | | A-7 (X$_4$=OCH$_3$, Y$_1$=CH$_3$) |
| Cl | —CH$_2$CH$_2$OCH$_2$CH$_2$— | | A-2 (X$_1$=CH$_3$, Y$_1$=CH$_2$) |
| Cl | —CH$_2$CH$_2$OCH$_2$CH$_2$— | | A-3 (X$_1$=CH$_3$) |
| Cl | —CH$_2$CH$_2$OCH$_2$CH$_2$— | | A-3 (X$_1$=OCH$_3$) |
| Cl | —CH$_2$CH$_2$OCH$_2$CH$_2$— | | A-4 (X$_1$=CH$_3$, Y$_3$=CH$_3$) |
| Cl | —CH$_2$CH$_2$OCH$_2$CH$_2$— | | A-4 (X$_1$=CH$_3$, Y$_3$=OCH$_3$) |
| Cl | —CH$_2$CH$_2$OCH$_2$CH$_2$— | | A-4 (X$_1$=OCH$_3$, Y$_3$=CH$_3$) |
| Cl | —CH$_2$CH$_2$OCH$_2$CH$_2$— | | A-5 (X$_2$=CH$_3$, Y$_2$=OCH$_3$) |
| Cl | —CH$_2$CH$_2$OCH$_2$CH$_2$— | | A-5 (X$_2$=CH$_3$, Y$_2$=SCH$_3$) |
| Cl | —CH$_2$CH$_2$OCH$_2$CH$_2$— | | A-6 (X$_3$=OCH$_3$) |
| Cl | —CH$_2$CH$_2$OCH$_2$CH$_2$— | | A-7 (X$_4$=OCH$_3$, Y$_4$=OCH$_3$) |
| Cl | —CH$_2$CH OCH$_2$CH$_2$— | | A-7 (X$_4$=CH$_3$, Y$_4$=OCH$_3$) |
| Cl | —CH$_2$CH$_2$OCH$_2$CH$_2$— | | A-7 (X$_4$=OCH$_3$, Y$_4$=CH$_3$) |
| CH$_3$ | H | H | A-2 (X$_1$=CH$_3$, Y$_1$=CH$_2$) |
| CH$_3$ | H | H | A-3 (X$_1$=CH$_3$) |
| CH$_3$ | H | H | A-3 (X$_1$=OCH$_3$) |
| CH$_3$ | H | H | A-4 (X$_1$=CH$_3$, Y$_3$=CH$_3$) |
| CH$_3$ | H | H | A-4 (X$_1$=CH$_3$, Y$_3$=OCH$_3$) |
| CH$_3$ | H | H | A-4 (X$_1$=OCH$_3$, Y$_3$=CH$_3$) |
| CH$_3$ | H | H | A-5 (X$_2$=CH$_3$, Y$_2$=OCH$_3$) |
| CH$_3$ | H | H | A-5 (X$_2$=CH$_3$, Y$_2$=SCH$_3$) |
| CH$_3$ | H | H | A-6 (X$_3$=OCH$_3$) |
| CH$_3$ | H | H | A-7 (X$_4$=OCH$_3$, Y$_4$=OCH$_3$) |
| CH$_3$ | H | H | A-7 (X$_4$=CH$_3$, Y$_4$=OCH$_3$) |
| CH$_3$ | H | H | A-7 (X$_4$=OCH$_3$, Y$_4$=CH$_3$) |
| CH$_3$ | H | CH$_3$ | A-2 (X$_1$=CH$_3$, Y$_1$=CH$_2$) |
| CH$_3$ | H | CH$_3$ | A-3 (X$_1$=CH$_3$) |
| CH$_3$ | H | CH$_3$ | A-3 (X$_1$=OCH$_3$) |
| CH$_3$ | H | CH$_3$ | A-4 (X$_1$=CH$_3$, Y$_3$=CH$_3$) |
| CH$_3$ | H | CH$_3$ | A-4 (X$_1$=CH$_3$, Y$_3$=OCH$_3$) |
| CH$_3$ | H | CH$_3$ | A-4 (X$_1$=OCH$_3$, Y$_3$=CH$_3$) |
| CH$_3$ | H | CH$_3$ | A-5 (X$_2$=CH$_3$, Y$_2$=OCH$_3$) |
| CH$_3$ | H | CH$_3$ | A-5 (X$_2$=CH$_3$, Y$_2$=SCH$_3$) |
| CH$_3$ | H | CH$_3$ | A-6 (X$_3$=OCH$_3$) |
| CH$_3$ | H | CH$_3$ | A-7 (X$_4$=OCH$_3$, Y$_4$=OCH$_3$) |
| CH$_3$ | H | CH$_3$ | A-7 (X$_4$=CH$_3$, Y$_4$=OCH$_3$) |
| CH$_3$ | H | CH$_3$ | A-7 (X$_4$=OCH$_3$, Y$_4$=CH$_3$) |
| CH$_3$ | H | CH$_2$CH$_3$ | A-2 (X$_1$=CH$_3$, Y$_1$=CH$_2$) |

TABLE II-continued
GENERAL STRUCTURE 3

| R$_1$ | R$_2$ | R$_3$ | A |
|---|---|---|---|
| CH$_3$ | H | CH$_2$CH$_3$ | A-3 (X$_1$=CH$_3$) |
| CH$_3$ | H | CH$_2$CH$_3$ | A-3 (X$_1$=OCH$_3$) |
| CH$_3$ | H | CH$_2$CH$_3$ | A-4 (X$_1$=CH$_3$, Y$_3$=CH$_3$) |
| CH$_3$ | H | CH$_2$CH$_3$ | A-4 (X$_1$=CH$_3$, Y$_3$=OCH$_3$) |
| CH$_3$ | H | CH$_2$CH$_3$ | A-4 (X$_1$=OCH$_3$, Y$_3$=CH$_3$) |
| CH$_3$ | H | CH$_2$CH$_3$ | A-5 (X$_2$=CH$_3$, Y$_2$=OCH$_3$) |
| CH$_3$ | H | CH$_2$CH$_3$ | A-5 (X$_2$CH$_3$, Y$_2$=SCH$_3$) |
| CH$_3$ | H | CH$_2$CH$_3$ | A-6 (X$_3$=OCH$_3$) |
| CH$_3$ | H | CH$_2$CH$_3$ | A-7 (X$_4$=OCH$_3$, Y$_4$=OCH$_3$) |
| CH$_3$ | H | CH$_2$CH$_3$ | A-7 (X$_4$=CH$_3$, Y$_4$=OCH$_3$) |
| CH$_3$ | H | CH$_2$CH$_3$ | A-7 (X$_4$=OCH$_3$, Y$_4$=CH$_3$) |
| CH$_3$ | CH$_2$CF$_3$ | H | A-2 (X$_1$=CH$_3$, Y$_1$=CH$_2$) |
| CH$_3$ | CH$_2$CF$_3$ | H | A-3 (X$_1$=CH$_3$) |
| CH$_3$ | CH$_2$CF$_3$ | H | A-3 (X$_1$=OCH$_3$) |
| CH$_3$ | CH$_2$CF$_3$ | H | A-4 (X$_1$=CH$_3$, Y$_3$=CH$_3$) |
| CH$_3$ | CH$_2$CF$_3$ | H | A-4 (X$_1$=CH$_3$, Y$_3$=OCH$_3$) |
| CH$_3$ | CH$_2$CF$_3$ | H | A-4 (X$_1$=OCH$_3$, Y$_3$=CH$_3$) |
| CH$_3$ | CH$_2$CF$_3$ | H | A-5 (X$_2$=CH$_3$, Y$_2$=OCH$_3$) |
| CH$_3$ | CH$_2$CF$_3$ | H | A-5 (X$_2$=CH$_3$, Y$_2$=SCH$_3$) |
| CH$_3$ | CH$_2$CF$_3$ | H | A-6 (X$_3$=OCH$_3$) |
| CH$_3$ | CH$_2$CH$_3$ | H | A-7 (X$_4$=OCH$_3$, Y$_4$=OCH$_3$) |
| CH$_3$ | CH$_2$CF$_3$ | H | A-7 (X$_4$=CH$_3$, Y$_4$=OCH$_3$) |
| CH$_3$ | CH$_2$CF$_3$ | H | A-7 (X$_4$=OCH$_3$, Y$_4$=CH$_3$) |
| CH$_3$ | CH$_2$CH$_2$Cl | H | A-2 (X$_1$=CH$_3$, Y$_1$=CH$_2$) |
| CH$_3$ | CH$_2$CH$_2$Cl | H | A-3 (X$_1$=CH$_3$) |
| CH$_3$ | CH$_2$CH$_2$Cl | H | A-3 (X$_1$=OCH$_3$) |
| CH$_3$ | CH$_2$CH$_2$Cl | H | A-4 (X$_1$=CH$_3$, Y$_3$=CH$_3$) |
| CH$_3$ | CH$_2$CH$_2$Cl | H | A-4 (X$_1$=CH$_3$, Y$_3$=OCH$_3$) |
| CH$_3$ | CH$_2$CH$_2$Cl | H | A-4 (X$_1$=OCH$_3$, Y$_3$=CH$_3$) |
| CH$_3$ | CH$_2$CH$_2$Cl | H | A-5 (X$_2$=CH$_3$, Y$_2$=OCH$_3$) |
| CH$_3$ | CH$_2$CH$_2$Cl | H | A-5 (X$_2$=CH$_3$, Y$_2$=SCH$_3$) |
| CH$_3$ | CH$_2$CH$_2$Cl | H | A-6 (X$_3$=OCH$_3$) |
| CH$_3$ | CH$_2$CH$_2$Cl | H | A-7 (X$_4$=OCH$_3$, Y$_4$=OCH$_3$) |
| CH$_3$ | CH$_2$CH$_2$Cl | H | A-7 (X$_4$=CH$_3$, Y$_4$=OCH$_3$) |
| CH$_3$ | CH$_2$CH$_2$Cl | H | A-7 (X$_4$=OCH$_3$, Y$_4$=CH$_3$) |
| CH$_3$ | CH$_2$CN | H | A-2 (X$_1$=CH$_3$, Y$_1$=CH$_2$) |
| CH$_3$ | CH$_2$CN | H | A-3 (X$_1$=CH$_3$) |
| CH$_3$ | CH$_2$CN | H | A-3 (X$_1$=OCH$_3$) |
| CH$_3$ | CH$_2$CN | H | A-4 (X$_1$=CH$_3$, Y$_3$=CH$_3$) |
| CH$_3$ | CH$_2$CN | H | A-4 (X$_1$=CH$_3$, Y$_3$=OCH$_3$) |
| CH$_3$ | CH$_2$CN | H | A-4 (X$_1$=OCH$_3$, Y$_3$=CH$_3$) |
| CH$_3$ | CH$_2$CN | H | A-5 (X$_2$=CH$_3$, Y$_2$=OCH$_3$) |
| CH$_3$ | CH$_2$CN | H | A-5 (X$_2$=CH$_3$, Y$_2$=SCH$_3$) |
| CH$_3$ | CH$_2$CN | H | A-6 (X$_3$=OCH$_3$) |
| CH$_3$ | CH$_2$CN | H | A-7 (X$_4$=OCH$_3$, Y$_4$=OCH$_3$) |
| CH$_3$ | CH$_2$CN | H | A-7 (X =CH$_3$, Y$_4$=OCH$_3$) |
| CH$_3$ | CH$_2$CN | H | A-7 (X$_4$=OCH$_3$, Y$_4$=CH$_3$) |
| CH$_3$ | CH$_2$CH$_2$OCH$_3$ | H | A-2 (X$_1$=CH$_3$, Y$_1$=CH$_2$) |
| CH$_3$ | CH$_2$CH$_2$OCH$_3$ | H | A-3 (X$_1$=CH$_3$) |
| CH$_3$ | CH$_2$CH$_2$OCH$_3$ | H | A-3 (X$_1$=OCH$_3$) |
| CH$_3$ | CH$_2$CH$_2$OCH$_3$ | H | A-4 (X$_1$=CH$_3$, Y$_3$=CH$_3$) |
| CH$_3$ | CH$_2$CH$_2$OCH$_3$ | H | A-4 (X$_1$=CH$_3$, Y$_3$=OCH$_3$) |
| CH$_3$ | CH$_2$CH$_2$OCH$_3$ | H | A-4 (X$_1$=OCH$_3$, Y$_3$=CH$_3$) |
| CH$_3$ | CH$_2$CH$_2$OCH$_3$ | H | A-5 (X$_2$=CH$_3$, Y$_2$=OCH$_3$) |
| CH$_3$ | CH$_2$CH$_2$OCH$_3$ | H | A-5 (X$_2$=CH$_3$, Y$_2$=SCH$_3$) |
| CH$_3$ | CH$_2$CH$_3$OCH$_3$ | H | A-6 (X$_3$=OCH$_3$) |
| CH$_3$ | CH$_2$CH$_2$OCH$_3$ | H | A-7 (X$_4$=OCH$_3$, Y$_4$=OCH$_3$) |
| CH$_3$ | CH$_2$CH$_2$OCH$_3$ | H | A-7 (X$_4$=CH$_3$, Y$_4$=OCH$_3$) |
| CH$_3$ | CH$_2$CH$_2$OCH$_3$ | H | A-7 (X$_4$=OCH$_3$, Y$_4$=CH$_3$) |
| CH$_3$ | CH$_2$CH=CH$_2$ | H | A-2 (X$_1$=CH$_3$, Y$_1$=CH$_2$) |
| CH$_3$ | CH$_2$CH=CH$_2$ | H | A-3 (X$_1$=CH$_3$) |
| CH$_3$ | CH$_2$CH=CH$_2$ | H | A-3 (X$_1$=OCH$_3$) |
| CH$_3$ | CH$_2$CH=CH$_2$ | H | A-4 (X$_1$=CH$_3$, Y$_3$=CH$_3$l |
| CH$_3$ | CH$_2$CH=CH$_2$ | H | A-4 (X$_1$=CH$_3$, Y$_3$=OCH$_3$) |
| CH$_3$ | CH$_2$CH=CH$_2$ | H | A-4 (X$_1$=OCH$_3$, Y$_3$=CH$_3$) |
| CH$_3$ | CH$_2$CH=CH$_2$ | H | A-4 (X$_1$=CH$_3$, Y$_3$=OCH$_3$) |
| CH$_3$ | CH$_2$CH=CH$_2$ | H | A-5 (X$_2$=CH$_3$, Y$_2$=OCH$_3$) |
| CH$_3$ | CH$_2$CH=CH$_2$ | H | A-5 (X$_2$=CH$_3$, Y$_2$=SCH$_3$) |
| CH$_3$ | CH$_2$CH=CH$_2$ | H | A-6 (X$_3$=OCH$_3$) |
| CH$_3$ | CH$_2$CH=CH$_2$ | H | A-7 (X$_4$=OCH$_3$, Y$_4$=OCH$_3$) |
| CH$_3$ | CH$_2$CH=CH$_2$ | H | A-7 (X$_4$=CH$_3$, Y$_4$=OCH$_3$) |
| CH$_3$ | CH$_2$CH=CH$_2$ | H | A-7 (X$_4$=OCH$_3$, Y$_4$=CH$_3$) |
| CH$_3$ | CH$_2$C≡CH | H | A-2 (X$_1$=*CH3*, Y$_1$=CH$_2$) |
| CH$_3$ | CH$_2$C≡CH | H | A-3 (X$_1$=CH$_3$) |
| CH$_3$ | CH$_2$C≡CH | H | A-3 (X$_1$=OCH$_3$) |
| CH$_3$ | CH$_2$C≡CH | H | A-4 (X$_1$=CH$_3$, Y$_3$=CH$_3$) |
| CH$_3$ | CH$_2$C≡CH | H | A-4 (X$_1$=CH$_3$, Y$_3$=OCH$_3$) |
| CH$_3$ | CH$_2$C≡CH | H | A-4 (X$_1$=OCH$_3$, Y$_3$=CH$_3$) |
| CH$_3$ | CH$_2$C≡CH | H | A-5 (X$_2$=CH$_3$, Y$_2$=OCH$_3$) |
| CH$_3$ | CH$_2$C≡CH | H | A-5 (X$_2$=CH$_3$, Y$_2$=SCH$_3$) |

TABLE II-continued

GENERAL STRUCTURE 3

| R₁ | R₂ | R₃ | A |
|---|---|---|---|
| $CH_3$ | $CH_2C\equiv CH$ | H | A-6 ($X_3=OCH_3$) |
| $CH_3$ | $CH_2C\equiv CH$ | H | A-7 ($X_4=OCH_3$, $Y_4=OCH_3$) |
| $CH_3$ | $CH_2C\equiv CH$ | H | A-7 ($X_4=CH_3$, $Y_4=CH_3$) |
| $CH_3$ | $CH_2C\equiv CH$ | H | A-7 ($X_4=OCH_3$, $Y_4=CH_3$) |
| $CH_3$ | cyclo-$C_3H_7$ | H | A-2 ($X_1=CH_3$, $Y=CH_2$) |
| $CH_3$ | cyclo-$C_3H_7$ | H | A-3 ($X_1=CH_3$) |
| $CH_3$ | cyclo-$C_3H_7$ | H | A-3 ($X_1=OCH_3$) |
| $CH_3$ | cyclo-$C_3H_7$ | H | A-4 ($X_1=CH_3$, $Y_3=CH_3$) |
| $CH_3$ | cyclo-$C_3H_7$ | H | A-4 ($X_1=CH_3$, $Y_3=OCH_3$) |
| $CH_3$ | cyclo-$C_3H_7$ | H | A-4 ($X_1=OCH_3$, $Y_3=CH_3$) |
| $CH_3$ | cyclo-$C_3H_7$ | H | A-5 ($X_2=CH_3$, $Y_2=OCH_3$) |
| $CH_3$ | cyclo-$C_3H_7$ | H | A-5 ($X_2=CH_3$, $Y_2=SCH_3$) |
| $CH_3$ | cyclo-$C_3H_7$ | H | A-6 ($X_3=OCH_3$) |
| $CH_3$ | cyclo-$C_3H_7$ | H | A-7 ($X_4=OCH_3$, $Y_4=OCH_3$) |
| $CH_3$ | cyclo-$C_3H_7$ | H | A-7 ($X_4=CH_3$, $Y=OCH_3$) |
| $CH_3$ | cyclo-$C_3H_7$ | H | A-7 ($X_4=OCH_3$, $Y_4=CH_3$) |
| $CH_3$ | $CH_3$ | $CH_3$ | A-2 ($X_1=CH_3$, $Y_1=CH_2$) |
| $CH_3$ | $CH_3$ | $CH_3$ | A-3 ($X_1=CH_3$) |
| $CH_3$ | $CH_3$ | $CH_3$ | A-3 ($X_1=OCH_3$) |
| $CH_3$ | $CH_3$ | $CH_3$ | A-4 ($X_1=CH_3$, $Y_3=CH_3$) |
| $CH_3$ | $CH_3$ | $CH_3$ | A-4 ($X_1=CH_3$, $Y_3=OCH_3$) |
| $CH_3$ | $CH_3$ | $CH_3$ | A-4 ($X_1=OCH_3$, $Y_3=CH_3$) |
| $CH_3$ | $CH_3$ | $CH_3$ | A-5 ($X_2=CH_3$, $Y_2=OCH_3$) |
| $CH_3$ | $CH_3$ | $CH_3$ | A-5 ($X_2=CH_3$, $Y_2=SCH_3$) |
| $CH_3$ | $CH_3$ | $CH_3$ | A-6 ($X_3=OCH_3$) |
| $CH_3$ | $CH_3$ | $CH_3$ | A-7 ($X_4=OCH_3$, $Y_4=OCH_3$) |
| $CH_3$ | $CH_3$ | $CH_3$ | A-7 ($X_4=CH_3$, $Y_4=OCH_3$) |
| $CH_3$ | $CH_3$ | $CH_3$ | A-7 ($X_4=OCH_3$, $Y_4=CH_3$) |
| $CH_3$ | $CH_2CH_3$ | $CH_3$ | A-2 ($X_1=CH_3$, $Y_1=CH_2$) |
| $CH_3$ | $CH_2CH_3$ | $CH_3$ | A-3 ($X_1=CH_3$) |
| $CH_3$ | $CH_2CH_3$ | $CH_3$ | A-3 ($X_1=OCH_3$) |
| $CH_3$ | $CH_2CH_3$ | $CH_3$ | A-4 ($X_1=CH_3$, $Y_3=CH_3$) |
| $CH_3$ | $CH_2CH_3$ | $CH_3$ | A-4 ($X_1=CH_3$, $Y_3=OCH_3$) |
| $CH_3$ | $CH_2CH_3$ | $CH_3$ | A-4 ($X_1=OCH_3$, $Y_3=CH_3$) |
| $CH_3$ | $CH_2CH_3$ | $CH_3$ | A-5 ($X_2=CH_3$, $Y_2=OCH_3$) |
| $CH_3$ | $CH_2CH_3$ | $CH_3$ | A-5 ($X_2=CH_3$, $Y_2SCH_3$) |
| $CH_3$ | $CH_2CH_3$ | $CH_3$ | A-6 ($X_3=OCH_3$) |
| $CH_3$ | $CH_2CH_3$ | $CH_3$ | A-6 ($X_4=OCH_3$, $Y_4=OCH_3$) |
| $CH_3$ | $CH_2CH_3$ | $CH_3$ | A-7 ($X_4=CH_3$, $Y_4=OCH_3$) |
| $CH_3$ | $CH_2CH_3$ | $CH_3$ | A-7 ($X_4=OCH_3$, $Y_4=CH_3$) |
| $CH_3$ | $CH_2CH_3$ | $CH_2CH$ | A-2 ($X_1=CH_3$, $Y_1=CH_2$) |
| $CH_3$ | $CH_2CH_3$ | $CH_2CH_3$ | A-3 ($X_1=CH_3$) |
| $CH_3$ | $CH_2CH_3$ | $CH_2CH_3$ | A-3 ($X_1=OCH_3$) |
| $CH_3$ | $CH_2CH_3$ | $CH_2CH_3$ | A-4 ($X_1=CH_3$, $Y_3=CH_3$) |
| $CH_3$ | $CH_2CH_3$ | $CH_2CH_3$ | A-4 ($X_1=CH_3$, $Y_3=OCH_3$) |
| $CH_3$ | $CH_2CH_3$ | $CH_2CH_3$ | A-4 ($X_1=OCH_3$, $Y_3=CH_3$) |
| $CH_3$ | $CH_2CH_3$ | $CH_2CH_3$ | A-5 ($X_2=CH_3$, $Y_2=OCH_3$) |
| $CH_3$ | $CH_2CH_3$ | $CH_2CH_3$ | A-5 ($X_2=CH_3$, $Y_2=SCH_3$) |
| $CH_3$ | $CH_2CH_3$ | $CH_2CH_3$ | A-6 ($X_3=OCH_3$) |
| $CH_3$ | $CH_2CH_3$ | $CH_2CH_3$ | A-7 ($X_4=OCH_3$, $Y_4=OCH_3$) |
| $CH_3$ | $CH_2CH_3$ | $CH_2CH_3$ | A-7 ($X_4=CH_3$, $Y_4=OCH_3$) |
| $CH_3$ | $CH_2CH_3$ | $CH_2CH_3$ | A-7 ($X_4=OCH_3$, $Y_4=CH_3$) |
| $CH_3$ | $OCH_3$ | $CH_3$ | A-2 ($X_1=CH_3$, $Y_1=CH_2$) |
| $CH_3$ | $OCH_3$ | $CH_3$ | A-3 ($X_1=CH_3$) |
| $CH_3$ | $OCH_3$ | $CH_3$ | A-3 ($X_1=OCH_3$) |
| $CH_3$ | $OCH_3$ | $CH_3$ | A-4 ($X_1=CH_3$, $Y_3=CH_3$) |
| $CH_3$ | $OCH_3$ | $CH_3$ | A-4 ($X_1=CH_3$, $Y_3=OCH_3$) |
| $CH_3$ | $OCH_3$ | $CH_3$ | A-4 ($X_1=OCH_3$, $Y_3=CH_3$) |
| $CH_3$ | $OCH_3$ | $CH_3$ | A-5 ($X_2=CH_3$, $Y_2=OCH_3$) |
| $CH_3$ | $OCH_3$ | $CH_3$ | A-5 ($X_2=CH_3$, $Y_2=SCH_3$) |
| $CH_3$ | $OCH_3$ | $CH_3$ | A-6 ($X_3=OCH_3$) |
| $CH_3$ | $OCH_3$ | $CH_3$ | A-7 ($X_4=OCH_3$, $Y_4=OCH_3$) |
| $CH_3$ | $OCH_3$ | $CH_3$ | A-7 ($X_4=CH_3$, $Y_4=OCH_3$) |
| $CH_3$ | $OCH_3$ | $CH_3$ | A-7 ($X_4=OCH_3$, $Y_4=CH_3$) |
| $CH_3$ | $NHCH_3$ | $CH_3$ | A-2 ($X_1=CH_3$, $Y_1=CH_2$) |
| $CH_3$ | $NHCH_3$ | $CH_3$ | A-3 ($X_1=CH_3$) |
| $CH_3$ | $NHCH_3$ | $CH_3$ | A-3 ($X_1=OCH_3$) |
| $CH_3$ | $NHCH_3$ | $CH_3$ | A-4 ($X_1=CH_3$, $Y_3=CH_3$) |
| $CH_3$ | $NHCH_3$ | $CH_3$ | A-4 ($X_1=CH_3$, $Y_3=OCH_3$) |
| $CH_3$ | $NHCH_3$ | $CH_3$ | A-4 ($X_1=OCH_3$, $Y_3=CH_3$) |
| $CH_3$ | $NHCH_3$ | $CH_3$ | A-5 ($X_2=CH_3$, $Y_2=OCH_3$) |
| $CH_3$ | $NHCH_3$ | $CH_3$ | A-5 ($X_2=CH_3$, $Y_2=SCH_3$) |
| $CH_3$ | $NHCH_3$ | $CH_3$ | A-6 ($X_3=OCH_3$) |
| $CH_3$ | $NHCH_3$ | $CH_3$ | A-7 ($X_4=OCH_3$, $Y_4=OCH_3$) |
| $CH_3$ | $NHCH_3$ | $CH_3$ | A-7 ($X_4=CH_3$, $Y_4=OCH_3$) |
| $CH_3$ | $NHCH_3$ | $CH_3$ | A-7 ($X_4=OCH_3$, $Y_4=CH_3$) |
| $CH_3$ | $N(CH_3)_2$ | $CH_3$ | A-2 ($X_1=CH_3$, $Y_1=CH_2$) |
| $CH_3$ | $N(CH_3)_2$ | $CH_3$ | A-3 ($X_1=CH_3$) |
| $CH_3$ | $N(CH_2)_2$ | $CH_3$ | A-3 ($X_1=OCH_3$) |

TABLE II-continued
GENERAL STRUCTURE 3

| $R_1$ | $R_2$ | $R_3$ | A |
|---|---|---|---|
| $CH_3$ | $N(CH_3)_2$ | $CH_3$ | A-4 ($X_1=CH_3$, $Y_3=CH_3$) |
| $CH_3$ | $N(CH_3)_2$ | $CH_3$ | A-4 ($X_1=CH_3$, $Y_3=OCH_3$) |
| $CH_3$ | $N(CH_3)_2$ | $CH_3$ | A-4 ($X_1=OCH_3$, $Y_3=CH_3$) |
| $CH_3$ | $N(CH_3)_2$ | $CH_3$ | A-5 ($X_2=CH_3$, $Y_2=OCH_3$) |
| $CH_3$ | $N(CH_3)_2$ | $CH_3$ | A-5 ($X_2=CH_3$, $Y_2=SCH_3$) |
| $CH_3$ | $N(CH_3)_2$ | $CH_3$ | A-6 ($X_3=OCH_3$) |
| $CH_3$ | $N(CH_3)_2$ | $CH_3$ | A-7 ($X_4=OCH_3$, $Y_4=OCH_3$) |
| $CH_3$ | $N(CH_3)_2$ | $CH_3$ | A-7 ($X_4=CH_3$, $Y_4=OCH_3$) |
| $CH_3$ | $N(CH_3)_2$ | $CH_3$ | A-7 ($X_4=OCH_3$, $Y_4=CH_3$) |
| $CH_3$ | $-CH_2CH_2CH_2-$ | | A-2 ($X_1CH_3$, $Y_1=CH_2$) |
| $CH_3$ | $-CH_2CH_2CH_2-$ | | A-3 ($X_1=CH_3$) |
| $CH_3$ | $-CH_2CH_2CH_2-$ | | A-3 ($X_1=OCH_3$) |
| $CH_3$ | $-CH_2CH_2CH_2-$ | | A-4 ($X_1=CH_3$, $Y_3=CH_3$) |
| $CH_3$ | $-CH_2CH_2CH_2-$ | | A-4 ($X_1=CH_3$, $Y_3=OCH_3$) |
| $CH_3$ | $-CH_2CH_2CH_2-$ | | A-4 ($X_1=OCH_3$, $Y_3=CH_3$) |
| $CH_3$ | $-CH_2CH_2CH_2-$ | | A-5 ($X_2=CH_3$, $Y_2=OCH_3$) |
| $CH_3$ | $-CH_2CH_2CH_2-$ | | A-5 ($X_2=CH_3$, $Y_2=SCH_3$) |
| $CH_3$ | $-CH_2CH_2CH_2-$ | | A-6 ($X_3=OCH_3$) |
| $CH_3$ | $-CH_2CH_2CH_2-$ | | A-7 ($X_4=OCH_3$, $Y_4=OCH_3$) |
| $CH_3$ | $-CH_2CH_2CH_2-$ | | A-7 ($X_4=CH_3$, $Y_4=OCH_3$) |
| $CH_3$ | $-CH_2CH_2CH_2-$ | | A-7 ($X_4=OCH_3$, $Y_4=CH_3$) |
| $CH_3$ | $-CH_2CH_2OCH_2CH_2-$ | | A-2 ($X_1=CH_3$, $Y_1=CH_2$) |
| $CH_3$ | $-CH_2CH_2OCH_2CH_2-$ | | A-3 ($X_1=CH_3$) |
| $CH_3$ | $-CH_2CH_3OCH_2CH_2-$ | | A-3 ($X_1=OCH_3$) |
| $CH_3$ | $-CH_2CH_2OCH_2CH_2-$ | | A-4 ($X_1=CH_3$, $Y_3=CH_3$) |
| $CH_3$ | $-CH_2CH_2OCH_2CH_2-$ | | A-4 ($X_1=CH_3$, $Y_3=OCH_3$) |
| $CH_3$ | $-CH_2CH_2OCH_2CH_2-$ | | A-4 ($X_1=OCH_3$, $Y_3=CH_3$) |
| $CH_3$ | $-CH_2CH_2OCH_2CH_2-$ | | A-5 ($X_2=CH_3$, $Y_2=OCH_3$) |
| $CH_3$ | $-CH_2CH_2OCH_2CH_2-$ | | A-5 ($X_2=CH_3$, $Y_2=SCH_3$) |
| $CH_3$ | $-CH_2CH_2OCH_2CH_2-$ | | A-6 ($X_3=OCH_3$) |
| $CH_3$ | $-CH_2CH_2OCH_2CH_2-$ | | A-7 ($X_4=OCH_3$, $Y_4=OCH_3$) |
| $CH_3$ | $-CH_2CH_2OCH_2CH_2-$ | | A-7 ($X_4=CH_3$, $Y_4=OCH_3$) |
| $CH_3$ | $-CH_2CH_2OCH_2CH_2-$ | | A-7 ($X_4=OCH_3$, $Y_4=CH_3$) |
| $SCH_3$ | H | H | A-2 ($X_1=CH_3$, $Y_1=CH_2$) |
| $SCH_3$ | H | H | A-3 ($X_1=CH_3$) |
| $SCH_3$ | H | H | A-3 ($X_1=OCH_3$) |
| $SCH_3$ | H | H | A-4 ($X_1=CH_3$, $Y_3=CH_3$) |
| $SCH_3$ | H | H | A-4 ($X_1=CH_3$, $Y_3=OCH_3$) |
| $SCH_3$ | H | H | A-4 ($X_1=OCH_3$, $Y_3=CH_3$) |
| $SCH_3$ | H | H | A-5 ($X_2=CH_3$, $Y_2=OCH_3$) |
| $SCH_3$ | H | H | A-5 ($X_2=CH_3$, $Y_2=SCH_3$) |
| $SCH_3$ | H | H | A-6 ($X_3=OCH_3$) |
| $SCH_3$ | H | H | A-7 ($X_4=OCH_3$, $Y_4=OCH_3$) |
| $SCH_3$ | H | H | A-7 ($X_4=CH_3$, $Y_4=OCH_3$) |
| $SCH_3$ | H | H | A-7 ($X_4=OCH_3$, $Y_4=CH_3$) |
| $SCH_3$ | H | $CH_3$ | A-2 ($X_1=CH_3$, $Y_1=CH_2$) |
| $SCH_3$ | H | $CH_3$ | A-3 ($X_1=CH_3$) |
| $SCH_3$ | H | $CH_3$ | A-3 ($X_1=OCH_3$) |
| $SCH_3$ | H | $CH_3$ | A-4 ($X_1=CH_3$, $Y_3=CH_3$) |
| $SCH_3$ | H | $CH_3$ | A-4 ($X_1=CH_3$, $Y_3=OCH_3$) |
| $SCH_3$ | H | $CH_3$ | A-4 ($X_1=OCH_3$, $Y_3=CH_3$) |
| $SCH_3$ | H | $CH_3$ | A-5 ($X_2=CH_3$, $Y_2=OCH_3$) |
| $SCH_3$ | H | $CH_3$ | A-5 ($X_2=CH_3$, $Y_2=SCH_3$) |
| $SCH_3$ | H | $CH_3$ | A-6 ($X_3=OCH_3$) |
| $SCH_3$ | H | $CH_3$ | A-7 ($X_4=OCH_3$, $Y_4=OCH_3$) |
| $SCH_3$ | H | $CH_3$ | A-7 ($X_4=CH_3$, $Y_4=OCH_3$) |
| $SCH_3$ | H | $CH_3$ | A-7 ($X_4=OCH_3$, $Y_4=CH_3$) |
| $SCH_3$ | H | $CH_2CH_3$ | A-2 ($X_1=CH_3$, $Y_1=CH_2$) |
| $SCH_3$ | H | $CH_2CH_3$ | A-3 ($X_1=CH_3$) |
| $SCH_3$ | H | $CH_2CH_3$ | A-3 ($X_1=OCH_3$) |
| $SCH_3$ | H | $CH_2CH_3$ | A-4 ($X_1=CH_3$, $Y_3=CH_3$) |
| $SCH_3$ | H | $CH_2CH_3$ | A-4 ($X_1=CH_3$, $Y_3=OCH_3$) |
| $SCH_3$ | H | $CH_2CH_3$ | A-4 ($X_1=OCH_3$, $Y_3=CH_3$) |
| $SCH_3$ | H | $CH_2CH_3$ | A-5 ($X_2=CH_3$, $Y_2=OCH_3$) |
| $SCH_3$ | H | $CH_2CH_3$ | A-5 ($X_2=CH_3$, $Y_2=SCH_3$) |
| $SCH_3$ | H | $CH_2CH_3$ | A-6 ($X_3=OCH_3$) |
| $SCH_3$ | H | $CH_2CH_3$ | A-7 ($X_4=OCH_3$, $Y_4=OCH_3$) |
| $SCH_3$ | H | $CH_2CH_3$ | A-7 ($X_4=CH_3$, $Y_4=OCH_3$) |
| $SCH_3$ | H | $CH_2CH_3$ | A-7 ($X_4=OCH_3$, $Y_4=CH_3$) |
| $SCH_3$ | $CH_2CF_3$ | H | A-2 ($X_1=CH_3$, $Y_1=CH_2$) |
| $SCH_3$ | $CH_2CF_3$ | H | A-3 ($X_1=CH_3$) |
| $SCH_3$ | $CH_2CF_3$ | H | A-3 ($X_1=OCH_3$) |
| $SCH_3$ | $CH_2CF_3$ | H | A-4 ($X_1=CH_3$, $Y_3=CH_3$) |
| $SCH_3$ | $CH_2CF_3$ | H | A-4 ($X_1=CH_3$, $Y_3=OCH_3$) |
| $SCH_3$ | $CH_2CF_3$ | H | A-4 ($X_1=OCH_3$, $Y_3=CH_3$) |
| $SCH_3$ | $CH_2CF_3$ | H | A-5 ($X_2=CH_3$, $Y_2=OCH_3$) |
| $SCH_3$ | $CH_2CF_3$ | H | A-5 ($X_2=CH_3$, $Y_2=SCH_3$) |
| $SCH_3$ | $CH_2CF_3$ | H | A-6 ($X_3=OCH_3$) |
| $SCH_3$ | $CH_2CF_3$ | H | A-7 ($X_4=OCH_3$, $Y_4=OCH_3$) |
| $SCH_3$ | $CH_2CF_3$ | H | A-7 ($X_4=CH_3$, $Y_4=OCH_3$) |

TABLE II-continued

GENERAL STRUCTURE 3

| R₁ | R₂ | R₃ | A |
|---|---|---|---|
| SCH$_3$ | CH$_2$CF$_3$ | H | A-7 (X$_4$=OCH$_3$, Y$_4$=CH$_3$) |
| SCH$_3$ | CH$_2$CH$_2$Cl | H | A-2 (X$_1$=CH$_3$, Y$_1$=CH$_3$) |
| SCH$_3$ | CH$_2$CH$_2$Cl | H | A-3 (X$_1$=CH$_3$) |
| SCH$_3$ | CH$_2$CH$_2$Cl | H | A-3 (X$_2$=OCH$_3$) |
| SCH$_3$ | CH$_2$CH$_2$Cl | H | A-4 (X$_1$=CH$_3$, Y$_3$=CH$_3$) |
| SCH$_3$ | CH$_2$CH$_2$Cl | H | A-4 (X$_1$=CH$_3$, Y$_3$=OCH$_3$) |
| SCH$_3$ | CH$_2$CH$_2$Cl | H | A-4 (X$_1$=OCH$_3$, Y$_3$=CH$_3$) |
| SCH$_3$ | CH$_2$CH$_2$Cl | H | A-5 (X$_2$=CH$_3$, Y$_1$=OCH$_3$) |
| SCH$_3$ | CH$_2$CH$_2$Cl | H | A-5 (X$_2$=CH$_3$, Y$_2$=SCH$_3$) |
| SCH$_3$ | CH$_2$CH$_2$Cl | H | A-6 (X$_3$=OCH$_3$) |
| SCH$_3$ | CH$_2$CH$_2$Cl | H | A-7 (X$_4$=OCH$_3$, Y$_4$=OCH$_3$) |
| SCH$_3$ | CH$_2$CH$_2$Cl | H | A-7 (X$_4$=CH$_3$, Y$_4$=OCH$_3$) |
| SCH$_3$ | CH$_2$CH$_2$Cl | H | A-7 (X$_4$=OCH$_3$, Y$_4$=CH$_3$) |
| SCH$_3$ | CH$_2$CN | H | A-2 (X$_1$=CH$_3$, Y$_1$=CH$_2$) |
| SCH$_3$ | CH$_2$CN | H | A-3 (X$_1$=CH$_3$) |
| SCH$_3$ | CH$_2$CN | H | A-3 (X$_1$=OCH$_3$) |
| SCH$_3$ | CH$_2$CN | H | A-4 (X$_1$=CH$_3$, Y$_3$=CH$_3$) |
| SCH$_3$ | CH$_2$CN | H | A-4 (X$_1$=CH$_3$, Y$_3$=OCH$_3$) |
| SCH$_3$ | CH$_2$CN | H | A-4 (X$_1$=OCH$_3$, Y$_3$=CH$_3$) |
| SCH$_3$ | CH$_2$CN | H | A-5 (X$_2$=CH$_3$, Y$_2$=OCH$_3$) |
| SCH$_3$ | CH$_2$CN | H | A-5 (X$_2$=CH$_3$, Y$_2$=SCH$_3$) |
| SCH$_3$ | CH$_2$CN | H | A-6 (X$_3$=OCH$_3$) |
| SCH$_3$ | CH$_2$CN | H | A-7 (X$_4$=OCH$_3$, Y$_4$=OCH$_3$) |
| SCH$_3$ | CH$_2$CN | H | A-7 (X$_4$=CH$_3$, Y$_4$=OCH$_3$) |
| SCH$_3$ | CH$_2$CN | H | A-7 (X$_4$=OCH$_3$, Y$_4$=CH$_3$) |
| SCH$_3$ | CH$_2$CH$_2$OCH$_3$ | H | A-2 (X$_1$=CH$_3$, Y$_1$=CH$_2$) |
| SCH$_3$ | CH$_2$CH$_2$OCH$_3$ | H | A-3 (X$_1$=CH$_3$) |
| SCH$_3$ | CH$_2$CH$_2$OCH$_3$ | H | A-3 (X$_1$=OCH$_3$) |
| SCH$_3$ | CH$_2$CH$_2$OCH$_3$ | H | A-4 (X$_1$=CH$_3$, Y$_3$=OCH$_3$) |
| SCH$_3$ | CH$_2$CH$_2$OCH$_3$ | H | A-4 (X$_1$=OCH$_3$, Y$_3$=CH$_3$) |
| SCH$_3$ | CH$_2$CH$_2$OCH$_3$ | H | A-5 (X$_2$=CH$_3$, Y$_2$=OCH$_3$) |
| SCH$_3$ | CH$_2$CH$_2$OCH$_3$ | H | A-5 (X$_2$=CH$_3$, Y$_2$=SCH$_3$) |
| SCH$_3$ | CH$_2$CH$_2$OCH$_3$ | H | A-6 (X$_3$=OCH$_3$) |
| SCH$_3$ | CH$_2$CH$_2$OCH$_3$ | H | A-7 (X$_4$=OCH$_3$, Y$_4$=OCH$_3$) |
| SCH$_3$ | CH$_2$CH$_2$OCH$_3$ | H | A-7 (X$_4$=CH$_3$, Y$_4$=OCH$_3$) |
| SCH$_3$ | CH$_2$CH$_2$OCH$_3$ | H | A-7 (X$_4$=OCH$_3$, Y$_4$=CH$_3$) |
| SCH$_3$ | CH$_2$CH=CH$_2$ | H | A-2 (X$_1$=CH$_3$, Y$_1$=CH$_2$) |
| SCH$_3$ | CH$_2$CH=CH$_2$ | H | A-3 (X$_1$=CH$_3$) |
| SCH$_3$ | CH$_2$CH=CH$_2$ | H | A-3 (X$_1$=OCH$_3$) |
| SCH$_3$ | CH$_2$CH=CH$_2$ | H | A-4 (X$_1$=CH$_3$, Y$_3$=CH$_3$) |
| SCH$_3$ | CH$_2$CH=CH$_2$ | H | A-4 (X$_1$=CH$_3$, Y$_3$=OCH$_3$) |
| SCH$_3$ | CH$_2$CH=CH$_2$ | H | A-4 (X$_1$=OCH$_3$, Y$_3$=CH$_3$) |
| SCH$_3$ | CH$_2$CH=CH$_2$ | H | A-5 (X$_2$=CH$_3$, Y$_2$=OCH$_3$) |
| SCH$_3$ | CH$_2$CH=CH$_2$ | H | A-5 (X$_2$=CH$_3$, Y$_2$=SCH$_3$) |
| SCH$_3$ | CH$_2$CH=CH$_2$ | H | A-6 (X$_3$=OCH$_3$) |
| SCH$_3$ | CH$_2$CH=CH$_2$ | H | A-7 (X$_4$=OCH$_3$, Y$_4$=OCH$_3$) |
| SCH$_3$ | CH$_2$CH=CH$_2$ | H | A-7 (X$_4$=CH$_3$, Y$_4$=OCH$_3$) |
| SCH$_3$ | CH$_2$CH=CH$_2$ | H | A-7 (X$_4$=OCH$_3$, Y$_4$=CH$_3$) |
| SCH$_3$ | CH$_2$C≡CH | H | A-2 (X$_1$=CH$_3$, Y$_1$=CH$_2$) |
| SCH$_3$ | CH$_2$C≡CH | H | A-3 (X$_1$=CH$_3$) |
| SCH$_3$ | CH$_2$C≡CH | H | A-3 (X$_1$=OCH$_3$) |
| SCH$_3$ | CH$_2$C≡CH | H | A-4 (X$_1$=CH$_3$, Y$_3$=CH$_3$) |
| SCH$_3$ | CH$_2$C≡CH | H | A-4 (X$_1$=CH$_3$, Y$_3$=OCH$_3$) |
| SCH$_3$ | CH$_2$C≡CH | H | A-4 (X$_1$=OCH$_3$, Y$_3$=CH$_3$) |
| SCH$_3$ | CH$_2$C≡CH | H | A-5 (X$_2$=CH$_3$, Y$_2$=OCH$_3$) |
| SCH$_3$ | CH$_2$C≡CH | H | A-5 (X$_2$=CH$_3$, Y$_2$=SCH$_3$) |
| SCH$_3$ | CH$_2$C≡CH | H | A-6 (X$_3$=OCH$_3$) |
| SCH$_3$ | CH$_2$C≡CH | H | A-7 (X$_4$=OCH$_3$, Y$_4$=OCH$_3$) |
| SCH$_3$ | CH$_2$C≡CH | H | A-7 (X$_4$=CH$_3$, Y$_4$=OCH$_3$) |
| SCH$_3$ | CH$_2$C≡CH | H | A-7 (X$_4$OCH$_3$, Y$_4$=CH$_3$) |
| SCH$_3$ | cyclo-C$_3$H$_7$ | H | A-2 (X$_1$=CH$_3$, Y$_1$=CH$_2$) |
| SCH$_3$ | cyclo-C$_3$H$_7$ | H | A-3 (X$_1$=CH$_3$) |
| SCH$_3$ | cyclo-C$_3$H$_7$ | H | A-3 (X$_1$=OCH$_3$) |
| SCH$_3$ | cyclo-C$_3$H$_7$ | H | A-4 (X$_1$=CH$_3$, Y$_3$=CH$_3$) |
| SCH$_3$ | cyclo-C$_3$H$_7$ | H | A-4 (X$_1$=CH$_3$, Y$_3$=OCH$_3$) |
| SCH$_3$ | cyclo-C$_3$H$_7$ | H | A-4 (X$_1$=OCH$_3$, Y$_3$=CH$_3$) |
| SCH$_3$ | cyclo-C$_3$H$_7$ | H | A-5 (X$_2$=CH$_3$, Y$_2$=OCH$_3$) |
| SCH$_3$ | cyclo-C$_3$H$_7$ | H | A-5 (X$_2$=CH$_3$, Y$_2$=SCH$_3$) |
| SCH$_3$ | cyclo-C$_3$H$_7$ | H | A-6 (X$_3$=OCH$_3$) |
| SCH$_3$ | cyclo-C$_3$H$_7$ | H | A-7 (X$_4$=OCH$_3$, Y$_4$=OCH$_3$) |
| SCH$_3$ | cyclo-C$_3$H$_7$ | H | A-7 (X$_4$=CH$_3$, Y$_4$=OCH$_3$) |
| SCH$_3$ | cyclo-C$_3$H$_7$ | H | A-7 (X$_4$=OCH$_3$, Y$_4$=CH$_3$) |
| SCH$_3$ | CH$_3$ | CH$_3$ | A-2 (X$_1$=CH$_3$, Y$_1$=CH$_2$) |
| SCH$_3$ | CH$_3$ | CH$_3$ | A-3 (X$_1$=CH$_3$) |
| SCH$_3$ | CH$_3$ | CH$_3$ | A-3 (X$_1$=OCH$_3$) |
| SCH$_3$ | CH$_3$ | CH$_3$ | A-4 (X$_1$=CH$_3$, Y$_3$=CH$_3$) |
| SCH$_3$ | CH$_3$ | CH$_3$ | A-4 (X$_1$=CH$_3$, Y$_3$=OCH$_3$) |
| SCH$_3$ | CH$_3$ | CH$_3$ | A-4 (X$_1$=OCH$_3$, Y$_3$=CH$_3$) |
| SCH$_3$ | CH$_3$ | CH$_3$ | A-5 (X$_2$=CH$_3$, Y$_2$=OCH$_3$) |
| SCH$_3$ | CH$_3$ | CH$_3$ | A-5 (X$_2$=CH$_3$, Y$_2$=SCH$_3$) |

TABLE II-continued
GENERAL STRUCTURE 3

| R$_1$ | R$_2$ | R$_3$ | A |
|---|---|---|---|
| SCH$_3$ | CH$_3$ | CH$_3$ | A-6 (X$_3$=OCH$_3$) |
| SCH$_3$ | CH$_3$ | CH$_3$ | A-7 (X$_4$=OCH$_3$, Y$_4$=OCH$_3$) |
| SCH$_3$ | CH$_3$ | CH$_3$ | A-7 (X$_4$=CH$_3$, Y$_4$=OCH$_3$) |
| SCH$_3$ | CH$_3$ | CH$_3$ | A-7 (X$_4$=OCH$_3$, Y$_4$=CH$_3$) |
| SCH$_3$ | CH$_2$CH$_3$ | CH$_3$ | A-2 (X$_1$=CH$_3$, Y$_1$=CH$_2$) |
| SCH$_3$ | CH$_2$CH$_3$ | CH$_3$ | A-3 (X$_1$=CH$_3$) |
| SCH$_3$ | CH$_2$CH$_3$ | CH$_3$ | A-3 (X$_1$=OCH$_3$) |
| SCH$_3$ | CH$_2$CH$_3$ | CH$_3$ | A-4 (X$_1$=CH$_3$, Y$_3$=CH$_3$) |
| SCH$_3$ | CH$_2$CH$_3$ | CH$_3$ | A-4 (X$_1$=CH$_3$, Y$_3$=OCH$_3$) |
| SCH$_3$ | CH$_2$CH$_3$ | CH$_3$ | A-4 (X$_1$=OCH$_3$, Y$_3$=CH$_3$) |
| SCH$_3$ | CH$_2$CH$_3$ | CH$_3$ | A-5 (X$_2$=CH$_3$, Y$_2$=OCH$_3$) |
| SCH$_3$ | CH$_2$CH$_3$ | CH$_3$ | A-5 (X$_2$=CH$_3$, Y$_2$=SCH$_3$) |
| SCH$_3$ | CH$_2$CH$_3$ | CH$_3$ | A-6 (X$_3$=OCH$_3$) |
| SCH$_3$ | CH$_2$CH$_3$ | CH$_3$ | A-7 (X$_4$=OCH$_3$, Y$_4$=OCH$_3$) |
| SCH$_3$ | CH$_2$CH$_3$ | CH$_3$ | A-7 (X$_4$=CH$_3$, Y$_4$=OCH$_3$) |
| SCH$_3$ | CH$_2$CH$_3$ | CH$_3$ | A-7 (X$_4$=OCH$_3$, Y$_4$=CH$_3$) |
| SCH$_3$ | CH$_2$CH$_3$ | CH$_2$CH$_3$ | A-2 (X$_1$=CH$_3$, Y$_1$=CH$_2$) |
| SCH$_3$ | CH$_2$CH$_3$ | CH$_2$CH$_3$ | A-3 (X$_1$=CH$_3$) |
| SCH$_3$ | CH$_2$CH$_3$ | CH$_2$CH$_3$ | A-3 (X$_1$=OCH$_3$) |
| SCH$_3$ | CH$_2$CH$_3$ | CH$_2$CH$_3$ | A-4 (X$_1$=CH$_3$, Y$_3$=CH$_3$) |
| SCH$_3$ | CH$_2$CH$_3$ | CH$_2$CH$_3$ | A-4 (X$_1$=CH$_3$, Y$_3$=OCH$_3$) |
| SCH$_3$ | CH$_2$CH$_3$ | CH$_2$CH$_3$ | A-4 (X$_1$=OCH$_3$, Y$_3$=CH$_3$) |
| SCH$_3$ | CH$_2$CH$_3$ | CH$_2$CH$_3$ | A-5 (X$_2$=CH$_3$, Y$_2$=OCH$_3$) |
| SCH$_3$ | CH$_2$CH$_3$ | CH$_2$CH$_3$ | A-5 (X$_2$=CH$_3$, Y$_2$=SCH$_3$) |
| SCH$_3$ | CH$_2$CH$_3$ | CH$_2$CH$_3$ | A-6 (X$_3$=OCH$_3$) |
| SCH$_3$ | CH$_2$CH$_3$ | CH$_2$CH$_3$ | A-7 (X$_4$=OCH$_3$, Y$_4$=OCH$_3$) |
| SCH$_3$ | CH$_2$CH$_3$ | CH$_2$CH$_3$ | A-7 (X$_4$=CH$_3$, Y$_4$=OCH$_3$) |
| SCH$_3$ | CH$_2$CH$_3$ | CH$_2$CH$_3$ | A-7 (X$_4$=OCH$_3$, Y$_4$=CH$_3$) |
| SCH$_3$ | OCH$_3$ | CH$_3$ | A-2 (X$_1$=CH$_3$, Y$_1$=CH$_2$) |
| SCH$_3$ | OCH$_3$ | CH$_3$ | A-3 (X$_1$=CH$_3$) |
| SCH$_3$ | OCH$_3$ | CH$_3$ | A-3 (X$_1$=OCH$_3$) |
| SCH$_3$ | OCH$_3$ | CH$_3$ | A-4 (X$_1$=CH$_3$, Y$_3$=CH$_3$) |
| SCH$_3$ | OCH$_3$ | CH$_3$ | A-4 (X$_1$=CH$_3$, Y$_3$=OCH$_3$) |
| SCH$_3$ | OCH$_3$ | CH$_3$ | A-4 (X$_1$=OCH$_3$, Y$_3$=CH$_3$) |
| SCH$_3$ | OCH$_3$ | CH$_3$ | A-5 (X$_2$=CH$_3$, Y$_2$=OCH$_3$) |
| SCH$_3$ | OCH$_3$ | CH$_3$ | A-5 (X$_2$=CH$_3$, Y$_2$=SCH$_3$) |
| SCH$_3$ | OCH$_3$ | CH$_3$ | A-6 (X$_3$=OCH$_3$) |
| SCH$_3$ | OCH$_3$ | CH$_3$ | A-7 (X$_4$=OCH$_3$, Y$_4$=OCH$_3$) |
| SCH$_3$ | OCH$_3$ | CH$_3$ | A-7 (X$_4$=CH$_3$, Y$_4$=OCH$_3$) |
| SCH$_3$ | OCH$_3$ | CH$_3$ | A-7 (X$_4$=OCH$_3$, Y$_4$=CH$_3$) |
| SCH$_3$ | NHCH$_3$ | CH$_3$ | A-2 (X$_1$=CH$_3$, Y$_1$=CH$_2$) |
| SCH$_3$ | NHCH$_3$ | CH$_3$ | A-3 (X$_1$=CH$_3$) |
| SCH$_3$ | NHCH$_3$ | CH$_3$ | A-3 (X$_1$=OCH$_3$) |
| SCH$_3$ | NHCH$_3$ | CH$_3$ | A-4 (X$_1$=CH$_3$, Y$_3$=CH$_3$) |
| SCH$_3$ | NHCH$_3$ | CH$_3$ | A-4 (X$_1$=CH$_3$, Y$_3$=OCH$_3$) |
| SCH$_3$ | NHCH$_3$ | CH$_3$ | A-4 (X$_1$=OCH$_3$, Y$_3$=CH$_3$) |
| SCH$_3$ | NHCH$_3$ | CH$_3$ | A-5 (X$_2$=CH$_3$, Y$_2$=OCH$_3$) |
| SCH$_3$ | NHCH$_3$ | CH$_3$ | A-5 (X$_2$=CH$_3$, Y$_2$=SCH$_3$) |
| SCH$_3$ | NHCH$_3$ | CH$_3$ | A-6 (X$_3$=OCH$_3$) |
| SCH$_3$ | NHCH$_3$ | CH$_3$ | A-7 (X$_4$=OCH$_3$, Y$_4$=OCH$_3$) |
| SCH$_3$ | NHCH$_3$ | CH$_3$ | A-7 (X$_4$=CH$_3$, Y$_4$=OCH$_3$) |
| SCH$_3$ | NHCH$_3$ | CH$_3$ | A-7 (X$_4$=OCH$_3$, Y$_4$=CH$_3$) |
| SCH$_3$ | N(CH$_3$)$_2$ | CH$_3$ | A-2 (X$_1$=CH$_3$, Y$_1$=CH$_2$) |
| SCH$_3$ | N(CH$_3$)$_2$ | CH$_3$ | A-3 (X$_1$=CH$_3$) |
| SCH$_3$ | N(CH$_3$)$_2$ | CH$_3$ | A-3 (X$_1$=OCH$_3$) |
| SCH$_3$ | N(CH$_3$)$_2$ | CH$_3$ | A-4 (X$_1$=CH$_3$, Y$_3$=CH$_3$) |
| SCH$_3$ | N(CH$_3$)$_2$ | CH$_3$ | A-4 (X$_1$=CH$_3$, Y$_3$=OCH$_3$) |
| SCH$_3$ | N(CH$_3$)$_2$ | CH$_3$ | A-4 (X$_1$=OCH$_3$, Y$_3$=CH$_3$) |
| SCH$_3$ | N(CH$_3$)$_2$ | CH$_3$ | A-5 (X$_2$=CH$_3$, Y$_2$=OCH$_3$) |
| SCH$_3$ | N(CH$_3$)$_2$ | CH$_3$ | A-5 (X$_2$=CH$_3$, Y$_2$=SCH$_3$) |
| SCH$_3$ | N(CH$_3$)$_2$ | CH$_3$ | A-6 (X$_3$=OCH$_3$) |
| SCH$_3$ | N(CH$_3$)$_2$ | CH$_3$ | A-7 (X$_4$=OCH$_3$, Y$_4$=OCH$_3$) |
| SCH$_3$ | N(CH$_3$)$_2$ | CH$_3$ | A-7 (X$_4$=CH$_3$, Y$_4$=OCH$_3$) |
| SCH$_3$ | N(CH$_3$)$_2$ | CH$_3$ | A-7 (X$_4$=OCH$_3$, Y$_4$=CH$_3$) |
| SCH$_3$ | —CH$_2$CH$_2$CH$_2$— | | A-2 (X$_1$=CH$_3$, Y$_1$=CH$_2$) |
| SCH$_3$ | —CH$_2$CH$_2$CH$_2$— | | A-3 (X$_1$=CH$_3$) |
| SCH$_3$ | —CH$_2$CH$_2$CH$_2$— | | A-3 (X$_1$=OCH$_3$) |
| SCH$_3$ | —CH$_2$CH$_2$CH$_2$— | | A-4 (X$_1$=CH$_3$, Y$_3$=CH$_3$) |
| SCH$_3$ | —CH$_2$CH$_2$CH$_2$— | | A-4 (X$_1$=CH$_3$, Y$_3$=OCH$_3$) |
| SCH$_3$ | —CH$_2$CH$_2$CH$_2$— | | A-4 (X$_1$=OCH$_3$, Y$_3$=CH$_3$) |
| SCH$_3$ | —CH$_2$CH$_2$CH$_2$— | | A-5 (X$_2$=CH$_3$, Y$_2$=OCH$_3$) |
| SCH$_3$ | —CH$_2$CH$_2$CH$_2$— | | A-5 (X$_2$=CH$_3$, Y$_2$=SCH$_3$) |
| SCH$_3$ | —CH$_2$CH$_2$CH$_2$— | | A-6 (X$_3$=OCH$_3$) |
| SCH$_3$ | —CH$_2$CH$_2$CH$_2$— | | A-7 (X$_4$=OCH$_3$, Y$_4$=OCH$_3$) |
| SCH$_3$ | —CH$_2$CH$_2$CH$_2$— | | A-7 (X$_4$=CH$_3$, Y$_4$=OCH$_3$) |
| SCH$_3$ | —CH$_2$CH$_2$CH$_2$— | | A-7 (X$_4$=OCH$_3$, Y$_4$=CH$_3$) |
| SCH$_3$ | —CH$_2$CH$_2$OCH$_2$CH$_2$— | | A-2 (X$_1$=CH$_3$, Y$_1$=CH$_2$) |
| SCH$_3$ | —CH$_2$CH$_2$OCH$_2$CH$_2$— | | A-3 (X$_1$=CH$_3$) |
| SCH$_3$ | —CH$_2$CH$_2$OCH$_2$CH$_2$— | | A-3 (X$_1$=OCH$_3$) |
| SCH$_3$ | —CH$_2$CH$_2$OCH$_2$CH$_2$— | | A-4 (X$_1$=CH$_3$, Y$_3$=CH$_3$) |

TABLE II-continued

GENERAL STRUCTURE 3

| R$_1$ | R$_2$ | R$_3$ | A |
|---|---|---|---|
| SCH$_3$ | —CH$_2$CH$_2$OCH$_2$CH$_2$— | | A-4 (X$_1$=CH$_3$, Y$_3$=OCH$_3$) |
| SCH$_3$ | —CH$_2$CH$_2$OCH$_2$CH$_2$— | | A-4 (X$_1$=OCH$_3$, Y$_3$=CH$_3$) |
| SCH$_3$ | —CH$_2$CH$_2$OCH$_2$CH$_2$— | | A-5 (X$_2$=CH$_3$, Y$_2$=OCH$_3$) |
| SCH$_3$ | —CH$_2$CH$_2$OCH$_2$CH$_2$— | | A-5 (X$_2$=CH$_3$, Y$_2$=SCH$_3$) |
| SCH$_3$ | —CH$_2$CH$_2$OCH$_2$CH$_2$— | | A-6 (X$_3$=OCH$_3$) |
| SCH$_3$ | —CH$_2$CH$_2$OCH$_2$CH$_2$— | | A-7 (X$_4$=OCH$_3$, Y$_4$=OCH$_3$) |
| SCH$_3$ | —CH$_2$CH$_2$OCH$_2$CH$_2$— | | A-7 (X$_4$=CH$_3$, Y$_4$=OCH$_3$) |
| SCH$_3$ | —CH$_2$CH$_2$OCH$_2$CH$_2$— | | A-7 (X$_4$=OCH$_3$, Y$_4$=CH$_3$) |
| SO$_2$CH$_2$CH$_3$ | H | H | A-2 (X$_1$=CH$_3$, Y$_1$=CH$_2$) |
| SO$_2$CH$_2$CH$_3$ | H | H | A-3 (X$_1$=CH$_3$) |
| SO$_2$CH$_2$CH$_3$ | H | H | A-3 (X$_1$=OCH$_3$) |
| SO$_2$CH$_2$CH$_3$ | H | H | A-4 (X$_1$=CH$_3$, Y$_3$=CH$_3$) |
| SO$_2$CH$_2$CH$_3$ | H | H | A-4 (X$_1$=CH$_3$, Y$_3$=OCH$_3$) |
| SO$_2$CH$_2$CH$_3$ | H | H | A-4 (X$_1$=OCH$_3$, Y$_3$=CH$_3$) |
| SO$_2$CH$_2$CH$_3$ | H | H | A-5 (X$_2$=CH$_3$, Y$_2$=OCH$_3$) |
| SO$_2$CH$_2$CH$_3$ | H | H | A-5 (X$_2$=CH$_3$, Y$_2$=SCH$_3$) |
| SO$_2$CH$_2$CH$_3$ | H | H | A-6 (X$_3$=OCH$_3$) |
| SO$_2$CH$_2$CH$_3$ | H | H | A-7 (X$_4$=OCH$_3$, Y$_4$=OCH$_3$) |
| SO$_2$CH$_2$CH$_3$ | H | H | A-7 (X$_4$=CH$_3$, Y$_4$=OCH$_3$) |
| SO$_2$CH$_2$CH$_3$ | H | H | A-7 (X$_4$=OCH$_3$, Y$_4$=CH$_3$) |
| SO$_2$CH$_2$CH$_3$ | H | CH$_3$ | A-2 (X$_1$=CH$_3$, Y$_1$=CH$_2$) |
| SO$_2$CH$_2$CH$_3$ | H | CH$_3$ | A-3 (X$_1$=CH$_3$) |
| SO$_2$CH$_2$CH$_3$ | H | CH$_3$ | A-3 (X$_1$=OCH$_3$) |
| SO$_2$CH$_2$CH$_3$ | H | CH$_3$ | A-4 (X$_1$=CH$_3$, Y$_3$=CH$_3$) |
| SO$_2$CH$_2$CH$_3$ | H | CH$_3$ | A-4 (X$_1$=CH$_3$, Y$_3$=OCH$_3$) |
| SO$_2$CH$_2$CH$_3$ | H | CH$_3$ | A-4 (X$_1$=OCH$_3$, Y$_3$=CH$_3$) |
| SO$_2$CH$_2$CH$_3$ | H | CH$_3$ | A-5 (X$_2$=CH$_3$, Y$_2$=OCH$_3$) |
| SO$_2$CH$_2$CH$_3$ | H | CH$_3$ | A-5 (X$_2$=CH$_3$, Y$_2$=SCH$_3$) |
| SO$_2$CH$_2$CH$_3$ | H | CH$_3$ | A-6 (X$_3$=OCH$_3$) |
| SO$_2$CH$_2$CH$_3$ | H | CH$_3$ | A-7 (X$_4$=OCH$_3$, Y$_4$=OCH$_3$) |
| SO$_2$CH$_2$CH$_3$ | H | CH$_3$ | A-7 (X$_4$=CH$_3$, Y$_4$=OCH$_3$) |
| SO$_2$CH$_2$CH$_3$ | H | CH$_3$ | A-7 (X$_4$=OCH$_3$, Y$_4$=CH$_3$) |
| SO$_2$CH$_2$CH$_3$ | H | CH$_2$CH$_3$ | A-2 (X$_1$=CH$_3$, Y$_1$=CH$_2$) |
| SO$_2$CH$_2$CH$_3$ | H | CH$_2$CH$_3$ | A-3 (X$_1$=CH$_3$) |
| SO$_2$CH$_2$CH$_3$ | H | CH$_2$CH$_3$ | A-3 (X$_1$=OCH$_3$) |
| SO$_2$CH$_2$CH$_3$ | H | CH$_2$CH$_3$ | A-4 (X$_1$=CH$_3$, Y$_3$=CH$_3$) |
| SO$_2$CH$_2$CH$_3$ | H | CH$_2$CH$_3$ | A-4 (X$_1$=CH$_3$, Y$_3$=OCH$_3$) |
| SO$_2$CH$_2$CH$_3$ | H | CH$_2$CH$_3$ | A-4 (X$_1$=OCH$_3$, Y$_3$=CH$_3$) |
| SO$_2$CH$_2$CH$_3$ | H | CH$_2$CH$_3$ | A-5 (X$_2$=CH$_3$, Y$_2$=OCH$_3$) |
| SO$_2$CH$_2$CH$_3$ | H | CH$_2$CH$_3$ | A-5 (X$_2$=CH$_3$, Y$_2$=SCH$_3$) |
| SO$_2$CH$_2$CH$_3$ | H | CH$_2$CH$_3$ | A-6 (X$_3$=OCH$_3$) |
| SO$_2$CH$_2$CH$_3$ | H | CH$_2$CH$_3$ | A-7 (X$_4$=OCH$_3$, Y$_4$=OCH$_3$) |
| SO$_2$CH$_2$CH$_3$ | H | CH$_2$CH$_3$ | A-7 (X$_4$=CH$_3$, Y$_4$=OCH$_3$) |
| SO$_2$CH$_2$CH$_3$ | H | CH$_2$CH$_3$ | A-7 (X$_4$=OCH$_3$, Y$_4$=CH$_3$) |
| SO$_2$CH$_2$CH$_3$ | CH$_2$CF$_3$ | H | A-2 (X$_1$=CH$_3$, Y$_1$=CH$_2$) |
| SO$_2$CH$_2$CH$_3$ | CH$_2$CF$_3$ | H | A-3 (X$_1$=CH$_3$) |
| SO$_2$CH$_2$CH$_3$ | CH$_2$CF$_3$ | H | A-3 (X$_1$=OCH$_3$) |
| SO$_2$CH$_2$CH$_3$ | CH$_2$CF$_3$ | H | A-4 (X$_1$=CH$_3$, Y$_3$=CH$_3$) |
| SO$_2$CH$_2$CH$_3$ | CH$_2$CF$_3$ | H | A-4 (X$_1$=CH$_3$, Y$_3$=OCH$_3$) |
| SO$_2$CH$_2$CH$_3$ | CH$_2$CF$_3$ | H | A-4 (X$_1$=OCH$_3$, Y$_3$=CH$_3$) |
| SO$_2$CH$_2$CH$_3$ | CH$_2$CF$_3$ | H | A-5 (X$_2$=CH$_3$, Y$_2$=OCH$_3$) |
| SO$_2$CH$_2$CH$_3$ | CH$_2$CF$_3$ | H | A-5 (X$_2$=CH$_3$, Y$_2$=SCH$_3$) |
| SO$_2$CH$_2$CH$_3$ | CH$_2$CF$_3$ | H | A-6 (X$_3$=OCH$_3$) |
| SO$_2$CH$_2$CH$_3$ | CH$_2$CF$_3$ | H | A-7 (X$_4$=OCH$_3$, Y$_4$=OCH$_3$) |
| SO$_2$CH$_2$CH$_3$ | CH$_2$CF$_3$ | H | A-7 (X$_4$=CH$_3$, Y$_4$=OCH$_3$) |
| SO$_2$CH$_2$CH$_3$ | CH$_2$CF$_3$ | H | A-7 (X$_4$=OCH$_3$, Y$_4$=CH$_3$) |
| SO$_2$CH$_2$CH$_3$ | CH$_2$CH$_2$Cl | H | A-2 (X$_1$=CH$_3$, Y$_1$=CH$_2$) |
| SO$_2$CH$_2$CH$_3$ | CH$_2$CH$_2$Cl | H | A-3 (X$_1$=CH$_3$) |
| SO$_2$CH$_2$CH$_3$ | CH$_2$CH$_2$Cl | H | A-3 (X$_1$=OCH$_3$) |
| SO$_2$CH$_2$CH$_3$ | CH$_2$CH$_2$Cl | H | A-4 (X$_1$=CH$_3$, Y$_3$=CH$_3$) |
| SO$_2$CH$_2$CH$_3$ | CH$_2$CH$_2$Cl | H | A-4 (X$_1$=CH$_3$, Y$_3$=OCH$_3$) |
| SO$_2$CH$_2$CH$_3$ | CH$_2$CH$_2$Cl | H | A-4 (X$_1$=OCH$_3$, Y$_3$=CH$_3$) |
| SO$_2$CH$_2$CH$_3$ | CH$_2$CH$_2$Cl | H | A-5 (X$_2$=CH$_3$, Y$_2$=OCH$_3$) |
| SO$_2$CH$_2$CH$_3$ | CH$_2$CH$_2$Cl | H | A-5 (X$_2$=CH$_3$, Y$_2$=SCH$_3$) |
| SO$_2$CH$_2$CH$_3$ | CH$_2$CH$_2$Cl | H | A-6 (X$_3$=OCH$_3$) |
| SO$_2$CH$_2$CH$_3$ | CH$_2$CH$_2$Cl | H | A-7 (X$_4$=OCH$_3$, Y$_4$=OCH$_3$) |
| SO$_2$CH$_2$CH$_3$ | CH$_2$CH$_2$Cl | H | A-7 (X$_4$=CH$_3$, Y$_4$=OCH$_3$) |
| SO$_2$CH$_2$CH$_3$ | CH$_2$CH$_2$Cl | H | A-7 (X$_4$=OCH$_3$, Y$_4$=CH$_3$) |
| SO$_2$CH$_2$CH$_3$ | CH$_2$CN | H | A-2 (X$_1$=CH$_3$, Y$_1$=CH$_2$) |
| SO$_2$CH$_2$CH$_3$ | CH$_2$CN | H | A-3 (X$_1$=CH$_3$) |
| SO$_2$CH$_2$CH$_3$ | CH$_2$CN | H | A-3 (X$_1$=OCH$_3$) |
| SO$_2$CH$_2$CH$_3$ | CH$_2$CN | H | A-4 (X$_1$=CH$_3$, Y$_3$=CH$_3$) |
| SO$_2$CH$_2$CH$_3$ | CH$_2$CN | H | A-4 (X$_1$=CH$_3$, Y$_3$=OCH$_3$) |
| SO$_2$CH$_2$CH$_3$ | CH$_2$CN | H | A-4 (X$_1$=OCH$_3$, Y$_3$=CH$_3$) |
| SO$_2$CH$_2$CH$_3$ | CH$_2$CN | H | A-5 (X$_2$=CH$_3$, Y$_2$=OCH$_3$) |
| SO$_2$CH$_2$CH$_3$ | CH$_2$CN | H | A-5 (X$_2$=CH$_3$, Y$_2$=SCH$_3$) |
| SO$_2$CH$_2$CH$_3$ | CH$_2$CN | H | A-6 (X$_3$=OCH$_3$) |
| SO$_2$CH$_2$CH$_3$ | CH$_2$CN | H | A-7 (X$_4$=OCH$_3$, Y$_4$=OCH$_3$) |
| SO$_2$CH$_2$CH$_3$ | CH$_2$CN | H | A-7 (X$_4$=CH$_3$, Y$_4$=OCH$_3$) |
| SO$_2$CH$_2$CH$_3$ | CH$_2$CH$_2$OCH$_3$ | H | A-2 (X$_1$=CH$_3$, Y$_1$=CH$_2$) |

TABLE II-continued

GENERAL STRUCTURE 3

| R₁ | R₂ | R₃ | A |
|---|---|---|---|
| SO$_2$CH$_2$CH$_3$ | CH$_2$CH$_2$OCH$_3$ | H | A-3 (X$_1$=CH$_3$) |
| SO$_2$CH$_2$CH$_3$ | CH$_2$CH$_2$OCH$_3$ | H | A-3 (X$_1$=OCH$_3$) |
| SO$_2$CH$_2$CH$_3$ | CH$_2$CH$_2$OCH$_3$ | H | A-4 (X$_1$=CH$_3$, Y$_3$=CH$_3$) |
| SO$_2$CH$_2$CH$_3$ | CH$_2$CH$_2$OCH$_3$ | H | A-4 (X$_1$=CH$_3$, Y$_3$=OCH$_3$) |
| SO$_2$CH$_2$CH$_3$ | CH$_2$CH$_2$OCH$_3$ | H | A-4 (X$_1$=OCH$_3$, Y$_3$=CH$_3$) |
| SO$_2$CH$_2$CH$_3$ | CH$_2$CH$_2$OCH$_3$ | H | A-5 (X$_2$=CH$_3$, Y$_2$=OCH$_3$) |
| SO$_2$CH$_2$CH$_3$ | CH$_2$CH$_2$OCH$_3$ | H | A-5 (X$_2$=CH$_3$, Y$_2$=SCH$_3$) |
| SO$_2$CH$_2$CH$_3$ | CH$_2$CH$_2$OCH$_3$ | H | A-6 (X$_3$=OCH$_3$) |
| SO$_2$CH$_2$CH$_3$ | CH$_2$CH$_2$OCH$_3$ | H | A-7 (X$_4$=OCH$_3$, Y$_4$=OCH$_3$) |
| SCH$_3$ | CH$_2$CF$_3$ | H | A-5 (X$_2$=CH$_3$, Y$_2$=OCH$_3$) |
| SCH$_3$ | CH$_2$CF$_3$ | H | A-5 (X$_2$=CH$_3$, Y$_2$=SCH$_3$) |
| SCH$_3$ | CH$_2$CF$_3$ | H | A-6 (X$_3$=OCH$_3$) |
| SCH$_3$ | CH$_2$CF$_3$ | H | A-7 (X$_4$=OCH$_3$, Y$_4$=OCH$_3$) |
| SCH$_3$ | CH$_2$CF$_3$ | H | A-7 (X$_4$=CH$_3$, Y$_4$=OCH$_3$) |
| SCH$_3$ | CH$_2$CF$_3$ | H | A-7 (X$_4$=OCH$_3$, Y$_4$=CH$_3$) |
| SCH$_3$ | CH$_2$CH$_2$Cl | H | A-2 (X$_1$=CH$_3$, Y$_1$=CH$_3$) |
| SCH$_3$ | CH$_2$CH$_2$Cl | H | A-3 (X$_1$=CH$_3$) |
| SCH$_3$ | CH$_2$CH$_2$Cl | H | A-3 (X$_1$=OCH$_3$) |
| SCH$_3$ | CH$_2$CH$_2$Cl | H | A-4 (X$_1$=CH$_3$, Y$_3$=CH$_3$) |
| SCH$_3$ | CH$_2$CH$_2$Cl | H | A-4 (X$_1$=CH$_3$, Y$_3$=OCH$_3$) |
| SCH$_3$ | CH$_2$CH$_2$Cl | H | A-4 (X$_1$=OCH$_3$, Y$_3$=CH$_3$) |
| SCH$_3$ | CH$_2$CH$_2$Cl | H | A-5 (X$_2$=CH$_3$, Y$_1$=OCH$_3$) |
| SCH$_3$ | CH$_2$CH$_2$Cl | H | A-5 (X$_2$=CH$_3$, Y$_2$=SCH$_3$) |
| SCH$_3$ | CH$_2$CH$_2$Cl | H | A-6 (X$_3$=OCH$_3$) |
| SCH$_3$ | CH$_2$CH$_2$Cl | H | A-7 (X$_4$=OCH$_3$, Y$_4$=OCH$_3$) |
| SCH$_3$ | CH$_2$CH$_2$Cl | H | A-7 (X$_4$=CH$_3$, Y$_4$=OCH$_3$) |
| SCH$_3$ | CH$_2$CH$_2$Cl | H | A-7 (X$_4$=OCH$_3$, Y$_4$=CH$_3$) |
| SCH$_3$ | CH$_2$CN | H | A-2 (X$_1$=CH$_3$, Y$_1$=CH$_2$) |
| SCH$_3$ | CH$_2$CN | H | A-3 (X$_1$=CH$_3$) |
| SCH$_3$ | CH$_2$CN | H | A-3 (X$_1$=OCH$_3$) |
| SCH$_3$ | CH$_2$CN | H | A-4 (X$_1$=CH$_3$, Y$_3$=CH$_3$) |
| SCH$_3$ | CH$_2$CN | H | A-4 (X$_1$=CH$_3$, Y$_3$=OCH$_3$) |
| SCH$_3$ | CH$_2$CN | H | A-4 (X$_1$=OCH$_3$, Y$_3$=CH$_3$) |
| SCH$_3$ | CH$_2$CN | H | A-5 (X$_2$=CH$_3$, Y$_2$=OCH$_3$) |
| SCH$_3$ | CH$_2$CN | H | A-5 (X$_2$CH$_3$, Y$_2$=SCH$_3$) |
| SCH$_3$ | CH$_2$CN | H | A-6 (X$_3$=OCH$_3$) |
| SCH$_3$ | CH$_2$CN | H | A-7 (X$_4$=OCH$_3$, Y$_4$=OCH$_3$) |
| SCH$_3$ | CH$_2$CN | H | A-7 (X$_4$=CH$_3$, Y$_4$=OCH$_3$) |
| SCH$_3$ | CH$_2$CN | H | A-7 (X$_4$=OCH$_3$, Y$_4$=CH$_3$) |
| SCH$_3$ | CH$_2$CH$_2$OCH$_3$ | H | A-2 (X$_1$=CH$_3$, Y$_1$=CH$_2$) |
| SCH$_3$ | CH$_2$CH$_2$OCH$_3$ | H | A-3 (X$_1$=CH$_3$) |
| SCH$_3$ | CH$_2$CH$_2$OCH$_3$ | H | A-3 (X$_1$=OCH$_3$) |
| SCH$_3$ | CH$_2$CH$_2$OCH$_3$ | H | A-4 (X$_1$=CH$_3$, Y$_3$=CH$_3$) |
| SCH$_3$ | CH$_2$CH$_2$OCH$_3$ | H | A-4 (X$_1$=CH$_3$, Y$_3$=OCH$_3$) |
| SCH$_3$ | CH$_2$CH$_2$OCH$_3$ | H | A-4 (X$_1$=OCH$_3$, Y$_3$=CH$_3$) |
| SCH$_3$ | CH$_2$CH$_2$OCH$_3$ | H | A-5 (X$_2$=CH$_3$, Y$_2$=OCH$_3$) |
| SCH$_3$ | CH$_2$CH$_2$OCH$_3$ | H | A-5 (X$_2$=CH$_3$, Y$_2$=SCH$_3$) |
| SCH$_3$ | CH$_2$CH$_2$OCH$_3$ | H | A-6 (X$_3$=OCH$_3$) |
| SCH$_3$ | CH$_2$CH$_2$OCH$_3$ | H | A-7 (X$_4$=OCH$_3$, Y$_4$=OCH$_3$) |
| SCH$_3$ | CH$_2$CH$_2$OCH$_3$ | H | A-7 (X$_4$=CH$_3$, Y$_4$=OCH$_3$) |
| SCH$_3$ | CH$_2$CH$_2$OCH$_3$ | H | A-7 (X$_4$=OCH$_3$, Y$_4$=CH$_3$) |
| SCH$_3$ | CH$_2$CH=CH$_2$ | H | A-2 (X$_1$=CH$_3$, Y$_1$=CH$_2$) |
| SCH$_3$ | CH$_2$CH=CH$_2$ | H | A-3 (X$_1$=CH$_3$) |
| SCH$_3$ | CH$_2$CH=CH$_2$ | H | A-3 (X$_1$=OCH$_3$) |
| SCH$_3$ | CH$_2$CH=CH$_2$ | H | A-4 (X$_1$=CH$_3$, Y$_3$=CH$_3$) |
| SCH$_3$ | CH$_2$CH=CH$_2$ | H | A-4 (X$_1$=CH$_3$, Y$_3$=OCH$_3$) |
| SCH$_3$ | CH$_2$CH=CH$_2$ | H | A-4 (X$_1$=OCH$_3$, Y$_3$=CH$_3$) |
| SCH$_3$ | CH$_2$CH=CH$_2$ | H | A-5 (X$_2$=CH$_3$, Y$_2$=OCH$_3$) |
| SCH$_3$ | CH$_2$CH=CH$_2$ | H | A-5 (X$_2$=CH$_3$, Y$_2$=SCH$_3$) |
| SCH$_3$ | CH$_2$CH=CH$_2$ | H | A-6 (X$_3$=OCH$_3$) |
| SCH$_3$ | CH$_2$CH=CH$_2$ | H | A-7 (X$_4$=OCH$_3$, Y$_4$=OCH$_3$) |
| SCH$_3$ | CH$_2$CH=CH$_2$ | H | A-7 (X$_4$=CH$_3$, Y$_4$=OCH$_3$) |
| SCH$_3$ | CH$_2$CH=CH$_2$ | H | A-7 (X$_4$=OCH$_3$, Y$_4$=CH$_3$) |
| SCH$_3$ | CH$_2$C≡CH | H | A-2 (X$_1$=CH$_3$, Y$_1$=CH$_2$) |
| SCH$_3$ | CH$_2$C≡CH | H | A-3 (X$_1$=CH$_3$) |
| SCH$_3$ | CH$_2$C≡CH | H | A-3 (X$_1$=OCH$_3$) |
| SCH$_3$ | CH$_2$C≡CH | H | A-4 (X$_1$=CH$_3$, Y$_3$=CH$_3$) |
| SCH$_3$ | CH$_2$C≡CH | H | A-4 (X$_1$=CH$_3$, Y$_3$=OCH$_3$) |
| SCH$_3$ | CH$_2$C≡CH | H | A-4 (X$_1$=OCH$_3$, Y$_3$=CH$_3$) |
| SCH$_3$ | CH$_2$C≡CH | H | A-5 (X$_2$=CH$_3$, Y$_2$=OCH$_3$) |
| SCH$_3$ | CH$_2$C≡CH | H | A-5 (X$_2$=CH$_3$, Y$_2$=SCH$_3$) |
| SCH$_3$ | CH$_2$C≡CH | H | A-6 (X$_3$=OCH$_3$) |
| SCH$_3$ | CH$_2$C≡CH | H | A-7 (X$_4$=OCH$_3$, Y$_4$=OCH$_3$) |
| SCH$_3$ | CH$_2$C≡CH | H | A-7 (X$_4$=CH$_3$, Y$_4$=OCH$_3$) |
| SCH$_3$ | CH$_2$C≡CH | H | A-7 (X$_4$=OCH$_3$, Y$_4$=CH$_3$) |
| SCH$_3$ | cyclo-C$_3$H$_7$ | H | A-2 (X$_1$=CH$_3$, Y$_1$=CH$_2$) |

-continued

| | | | |
|---|---|---|---|
| SCH$_3$ | cyclo-C$_3$H$_7$ | H | A-3 (X$_1$=CH$_3$) |
| SCH$_3$ | cyclo-C$_3$H$_7$ | H | A-3 (X$_1$=OCH$_3$) |
| SCH$_3$ | cyclo-C$_3$H$_7$ | H | A-4 (X$_1$=CH$_3$, Y$_3$=CH$_3$) |
| SCH$_3$ | cyclo-C$_3$H$_7$ | H | A-4 (X$_1$=CH$_3$, Y$_3$=OCH$_3$) |
| SCH$_3$ | cyclo-C$_3$H$_7$ | H | A-4 (X$_1$=OCH$_3$, Y$_3$=CH$_3$) |
| SCH$_3$ | cyclo-C$_3$H$_7$ | H | A-5 (X$_2$=CH$_3$, Y$_2$=OCH$_3$) |
| SCH$_3$ | cyclo-C$_3$H$_7$ | H | A-5 (X$_2$=CH$_3$, Y$_2$=SCH$_3$) |
| SCH$_3$ | cyclo-C$_3$H$_7$ | H | A-6 (X$_3$=OCH$_3$) |
| SCH$_3$ | cyclo-C$_3$H$_7$ | H | A-7 (X$_4$=OCH$_3$, Y$_4$=OCH$_3$) |
| SCH$_3$ | cyclo-C$_3$H$_7$ | H | A-7 (X$_4$=CH$_3$, Y$_4$=OCH$_3$) |
| SCH$_3$ | cyclo-C$_3$H$_7$ | H | A-7 (X$_4$=OCH$_3$, Y$_4$=CH$_3$) |
| SCH$_3$ | CH$_3$ | CH$_3$ | A-2 (X$_1$=CH$_3$, Y$_1$=CH$_2$) |
| SCH$_3$ | CH$_3$ | CH$_3$ | A-3 (X$_1$=CH$_3$) |
| SCH$_3$ | CH$_3$ | CH$_3$ | A-3 (X$_1$=OCH$_3$) |
| SCH$_3$ | CH$_3$ | CH$_3$ | A-4 (X$_1$=CH$_3$, Y$_3$=CH$_3$) |
| SCH$_3$ | CH$_3$ | CH$_3$ | A-4 (X$_1$=CH$_3$, Y$_3$=OCH$_3$) |
| SCH$_3$ | CH$_3$ | CH$_3$ | A-4 (X$_1$=OCH$_3$, Y$_3$=CH$_3$) |
| SCH$_3$ | CH$_3$ | CH$_3$ | A-5 (X$_2$=CH$_3$, Y$_2$=OCH$_3$) |
| SCH$_3$ | CH$_3$ | CH$_3$ | A-5 (X$_2$=CH$_3$, Y$_2$=SCH$_3$) |
| SCH$_3$ | CH$_3$ | CH$_3$ | A-6 (X$_3$=OCH$_3$) |
| SCH$_3$ | CH$_3$ | CH$_3$ | A-7 (X$_4$=OCH$_3$, Y$_4$=OCH$_3$) |
| SCH$_3$ | CH$_3$ | CH$_3$ | A-7 (X$_4$=CH$_3$, Y$_4$=OCH$_3$) |
| SCH$_3$ | CH$_3$ | CH$_3$ | A-7 (X$_4$=OCH$_3$, Y$_4$=CH$_3$) |
| SCH$_3$ | CH$_2$CH$_3$ | CH$_3$ | A-2 (X$_1$=CH$_3$, Y$_1$=CH$_2$) |
| SCH$_3$ | CH$_2$CH$_3$ | CH$_3$ | A-3 (X$_1$=CH$_3$) |
| SCH$_3$ | CH$_2$CH$_3$ | CH$_3$ | A-3 (X$_1$=OCH$_3$) |
| SCH$_3$ | CH$_2$CH$_3$ | CH$_3$ | A-4 (X$_1$=CH$_3$, Y$_3$=CH$_3$) |
| SCH$_3$ | CH$_2$CH$_3$ | CH$_3$ | A-4 (X$_1$=CH$_3$, Y$_3$=OCH$_3$) |
| SCH$_3$ | CH$_2$CH$_3$ | CH$_3$ | A-4 (X$_1$=OCH$_3$, Y$_3$=CH$_3$) |
| SCH$_3$ | CH$_2$CH$_3$ | CH$_3$ | A-5 (X$_2$=CH$_3$, Y$_2$=OCH$_3$) |
| SCH$_3$ | CH$_2$CH$_3$ | CH$_3$ | A-5 (X$_2$=CH$_3$, Y$_2$=SCH$_3$) |
| SCH$_3$ | CH$_2$CH$_3$ | CH$_3$ | A-6 (X$_3$=OCH$_3$) |
| SCH$_3$ | CH$_2$CH$_3$ | CH$_3$ | A-7 (X$_4$=OCH$_3$, Y$_4$=OCH$_3$) |
| SCH$_3$ | CH$_2$CH$_3$ | CH$_3$ | A-7 (X$_4$=CH$_3$, Y$_4$=OCH$_3$) |
| SCH$_3$ | CH$_2$CH$_3$ | CH$_3$ | A-7 (X$_4$=OCH$_3$, Y$_4$=CH$_3$) |
| SCH$_3$ | CH$_2$CH$_3$ | CH$_2$CH$_3$ | A-2 (X$_1$=CH$_3$, Y$_1$=CH$_2$) |
| SCH$_3$ | CH$_2$CH$_3$ | CH$_2$CH$_3$ | A-3 (X$_1$=CH$_3$) |
| SCH$_3$ | CH$_2$CH$_3$ | CH$_2$CH$_3$ | A-3 (X$_1$=OCH$_3$) |
| SCH$_3$ | CH$_2$CH$_3$ | CH$_2$CH$_3$ | A-4 (X$_1$=CH$_3$, Y$_3$=CH$_3$) |
| SCH$_3$ | CH$_2$CH$_3$ | CH$_2$CH$_3$ | A-4 (X$_1$=CH$_3$, Y$_3$=OCH$_3$) |
| SCH$_3$ | CH$_2$CH$_3$ | CH$_2$CH$_3$ | A-4 (X$_1$=OCH$_3$, Y$_3$=CH$_3$) |
| SCH$_3$ | CH$_2$CH$_3$ | CH$_2$CH$_3$ | A-5 (X$_2$=CH$_3$, Y$_2$=OCH$_3$) |
| SCH$_3$ | CH$_2$CH$_3$ | CH$_2$CH$_3$ | A-5 (X$_2$=CH$_3$, Y$_2$=SCH$_3$) |
| SCH$_3$ | CH$_2$CH$_3$ | CH$_2$CH$_3$ | A-6 (X$_3$=OCH$_3$) |
| SCH$_3$ | CH$_2$CH$_3$ | CH$_2$CH$_3$ | A-7 (X$_4$=OCH$_3$, Y$_4$=OCH$_3$) |
| SCH$_3$ | CH$_2$CH$_3$ | CH$_2$CH$_3$ | A-7 (X$_4$=CH$_3$, Y$_4$=OCH$_3$) |
| SCH$_3$ | CH$_2$CH$_3$ | CH$_2$CH$_3$ | A-7 (X$_4$=OCH$_3$, Y$_4$=CH$_3$) |
| SCH$_3$ | OCH$_3$ | CH$_3$ | A-2 (X$_1$=CH$_3$, Y$_1$=CH$_2$) |
| SCH$_3$ | OCH$_3$ | CH$_3$ | A-3 (X$_1$=CH$_3$) |
| SCH$_3$ | OCH$_3$ | CH$_3$ | A-3 (X$_1$=OCH$_3$) |
| SCH$_3$ | OCH$_3$ | CH$_3$ | A-4 (X$_1$=CH$_3$, Y$_3$=CH$_3$) |
| SCH$_3$ | OCH$_3$ | CH$_3$ | A-4 (X$_1$=CH$_3$, Y$_3$=OCH$_3$) |
| SCH$_3$ | OCH$_3$ | CH$_3$ | A-4 (X$_1$=OCH$_3$, Y$_3$=CH$_3$) |
| SCH$_3$ | OCH$_3$ | CH$_3$ | A-5 (X$_2$=CH$_3$, Y$_2$=OCH$_3$) |
| SCH$_3$ | OCH$_3$ | CH$_3$ | A-5 (X$_2$=CH$_3$, Y$_2$=SCH$_3$) |
| SCH$_3$ | OCH$_3$ | CH$_3$ | A-7 (X$_4$=OCH$_3$, Y$_4$=OCH$_3$) |
| SCH$_3$ | OCH$_3$ | CH$_3$ | A-7 (X$_4$=CH$_3$, Y$_4$=OCH$_3$) |
| SCH$_3$ | OCH$_3$ | CH$_3$ | A-7 (X$_4$=OCH$_3$, Y$_4$=CH$_3$) |
| SCH$_3$ | NHCH$_3$ | CH$_3$ | A-2 (X$_1$=CH$_3$, Y$_1$=CH$_2$) |
| SCH$_3$ | NHCH$_3$ | CH$_3$ | A-3 (X$_1$=CH$_3$) |
| SCH$_3$ | NHCH$_3$ | CH$_3$ | A-3 (X$_1$=OCH$_3$) |
| SCH$_3$ | NHCH$_3$ | CH$_3$ | A-4 (X$_1$=CH$_3$, Y$_3$=CH$_3$) |
| SCH$_3$ | NHCH$_3$ | CH$_3$ | A-4 (X$_1$=CH$_3$, Y$_3$=OCH$_3$) |
| SCH$_3$ | NHCH$_3$ | CH$_3$ | A-4 (X$_1$=OCH$_3$, Y$_3$=CH$_3$) |
| SCH$_3$ | NHCH$_3$ | CH$_3$ | A-5 (X$_2$=CH$_3$, Y$_2$=OCH$_3$) |
| SCH$_3$ | NHCH$_3$ | CH$_3$ | A-5 (X$_2$=CH$_3$, Y$_2$=SCH$_3$) |
| SCH$_3$ | NHCH$_3$ | CH$_3$ | A-6 (X$_3$=OCH$_3$) |
| SCH$_3$ | NHCH$_3$ | CH$_3$ | A-7 (X$_4$=OCH$_3$, Y$_4$=OCH$_3$) |
| SCH$_3$ | NHCH$_3$ | CH$_3$ | A-7 (X$_4$=CH$_3$, Y$_4$=OCH$_3$) |
| SCH$_3$ | NHCH$_3$ | CH$_3$ | A-7 (X$_4$=OCH$_3$, Y$_4$=CH$_3$) |
| SCH$_3$ | N(CH$_3$)$_2$ | CH$_3$ | A-2 (X$_1$=CH$_3$, Y$_1$=CH$_2$) |
| SCH$_3$ | N(CH$_3$)$_2$ | CH$_3$ | A-3 (X$_1$=CH$_3$) |
| SCH$_3$ | N(CH$_3$)$_2$ | CH$_3$ | A-3 (X$_1$=OCH$_3$) |
| SCH$_3$ | N(CH$_3$)$_2$ | CH$_3$ | A-4 (X$_1$=CH$_3$, Y$_3$=CH$_3$) |
| SCH$_3$ | N(CH$_3$)$_2$ | CH$_3$ | A-4 (X$_1$=CH$_3$, Y$_3$=OCH$_3$) |
| SCH$_3$ | N(CH$_3$)$_2$ | CH$_3$ | A-4 (X$_1$=OCH$_3$, Y$_3$=CH$_3$) |
| SCH$_3$ | N(CH$_3$)$_2$ | CH$_3$ | A-5 (X$_2$=CH$_3$, Y$_2$=OCH$_3$) |
| SCH$_3$ | N(CH$_3$)$_2$ | CH$_3$ | A-5 (X$_2$=CH$_3$, Y$_2$=SCH$_3$) |
| SCH$_3$ | N(CH$_3$)$_2$ | CH$_3$ | A-6 (X$_3$=OCH$_3$) |
| SCH$_3$ | N(CH$_3$)$_2$ | CH$_3$ | A-7 (X$_4$=OCH$_3$, Y$_4$=OCH$_3$) |
| SCH$_3$ | N(CH$_3$)$_2$ | CH$_3$ | A-7 (X$_4$=CH$_3$, Y$_4$=OCH$_3$) |
| SCH$_3$ | N(CH$_3$)$_2$ | CH$_3$ | A-7 (X$_4$=OCH$_3$, Y$_4$=CH$_3$) |

-continued

| | | | |
|---|---|---|---|
| SCH$_3$ | —CH$_2$CH$_2$CH$_2$— | | A-2 (X$_1$=CH$_3$, Y$_1$=CH$_2$) |
| SCH$_3$ | —CH$_2$CH$_2$CH$_2$— | | A-3 (X$_1$=CH$_3$) |
| SCH$_3$ | —CH$_2$CH$_2$CH$_2$— | | A-3 (X$_1$=OCH$_3$) |
| SCH$_3$ | —CH$_2$CH$_2$CH$_2$— | | A-4 (X$_1$=CH$_3$, Y$_3$=CH$_3$) |
| SCH$_3$ | —CH$_2$CH$_2$CH$_2$ | | A-4 (X$_1$=CH$_3$, Y$_3$=OCH$_3$) |
| SCH$_3$ | —CH$_2$CH$_2$CH$_2$— | | A-4 (X$_1$=OCH$_3$, Y$_3$=CH$_3$) |
| SCH$_3$ | —CH$_2$CH$_2$CH$_2$— | | A-5 (X$_2$=CH$_3$, Y$_2$=OCH$_3$) |
| SCH$_3$ | —CH$_2$CH$_2$CH$_2$— | | A-5 (X$_2$=CH$_3$, Y$_2$=SCH$_3$) |
| SCH$_3$ | —CH$_2$CH$_2$CH$_2$— | | A-6 (X$_3$=OCH$_3$) |
| SCH$_3$ | —CH$_2$CH$_2$CH$_2$— | | A-7 (X$_4$=OCH$_3$, Y$_4$=OCH$_3$) |
| SCH$_3$ | —CH$_2$CH$_2$CH$_2$— | | A-7 (X$_4$=CH$_3$, Y$_4$=OCH$_3$) |
| SCH$_3$ | —CH$_2$CH$_2$CH$_2$— | | A-7 (X$_4$=OCH$_3$, Y$_4$=CH$_3$) |
| SCH$_3$ | —CH$_2$CH$_2$OCH$_2$CH$_2$— | | A-2 (X$_1$=CH$_3$, Y$_1$=CH$_2$) |
| SCH$_3$ | —CH$_2$CH$_2$OCH$_2$CH$_2$— | | A-3 (X$_1$=CH$_3$) |
| SCH$_3$ | —CH$_2$CH$_2$OCH$_2$CH$_2$— | | A-3 (X$_1$=OCH$_3$) |
| SCH$_3$ | —CH$_2$CH$_2$OCH$_2$CH$_2$— | | A-4 (X$_1$=CH$_3$, Y$_3$=CH$_3$) |
| SCH$_3$ | —CH$_2$CH$_2$OCH$_2$CH$_2$— | | A-4 (X$_1$=CH$_3$, Y$_3$=OCH$_3$) |
| SCH$_3$ | —CH$_2$CH$_2$OCH$_2$CH$_2$— | | A-4 (X$_1$=OCH$_3$, Y$_3$=CH$_3$) |
| SCH$_3$ | —CH$_2$CH$_2$OCH$_2$CH$_2$— | | A-5 (X$_2$=CH$_3$, Y$_2$=OCH$_3$) |
| SCH$_3$ | —CH$_2$CH$_2$OCH$_2$CH$_2$— | | A-5 (X$_2$=CH$_3$, Y$_2$=SCH$_3$) |
| SCH$_3$ | —CH$_2$CH$_2$OCH$_2$CH$_2$— | | A-6 (X$_3$=OCH$_3$) |
| SCH$_3$ | —CH$_2$CH$_2$OCH$_2$CH$_2$— | | A-7 (X$_4$=OCH$_3$, Y$_4$=OCH$_3$) |
| SCH$_3$ | —CH$_2$CH$_2$OCH$_2$CH$_2$— | | A-7 (X$_4$=CH$_3$, Y$_4$=OCH$_3$) |
| SCH$_3$ | —CH$_2$CH$_2$OCH$_2$CH$_2$— | | A-7 (X$_4$=OCH$_3$, Y$_4$=CH$_3$) |
| SO$_2$CH$_2$CH$_3$ | H | H | A-2 (X$_1$=CH$_3$, Y$_1$=CH$_2$) |
| SO$_2$CH$_2$CH$_3$ | H | H | A-3 (X$_1$=CH$_3$) |
| SO$_2$CH$_2$CH$_3$ | H | H | A-3 (X$_1$=OCH$_3$) |
| SO$_2$CH$_2$CH$_3$ | H | H | A-4 (X$_1$=CH$_3$, Y$_3$=CH$_3$) |
| SO$_2$CH$_2$CH$_3$ | H | H | A-4 (X$_1$=CH$_3$, Y$_3$=OCH$_3$) |
| SO$_2$CH$_2$CH$_3$ | H | H | A-4 (X$_1$=OCH$_3$, Y$_3$=CH$_3$) |
| SO$_2$CH$_2$CH$_3$ | H | H | A-5 (X$_2$=CH$_3$, Y$_2$=OCH$_3$) |
| SO$_2$CH$_2$CH$_3$ | H | H | A-5 (X$_2$=CH$_3$, Y$_2$=SCH$_3$) |
| SO$_2$CH$_2$CH$_3$ | H | H | A-6 (X$_3$=OCH$_3$) |
| SO$_2$CH$_2$CH$_3$ | H | H | A-7 (X$_4$=OCH$_3$, Y$_4$=OCH$_3$) |
| SO$_2$CH$_2$CH$_3$ | H | H | A-7 (X$_4$=CH$_3$, Y$_4$=OCH$_3$) |
| SO$_2$CH$_2$CH$_3$ | H | H | A-7 (X$_4$=OCH$_3$, Y$_4$=CH$_3$) |
| SO$_2$CH$_2$CH$_3$ | H | CH$_3$ | A-2 (X$_1$=CH$_3$, Y$_1$=CH$_2$) |
| SO$_2$CH$_2$CH$_3$ | H | CH$_3$ | A-3 (X$_1$=CH$_3$) |
| SO$_2$CH$_2$CH$_3$ | H | CH$_3$ | A-3 (X$_1$=OCH$_3$) |
| SO$_2$CH$_2$CH$_3$ | H | CH$_3$ | A-4 (X$_1$=CH$_3$, Y$_3$=CH$_3$) |
| SO$_2$CH$_2$CH$_3$ | H | CH$_3$ | A-4 (X$_1$=CH$_3$, Y$_3$=OCH$_3$) |
| SO$_2$CH$_2$CH$_3$ | H | CH$_3$ | A-4 (X$_2$=OCH$_3$, Y$_3$=CH$_3$) |
| SO$_2$CH$_2$CH$_3$ | H | CH$_3$ | A-5 (X$_2$=CH$_3$, Y$_2$=OCH$_3$) |
| SO$_2$CH$_2$CH$_3$ | H | CH$_3$ | A-5 (X$_2$=CH$_3$, Y$_2$=SCH$_3$) |
| SO$_2$CH$_2$CH$_3$ | H | CH$_3$ | A-6 (X$_3$=OCH$_3$) |
| SO$_2$CH$_2$CH$_3$ | H | CH$_3$ | A-7 (X$_4$=OCH$_3$, Y$_4$=OCH$_3$) |
| SO$_2$CH$_2$CH$_3$ | H | CH$_3$ | A-7 (X$_4$=CH$_3$, Y$_4$=OCH$_3$) |
| SO$_2$CH$_2$CH$_3$ | H | CH$_3$ | A-7 (X$_4$=OCH$_3$, Y$_4$=CH$_3$) |
| SO$_2$CH$_2$CH$_3$ | H | CH$_2$CH$_3$ | A-2 (X$_1$=CH$_3$, Y$_1$=CH$_2$) |
| SO$_2$CH$_2$CH$_3$ | H | CH$_2$CH$_3$ | A-3 (X$_1$=CH$_3$) |
| SO$_2$CH$_2$CH$_3$ | H | CH$_2$CH$_3$ | A-3 (X$_1$=OCH$_3$) |
| SO$_2$CH$_2$CH$_3$ | H | CH$_2$CH$_3$ | A-4 (X$_1$=CH$_3$, Y$_3$=CH$_3$) |
| SO$_2$CH$_2$CH$_3$ | H | CH$_2$CH$_3$ | A-4 (X$_1$=CH$_3$, Y$_3$=OCH$_3$) |
| SO$_2$CH$_2$CH$_3$ | H | CH$_2$CH$_3$ | A-4 (X$_1$=OCH$_3$, Y$_3$=CH$_3$) |
| SO$_2$CH$_2$CH$_3$ | H | CH$_2$CH$_3$ | A-5 (X$_2$=CH$_3$, Y$_2$=OCH$_3$) |
| SO$_2$CH$_2$CH$_3$ | H | CH$_2$CH$_3$ | A-5 (X$_2$=CH$_3$, Y$_2$=SCH$_3$) |
| SO$_2$CH$_2$CH$_3$ | H | CH$_2$CH$_3$ | A-6 (X$_3$=OCH$_3$) |
| SO$_2$CH$_2$CH$_3$ | H | CH$_2$CH$_3$ | A-7 (X$_4$=OCH$_3$, Y$_4$=OCH$_3$) |
| SO$_2$CH$_2$CH$_3$ | H | CH$_2$CH$_3$ | A-7 (X$_4$=CH$_3$, Y$_4$=OCH$_3$) |
| SO$_2$CH$_2$CH$_3$ | H | CH$_2$CH$_3$ | A-7 (X$_4$=OCH$_3$, Y$_4$=CH$_3$) |
| SO$_2$CH$_2$CH$_3$ | CH$_2$CF$_3$ | H | A-2 (X$_1$=CH$_3$, Y$_1$=CH$_2$) |
| SO$_2$CH$_2$CH$_3$ | CH$_2$CF$_3$ | H | A-3 (X$_1$=CH$_3$) |
| SO$_2$CH$_2$CH$_3$ | CH$_2$CF$_3$ | H | A-3 (X$_1$=OCH$_3$) |
| SO$_2$CH$_2$CH$_3$ | CH$_2$CF$_3$ | H | A-4 (X$_1$=CH$_3$, Y$_3$=CH$_3$) |
| SO$_2$CH$_2$CH$_3$ | CH$_2$CF$_3$ | H | A-4 (X$_1$=CH$_3$, Y$_3$=OCH$_3$) |
| SO$_2$CH$_2$CH$_3$ | CH$_2$CF$_3$ | H | A-4 (X$_1$=OCH$_3$ y$_3$=CH$_3$) |
| SO$_2$CH$_2$CH$_3$ | CH$_2$CF$_3$ | H | A-5 (X$_2$=CH$_3$, Y$_2$=OCH$_3$) |
| SO$_2$CH$_2$CH$_3$ | CH$_2$CF$_3$ | H | A-5 (X$_2$=CH$_3$, Y$_2$=SCH$_3$) |
| SO$_2$CH$_2$CH$_3$ | CH$_2$CF$_3$ | H | A-6 (X$_3$=OCH$_3$) |
| SO$_2$CH$_2$CH$_3$ | CH$_2$CF$_3$ | H | A-7 (X$_4$=OCH$_3$, Y$_4$=OCH$_3$) |
| SO$_2$CH$_2$CH$_3$ | CH$_2$CF$_3$ | H | A-7 (X$_4$=CH$_3$, Y$_4$=OCH$_3$) |
| SO$_2$CH$_2$CH$_3$ | CH$_2$CF$_3$ | H | A-7 (X$_4$=OCH$_3$, Y$_4$=CH$_3$) |
| SO$_2$CH$_2$CH$_3$ | CH$_2$CH$_2$Cl | H | A-2 (X$_1$=CH$_3$, Y$_1$=CH$_2$) |
| SO$_2$CH$_2$CH$_3$ | CH$_2$CH$_2$Cl | H | A-3 (X$_1$=CH$_3$) |
| SO$_2$CH$_2$CH$_3$ | CH$_2$CH$_2$Cl | H | A-3 (X$_1$=OCH$_3$) |
| SO$_2$CH$_2$CH$_3$ | CH$_2$CH$_2$Cl | H | A-4 (X$_1$=CH$_3$, Y |
| SO$_2$CH$_2$CH$_3$ | CH$_2$CH$_2$Cl | H | A-4 (X =CH$_3$, Y$_3$=OCH$_3$) |
| SO$_2$CH$_2$CH$_3$ | CH$_2$CH$_2$Cl | H | A-4 (X$_1$=OCH$_3$, Y$_3$=CH$_3$) |
| SO$_2$CH$_2$CH$_3$ | CH$_2$CH$_2$Cl | H | A-5 (X$_2$=CH$_3$, Y$_2$=OCH$_3$) |
| SO$_2$CH$_2$CH$_3$ | CH$_2$CH$_2$Cl | H | A-5 (X$_2$=CH$_3$, Y$_2$=SCH$_3$) |
| SO$_2$CH$_2$CH$_3$ | CH$_2$CH$_2$Cl | H | A-6 (X$_3$=OCH$_3$) |
| SO$_2$CH$_2$CH$_3$ | CH$_2$CH$_2$Cl | H | A-7 (X$_4$=OCH$_3$, Y$_4$=OCH$_3$) |

-continued

| | | | |
|---|---|---|---|
| SO$_2$CH$_2$CH$_3$ | CH$_2$CH$_2$Cl | H | A-7 (X$_4$=CH$_3$, Y$_4$=OCH$_3$) |
| SO$_2$CH$_2$CH$_3$ | CH$_2$CH$_2$Cl | H | A-7 (X$_4$=OCH$_3$, Y$_4$=CH$_3$) |
| SO$_2$CH$_2$CH$_3$ | CH$_2$CN | H | A-2 (X$_1$=CH$_3$, Y$_1$=CH$_2$) |
| SO$_2$CH$_2$CH$_3$ | CH$_2$CN | H | A-3 (XI=CH$_3$) |
| SO$_2$CH$_2$CH$_3$ | CH$_2$CN | H | A-3 (X$_1$=OCH$_3$) |
| SO$_2$CH$_2$CH$_3$ | CH$_2$CN | H | A-4 (X =CH$_3$, Y$_3$=CH$_3$) |
| SO$_2$CH$_2$CH$_3$ | CH$_2$CN | H | A-4 (X$_1$=CH$_3$, Y$_3$=OCH$_3$) |
| SO$_2$CH$_2$CH$_3$ | CH$_2$CN | H | A-4 (X$_1$=OCH$_3$, Y$_3$=CH$_3$) |
| SO$_2$CH$_2$CH$_3$ | CH$_2$CN | H | A-5 (X$_2$=CH$_3$, Y$_2$=OCH$_3$) |
| SO$_2$CH$_2$CH$_3$ | CH$_2$CN | H | A-5 (X$_2$=CH$_3$, Y$_2$=SCH$_3$) |
| SO$_2$CH$_2$CH$_3$ | CH$_2$CN | H | A-6 (X$_3$=OCH$_3$) |
| SO$_2$CH$_2$CH$_3$ | CH$_2$CN | H | A-7 (X$_4$=OCH$_3$, Y$_4$=OCH$_3$) |
| SO$_2$CH$_2$CH$_3$ | CH$_2$CN | H | A-7 (X$_4$=CH$_3$, Y$_4$=OCH$_3$) |
| SO$_2$CH$_2$CH$_3$ | CH$_2$CN | H | A-7 (X$_4$=OCH$_3$, Y$_4$=CH$_3$) |
| SO$_2$CH$_2$CH$_3$ | CH$_2$CH$_2$OCH$_3$ | H | A-2 (X$_1$=CH$_3$, Y$_1$=CH$_2$) |
| SO$_2$CH$_2$CH$_3$ | CH$_2$CH$_2$OCH$_3$ | H | A-3 (X$_1$=CH$_3$) |
| SO$_2$CH$_2$CH$_3$ | CH$_2$CH$_2$OCH$_3$ | H | A-3 (X$_1$=OCH$_3$) |
| SO$_2$CH$_2$CH$_3$ | CH$_2$CH$_2$OCH$_3$ | H | A-3 (X$_1$=CH$_3$, Y$_3$=CH$_3$) |
| SO$_2$CH$_2$CH$_3$ | CH$_2$CH$_2$OCH$_3$ | H | A-4 (X$_1$=CH$_3$, y$_3$=OCH$_3$) |
| SO$_2$CH$_2$CH$_3$ | CH$_2$CH$_2$OCH$_3$ | H | A-4 (X$_1$=OCH$_3$, Y$_3$=CH$_3$) |
| SO$_2$CH$_2$CH$_3$ | CH$_2$CH$_2$OCH$_3$ | H | A-5 (X$_2$=CH$_3$, Y$_2$=OCH$_3$) |
| SO$_2$CH$_2$CH$_3$ | CH$_2$CH$_2$OCH$_3$ | H | A-5 (X$_2$=CH$_3$, Y$_2$=SCH$_3$) |
| SO$_2$CH$_2$CH$_3$ | CH$_2$CH$_2$OCH$_3$ | H | A-6 (X$_3$=OCH$_3$) |
| SO$_2$CH$_2$CH$_3$ | CH$_2$CH$_2$OCH$_3$ | H | A-7 (X$_4$=OCH$_3$, Y$_4$=OCH$_3$) |
| SO$_2$CH$_2$CH$_3$ | CH$_2$CH$_2$OCH$_3$ | H | A-7 (X$_4$=CH$_3$, Y$_4$=OCH$_3$) |
| SO$_2$CH$_2$CH$_3$ | CH$_2$CH$_2$OCH$_3$ | H | A-7 (X$_4$=OCH$_3$, Y$_4$=CH$_3$) |
| SO$_2$CH$_2$CH$_3$ | CH$_2$CH=CH$_2$ | H | A-2 (X$_1$=CH$_3$, Y$_1$=CH$_2$) |
| SO$_2$CH$_2$CH$_3$ | CH$_2$CH=CH$_2$ | H | A-3 (X$_1$=CH$_3$) |
| SO$_2$CH$_2$CH$_3$ | CH$_2$CH=CH$_2$ | H | A-3 (X$_1$=OCH$_3$) |
| SO$_2$CH$_2$CH$_3$ | CH$_2$CH=CH$_2$ | H | A-4 (X$_1$=CH$_3$, Y$_3$=CH$_3$) |
| SO$_2$CH$_2$CH$_3$ | CH$_2$CH=CH$_2$ | H | A-4 (X$_1$=CH$_3$, Y$_3$=OCH$_3$) |
| SO$_2$CH$_2$CH$_3$ | CH$_2$CH=CH$_2$ | H | A-4 (X$_3$=OCH$_3$, Y$_3$=CH) |
| SO$_2$CH$_2$CH$_3$ | CH$_2$CH=CH$_2$ | H | A-5 (X$_2$=CH$_3$, Y$_2$=OCH$_3$) |
| SO$_2$CH$_2$CH$_3$ | CH$_2$CH=CH$_2$ | H | A-5 (X$_2$=CH$_3$, Y$_2$=SCH$_3$) |
| SO$_2$CH$_2$CH$_3$ | CH$_2$CH=CH$_2$ | H | A-6 (X$_3$=OCH$_3$) |
| SO$_2$CH$_2$CH$_3$ | CH$_2$CH=CH$_2$ | H | A-7 (X$_4$=OCH$_3$, Y$_4$=OCH$_3$) |
| SO$_2$CH$_2$CH$_3$ | CH$_2$CH=CH$_2$ | H | A-7 (X$_4$=CH$_3$, Y$_4$=OCH$_3$) |
| SO$_2$CH$_2$CH$_3$ | CH$_2$CH=CH$_2$ | H | A-7 (X$_4$=OCH$_3$, Y$_4$=CH$_3$) |
| SO$_2$CH$_2$CH$_3$ | CH$_2$C≡CH | H | A-2 (X$_1$=CH$_3$, Y$_1$=CH$_2$) |
| SO$_2$CH$_2$CH$_3$ | CH$_2$C≡CH | H | A-3 (X$_1$=CH$_3$) |
| SO$_2$CH$_2$CH$_3$ | CH$_2$C≡CH | H | A-3 (X$_1$=OCH$_3$) |
| SO$_2$CH$_2$CH$_3$ | CH$_2$C≡CH | H | A-4 (X$_1$=CH$_3$, Y$_3$=CH$_3$) |
| SO$_2$CH$_2$CH$_3$ | CH$_2$C≡CH | H | A-4 (X$_1$=CH$_3$, Y$_3$=OCH$_3$) |
| SO$_2$CH$_2$CH$_3$ | CH$_2$C≡CH | H | A-4 (X$_1$=OCH$_3$, Y$_3$=CH$_3$) |
| SO$_2$CH$_2$CH$_3$ | CH$_2$C≡CH | H | A-5 (X$_2$=CH$_3$, Y$_2$=OCH$_3$) |
| SO$_2$CH$_2$CH$_3$ | CH$_2$C≡CH | H | A-5 (X$_2$=CH$_3$, Y$_2$=SCH$_3$) |
| SO$_2$CH$_2$CH$_3$ | CH$_2$C≡CH | H | A-6 (X$_3$=OCH$_3$) |
| SO$_2$CH$_2$CH$_3$ | CH$_2$C≡CH | H | A-7 (X$_4$=OCH$_3$, Y$_4$=OCH$_3$) |
| SO$_2$CH$_2$CH$_3$ | CH$_2$C≡CH | H | A-7 (X$_4$=CH$_3$, Y$_4$=OCH$_3$) |
| SO$_2$CH$_2$CH$_3$ | CH$_2$C≡CH | H | A-7 (X$_4$=OCH$_3$, Y$_4$=CH$_3$) |
| SO$_2$CH$_2$CH$_3$ | cyclo-C$_3$H$_7$ | H | A-2 (X$_1$=CH$_3$, Y$_1$=CH$_2$) |
| SO$_2$CH$_2$CH$_3$ | cyclo-C$_3$H$_7$ | H | A-3 (X$_1$=CH$_3$) |
| SO$_2$CH$_2$CH$_3$ | cyclo-C$_3$H$_7$ | H | A-3 (X$_1$=OCH$_3$) |
| SO$_2$CH$_2$CH$_3$ | cyclo-C$_3$H$_7$ | H | A-4 (X$_1$=CH$_3$, Y$_3$=CH$_3$) |
| SO$_2$CH$_2$CH$_3$ | cyclo-C$_3$H$_7$ | H | A-4 (X$_1$=CH$_3$, Y$_3$=OCH$_3$) |
| SO$_2$CH$_2$CH$_3$ | cyclo-C$_3$H$_7$ | H | A-4 (X$_1$=OCH$_3$, Y$_3$=CH$_3$) |
| SO$_2$CH$_2$CH$_3$ | cyclo-C$_3$H$_7$ | H | A-5 (X$_2$=CH$_3$, Y$_2$=OCH$_3$) |
| SO$_2$CH$_2$CH$_3$ | cyclo-C$_3$H$_7$ | H | A-5 (X$_2$=CH$_3$, Y$_2$=SCH$_3$) |
| SO$_2$CH$_2$CH$_3$ | cyclo-C$_3$H$_7$ | H | A-6 (X$_3$=OCH$_3$) |
| SO$_2$CH$_2$CH$_3$ | cyclo-C$_3$H$_7$ | H | A-7 (X$_4$=OCH$_3$, Y$_4$=OCH$_3$) |
| SO$_2$CH$_2$CH$_3$ | cyclo-C$_3$H$_7$ | H | A-7 (X$_4$=CH$_3$, Y$_4$=OCH$_3$) |
| SO$_2$CH$_2$CH$_3$ | cyclo-C$_3$H$_7$ | H | A-7 (X$_4$=OCH$_3$, Y$_4$=CH$_3$) |
| SO$_2$CH$_2$CH$_3$ | CH$_3$ | CH$_3$ | A-2 (X$_1$=CH$_3$, Y$_1$=CH$_2$) |
| SO$_2$CH$_2$CH$_3$ | CH$_3$ | CH$_3$ | A-3 (X$_1$=CH$_3$) |
| SO$_2$CH$_2$CH$_3$ | CH$_3$ | CH$_3$ | A-3 (X$_1$=OCH$_3$) |
| SO$_2$CH$_2$CH$_3$ | CH$_3$ | CH$_3$ | A-4 (X$_1$=CH$_3$, Y$_3$=CH$_3$) |
| SO$_2$CH$_2$CH$_3$ | CH$_3$ | CH$_3$ | A-4 (X$_1$=CH$_3$, Y$_3$=OCH$_3$) |
| SO$_2$CH$_2$CH$_3$ | CH$_3$ | CH$_3$ | A-4 (X$_1$=OCH$_3$, Y$_3$=CH$_3$) |
| SO$_2$CH$_2$CH$_3$ | CH$_3$ | CH$_3$ | A-5 (X$_2$=CH$_3$, Y$_2$=OCH$_3$) |
| SO$_2$CH$_2$CH$_3$ | CH$_3$ | CH$_3$ | A-5 (X$_2$=CH$_3$, Y$_2$=SCH$_3$) |
| SO$_2$CH$_2$CH$_3$ | CH$_3$ | CH$_3$ | A-6 (X$_3$=OCH$_3$) |
| SO$_2$CH$_2$CH$_3$ | CH$_3$ | CH$_3$ | A-7 (X$_4$=OCH$_3$, Y$_4$=OCH$_3$) |
| SO$_2$CH$_2$CH$_3$ | CH$_3$ | CH$_3$ | A-7 (X$_4$=CH$_3$, Y$_4$=OCH$_3$) |
| SO$_2$CH$_2$CH$_3$ | CH$_3$ | CH$_3$ | A-7 (X$_4$=OCH$_3$, Y$_4$=CH$_3$) |
| SO$_2$CH$_2$CH$_3$ | CH$_2$CH$_3$ | CH$_3$ | A-2 (X$_1$=CH$_3$, Y$_1$=CH$_2$) |
| SO$_2$CH$_2$CH$_3$ | CH$_2$CH$_3$ | CH$_3$ | A-3 (X$_1$=CH$_3$) |
| SO$_2$CH$_2$CH$_3$ | CH$_2$CH$_3$ | CH$_3$ | A-3 (X$_1$=OCH$_3$) |
| SO$_2$CH$_2$CH$_3$ | CH$_2$CH$_3$ | CH$_3$ | A-4 (X$_1$=CH$_3$, Y$_3$=CH$_3$) |

-continued

| | | | |
|---|---|---|---|
| SO₂CH₂CH₃ | CH₂CH₃ | CH₃ | A-4 (X₁=CH₃, Y₃=OCH₃) |
| SO₂CH₂CH₃ | CH₂CH₃ | CH₃ | A-4 (X₁=OCH₃, Y₃=CH₃) |
| SO₂CH₂CH₃ | CH₂CH₃ | CH₃ | A-5 (X₂=CH₃, Y₂=OCH₃) |
| SO₂CH₂CH₃ | CH₂CH₃ | CH₃ | A-5 (X₂=CH₃, Y₂=SCH₃) |
| SO₂CH₂CH₃ | CH₂CH₃ | CH₃ | A-6 (X₃=OCH₃) |
| SO₂CH₂CH₃ | CH₂CH₃ | CH₃ | A-7 (X₄=OCH₃, Y₄=OCH₃) |
| SO₂CH₂CH₃ | CH₂CH₃ | CH₃ | A-7 (X₄=CH₃, Y₄=OCH₃) |
| SO₂CH₂CH₃ | CH₂CH₃ | CH₃ | A-7 (X₄=OCH₃, Y₄=CH₃) |
| SO₂CH₂CH₃ | CH₂CH₃ | CH₂CH₃ | A-2 (X₁=CH₃, Y₁=CH₂) |
| SO₂CH₂CH₃ | CH₂CH₃ | CH₂CH₃ | A-3 (X₁=CH₃) |
| SO₂CH₂CH₃ | CH₂CH₃ | CH₂CH₃ | A-3 (X₁=OCH₃) |
| SO₂CH₂CH₃ | CH₂CH₃ | CH₂CH₃ | A-4 (X₁=CH₃, Y₃=CH₃) |
| SO₂CH₂CH₃ | CH₂CH₃ | CH₂CH₃ | A-4 (X₁=CH₃, Y₃=OCH₃) |
| SO₂CH₂CH₃ | CH₂CH₃ | CH₂CH₃ | A-4 (X₁=OCH₃, Y₃=CH₃) |
| SO₂CH₂CH₃ | CH₂CH₃ | CH₂CH₃ | A-5 (X₂=CH₃, Y₂=OCH₃) |
| SO₂CH₂CH₃ | CH₂CH₃ | CH₂CH₃ | A-5 (X₂=CH₃, Y₂=SCH₃) |
| SO₂CH₂CH₃ | CH₂CH₃ | CH₂CH₃ | A-6 (X₃=OCH₃) |
| SO₂CH₂CH₃ | CH₂CH₃ | CH₂CH₃ | A-7 (X₄=OCH₃, Y₄=OCH₃) |
| SO₂CH₂CH₃ | CH₂CH₃ | CH₂CH₃ | A-7 (X₄=CH₃, Y₄=OCH₃) |
| SO₂CH₂CH₃ | CH₂CH₃ | CH₂CH₃ | A-7 (X₄=OCH₃, Y₄=CH₃) |
| SO₂CH₂CH₃ | OCH₃ | CH₃ | A-2 (X₁=CH₃, Y₁=CH₂) |
| SO₂CH₂CH₃ | OCH₃ | CH₃ | A-3 (X₁=CH₃) |
| SO₂CH₂CH₃ | OCH₃ | CH₃ | A-3 (X₁=OCH₃) |
| SO₂CH₂CH₃ | OCH₃ | CH₃ | A-4 (X₁=CH₃, Y₃=CH₃) |
| SO₂CH₂CH₃ | OCH₃ | CH₃ | A-4 (X₁=CH₃, Y₃=OCH₃) |
| SO₂CH₂CH₃ | OCH₃ | CH₃ | A-4 (X₁=OCH₃, Y₃=CH₃) |
| SO₂CH₂CH₃ | OCH₃ | CH₃ | A-5 (X₂=CH₃, Y₂=OCH₃) |
| SO₂CH₂CH₃ | OCH₃ | CH₃ | A-5 (X₂=CH₃, Y₂=SCH₃) |
| SO₂CH₂CH₃ | OCH₃ | CH₃ | A-6 (X₃=OCH₃) |
| SO₂CH₂CH₃ | OCH₃ | CH₃ | A-7 (X₄=OCH₃, Y₄=OCH₃) |
| SO₂CH₂CH₃ | OCH₃ | CH₃ | A-7 (X₄=CH₃, Y₄=OCH₃) |
| SO₂CH₂CH₃ | OCH₃ | CH₃ | A-7 (X₄=OCH₃, Y₄=CH₃) |
| SO₂CH₂CH₃ | NHCH₃ | CH₃ | A-2 (X₁=CH₃, Y₁=CH₂) |
| SO₂CH₂CH₃ | NHCH₃ | CH₃ | A-3 (X₁=CH₃) |
| SO₂CH₂CH₃ | NHCH₃ | CH₃ | A-3 (X₁=OCH₃) |
| SO₂CH₂CH₃ | NHCH₃ | CH₃ | A-4 (X₁=CH₃, Y₃=CH₃) |
| SO₂CH₂CH₃ | NHCH₃ | CH₃ | A-4 (X₁=CH₃, Y₃=OCH₃) |
| SO₂CH₂CH₃ | NHCH₃ | CH₃ | A-4 (X₁=OCH₃, Y₃=CH₃) |
| SO₂CH₂CH₃ | NHCH₃ | CH₃ | A-5 (X₂=CH₃, Y₂=OCH₃) |
| SO₂CH₂CH₃ | NHCH₃ | CH₃ | A-5 (X₂=CH₃, Y₂=SCH₃) |
| SO₂CH₂CH₃ | NHCH₃ | CH₃ | A-6 (X₃=OCH₃) |
| SO₂CH₂CH₃ | NHCH₃ | CH₃ | A-7 (X₄=OCH₃, Y₄=OCH₃) |
| SO₂CH₂CH₃ | NHCH₃ | CH₃ | A-7 (X₄=CH₃, Y₄=OCH₃) |
| SO₂CH₂CH₃ | NHCH₃ | CH₃ | A-7 (X₄=OCH₃, Y₄=CH₃) |
| SO₂CH₂CH₃ | N(CH₃)₂ | CH₃ | A-2 (X₁=CH₃, Y₁=CH₂) |
| SO₂CH₂CH₃ | N(CH₃)₂ | CH₃ | A-3 (X₁=CH₃) |
| SO₂CH₂CH₃ | N(CH₃)₂ | CH₃ | A-3 (X₁=OCH₃) |
| SO₂CH₂CH₃ | N(CH₃)₂ | CH₃ | A-4 (X₁=CH₃, Y₃=CH₃) |
| SO₂CH₂CH₃ | N(CH₃)₂ | CH₃ | A-4 (X₁=CH₃, Y₃=OCH₃) |
| SO₂CH₂CH₃ | N(CH₃)₂ | CH₃ | A-4 (X₁=OCH₃, Y₃=CH₃) |
| SO₂CH₂CH₃ | N(CH₃)₂ | CH₃ | A-5 (X₂=CH₃, Y₂=OCH₃) |
| SO₂CH₂CH₃ | N(CH₃)₂ | CH₃ | A-5 (X₂=CH₃, Y₂=SCH₃) |
| SO₂CH₂CH₃ | N(CH₃)₂ | CH₃ | A-6 (X₃=OCH₃) |
| SO₂CH₂CH₃ | N(CH₃)₂ | CH₃ | A-7 (X₄=OCH₃, Y₄=OCH₃) |
| SO₂CH₂CH₃ | N(CH₃)₂ | CH₃ | A-7 (X₄=CH₃, Y₄=OCH₃) |
| SO₂CH₂CH₃ | N(CH₃)₂ | CH₃ | A-7 (X₄=OCH₃, Y₄=CH₃) |
| SO₂CH₂CH₃ | —CH₂CH₂CH₂— | | A-2 (X₁=CH₃, Y₁=CH₂) |
| SO₂CH₂CH₃ | —CH₂CH₂CH₂— | | A-3 (X₁=CH₃) |
| SO₂CH₂CH₃ | —CH₂CH₂CH₂— | | A-3 (X₁=OCH₃) |
| SO₂CH₂CH₃ | —CH₂CH₂CH₂— | | A-4 (X₁=CH₃, Y₃=CH₃) |
| SO₂CH₂CH₃ | —CH₂CH₂CH₂— | | A-4 (X₁=CH₃, Y₃=OCH₃) |
| SO₂CH₂CH₃ | —CH₂CH₂CH₂— | | A-4 (X₁=OCH₃, Y₃=CH₃) |
| SO₂CH₂CH₃ | —CH₂CH₂CH₂— | | A-5 (X₂=CH₃, Y₂=OCH₃) |
| SO₂CH₂CH₃ | —CH₂CH₂CH₂— | | A-5 (X₂=CH₃, Y₂=SCH₃) |
| SO₂CH₂CH₃ | —CH₂CH₂CH₂— | | A-6 (X₃=OCH₃) |
| SO₂CH₂CH₃ | —CH₂CH₂CH₂— | | A-7 (X₄=OCH₃, Y₄=OCH₃) |
| SO₂CH₂CH₃ | —CH₂CH₂CH₂— | | A-7 (X₄=CH₃, Y₄=OCH₃) |
| SO₂CH₂CH₃ | —CH₂CH₂CH₂— | | A-7 (X₄=OCH₃, Y₄=CH₃) |
| SO₂CH₂CH₃ | —CH₂CH₂OCH₂CH₂— | | A-2 (X₁=CH₃, Y₁=CH₂) |
| SO₂CH₂CH₃ | —CH₂CH₂OCH₂CH₂— | | A-3 (X₁=CH₃) |
| SO₂CH₂CH₃ | —CH₂CH₂OCH₂CH₂— | | A-3 (X₁=OCH₃) |
| SO₂CH₂CH₃ | —CH₂CH₂OCH₂CH₂— | | A-4 (X₁=CH₃, Y₃=CH₃) |
| SO₂CH₂CH₃ | —CH₂CH₂OCH₂CH₂— | | A-4 (X₁=CH₃, Y₃=OCH₃) |
| SO₂CH₂CH₃ | —CH₂CH₂OCH₂CH₂— | | A-4 (X₁=OCH₃, Y₃=CH₃) |
| SO₂CH₂CH₃ | —CH₂CH₂OCH₂CH₂— | | A-5 (X₂=CH₃, Y₂=OCH₃) |
| SO₂CH₂CH₃ | —CH₂CH₂OCH₂CH₂— | | A-5 (X₂=CH₃, Y₂=SCH₃) |
| SO₂CH₂CH₃ | —CH₂CH₂OCH₂CH₂— | | A-6 (X₃=OCH₃) |
| SO₂CH₂CH₃ | —CH₂CH₂OCH₂CH₂— | | A-7 (X₄=OCH₃, Y₄=OCH₃) |
| SO₂CH₂CH₃ | —CH₂CH₂OCH₂CH₂— | | A-7 (X₄=CH₃, Y₄=OCH₃) |
| SO₂CH₂CH₃ | —CH₂CH₂OCH₂CH₂— | | A-7 (X₄=OCH₃, Y₄=CH₃) |
| Br | CH₃ | H | A-2 (X₁=CH₃, Y₁=CH₂) |
| Br | CH₃ | H | A-3 (X₁=CH₃) |

-continued

| | | | |
|---|---|---|---|
| Br | CH$_3$ | H | A-3 (X$_1$=OCH$_3$) |
| Br | CH$_3$ | H | A-4 (X$_1$=CH$_3$, Y$_3$=CH$_3$) |
| Br | CH$_3$ | H | A-4 (X$_1$=CH$_3$, Y$_3$=OCH$_3$) |
| Br | CH$_3$ | H | A-4 (X$_1$=OCH$_3$, Y$_3$=CH$_3$) |
| Br | CH$_3$ | H | A-5 (X$_2$=CH$_3$, Y$_2$=OCH$_3$) |
| Br | CH$_3$ | H | A-5 (X$_2$=CH$_3$, Y$_2$=SCH$_3$) |
| Br | CH$_3$ | H | A-6 (X$_3$=OCH$_3$) |
| Br | CH$_3$ | H | A-7 (X$_4$=OCH$_3$, Y$_4$=OCH$_3$) |
| Br | CH$_3$ | H | A-7 (X$_4$=CH$_3$, Y$_4$=OCH$_3$) |
| Br | CH$_3$ | H | A-7 (X$_4$=OCH$_3$, Y$_4$=CH$_3$) |
| Br | CH$_3$ | CH$_3$ | A-2 (X$_1$=CH$_3$, Y$_1$=CH$_2$) |
| Br | CH$_3$ | CH$_3$ | A-3 (X$_1$=CH$_3$) |
| Br | CH$_3$ | CH$_3$ | A-3 (X$_1$=OCH$_3$) |
| Br | CH$_3$ | CH$_3$ | A-4 (X$_1$=CH$_3$, Y$_3$=CH$_3$) |
| Br | CH$_3$ | CH$_3$ | A-4 (X$_1$=CH$_3$, Y$_3$=OCH$_3$) |
| Br | CH$_3$ | CH$_3$ | A-4 (X$_1$=OCH$_3$, Y$_3$=CH$_3$) |
| Br | CH$_3$ | CH$_3$ | A-5 (X$_2$=CH$_3$, Y$_2$=OCH$_3$) |
| Br | CH$_3$ | CH$_3$ | A-5 (X$_2$=CH$_3$, Y$_2$=SCH$_3$) |
| Br | CH$_3$ | CH$_3$ | A-6 (X$_3$=OCH$_3$) |
| Br | CH$_3$ | CH$_3$ | A-7 (X$_4$=OCH$_3$, Y$_4$=OCH$_3$) |
| Br | CH$_3$ | CH$_3$ | A-7 (X$_4$=CH$_3$, Y$_4$=OCH$_3$) |
| Br | CH$_3$ | CH$_3$ | A-7 (X$_4$=OCH$_3$, Y$_4$=CH$_3$) |
| Br | CH$_2$CH=CH$_2$ | H | A-2 (X$_1$=CH$_3$, Y$_1$=CH$_2$) |
| Br | CH$_2$CH=CH$_2$ | H | A-3 (X$_1$=CH$_3$) |
| Br | CH$_2$CH=CH$_2$ | H | A-3 (X$_1$=OCH$_3$) |
| Br | CH$_2$CH=CH$_2$ | H | A-4 (X$_1$=CH$_3$, Y$_3$=CH$_3$) |
| Br | CH$_2$CH=CH$_2$ | H | A-4 (X$_1$=CH$_3$, Y$_3$=OCH$_3$) |
| Br | CH$_2$CH=CH$_2$ | H | A-4 (X$_1$=OCH$_3$, Y$_3$=CH$_3$) |
| Br | CH$_2$CH=CH$_2$ | H | A-5 (X$_2$=CH$_3$, Y$_2$=OCH$_3$) |
| Br | CH$_2$CH=CH$_2$ | H | A-5 (X$_2$=CH$_3$, Y$_2$=SCH$_3$) |
| Br | CH$_2$CH=CH$_2$ | H | A-6 (X$_3$=OCH$_3$) |
| Br | CH$_2$CH=CH$_2$ | H | A-7 (X$_4$=OCH$_3$, Y$_4$=OCH$_3$) |
| Br | CH$_2$CH=CH$_2$ | H | A-7 (X$_4$=CH$_3$, Y$_4$=OCH$_3$) |
| Br | CH$_2$CH=CH$_2$ | H | A-7 (X$_4$=OCH$_3$, Y$_4$=CH$_3$) |
| CH$_2$CH$_3$ | CH$_3$ | H | A-2 (X$_1$=CH$_3$, Y$_1$=CH$_2$) |
| CH$_2$CH$_3$ | CH$_3$ | H | A-3 (X$_1$=CH$_3$) |
| CH$_2$CH$_3$ | CH$_3$ | H | A-3 (X$_1$=OCH$_3$) |
| CH$_2$CH$_3$ | CH$_3$ | H | A-4 (X$_1$=CH$_3$, Y$_3$=CH$_3$) |
| CH$_2$CH$_3$ | CH$_3$ | H | A-4 (X$_1$=CH$_3$, Y$_3$=OCH$_3$) |
| CH$_2$CH$_3$ | CH$_3$ | H | A-4 (X$_1$=OCH$_3$, Y$_3$=CH$_3$) |
| CH$_2$CH$_3$ | CH$_3$ | H | A-5 (X$_2$=CH$_3$, Y$_2$=OCH$_3$) |
| CH$_2$CH$_3$ | CH$_3$ | H | A-5 (X$_2$=CH$_3$, Y$_2$=SCH$_3$) |
| CH$_2$CH$_3$ | CH$_3$ | H | A-6 (X$_3$=OCH$_3$) |
| CH$_2$CH$_3$ | CH$_3$ | H | A-7 (X$_4$=OCH$_3$, Y$_4$=OCH$_3$) |
| CH$_2$CH$_3$ | CH$_3$ | H | A-7 (X$_4$=CH$_3$, Y$_4$=OCH$_3$) |
| CH$_2$CH$_3$ | CH$_3$ | H | A-7 (X$_4$=OCH$_3$, Y$_4$=CH$_3$) |
| CH$_2$CH$_3$ | CH$_3$ | CH$_3$ | A-2 (X$_1$=CH$_3$, Y$_1$=CH$_2$) |
| CH$_2$CH$_3$ | CH$_3$ | CH$_3$ | A-3 (X$_1$=CH$_3$) |
| CH$_2$CH$_3$ | CH$_3$ | CH$_3$ | A-3 (X$_1$=OCH$_3$) |
| CH$_2$CH$_3$ | CH$_3$ | CH$_3$ | A-4 (X$_1$=CH$_3$, Y$_3$=CH$_3$) |
| CH$_2$CH$_3$ | CH$_3$ | CH$_3$ | A-4 (X$_1$=CH$_3$, Y$_3$=OCH$_3$) |
| CH$_2$CH$_3$ | CH$_3$ | CH$_3$ | A-4 (X$_1$=OCH$_3$, Y$_3$=CH$_3$) |
| CH$_2$CH$_3$ | CH$_3$ | CH$_3$ | A-5 (X$_2$=CH$_3$, Y$_2$=OCH$_3$) |
| CH$_2$CH$_3$ | CH$_3$ | CH$_3$ | A-5 (X$_2$=CH$_3$, Y$_2$=SCH$_3$) |
| CH$_2$CH$_3$ | CH$_3$ | CH$_3$ | A-6 (X$_3$=OCH$_3$) |
| CH$_2$CH$_3$ | CH$_3$ | CH$_3$ | A-7 (X$_4$=OCH$_3$, Y$_4$=OCH$_3$) |
| CH$_2$CH$_3$ | CH$_3$ | CH$_3$ | A-7 (X$_4$=CH$_3$, Y$_4$=OCH$_3$) |
| CH$_2$CH$_3$ | CH$_3$ | CH$_3$ | A-7 (X$_4$=OCH$_3$, Y$_4$=CH$_3$) |
| CH$_2$CH$_3$ | CH$_2$CH=CH$_2$ | H | A-2 (X$_1$=CH$_3$, Y$_1$=CH$_2$) |
| CH$_2$CH$_3$ | CH$_2$CH=CH$_2$ | H | A-3 (X$_1$=CH$_3$) |
| CH$_2$CH$_3$ | CH$_2$CH=CH$_2$ | H | A-3 (X$_1$=OCH$_3$) |
| CH$_2$CH$_3$ | CH$_2$CH=CH$_2$ | H | A-4 (X$_1$=CH$_3$, Y$_3$=CH$_3$) |
| CH$_2$CH$_3$ | CH$_2$CH=CH$_2$ | H | A-4 (X$_1$=CH$_3$, Y$_3$=OCH$_3$) |
| CH$_2$CH$_3$ | CH$_2$CH=CH$_2$ | H | A-4 (X$_1$=OCH$_3$, Y$_3$=CH$_3$) |
| CH$_2$CH$_3$ | CH$_2$CH=CH$_2$ | H | A-5 (X$_2$=CH$_3$, Y$_2$=OCH$_3$) |
| CH$_2$CH$_3$ | CH$_2$CH=CH$_2$ | H | A-5 (X$_2$=CH$_3$, Y$_2$=SCH$_3$) |
| CH$_2$CH$_3$ | CH$_2$CH=CH$_2$ | H | A-6 (X$_3$=OCH$_3$) |
| CH$_2$CH$_3$ | CH$_2$CH=CH$_2$ | H | A-7 (X$_4$=OCH$_3$, Y$_4$=OCH$_3$) |
| CH$_2$CH$_3$ | CH$_2$CH=CH$_2$ | H | A-7 (X$_4$=CH$_3$, Y$_4$=OCH$_3$) |
| CH$_2$CH$_3$ | CH$_2$CH=CH$_2$ | H | A-7 (X$_4$=OCH$_3$, Y$_4$=CH$_3$) |
| CF$_3$ | CH$_3$ | H | A-2 (X$_1$=CH$_3$, Y$_1$=CH$_2$) |
| CF$_3$ | CH$_3$ | H | A-3 (X$_1$=CH$_3$) |
| CF$_3$ | CH$_3$ | H | A-3 (X$_1$=OCH$_3$) |
| CF$_3$ | CH$_3$ | H | A-4 (X$_1$=CH$_3$, Y$_3$=CH$_3$) |
| CF$_3$ | CH$_3$ | H | A-4 (X$_1$=CH$_3$, Y$_3$=OCH$_3$) |
| CF$_3$ | CH$_3$ | H | A-4 (X$_1$=OCH$_3$, Y$_3$=CH$_3$) |
| CF$_3$ | CH$_3$ | H | A-5 (X$_2$=CH$_3$, Y$_2$=OCH$_3$) |
| CF$_3$ | CH$_3$ | H | A-5 (X$_2$=CH$_3$, Y$_2$=SCH$_3$) |
| CF$_3$ | CH$_3$ | H | A-6 (X$_3$=OCH$_3$) |
| CF$_3$ | CH$_3$ | H | A-7 (X$_4$=OCH$_3$, Y$_4$=OCH$_3$) |
| CF$_3$ | CH$_3$ | H | A-7 (X$_4$=CH$_3$, Y$_4$=OCH$_3$) |
| CF$_3$ | CH$_3$ | H | A-7 (X$_4$=OCH$_3$, Y$_4$=CH$_3$) |

-continued

| | | | |
|---|---|---|---|
| CF$_3$ | CH$_3$ | CH$_3$ | A-2 (X$_1$=CH$_3$, Y$_1$=CH$_2$) |
| CF$_3$ | CH$_3$ | CH$_3$ | A-3 (X$_1$=CH$_3$) |
| CF$_3$ | CH$_3$ | CH$_3$ | A-3 (X$_1$=OCH$_3$) |
| CF$_3$ | CH$_3$ | CH$_3$ | A-4 (X$_1$=CH$_3$, Y$_3$=CH$_3$) |
| CF$_3$ | CH$_3$ | CH$_3$ | A-4 (X$_1$=CH$_3$, Y$_3$=OCH$_3$) |
| CF$_3$ | CH$_3$ | CH$_3$ | A-4 (X$_1$=OCH$_3$, Y$_3$=CH$_3$) |
| CF$_3$ | CH$_3$ | CH$_3$ | A-5 (X$_2$=CH$_3$, Y$_2$=OCH$_3$) |
| CF$_3$ | CH$_3$ | CH$_3$ | A-5 (X$_2$=CH$_3$, Y$_2$=SCH$_3$) |
| CF$_3$ | CH$_3$ | CH$_3$ | A-6 (X$_3$=OCH$_3$) |
| CF$_3$ | CH$_3$ | CH$_3$ | A-7 (X$_4$=OCH$_3$, Y$_4$=OCH$_3$) |
| CF$_3$ | CH$_3$ | CH$_3$ | A-7 (X$_4$=CH$_3$, Y$_4$=OCH$_3$) |
| CF$_3$ | CH$_3$ | CH$_3$ | A-7 (X$_4$=OCH$_3$, Y$_4$=CH$_3$) |
| CF$_3$ | CH$_2$CH=CH$_2$ | H | A-2 (X$_1$=CH$_3$, Y$_1$=CH$_2$) |
| CF$_3$ | CH$_2$CH=CH$_2$ | H | A-3 (X$_1$=CH$_3$) |
| CF$_3$ | CH$_2$CH=CH$_2$ | H | A-3 (X$_1$=OCH$_3$) |
| CF$_3$ | CH$_2$CH=CH$_2$ | H | A-4 (X$_1$=CH$_3$, Y$_3$=CH$_3$) |
| CF$_3$ | CH$_2$CH=CH$_2$ | H | A-4 (X$_1$=CH$_3$, Y$_3$=OCH$_3$) |
| CF$_3$ | CH$_2$CH=CH$_2$ | H | A-4 (X$_1$=OCH$_3$, Y$_3$=CH$_3$) |
| CF$_3$ | CH$_2$CH=CH$_2$ | H | A-5 (X$_2$=CH$_3$, Y$_2$=OCH$_3$) |
| CF$_3$ | CH$_2$CH=CH$_2$ | H | A-5 (X$_2$=CH$_3$, Y$_2$=SCH$_3$) |
| CF$_3$ | CH$_2$CH=CH$_2$ | H | A-6 (X$_3$=OCH$_3$) |
| CF$_3$ | CH$_2$CH=CH$_2$ | H | A-7 (X$_4$=OCH$_3$, Y$_4$=OCH$_3$) |
| CF$_3$ | CH$_2$CH=CH$_2$ | H | A-7 (X$_4$=CH$_3$, Y$_4$=OCH$_3$) |
| CF$_3$ | CH$_2$CH=CH$_2$ | H | A-7 (X$_4$=OCH$_3$, Y$_4$=CH$_3$) |
| OCH$_3$ | CH$_3$ | H | A-2 (X$_1$=CH$_3$, Y$_1$=CH$_2$) |
| OCH$_3$ | CH$_3$ | H | A-3 (X$_1$=CH$_3$) |
| OCH$_3$ | CH$_3$ | H | A-3 (X$_1$=OCH$_3$) |
| OCH$_3$ | CH$_3$ | H | A-4 (X$_1$=CH$_3$, Y$_3$=CH$_3$) |
| OCH$_3$ | CH$_3$ | H | A-4 (X$_1$=CH$_3$, Y$_3$=OCH$_3$) |
| OCH$_3$ | CH$_3$ | H | A-4 (X$_1$=OCH$_3$, Y$_3$=CH$_3$) |
| OCH$_3$ | CH$_3$ | H | A-5 (X$_2$=CH$_3$, Y$_2$=OCH$_3$) |
| OCH$_3$ | CH$_3$ | H | A-5 (X$_2$=CH$_3$, Y$_2$=SCH$_3$) |
| OCH$_3$ | CH$_3$ | H | A-6 (X$_3$=OCH$_3$) |
| OCH$_3$ | CH$_3$ | H | A-7 (X$_4$=OCH$_3$, Y$_4$=OCH$_3$) |
| OCH$_3$ | CH$_3$ | H | A-7 (X$_4$=CH$_3$, Y$_4$=OCH$_3$) |
| OCH$_3$ | CH$_3$ | H | A-7 (X$_4$=OCH$_3$, Y$_4$=CH$_3$) |
| OCH$_3$ | CH$_3$ | CH$_3$ | A-2 (X$_1$=CH$_3$, Y$_1$=CH$_2$) |
| OCH$_3$ | CH$_3$ | CH$_3$ | A-3 (X$_1$=CH$_3$) |
| OCH$_3$ | CH$_3$ | CH$_3$ | A-3 (X$_1$=OCH$_3$) |
| OCH$_3$ | CH$_3$ | CH$_3$ | A-4 (X$_1$=CH$_3$, Y$_3$=CH$_3$) |
| OCH$_3$ | CH$_3$ | CH$_3$ | A-4 (X$_1$=CH$_3$, Y$_3$=OCH$_3$) |
| OCH$_3$ | CH$_3$ | CH$_3$ | A-4 (X$_1$=OCH$_3$, Y$_3$=CH$_3$) |
| OCH$_3$ | CH$_3$ | CH$_3$ | A-5 (X$_2$=CH$_3$, Y$_2$=OCH$_3$) |
| OCH$_3$ | CH$_3$ | CH$_3$ | A-5 (X$_2$=CH$_3$, Y$_2$=SCH$_3$) |
| OCH$_3$ | CH$_3$ | CH$_3$ | A-6 (X$_3$=OCH$_3$) |
| OCH$_3$ | CH$_3$ | CH$_3$ | A-7 (X$_4$=OCH$_3$, Y$_4$=OCH$_3$) |
| OCH$_3$ | CH$_3$ | CH$_3$ | A-7 (X$_4$=CH$_3$, Y$_4$=OCH$_3$) |
| OCH$_3$ | CH$_3$ | CH$_3$ | A-7 (X$_4$=OCH$_3$, Y$_4$=CH$_3$) |
| OCH$_3$ | CH$_2$CH=CH$_2$ | H | A-2 (X$_1$=CH$_3$, Y$_1$=CH$_2$) |
| OCH$_3$ | CH$_2$CH=CH$_2$ | H | A-3 (X$_1$=CH$_3$) |
| OCH$_3$ | CH$_2$CH=CH$_2$ | H | A-3 (X$_1$=OCH$_3$) |
| OCH$_3$ | CH$_2$CH=CH$_2$ | H | A-4 (X$_1$=CH$_3$, Y$_3$=CH$_3$) |
| OCH$_3$ | CH$_2$CH=CH$_2$ | H | A-4 (X$_1$=CH$_3$, Y$_3$=OCH$_3$) |
| OCH$_3$ | CH$_2$CH=CH$_2$ | H | A-4 (X$_1$=OCH$_3$, Y$_3$=CH$_3$) |
| OCH$_3$ | CH$_2$CH=CH$_2$ | H | A-5 (X$_2$=CH$_3$, Y$_2$=OCH$_3$) |
| OCH$_3$ | CH$_2$CH=CH$_2$ | H | A-5 (X$_2$=CH$_3$, Y$_2$=SCH$_3$) |
| OCH$_3$ | CH$_2$CH=CH$_2$ | H | A-6 (X$_3$=OCH$_3$) |
| OCH$_3$ | CH$_2$CH=CH$_2$ | H | A-7 (X$_4$=OCH$_3$, Y$_4$=OCH$_3$) |
| OCH$_3$ | CH$_2$CH=CH$_2$ | H | A-7 (X$_4$=CH$_3$, Y$_4$=OCH$_3$) |
| OCH$_3$ | CH$_2$CH=CH$_2$ | H | A-7 (X$_4$=OCH$_3$, Y$_4$=CH$_3$) |
| OCF$_2$H | CH$_3$ | H | A-2 (X$_1$=CH$_3$, Y$_1$=CH$_2$) |
| OCF$_2$H | CH$_3$ | H | A-3 (X$_1$=CH$_3$) |
| OCF$_2$H | CH$_3$ | H | A-3 (X$_1$=OCH$_3$) |
| OCF$_2$H | CH$_3$ | H | A-4 (X$_1$=CH$_3$, Y$_3$=CH$_3$) |
| OCF$_2$H | CH$_3$ | H | A-4 (X$_1$=CH$_3$, Y$_3$=OCH$_3$) |
| OCF$_2$H | CH$_3$ | H | A-4 (X$_1$=OCH$_3$, Y$_3$=CH$_3$) |
| OCF$_2$H | CH$_3$ | H | A-5 (X$_2$=CH$_3$, Y$_2$=OCH$_3$) |
| OCF$_2$H | CH$_3$ | H | A-5 (X$_2$=CH$_3$, Y$_2$=SCH$_3$) |
| OCF$_2$H | CH$_3$ | H | A-6 (X$_3$=OCH$_3$) |
| OCF$_2$H | CH$_3$ | H | A-7 (X$_4$=OCH$_3$, Y$_4$=OCH$_3$) |
| OCF$_2$H | CH$_3$ | H | A-7 (X$_4$=CH$_3$, Y$_4$=OCH$_3$) |
| OCF$_2$H | CH$_3$ | H | A-7 (X$_4$=OCH$_3$, Y$_4$=CH$_3$) |
| OCF$_2$H | CH$_3$ | CH$_3$ | A-2 (X$_1$=CH$_3$, Y$_1$=CH$_2$) |
| OCF$_2$H | CH$_3$ | CH$_3$ | A-3 (X$_1$=CH$_3$) |
| OCF$_2$H | CH$_3$ | CH$_3$ | A-3 (X$_1$=OCH$_3$) |
| OCF$_2$H | CH$_3$ | CH$_3$ | A-4 (X$_1$=CH$_3$, Y$_3$=CH$_3$) |
| OCF$_2$H | CH$_3$ | CH$_3$ | A-4 (X$_1$=CH$_3$, Y$_3$=OCH$_3$) |
| OCF$_2$H | CH$_3$ | CH$_3$ | A-4 (X$_1$=OCH$_3$, Y$_3$=CH$_3$) |
| OCF$_2$H | CH$_3$ | CH$_3$ | A-5 (X$_2$=CH$_3$, Y$_2$=OCH$_3$) |
| OCF$_2$H | CH$_3$ | CH$_3$ | A-5 (X$_2$=CH$_3$, Y$_2$=SCH$_3$) |
| OCF$_2$H | CH$_3$ | CH$_3$ | A-6 (X$_3$=OCH$_3$) |
| OCF$_2$H | CH$_3$ | CH$_3$ | A-7 (X$_4$=OCH$_3$, Y$_4$=OCH$_3$) |

-continued

| | | | |
|---|---|---|---|
| OCF$_2$H | CH$_3$ | CH$_3$ | A-7 (X$_4$=CH$_3$, Y$_4$=OCH$_3$) |
| OCF$_2$H | CH$_3$ | CH$_3$ | A-7 (X$_4$=OCH$_3$, Y$_4$=CH$_3$) |
| OCF$_2$H | CH$_2$CH=CH$_2$ | H | A-2 (X$_1$=CH$_3$, Y$_1$=CH$_2$) |
| OCF$_2$H | CH$_2$CH=CH$_2$ | H | A-3 (X$_1$=CH$_3$) |
| OCF$_2$H | CH$_2$CH=CH$_2$ | H | A-3 (X$_1$=OCH$_3$) |
| OCF$_2$H | CH$_2$CH=CH$_2$ | H | A-4 (X$_1$=CH$_3$, Y$_3$=CH$_3$) |
| OCF$_2$H | CH$_2$CH=CH$_2$ | H | A-4 (X$_1$=CH$_3$, Y$_3$=OCH$_3$) |
| OCF$_2$H | CH$_2$CH=CH$_2$ | H | A-4 (X$_1$=OCH$_3$, Y$_3$=CH$_3$) |
| OCF$_2$H | CH$_2$CH=CH$_2$ | H | A-5 (X$_2$=CH$_3$, Y$_2$=OCH$_3$) |
| OCF$_2$H | CH$_2$CH=CH$_2$ | H | A-5 (X$_2$=CH$_3$, Y$_2$=SCH$_3$) |
| OCF$_2$H | CH$_2$CH=CH$_2$ | H | A-6 (X$_3$=OCH$_3$) |
| OCF$_2$H | CH$_2$CH=CH$_2$ | H | A-7 (X$_4$=OCH$_3$, Y$_4$=OCH$_3$) |
| OCF$_2$H | CH$_2$CH=CH$_2$ | H | A-7 (X$_4$=CH$_3$, Y$_4$=OCH$_3$) |
| OCF$_2$H | CH$_2$CH=CH$_2$ | H | A-7 (X$_4$=OCH$_3$, Y$_4$=CH$_3$) |
| SCF$_2$H | CH$_3$ | H | A-2 (X$_1$=CH$_3$, Y$_1$=CH$_2$) |
| SCF$_2$H | CH$_3$ | H | A-3 (X$_1$=CH$_3$) |
| SCF$_2$H | CH$_3$ | H | A-3 (X$_1$=OCH$_3$) |
| SCF$_2$H | CH$_3$ | H | A-4 (X$_1$=CH$_3$, Y$_3$=CH$_3$) |
| SCF$_2$H | CH$_3$ | H | A-4 (X$_1$=CH$_3$, Y$_3$=OCH$_3$) |
| SCF$_2$H | CH$_3$ | H | A-4 (X$_1$=OCH$_3$, Y$_3$=CH$_3$) |
| SCF$_2$H | CH$_3$ | H | A-5 (X$_2$=CH$_3$, Y$_2$=OCH$_3$) |
| SCF$_2$H | CH$_3$ | H | A-5 (X$_2$=CH$_3$, Y$_2$=SCH$_3$) |
| SCF$_2$H | CH$_3$ | H | A-6 (X$_3$=OCH$_3$) |
| SCF$_2$H | CH$_3$ | H | A-7 (X$_4$=OCH$_3$, Y$_4$=OCH$_3$) |
| SCF$_2$H | CH$_3$ | H | A-7 (X$_4$=CH$_3$, Y$_4$=OCH$_3$) |
| SCF$_2$H | CH$_3$ | H | A-7 (X$_4$=OCH$_3$, Y$_4$=CH$_3$) |
| SCF$_2$H | CH$_3$ | CH$_3$ | A-2 (X$_1$=CH$_3$, Y$_1$=CH$_2$) |
| SCF$_2$H | CH$_3$ | CH$_3$ | A-3 (X$_1$=CH$_3$) |
| SCF$_2$H | CH$_3$ | CH$_3$ | A-3 (X$_1$=OCH$_3$) |
| SCF$_2$H | CH$_3$ | CH$_3$ | A-4 (X$_1$=CH$_3$, Y$_3$=CH$_3$) |
| SCF$_2$H | CH$_3$ | CH$_3$ | A-4 (X$_1$=CH$_3$, Y$_3$=OCH$_3$) |
| SCF$_2$H | CH$_3$ | CH$_3$ | A-4 (X$_1$=OCH$_3$, Y$_3$=CH$_3$) |
| SCF$_2$H | CH$_3$ | CH$_3$ | A-5 (X$_2$=CH$_3$, Y$_2$=OCH$_3$) |
| SCF$_2$H | CH$_3$ | CH$_3$ | A-5 (X$_2$=CH$_3$, Y$_2$=SCH$_3$) |
| SCF$_2$H | CH$_3$ | CH$_3$ | A-6 (X$_3$=OCH$_3$) |
| SCF$_2$H | CH$_3$ | CH$_3$ | A-7 (X$_4$=OCH$_3$, Y$_4$=OCH$_3$) |
| SCF$_2$H | CH$_3$ | CH$_3$ | A-7 (X$_4$=CH$_3$, Y$_4$=OCH$_3$) |
| SCF$_2$H | CH$_3$ | CH$_3$ | A-7 (X$_4$=OCH$_3$, Y$_4$=CH$_3$) |
| SCF$_2$H | CH$_2$CH=CH$_2$ | H | A-2 (X$_1$=CH$_3$, Y$_1$=CH$_2$) |
| SCF$_2$H | CH$_2$CH=CH$_2$ | H | A-3 (X$_1$=CH$_3$) |
| SCF$_2$H | CH$_2$CH=CH$_2$ | H | A-3 (X$_1$=OCH$_3$) |
| SCF$_2$H | CH$_2$CH=CH$_2$ | H | A-4 (X$_1$=CH$_3$, Y$_3$=CH$_3$) |
| SCF$_2$H | CH$_2$CH=CH$_2$ | H | A-4 (X$_1$=CH$_3$, Y$_3$=OCH$_3$) |
| SCF$_2$H | CH$_2$CH=CH$_2$ | H | A-4 (X$_1$=OCH$_3$, Y$_3$=CH$_3$) |
| SCF$_2$H | CH$_2$CH=CH$_2$ | H | A-5 (X$_2$=CH$_3$, Y$_2$=OCH$_3$) |
| SCF$_2$H | CH$_2$CH=CH$_2$ | H | A-5 (X$_2$=CH$_3$, Y$_2$=SCH$_3$) |
| SCF$_2$H | CH$_2$CH=CH$_2$ | H | A-6 (X$_3$=OCH$_3$) |
| SCF$_2$H | CH$_2$CH=CH$_2$ | H | A-7 (X$_4$=OCH$_3$, Y$_4$=OCH$_3$) |
| SCF$_2$H | CH$_2$CH=CH$_2$ | H | A-7 (X$_4$=CH$_3$, Y$_4$=OCH$_3$) |
| SCF$_2$H | CH$_2$CH=CH$_2$ | H | A-7 (X$_4$=OCH$_3$, Y$_4$=CH$_3$) |
| SCF$_2$H | CH$_3$ | H | A-2 (X$_1$=CH$_3$, Y$_1$=CH$_2$) |
| SCF$_2$H | CH$_3$ | H | A-3 (X$_1$=CH$_3$) |
| SCF$_2$H | CH$_3$ | H | A-3 (X$_1$=OCH$_3$) |
| SCF$_2$H | CH$_3$ | H | A-4 (X$_1$=CH$_3$, Y$_3$=CH$_3$) |
| SCF$_2$H | CH$_3$ | H | A-4 (X$_1$=CH$_3$, Y$_3$=OCH$_3$) |
| SCF$_2$H | CH$_3$ | H | A-4 (X$_1$=OCH$_3$, Y$_3$=CH$_3$) |
| SCF$_2$H | CH$_3$ | H | A-5 (X$_2$=CH$_3$, Y$_2$=OCH$_3$) |
| SCF$_2$H | CH$_3$ | H | A-5 (X$_2$=CH$_3$, Y$_2$=SCH$_3$) |
| SCF$_2$H | CH$_3$ | H | A-6 (X$_3$=OCH$_3$) |
| SCF$_2$H | CH$_3$ | H | A-7 (X$_4$=OCH$_3$, Y$_4$=OCH$_3$) |
| SCF$_2$H | CH$_3$ | H | A-7 (X$_4$=CH$_3$, Y$_4$=OCH$_3$) |
| SCF$_2$H | CH$_3$ | H | A-7 (X$_4$=OCH$_3$, Y$_4$=CH$_3$) |
| SCF$_2$H | CH$_3$ | CH$_3$ | A-2 (X$_1$=CH$_3$, Y$_1$=CH$_2$) |
| SCF$_2$H | CH$_3$ | CH$_3$ | A-3 (X$_1$=CH$_3$) |
| SCF$_2$H | CH$_3$ | CH$_3$ | A-3 (X$_1$=OCH$_3$) |
| SCF$_2$H | CH$_3$ | CH$_3$ | A-4 (X$_1$=CH$_3$, Y$_3$=CH$_3$) |
| SCF$_2$H | CH$_3$ | CH$_3$ | A-4 (X$_1$=CH$_3$, Y$_3$=OCH$_3$) |
| SCF$_2$H | CH$_3$ | CH$_3$ | A-4 (X$_1$=OCH$_3$, Y$_3$=CH$_3$) |
| SCF$_2$H | CH$_3$ | CH$_3$ | A-5 (X$_2$=CH$_3$, Y$_2$=OCH$_3$) |
| SCF$_2$H | CH$_3$ | CH$_3$ | A-5 (X$_2$=CH$_3$, Y$_2$=SCH$_3$) |
| SCF$_2$H | CH$_3$ | CH$_3$ | A-6 (X$_3$=OCH$_3$) |
| SCF$_2$H | CH$_3$ | CH$_3$ | A-7 (X$_4$=OCH$_3$, Y$_4$=OCH$_3$) |
| SCF$_2$H | CH$_3$ | CH$_3$ | A-7 (X$_4$=CH$_3$, Y$_4$=OCH$_3$) |
| SCF$_2$H | CH$_3$ | CH$_3$ | A-7 (X$_4$=OCH$_3$, Y$_4$=CH$_3$) |
| SCF$_2$H | CH$_2$CH=CH$_2$ | H | A-2 (X$_1$=CH$_3$, Y$_1$=CH$_2$) |
| SCF$_2$H | CH$_2$CH=CH$_2$ | H | A-3 (X$_1$=CH$_3$) |
| SCF$_2$H | CH$_2$CH=CH$_2$ | H | A-3 (X$_1$=OCH$_3$) |
| SCF$_2$H | CH$_2$CH=CH$_2$ | H | A-4 (X$_1$=CH$_3$, Y$_3$=CH$_3$) |
| SCF$_2$H | CH$_2$CH=CH$_2$ | H | A-4 (X$_1$=CH$_3$, Y$_3$=OCH$_3$) |
| SCF$_2$H | CH$_2$CH=CH$_2$ | H | A-4 (X$_1$=OCH$_3$, Y$_3$=CH$_3$) |
| SCF$_2$H | CH$_2$CH=CH$_2$ | H | A-5 (X$_2$=CH$_3$, Y$_2$=OCH$_3$) |
| SCF$_2$H | CH$_2$CH=CH$_2$ | H | A-5 (X$_2$=CH$_3$, Y$_2$=SCH$_3$) |

-continued

| | | | |
|---|---|---|---|
| SCF$_2$H | CH$_2$CH=CH$_2$ | H | A-6 (X$_3$=OCH$_3$) |
| SCF$_2$H | CH$_2$CH=CH$_2$ | H | A-7 (X$_4$=OCH$_3$, Y$_4$=OCH$_3$) |
| SCF$_2$H | CH$_2$CH=CH$_2$ | H | A-7 (X$_4$=CH$_3$, Y$_4$=OCH$_3$) |
| SCF$_2$H | CH$_2$CH=CH$_2$ | H | A-7 (X$_4$=OCH$_3$, Y$_4$=CH$_3$) |

TABLE IV

GENERAL STRUCTURE 4

| R$_1$ | R$_2$ | R$_3$ | A |
|---|---|---|---|
| H | H | H | A-2 (X$_1$=CH$_3$, Y$_1$=CH$_2$) |
| H | H | H | A-3 (X$_1$=OCH$_3$) |
| H | H | H | A-4 (X$_1$=OCH$_3$, Y$_3$=CH$_3$) |
| H | H | H | A-5 (X$_2$=CH$_3$, Y$_2$=OCH$_3$) |
| H | H | H | A-6 (X$_3$=OCH$_3$) |
| H | H | H | A-7 (X$_4$=OCH$_3$, Y$_4$=OCH$_3$) |
| H | CH$_3$ | H | A-2 (X$_1$=CH$_3$, Y$_1$=CH$_2$) |
| H | CH$_3$ | H | A-3 (X$_1$=OCH$_3$) |
| H | CH$_3$ | H | A-4 (X$_1$=OCH$_3$, Y$_3$=CH$_3$) |
| H | CH$_3$ | H | A-5 (X$_2$=CH$_3$, Y$_2$=OCH$_3$) |
| H | CH$_3$ | H | A-6 (X$_3$=OCH$_3$) |
| H | CH$_3$ | H | A-7 (X$_4$=OCH$_3$, Y$_4$=OCH$_3$) |
| H | CH$_2$CH$_3$ | H | A-2 (X$_1$=CH$_3$, Y$_1$=CH$_2$) |
| H | CH$_2$CH$_3$ | H | A-3 (X$_1$=OCH$_3$) |
| H | CH$_2$CH$_3$ | H | A-4 (X$_1$=OCH$_3$, Y$_3$=CH$_3$) |
| H | CH$_2$CH$_3$ | H | A-5 (X$_2$=CH$_3$, Y$_2$=OCH$_3$) |
| H | CH$_2$CH$_3$ | H | A-6 (X$_3$=OCH$_3$) |
| H | CH$_2$CH$_3$ | H | A-7 (X$_4$=OCH$_3$, Y$_4$=OCH$_3$) |
| H | CH$_2$CF$_3$ | H | A-2 (X$_1$=CH$_3$, Y$_1$=CH$_2$) |
| H | CH$_2$CF$_3$ | H | A-3 (X$_1$=OCH$_3$) |
| H | CH$_2$CF$_3$ | H | A-4 (X$_1$=OCH$_3$, Y$_3$=CH$_3$) |
| H | CH$_2$CF$_3$ | H | A-5 (X$_2$=CH$_3$, Y$_2$=OCH$_3$) |
| H | CH$_2$CF$_3$ | H | A-6 (X$_3$=OCH$_3$) |
| H | CH$_2$CF$_3$ | H | A-7 (X$_4$=OCH$_3$, Y$_4$=OCH$_3$) |
| H | CH$_2$CH$_2$Cl | H | A-2 (X$_1$=CH$_3$, Y$_1$=CH$_2$) |
| H | CH$_2$CH$_2$Cl | H | A-3 (X$_1$=OCH$_3$) |
| H | CH$_2$CH$_2$Cl | H | A-4 (X$_1$=OCH$_3$, Y$_3$=CH$_3$) |
| H | CH$_2$CH$_2$Cl | H | A-5 (X$_2$=CH$_3$, Y$_2$=OCH$_3$) |
| H | CH$_2$CH$_2$Cl | H | A-6 (X$_3$=OCH$_3$) |
| H | CH$_2$CH$_2$Cl | H | A-7 (X$_4$=OCH$_3$, Y$_4$=OCH$_3$) |
| H | CH$_2$CN | H | A-2 (X$_1$=CH$_3$, Y$_1$=CH$_2$) |
| H | CH$_2$CN | H | A-3 (X$_1$=OCH$_3$) |
| H | CH$_2$CN | H | A-4 (X$_1$=OCH$_3$, Y$_3$=CH$_3$) |
| H | CH$_2$CN | H | A-5 (X$_2$=CH$_3$, Y$_2$=OCH$_3$) |
| H | CH$_2$CN | H | A-6 (X$_3$=OCH$_3$) |
| H | CH$_2$CN | H | A-7 (X$_4$=OCH$_3$, Y$_4$=OCH$_3$) |
| H | CH$_2$CH$_2$OCH$_3$ | H | A-2 (X$_1$=CH$_3$, Y$_1$=CH$_2$) |
| H | CH$_2$CH$_2$OCH$_3$ | H | A-3 (X$_1$=OCH$_3$) |
| H | CH$_2$CH$_2$OCH$_3$ | H | A-4 (X$_1$=OCH$_3$, Y$_3$=CH$_3$) |
| H | CH$_2$CH$_2$OCH$_3$ | H | A-5 (X$_2$=CH$_3$, Y$_2$=OCH$_3$) |
| H | CH$_2$CH$_2$OCH$_3$ | H | A-6 (X$_3$=OCH$_3$) |
| H | CH$_2$CH$_2$OCH$_3$ | H | A-7 (X$_4$=OCH$_3$, Y$_4$=OCH$_3$) |
| H | CH$_2$CH=CH$_2$ | H | A-2 (X$_1$=CH$_3$, Y$_1$=CH$_2$) |
| H | CH$_2$CH=CH$_2$ | H | A-3 (X$_1$=OCH$_3$) |
| H | CH$_2$CH=CH$_2$ | H | A-4 (X$_1$=OCH$_3$, Y$_3$=CH$_3$) |
| H | CH$_2$CH=CH$_2$ | H | A-5 (X$_2$=CH$_3$, Y$_2$=OCH$_3$) |
| H | CH$_2$CH=CH$_2$ | H | A-6 (X$_3$=OCH$_3$) |
| H | CH$_2$CH=CH$_2$ | H | A-7 (X$_4$=OCH$_3$, Y$_4$=OCH$_3$) |
| H | CH$_2$C≡CH | H | A-2 (X$_1$=CH$_3$, Y$_1$=CH$_2$) |
| H | CH$_2$C≡CH | H | A-3 (X$_1$=OCH$_3$) |
| H | CH$_2$C≡CH | H | A-4 (X$_1$=OCH$_3$, Y$_3$=CH$_3$) |
| H | CH$_2$C≡CH | H | A-5 (X$_2$=CH$_3$, Y$_2$=OCH$_3$) |
| H | CH$_2$C≡CH | H | A-6 (X$_3$=OCH$_3$) |
| H | CH$_2$C≡CH | H | A-7 (X$_4$=OCH$_3$, Y$_4$=OCH$_3$) |
| H | cyclo-C$_3$H$_7$ | H | A-2 (X$_1$=CH$_3$, Y$_1$=CH$_2$) |
| H | cyclo-C$_3$H$_7$ | H | A-3 (X$_1$=OCH$_3$) |
| H | cyclo-C$_3$H$_7$ | H | A-4 (X$_1$=OCH$_3$, Y$_3$=CH$_3$) |
| H | cyclo-C$_3$H$_7$ | H | A-5 (X$_2$=CH$_3$, Y$_2$=OCH$_3$) |
| H | cyclo-C$_3$H$_7$ | H | A-6 (X$_3$=OCH$_3$) |
| H | cyclo-C$_3$H$_7$ | H | A-7 (X$_4$=OCH$_3$, Y$_4$=OCH$_3$) |
| H | CH$_3$ | CH$_3$ | A-2 (X$_1$=CH$_3$, Y$_1$=CH$_2$) |
| H | CH$_3$ | CH$_3$ | A-3 (X$_1$=OCH$_3$) |
| H | CH$_3$ | CH$_3$ | A-4 (X$_1$=OCH$_3$, Y$_3$=CH$_3$) |
| H | CH$_3$ | CH$_3$ | A-5 (X$_2$=CH$_3$, Y$_2$=OCH$_3$) |
| H | CH$_3$ | CH$_3$ | A-6 (X$_3$=OCH$_3$) |
| H | CH$_3$ | CH$_3$ | A-7 (X$_4$=OCH$_3$, Y$_4$=OCH$_3$) |
| H | CH$_2$CH$_3$ | CH$_3$ | A-2 (X$_1$=CH$_3$, Y$_1$=CH$_2$) |
| H | CH$_2$CH$_3$ | CH$_3$ | A-3 (X$_1$=OCH$_3$) |
| H | CH$_2$CH$_3$ | CH$_3$ | A-4 (X$_1$=OCH$_3$, Y$_3$=CH$_3$) |
| H | CH$_2$CH$_3$ | CH$_3$ | A-5 (X$_2$=CH$_3$, Y$_2$=(OCH$_3$) |
| H | CH$_2$CH$_3$ | CH$_3$ | A-6 (X$_3$=OCH$_3$) |
| H | CH$_2$CH$_3$ | CH$_3$ | A-7 (X$_4$=OCH$_3$, Y$_4$=OCH$_3$) |

TABLE IV-continued
GENERAL STRUCTURE 4

| $R_1$ | $R_2$ | $R_3$ | A |
|---|---|---|---|
| H | $CH_2CH_3$ | $CH_2CH_3$ | A-2 ($X_1=CH_3$, $Y_1=CH_2$) |
| H | $CH_2CH_3$ | $CH_2CH_3$ | A-3 ($X_1=OCH_3$) |
| H | $CH_2CH_3$ | $CH_2CH_3$ | A-4 ($X_1=OCH_3$, $Y_3=CH_3$) |
| H | $CH_2CH_3$ | $CH_2CH_3$ | A-5 ($X_2=CH_3$, $Y_2=OCH_3$) |
| H | $CH_2CH_3$ | $CH_2CH_3$ | A-6 ($X_3=OCH_3$) |
| H | $CH_2CH_3$ | $CH_2CH_3$ | A-7 ($X_4=OCH_3$, $Y_4=OCH_3$) |
| H | $OCH_3$ | $CH_3$ | A-2 ($X_1=CH_3$, $Y_1=CH_2$) |
| H | $OCH_3$ | $CH_3$ | A-3 ($X_1=OCH_3$) |
| H | $OCH_3$ | $CH_3$ | A-4 ($X_1=OCH_3$, $Y_3=CH_3$) |
| H | $OCH_3$ | $CH_3$ | A-5 ($X_2=CH_3$, $Y_2=OCH_3$) |
| H | $OCH_3$ | $CH_3$ | A-6 ($X_3=OCH_3$) |
| H | $OCH_3$ | $CH_3$ | A-7 ($X_4=OCH_3$, $Y_4=OCH_3$) |
| H | $NHCH_3$ | $CH_3$ | A-2 ($X_1=CH_3$, $Y_1=CH_2$) |
| H | $NHCH_3$ | $CH_3$ | A-3 ($X_1=OCH_3$) |
| H | $NHCH_3$ | $CH_3$ | A-4 ($X_1=OCH_3$, $Y_3=CH_3$) |
| H | $NHCH_3$ | $CH_3$ | A-5 ($X_2=CH_3$, $Y_2=OCH_3$) |
| H | $NHCH_3$ | $CH_3$ | A-6 ($X_3=OCH_3$) |
| H | $NHCH_3$ | $CH_3$ | A-7 ($X_4=OCH_3$, $Y_4=OCH_3$) |
| H | $N(CH_3)_2$ | $CH_3$ | A-2 ($X_1=OCH_3$, $Y_1=CH_2$) |
| H | $N(CH_3)_2$ | $CH_3$ | A-3 ($X_1=OCH_3$) |
| H | $N(CH_3)_2$ | $CH_3$ | A-4 ($X_1=OCH_3$, $Y_3=CH_3$) |
| H | $N(CH_3)_2$ | $CH_3$ | A-5 ($X_2=CH_3$, $Y_2=OCH_3$) |
| H | $N(CH_3)_2$ | $CH_3$ | A-6 ($X_3=OCH_3$) |
| H | $N(CH_3)_2$ | $CH_3$ | A-7 ($X_4=OCH_3$, $Y_4=OCH_3$) |
| H | $-CH_2CH_2CH_2-$ | | A-2 ($X_1=CH_3$, $Y_1=CH_2$) |
| H | $-CH_2CH_2CH_2-$ | | A-3 ($X_1=OCH_3$) |
| H | $-CH_2CH_2CH_2-$ | | A-4 ($X_1=OCH_3$, $Y_3=CH_3$) |
| H | $-CH_2CH_2CH_2-$ | | A-5 ($X_2=CH_3$, $Y_2=OCH_3$) |
| H | $-CH_2CH_2CH_2-$ | | A-6 ($X_3=OCH_3$) |
| H | $-CH_2CH_2CH_2-$ | | A-7 ($X_4=OCH_3$, $Y_4=OCH_3$) |
| H | $-CH_2CH_2OCH_2CH_2-$ | | A-2 ($X_1=CH_3$, $Y_1=CH_2$) |
| H | $-CH_2CH_2OCH_2CH_2-$ | | A-3 ($X_1=OCH_3$) |
| H | $-CH_2CH_2OCH_2CH_2-$ | | A-4 ($X_1=OCH_3$, $Y_3=CH_3$) |
| H | $-CH_2CH_2OCH_2CH_2-$ | | A-5 ($X_2=CH_3$, $Y_2=(OCH_3)$) |
| H | $-CH_2CH_2OCH_2CH_2-$ | | A-6 ($X_3=OCH_3$) |
| H | $-CH_2CH_2OCH_2CH_2-$ | | A-7 ($X_4=OCH_3$, $Y_4=OCH_3$) |
| Cl | H | H | A-2 ($X_1=CH_3$, $Y_1=CH_2$) |
| Cl | H | H | A-3 ($X_1=OCH_3$) |
| Cl | H | H | A-4 ($X_1=OCH_3$, $Y_3=CH_3$) |
| Cl | H | H | A-5 ($X_2=CH_3$, $Y_2=OCH_3$) |
| Cl | H | H | A-6 ($X_3=OCH_3$) |
| Cl | H | H | A-7 ($X_4=OCH_3$, $Y_4=OCH_3$) |
| Cl | $CH_3$ | H | A-2 ($X_1=CH_3$, $Y_1=CH_2$) |
| Cl | $CH_3$ | H | A-3 ($X_1=OCH_3$) |
| Cl | $CH_3$ | H | A-4 ($X_1=OCH_3$, $Y_3=CH_3$) |
| Cl | $CH_3$ | H | A-5 ($X_2=CH_3$, $Y_2=OCH_3$) |
| Cl | $CH_3$ | H | A-6 ($X_3=OCH_3$) |
| Cl | $CH_3$ | H | A-7 ($X_4=OCH_3$, $Y_4=OCH_3$) |
| Cl | $CH_2CH_3$ | H | A-2 ($X_1=CH_3$, $Y_1=CH_2$) |
| Cl | $CH_2CH_3$ | H | A-3 ($X_1=OCH_3$) |
| Cl | $CH_2CH_3$ | H | A-4 ($X_1=OCH_3$, $Y_3=CH_3$) |
| Cl | $CH_2CH_3$ | H | A-5 ($X_2=CH_3$, $Y_2=OCH_3$) |
| Cl | $CH_2CH_3$ | H | A-6 ($X_3=OCH_3$) |
| Cl | $CH_2CH_3$ | H | A-7 ($X_4=OCH_3$, $Y_4=OCH_3$) |
| Cl | $CH_2CF_3$ | H | A-2 ($X_1=CH_3$, $Y_1=CH_2$) |
| Cl | $CH_2CF_3$ | H | A-3 ($X_1=OCH_3$) |
| Cl | $CH_2CF_3$ | H | A-4 ($X_1=OCH_3$, $Y_3=CH_3$) |
| Cl | $CH_2CF_3$ | H | A-5 ($X_2=CH_3$, $Y_2=OCH_3$) |
| Cl | $CH_2CF_3$ | H | A-6 ($X_3=OCH_3$) |
| Cl | $CH_2CF_3$ | H | A-7 ($X_4=OCH_3$, $Y_4=OCH_3$) |
| Cl | $CH_2CH_2Cl$ | H | A-2 ($X_1=CH_3$, $Y_1=CH_2$) |
| Cl | $CH_2CH_2Cl$ | H | A-3 ($X_1=OCH_3$) |
| Cl | $CH_2CH_2Cl$ | H | A-4 ($X_1=OCH_3$, $Y_3=CH_3$) |
| Cl | $CH_2CH_2Cl$ | H | A-5 ($X_2=CH_3$, $Y_2=OCH_3$) |
| Cl | $CH_2CH_2Cl$ | H | A-6 ($X_3=OCH_3$) |
| Cl | $CH_2CH_2Cl$ | H | A-7 ($X_4=OCH_3$, $Y_4=OCH_3$) |
| Cl | $CH_2CN$ | H | A-2 ($X_1=CH_3$, $Y_1=CH_2$) |
| Cl | $CH_2CN$ | H | A-3 ($X_1=OCH_3$) |
| Cl | $CH_2CN$ | H | A-4 ($X_1=OCH_3$, $Y_3=CH_3$) |
| Cl | $CH_2CN$ | H | A-5 ($X_2=CH_3$, $Y_2=(OCH_3)$) |
| Cl | $CH_2CN$ | H | A-6 ($X_3=OCH_3$) |
| Cl | $CH_2CN$ | H | A-7 ($X_4=OCH_3$, $Y_4=OCH_3$) |
| Cl | $CH_2CH_2OCH_3$ | H | A-2 ($X_1=CH_3$, $Y_1=CH_2$) |
| Cl | $CH_2CH_2OCH_3$ | H | A-3 ($X_1=OCH_3$) |
| Cl | $CH_2CH_2OCH_3$ | H | A-4 ($X_1=OCH_3$, $Y_3=CH_3$) |
| Cl | $CH_2CH_2OCH_3$ | H | A-5 ($X_2=CH_3$, $Y_2=OCH_3$) |
| Cl | $CH_2CH_2OCH_3$ | H | A-6 ($X_3=OCH_3$) |
| Cl | $CH_2CH_2OCH_3$ | H | A-7 ($X_4=OCH_3$, $Y_4=OCH_3$) |
| Cl | $CH_2CH=CH_2$ | H | A-2 ($X_1=CH_3$, $Y_1=CH_2$) |
| Cl | $CH_2CH=CH_2$ | H | A-3 ($X_1=OCH_3$) |

TABLE IV-continued
GENERAL STRUCTURE 4

| R$_1$ | R$_2$ | R$_3$ | A |
|---|---|---|---|
| Cl | CH$_2$CH=CH$_2$ | H | A-4 (X$_1$=OCH$_3$, Y$_3$=CH$_3$) |
| Cl | CH$_2$CH=CH$_2$ | H | A-5 (X$_2$=CH$_3$, Y$_2$=OCH$_3$) |
| Cl | CH$_2$CH=CH$_2$ | H | A-6 (X$_3$=OCH$_3$) |
| Cl | CH$_2$CH=CH$_2$ | H | A-7 (X$_4$=OCH$_3$, Y$_4$=OCH$_3$) |
| Cl | CH$_2$C≡CH | H | A-2 (X$_1$=CH$_3$, Y$_1$=CH$_2$) |
| Cl | CH$_2$C≡CH | H | A-3 (X$_1$=OCH$_3$) |
| Cl | CH$_2$C≡CH | H | A-4 (X$_1$=OCH$_3$, Y$_3$=CH$_3$) |
| Cl | CH$_2$C≡CH | H | A-5 (X$_2$=CH$_3$, Y$_2$=OCH$_3$) |
| Cl | CH$_2$C≡CH | H | A-6 (X$_3$=OCH$_3$) |
| Cl | CH$_2$C≡CH | H | A-7 (X$_4$=OCH$_3$, Y$_4$=OCH$_3$) |
| Cl | cyclo-C$_3$H$_7$ | H | A-2 (X$_1$=CH$_3$, Y$_1$=CH$_2$) |
| Cl | cyclo-C$_3$H$_7$ | H | A-3 (X$_1$=OCH$_3$) |
| Cl | cyclo-C$_3$H$_7$ | H | A-4 (X$_1$=OCH$_3$, Y$_3$=CH$_3$) |
| Cl | cyclo-C$_3$H$_7$ | H | A-5 (X$_2$=CH$_3$, Y$_2$=OCH$_3$) |
| Cl | cyclo-C$_3$H$_7$ | H | A-6 (X$_3$=OCH$_3$) |
| Cl | cyclo-C$_3$H$_7$ | H | A-7 (X$_4$=OCH$_3$, Y$_4$=OCH$_3$) |
| Cl | CH$_3$ | CH$_3$ | A-2 (X$_1$=CH$_3$, Y$_1$=CH$_2$) |
| Cl | CH$_3$ | CH$_3$ | A-3 (X$_1$=OCH$_3$) |
| Cl | CH$_3$ | CH$_3$ | A-4 (X$_1$=OCH$_3$, Y$_3$=CH$_3$) |
| Cl | CH$_3$ | CH$_3$ | A-5 (X$_2$=CH$_3$, Y$_2$=OCH$_3$) |
| Cl | CH$_3$ | CH$_3$ | A-6 (X$_3$=OCH$_3$) |
| Cl | CH$_3$ | CH$_3$ | A-7 (X$_4$=OCH$_3$, Y$_4$=OCH$_3$) |
| Cl | CH$_2$CH$_3$ | CH$_3$ | A-2 (X$_1$=CH$_3$, Y$_1$=CH$_2$) |
| Cl | CH$_2$CH$_3$ | CH$_3$ | A-3 (X$_1$=OCH$_3$) |
| Cl | CH$_2$CH$_3$ | CH$_3$ | A-4 (X$_1$=OCH$_3$, Y$_3$=CH$_3$) |
| Cl | CH$_2$CH$_3$ | CH$_3$ | A-5 (X$_2$=CH$_3$, Y$_2$=OCH$_3$) |
| Cl | CH$_2$CH$_3$ | CH$_3$ | A-6 (X$_3$=OCH$_3$) |
| Cl | CH$_2$CH$_3$ | CH$_3$ | A-7 (X$_4$=OCH$_3$, Y$_4$=OCH$_3$) |
| Cl | CH$_2$CH$_3$ | CH$_2$CH$_3$ | A-2 (X$_1$=CH$_3$, Y$_1$=CH$_2$) |
| Cl | CH$_2$CH$_3$ | CH$_2$CH$_3$ | A-3 (X$_1$=OCH$_3$) |
| Cl | CH$_2$CH$_3$ | CH$_2$CH$_3$ | A-4 (X$_1$=OCH$_3$, Y$_3$=CH$_3$) |
| Cl | CH$_2$CH$_3$ | CH$_2$CH$_3$ | A-5 (X$_2$=CH$_3$, Y$_2$=OCH$_3$) |
| Cl | CH$_2$CH$_3$ | CH$_2$CH$_3$ | A-6 (X$_3$=OCH$_3$) |
| Cl | CH$_2$CH$_3$ | CH$_2$CH$_3$ | A-7 (X$_4$=OCH$_3$, Y$_4$=OCH$_3$) |
| Cl | OCH$_3$ | CH$_3$ | A-2 (X$_1$=CH$_3$, Y$_1$=CH$_2$) |
| Cl | OCH$_3$ | CH$_3$ | A-3 (X$_1$=OCH$_3$) |
| Cl | OCH$_3$ | CH$_3$ | A-4 (X$_1$=OCH$_3$, Y$_3$=CH$_3$) |
| Cl | OCH$_3$ | CH$_3$ | A-5 (X$_2$=CH$_3$, Y$_2$=OCH$_3$) |
| Cl | OCH$_3$ | CH$_3$ | A-6 (X$_3$=OCH$_3$) |
| Cl | OCH$_3$ | CH$_3$ | A-7 (X$_4$=OCH$_3$, Y$_4$=OCH$_3$) |
| Cl | NHCH$_3$ | CH$_3$ | A-2 (X$_1$=CH$_3$, Y$_1$=CH$_2$) |
| Cl | NHCH$_3$ | CH$_3$ | A-3 (X$_1$=OCH$_3$) |
| Cl | NHCH$_3$ | CH$_3$ | A-4 (X$_1$=OCH$_3$, Y$_3$=CH$_3$) |
| Cl | NHCH$_3$ | CH$_3$ | A-5 (X$_2$=CH$_3$, Y$_2$=OCH$_3$) |
| Cl | NHCH$_3$ | CH$_3$ | A-6 (X$_3$=OCH$_3$) |
| Cl | NHCH$_3$ | CH$_3$ | A-7 (X$_4$=OCH$_3$, Y$_4$=OCH$_3$) |
| Cl | N(CH$_3$)$_2$ | CH$_3$ | A-2 (X$_1$=CH$_3$, Y$_1$=CH$_2$) |
| Cl | N(CH$_3$)$_2$ | CH$_3$ | A-3 (X$_1$=OCH$_3$) |
| Cl | N(CH$_3$)$_2$ | CH$_3$ | A-4 (X$_1$=OCH$_3$, Y$_3$=CH$_3$) |
| Cl | N(CH$_3$)$_2$ | CH$_3$ | A-5 (X$_2$=CH$_3$, Y$_2$=OCH$_3$) |
| Cl | N(CH$_3$)$_2$ | CH$_3$ | A-6 (X$_3$=OCH$_3$) |
| Cl | N(CH$_3$)$_2$ | CH$_3$ | A-7 (X$_4$=OCH$_3$, Y$_4$=OCH$_3$) |
| Cl | —CH$_2$CH$_2$CH$_2$— | | A-2 (X$_1$=CH$_3$, Y$_1$=CH$_2$) |
| Cl | —CH$_2$CH$_2$CH$_2$— | | A-3 (X$_1$=OCH$_3$) |
| Cl | —CH$_2$CH$_2$CH$_2$— | | A-4 (X$_1$=OCH$_3$, Y$_3$=CH$_3$) |
| Cl | —CH$_2$CH$_2$CH$_2$— | | A-5 (X$_2$=CH$_3$, Y$_2$=OCH$_3$) |
| Cl | —CH$_2$CH$_2$CH$_2$— | | A-6 (X$_3$=OCH$_3$) |
| Cl | —CH$_2$CH$_2$CH$_2$— | | A-7 (X$_4$=OCH$_3$, Y$_4$=OCH$_3$) |
| Cl | —CH$_2$CH$_2$OCH$_2$CH$_2$— | | A-2 (X$_1$=CH$_3$, Y$_1$=CH$_2$) |
| Cl | —CH$_2$CH$_2$OCH$_2$CH$_2$— | | A-3 (X$_1$=OCH$_3$) |
| Cl | —CH$_2$CH$_2$OCH$_2$CH$_2$— | | A-4 (X$_1$=OCH$_3$, Y$_3$=CH$_3$) |
| Cl | —CH$_2$CH$_2$OCH$_2$CH$_2$— | | A-5 (X$_2$=CH$_3$, Y$_2$=(OCH$_3$) |
| Cl | —CH$_2$CH$_2$OCH$_2$CH$_2$— | | A-6 (X$_3$=OCH$_3$) |
| Cl | —CH$_2$CH$_2$OCH$_2$CH$_2$— | | A-7 (X$_4$=OCH$_3$, Y$_4$=OCH$_3$) |
| CH$_3$ | H | H | A-2 (X$_1$=CH$_3$, Y$_1$=CH$_2$) |
| CH$_3$ | H | H | A-3 (X$_1$=OCH$_3$) |
| CH$_3$ | H | H | A-4 (X$_1$=OCH$_3$, Y$_3$=CH$_3$) |
| CH$_3$ | H | H | A-5 (X$_2$=CH$_3$, Y$_2$=OCH$_3$) |
| CH$_3$ | H | H | A-6 (X$_3$=OCH$_3$) |
| CH$_3$ | H | H | A-7 (X$_4$=OCH$_3$, Y$_4$=OCH$_3$) |
| CH$_3$ | CH$_3$ | H | A-2 (X$_1$=CH$_3$, Y$_1$=CH$_2$) |
| CH$_3$ | CH$_3$ | H | A-3 (X$_1$=OCH$_3$) |
| CH$_3$ | CH$_3$ | H | A-4 (X$_1$=OCH$_3$, Y$_3$=CH$_3$) |
| CH$_3$ | CH$_3$ | H | A-5 (X$_2$=CH$_3$, Y$_2$=OCH$_3$) |
| CH$_3$ | CH$_3$ | H | A-6 (X$_3$=OCH$_3$) |
| CH$_3$ | CH$_3$ | H | A-7 (X$_4$=OCH$_3$, Y$_4$=OCH$_3$) |
| CH$_3$ | CH$_2$CH$_3$ | H | A-2 (X$_1$=CH$_3$, Y$_1$=CH$_2$) |
| CH$_3$ | CH$_2$CH$_3$ | H | A-3 (X$_1$=OCH$_3$) |
| CH$_3$ | CH$_2$CH$_3$ | H | A-4 (X$_1$=OCH$_3$, Y$_3$=CH$_3$) |
| CH$_3$ | CH$_2$CH$_3$ | H | A-5 (X$_2$=CH$_3$, Y$_2$=OCH$_3$) |

TABLE IV-continued

GENERAL STRUCTURE 4

| $R_1$ | $R_2$ | $R_3$ | A |
|---|---|---|---|
| $CH_3$ | $CH_2CH_3$ | H | A-6 ($X_3$=$OCH_3$) |
| $CH_3$ | $CH_2CH_3$ | H | A-7 ($X_4$=$OCH_3$, $Y_4$=$OCH_3$) |
| $CH_3$ | $CH_2CF_3$ | H | A-2 ($X_1$=$CH_3$, $Y_1$=$CH_2$) |
| $CH_3$ | $CH_2CF_3$ | H | A-3 ($X_1$=$OCH_3$) |
| $CH_3$ | $CH_2CF_3$ | H | A-4 ($X_1$=$OCH_3$, $Y_3$=$CH_3$) |
| $CH_3$ | $CH_2CF_3$ | H | A-5 ($X_2$=$CH_3$, $Y_2$=$OCH_3$) |
| $CH_3$ | $CH_2CF_3$ | H | A-6 ($X_3$=$OCH_3$) |
| $CH_3$ | $CH_2CF_3$ | H | A-7 ($X_4$=$OCH_3$, $Y_4$=$OCH_3$) |
| $CH_3$ | $CH_2CH_2Cl$ | H | A-2 ($X_1$=$CH_3$, $Y_1$=$CH_2$) |
| $CH_3$ | $CH_2CH_2Cl$ | H | A-3 ($X_1$=$OCH_3$) |
| $CH_3$ | $CH_2CH_2Cl$ | H | A-4 ($X_1$=$OCH_3$, $Y_3$=$CH_3$) |
| $CH_3$ | $CH_2CH_2Cl$ | H | A-5 ($X_2$=$CH_3$, $Y_2$=$OCH_3$) |
| $CH_3$ | $CH_2CH_2Cl$ | H | A-6 ($X_3$=$OCH_3$) |
| $CH_3$ | $CH_2CH_2Cl$ | H | A-7 ($X_4$=$OCH_3$, $Y_4$=$OCH_3$) |
| $CH_3$ | $CH_2CN$ | H | A-2 ($X_1$=$CH_3$, $Y_1$=$CH_2$) |
| $CH_3$ | $CH_2CN$ | H | A-3 ($X_1$=$OCH_3$) |
| $CH_3$ | $CH_2CN$ | H | A-4 ($X_1$=$OCH_3$, $Y_3$=$CH_3$) |
| $CH_3$ | $CH_2CN$ | H | A-5 ($X_2$=$CH_3$, $Y_2$=($OCH_3$)) |
| $CH_3$ | $CH_2CN$ | H | A-6 ($X_3$=$OCH_3$) |
| $CH_3$ | $CH_2CN$ | H | A-7 ($X_4$=$OCH_3$, $Y_4$=$OCH_3$) |
| $CH_3$ | $CH_2CH_2OCH_3$ | H | A-2 ($X_1$=$CH_3$, $Y_1$=$CH_2$) |
| $CH_3$ | $CH_2CH_2OCH_3$ | H | A-3 ($X_1$=$OCH_3$) |
| $CH_3$ | $CH_2CH_2OCH_3$ | H | A-4 ($X_1$=$OCH_3$, $Y_3$=$CH_3$) |
| $CH_3$ | $CH_2CH_2OCH_3$ | H | A-5 ($X_2$=$CH_3$, $Y_2$=$OCH_3$) |
| $CH_3$ | $CH_2CH_2OCH_3$ | H | A-6 ($X_3$=$OCH_3$) |
| $CH_3$ | $CH_2CH_2OCH_3$ | H | A-7 ($X_4$=$OCH_3$, $Y_4$=$OCH_3$) |
| $CH_3$ | $CH_2CH$=$CH_2$ | H | A-2 ($X_1$=$CH_3$, $Y_1$=$CH_2$) |
| $CH_3$ | $CH_2CH$=$CH_2$ | H | A-3 ($X_1$=$OCH_3$) |
| $CH_3$ | $CH_2CH$=$CH_2$ | H | A-4 ($X_1$=$OCH_3$, $Y_3$=$CH_3$) |
| $CH_3$ | $CH_2CH$=$CH_2$ | H | A-5 ($X_2$=$CH_3$, $Y_2$=$OCH_3$) |
| $CH_3$ | $CH_2CH$=$CH_2$ | H | A-6 ($X_3$=$OCH_3$) |
| $CH_3$ | $CH_2CH$=$CH_2$ | H | A-7 ($X_4$=$OCH_3$, $Y_4$=$OCH_3$) |
| $CH_3$ | $CH_2C$≡$CH$ | H | A-2 ($X_1$=$CH_3$, $Y_1$=$CH_2$) |
| $CH_3$ | $CH_2C$≡$CH$ | H | A-3 ($X_1$=$OCH_3$) |
| $CH_3$ | $CH_2C$≡$CH$ | H | A-4 ($X_1$=$OCH_3$, $Y_3$=$CH_3$) |
| $CH_3$ | $CH_2C$≡$CH$ | H | A-5 ($X_2$=$CH_3$, $Y_2$=$OCH_3$) |
| $CH_3$ | $CH_2C$≡$CH$ | H | A-6 ($X_3$=$OCH_3$) |
| $CH_3$ | $CH_2C$≡$CH$ | H | A-7 ($X_4$=$OCH_3$, $Y_4$=$OCH_3$) |
| $CH_3$ | cyclo-$C_3H_7$ | H | A-2 ($X_1$=$CH_3$, $Y_1$=$CH_2$) |
| $CH_3$ | cyclo-$C_3H_7$ | H | A-3 ($X_1$=$OCH_3$) |
| $CH_3$ | cyclo-$C_3H_7$ | H | A-4 ($X_1$=$OCH_3$, $Y_3$=$CH_3$) |
| $CH_3$ | cyclo-$C_3H_7$ | H | A-5 ($X_2$=$CH_3$, $Y_2$=$OCH_3$) |
| $CH_3$ | cyclo-$C_3H_7$ | H | A-6 ($X_3$=$OCH_3$) |
| $CH_3$ | cyclo-$C_3H_7$ | H | A-7 ($X_4$=$OCH_3$, $Y_4$=$OCH_3$) |
| $CH_3$ | $CH_3$ | $CH_3$ | A-2 ($X_1$=$CH_3$, $Y_1$=$CH_2$) |
| $CH_3$ | $CH_3$ | $CH_3$ | A-3 ($X_1$=$OCH_3$) |
| $CH_3$ | $CH_3$ | $CH_3$ | A-4 ($X_1$=$OCH_3$, $Y_3$=$CH_3$) |
| $CH_3$ | $CH_3$ | $CH_3$ | A-5 ($X_2$=$CH_3$, $Y_2$=$OCH_3$) |
| $CH_3$ | $CH_3$ | $CH_3$ | A-6 ($X_3$=$OCH_3$) |
| $CH_3$ | $CH_3$ | $CH_3$ | A-7 ($X_4$=$OCH_3$, $Y_4$=$OCH_3$) |
| $CH_3$ | $CH_2CH_3$ | $CH_3$ | A-2 ($X_1$=$CH_3$, $Y_1$=$CH_2$) |
| $CH_3$ | $CH_2CH_3$ | $CH_3$ | A-3 ($X_1$=$OCH_3$) |
| $CH_3$ | $CH_2CH_3$ | $CH_3$ | A-4 ($X_1$=$OCH_3$, $Y_3$=$CH_3$) |
| $CH_3$ | $CH_2CH_3$ | $CH_3$ | A-5 ($X_2$=$CH_3$, $Y_2$=($OCH_3$)) |
| $CH_3$ | $CH_2CH_3$ | $CH_3$ | A-6 ($X_3$=$OCH_3$) |
| $CH_3$ | $CH_2CH_3$ | $CH_3$ | A-7 ($X_4$=$OCH_3$, $Y_4$=$OCH_3$) |
| $CH_3$ | $CH_2CH_3$ | $CH_2CH_3$ | A-2 ($X_1$=$CH_3$, $Y_1$=$CH_2$) |
| $CH_3$ | $CH_2CH_3$ | $CH_2CH_3$ | A-3 ($X_1$=$OCH_3$) |
| $CH_3$ | $CH_2CH_3$ | $CH_2CH_3$ | A-4 ($X_1$=$OCH_3$, $Y_3$=$CH_3$) |
| $CH_3$ | $CH_2CH_3$ | $CH_2CH_3$ | A-5 ($X_2$=$CH_3$, $Y_2$=$OCH_3$) |
| $CH_3$ | $CH_2CH_3$ | $CH_2CH_3$ | A-6 ($X_3$=$OCH_3$) |
| $CH_3$ | $CH_2CH_3$ | $CH_2CH_3$ | A-7 ($X_4$=$OCH_3$, $Y_4$=$OCH_3$) |
| $CH_3$ | $OCH_3$ | $CH_3$ | A-2 ($X_1$=$CH_3$, $Y_1$=$CH_2$) |
| $CH_3$ | $OCH_3$ | $CH_3$ | A-3 ($X_1$=$OCH_3$) |
| $CH_3$ | $OCH_3$ | $CH_3$ | A-4 ($X_1$=$OCH_3$, $Y_3$=$CH_3$) |
| $CH_3$ | $OCH_3$ | $CH_3$ | A-5 ($X_2$=$CH_3$, $Y_2$=$OCH_3$) |
| $CH_3$ | $OCH_3$ | $CH_3$ | A-6 ($X_3$=$OCH_3$) |
| $CH_3$ | $OCH_3$ | $CH_3$ | A-7 ($X_4$=$OCH_3$, $Y_4$=$OCH_3$) |
| $CH_3$ | $NHCH_3$ | $CH_3$ | A-2 ($X_1$=$CH_3$, $Y_1$=$CH_2$) |
| $CH_3$ | $NHCH_3$ | $CH_3$ | A-3 ($X_1$=$OCH_3$) |
| $CH_3$ | $NHCH_3$ | $CH_3$ | A-4 ($X_1$=$OCH_3$, $Y_3$=$CH_3$) |
| $CH_3$ | $NHCH_3$ | $CH_3$ | A-5 ($X_2$=$CH_3$, $Y_2$=$OCH_3$) |
| $CH_3$ | $NHCH_3$ | $CH_3$ | A-6 ($X_3$=$OCH_3$) |
| $CH_3$ | $NHCH_3$ | $CH_3$ | A-7 ($X_4$=$OCH_3$, $Y_4$=$OCH_3$) |
| $CH_3$ | $N(CH_3)_2$ | $CH_3$ | A-2 ($X_1$=$CH_3$, $Y_1$=$CH_2$) |
| $CH_3$ | $N(CH_3)_2$ | $CH_3$ | A-3 ($X_1$=$OCH_3$) |
| $CH_3$ | $N(CH_3)_2$ | $CH_3$ | A-4 ($X_1$=$OCH_3$, $Y_3$=$CH_3$) |
| $CH_3$ | $N(CH_3)_2$ | $CH_3$ | A-5 ($X_2$=$CH_3$, $Y_2$=$OCH_3$) |
| $CH_3$ | $N(CH_3)_2$ | $CH_3$ | A-6 ($X_3$=$OCH_3$) |
| $CH_3$ | $N(CH_3)_2$ | $CH_3$ | A-7 ($X_4$=$OCH_3$, $Y_4$=$OCH_3$) |

TABLE IV-continued

GENERAL STRUCTURE 4

| R₁ | R₂ | R₃ | A |
|---|---|---|---|
| CH₃ | —CH₂CH₂CH₂— | | A-2 (X₁=CH₃, Y₁=CH₂) |
| CH₃ | —CH₂CH₂CH₂— | | A-3 (X₁=OCH₃) |
| CH₃ | —CH₂CH₂CH₂— | | A-4 (X₁=OCH₃, Y₃=CH₃) |
| CH₃ | —CH₂CH₂CH₂— | | A-5 (X₂=CH₃, Y₂=OCH₃) |
| CH₃ | —CH₂CH₂CH₂— | | A-6 (X₃=OCH₃) |
| CH₃ | —CH₂CH₂CH₂— | | A-7 (X₄=OCH₃, Y₄=OCH₃) |
| CH₃ | —CH₂CH₂OCH₂CH₂— | | A-2 (X₁=CH₃, Y₁=CH₂) |
| CH₃ | —CH₂CH₂OCH₂CH₂— | | A-3 (X₁=OCH₃) |
| CH₃ | —CH₂CH₂OCH₂CH₂— | | A-4 (X₁=OCH₃, Y₃=CH₃) |
| CH₃ | —CH₂CH₂OCH₂CH₂— | | A-5 (X₂=CH₃, Y₂=(OCH₃)) |
| CH₃ | —CH₂CH₂OCH₂CH₂— | | A-6 (X₃=OCH₃) |
| CH₃ | —CH₂CH₂OCH₂CH₂— | | A-7 (X₄=OCH₃, Y₄=OCH₃) |
| SCH₃ | H | H | A-2 (X₁=CH₃, Y₁=CH₂) |
| SCH₃ | H | H | A-3 (X₁=OCH₃) |
| SCH₃ | H | H | A-4 (X₁=OCH₃, Y₃=CH₃) |
| SCH₃ | H | H | A-5 (X₂=CH₃, Y₂=OCH₃) |
| SCH₃ | H | H | A-6 (X₃=OCH₃) |
| SCH₃ | H | H | A-7 (X₄=OCH₃, Y₄=OCH₃) |
| SCH₃ | CH₃ | H | A-2 (X₁=CH₃, Y₁=CH₂) |
| SCH₃ | CH₃ | H | A-3 (X₁=OCH₃) |
| SCH₃ | CH₃ | H | A-4 (X₁=OCH₃, Y₃=CH₃) |
| SCH₃ | CH₃ | H | A-5 (X₂=CH₃, Y₂=OCH₃) |
| SCH₃ | CH₃ | H | A-6 (X₃=OCH₃) |
| SCH₃ | CH₃ | H | A-7 (X₄=OCH₃, Y₄=OCH₃) |
| SCH₃ | CH₂CH₃ | H | A-2 (X₁=CH₃, Y₁=CH₂) |
| SCH₃ | CH₂CH₃ | H | A-3 (X₁=OCH₃) |
| SCH₃ | CH₂CH₃ | H | A-4 (X₁=OCH₃, Y₃=CH₃) |
| SCH₃ | CH₂CH₃ | H | A-5 (X₂=CH₃, Y₂=OCH₃) |
| SCH₃ | CH₂CH₃ | H | A-6 (X₃=OCH₃) |
| SCH₃ | CH₂CH₃ | H | A-7 (X₄=OCH₃, Y₄=OCH₃) |
| SCH₃ | CH₂CF₃ | H | A-2 (X₁=CH₃, Y₁=CH₂) |
| SCH₃ | CH₂CF₃ | H | A-3 (X₁=OCH₃) |
| SCH₃ | CH₂CF₃ | H | A-4 (X₁=OCH₃, Y₃=CH₃) |
| SCH₃ | CH₂CF₃ | H | A-5 (X₂=CH₃, Y₂=OCH₃) |
| SCH₃ | CH₂CF₃ | H | A-6 (X₃=OCH₃) |
| SCH₃ | CH₂CF₃ | H | A-7 (X₄=OCH₃, Y₄=OCH₃) |
| SCH₃ | CH₂CH₂Cl | H | A-2 (X₁=CH₃, Y₁=CH₂) |
| SCH₃ | CH₂CH₂Cl | H | A-3 (X₁=OCH₃) |
| SCH₃ | CH₂CH₂Cl | H | A-4 (X₁=OCH₃, Y₃=CH₃) |
| SCH₃ | CH₂CH₂Cl | H | A-5 (X₂=CH₃, Y₂=OCH₃) |
| SCH₃ | CH₂CH₂Cl | H | A-6 (X₃=OCH₃) |
| SCH₃ | CH₂CH₂Cl | H | A-7 (X₄=OCH₃, Y₄=OCH₃) |
| SCH₃ | CH₂CN | H | A-2 (X₁=CH₃, Y₁=CH₂) |
| SCH₃ | CH₂CN | H | A-3 (X₁=OCH₃) |
| SCH₃ | CH₂CN | H | A-4 (X₁=OCH₃, Y₃=CH₃) |
| SCH₃ | CH₂CN | H | A-5 (X₂=CH₃, Y₂=(OCH₃)) |
| SCH₃ | CH₂CN | H | A-6 (X₃=OCH₃) |
| SCH₃ | CH₂CN | H | A-7 (X₄=OCH₃, Y₄=OCH₃) |
| SCH₃ | CH₂CH₂OCH₃ | H | A-2 (X₁=CH₃, Y₁=CH₂) |
| SCH₃ | CH₂CH₂OCH₃ | H | A-3 (X₁=OCH₃) |
| SCH₃ | CH₂CH₂OCH₃ | H | A-4 (X₁=OCH₃, Y₃=CH₃) |
| SCH₃ | CH₂CH₂OCH₃ | H | A-5 (X₂=CH₃, Y₂=OCH₃) |
| SCH₃ | CH₂CH₂OCH₃ | H | A-6 (X₃=OCH₃) |
| SCH₃ | CH₂CH₂OCH₃ | H | A-7 (X₄=OCH₃, Y₄=OCH₃) |
| SCH₃ | CH₂CH=CH₂ | H | A-2 (X₁=CH₃, Y₁=CH₂) |
| SCH₃ | CH₂CH=CH₂ | H | A-3 (X₁=OCH₃) |
| SCH₃ | CH₂CH=CH₂ | H | A-4 (X₁=OCH₃, Y₃=CH₃) |
| SCH₃ | CH₂CH=CH₂ | H | A-5 (X₂=CH₃, Y₂=OCH₃) |
| SCH₃ | CH₂CH=CH₂ | H | A-6 (X₃=OCH₃) |
| SCH₃ | CH₂CH=CH₂ | H | A-7 (X₄=OCH₃, Y₄=OCH₃) |
| SCH₃ | CH₂C≡CH | H | A-2 (X₁=CH₃, Y₁=CH₂) |
| SCH₃ | CH₂C≡CH | H | A-3 (X₁=OCH₃) |
| SCH₃ | CH₂C≡CH | H | A-4 (X₁=OCH₃, Y₃=CH₃) |
| SCH₃ | CH₂C≡CH | H | A-5 (X₂=CH₃, Y₂=OCH₃) |
| SCH₃ | CH₂C≡CH | H | A-6 (X₃=OCH₃) |
| SCH₃ | CH₂C≡CH | H | A-7 (X₄=OCH₃, Y₄=OCH₃) |
| SCH₃ | cyclo-C₃H₇ | H | A-2 (X₁=CH₃, Y₁=CH₂) |
| SCH₃ | cyclo-C₃H₇ | H | A-3 (X₁=OCH₃) |
| SCH₃ | cyclo-C₃H₇ | H | A-4 (X₁=OCH₃, Y₃=CH₃) |
| SCH₃ | cyclo-C₃H₇ | H | A-5 (X₂=CH₃, Y₂=OCH₃) |
| SCH₃ | cyclo-C₃H₇ | H | A-6 (X₃=OCH₃) |
| SCH₃ | cyclo-C₃H₇ | H | A-7 (X₄=OCH₃, Y₄=OCH₃) |
| SCH₃ | CH₃ | CH₃ | A-2 (X₁=CH₃, Y₁=CH₂) |
| SCH₃ | CH₃ | CH₃ | A-3 (X₁=OCH₃) |
| SCH₃ | CH₃ | CH₃ | A-4 (X₁=OCH₃, Y₃=CH₃) |
| SCH₃ | CH₃ | CH₃ | A-5 (X₂=CH₃, Y₂=OCH₃) |
| SCH₃ | CH₃ | CH₃ | A-6 (X₃=OCH₃) |
| SCH₃ | CH₃ | CH₃ | A-7 (X₄=OCH₃, Y₄=OCH₃) |
| SCH₃ | CH₂CH₃ | CH₃ | A-2 (X₁=CH₃, Y₁=CH₂) |
| SCH₃ | CH₂CH₃ | CH₃ | A-3 (X₁=OCH₃) |

TABLE IV-continued

GENERAL STRUCTURE 4

| R₁ | R₂ | R₃ | A |
|---|---|---|---|
| SCH$_3$ | CH$_2$CH$_3$ | CH$_3$ | A-4 (X$_1$=OCH$_3$, Y$_3$=CH$_3$) |
| SCH$_3$ | CH$_2$CH$_3$ | CH$_3$ | A-5 (X$_2$=CH$_3$, Y$_2$=(OCH$_3$) |
| SCH$_3$ | CH$_2$CH$_3$ | CH$_3$ | A-6 (X$_3$=OCH$_3$) |
| SCH$_3$ | CH$_2$CH$_3$ | CH$_3$ | A-7 (X$_4$=OCH$_3$, Y$_4$=OCH$_3$) |
| SCH$_3$ | CH$_2$CH$_3$ | CH$_2$CH$_3$ | A-2 (X$_1$=CH$_3$, Y$_1$=CH$_2$) |
| SCH$_3$ | CH$_2$CH$_3$ | CH$_2$CH$_3$ | A-3 (X$_1$=OCH$_3$) |
| SCH$_3$ | CH$_2$CH$_3$ | CH$_2$CH$_3$ | A-4 (X$_1$=OCH$_3$, Y$_3$=CH$_3$) |
| SCH$_3$ | CH$_2$CH$_3$ | CH$_2$CH$_3$ | A-5 (X$_2$=CH$_3$, Y$_2$=OCH$_3$) |
| SCH$_3$ | CH$_2$CH$_3$ | CH$_2$CH$_3$ | A-6 (X$_3$=OCH$_3$) |
| SCH$_3$ | CH$_2$CH$_3$ | CH$_2$CH$_3$ | A-7 (X$_4$=OCH$_3$, Y$_4$=OCH$_3$) |
| SCH$_3$ | OCH$_3$ | CH$_3$ | A-2 (X$_1$=CH$_3$, Y$_1$=CH$_2$) |
| SCH$_3$ | OCH$_3$ | CH$_3$ | A-3 (X$_1$=OCH$_3$) |
| SCH$_3$ | OCH$_3$ | CH$_3$ | A-4 (X$_1$=OCH$_3$, Y$_3$=CH$_3$) |
| SCH$_3$ | OCH$_3$ | CH$_3$ | A-5 (X$_2$=CH$_3$, Y$_2$=OCH$_3$) |
| SCH$_3$ | OCH$_3$ | CH$_3$ | A-6 (X$_3$=OCH$_3$) |
| SCH$_3$ | OCH$_3$ | CH$_3$ | A-7 (X$_4$=OCH$_3$, Y$_4$=OCH$_3$) |
| SCH$_3$ | NHCH$_3$ | CH$_3$ | A-2 (X$_1$=CH$_3$, Y$_1$=CH$_2$) |
| SCH$_3$ | NHCH$_3$ | CH$_3$ | A-3 (X$_1$=OCH$_3$) |
| SCH$_3$ | NHCH$_3$ | CH$_3$ | A-4 (X$_1$=OCH$_3$, Y$_3$=CH$_3$) |
| SCH$_3$ | NHCH$_3$ | CH$_3$ | A-5 (X$_2$=CH$_3$, Y$_2$=OCH$_3$) |
| SCH$_3$ | NHCH$_3$ | CH$_3$ | A-6 (X$_3$=OCH$_3$) |
| SCH$_3$ | NHCH$_3$ | CH$_3$ | A-7 (X$_4$=OCH$_3$, Y$_4$=OCH$_3$) |
| SCH$_3$ | N(CH$_3$)$_2$ | CH$_3$ | A-2 (X$_1$=CH$_3$, Y$_1$=CH$_2$) |
| SCH$_3$ | N(CH$_3$)$_2$ | CH$_3$ | A-3 (X$_1$=OCH$_3$) |
| SCH$_3$ | N(CH$_3$)$_2$ | CH$_3$ | A-4 (X$_1$=OCH$_3$, Y$_3$=CH$_3$) |
| SCH$_3$ | N(CH$_3$)$_2$ | CH$_3$ | A-5 (X$_2$=CH$_3$, Y$_2$=OCH$_3$) |
| SCH$_3$ | N(CH$_3$)$_2$ | CH$_3$ | A-6 (X$_3$=OCH$_3$) |
| SCH$_3$ | N(CH$_3$)$_2$ | CH$_3$ | A-7 (X$_4$=OCH$_3$, Y$_4$=OCH$_3$) |
| SCH$_3$ | —CH$_2$CH$_2$CH$_2$— | | A-2 (X$_1$=CH$_3$, Y$_1$=CH$_2$) |
| SCH$_3$ | —CH$_2$CH$_2$CH$_2$— | | A-3 (X$_1$=OCH$_3$) |
| SCH$_3$ | —CH$_2$CH$_2$CH$_2$— | | A-4 (X$_1$=OCH$_3$, Y$_3$=CH$_3$) |
| SCH$_3$ | —CH$_2$CH$_2$CH$_2$— | | A-5 (X$_2$=CH$_3$, Y$_2$=OCH$_3$) |
| SCH$_3$ | —CH$_2$CH$_2$CH$_2$— | | A-6 (X$_3$=OCH$_3$) |
| SCH$_3$ | —CH$_2$CH$_2$CH$_2$— | | A-7 (X$_4$=OCH$_3$, Y$_4$=OCH$_3$) |
| SCH$_3$ | —CH$_2$CH$_2$OCH$_2$CH$_2$— | | A-2 (X$_1$=CH$_3$, Y$_1$=CH$_2$) |
| SCH$_3$ | —CH$_2$CH$_2$OCH$_2$CH$_2$— | | A-3 (X$_1$=OCH$_3$) |
| SCH$_3$ | —CH$_2$CH$_2$OCH$_2$CH$_2$— | | A-4 (X$_1$=OCH$_3$, Y$_3$=CH$_3$) |
| SCH$_3$ | —CH$_2$CH$_2$OCH$_2$CH$_2$— | | A-5 (X$_2$=CH$_3$, Y$_2$=(OCH$_3$) |
| SCH$_3$ | —CH$_2$CH$_2$OCH$_2$CH$_2$— | | A-6 (X$_3$=OCH$_3$) |
| SCH$_3$ | —CH$_2$CH$_2$OCH$_2$CH$_2$— | | A-7 (X$_4$=OCH$_3$, Y$_4$=OCH$_3$) |
| SO$_2$CH$_2$CH$_3$ | H | H | A-2 (X$_1$=CH$_3$, Y$_1$=CH$_2$) |
| SO$_2$CH$_2$CH$_3$ | H | H | A-3 (X$_1$=OCH$_3$) |
| SO$_2$CH$_2$CH$_3$ | H | H | A-4 (X$_1$=OCH$_3$, Y$_3$=CH$_3$) |
| SO$_2$CH$_2$CH$_3$ | H | H | A-5 (X$_2$=CH$_3$, Y$_2$=OCH$_3$) |
| SO$_2$CH$_2$CH$_3$ | H | H | A-6 (X$_3$=OCH$_3$) |
| SO$_2$CH$_2$CH$_3$ | H | H | A-7 (X$_4$=OCH$_3$, Y$_4$=OCH$_3$) |
| SO$_2$CH$_2$CH$_3$ | CH$_3$ | H | A-2 (X$_1$=CH$_3$, Y$_1$=CH$_2$) |
| SO$_2$CH$_2$CH$_3$ | CH$_3$ | H | A-3 (X$_1$=OCH$_3$) |
| SO$_2$CH$_2$CH$_3$ | CH$_3$ | H | A-4 (X$_1$=OCH$_3$, Y$_3$=CH$_3$) |
| SO$_2$CH$_2$CH$_3$ | CH$_3$ | H | A-5 (X$_2$=CH$_3$, Y$_2$=OCH$_3$) |
| SO$_2$CH$_2$CH$_3$ | CH$_3$ | H | A-6 (X$_3$=OCH$_3$) |
| SO$_2$CH$_2$CH$_3$ | CH$_3$ | H | A-7 (X$_4$=OCH$_3$, Y$_4$=OCH$_3$) |
| SO$_2$CH$_2$CH$_3$ | CH$_2$CH$_3$ | H | A-2 (X$_1$=CH$_3$, Y$_1$=CH$_2$) |
| SO$_2$CH$_2$CH$_3$ | CH$_2$CH$_3$ | H | A-3 (X$_1$=OCH$_3$) |
| SO$_2$CH$_2$CH$_3$ | CH$_2$CH$_3$ | H | A-4 (X$_1$=OCH$_3$, Y$_3$=CH$_3$) |
| SO$_2$CH$_2$CH$_3$ | CH$_2$CH$_3$ | H | A-5 (X$_2$=CH$_3$, Y$_2$=OCH$_3$) |
| SO$_2$CH$_2$CH$_3$ | CH$_2$CH$_3$ | H | A-6 (X$_3$=OCH$_3$) |
| SO$_2$CH$_2$CH$_3$ | CH$_2$CH$_3$ | H | A-7 (X$_4$=OCH$_3$, Y$_4$=OCH$_3$) |
| SO$_2$CH$_2$CH$_3$ | CH$_2$CF$_3$ | H | A-2 (X$_1$=CH$_3$, Y$_1$=CH$_2$) |
| SO$_2$CH$_2$CH$_3$ | CH$_2$CF$_3$ | H | A-3 (X$_1$=OCH$_3$) |
| SO$_2$CH$_2$CH$_3$ | CH$_2$CF$_3$ | H | A-4 (X$_1$=OCH$_3$, Y$_3$=CH$_3$) |
| SO$_2$CH$_2$CH$_3$ | CH$_2$CF$_3$ | H | A-5 (X$_2$=CH$_3$, Y$_2$=OCH$_3$) |
| SO$_2$CH$_2$CH$_3$ | CH$_2$CF$_3$ | H | A-6 (X$_3$=OCH$_3$) |
| SO$_2$CH$_2$CH$_3$ | CH$_2$CF$_3$ | H | A-7 (X$_4$=OCH$_3$, Y$_4$=OCH$_3$) |
| SO$_2$CH$_2$CH$_3$ | CH$_2$CH$_2$Cl | H | A-2 (X$_1$=CH$_3$, Y$_1$=CH$_2$) |
| SO$_2$CH$_2$CH$_3$ | CH$_2$CH$_2$Cl | H | A-3 (X$_1$=OCH$_3$) |
| SO$_2$CH$_2$CH$_3$ | CH$_2$CH$_2$Cl | H | A-4 (X$_1$=OCH$_3$, Y$_3$=CH$_3$) |
| SO$_2$CH$_2$CH$_3$ | CH$_2$CH$_2$Cl | H | A-5 (X$_2$=CH$_3$, Y$_2$=OCH$_3$) |
| SO$_2$CH$_2$CH$_3$ | CH$_2$CH$_2$Cl | H | A-6 (X$_3$=OCH$_3$) |
| SO$_2$CH$_2$CH$_3$ | CH$_2$CH$_2$Cl | H | A-7 (X$_4$=OCH$_3$, Y$_4$=OCH$_3$) |
| SO$_2$CH$_2$CH$_3$ | CH$_2$CN | H | A-2 (X$_1$=CH$_3$, Y$_1$=CH$_2$) |
| SO$_2$CH$_2$CH$_3$ | CH$_2$CN | H | A-3 (X$_1$=OCH$_3$) |
| SO$_2$CH$_2$CH$_3$ | CH$_2$CN | H | A-4 (X$_1$=OCH$_3$, Y$_3$=CH$_3$) |
| SO$_2$CH$_2$CH$_3$ | CH$_2$CN | H | A-5 (X$_2$=CH$_3$, Y$_2$=(OCH$_3$) |
| SO$_2$CH$_2$CH$_3$ | CH$_2$CN | H | A-6 (X$_3$=OCH$_3$) |
| SO$_2$CH$_2$CH$_3$ | CH$_2$CN | H | A-7 (X$_4$=OCH$_3$, Y$_4$=OCH$_3$) |
| SO$_2$CH$_2$CH$_3$ | CH$_2$CH$_2$OCH$_3$ | H | A-2 (X$_1$=CH$_3$, Y$_1$=CH$_2$) |
| SO$_2$CH$_2$CH$_3$ | CH$_2$CH$_2$OCH$_3$ | H | A-3 (X$_1$=OCH$_3$) |
| SO$_2$CH$_2$CH$_3$ | CH$_2$CH$_2$OCH$_3$ | H | A-4 (X$_1$=OCH$_3$, Y$_3$=CH$_3$) |
| SO$_2$CH$_2$CH$_3$ | CH$_2$CH$_2$OCH$_3$ | H | A-5 (X$_2$=CH$_3$, Y$_2$=OCH$_3$) |

TABLE IV-continued
GENERAL STRUCTURE 4

| R$_1$ | R$_2$ | R$_3$ | A |
|---|---|---|---|
| SO$_2$CH$_2$CH$_3$ | CH$_2$CH$_2$OCH$_3$ | H | A-6 (X$_3$=OCH$_3$) |
| SO$_2$CH$_2$CH$_3$ | CH$_2$CH$_2$OCH$_3$ | H | A-7 (X$_4$=OCH$_3$, Y$_4$=OCH$_3$) |
| SO$_2$CH$_2$CH$_3$ | CH$_2$CH=CH$_2$ | H | A-2 (X$_1$=CH$_3$, Y$_1$=CH$_2$) |
| SO$_2$CH$_2$CH$_3$ | CH$_2$CH=CH$_2$ | H | A-3 (X$_1$=OCH$_3$) |
| SO$_2$CH$_2$CH$_3$ | CH$_2$CH=CH$_2$ | H | A-4 (X$_1$=OCH$_3$, Y$_3$=CH$_3$) |
| SO$_2$CH$_2$CH$_3$ | CH$_2$CH=CH$_2$ | H | A-5 (X$_2$=CH$_3$, Y$_2$=OCH$_3$) |
| SO$_2$CH$_2$CH$_3$ | CH$_2$CH=CH$_2$ | H | A-6 (X$_3$=OCH$_3$) |
| SO$_2$CH$_2$CH$_3$ | CH$_2$CH=CH$_2$ | H | A-7 (X$_4$=OCH$_3$, Y$_4$=OCH$_3$) |
| SO$_2$CH$_2$CH$_3$ | CH$_2$C≡CH | H | A-2 (X$_1$=CH$_3$, Y$_1$=CH$_2$) |
| SO$_2$CH$_2$CH$_3$ | CH$_2$C≡CH | H | A-3 (X$_1$=OCH$_3$) |
| SO$_2$CH$_2$CH$_3$ | CH$_2$C≡CH | H | A-4 (X$_1$=OCH$_3$, Y$_3$=CH$_3$) |
| SO$_2$CH$_2$CH$_3$ | CH$_2$C≡CH | H | A-5 (X$_2$CH$_3$, Y$_2$=OCH$_3$) |
| SO$_2$CH$_2$CH$_3$ | CH$_2$C≡CH | H | A-6 (X$_3$=OCH$_3$) |
| SO$_2$CH$_2$CH$_3$ | CH$_2$C≡CH | H | A-7 (X$_4$=OCH$_3$, Y$_4$=OCH$_3$) |
| SO$_2$CH$_2$CH$_3$ | cyclo-C$_3$H$_7$ | H | A-2 (X$_1$=CH$_3$, Y$_1$=CH$_2$) |
| SO$_2$CH$_2$CH$_3$ | cyclo-C$_3$H$_7$ | H | A-3 (X$_1$=OCH$_3$) |
| SO$_2$CH$_2$CH$_3$ | cyclo-C$_3$H$_7$ | H | A-4 (X$_1$=OCH$_3$, Y$_3$=CH$_3$) |
| SO$_2$CH$_2$CH$_3$ | cyclo-C$_3$H$_7$ | H | A-5 (X$_2$=CH$_3$, Y$_2$=OCH$_3$) |
| SO$_2$CH$_2$CH$_3$ | cyclo-C$_3$H$_7$ | H | A-6 (X$_3$=OCH$_3$) |
| SO$_2$CH$_2$CH$_3$ | cyclo-C$_3$H$_7$ | H | A-7 (X$_4$=OCH$_3$, Y$_4$=OCH$_3$) |
| SO$_2$CH$_2$CH$_3$ | CH$_3$ | CH$_3$ | A-2 (X$_1$=CH$_3$, Y$_1$=CH$_2$) |
| SO$_2$CH$_2$CH$_3$ | CH$_3$ | CH$_3$ | A-3 (X$_1$=OCH$_3$) |
| SO$_2$CH$_2$CH$_3$ | CH$_3$ | CH$_3$ | A-4 (X$_1$=OCH$_3$, Y$_3$=CH$_3$) |
| SO$_2$CH$_2$CH$_3$ | CH$_3$ | CH$_3$ | A-5 (X$_2$=CH$_3$, Y$_2$=OCH$_3$) |
| SO$_2$CH$_2$CH$_3$ | CH$_3$ | CH$_3$ | A-6 (X$_3$=OCH$_3$) |
| SO$_2$CH$_2$CH$_3$ | CH$_3$ | CH$_3$ | A-7 (X$_4$=OCH$_3$, Y$_4$=OCH$_3$) |
| SO$_2$CH$_2$CH$_3$ | CH$_2$CH$_3$ | CH$_3$ | A-2 (X$_1$=CH$_3$, Y$_1$=CH$_2$) |
| SO$_2$CH$_2$CH$_3$ | CH$_2$CH$_3$ | CH$_3$ | A-3 (X$_1$=OCH$_3$) |
| SO$_2$CH$_2$CH$_3$ | CH$_2$CH$_3$ | CH$_3$ | A-4 (X$_1$=OCH$_3$, Y$_3$=CH$_3$) |
| SO$_2$CH$_2$CH$_3$ | CH$_2$CH$_3$ | CH$_3$ | A-5 (X$_2$=CH$_3$, Y$_2$=(OCH$_3$) |
| SO$_2$CH$_2$CH$_3$ | CH$_2$CH$_3$ | CH$_3$ | A-6 (X$_3$=OCH$_3$) |
| SO$_2$CH$_2$CH$_3$ | CH$_2$CH$_3$ | CH$_3$ | A-7 (X$_4$=OCH$_3$, Y$_4$=OCH$_3$) |
| SO$_2$CH$_2$CH$_3$ | CH$_2$CH$_3$ | CH$_2$CH$_3$ | A-2 (X$_1$=CH$_3$, Y$_1$=CH$_2$) |
| SO$_2$CH$_2$CH$_3$ | CH$_2$CH$_3$ | CH$_2$CH$_3$ | A-3 (X$_1$=OCH$_3$) |
| SO$_2$CH$_2$CH$_3$ | CH$_2$CH$_3$ | CH$_2$CH$_3$ | A-4 (X$_1$=OCH$_3$, Y$_3$=CH$_3$) |
| SO$_2$CH$_2$CH$_3$ | CH$_2$CH$_3$ | CH$_2$CH$_3$ | A-5 (X$_2$=CH$_3$, Y$_2$=OCH$_3$) |
| SO$_2$CH$_2$CH$_3$ | CH$_2$CH$_3$ | CH$_2$CH$_3$ | A-6 (X$_3$=OCH$_3$) |
| SO$_2$CH$_2$CH$_3$ | CH$_2$CH$_3$ | CH$_2$CH$_3$ | A-7 (X$_4$=OCH$_3$, Y$_4$=OCH$_3$) |
| SO$_2$CH$_2$CH$_3$ | OCH$_3$ | CH$_3$ | A-2 (X$_1$=CH$_3$, Y$_1$=CH$_2$) |
| SO$_2$CH$_2$CH$_3$ | OCH$_3$ | CH$_3$ | A-3 (X$_1$=OCH$_3$) |
| SO$_2$CH$_2$CH$_3$ | OCH$_3$ | CH$_3$ | A-4 (X$_1$=OCH$_3$, Y$_3$=CH$_3$) |
| SO$_2$CH$_2$CH$_3$ | OCH$_3$ | CH$_3$ | A-5 (X$_2$=CH$_3$, Y$_2$=OCH$_3$) |
| SO$_2$CH$_2$CH$_3$ | OCH$_3$ | CH$_3$ | A-6 (X$_3$=OCH$_3$) |
| SO$_2$CH$_2$CH$_3$ | OCH$_3$ | CH$_3$ | A-7 (X$_4$=OCH$_3$, Y$_4$=OCH$_3$) |
| SO$_2$CH$_2$CH$_3$ | NHCH$_3$ | CH$_3$ | A-2 (X$_1$=CH$_3$, Y$_1$=CH$_2$) |
| SO$_2$CH$_2$CH$_3$ | NHCH$_3$ | CH$_3$ | A-3 (X$_1$=OCH$_3$) |
| SO$_2$CH$_2$CH$_3$ | NHCH$_3$ | CH$_3$ | A-4 (X$_1$=OCH$_3$, Y$_3$=CH$_3$) |
| SO$_2$CH$_2$CH$_3$ | NHCH$_3$ | CH$_3$ | A-5 (X$_2$=CH$_3$, Y$_2$=OCH$_3$) |
| SO$_2$CH$_2$CH$_3$ | NHCH$_3$ | CH$_3$ | A-6 (X$_3$=OCH$_3$) |
| SO$_2$CH$_2$CH$_3$ | NHCH$_3$ | CH$_3$ | A-7 (X$_4$=OCH$_3$, Y$_4$=OCH$_3$) |
| SO$_2$CH$_2$CH$_3$ | N(CH$_3$)$_2$ | CH$_3$ | A-2 (X$_1$=CH$_3$, Y$_1$=CH$_2$) |
| SO$_2$CH$_2$CH$_3$ | N(CH$_3$)$_2$ | CH$_3$ | A-3 (X$_1$=OCH$_3$) |
| SO$_2$CH$_2$CH$_3$ | N(CH$_3$)$_2$ | CH$_3$ | A-4 (X$_1$=OCH$_3$, Y$_3$=CH$_3$) |
| SO$_2$CH$_2$CH$_3$ | N(CH$_3$)$_2$ | CH$_3$ | A-5 (X$_2$=CH$_3$, Y$_2$=OCH$_3$) |
| SO$_2$CH$_2$CH$_3$ | N(CH$_3$)$_2$ | CH$_3$ | A-6 (X$_3$=OCH$_3$) |
| SO$_2$CH$_2$CH$_3$ | N(CH$_3$)$_2$ | CH$_3$ | A-7 (X$_4$=OCH$_3$, Y$_4$=OCH$_3$) |
| SO$_2$CH$_2$CH$_3$ | —CH$_2$CH$_2$CH$_2$— | | A-2 (X$_1$=CH$_3$, Y$_1$=CH$_2$) |
| SO$_2$CH$_2$CH$_3$ | —CH$_2$CH$_2$CH$_2$— | | A-3 (X$_1$=OCH$_3$) |
| SO$_2$CH$_2$CH$_3$ | —CH$_2$CH$_2$CH$_2$— | | A-4 (X$_1$=OCH$_3$, Y$_3$=CH$_3$) |
| SO$_2$CH$_2$CH$_3$ | —CH$_2$CH$_2$CH$_2$— | | A-5 (X$_2$=CH$_3$, Y$_2$=OCH$_3$) |
| SO$_2$CH$_2$CH$_3$ | —CH$_2$CH$_2$CH$_2$— | | A-6 (X$_3$=OCH$_3$) |
| SO$_2$CH$_2$CH$_3$ | —CH$_2$CH$_2$CH$_2$— | | A-7 (X$_4$=OCH$_3$, Y$_4$=OCH$_3$) |
| SO$_2$CH$_2$CH$_3$ | —CH$_2$CH$_2$OCH$_2$CH$_2$— | | A-2 (X$_1$=CH$_3$, Y$_1$=CH$_2$) |
| SO$_2$CH$_2$CH$_3$ | —CH$_2$CH$_2$OCH$_2$CH$_2$— | | A-3 (X$_1$=OCH$_3$) |
| SO$_2$CH$_2$CH$_3$ | —CH$_2$CH$_2$OCH$_2$CH$_2$— | | A-4 (X$_1$=OCH$_3$, Y$_3$=CH$_3$) |
| SO$_2$CH$_2$CH$_3$ | —CH$_2$CH$_2$OCH$_2$CH$_2$— | | A-5 (X$_2$=CH$_3$, Y$_2$=(OCH$_3$) |
| SO$_2$CH$_2$CH$_3$ | —CH$_2$CH$_2$OCH$_2$CH$_2$— | | A-6 (X$_3$=OCH$_3$) |
| SO$_2$CH$_2$CH$_3$ | —CH$_2$CH$_2$OCH$_2$CH$_2$— | | A-7 (X$_4$=OCH$_3$, Y$_4$=OCH$_3$) |
| Br | CH$_3$ | H | A-2 (X$_1$=CH$_3$, Y$_1$=CH$_2$) |
| Br | CH$_3$ | H | A-3 (X$_1$=OCH$_3$) |
| Br | CH$_3$ | H | A-4 (X$_1$=OCH$_3$, Y$_3$=CH$_3$) |
| Br | CH$_3$ | H | A-5 (X$_2$=CH$_3$, Y$_2$=OCH$_3$) |
| Br | CH$_3$ | H | A-6 (X$_3$=OCH$_3$) |
| Br | CH$_3$ | H | A-7 (X$_4$=OCH$_3$, Y$_4$=OCH$_3$) |
| Br | CH$_3$ | CH$_3$ | A-2 (X$_1$=CH$_3$, Y$_1$=CH$_2$) |
| Br | CH$_3$ | CH$_3$ | A-3 (X$_1$=OCH$_3$) |
| Br | CH$_3$ | CH$_3$ | A-4 (X$_1$=OCH$_3$, Y$_3$=CH$_3$) |
| Br | CH$_3$ | CH$_3$ | A-5 (X$_2$=CH$_3$, Y$_2$=OCH$_3$) |
| Br | CH$_3$ | CH$_3$ | A-6 (X$_3$=OCH$_3$) |
| Br | CH$_3$ | CH$_3$ | A-7 (X$_4$=OCH$_3$, Y$_4$=OCH$_3$) |

TABLE IV-continued
GENERAL STRUCTURE 4

| R₁ | R₂ | R₃ | A |
|---|---|---|---|
| Br | CH₂CH=CH₂ | H | A-2 (X₁=CH₃, Y₁=CH₂) |
| Br | CH₂CH=CH₂ | H | A-3 (X₁=OCH₃) |
| Br | CH₂CH=CH₂ | H | A-4 (X₁=OCH₃, Y₃=CH₃) |
| Br | CH₂CH=CH₂ | H | A-5 (X₂=CH₃, Y₂=OCH₃) |
| Br | CH₂CH=CH₂ | H | A-6 (X₃=OCH₃) |
| Br | CH₂CH=CH₂ | H | A-7 (X₄=OCH₃, Y₄=OCH₃) |
| CH₂CH₃ | CH₃ | H | A-2 (X₁=CH₃, Y₁=CH₂) |
| CH₂CH₃ | CH₃ | H | A-3 (X₁=OCH₃) |
| CH₂CH₃ | CH₃ | H | A-4 (X₁=OCH₃, Y₃=CH₃) |
| CH₂CH₃ | CH₃ | H | A-5 (X₂=CH₃, Y₂=OCH₃) |
| CH₂CH₃ | CH₃ | H | A-6 (X₃=OCH₃) |
| CH₂CH₃ | CH₃ | H | A-7 (X₄=OCH₃, Y₄=OCH₃) |
| CH₂CH₃ | CH₃ | CH₃ | A-2 (X₁=CH₃, Y₁=CH₂) |
| CH₂CH₃ | CH₃ | CH₃ | A-3 (X₁=OCH₃) |
| CH₂CH₃ | CH₃ | CH₃ | A-4 (X₁=OCH₃, Y₃=CH₃) |
| CH₂CH₃ | CH₃ | CH₃ | A-5 (X₂=CH₃, Y₂=OCH₃) |
| CH₂CH₃ | CH₃ | CH₃ | A-6 (X₃=OCH₃) |
| CH₂CH₃ | CH₃ | CH₃ | A-7 (X₄=OCH₃, Y₄=OCH₃) |
| CH₂CH₃ | CH₂CH=CH₂ | H | A-2 (X₁=CH₃, Y₁=CH₂) |
| CH₂CH₃ | CH₂CH=CH₂ | H | A-3 (X₁=OCH₃) |
| CH₂CH₃ | CH₂CH=CH₂ | H | A-4 (X₁=OCH₃, Y₃=CH₃) |
| CH₂CH₃ | CH₂CH=CH₂ | H | A-5 (X₂=CH₃, Y₂=(OCH₃) |
| CH₂CH₃ | CH₂CH=CH₂ | H | A-6 (X₃=OCH₃) |
| CH₂CH₃ | CH₂CH=CH₂ | H | A-7 (X₄=OCH₃, Y₄=OCH₃) |
| CF₃ | CH₃ | H | A-2 (X₁=CH₃, Y₁=CH₂) |
| CF₃ | CH₃ | H | A-3 (X₁=OCH₃) |
| CF₃ | CH₃ | H | A-4 (X₁=OCH₃, Y₃=CH₃) |
| CF₃ | CH₃ | H | A-5 (X₂=CH₃, Y₂=OCH₃) |
| CF₃ | CH₃ | H | A-6 (X₃=OCH₃) |
| CF₃ | CH₃ | H | A-7 (X₄=OCH₃, Y₄=OCH₃) |
| CF₃ | CH₃ | CH₃ | A-2 (X₁=CH₃, Y₁=CH₂) |
| CF₃ | CH₃ | CH₃ | A-3 (X₁=OCH₃) |
| CF₃ | CH₃ | CH₃ | A-4 (X₁=OCH₃, Y₃=CH₃) |
| CF₃ | CH₃ | CH₃ | A-5 (X₂=CH₃, Y₂=OCH₃) |
| CF₃ | CH₃ | CH₃ | A-6 (X₃=OCH₃) |
| CF₃ | CH₃ | CH₃ | A-7 (X₄=OCH₃, Y₄=OCH₃) |
| CF₃ | CH₂CH=CH₂ | H | A-2 (X₁=CH₃, Y₁=CH₂) |
| CF₃ | CH₂CH=CH₂ | H | A-3 (X₁=OCH₃) |
| CF₃ | CH₂CH=CH₂ | H | A-4 (X₁=OCH₃, Y₃=CH₃) |
| CF₃ | CH₂CH=CH₂ | H | A-5 (X₂=CH₃, Y₂=OCH₃) |
| CF₃ | CH₂CH=CH₂ | H | A-6 (X₃=OCH₃) |
| CF₃ | CH₂CH=CH₂ | H | A-7 (X₄=OCH₃, Y₄=OCH₃) |
| OCH₃ | CH₃ | H | A-2 (X₁=CH₃, Y₁=CH₂) |
| OCH₃ | CH₃ | H | A-3 (X₁=OCH₃) |
| OCH₃ | CH₃ | H | A-4 (X₁=OCH₃, Y₃=CH₃) |
| OCH₃ | CH₃ | H | A-5 (X₂=CH₃, Y₂=OCH₃) |
| OCH₃ | CH₃ | H | A-6 (X₃=OCH₃) |
| OCH₃ | CH₃ | H | A-7 (X₄=OCH₃, Y₄=OCH₃) |
| OCH₃ | CH₃ | CH₃ | A-2 (X₁=CH₃, Y₁=CH₂) |
| OCH₃ | CH₃ | CH₃ | A-3 (X₁=OCH₃) |
| OCH₃ | CH₃ | CH₃ | A-4 (X₁=OCH₃, Y₃=CH₃) |
| OCH₃ | CH₃ | CH₃ | A-5 (X₂=CH₃, Y₂=OCH₃) |
| OCH₃ | CH₃ | CH₃ | A-6 (X₃=OCH₃) |
| OCH₃ | CH₃ | CH₃ | A-7 (X₄=OCH₃, Y₄=OCH₃) |
| OCH₃ | CH₂CH=CH₂ | H | A-2 (X₁=CH₃, Y₁=CH₂) |
| OCH₃ | CH₂CH=CH₂ | H | A-3 (X₁=OCH₃) |
| OCH₃ | CH₂CH=CH₂ | H | A-4 (X₁=OCH₃, Y₃=CH₃) |
| OCH₃ | CH₂CH=CH₂ | H | A-5 (X₂=CH₃, Y₂=(OCH₃) |
| OCH₃ | CH₂CH=CH₂ | H | A-6 (X₃=OCH₃) |
| OCH₃ | CH₂CH=CH₂ | H | A-7 (X₄=OCH₃, Y₄=OCH₃) |
| OCF₂H | CH₃ | H | A-2 (X₁=CH₃, Y₁=CH₂) |
| OCF₂H | CH₃ | H | A-3 (X₁=OCH₃) |
| OCF₂H | CH₃ | H | A-4 (X₁=OCH₃, Y₃=CH₃) |
| OCF₂H | CH₃ | H | A-5 (X₂=CH₃, Y₂=OCH₃) |
| OCF₂H | CH₃ | H | A-6 (X₃=OCH₃) |
| OCF₂H | CH₃ | H | A-7 (X₄=OCH₃, Y₄=OCH₃) |
| OCF₂H | CH₃ | CH₃ | A-2 (X₁=CH₃, Y₁=CH₂) |
| OCF₂H | CH₃ | CH₃ | A-3 (X₁=OCH₃) |
| OCF₂H | CH₃ | CH₃ | A-4 (X₁=OCH₃, Y₃=CH₃) |
| OCF₂H | CH₃ | CH₃ | A-5 (X₂=CH₃, Y₂=OCH₃) |
| OCF₂H | CH₃ | CH₃ | A-6 (X₃=OCH₃) |
| OCF₂H | CH₃ | CH₃ | A-7 (X₄=OCH₃, Y₄=OCH₃) |
| OCF₂H | CH₂CH=CH₂ | H | A-2 (X₁=CH₃, Y₁=CH₂) |
| OCF₂H | CH₂CH=CH₂ | H | A-3 (X₁=OCH₃) |
| OCF₂H | CH₂CH=CH₂ | H | A-4 (X₁=OCH₃, Y₃=CH₃) |
| OCF₂H | CH₂CH=CH₂ | H | A-5 (X₂=CH₃, Y₂=OCH₃) |
| OCF₂H | CH₂CH=CH₂ | H | A-6 (X₃=OCH₃) |
| OCF₂H | CH₂CH=CH₂ | H | A-7 (X₄=OCH₃, Y₄=OCH₃) |
| SCF₂H | CH₃ | H | A-2 (X₁=CH₃, Y₁=CH₂) |
| SCF₂H | CH₃ | H | A-3 (X₁=OCH₃) |

TABLE IV-continued

GENERAL STRUCTURE 4

| R$_1$ | R$_2$ | R$_3$ | A |
|---|---|---|---|
| SCF$_2$H | CH$_3$ | H | A-4 (X$_1$=OCH$_3$, Y$_3$=CH$_3$) |
| SCF$_2$H | CH$_3$ | H | A-5 (X$_2$=CH$_3$, Y$_2$=OCH$_3$) |
| SCF$_2$H | CH$_3$ | H | A-6 (X$_3$=OCH$_3$) |
| SCF$_2$H | CH$_3$ | H | A-7 (X$_4$=OCH$_3$, Y$_4$=OCH$_3$) |
| SCF$_2$H | CH$_3$ | CH$_3$ | A-2 (X$_1$=CH$_3$, Y$_1$=CH$_2$) |
| SCF$_2$H | CH$_3$ | CH$_3$ | A-3 (X$_1$=OCH$_3$) |
| SCF$_2$H | CH$_3$ | CH$_3$ | A-4 (X$_1$=OCH$_3$, Y$_3$=CH$_3$) |
| SCF$_2$H | CH$_3$ | CH$_3$ | A-5 (X$_2$=CH$_3$, Y$_2$=OCH$_3$) |
| SCF$_2$H | CH$_3$ | CH$_3$ | A-6 (X$_3$=OCH$_3$) |
| SCF$_2$H | CH$_3$ | CH$_3$ | A-7 (X$_4$=OCH$_3$, Y$_4$=OCH$_3$) |
| SCF$_2$H | CH$_2$CH=CH$_2$ | H | A-2 (X$_1$=CH$_3$, Y$_1$=CH$_2$) |
| SCF$_2$H | CH$_2$CH=CH$_2$ | H | A-3 (X$_1$=OCH$_3$) |
| SCF$_2$H | CH$_2$CH=CH$_2$ | H | A-4 (X$_1$=OCH$_3$, Y$_3$=CH$_3$) |
| SCF$_2$H | CH$_2$CH=CH$_2$ | H | A-5 (X$_2$=CH$_3$, Y$_2$=(OCH$_3$)) |
| SCF$_2$H | CH$_2$CH=CH$_2$ | H | A-6 (X$_3$=OCH$_3$) |
| SCF$_2$H | CH$_2$CH=CH$_2$ | H | A-7 (X$_4$=OCH$_3$, Y$_4$=OCH$_3$) |
| SO$_2$CF$_2$H | CH$_3$ | H | A-2 (X$_1$=CH$_3$, Y$_1$=CH$_2$) |
| SO$_2$CF$_2$H | CH$_3$ | H | A-3 (X$_1$=OCH$_3$) |
| SO$_2$CF$_2$H | CH$_3$ | H | A-4 (X$_1$=OCH$_3$, Y$_3$=CH$_3$) |
| SO$_2$CF$_2$H | CH$_3$ | H | A-5 (X$_2$=CH$_3$, Y$_2$=OCH$_3$) |
| SO$_2$CF$_2$H | CH$_3$ | H | A-6 (X$_3$=OCH$_3$) |
| SO$_2$CF$_2$H | CH$_3$ | H | A-7 (X$_4$=OCH$_3$, Y$_4$=OCH$_3$) |
| SO$_2$CF$_2$H | CH$_3$ | CH$_3$ | A-2 (X$_1$=CH$_3$, Y$_1$=CH$_2$) |
| SO$_2$CF$_2$H | CH$_3$ | CH$_3$ | A-3 (X$_1$=OCH$_3$) |
| SO$_2$CF$_2$H | CH$_3$ | CH$_3$ | A-4 (X$_1$=OCH$_3$, Y$_3$=CH$_3$) |
| SO$_2$CF$_2$H | CH$_3$ | CH$_3$ | A-5 (X$_2$=CH$_3$, Y$_2$=OCH$_3$) |
| SO$_2$CF$_2$H | CH$_3$ | CH$_3$ | A-6 (X$_3$=OCH$_3$) |
| SO$_2$CF$_2$H | CH$_3$ | CH$_3$ | A-7 (X$_4$=OCH$_3$, Y$_4$=OCH$_3$) |
| SO$_2$CF$_2$H | CH$_2$CH=CH$_2$ | H | A-2 (X$_1$=CH$_3$, Y$_1$=CH$_2$) |
| SO$_2$CF$_2$H | CH$_2$CH=CH$_2$ | H | A-3 (X$_1$=OCH$_3$) |
| SO$_2$CF$_2$H | CH$_2$CH=CH$_2$ | H | A-4 (X$_1$=OCH$_3$, Y$_3$=CH$_3$) |
| SO$_2$CF$_2$H | CH$_2$CH=CH$_2$ | H | A-5 (X$_2$=CH$_3$, Y$_2$=OCH$_3$) |
| SO$_2$CF$_2$H | CH$_2$CH=CH$_2$ | H | A-6 (X$_3$=OCH$_3$) |
| SO$_2$CF$_2$H | CH$_2$CH=CH$_2$ | H | A-7 (X$_4$=OCH$_3$, Y$_4$=OCH$_3$) |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid inert diluent(s). More specifically, they will contain these ingredients in the following approximate proportions:

| | Weight Percent* | | |
|---|---|---|---|
| | Active Ingredient | Diluent(s) | Surfactant(s) |
| Wettable Powders | 20–90 | 0–74 | 1–10 |
| Oil Suspensions, Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", Chemical Engineering, Dec. 4, 1967, pp. 147ff. and "Perry's Chemical Engineer's Handbook", 5th Ed., McGraw-Hill, New York, 1973, pp. 8–57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, June 23, 1959, Col. 3, line 66 through Col. 5, line 17 and Examples 1–4;

G. C. Klingman, "Weed Control as a Science", John Wiley and Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

In the following Examples, all parts are by weight unless otherwise indicated.

EXAMPLE 2

Wettable Powder

| | |
|---|---|
| N-[[(4,6-Dimethoxy-2-pyrimidinyl)amino]carbonyl]-6-(diethylamino)-2-pyridinesulfonamide | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

EXAMPLE 3

| | |
|---|---|
| 6-(Dimethylamino)-N-[[(4-ethoxy-6-(methylamino)-1,3,5-triazin-2-yl]amino]carbonyl]-2-pyridinesulfonamide | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 4

Granule

| | |
|---|---|
| Wettable Powder of Example 3 | 5% |
| attapulgite granules (U.S.S. 20 to 40 mesh; 0.84–0.42 mm) | 95% |

A slurry of wettable powder containing 25 % solids is sprayed on the surface of attapulgite granules in a double-cone blender. The granules are dried and packaged.

EXAMPLE 5

Extruded Pellet

| | |
|---|---|
| N-[[[(4-Ethoxy-6-(dimethylamino)-1,3,5-triazin-2-yl]amino]carbonyl]-6-(methylamino)-2-pyridinesulfonamide | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 6

Low Strength Granule

| | |
|---|---|
| N-[[(4,6-Dimethoxy-2-pyrimidinyl)amino]carbonyl]-6-(dimethylamino)-2-pyridinesulfonamide | 0.1% |
| attapulgite granules (U.S.S. 20 to 40 mesh) | 99.9% |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 7

Granule

| | |
|---|---|
| 6-(Diethylamino)-N-[[(4-ethoxy-6-(methylamino)-1,3,5-triazin-2-yl]amino]carbonyl]-2-pyridinesulfonamide | 80% |
| wetting agent | 1% |
| crude ligninsulfonate salt (containing 5 to 20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed into the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14 to 100 mesh (1410 to 149 microns), and packaged for use.

EXAMPLE 8

Low Strength Granule

| | |
|---|---|
| N-[[[(4-Ethoxy-6-(dimethylamino)-1,3,5-triazin-2-yl]amino]carbonyl]-6-(methylamino)-2-pyridinesulfonamide | 1% |
| N,N-dimethylformamide | 9% |
| attapulgite granules (U.S.S. 20 to 40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 9

Aqueous Suspension

| | |
|---|---|
| N-[[(4,6-Dimethoxy-2-pyrimidinyl)amino]-carbonyl]-6-(dimethylamino)-2-pyridine-sulfonamide | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 10

Solution

| | |
|---|---|
| 6-(Dimethylamino)-N-[[(4-ethoxy-6-(methyl-amino)-1,3,5-triazin-2-yl]amino]carbonyl]-2-pyridinesulfonamide, sodium salt | 5% |
| water | 95% |

The salt is added directly to the water with stirring to produce the solution, which may then be packaged for use.

EXAMPLE 11

High strength Concentrate

| | |
|---|---|
| N-[[[(4-Ethoxy-6-(dimethylamino)-1,3,5-triazin-2-yl]amino]carbonyl]-6-(methyl-amino)-2-pyridinesulfonamide | 99% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

EXAMPLE 12

Wettable Powder

| | |
|---|---|
| N-[[(4,6-Dimethoxy-2-pyrimidinyl)amino]-carbonyl]-6-(dimethylamino)-2-pyridine-sulfonamide | 90% |
| dioctyl sodium sulfosuccinate | 0.1% |
| synthetic fine silica | 9.9% |

The ingredients are blended and ground in a hammer-mill to produce particles essentially all below 100 microns. The material is sifted through a U.S.S. No. 50 screen and then packaged.

EXAMPLE 13

Wettable Powder

| | |
|---|---|
| 6-(Dimethylamino)-N-[[(4-ethoxy-6-(methyl-amino)-1,3,5-triazin-2-yl]amino]carbonyl]-2-pyridinesulfonamide | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 14

Oil Suspension

| | |
|---|---|
| N-[[[(4-Ethoxy-6-(dimethylamino)-1,3,5-triazin-2-yl]amino]carbonyl]-6-(methyl-amino)-2-pyridinesulfonamide | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

EXAMPLE 15

Dust

| | |
|---|---|
| N-[[(4,6-Dimethoxy-2-pyrimidinyl)amino]-carbonyl]-6-(dimethylamino)-2-pyridine-sulfonamide | 10% |
| attapulgite | 10% |
| Pyrophyllite | 80% |

The active ingredient is blended with attapulgite and then passed through a hammer-mill to produce particles substantially all below 200 microns. The ground concentrate is then blended with powdered pyrophyllite until homogeneous.

EXAMPLE 16

Oil Suspension

| | |
|---|---|
| 6-(Dimethylamino)-N-[[(4-ethoxy-6-(methyl-amino)-1,3,5-triazin-2-yl]amino]carbonyl]-2-pyridinesulfonamide | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 17

Wettable Powder

| | |
|---|---|
| N-[[[(4-Ethoxy-6-(dimethylamino)-1,3,5-triazin-2-yl]amino]carbonyl]-6-(methyl-amino)-2-pyridinesulfonamide | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve (0.3 mm opening) and packaged.

Utility

Test results indicate that the compounds of the present invention are highly active preemergent or postemergent herbicides or plant growth regulants. Many of them have utility for broad-spectrum pre- and/or post-emergence weed control in areas where complete control of all vegetation is desired, such as around storage tanks, parking lots, drive-in theaters, billboards, highways, and railroad structures. Some compounds have utility for selective weed control in cereal crops, such as wheat and barley, corn, cotton, rape, soybean and sugarbeet, and for weed control in fallow. Some of the compounds are particularly useful for the control of grass weeds, such as wild oat, in cereal crops, such as wheat and barley. Also, some of the compounds are particularly useful for the control of weeds in cotton and/or rape. Alternatively, the subject compounds are useful to modify plant growth.

The rates of application for the compounds of the invention are determined by a number of factors, including their use as plant growth modifiers or as herbicides, the crop species involved, the types of weeds to be controlled, weather and climate, formulations selected, mode of application, amount of foliage present, etc. In general terms, the subject compounds should be applied at levels of around 0.0005 to 20 kg/ha, the lower rates being suggested for use on lighter soils and/or those having a low organic matter content, for plant growth modification or for situations where only short-term persistence is required such as herbicide for fallow land.

The compounds of this invention may be used in combination with other commercial herbicides, insecticides or fungicides. The following list exemplifies some of the herbicides suitable for use in mixtures.

| Common Name | Chemical Name |
| --- | --- |
| acetochlor | 2-chloro-N-(ethoxymethyl)-N-(2-ethyl-6-methylphenyl)acetamide |
| acifluorfen | 5-[2-chloro-4-(trifluoromethyl)phenoxy]-2-nitrobenzoic acid |
| acrolein | 2-propenal |
| alachlor | 2-chloro-N-(2,6-diethylphenyl)-N-(methoxymethyl)acetamide |
| ametryn | N-ethyl-N'-(1-methylethyl)-6-(methylthio)-1,3,5-triazine-2,4-diamine |
| amitrole | 1H-1,2,4-triazol-3-amine |
| AMS | ammonium sulfamate |
| asulam | methyl [(4-aminophenyl)sulfonyl]carbamate |
| atrazine | 6-chloro-N-ethyl-N'-(1-methylethyl)-1,3,5-triazine-2,4-diamine |
| barban | 4-chloro-2-butynyl 3-chlorocarbamate |
| benefin | N-butyl-N-ethyl-2,6-dinitro-4-(trifluoromethyl)benzenamine |
| bensulfuron methyl | 2-[[[[(4,6-dimethoxy-2-pyrimidinyl)amino]methylcarbonyl]amino]sulfonyl]methyl]benzoic acid, methyl ester |
| bensulide | O,O-bis(1-methylethyl) S-[2-[(phenylsulfonyl)amino]ethyl]phosphorodithioate |
| bentazon | 3-(1-methylethyl)-(1H)-2,1,3-benzothiadiazin-4(3H)-one, 2,2-dioxide |
| benzofluor | N-[4-(ethylthio)-2-(trifluoromethyl)phenyl]methanesulfonamide |
| benzoylprop | N-benzoyl-N-(3,4-dichlorophenyl)-DL-alanine |
| bifenox | methyl 5-(2,4-dichlorophenoxy)-2-nitrobenzoate |
| bromacil | 5-bromo-6-methyl-3-(1-methylpropyl)-2,4(1H,3H)pyrimidinedione |
| bromoxynil | 3,5-dibromo-4-hydroxybenzonitrile |
| butachlor | N-(butoxymethyl)-2-chloro-N-(2,6-diethylphenyl)acetamide |
| buthidazole | 3-[5-(1,1-dimethylethyl)-1,3,4-thiadiazol-2-yl]-4-hydroxy-1-methyl-2-imidazolidinone |
| butralin | 4-(1,1-dimethylethyl)-N-(1-methylpropyl)-2,6-dinitrobenzenamine |
| butylate | S-ethyl bis(2-methylpropyl)carbamothioate |
| cacodylic acid | dimethyl arsinic oxide |
| CDAA | 2-chloro-N,N-di-2-propenylacetamide |
| CDEC | 2-chloroallyl diethyldithiocarbamate |
| chloramben | 3-amino-2,5-dichlorobenzoic acid |
| chlorbromuron | 3-(4-bromo-3-chlorophenyl)-1-methoxy-1-methylurea |
| chlorimuron | 2-[[[[(4-chloro-6-methoxy-2-pyrimidinyl)ethylamino]carbonyl]amino]sulfonyl]benzoic acid, ethyl ester |
| chloroxuron | N'-[4-(4-chlorophenoxy)phenyl]-N,N-dimethylurea |
| chlorpropham | 1-methylethyl 3-chlorophenylcarbamate |
| chlorsulfuron | 2-chloro-N-[[(4-methoxy-6-methyl-1,3,5-triazin-2-yl)amino]carbonyl]benzenesulfonamide |
| chlortoluron | N'-(3-chloro-4-methylphenyl)-N,N-dimethylurea |
| cinmethylin | exo-1-methyl-4-(1-methylethyl)-2-[(2-methylphenyl)methoxy]-7-oxabicyclo[2.2.1]heptane |
| clethodim | (E,E)-(±)-2-[1-[[(3-chloro-2-propenyl)oxy]imino]propyl]-5-[2-(ethylthio)propyl]-3-hydroxy-2-cyclohexen-1-one |
| clomazone | 2-[(2-chlorophenyl)methyl]-4,4-dimethyl-3-isoxazolidinone |
| cloproxydim | (E,E)-2-[1-[[(3-chloro-2-propenyl)oxy]imino]butyl]-5-[2-(ethylthio)propyl]-3-hydroxy-2-cyclohexen-1-one |
| clopyralid | 3,6-dichloro-2-pyridinecarboxylic acid |
| CMA | calcium salt of MAA |
| cyanazine | 2-[[4-chloro-6-(ethylamino)-1,3,5-triazin-2-yl]amino]-2-methylpropanenitrile |
| cycloate | S-ethyl cyclohexylethylcarbamothioate |
| cycluron | 3-cyclooctyl-1,1-dimethylurea |
| cyperquat | 1-methyl-4-phenylpyridinium |
| cyprazine | 2-chloro-4-(cyclopropylamino)-6-(isopropylamino)-s-triazine |
| cyprazole | N-[5-(2-chloro-1,1-dimethylethyl)-1,3,4-thiadiazol-2-yl]cyclopropanecarboxamide |
| cypromid | 3',4'-dichlorocyclopropanecarboxanilide |
| dalapon | 2,2-dichloropropanoic acid |
| dazomet | tetrahydro-3,5-dimethyl-2H-1,3,5-thiadiazine-2-thione |
| DCPA | dimethyl 2,3,5,6-tetrachloro-1,4-benzenedicarboxylate |
| desmediphan | ethyl [3-[[(phenylamino)carbonyl]oxy]phenyl]carbamate |
| desmetryn | 2-(isopropylamino)-4-(methylamino)-6-(methylthio)-s-triazine |
| diallate | S-(2,3-dichloro-2-propenyl)bis(1-methylethyl)carbamothioate |
| dicamba | 3,6-dichloro-2-methoxybenzoic acid |
| dichlobenil | 2,6-dichlorobenzonitrile |
| dichlorprop | (±)-2-(2,4-dichlorophenoxy)propanoic acid |
| dichlofop-methyl | (±)-2-[4-(2,4-dichlorophenoxy)phenoxy]propanoic acid, methyl ester |
| diethatyl | N-(chloroacetyl)-N-(2,6-diethylphenyl)glycine |
| difenzoquat | 1,2-dimethyl-3,5-diphenyl-1H-pyrazolium |
| dinitramine | $N^3,N^3$-diethyl-2,4-dinitro-6-(trifluoromethyl)-1,3-benzenediamine |
| dinoseb | 2-(1-methylpropyl)-4,6-dinitrophenol |
| diphenamid | N,N-dimethyl-α-phenylbenzeneacetamide |

| Common Name | Chemical Name |
|---|---|
| dipropetryn | 6-(ethylthio)-N,N'-bis(1-methylethyl)-1,3,5-triazine-2,4-diamine |
| diquat | 6,7-dihydrodipyrido[1,2-a:2',1'-c]-pyrazinedium ion |
| diuron | N'-(3,4-dichlorophenyl)-N,N-dimethylurea |
| DNOC | 2-methyl-4,6-dinitrophenol |
| DPX-M6316 | 3-[[[[(4-methoxy-6-methyl-1,3,5-triazin-2-yl)amino]carbonyl]amino]sulfonyl]-2-thiophenecarboxylic acid, methyl ester |
| DSMA | disodium salt of MAA |
| endothall | 7-oxabicyclo[2.2.1]heptane-2,3-dicarboxylic acid |
| EPTC | S-ethyl dipropylcarbamothioate |
| ethalfluralin | N-ethyl-N-(2-methyl-2-propenyl)-2,6-dinitro-4-(trifluoromethyl)-benzenamine |
| ethofumesate | (±)-2-ethoxy-2,3-dihydro-3,3-dimethyl-5-benzofuranyl methanesulfonate |
| Express ® | 2-[[[[N-(4-methoxy-6-methyl-1,3,5-triazine-2-yl)-N-methylamino]-carbonyl]amino]sulfonyl]benzoic acid, methyl ester |
| fenac | 2,3,6-trichlorobenzeneacetic acid |
| fenoxaprop | (±)-2-[4-[(6-chloro-2-benzoxazolyl)oxy]phenoxy]propanoic acid |
| fenuron | N,N-dimethyl-N'-phenylurea |
| fenuron TCA | Salt of fenuron and TCA |
| flamprop | N-benzoyl-N-(3-chloro-4-fluorophenyl)-DL-alanine |
| fluazifop | (±)-2-[4-[[5-(trifluoromethyl)-2-pyridinyl]oxy]phenoxy]propanoic acid |
| fluazifop-P | (R)-2-[4-[[5-(trifluoromethyl)-2-pyridinyl]oxy]phenoxy]propanoic acid |
| fluchloralin | N-(2-chloroethyl)-2,6-dinitro-N-propyl-4-(trifluoromethyl)benzenamine |
| fluometuron | N,N,-dimethylN'-[3-(trifluoromethyl)-phenyl]urea |
| fluorochlor-idone | 3-chloro-4-(chloromethyl)-1-[3-(trifluoromethyl)phenyl]-2-pyrrolidinone |
| fluorodifen | p-nitrophenyl α,α,α-trifluoro-2-nitro-p-tolyl ether |
| fluorogly-cofen | carboxymethyl 5-[2-chloro-4-(trifluoromethyl)phenoxy]-2-nitrobenzoate |
| fluridone | 1-methyl-3-phenyl-5-[3-(trifluoromethyl)phenyl]-4(1H)-pyridinone |
| fomesafen | 5-[2-chloro-4-(trifluoromethyl)phenoxy]-N-(methylsulfonyl)-2-nitrobenzamide |
| fosamine | ethyl hydrogen (aminocarbonyl)-phosphate |
| glyphosate | N-(phosphonomethyl)glycine |
| haloxyfop | 2-[4-[[3-chloro-5-(trifluoromethyl)-2-pyridinyl]oxy]phenoxy]propanoic acid |
| hexaflurate | potassium hexafluoroarsenate |
| hexazinone | 3-cyclohexyl-6-(dimethylamino)-1-methyl-1,3,5-triazine-2,4(1H,3H)-dione |
| imazametha-benz | 6-(4-isopropyl-4-methyl-5-oxo-2-imidazolin-2-yl)--toluic acid, methyl ester and 6-(4-isopropyl-4-methyl-5-oxo-2-imidazolin-2-yl)-p-toluic acid, methyl ester |
| imazapyr | (±)-2-[4,5-dihydro-4-methyl-4-(1-methylethyl)-5-oxo-1H-imidazol-2-yl]-3-pyridinecarboxylic acid |
| imazaquin | 2-[4,5-dihydro-4-methyl-4-(1-methylethyl)-5-oxo-1H-imidazol-2-yl]-3-quinolinecarboxylic acid |
| imazethapyr | (±)-2-[4,5-dihydro-4-methyl-4-(1-methylethyl)-5-oxo-1H-imidazol-2-yl]-5-ethyl-3-pyridinecarboxylic acid |
| ioxynil | 4-hydroxy-3,5-diiodobenzonitrile |
| isopropalin | 4-(1-methylethyl)-2,6-dinitro-N,N-dipropylbenzenamine |
| isoproturon | N-(4-isopropylphenyl)-N',N'-dimethylurea |
| isouron | N'-[5-(1,1-dimethylethyl)-3-isoxazolyl]-N,N-dimethylurea |
| isoxaben | N-[3-(1-ethyl-1-methylpropyl)-5-isoxazolyl]-2,6-dimethoxybenzamide |
| karbutilate | 3-[[(dimethylamino)carbonyl]amino]-phenyl-(1,1-dimethylethyl)carbamate |
| lactofen | (±)-2-ethoxy-1-methyl-2-oxoethyl 5-[2-chloro-4-(trifluoromethyl)phenoxy]-2-nitrobenzoate |
| lenacil | 3-cyclohexyl-6,7-dihydro-1H-cyclopenta-pyrimidine-2,4(3H,5H)-dione |
| linuron | N'-(3,4-dichlorophenyl)-N-methoxy-N-methylurea |
| MAA | methylarsonic acid |
| MAMA | monoammonium salt of MAA |
| MCPA | (4-chloro-2-methylphenoxy)acetic acid |
| MCPB | 4-(4-chloro-2-methylphenoxy)butanoic acid |
| mecoprop | (±)-2-(4-chloro-2-methylphenoxy)-propanoic acid |
| mefluidide | N-[2,4-dimethyl-5-[[(trifluoromethyl)-sulfonyl]amino]phenyl]acetamide |
| methal-propalin | N-(2-methyl-2-propenyl)-2,6-dinitro-N-propyl-4-(trifluoromethyl)benzenamide |
| methabenz-thiazuron | 1,3-dimethyl-3-(2-benzothiazolyl)urea |
| metham | methylcarbamodithioic acid |
| methazole | 2-(3,4-dichlorophenyl)-4-methyl-1,2,4-oxadiazolidine-3,5-dione |
| methoxuron | N'-(3-chloro-4-methoxyphenyl)-N,N-dimethylurea |
| metolachlor | 2-chloro-N-(2-ethyl-6-methylphenyl)-N-(2-methoxy-1-methylethyl)acetamide |
| metribuzin | 4-amino-6-(1,1-dimethylethyl)-3-(methylthio)-1,2,4-triazin-5(4H)-one |
| metsulfuron methyl | 2-[[[[(4-methoxy-6-methyl-1,3,5-triazin-2-yl)amino]carbonyl]-amino]sulfonyl]benzoic acid, methyl ester |
| MH | 1,2-dihydro-3,6-pyridazinedione |
| molinate | S-ethyl hexahydro-1H-azepine-1-carbothioate |
| monolinuron | 3-(p-chlorophenyl)-1-methoxy-1-methylurea |
| monuron | N'-(4-chlorophenyl)-N,N-dimethylurea |
| monuron TCA | Salt of monuron and TCA |
| MSMA | monosodium salt of MAA |
| napromide | N,N-diethyl-2-(1-naphthalenyloxy)-propanamide |
| naptalam | 2-[(1-naphthalenylamino)carbonyl]-benzoic acid |
| neburon | 1-butyl-3-(3,4-dichlorophenyl)-1-methylurea |
| nitralin | 4-(methylsulfonyl)-2,6-dinitro-N,N-dipropylaniline |
| nitrofen | 2,4-dichloro-1-(4-nitrophenoxy)benzene |
| nitrofluorfen | 2-chloro-1-(4-nitrophenoxy)-4-(trifluoromethyl)benzene |
| norea | N,N-dimethyl-N'-(octahydro-4,7-methano-1H-inden-5-yl)urea 3a,-4α,5α,7α,7aα-isomer |
| norflurazon | 4-chloro-5-(methylamino)-2-[3-(trifluoromethyl)phenyl]-3(2H)-pyridazinone |
| oryzalin | 4-(dipropylamino)-3,5-dinitro-benzenesulfonamide |
| oxadiazon | 3-[2,4-dichloro-5-(1-methylethoxy)-phenyl]-5-(1,1-dimethylethyl)-1,3,4-oxadiazol-2(3H)-one |
| oxyfluorfen | 2-chloro-1-(3-ethoxy-4-nitrophenoxy)-4-(trifluoromethyl)benzene |
| paraquat | 1,1'-dimethyl-4,4'-dipyridinium ion |
| pebulate | S-propyl butylethylcarbamothioate |
| pendimethalin | N-(1-ethylpropyl)-3,4-dimethyl-2,6-dinitrobenzenamine |
| perfluidone | 1,1,1-trifluoro-N-[2-methyl-4-(phenylsulfonyl)phenyl]methanesulfonamide |
| phenmedipham | 3-[(methoxycarbonyl)amino]phenyl (3-methylphenyl)carbamate |
| picloram | 4-amino-3,5,6-trichloro-2-pyridine-carboxylic acid |
| PPG-1013 | 5-[2-chloro-4-(trifluoromethyl)-phenoxy]-2-nitroacetophenone oxime-O-acetic acid, methyl ester |
| procyazine | 2-[[4-chloro-6-(cyclopropylamino)-1,3,5-triazin-2-yl]amino]-2-methylpropane-nitrile |

-continued

| Common Name | Chemical Name |
|---|---|
| profluralin | N-(cyclopropylmethyl)-2,6-dinitro-N-propyl-4-(trifluoromethyl)benzenamine |
| prometon | 6-methoxy-N,N'-bis(1-methylethyl)-1,3,5-triazine-2,4-diamine |
| prometryn | N,N'-bis(1-methylethyl)-6-(methylthio)-1,3,5-triazine-2,4-diamine |
| pronamide | 3,5-dichloro-N-(1,1-dimethyl-2-propynyl)benzamide |
| propachlor | 2-chloro-N-(1-methylethyl)-N-phenylacetamide |
| propanil | N-(3,4-dichlorophenyl)propanamide |
| propazine | 6-chloro-N,N'-bis(1-methylethyl)-1,3,5-triazine-2,4-diamine |
| propham | 1-methylethyl phenylcarbamate |
| prosulfalin | N-[[4-(dipropylamino)-3,5-dinitrophenyl]sulfonyl]-S,S-dimethylsulfilimine |
| prynachlor | 2-chloro-N-(1-methyl-2-propynyl)acetanilide |
| pyrazon | 5-amino-4-chloro-2-phenyl-3(2H)-pyridazinone |
| quizalofop ethyl | (±)-2-[4-[(6-chloro-2-quinoxalinyl)oxy]phenoxy]propanoic acid, ethyl ester |
| secbumeton | N-ethyl-6-methoxy-N'-(1-methylpropyl)-1,3,5-triazine-2,4-diamine |
| sethoxydim | 2-[1-(ethoxyimino)butyl]-5-[2-(ethylthio)propyl]-3-hydroxy-2-cyclohexen-1-one |
| siduron | N-(2-methylcyclohexyl)-N'-phenylurea |
| simazine | 6-chloro-N,N'-diethyl-1,3,5-triazine-2,4-diamine |
| sulfometuron methyl | 2-[[[[(4,6-dimethyl-2-pyrimidinyl)amino]carbonyl]amino]sulfonyl]benzoic acid, methyl ester |
| TCA | trichloroacetic acid |
| tebuthiuron | N-[5-(1,1-dimethylethyl)-1,3,4-thiadiazol-2-yl]-N,N'-dimethylurea |
| terbacil | 5-chloro-3-(1,1-dimethylethyl)-6-methyl-2,4(1H,3H)-pyrimidinedione phenyl]-5-(1,1-dimethylethYl)- |
| terbuchlor | N-(butoxymethyl)-2-chloro-N-[2-(1,1-dimethylethyl)-6-methylphenyl]-acetamide |
| terbuthylazine | 2-(tert-butylamino)-4-chloro-6-(ethylamino)-s-triazine |
| terbutol | 2,6-di-tert-butyl-p-tolyl methylcarbamate |
| terbutryn | N-(1,1-dimethylethyl)-N'-ethyl-6-(methylthio)-1,3,5-triazine-2,4-diamine |
| thiobencarb | S-[(4-chlorophenyl)methyl] diethylcarbamothioate |
| triallate | S-(2,3,3-trichloro-2-propenyl) bis(1-methylethyl)carbamothioate |
| triclopyr | [(3,5,6-trichloro-2-pyridinyl)oxy]acetic acid |
| tridiphane | 2-(3,5-dichlorophenyl)-2-(2,2,2-trichloroethyl)oxirane |
| trifluralin | 2,6-dinitro-N,N-dipropyl-4-(trifluoromethyl)benzenamine |
| trimeturon | 1-(p-chlorophenyl)-2,3,3-trimethylpseudourea |
| 2,4-D | (2,4-dichlorophenoxy)acetic acid |
| 2,4-DB | 4-(2,4-dichlorophenoxy)butanoic acid |
| vernolate | S-propyl dipropylcarbamothioate |
| xylachlor | 2-chloro-N-(2,3-dimethylphenyl)-N-(1-methylethyl)acetamide |

Herbicidal properties of the subject compounds were discovered in a number of greenhouse tests. Test procedures and results follow.

Herbicidal properties of the subject compounds were discovered in a number of greenhouse tests. Test procedures and results follow.

COMPOUNDS

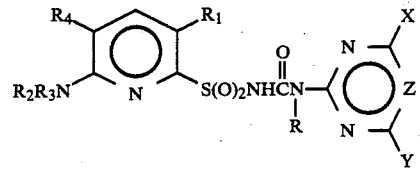

| CMPD | R$_2$ | R$_3$ | R$_1$ | R$_4$ | R | X | Y | Z | m.p. (°C.) |
|---|---|---|---|---|---|---|---|---|---|
| 1 | CH$_3$ | CH$_3$ | H | H | H | OCH$_3$ | OCH$_3$ | CH | 141–143 |
| 2 | CH$_3$ | CH$_3$ | H | H | H | Cl | OCH$_3$ | CH | 161–164 |
| 3 | CH$_3$ | CH$_3$ | H | H | H | CH$_3$ | OCH$_3$ | CH | 163–166 |
| 4 | CH$_3$ | CH$_3$ | H | H | H | CH$_3$ | CH$_3$ | CH | 165–167 |
| 5 | CH$_3$ | CH$_3$ | H | H | H | OCH$_3$ | OCH$_3$ | N | 110–122 |
| 6 | CH$_3$ | CH$_3$ | H | H | H | CH$_3$ | OCH$_3$ | N | 170–172 |
| 7 | CH$_3$ | CH$_3$ | H | H | CH$_3$ | CH$_3$ | OCH$_3$ | N | 152–154 |
| 8 | CH$_3$ | CH$_3$ | H | H | H | NHCH$_3$ | OEt | N | 186–188 |
| 9 | CH$_3$ | CH$_3$ | H | H | H | NMe$_2$ | OEt | N | 185–187 |
| 10 | CH$_3$ | CH$_3$ | H | H | H | OEt | OEt | N | 124–125 |
| 11 | CH$_3$ | CH$_3$ | H | H | H | NMe$_2$ | OCH$_2$CF$_3$ | N | 122–124 |
| 12 | CH$_3$ | CH$_3$ | H | H | H | NMe$_2$ | OCH$_3$ | N | 143–145 |
| 13 | —CH$_2$CH$_2$CH$_2$— | | H | H | H | OCH$_3$ | OCH$_3$ | CH | 143–150 |
| 14 | —CH$_2$CH$_2$CH$_2$— | | H | H | H | Cl | OCH$_3$ | CH | 110–120 |
| 15 | —CH$_2$CH$_2$CH$_2$— | | H | H | H | CH$_3$ | OCH$_3$ | CH | 170–179 |
| 16 | —CH$_2$CH$_2$CH$_2$— | | H | H | H | CH$_3$ | CH$_3$ | CH | 130–142 |
| 17 | —CH$_2$CH$_2$CH$_2$— | | H | H | H | OCH$_3$ | OCH$_3$ | N | 178–184 |
| 18 | —CH$_2$CH$_2$CH$_2$— | | H | H | H | CH$_3$ | OCH$_3$ | N | 112–167 |
| 19 | —CH$_2$CH$_2$CH$_2$— | | H | H | CH$_3$ | CH$_3$ | OCH$_3$ | N | 132–140 |
| 20 | CH$_3$ | H | H | H | H | OCH$_3$ | OCH$_3$ | CH | 166–168 |
| 21 | CH$_3$ | H | H | H | H | Cl | OCH$_3$ | CH | 100–102 |
| 22 | CH$_3$ | H | H | H | H | OCH$_3$ | OCH$_3$ | N | 164–165 |
| 23 | CH$_3$ | H | H | H | H | CH$_3$ | OCH$_3$ | N | 168–170 |
| 24 | CH$_3$ | H | H | H | CH$_3$ | CH$_3$ | OCH$_3$ | N | 118–120 |
| 25 | CH$_3$ | H | H | H | H | CH$_3$ | OCH$_3$ | CH | 160–162 |
| 26 | CH$_3$ | H | H | H | H | CH$_3$ | CH$_3$ | CH | 182–184 |
| 27 | CH$_3$ | H | H | H | H | OEt | OEt | N | 79–81 |

COMPOUNDS-continued

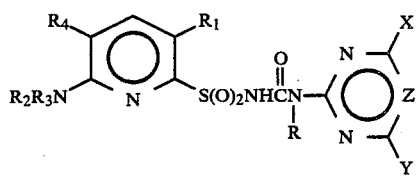

| CMPD | R₂ | R₃ | R₁ | R₄ | R | X | Y | Z | m.p. (°C.) |
|---|---|---|---|---|---|---|---|---|---|
| 28 | CH₃ | H | H | H | H | NMe₂ | OEt | N | 116–117 |
| 29 | CH₃ | H | H | H | H | NMe₂ | OMe | N | 194–195 |
| 30 | CH₃ | H | H | H | H | NMe₂ | OCH₂CF₃ | N | 115–116 |
| 31 | CH₃ | H | H | H | H | NHCH₃ | OEt | N | 114–115 |
| 32 | —CH₂CH₂OCH₂CH₂— |  | H | H | H | OCH₃ | OCH₃ | CH | 176–178 |
| 33 | —CH₂CH₂OCH₂CH₂— |  | H | H | H | Cl | OCH₃ | CH | 153–155 |
| 34 | —CH₂CH₂OCH₂CH₂— |  | H | H | H | CH₃ | OCH₃ | CH | 172–174 |
| 35 | —CH₂CH₂OCH₂CH₂— |  | H | H | H | OCH₃ | OCH₃ | N | 193–195 |
| 36 | —CH₂CH₂OCH₂CH₂— |  | H | H | H | CH₃ | OCH₃ | N | 118–119 |
| 37 | —CH₂CH₂OCH₂CH₂— |  | H | H | CH₃ | CH₃ | OCH₃ | N | 128–130 |
| 38 | —CH₂CH₂OCH₂CH₂— |  | H | H | H | OCH₃ | OCH₃ | N | 199–202 |
| 39 | —CH₂CH₂OCH₂CH₂— |  | H | H | H | NHCH₃ | OEt | N | 197–200 |
| 40 | CH₃ | OCH₃ | H | H | H | OCH₃ | OCH₃ | CH | 148–149 |
| 41 | CH₃ | OCH₃ | H | H | H | Cl | OCH₃ | CH | 104–105 |
| 42 | CH₃ | OCH₃ | H | H | H | CH₃ | OCH₃ | CH | 124–126 |
| 43 | CH₃ | OCH₃ | H | H | H | CH₃ | CH₃ | CH | 167–168 |
| 44 | CH₃ | OCH₃ | H | H | H | OCH₃ | OCH₃ | N | 159–160 |
| 45 | CH₃ | OCH₃ | H | H | H | CH₃ | OCH₃ | N | 160–161 |
| 46 | CH₃ | OCH₃ | H | H | H | NHCH₃ | OEt | N | 167–169 |
| 47 | CH₂CH₃ | H | H | H | H | OCH₃ | OCH₃ | CH | 138–140 |
| 48 | CH₂CH₃ | H | H | H | H | Cl | OCH₃ | CH | 155–156 |
| 49 | CH₂CH₃ | H | H | H | H | CH₃ | OCH₃ | CH | 197–199 |
| 50 | CH₂CH₃ | H | H | H | H | OCH₃ | OCH₃ | N | 153–155 |
| 51 | CH₂CH₃ | H | H | H | H | CH₃ | OCH₃ | N | 144–146 |
| 52 | CH₂CH₃ | H | H | H | H | NMe₂ | OCH₃ | N | 160–162 |
| 53 | CH₂CH₃ | H | H | H | H | NMe₂ | OCH₂CF₃ | N | 138–139 |
| 54 | CH₂CH=CH₂ | H | H | H | H | OCH₃ | OCH₃ | CH | 159–160 |
| 55 | CH₂CH=CH₂ | H | H | H | H | Cl | OCH₃ | CH | 168–170 |
| 56 | CH₂CH=CH₂ | H | H | H | H | CH₃ | OCH₃ | CH | 162 |
| 57 | CH₂CH=CH₂ | H | H | H | H | CH₃ | CH₃ | CH | 107–108 |
| 58 | CH₂CH=CH₂ | H | H | H | H | OCH₃ | OCH₃ | N | 115–117 |
| 59 | CH₂CH=CH₂ | H | H | H | H | CH₃ | OCH₃ | N | 99–100 |
| 60 | CH₂C≡CH | H | H | H | H | OCH₃ | OCH₃ | CH | 156–157 |
| 61 | CH₂C≡CH | H | H | H | H | CH₃ | OCH₃ | CH | 159–160 |
| 62 | CH₂C≡CH | H | H | H | H | OCH₃ | OCH₃ | N | 150–151 |
| 63 | CH₂C≡CH | H | H | H | H | CH₃ | OCH₃ | N | 108–109 |
| 64 | CH₃ | CH₃ | S(O)₂CH₃ | H | H | OCH₃ | OCH₃ | CH | 217–219 |
| 65 | CH₂CF₃ | H | H | H | H | OCH₃ | OCH₃ | CH | 139–145 |
| 66 | CH₂CF₃ | H | H | H | H | CH₃ | OCH₃ | CH | 177–181 |
| 67 | cyclopropyl | H | H | H | H | OCH₃ | OCH₃ | CH | 117–122 |
| 68 | cyclopropyl | H | H | H | H | CH₃ | OCH₃ | CH | 175–178 |
| 69 | cyclopropyl | H | H | H | H | OCH₃ | OCH₃ | N | 120–122 |
| 70 | cyclopropyl | H | H | H | H | CH₃ | OCH₃ | N | 115–120 |
| 71 | cyclopropyl | H | H | H | H | NMe₂ | OCH₃ | N | 175–177 |
| 72 | CH₂C≡CH | CH₃ | H | H | H | OCH₃ | OCH₃ | CH | 195–199 |
| 73 | CH₂C≡CH | CH₃ | H | H | H | Cl | OCH₃ | CH | 165–169 |
| 74 | CH₂C≡CH | CH₃ | H | H | H | CH₃ | OCH₃ | CH | 158–161 |
| 75 | CH₂C≡CH | CH₃ | H | H | H | CH₃ | CH₃ | CH | 159–170 |
| 76 | CH₂C≡CH | CH₃ | H | H | H | OCH₃ | OCH₃ | N | 169–175 |
| 77 | CH₂C≡CH | CH₃ | H | H | H | CH₃ | OCH₃ | N | 160–173 |
| 78 | CH₂C≡CH | CH₃ | H | H | H | NMe₂ | OCH₃ | N | 160–173 |
| 79 | CH₂C≡CH | CH₃ | H | H | H | NMe₂ | OCH₂CF₃ | N | 158–175(d) |
| 80 | CH₂CH₂OH | CH₃ | H | H | H | OCH₃ | OCH₃ | CH | 150–153 |
| 81 | CH₂CH₂OH | CH₃ | H | H | H | CH₃ | OCH₃ | CH | 148–150 |
| 82 | CH₂CH₂OH | CH₃ | H | H | H | CH₃ | OCH₃ | N | 155–158 |
| 83 | CH₃ | CH₃ | Cl | Cl | H | OCH₃ | OCH₃ | CH | 139–145 |
| 84 | CH₃ | CH₃ | Cl | Cl | H | Cl | CH₃ | CH | 175–182 |
| 85 | CH₃ | CH₃ | Cl | Cl | H | CH₃ | OCH₃ | CH | 147–150 |
| 86 | CH₃ | CH₃ | Cl | Cl | H | CH₃ | CH₃ | CH | 138–143 |
| 87 | CH₃ | CH₃ | Cl | Cl | H | OCH₃ | OCH₃ | N | 185–193 |
| 88 | CH₃ | CH₃ | Cl | Cl | H | CH₃ | OCH₃ | N | 160–166 |
| 89 | CH₃ | CH₃ | Cl | Cl | H | OEt | OEt | N | 119–122 |
| 90 | CH₃ | CH₃ | Cl | Cl | H | NHCH₃ | OEt | N | 165–182 |
| 91 | CH₃ | CH₃ | Cl | Cl | H | NMe₂ | OEt | N | 128–192 |
| 92 | CH₃ | CH₃ | Cl | Cl | H | NMe₂ | OCH₃ | N | 103–165 |
| 93 | CH₃ | CH₃ | Cl | Cl | H | NHCH₃ | OCH₂CF₃ | N | 120–195 |
| 94 | CH₃ | CH₃ | Cl | Cl | H | NMe₂ | OCH₂CF₃ | N | 115–145 |
| 95 | CH₃ | CH₃ | S(O)₂CH₂CH₂ | H | H | OCH₃ | OCH₃ | CH | 228–231 |
| 96 | CH₃ | CH₃ | S(O)₂CH₂CH₂ | H | H | CH₃ | OCH₃ | CH | 208–213 |
| 97 | CH₃ | CH₃ | S(O)₂CH₂CH₂ | H | H | Cl | OCH₃ | CH | 205–209 |

COMPOUNDS-continued

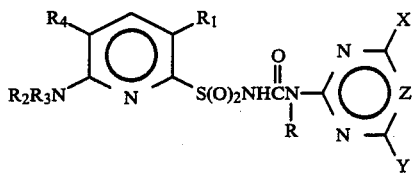

| CMPD | R$_2$ | R$_3$ | R$_1$ | R$_4$ | R | X | Y | Z | m.p. (°C.) |
|---|---|---|---|---|---|---|---|---|---|
| 98 | CH$_3$ | CH$_3$ | S(O)$_2$CH$_2$CH$_2$ | H | H | CH$_3$ | CH$_3$ | CH | 238–246 | wherein Me denotes CH$_3$ and Et denotes CH$_2$CH$_3$.

CL TEST A

Seeds of barley (*Hordeum vulgare*), barnyardgrass (*Echinochloa crus-galli*), cheatgrass (*Bromus secalinus*) or downy brome (*Bromus tectorum*), cocklebur (*Xanthium pensylvanicum*), corn (*Zea mays*), cotton (*Gossypium hirsutum*), crabgrass (Digitaria spp.), giant foxtail (*Setaria faberi*), morningglory (Ipomoea spp.), rice (*Oryza sativa*), sorghum (*Sorghum bicolor*), soybean (*Glycine max*), sugarbeet (*Beta vulgaris*), velvetleaf (*Abutilon theophrasti*), wheat (*Triticum aestivum*), and wild oat (*Avena fatua*) and purple nutsedge (*Cyperus rotundus*) tubers were planted and treated preemergence with test chemicals dissolved in a non-phytotoxic solvent. At the same time, these crop and weed species were also treated with postemergence applications of test chemicals. Plants ranged in height from two to eighteen cm for postemergence treatments. Treated plants and controls were maintained in a greenhouse for sixteen days, after which all species were compared to controls and visually evaluated. The ratings, summarized in Table A, are based on a scale of 0 to 10 where 0 is no effect and 10 is complete control. A dash (—) response means no test. The accompanying descriptive symbols have the following meanings:

C=chlorosis/necrosis;
E=inhibition of emergence;
G=growth retardation;
H=formative effect; and
U=unusual pigmentation.

TABLE A

| | CMPD 1 | | CMPD 2 | | CMPD 3 | | CMPD 4 | | CMPD 5 | | CMPD 6 | | CMPD 7 | | CMPD 8 | | CMPD 9 | | CMPD 10 | |
|---|---|---|---|---|---|---|---|---|---|---|---|---|---|---|---|---|---|---|---|---|
| RATE = KG/HA | 0.05 | 0.01 | 0.05 | 0.01 | 0.05 | 0.01 | 0.05 | 0.01 | 0.05 | 0.01 | 0.05 | 0.01 | 0.05 | 0.4 | 0.05 | 0.01 | 0.05 | 0.01 | 0.05 | 0.01 |
| POSTEMERGENCE | | | | | | | | | | | | | | | | | | | | |
| COTTON | 5C,9G | 2C,9G | 5C,9G | 3C,9G | 9C | 3C,9G | 3C,9G | 2C,7G | 5C,9G | 3C,7G | 7G | 5C,9G | 9C | 4C,8G | 3C,8G | 6G | 10C | 3C,6G |
| MORNINGGLORY | 9C | 10C | 10C | 9C | 10C | 10C | 10C | 3C,8H | 10C | 3C,8G | 9C | 3C,8G | 5C,9G | 10C | 4C,8G | 10C | 4C,8G |
| COCKLEBUR | 10C | 10C | 10C | 10C | 10C | 10C | 5C,9H | 4C,9H | 10C | 10C | 10C | 5C,9G | 10C | 2C,8G | 10C | 2C,8G | 9C |
| NUTSEDGE | 10C | 10C | 10C | 10C | 10C | 10C | 9C | 4C,9H | 6G | 0 | 9C | 9C | 2G | 3C,6G | 4G | 9G | 0 |
| CRABGRASS | 6C,9G | 8G | 9C | 0 | 10C | 8G | 8G | 6G | 4G | 4G | 2C,4G | 3G | 3C,8H | 4G | 0 |
| BARNYARDGRASS | 9C | 9C | 10C | 5C,9G | 9C | 4C,9G | 3C,8G | 3C,8G | 5C,9G | 3C,8G | 9C | 4G | 2C,9G | 9C | 4C,9H | 0 | 4C,9G |
| WILD OATS | 5C,9G | 4C,8G | 5C,9G | 5C,9G | 3C,9G | 3C,9G | 3C,9G | 9G | 3C,9G | 0 | 10C | 9C | 4G | 0 | 3C,8H | 0 | 0 |
| WHEAT | 9C | 4G | 6G | 6G | 9G | 8G | 9G | 6G | 9G | 8G | 10C | 10C | 2G | 10C | 2G | 0 |
| CORN | 9C | 5C,9G | 10C | 5C,9G | 9C | 9C | 10C | 9G | 9C | 8G | 10C | 2C,9G | 2G | 10C | 10C | 10C |
| SOYBEANS | 9C | 6C,9G | 5C,9G | 5C,9G | 5C,9G | 4G | 6C,9G | 9G | 10C | 5C,9G | 6C,6G | 5C,9G | 10C | 5C,9G | 4C,8G | 6C,9G | 5C,9G |
| RICE | 6C,9G | 9C | 6C,9G | 9C/9C | 9C | 5C,9G | 5C,9G | 9C | 4C,9G | 9G | 5C,9G | 9C | 4C,8G | 3C,8G | 3C,8G |
| SORGHUM | 9C | 3C,9G | 9C | 6C,9G | 9C | 3C,9G | 6C,9G | 4C,9G | 4C,9G | 9G | 9G | 5C,9G | 5C,9G | 10C | 10C | 2C,8G |
| CHEATGRASS | 5C,9G | 5C,9G | 9C | 10C | 10C | 4C,9G | 10C | 9C | 10C | 9C | 3G | — | 3C,9G | 10C | 9C | — |
| SUGARBEETS | 10C | 10C | 10C | — | 10C | 9C | 9C | 9C | 9C | 5C,9H | 9C | 5C,9G | 3C,9G | 10C | 5C,9G | 8H | 10C |
| VELVETLEAF | 9C | 9C | 9C | 9C | 10C | 10C | 5C,9H | 3C,9G | 9C | 3C,9G | 8G | 5C,9G | 5C,9G | 7G | 3C,8G |
| GIANT FOXTAIL | 9C | 4C,9G | 9C | 5C,9G | 5C,9G | 3C,9G | 4C,9G | 4C,9G | 4C,9G | 6G | 5C,9G | 3G | 4C,9G | 2C,7G | 8G | 4C,9G | 2C,4G |
| BARLEY | 5C,9G | 7G | 3C,8G | — | 3C,8G | 4C,9G | 8G | 5G | 9G | 4G | 4G | 2G | 3C,7G | 5C,9G | 6G | 4G | 2G |
| DOWNY BROME | — | | — | | — | | — | | — | | — | | — | | 3C,7G | 3C,8G | 4C,9G | 4G |
| PREEMERGENCE | | | | | | | | | | | | | | | | | | | | |
| COTTON | 8G | 7G | 8G | 7G | 7G | 7G | 8G | 7G | 5G | 0 | 0 | 8G | 0 | 0 | 3C,8G | 0 |
| MORNINGGLORY | 9G | 7G | 9G | 8G | 2C,9G | 6G | 3C,8H | 6G | 9G | 7H | 6G | 4G | 0 | 2C,5G | 0 | 2G |
| COCKLEBUR | 3C,7H | 5G | 3C,7H | 6H | 3C,8H | 2C,4H | 10E | 2C,4G | 3C,8H | 3C,6H | 2G | 0 | 0 | 1C | 0 | — | 1C | 0 |
| NUTSEDGE | 10E | 10E | 10E | 9G | 10E | 10C | 10C | 5G | 3C,9G | 3C,8G | 2G | 0 | 0 | 2G | 0 | 0 |
| CRABGRASS | 7G | 4G | 8G | 7G | 4C,9G | 2C,4G | 8G | 2G | 5C,9G | 3C,8G | 0 | 2C | 0 | 2C |
| BARNYARDGRASS | 3C,9H | 2G | 3C,8H | 2C,4H | 9H | 2C,6G | 5G | 2G | 4C,9H | 4C,9H | 4C,9G | 0 | 1C | 4C,9H | 3C,6H | 2C,7G | 4C,9H | 3C,8G |
| WILD OATS | 5G | 0 | 3C,8G | 3G | 2C,8G | 2C,2G | 2G | 4G | 3C,8G | 4C,9H | 4C,8G | 0 | 3C,9G | 2C,5G | 3C,8G | 2C,3G |
| WHEAT | 6G | 3C,3G | 8G | 3G | 2C,8G | 2C,2G | 4G | 4C,8H | 9G | 3C,8G | 9G | 0 | 0 | 4C,4G | 2C,6H | 3C,7G |
| CORN | 2C,7H | 1C,4G | 8G | 2C,3G | 2C,6G | 3G | 3C,9G | 2C,6G | 9C | 9G | 4C,9G | 0 | 0 | 9C | 3C,6H |
| SOYBEANS | 4C,9H | 2G | 4C,8G | 7G | 2C,8G | 4C,8H | 4C,7G | 5G | 10E | 3C,8H | 4C,8H | 0 | 3C,9H | 3C,9H | 3C,8H |
| RICE | 4C,9H | 8G | 9C | 9C | 9H | 9H | 9H | 4G | 10E | 9H | 10H | 3C,4H | 10H | 1C | 3C,6H |
| SORGHUM | 10H | 8G | 9G | 2C,8H | 3C,8H | 3C,8H | 9H | 9H | 4C,9H | 10H | 7G | 9H | 3C,8H | 10H |
| CHEATGRASS | 8G | 2G | 3C,8G | 3G | 8G | 7G | 3C,8H | 5C,9G | 3C,8G | — | 5C,9G | 3C,8G | 2C,7G | 2C,4G |
| SUGARBEETS | 1C,3G | 3G | 2C,7G | 5G | 2C,8G | 6C,9G | 6H | 9G | 3C,7H | 4C,9G | 3H | 8G | 2C | 8G | 3C,8H |
| VELVETLEAF | 3C,8G | 6G | 3C,8G | 2C,7G | 3C,8G | 4C,9G | 7G | 0 | 4C,9G | 3C,6H | 8G | 6H | 4H | 2H |
| GIANT FOXTAIL | 3C,9H | 6G | 3C,9H | 9H | 3C,9H | 4C,8G | 7G | 7G | 4C,9H | 10H | 2C | 2C |
| BARLEY | 8G | 2G | 3C,8G | 0 | 2C,9H | 3C,9H | 3C,8H | 3C,7G | 3G | 4G | 4G | 8G | 8G | 3C,8H |
| DOWNY BROME | — | | — | | 9G | | 8G | | — | | 9H | | | | 7G | 3C,8H |

| | CMPD 11 | | CMPD 12 | | CMPD 13 | | CMPD 14 | | CMPD 15 | | CMPD 16 | | CMPD 17 | | CMPD 18 | | CMPD 19 | | CMPD 20 | |
|---|---|---|---|---|---|---|---|---|---|---|---|---|---|---|---|---|---|---|---|---|
| RATE = KG/HA | 0.05 | 0.01 | 0.05 | 0.01 | 0.05 | 0.01 | 0.05 | 0.01 | 0.05 | K0.01 | 0.05 | 0.01 | 0.05 | 0.01 | 0.05 | 0.01 | 0.05 | 0.4 | 0.05 | 0.01 |
| POSTEMERGENCE | | | | | | | | | | | | | | | | | | | | |
| COTTON | 5G | 2G | 5C,9G | 7G | 5C,9G | 5C,9G | 2C,8G | 7G | 9C | 3C,8G | 7G | 0 | 4C,8G | 5G | 3C,8G | 2C,7G | 8G | 5C,9G | 3C,8G |
| MORNINGGLORY | 10C | 4C,8G | 10C | 4C,8G | 5C,9G | 5C,9G | 3C,7G | 2C,4G | 10C | 4C,9G | 3C,5H | 3C,7H | 5C,9G | 2C,5G | 4C,8G | 10C | 4C,8G | 9C |
| COCKLEBUR | 10C | 3C,8G | 10C | 4C,9G | 5C,9H | 5C,9H | 10C | 4C,9H | 5C,9H | 4C,9H | 10C | 10C | 10C | 10C | 0 | 4C,9H | 6C,9G | 10C |
| NUTSEDGE | 3C,5G | 4G | 10C | 0 | 8G | 6G | 3G | 0 | 4C,9G | 9G | 4G | 3G | 0 | 9G | — | 10C | 9G |
| CRABGRASS | 3C,8G | 3G | 3C,7G | 2C,5G | 2C,7G | 3G | 2G | 2C,4G | 7G | 5G 4G | 2G | 5G | 2C | 0 | 10C | 4C,9H |
| BARNYARDGRASS | 3C,9G | 6G | 3C,7G | 6G | 3C,7G | 4C,9H | 4C,8H | 3C,7H | 4C,9H | 10C | 5G | 4H | 9C | 2C,6H | 10C | 10C |
| WILD OATS | 2C,7G | 3C,3G | 3C,7G | 5G | 3C,9G | 5G | 5G | 2C,4G | 3C,9G | 2C,4G | 2G | 2C,4G | 3G | 9G | 2C,3G | 9G |
| WHEAT | 2C,5G | 0 | 2C,5G | 2C,5G | 2C,5G | 2G | 2G | 0 | 9G | 4G | 3G | 5G | 2C,4G | 9G | 2G | 6G |

TABLE A-continued

| | CMPD 21 | | CMPD 22 | | CMPD 23 | | CMPD 24 | | CMPD 25 | | CMPD 26 | | CMPD 27 | | CMPD 28 | | CMPD 29 | | CMPD 30 | |
|---|---|---|---|---|---|---|---|---|---|---|---|---|---|---|---|---|---|---|---|---|
| RATE = KG/HA | 0.05 | 0.01 | 0.05 | 0.01 | 0.05 | 0.01 | 0.4 | 0.05 | 0.05 | 0.01 | 0.05 | 0.01 | 0.05 | 0.01 | 0.05 | 0.01 | 0.05 | 0.01 | 0.05 | 0.01 |
| CORN | 10C | 3U,9G | 10C | 10C | 10C | 5C,9G | 2C,8G | 9C | 10C | 9C | 3C,9G | 3C,9G | 9C | 9G | 5C,9G | 2C,6G | 3C,8H | 10C | 0 |
| SOYBEANS | 5C,9G | 4C,8H | 9C | 3C,8G | 6G | 3C,7G | 2C,7H | 6C,9G | 4C,9G | 2C,7G | 4C,8G | 5C,9G | 4C,9G | 6H | 2C,7H | 5C,9G | 3C,8H |
| RICE | 4C,8G | 3C,8G | 10C | 4C,8G | 9C | 4C,9G | 2C,3G | 9C | 3C,8G | 3C,8G | 5C,9G | 5C,9G | 9C | 7G | 3C,8G | 9C | 4C,9G |
| SORGHUM | 3C,9G | 3C,9G | 10C | 10C | 9G | 9G | 8G | 9G | 8G | 3C,8G | 6G | 9C | 3C,9G | 9C |
| CHEATGRASS | — | — | — | — | — | — | 0 | 8G | — | 0 | 4C,9G | 7G | 8G | 0 | 3C,6H | — | 8G |
| SUGARBEETS | 9C | 4C,8G | 10C | — | 5C,9G | 9C | 2C,5H | 9C | 10C | 3C,9G | 10C | 8G | 3C,8G | 7G | 3C,7H | 3C,6H | 3C,5G |
| VELVETLEAF | 3C,7G | 6G | 9C | 9C | 10C | 3C,8H | 6G | 4C,8G | 9C | 3C,9G | 5C,9G | 3C,6H | 9C | 5H | 4C,9G | 3C,7H |
| GIANT FOXTAIL | 4C,9G | 2C,5G | 5C,9G | 5G | 9C | 5C,9G | 6G | 9C | 5C,9H | 3C,5G | 5C,9H | 5C,9G | 4C,9G | 0 | 0 | 8G |
| BARLEY | 3C,6G | 2G | 9C | 3C,8G | 5C,9G | 9C | 3G | 5C,9G | 2C,6G | 3C,5G | 6G | 6G | 9C | 7G | 4G | 0 | 2C,9G | 6G |
| DOWNY BROME | 9C | 2G | 10C | 5G | 3C,9G | — | 2G | 9G | 6G | 2G | 3C,9G | 5G | 3G | — | — | 7G | 10C | 9C |
| PREEMERGENCE | | | | | | | | | | | | | | | | | | | | |
| COTTON | 0 | 0 | 0 | 0 | 4G | 7G | 0 | 4G | 0 | 0 | 0 | 0 | 0 | 0 | 0 | 6G | 7G |
| MORNINGGLORY | 1C | 0 | 2C,6H | 0 | 2G | 2C,5G | 0 | 2C,4G | 0 | 0 | 6G | 2C,8H | 0 | 4C,9G | 1C | 9G |
| COCKLEBUR | 0 | 0 | 5G | 5G | 2G | 7G | 0 | 3C,7H | 0 | 0 | 2C,5G | 2C,8H | 2C,5G | 3G | 7G | 8H | 7G |
| NUTSEDGE | 2C,4G | 0 | 2G | 0 | 0 | 0 | 0 | 9G | 0 | 10E | 0 | 2G | 0 | 0 | 0 | 10E | 0 |
| CRABGRASS | 2C,6H | 0 | 0 | 0 | 3C,7G | 2C,6G | 0 | 5C,9G | 5C,9G | 0 | 6G | 2C,7H | 0 | 4G | 3G | 0 | 3C,9G |
| BARNYARDGRASS | 2C,6G | 0 | 2G | 0 | 4C,9H | 3G | 0 | 2C,6H | 2C,5G | 0 | 2C,7H | 4C,8H | 4G | 0 | 0 | 9H |
| WILD OATS | 8G | 0 | 2C,6G | 0 | 3C,6G | 0 | 0 | 2C,5G | 0 | 0 | 2C,7G | 3G | 5G | 3G | 2G | 3C,8G |
| WHEAT | 9G | 0 | 7G | 0 | 8G | 2G | 0 | 3G | 0 | 0 | 8G | 0 | 8G | 6G | 0 | 3C,8G |
| CORN | 9G | 3C,7H | 3C,7H | 4C,9G | 2C,5G | 4C,9G | 2G | 4C,9G | 0 | 0 | 3C,9G | 8G | 3C,9G | 0 | 2C,6G | 9G |
| SOYBEANS | 3C,8H | 2C,7G | 2C,7G | 7G | 3G | 7G | 2G | 3C,8H | 2C,3G | 0 | 3C,8H | 10H | 4C,8G | 0 | 0 | 4C,8H |
| RICE | 3C,8H | 3C,8H | 9H | 10H | 2C,8H | 10H | 3G | 4C,9H | 1C,2G | 0 | 10E | 4C,9H | 4C,8H | 4C,9H | 7G | 4C,8H |
| SORGHUM | 9H | 3C,7H | 9H | 3C,8H | 3FC,8H | 3C,7H | 3C,7H | 9H | 2C,8G | 0 | 3C,8H | 3C,7H | 3C,9H | 3C,7H | 2G | 9H |
| CHEATGRASS | — | — | — | 8H | 8G | 7G | 0 | 3G | 3G | 0 | 9H | 6H | 9H | 2G | 9H |
| SUGARBEETS | 2C,5H | 0 | 7H | — | 5G | 9G | 0 | 8H | 7G | 10E | 2G | 3G | 9H | 7G | 9G | 9G |
| VELVETLEAF | 0 | 0 | 6H | 0 | 3C,8H | 0 | 0 | 2C,5G | 8G | 0 | 2G | 2C,5G | 5C,9G | 4H | 2C,4G | 3C,9G |
| GIANT FOXTAIL | 5G | 0 | 0 | 2G | 2C,4G | 5G | 0 | 2C,7G | 3H | 0 | 2C,7G | 9C | 0 | 0 | 5G | 7G |
| BARLEY | 8G | 0 | 3C,9H | 0 | 7G | 4G | 3G | 7G | 2G | 0 | 7G | 2G | 0 | 0 | 5G | 0 |
| DOWNY BROME | 7G | 0 | 0 | 2G | 4G | 5G | 0 | 8G | 2G | 0 | 8G | 6G | 0 | 0 | — | 8G |
| POSTEMERGENCE | | | | | | | | | | | | | | | | | | | | |
| COTTON | 4C,9G | — | 4C,8G | 3G | — | 6G | 9C | 5C,9G | 0 | 7G | 5G | 9G | 5C,9G | 2C,7G | 0 |
| MORNINGGLORY | 9C | 0 | 10C | 4C,8G | 10C | 9C | 9C | 10C | 3G | 5C,9G | 9C | 3C,9H | 10C | 3C,7G | 3C,8H |
| COCKLEBUR | 9C | 3C,8G | 10C | 10C | 10C | 5C,9H | 9C | 10C | 7H | 10C | 3C,8G | 2C,9G | 9C | 2C,8H | 2C,8H |
| NUTSEDGE | 9C | 0 | 10C | 3G | 10C | 0 | 4C,8G | 10C | 3C,9G | 5C,9G | 5C,9G | 2C,9G | 9C | 5C,9G | 0 |
| CRABGRASS | 3C,6G | 0 | 10C | 10C | 2C,5G | 0 | 2C,6G | 4C,9G | 5G | 5G | 4C,9H | 2C,6G | 4C,8G | 9C | 0 |
| BARNYARDGRASS | 9C | 3C,8G | 9C | 9C | 9C | 2G | 4G | 9C | 2G | 2G | 9G | 3C,5H | 4C,9G | 9C | 3C,7H |
| WILD OATS | 6G | 0 | 4C,9G | 3C,9G | 4C,9G | 2G | 4G | 3C,5G | 3C,5G | 3C,7G | 3G | 2C,5H | 4C,9G | 4C,9G | 0 |
| WHEAT | 0 | 6C,9G | 9C | 8G | 10C | 4C,9G | 3G | 3C,5G | 2G | 7G | 3C,9G | 9G | 3G | 9G | 5G |
| CORN | 4C,9G | 0 | 10C | 10C | 10C | 3C,5G | 3C,9G | 4C,9G | 3C,5G | 8G | 3C,9G | 10C | 9G | 5C,9G | 4C,9G | 3C,9G |
| SOYBEANS | 5C,9G | 2C,6H | 6C,9G | 5C,9G | 10C | 5C,9G | 5C,9G | 3C,5G | 3C,7H | 3C,9G | 4C,9G | 4C,8G | 9C | 5C,9G | 4C,9G |
| RICE | 4C,9G | 8G | 9C | 4C,9G | 4C,9G | 7G | 9C | 4C,9G | 2G | 4C,9G | 4C,9G | 5C,9G | 9C | 9C | 5C,9G |
| SORGHUM | 9G | 9G | 3C,9G | 9G | 5C,9G | 2G | 9G | 5C,9G | 3C,7H | 3C,9G | 3C,9G | 3C,9G | 9C | 4C,9G | 3C,9G |
| CHEATGRASS | — | — | — | — | 5C,9G | 3C,5G | 5C,9G | 3C,9G | 4C,9G | 3C,9G | 6G | 3C,6G | 9C | 5C,9G | 3C,7G |
| SUGARBEETS | 5C,9G | 4G | 10C | 10C | 10C | 3C,5G | 5C,9G | 5C,9G | 3C,5G | 9C | 4C,9G | 4C,8H | 9C | 5C,9G | 3C,5G |
| VELVETLEAF | 8G | 7G | 4C,9G | 5C,9G | 4C,8G | 3C,9G | 4C,8G | 9C | 3C,9H | 8G | 4C,9H | 4C,8G | 9C | 3C,8G | 3C,8H |
| GIANT FOXTAIL | 6G | 2G | 9C | 9C | 3C,7G | 0 | 2C,3G | 3C,5G | 3C,7G | 3C,7G | 4C,9G | 3C,9G | 9C | 4C,9G | 3C,7G |
| BARLEY | 0 | 0 | 7G | 3C,8G | 5G | 3G | 0 | 3C,7G | 4G | 4G | 7G | 2G | 8G | 3C,8G | 7G |
| DOWNY BROME | 5C,9G | 0 | 10C | 10C | 9C | 2C,4G | 4C,9G | 9C | 6G | 6G | 9C | 6G | — | — | — |
| PREEMERGENCE | | | | | | | | | | | | | | | | | | | | |

TABLE A-continued

| | CMPD 31 | | CMPD 32 | | CMPD 33 | | CMPD 34 | | CMPD 35 | | CMPD 36 | | CMPD 37 | | CMPD 38 | | CMPD 39 | | CMPD 40 | |
|---|---|---|---|---|---|---|---|---|---|---|---|---|---|---|---|---|---|---|---|---|
| RATE = KG/HA | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| POSTEMERGENCE | | | | | | | | | | | | | | | | | | | | |
| COTTON | 0 | 0 | 0 | 0 | 0 | 0 | 8G | 0 | 7G | 5G | 6G | 0 | 0 | 0 | 0 | 0 | 7G | 0 | 0 | 0 |
| MORNINGGLORY | 7G | 0 | 8G | 6G | 8G | 8G | 8G | 3G | 9G | 3G | 8H | 7G | 0 | 0 | 0 | 0 | 3G | 0 | 0 | 0 |
| COCKLEBUR | 2C,2H | 0 | 3C,8H | 2G | 9G | 7H | 2C,6H | 0 | 3C,5H | 0 | 8H | 6G | 0 | 0 | 0 | 0 | 2C,3G | 0 | 0 | 0 |
| NUTSEDGE | 0 | 0 | 0 | 0 | 8H | 7G | 0 | 0 | 0 | 2C,6G | 10E | 0 | 0 | 0 | 0 | 0 | 0 | 0 | 0 | 0 |
| CRABGRASS | 4C,9G | 0 | 5C,9G | 3C,6G | 5C,9H | 4C,8G | 3C,8G | 0 | 2C,6G | 5H | 7G | 0 | 0 | 0 | 4G | 0 | 2G | 0 | 0 | 0 |
| BARNYARDGRASS | 6H | 4G | 4C,8H | 2C,5H | 5C,9H | 7H | 0 | 0 | 3H | 3G | 0 | 0 | 0 | 0 | 2H | 0 | 2C,7H | 0 | 0 | 0 |
| WILD OATS | 2G | 0 | 3C,8G | 2C,4G | 3C,8G | 3C,6G | 0 | 0 | 3G | 3G | 0 | 0 | 0 | 0 | 3G | 0 | 2C,7G | 0 | 0 | 0 |
| WHEAT | 0 | 0 | 9G | 8G | 9G | 8G | 0 | 0 | 3G | 4G | 0 | 0 | 0 | 0 | 3G | 0 | 8G | 0 | 0 | 0 |
| CORN | 3C,8H | 0 | 3C,9G | 4G | 9C | 0 | 5G | 0 | 3C,8H | 0 | 4G | 0 | 0 | 0 | 3C,6H | 0 | 3C,7G | 2G | 2C,8H | 2G |
| SOYBEANS | 3C,6G | 1C,2G | 5C,9H | 3C,7H | 9H | 0 | 4C,6G | 3G | 5C,9H | 5C,9H | 5G | 0 | 0 | 0 | 3C,5H | 1C,3G | 8H | 0 | 3C,3H | 0 |
| RICE | 8G | 8G | 9H | 3C,8G | 9H | 2C,5G | 3C,8H | 0 | 9H | 7H | 3G | 5G | 0 | 0 | 6H | 2G | 3C,9G | 6G | 4G | 0 |
| SORGHUM | 8H | 7G | 5C,9H | 9G | 10H | 3H | 7H | 0 | 9H | 10H | 8H | 6G | 0 | 0 | 0 | 0 | 9G | 6G | 3C,9H | 0 |
| CHEATGRASS | — | — | 9H | 0 | 10H | 0 | 3C,8H | 0 | 3C,9H | 10H | 8H | 8H | 0 | 0 | 8G | 0 | 8G | 0 | 8G | 0 |
| SUGARBEETS | 2C,2G | 0 | 2C,3H | 2H | 3C,9G | 0 | 6G | 2G | 9G | 6H | 7G | 6H | 0 | 0 | 2C,4G | 0 | 3G | 0 | 3G | 0 |
| VELVETLEAF | 2C,6H | 0 | 0 | 0 | 6H | 6H | 7H | 0 | 9G | 7H | 2H | 1H | 0 | 0 | 2H | 0 | 3G | 0 | 2G | 0 |
| GIANT FOXTAIL | 6G | 0 | 4G | 0 | 7G | 2G | 0 | 0 | 3C,9G | 6G | 2G | 2G | 0 | 0 | 2C,6G | 2G | 5G | 0 | 3G | 0 |
| BARLEY | 0 | 0 | 8G | 8G | 8G | 3G | 6G | 5G | 3C,7G | 2C,7G | 8G | 0 | 0 | 2G | 5G | 0 | 3C,7G | 0 | 3G | 0 |
| DOWNY BROME | 5G | 0 | 3C,8G | 6G | 9H | 7G | — | — | 9H | 2C,3G | 9G | 8G | — | — | — | — | — | — | 2C,4G | 0 |
| PREEMERGENCE | | | | | | | | | | | | | | | | | | | | |
| COTTON | | | 4G | 0 | 0 | 0 | 4C,9H | 3C,8G | 9H | 2C,5G | 3C,6G | 3C,7G | 0 | 0 | 4C,9H | 7G | 3C,9H | 4G | 5C,9G | 5G |
| MORNINGGLORY | | | 4G | 2G | 2G | 2G | 9C | 2C,6H | 4C,9H | 3C,7H | 1C | 0 | 0 | 0 | 2C,9G | 3C,7G | 4C,9G | 3C,6H | 9C | 2C,4G |
| COCKLEBUR | | | 9H | 0 | 2H | 0 | 9C | 5C,9G | 2C,5H | 32C,5G | 2C | 0 | 0 | 0 | 5C,9G | 3C,6HJ | 9C | 3C,6H | 10C | 10E |
| NUTSEDGE | | | 0 | 8G | 0 | 0 | 3C,7G | 0 | 0 | 0 | 2C | 0 | 0 | 0 | 0 | 2G | 3C,8G | 0 | 10C | 10E |
| CRABGRASS | | | 3C,7G | 0 | 4C,9G | 0 | 1C | 2C,3G | 3C,7H | 2C,2G | 3C,2G | 2C,5G | 0 | 0 | 3C,6G | 0 | 0 | 3C,6H | 4C,9G | 2C,4G |
| BARNYARDGRASS | | | 2C,5G | 3C,7G | 0 | 3H | 2C,6G | 0 | 2C,8G | 4C,9H | 3C,6G | 0 | 0 | 0 | 3C,7G | 4C,9G | 4C,8H | 0 | 9C | 3C,5G |
| WILD OATS | | | 0 | 0 | 0 | 0 | 2C,6G | 0 | 3C,6G | 3C,6G | 3C,8G | 0 | 0 | 0 | 3C,8G | 2G | 0 | 3C,6H | 9C | 3C,7G |
| WHEAT | | | 2G | 2G | 2G | 0 | 4C,9G | 3C,7G | 2C,4G | 0 | 9C | 6G | 0 | 0 | 3U,9G | 3G | 4C,9G | 0 | 3C,9G | 6G |
| CORN | | | 5G | 0 | 3G | 0 | 3C,8H | 4C,8G | 5G | 0 | 8G | 8G | 0 | 0 | 4C,9G | 3C,8H | 4C,9G | 4C,9G | 9C | 7G |
| SOYBEANS | | | 2G | 2G | 5C,9G | 5G | 2C,9G | 3C,5G | 5G | 2C,7H | 9C | 2C,2G | 0 | 0 | 9C | 4C,9G | 2C,8H | 2C,5G | 3C,9G | 9C |
| RICE | | | 5C,9G | 9C | 5C,9G | 9C | 9C | 3C,8G | 9C | 5C,9G | 9C | 2C,2G | 0 | 0 | 3C,7G | 3C,7G | 5C,9G | 4C,9G | 5C,9G | 5C,9G |
| SORGHUM | | | 4C,9G | 4C,9G | 3C,9G | 2C,9G | 2C,9G | 2C,5G | 4C,9G | 1C,2G | 4C,9G | 1C | 0 | 0 | 4C,9G | 3C,8G | 2C,8H | 2C,5G | 5C,9G | 5C,9G |
| CHEATGRASS | | | 5C,9G | 9C | — | — | — | — | 3C,7G | 3C,6G | 3C,8H | 3C,7G | 0 | 2G | 3C,3H | 3C,7G | 3C,3H | — | 9C | 9C |
| SUGARBEETS | | | 9C | 10C | 9C | 4C,9G | 10C | 10C | 7H | 3C,6G | 3C,7G | 2C,5G | 0 | 0 | 3C,5H | 3C,5H | 3C,6G | 2C,3G | 10C | 10C |
| VELVETLEAF | | | 9C | 4C,9G | 5C,9G | 3G | 3C,7G | 4G | 2G | 1C | 4C,9G | 2C,2G | 0 | 0 | 4C,9G | 0 | 9C | 5G | 9C | 4C,9G |
| GIANT FOXTAIL | | | 4C,9G | 3C,9G | 2G | 2G | 9C | 3C,7G | 5C,9G | 2C,8G | 9C | 4G | 0 | 0 | 2C,7G | 2G | 3C,6G | 3G | 9G | 5C,9G |
| BARLEY | | | 3C,9G | 7G | 3G | 3G | 9C | 9C | 9G | 2C,3G | 4G | 3G | 0 | 0 | 9C | 3C,8G | 4C,8G | 0 | 9C | 3C,7G |
| DOWNY BROME | — | — | — | — | 2G | 2G | | | | | | | | | | | | | 6G | 6G |
| PREEMERGENCE | | | | | | | | | | | | | | | | | | | | |
| COTTON | | | 2G | 0 | 0 | 0 | 2G | 2G | 0 | 0 | | | 0 | 0 | 0 | 0 | 2G | 0 | 8G | 5G |
| MORNINGGLORY | | | 2G | 2G | 2G | 2G | 2G | 2G | 0 | 0 | | | 0 | 0 | 0 | 0 | 3G | 0 | 5G | 2C,4G |
| COCKLEBUR | | | 0 | 0 | 0 | 2H | 2H | 5G | 8G | 2G | | | 0 | 0 | 0 | 0 | 3G | 0 | 3C,6H | 0 |
| NUTSEDGE | | | 8G | 0 | 0 | 0 | 5G | 0 | 0 | 0 | | | 0 | 0 | 0 | 0 | 10E | 0 | 10E | 10E |
| CRABGRASS | | | 0 | 3C,7G | 3C,7G | 0 | 0 | 0 | 0 | 0 | | | 0 | 0 | 0 | 0 | 2C | 0 | 4C,9G | 2C,4G |
| BARNYARDGRASS | | | 3C,8H | 0 | 0 | 0 | 2C,7G | 0 | 0 | 2C,8G | | | 0 | 0 | 0 | 0 | 0 | 0 | 3C,9H | 3C,5G |
| WILD OATS | | | 1C | 0 | 0 | 0 | 0 | 0 | 0 | 2G | | | 0 | 0 | 0 | 0 | 0 | 0 | 3C,9H | 3C,7G |
| WHEAT | | | 4G | 2G | 0 | 2G | 2G | 0 | 5G | 2C,7G | | | 0 | 0 | 3G | 2G | 0 | 0 | 9G | 6G |
| CORN | | | 3C,8H | 0 | 3G | 0 | 5G | 0 | 3C,5H | 0 | | | 0 | 0 | 2G | 3G | 0 | 0 | 2C,9G | 6G |
| SOYBEANS | | | 2G | 2G | 2C,4G | 2C,7G | 2C,7G | 0 | 8G | 2C,8G | | | 0 | 0 | 3C,3G | 0 | 0 | 0 | 3C,9G | 3C,4G |
| RICE | | | 3C,7G | 2G | 2G | 0 | 0 | 0 | 3C,5H | 2G | | | 0 | 0 | 2C,5G | 0 | 3C,7G | 0 | 3C,8H | 8G |
| SORGHUM | | | 3C,5G | 0 | 0 | 0 | 2C | 0 | 2C | 1C | | | 0 | 0 | 2C,4G | 0 | 2C,5G | 0 | 9H | 3C,9H |

TABLE A-continued

| | CMPD 41 | | CMPD 42 | | CMPD 43 | | CMPD 44 | | CMPD 45 | | CMPD 46 | | CMPD 47 | | CMPD 48 | | CMPD 49 | | CMPD 50 | |
|---|---|---|---|---|---|---|---|---|---|---|---|---|---|---|---|---|---|---|---|---|
| RATE = KG/HA | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| CHEATGRASS | 3C,7G | 8G | — | — | — | 5G | — | 8G | — | 4C,8H | — | 3C,7H | — | 10C | — | 2H | — | 3H | — | 4C,9G |
| SUGARBEETS | 4C,9G | 0 | 8G | 2G | — | 2H | 8G | 0 | — | 0 | — | 0 | — | 10C | — | 0 | — | 0 | — | 7G |
| VELVETLEAF | 9C | 2H | 4H | 0 | — | 0 | 1C | 0 | — | 0 | — | 0 | — | 10C | — | 0 | — | 0 | — | 0 |
| GIANT FOXTAIL | 2C,5G | 0 | 3C,8G | 4G | — | 2G | 7G | 0 | 2G | 0 | — | 0 | — | 5C,9G | — | 3G | — | 3G | — | 3C,5G |
| BARLEY | 3G | 0 | 9G | 0 | — | 3G | 2G | 0 | 4G | 0 | — | 0 | — | 9G | — | 2G | — | 9H | — | 2C,8G |
| DOWNY BROME | — | — | 5G | 0 | — | — | — | — | — | — | — | — | — | 8G | — | — | — | 3C,9G | — | 8G |
| POSTEMERGENCE | | | | | | | | | | | | | | | | | | | | |
| COTTON | 3C,7G | 1C | 9C | 4C,8H | 4C,8H | 3C,5G | 5C,9G | 3C,8H | 4C,9H | 3C,7H | 3C,7H | 10C | 9C | 10C | 9C | 10C | 10C |
| MORNINGGLORY | 4C,9G | 3C,7H | 10C | 4C,9G | 3C,7G | 2C,4G | 9C | 4C,8H | 4C,9G | 3C,7G | 10C | 10C | 10C | 9C | 10C | 10C | 8G |
| COCKLEBUR | 9C | 2C,5G | 10C | 5C,9G | 4C,9G | 2C,8H | 4C,8H | 4C,9G | 4C,9G | 3C,7H | 5C,9G | 3C,9G | 5C,9G | 4C,9G | 10C | 5C,9G | 9C |
| NUTSEDGE | 2C,5G | 0 | 5C,9G | 9C | 2C | 0 | 2G | 3C,8G | 0 | 0 | 5G | 2C,6G | 4G | 6C,9G | 10C | — | |
| CRABGRASS | 2G | 0 | 3C,7G | 3G | 0 | 0 | 3C,9G | 3C,8G | 3C,7G | 0 | 5C,9G | 9C | 3C,9G | 9G | 10C | 9C | 3C,8G |
| BARNYARDGRASS | 3C,8H | 0 | 4C,9H | 0 | 2C | 0 | 4C,9H | 3C,9G | 4C,9G | 3C,5H | 9C | 9C | 9C | 5C,9G | 9C | 4C,8G | 5C,9G |
| WILD OATS | 2C,6G | 0 | 2C,8H | 2C | 0 | 0 | 5G | 5C,9G | 5C,9G | 3G | 3C,9G | 9C | 5C,9G | 8G | 9C | 9C | 9G |
| WHEAT | 7G | 0 | 5C,9G | 3C,8G | 3G | 0 | 8H | 9C | 9C | 4C,9G | 3C,9G | 7G | 3C,9G | 4G | 5C,9G | 3C,9G | 9G |
| CORN | 5C,9G | 3C,8H | 10C | 2C,8G | 5G | 2C | 3C,7H | 10C | 5C,9G | 9G | 9C | 9C | 5C,9G | 4G | 10C | 9G | 4C,9G |
| SOYBEANS | 3C,6G | 2C,2H | 3C,6H | 9C | 4C,9G | 3C | 3C,7H | 5C,9G | 5C,9G | 4C,9G | 5C,9G | 7G | 3C,9G | 5C,9G | 9C | 10C | 9C |
| RICE | 9C | 0 | 3C,7G | 3C,9G | 3C,8H | 4C,9G | 3C,7H | 5C,9G | 5C,9G | 3G | 9C | 9C | 4C,9G | 4C,9G | 9C | 9C | 9C |
| SORGHUM | 4C,9G | 3C,8G | 3C,6G | 4C,9G | 4C,8H | 3G | 3C,7H | 9G | 5C,9G | 4C,9G | 4C,8G | 9C | 5C,9G | 5G | 6C,9G | 4C,9G |
| CHEATGRASS | — | — | 5C,9G | 4C,9H | — | 5C,9G | 9G | 4C,9G | 9G | — | — | — | 5C,9G | — | 5C,9G | — |
| SUGARBEETS | 4C,8H | 3C,5G | 10C | 10C | 5C,9G | 9C | 5C,9G | 9C | 2H | 9C | 4C,8G | 10C | 2C,6G | 10C | 10C | 3C,9G | 9C |
| VELVETLEAF | 4C,9G | 2C,5G | 9C | 3C,8G | 5C,9G | 4C,7H | 3C,7H | 3C,8H | 3C,8G | 9C | 9C | 3C,8G | 10C | 10C | 3C,8G |
| GIANT FOXTAIL | 3C,7G | 0 | 5C,9G | 3C,7G | 0 | 3C,8H | 3C,7G | 3C,6G | 3C,9G | 2G | 5C,9G | 10C | 6G | 10C | 4C,9G | 5G | 4C,9G |
| BARLEY | 5G | 0 | 8G | 2C,5G | 0 | 5G | 4G | 5G | 4G | 7G | 3C,9G | 4G | 3G | — | — | 5C,9G | 8G |
| DOWNY BROME | 7G | — | 5C,9G | 7G | 4G | 4C,9G | 3C,8G | 5C,9G | 8G | 3C,9G | — | 6G | — | — | — | — |
| PREEMERGENCE | | | | | | | | | | | | | | | | | | | | |
| COTTON | 0 | 0 | 2C,8H | 0 | 0 | 3C,8H | 1C | 3C,4G | 2C,4G | 2G | 9G | 9G | 3G | 9G | 7G | 2G |
| MORNINGGLORY | 2C,2G | 0 | 8H | 3C,5H | 0 | 3C,9G | 2C,3H | 3C,5H | 3C,5H | 0 | 9G | 8G | 5G | 3C,9G | 4G | 7G |
| COCKLEBUR | 2C,2G | 0 | 8H | 3C,3H | 2C | 9H | 7H | 3C,2H | 3C,2H | 0 | 3C,7G | 7G | 2G | 3C,7H | 3G | 8H |
| NUTSEDGE | 10E | 0 | 10E | 0 | 10E | 10E | 0 | 10E | 10E | 3G | 8G | 5G | 4G | 5G | 0 | 10E |
| CRABGRASS | 3C,5G | 0 | 4C,9G | 3C,5G | 3G | 5C,9G | 3C,7G | 5C,9G | 4C,8G | 3G | 4C,9H | 5C,9G | 4G | 5C,9H | 2C,7H | 3C,9H |
| BARNYARDGRASS | 3C,7G | 0 | 3C,6G | 2C | 0 | 3C,8H | 5G | 9H | 5C,9G | 3H | 2G | 3C,8H | 2G | 5C,9H | 0 | 2C,6H |
| WILD OATS | 6G | 0 | 2C,8H | 2C,6G | 0 | 3C,8G | 5G | 3C,7H | 3C,8H | 0 | 8G | 3C,8H | 2G | 3C,7G | 0 | 5G |
| WHEAT | 7G | 2C,5G | 2C,8H | 6G | 2G | 9H | 8H | 3C,7H | 3C,9H | 3G | 9H | 2G | 4G | 8G | 2G | 3C,7G |
| CORN | 3C,8G | 0 | 3C,9G | 3C,3G | 2C | 4C,9H | 3C,7H | 4C,6G | 4C,6G | 3C,5G | 4C,9H | 3C,8H | 2C,6G | 3C,9H | 2C,6H | 2C,2G |
| SOYBEANS | 3C,7H | 1C | 3C,8H | 3C,6H | 3C,3H | 4C,8H | 3C,7H | 3C,7G | 4C,6G | 3C,6G | 3C,8H | 2C,7G | 9H | 3C,8G | 2C,6G | 6G |
| RICE | 9H | 8H | 9H | 3C,7G | 5G | 10H | 10H | 10E | 10E | 5G | 5C,9H | 5G | 4C,8H | 9H | 5G | 3G |
| SORGHUM | 9H | 3C,5G | 3C,9H | 3C,6G | 2C,3G | 9H | 3C,7H | 9H | 9H | 7G | 9H | 4G | 3C,9H | 4C,8H | 2C,3G | 3C,7G |
| CHEATGRASS | 3C,3H | 2G | 5C,9G | 5C,9G | — | 5C,9G | 8H | — | — | 3C,5H | 3C,9G | 6G | 3C,9G | 4C,9G | 3G | 3G |
| SUGARBEETS | 0 | 0 | 4C,8H | 3C,8H | 0 | 6H | 2C,2H | 4H | 0 | 5H | 3C,8H | 2C,6G | 3C,8G | 4C,9G | 6G | 7G |
| VELVETLEAF | 5G | 0 | 4C,9G | 5G | 0 | 3C,7G | 7G | 3G | 3C,8H | 3C,8G | 5G | 3C,8G | 4C,9G | 3C,9H | 6H | 0 |
| GIANT FOXTAIL | 6G | 0 | 3C,8G | 7G | 0 | 9H | 9H | 9H | 9H | 3C,7G | 6G | 3G | 3C,9H | 4C,8G | 3C,9H | 2G |
| BARLEY | 7G | 5G | 9H | 7G | 0 | 9H | 7G | 8G | 8G | 4G | — | 7G | 9H | 3C,9H | 8G | 0 |
| DOWNY BROME | — | — | — | — | — | — | — | — | — | — | — | — | — | — | — | — |

| | CMPD 51 | | CMPD 52 | | CMPD 53 | | CMPD 54 | | CMPD 55 | | CMPD 56 | | CMPD 57 | | CMPD 58 | | CMPD 59 | | CMPD 60 | |
|---|---|---|---|---|---|---|---|---|---|---|---|---|---|---|---|---|---|---|---|---|---|---|
| RATE = KG/HA | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| POSTEMERGENCE | | | | | | | | | | | | | | | | | | | | | | |
| COTTON | 10C | 10C | 10C | 9C | 3C,9G | 9G | 10C | 9C | 9C | 9C | 9C | 9C | 9C | 9C | 9C | 9C | 10C | 10C | 9C | 10C |

TABLE A-continued

| | | | | | | | | | | | | | | | | | | |
|---|---|---|---|---|---|---|---|---|---|---|---|---|---|---|---|---|---|---|
| MORNINGGLORY | 10C | 9C | 10C | 5C,9G | 5C,9G | 5C,9G | 10C | 10C | 10C | 9C | 9C | 3C,8G | 9C | 3C,8H | 10C | 10C | 9C | 9C |
| COCKLEBUR | 9C | 10C | 10C | 9C | 4C,9G | 3C,8H | 9C | 5C,9G | 5C,9H | 9C | 5C,9G | 3C,8G | 9C | 4C,9G | 3G | 10C | 10C | 10C |
| NUTSEDGE | 3C,5G | 3G | — | 6G | 9G | 7G | 9G | 4C,9G | 7G | 8G | 7G | 7G | 10C | 3G | 3G | 3G | 10C | 9C |
| CRABGRASS | 9C | 3C,9G | 4C,9H | 3C,6G | 8G | 4G | 5C,9G | 3C,7G | 3G | 9G | 3C,7G | 3C,5G | 7G | 3C,5G | 4C,9H | 4C,9H | 9C | 9H |
| BARNYARDGRASS | 10C | 5C,9G | 10C | 5C,9G | 4C,9G | 4C,9G | 10C | 4C,9G | 3G | 3C,9H | 2C,5G | 2C,5G | 9C | 3C,8G | 4C,9H | 4C,9H | 9C | 9H |
| WILD OATS | 5C,9G | 9G | 5C,9G | 5C,9G | 6G | 5G | 9G | 9G | 2G | 9G | 4C,9G | 4G | 3C,9G | 9G | 8G | 8G | 3C,9G | 2C,9G |
| WHEAT | 5C,9G | 9G | 4C,9G | 8G | 5G | 3C,9G | 9G | 5G | 2G | 8G | 5G | 4G | 9G | 9G | 4C,9G | 8G | 9G | 9G |
| CORN | 10C | 4U,9G | 9C | 9C | 3C,9G | 9C | 4C,9G | 3C,9G | 3C,9G | 3C,9G | 4C,9G | 4C,9G | 9C | 4C,9H | 4C,9G | 4C,9G | 5C,9G | 5C,9G |
| SOYBEANS | 9C | 5C,8G | 9C | 5C,9G | 5C,9G | 3C,8G | 5C,9G | 3H,7G | 3C,4H | 9C | 9C | 3H,7G | 9C | 9C | 9C | 9C | 9C | 9C |
| RICE | 9C | 9C | 9C | 9C | 4C,8G | 3C,9G | 5C,9G | 4C,9G | 8G | 9C | 9C | 4C,8G | 9C | 9C | 9C | 9C | 6C,9G | 6C,9G |
| SORGHUM | 10C | 5C,9G | 10C | 3C,9G | 3C,9G | 5C,9G | 3C,9G | 4C,9G | 3C,8H | 3C,9G | 4C,9G | 4C,9G | 4C,9G | 4C,9H | 4C,9G | 4C,9G | 6C,9G | 4C,9G |
| CHEATGRASS | 10C | 5C,9G | 5C,9G | 4C,9G | 8G | 4C,9G | 3C,9G | 4C,9G | 3G | 3C,9G | 3C,9G | 7G | 5C,7G | 5C,9G | 5C,9G | 5C,9G | 2C,8G | 2C,8G |
| SUGARBEETS | 6C,9G | 9C | 9C | 5C,9G | 4C,8G | 3C,8G | 5C,9G | 4C,9G | 3H | 4C,9H | 5C,9G | 5C,9G | 9C | 3C,7H | 4C,8H | 4C,8H | 9C | 9C |
| VELVETLEAF | 9C | 3C,8G | 9C | 8G | 8G | 4C,8G | 9C | 10C | 3C,9G | 10C | 9C | 4C,9G | 10C | 4C,9G | 4C,9G | 4C,9G | 10C | 4C,9G |
| GIANT FOXTAIL | 9C | 5C,9G | 5C,9G | 9C | 6G | 3C,9G | 3C,8G | 9C | 6G | 4C,9G | 3C,8G | 3C,7G | 9C | 3C,7G | 5C,9G | 5C,9G | 9C | 4C,9G |
| BARLEY | 8G | 6G | 5C,9G | 9G | 5G | 7G | 2C,9G | 3C,7G | 0 | 3C,7G | 6G | 4G | 3C,7G | 3C,5G | 4G | 4G | 2C,9G | 8G |
| DOWNY BROME | — | — | — | — | — | — | — | — | — | — | — | — | — | — | — | — | — | — |
| PREEMERGENCE | | | | | | | | | | | | | | | | | | |
| COTTON | 9G | 6G | 0 | 4G | 0 | 9G | 9G | 4G | 0 | 9G | 8G | 2G | 8G | 7G | 7G | 6G |
| MORNINGGLORY | 9G | 9G | 2C,3G | 2G | 0 | 9G | 9G | 8H | 0 | 9G | 7G | 4G | 9G | 8G | 8G | 6G |
| COCKLEUR | 9G | 3C,7G | 2G | 6G | 2G | 5G | 5G | 9H | 0 | 5H | 2G | 1H | 7H | 0 | 5G | 3G |
| NUTSEDGE | 7G | 10E | 4G | 10E | 0 | 5G | 5G | 0 | 0 | 9G | 6H | 0 | 5G | 0 | 0 | 10E |
| CRABGRASS | 5C,9H | 3C,9H | 2C,8H | 2C,5G | 0 | 3C,9H | 3C,9G | 2C,8H | 2C,5G | 3C,9H | 4G | 5G | 4G | 5G | 3C,8G | 6G |
| BARNYARDGRASS | 5C,9H | 3C,9H | 4G | 2C,5H | 0 | 9H | 7H | 7H | 0 | 3G | 8H | 0 | 7G | 0 | 2C,6G | 8G |
| WILD OATS | 3C,8G | 4G | 0 | 0 | 0 | 6G | 0 | 0 | 0 | 3C,6G | 0 | 0 | 8H | 0 | 0 | 6G |
| WHEAT | 3C,9H | 7G | 2G | 0 | 0 | 7G | 2G | 0 | 0 | 8G | 2G | 0 | 7G | 0 | 7G | 8G |
| CORN | 5C,9H | 2C,4H | 3C,6H | 2G | 0 | 3C,9H | 3C,5G | 3C,7H | 0 | 3C,9G | 3C,6G | 2G | 3C,9H | 3C,3H | 2C,9G | 3C,7G |
| SOYBEANS | 9H | 3C,6G | 2G | 3G | 0 | 8H | 6H | 2H | 0 | 9H | 5H | 2G | 4C,8H | 5G | 9H | 4G |
| RICE | 6C,9H | 3C,8H | 2C,7H | 0 | 0 | 9H | 7G | 9G | 0 | 8H | 8H | 2G | 9G | 8G | 9H | 8G |
| SORGHUM | 4C,9H | 4C,9H | 3C,9H | 3C,7H | 2C,5G | 3C,9H | 2C,8G | 3C,7G | 2C,5G | 3C,9H | 3C,8H | 2C,7G | 3C,8G | 3C,9G | 2C,9H | 3C,7G |
| CHEATGRASS | 4C,9G | 3C,8G | 2C,7G | 6G | 0 | 4G | 9H | 4G | 0 | 7G | 2G | 0 | 4C,9G | 4G | 4G | 2G |
| SUGARBEETS | 9G | 8G | 3C,8G | 3G | 0 | 2H | 5G | 4G | 0 | 6G | 6G | 0 | 3G | 4G | 3G | 6G |
| VELVETLEAF | 4C,9G | 2G | 6G | 10E | 3G | 3G | 8H | 2G | 0 | 7G | 5H | 0 | 3C,8G | 3G | 3G | 3G |
| GIANT FOXTAIL | 4C,9H | 3H | 3C,8H | 2C,7H | 0 | 3C,6G | 5G | 0 | 0 | 8G | 3G | 0 | 7H | 2G | 7G | 3G |
| BARLEY | 8G | 2G | 6G | 2G | 0 | 3G | 4G | 4G | 0 | 4G | 3G | 2G | 2G | 1C | 7G | 3G |
| DOWNY BROME | — | — | — | — | — | — | — | — | — | — | — | — | — | — | — | — |

| RATE = KG/HA | CMPD 61 | | CMPD 62 | | CMPD 63 | | COMPD 64 | | CMPD 65 | | CMPD 66 | | CMPD 67 | | CMPD 68 | | CMPD 69 | | CMPD 70 | |
|---|---|---|---|---|---|---|---|---|---|---|---|---|---|---|---|---|---|---|---|---|
| | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| POSTEMERGENCE | | | | | | | | | | | | | | | | | | | | |
| COTTON | 9C | 5C,9G | 9C | 9G | 10C | 9C | 9C | 9C | 9C | 9C | 10C | 10C | 9C | 9C | 10C | 10C | 9C | 4C,9G | 5C,9G | 10C |
| MORNINGGLORY | 10C | 9C | 10C | 9C | 10C | 9C | 10C | 10C | 10C | 10C | 10C | 10C | 10C | 10C | 4C,9G | 4C,9G | 5C,9G | 1H | 9C | 10C |
| COCKLEBUR | 9C | 3C,8G | 10C | 5C,9G | 10C | 5C,9G | 10C | 0C | 9C | 9C | 10C | 3C,9G | 3C,9G | 3C,9G | 4C,9G | 4C,9G | 9C | 3C,9G | 10C | 9C |
| NUTSEDGE | 9G | 5G | 8G | | 10C | 2G | 3C,9G | 3C,9G | 9C | 9G | C,9G | 10C | — | 8G | 7G | 7G | 5G | — | 7G | 4G |
| CRABGRASS | 4C,8G | 7G | 9C | 2G | 3C,9G | 8G | 10C | 10C | 3C,8G | 3G | 5C,9G | 5G | 4G | 3G | 6G | 6G | 9H | 3G | 8G | — |
| BARNYARDGRASS | 9C | 9H | 9C | 8G | 10C | 5C,9G | 9C | 4C,9G | 5C,9G | 3C,9G | 9C | 3C,8G | 3C,9G | 3C,9G | 2C,8G | 2C,5H | 4C,9G | 3C,6G | 6C,9G | 4C,9H |
| WILD OATS | 5C,9G | 2C,9G | 5C,9H | 3C,9G | 4C,9G | 8G | 5C,9G | 9G | 9G | 9G | 4C,9G | 3C,9G | 9G | 9G | 3C,9G | 9G | 9H | 2C,7G | 4C,9G | 8G |
| WHEAT | 2C,9G | 4C,9G | 9H | 2C,9G | 9G | 9G | 4C,9G | 4C,9G | 9G | 9G | 5C,9G | 3C,9G | 9G | 5G | 9G | 4G | 4C,9G | 4G | 6G | — |
| CORN | 10C | 9C | 5C,9G | 5C,9G | 10C | 10C | 9C | 4C,9G | 3C,9G | 9G | 4C,9G | 4C,9G | 3C,9H | 2C,9G | 5C,9G | 9G | 5C,9G | 4C,9G | 5C,9G | 4C,9G |
| SOYBEANS | 9C | 4C,9G | 5C,9G | 2C,9G | 10C | 6C,9G | 9C | 4C,9G | 9G | 5C,9G | 4C,9G | 4C,9G | 3C,9H | 4C,9G | 4C,9H | 3C,7H | 4C,9H | 5C,9G | 6C,9G | 4C,9G |
| RICE | 9C | 9C | 5C,9G | 2C,9G | 9G | 9G | 9C | 9C | 9G | 4C,9G | 4C,9G | 4C,9G | 9C | 3C,9H | 5C,9G | 2C,9G | 4C,9G | 4C,9G | 5C,9G | 4C,9G |
| SORGHUM | 6C,9G | 6C,9G | 9C | 4C,9G | 5C,9G | 8G | 10C | 10C | 9G | 9G | 9G | 4C,8G | 5C,9H | 4C,9G | 3C,9H | 3C,7H | 4C,9G | 4C,9G | 4C,9G | 4C,9G |
| CHEATGRASS | 6C,9G | 4C,9G | 5C,9G | 7G | 4C,9G | 9G | 3C,9G | 4C,9G | 4C,9G | 4C,8G | 5C,9G | 5C,9G | 5C,9H | 9C | 2C,9G | 2C,8G | 4C,9H | 5C,9G | 5C,9G | 4C,9G |
| SUGARBEETS | 9C | 9C | 10C | 3C,7G | 9C | 9G | 5C,9H | 5C,9H | 10C | 9C | 10C | 10C | 9C | 4C,9G | 9C | 5C,9H | 4C,8H | 4C,8H | 9C | 5C,9G |
| VELVETLEAF | 9C | 9C | 9C | 4C,9G | 5C,9G | 4C,8G | 10C | 10C | 3C,9G | 3C,9G | 10C | 10C | 4C,9G | 2C,7G | 4C,8G | 3C,8G | 3C,7G | 3C,7G | 4C,9G | 4C,8H |
| GIANT FOXTAIL | 9C | 4C,9G | 5C,9G | 5C,9G | 9C | 3C,8G | 10C | 5C,9G | 3C,9G | 2C,6G | 5C,9G | 3C,7G | 4C,9G | 3C,6G | 2C,8G | 3C,8G | 4C,9G | 3C,8G | 4C,8G | 4C,8G |
| BARLEY | 3C,9G | 7G | 3C,9G | 3C,8G | 8G | 6G | 4C,9G | 8G | 4C,9G | 9G | 4C,9G | 2C,9G | 8G | 2G | 5G | 2G | 2C,8G | 5G | 2C,8G | 5G |
| DOWNY BROME | — | | — | | — | | — | | — | | — | | — | | — | | — | | — | |
| PREEMERGENCE | | | | | | | | | | | | | | | | | | | | |
| COTTON | 9G | 6G | 7G | 4G | 9G | 9G | 9G | 2C,2G | 9G | 8G | 9G | 9G | 3G | 2G | 8G | 2G | 2G | 0 | 5G | 0 |
| MORNINGGLORY | 9G | 9G | 9G | 3G | 9G | 9G | 3C,9H | 2G | 9G | 7G | 8G | 8G | 8G | 0 | 8G | 2G | 0 | 0 | 8G | 2C,8G |
| COCKLEBUR | 5H | 6G | 3H | 3G | 6G | 6G | 8H | 2C,5G | 3G | 3G | 8H | 8H | 2G | 0 | 2G | 0 | 0 | 0 | 10E | 0 |
| NUTSEDGE | 9G | 0 | 10E | 0 | 2G | — | 9G | 9G | 7G | 7G | 4G | 4G | 7G | 4G | 7G | 4G | 0 | 0 | — | 3G |
| CRABGRASS | 8G | 3G | 7G | 2G | 2C,3G | 0 | 2C,6H | 2C,6H | 2C,7H | 5H | 4C,8G | 2C,4G | 5G | 2G | 2C,7H | 2H | 2G | 4G | 5G | 2G |
| BARNYARDGRASS | 8H | 1H | 8H | 4G | 4C,9H | 3C,7H | 3C,6H | 3G | 3C,7G | 4G | 3C,8H | 3C,6G | 2C,8G | 4G | 3H | 0 | 2C,3G | 0 | 3C,6H | 3G |
| WILD OATS | 6G | 2G | 5G | 3G | 3G | 0 | 3C,6G | 2C,8G | 3C,7G | 4G | 4C,8H | 4C,6G | 2C,6G | 2G | 3G | 0 | 0 | 0 | 2C,2G | 0 |
| WHEAT | 9G | 5G | 8H | 8G | 3C,9G | 8G | 4C,8G | 4C,8G | 8G | 8G | 4C,9H | 4C,9G | 6G | 3C,6G | 4G | 0 | 5G | 0 | 5G | 0 |
| CORN | 2C,8G | 8H | 6H | 2G | 9G | 3C,6G | 4C,9G | 4C,6G | 5C,9G | 2C,9G | 9H | 9H | 2C,9H | 3C,6G | 2C,9G | 2C,9G | 2C,3G | 0 | 3C,9G | 2C,3G |
| SOYBEANS | 9H | 3G | 6H | 2G | 9H | 9H | 9H | 8H | 9H | 1C | 10H | 9H | 9H | 2C,5G | 9H | 5H | 2C,5H | 0 | 8H | 5G |
| RICE | 3C,9G | 3C,5H | 6H | 2G | 10H | 4C,9H | 5C,9H | 4C,7H | 3C,9H | 3C,9H | 10H | 10H | 9H | 3C,5G | 10H | 5H | 2C,5G | 0 | 10H | 3G |
| SORGHUM | 4C,9G | 3C,4G | 4C,9H | 3C,5G | 3C,9H | 4C,8H | 5C,9H | 8G | 2G | 2G | 4C,9G | 4C,9H | 9H | 3C,7H | 3C,7H | 2C,4H | 7G | 0 | 4C,9H | 2G |
| CHEATGRASS | 7G | 3G | 8H | 5G | 3C,8G | 7G | 8G | 4C,7H | 3C,7G | 2G | 5C,9G | 5C,9G | 5G | 2G | 6G | 4G | 2G | 0 | 8H | 0 |
| SUGARBEETS | 9G | 5H | 3C,9G | 7G | 4C,9G | 3G | 7G | 3G | 3C,9G | 6G | 9G | 4C,8H | 2G | 2G | 3G | 3G | 5G | 0 | 5G | 0 |
| VELVETLEAF | 2C,8G | 8H | 6H | 2G | 3C,9G | 8G | 2C,9G | 2C,5H | 5C,9G | 2C,7G | 5C,9G | 4C,8H | 8G | 0 | 2C,8G | 2C,7G | 2H | 5H | 0 | 0 |
| GIANT FOXTAIL | 8H | 3G | 6H | 2G | 6G | 2G | 6C,9G | 2C,6G | 5C,9G | 3G | 5C,9G | 3C,7G | 2C,9H | 3G | 2C,7G | 3C,8H | 0 | 2G | 2C,7G | 3G |
| BARLEY | 8G | 5G | 9G | 3U,9G | 9G | 3G | 4C,9G | 8G | 8G | 6G | 9H | 9G | 7G | 3G | 3C,8H | 6G | 2G | 0 | 2C,4G | 0 |
| DOWNY BROME | — | | — | | — | | — | | — | | — | | — | | — | | — | | — | |

| RATE = KG/HA | CMPD 71 | | CMPD 72 | | CMPD 73 | | CMPD 74 | | CMPD 75 | | CMPD 76 | | CMPD 77 | | CMPD 78 | | CMPD 79 | | CMPD 80 | |
|---|---|---|---|---|---|---|---|---|---|---|---|---|---|---|---|---|---|---|---|---|
| | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| COTTON | 9C | 5C,9G | 9C | 9C | 9C | 9C | 9C | 9C | 9C | 7C | 5C,9G | 4C,9G | 5C,9G | 5C,9G | 4C,9G | 7G | 4C,9G | 2C,3G | 10C | 5C,9G |
| MORNINGGLORY | 9C | 3C,7G | 10C | 9C | 10C | 9C | 10C | 10C | 5C,9G | 3C,7G | 10C | 5C,9G | 9C | 9C | 10C | 4C,9H | 5C,9G | 3C,8H | 4C,9G | 2C,5G |
| COCKLEBUR | 4C,9G | 3C,8G | 10C | 10C | 9C | 5C,9G | 10C | 5C,9G | 3C,9G | 2C,7G | 9C | 4C,9H | 10C | 10C | 10C | 3C,7H | 4C,9G | 2C,7H | 10C | 3C,9H |
| NUTSEDGE | — | 5G | 10C | 10C | 5G | 5G | 5C,9G | 4C,8G | 4C,9G | 2C,7G | — | 3C,7G | 4C,8G | 4C,8G | 9C | 2C,5G | 3G | 0 | 9C | 9C |
| CRABGRASS | 2C,5G | 2C,4G | 9C | 4C,7G | 3C,8G | 4C,9G | 9C | 4C,8G | 4C,9G | 2C,8G | 5C,9G | 2C,6G | 10C | 4C,8G | 4C,8G | 3G | 4C,8G | 2G | 3C,7G | 9C |
| BARNYARDGRASS | 3C,9H | 2C,5G | 9C | 5C,9H | 4C,9G | 4C,9G | 6C,9G | 3C,9H | 4C,8H | 3C,5G | 5C,9G | 3C,7H | 5C,9G | 4C,8G | 3C,8H | 3C,5H | 3C,8H | 2G | 9C | 5C,9G |
| WILD OATS | 3C,9G | 7G | 6H | 9G | 5C,9G | 4C,9G | 6C,9G | 3C,9H | 8G | 5G | 4C,9G | 3C,8G | 5C,9G | 3C,8G | 4C,9G | 2C,5G | 4C,9G | 3C,8H | 9C | 5C,9G |
| WHEAT | 3C,9G | 5G | 6H | 2C,9G | 2C,8G | 6G | 4C,9G | 2C,6G | 5C,9G | 5G | 4C,9G | 3C,7G | 5C,9G | 3G | 4G | 4G | 9G | 3G | 4C,9G | 6G |
| CORN | 2C,9G | 9G | 6H | 3U,9G | 9G | 9G | 3C,9G | 8G | 9G | 6G | 9C | 5U,9G | 9C | 5U,9C | 5C,9G | 3C,9G | 4C,9G | 4C,9G | 10C | 3U,9G |

| | | | | | | | | | -continued | | | | | | | | | |
|---|---|---|---|---|---|---|---|---|---|---|---|---|---|---|---|---|---|---|
| SOYBEANS | 3C,9H | 3C,7H | 9C | 9C | 3C,8H | 5H | 6C,9G | 5C,9G | 2C,8G | 9C | 5C,9G | 5C,9G | 5C,9G | 2C,8H | 5C,9G | 3C,9H | 9C | 3C,8G |
| RICE | 5C,9G | 3C,9G | 9C | 6C,9G | 5C,9G | 8G | 6C,9G | 4C,9G | 5C,9G | 9C | 5C,9G | 4C,9G | 9C | 9C | 4C,9G | 3C,7G | 9C | 5C,9G |
| SORGHUM | 3C,9G | 3C,9G | 9C | 4C,9G | 4C,9G | 2C,8G | 4C,9G | 4C,9G | 4C,9G | 9C | 4C,9G | 9C | 4C,9G | 3C,9G | 4C,9G | 4C,9G | 3C,9G | 2C,9G |
| CHEATGRASS | 3C,8G | 6G | 9C | 6C,9G | 2C,8G | 2G | 6C,9G | 3C,9G | 2C,8G | 9C | 4C,9G | 4C,9G | 4C,9G | 3C,9G | 4C,9G | 2C,5G | 5C,9G | 3C,8G |
| SUGAR BEETS | 4C,8H | 3C,9H | 9C | 9C | 7C | 5C,9G | 10C | 10C | 9C | 10C | 10C | 10C | 4C,9H | 4C,9H | 3C,7G | 3C,8G | 10C | 9C |
| VELVETLEAF | 3C,7G | 2C,7G | 9C | 5C,9G | 2C,8G | 2C,6G | 10C | 5C,9G | 3C,7G | 9C | 5C,9G | 4C,8H | 4C,8H | 2C,6G | 3C,7G | 5G | 3C,8G | 3C,9G |
| GIANT FOXTAIL | 3C,9G | 9G | 9C | 4C,9G | 3C,8G | 3C,6G | 9C | 4C,8G | 3C,7G | 9C | 4C,9G | 4C,9G | 4C,9G | 2C,6G | 2C,8G | 3C,7G | 10C | 5C,9G |
| BARLEY | 3C,8G | 4G | 2C,9G | 7G | 5G | 2G | 3C,9G | 3C,5G | 5G | 2C,7G | 5G | 5G | 5G | — | — | 3G | 3C,9G | 2C,9G |
| DOWNY BROME | — | — | — | — | — | — | — | — | — | — | — | — | — | — | — | — | — | — |
| PREEMERGENCE | | | | | | | | | | | | | | | | | | |
| COTTON | 0 | 0 | 8G | 5G | 3G | 0 | 8G | 7G | 2G | 9G | 9G | 2G | 5G | 0 | 3G | 0 | 8G | 4G |
| MORNINGGLORY | 4G | 2G | 8G | 6G | 3H | 4G | 9G | 4G | 0 | 9H | 9G | 4G | 3G | 0 | 6G | 2G | 8G | 6G |
| COCKLEBUR | 3G | 3G | 6H | 6G | 3H | 4G | 8H | 3G | 0 | 9H | 7H | 3G | 3G | 0 | 0 | 0 | 3C,6G | 2G |
| NUTSEDGE | 0 | 0 | 9G | 6G | 9G | 10E | 10E | 3G | 0 | 5G | 9G | 0 | 0 | 2G | 10E | — | 9G | 0 |
| CRABGRASS | 2G | 0 | 8G | 6G | 2C,8G | 6G | 4C,9G | 7G | 5G | 3C,6G | 3C,6G | 3C,6G | 5C,9G | 0 | 4G | 0 | 9G | 8H |
| BARNYARDGRASS | 0 | 2G | 3C,8H | 3C,5G | 9H | 6G | 8H | 3C,7G | 6H | 9H | 3C,7H | 3C,6G | 3C,7H | 0 | 5G | 0 | 3C,8H | 2H |
| WILD OATS | 0 | 0 | 2C,8G | 3G | 0 | 0 | 3C,6G | 3G | 0 | 3C,8G | 3C,7G | 0 | 0 | 0 | 5G | 0 | 2C,8G | 3C,7G |
| WHEAT | 0 | 0 | 2C,9G | 3G | 0 | 0 | 2C,8G | 2G | 0 | 3C,9G | 3C,8G | 0 | 3C,8G | 0 | 2G | 0 | 2C,8G | 5G |
| CORN | 0 | 0 | 2U,9G | 3C,8H | 4C,9G | 3C,9G | 3C,9G | 9G | 3C,8G | 4C,9H | 4C,9G | 2C,8G | 4C,9G | 3C,8G | 3C,7G | 2C,3G | 9G | 3C,8G |
| SOYBEANS | 3G | 0 | 3C,9H | 2C,7G | 3C,6H | 3G | 9H | 3C,5H | 1H | 9H | 9H | 3C,7H | 4C,8H | 3H | 3H | 2G | 4C,9G | 3C,7G |
| RICE | 0 | 3G | 4C,9H | 4C,8G | 4C,9H | 8G | 9H | 3C,9H | 9H | 10H | 9H | 9H | 10H | 9H | 4G | 0 | 4C,9G | 7G |
| SORGHUM | 2G | 0 | 9G | 5G | 3C,8G | 2C,8G | 9H | 3C,5H | 3C,8H | 10E | 10H | 10E | 10H | 2G | 3C,8G | 2G | 3C,8G | 3C,9G |
| CHEATGRASS | 0 | 0 | 4C,8G | 7G | 4C,9H | 4G | 8H | 3C,9H | 2C,9G | 9H | 2C,8G | 9G | 4C,9H | 0 | 7G | 2G | 9G | 6G |
| SUGARBEETS | 2G | 0 | 9G | 5G | 5G | 3G | 5C,9G | 8H | 6G | 9G | 8G | 7G | 9G | — | 4G | 3G | 9G | 0 |
| VELVETLEAF | 0 | 0 | 4C,9G | 7G | 5H | 0 | 4C,9G | 3H | 1H | 7H | 7G | 5G | 7G | 1H | 5G | 0 | 6G | 8H |
| GIANT FOXTAIL | 2G | 2G | 4C,9H | 1H | 5H | 0 | 4C,8H | 6G | 4G | 4C,9G | 7H | 1H | 3C,6G | 3C,8G | 5G | 0 | 3C,9H | 7G |
| BARLEY | 5G | 0 | 3C,8H | 6G | 2C,7G | 0 | 3C,8G | 4G | 0 | 7H | 3C,8G | 3C,8G | 3C,5G | 2G | 5G | 0 | 2C,7G | 7G |
| DOWNY BROME | 0 | 0 | 4C,8G | 1C | 2C,2G | 0 | 9G | 4G | 0 | 9H | 3C,9G | 2C,2G | 3C,2G | 0 | 2C,3G | 0 | 2C,7G | 2C,2G |

| RATE = KG/HA | CMPD 81 | | CMPD 82 | | CMPD 83 | | CMPD 84 | | CMPD 85 | | CMPD 86 | | CMPD 87 | | CMPD 88 | | CMPD 89 | | CMPD 90 | |
|---|---|---|---|---|---|---|---|---|---|---|---|---|---|---|---|---|---|---|---|---|
| | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| POSTEMERGENCE | | | | | | | | | | | | | | | | | | | | |
| COTTON | 4C,9G | 10C | 2C,9H | 2G | 10C | 9C | 10C | 3C,5G | 9C | 9C | 3G | 3G | 5C,9G | 4C,9G | 10C | 4C,8G | 4C,9G | 5G | 5C,8G | 3C,6G |
| MORNINGGLORY | 10C | 3C,8H | 3C,7G | 2G | 8G | 10C | 9C | 3C,9G | 10C | 4C,8G | 1H | 9C | 9C | 4C,8H | 10C | 9C | 10C | 10C | 5C,9G | 4C,8G |
| COCKLEBUR | 10C | 3C,8H | 6G | 2H | 10C | 4C,9G | 9C | 6G | 10C | 4C,9G | 5C,9G | 4C,9G | 10C | 3C,7H | 10C | 5C,9G | 6C,9G | 3C,7G | 5C,9G | 3G |
| NUTSEDGE | — | 8G | 6G | — | 5C,9G | 6C,9G | 4C,9G | 0 | 6C,9G | 3C,9G | 0 | 0 | 4C,9G | 0 | 5C,9G | 0 | 3C,5G | 0 | 5G | 0 |
| CRABGRASS | 4C,8G | 3C,5G | 3C,8G | 5G | 4C,8G | 2G | 0 | 3C,8H | 3C,5G | 1C | 3G | 0 | 3G | — | 5G | 0 | 3C,7H | 0 | 2C | 0 |
| BARNYARDGRASS | 9C | 3C,8H | 4C,9G | 7H | 10C | 9C | 9C | 2G | 6C,9G | 4C,9G | 4C,8G | 3G | 4C,9H | 3C,5G | 10C | 5C,9H | 3C,7H | 0 | 3C,7H | 2C,3G |
| WILD OATS | 9G | 5G | 3C,8G | 3G | 9C | 4C,8G | 2C,5G | 0 | 3C,6G | 3G | 4C,8G | 3G | 2C,6G | 4G | 10C | 3C,6G | 3C,5G | 0 | 3C,5G | 0 |
| WHEAT | 8G | 3G | 3C,9G | 4G | 10C | 8G | 5G | 2G | 3C,6G | 0 | 4C,8G | 4G | 5C,9G | 2C,9C | 10C | 5C,9G | 4G | 0 | 2C,6G | 4G |
| CORN | 5C,9G | 3C,9H | 9C | 3C,7H | 10C | 10C | 5U,9G | 4C,9G | 10C | 10C | 5U,9G | 2C,8G | 10C | 5U,9C | 10C | 10C | 4C,9G | 3C,8G | 4C,9G | 3C,9G |
| SOYBEANS | 9C | 3C,8H | 4C,9G | 4G | 6C,9G | 5C,9G | 4C,8H | 7G | 4C,9G | 4C,9G | 3C,8H | 3C,7G | 9C | 4C,9G | 9C | 9C | 5C,9G | 4C,9G | 5C,9G | 4C,8G |
| RICE | 9C | 4C,9G | 5C,9G | 3C,7G | 9C | 9C | 2G | 6G | 9C | 10C | 9C | 3C,8G | 9C | 9C | 9C | 9C | 9C | 3C,6G | 4C,9G | 3C,6G |
| SORGHUM | 5C,9G | 3C,6G | 4C,9G | 3C,8G | 10C | 9C | 4C,8G | 4C,8G | 6C,9G | 3C,7G | 9C | 3C,7G | 5C,9G | 2C,9G | 9C | 4C,9G | 5C,9G | 3C,6G | 5C,9G | 4C,8H |
| CHEATGRASS | 5C,9G | 3C,6G | 7G | 2G | 9C | 4C,8G | 5G | 5G | 7G | 7G | 5G | 3C,7G | 9C | 3C,8G | 9C | 3C,8G | 3C,8G | 3C,7G | 3C,8G | 2C,5G |
| SUGARBEETS | 10C | 3C,9G | 3C,9G | 3H | 10C | 5C,9G | 4C,8H | 5G | 9C | 4C,9G | 5G | 2C,4G | 10C | 2C,8H | 9C | 2C,4H | 9C | 0 | 3C,7H | 3C,7H |
| VELVETLEAF | 3C,8G | 6G | 0 | 0 | 9C | 10C | 4C,8G | 2G | 10C | 4C,9G | 2C,4G | 3C,7H | 3C,7G | 2G | 6C,9G | 2C,4H | 2C,4G | 5G | 3C,7G | 2C,5G |
| GIANT FOXTAIL | 9C | 4C,9G | 3C,7G | 2G | 5C,9G | 3C,7G | 4C,8G | 2C,5G | 9C | 2C,8G | 2C,3G | 2G | 6C,9G | 5G | 5C,9G | 3C,5G | 3C,5G | 0 | 4C,8G | 2C,5G |
| BARLEY | 5C,9G | 3C,7G | 3C,8G | 3C,4G | 5C,9G | 3C,7G | 2G | 2G | 3C,9G | 3C,6G | 4G | — | 6C,9G | 5G | 2C,9G | 2C,5G | 0 | 0 | 3C,5G | 0 |
| DOWNY BROME | — | — | — | — | — | — | — | — | — | — | — | — | — | — | — | — | — | — | — | — |
| PREEMERGENCE | | | | | | | | | | | | | | | | | | | | |
| COTTON | 8G | 7G | 8G | 5G | 6G | 5G | 5G | 2G | 3C,8G | 4G | 0 | 0 | 3C,8G | 6G | 3C,8H | 2C,5G | 3G | 0 | 0 | 0 |
| MORNINGGLORY | 8G | 2H | 9G | 2G | 1C | 3G | 0 | 0 | 3C,5G | 0 | 0 | 0 | 3C,5G | 2G | 2C,8H | 1C | 0 | 0 | 1C | 0 |
| COCKLEBUR | 8H | 0 | 7H | 2H | 2C,5G | 0 | 5G | 0 | 3C,6H | — | 0 | 0 | 3C,4G | 0 | 3C,6H | 1C | 0 | 0 | 0 | 0 |
| NUTSEDGE | 9G | 3G | 8G | 8G | 9G | 9G | 0 | 0 | 2C | 0 | 0 | 0 | 0 | 0 | 2C | 3G | 0 | 0 | 5G | 0 |
| CRABGRASS | 4C,9H | 8G | 9C | 3C,8H | 3G | 8H | 5G | 2G | 2C,8G | 2H | 0 | 0 | 3G | 3G | 2C,8G | 2C,3G | 0 | 0 | 0 | 0 |
| BARNYARDGRASS | 3C,9H | 3C,7H | 4C,9G | 2C,7G | 8H | 4G | 7G | 0 | 4C,9H | 2G | 0 | 0 | 1C | 2G | 3C,8G | 2G | 3G | 0 | 0 | 0 |
| WILD OATS | 4C,8G | 2C,8H | 3C,9H | 2C,7G | 2C,8G | 2G | 2G | 0 | 3C,7G | 5G | 0 | 0 | 3C,5G | 2G | 3C,6G | 7G | 0 | 0 | 0 | 0 |
| WHEAT | 8G | 6G | 3C,9G | 3C,7G | 6G | 2G | 0 | 3C,7G | 2C,8G | 5G | 0 | 0 | 3C,8G | 7G | 3C,9G | 3C,3G | 0 | 0 | 0 | 0 |
| CORN | 2U,9G | 2C,8H | 3C,9G | 2C,5G | 3C,8G | 0 | 0 | 2C,2H | 2C,8G | 3C,5H | 0 | 0 | 4C,9G | 3C,5G | 3C,9G | 2G | 0 | 0 | 1C,1H | 0 |
| SOYBEANS | 3C,9H | 2C,7H | 4C,9G | 2C,5G | 6H | 3C,5G | 2C,2H | 0 | 3C,7H | 3C,5H | 1C,2H | 0 | 3C,8H | 2C,7H | 4C,9G | 3C,5H | 2H | 0 | 2C | 0 |
| RICE | 3C,9G | 3C,8G | 4C,9G | 2C,5G | 9G | 9G | 9G | 7G | 4C,9G | 8G | 3G | 0 | 5C,9G | 4C,8G | 10E | 9H | 0 | 0 | 5G | 0 |
| SORGHUM | 2C,9G | 3C,8H | 9H | 3C,8H | 9G | 9G | 9G | 2C,6G | 3C,9G | 3C,7G | 2C,3G | 0 | 8G | 3G | 4C,9G | 3C,9G | 3G | 0 | 0 | 0 |
| CHEATGRASS | 5C,9G | 8G | 3C,9G | 8G | 8G | 7G | 4G | 2G | 8G | 8G | 0 | 0 | 8G | 3G | 9H | 8G | 0 | 0 | 2H | 0 |
| SUGARBEETS | 6G | 0 | 4C,9G | 0 | 8G | 1H | 6G | 2G | 5H | 5H | 0 | 0 | 2C,2H | 3C,7G | 7H | 2H | 3G | 0 | 1H | 0 |
| VELVETLEAF | 2H,5G | 6H | 6H | 0 | 5G | 1H | 2G | 0 | 7H | 2H | 0 | 0 | 3C,7G | 2H | 3C,6H | 2C | 0 | 0 | 0 | 0 |
| GIANT FOXTAIL | 3C,9H | 3C,9G | 3C,8G | 3G | 5G | 4G | 2G | 0 | 3C,8G | 2G | 1C,2H | 0 | 3C,8H | 7G | 3C,8G | 2C | 0 | 0 | 0 | 0 |
| BARLEY | 2C,8G | 3C,7H | 3C,9G | 3C,4G | 8G | 0 | 3G | 0 | 3C,8G | 7G | 2C,3G | 0 | 4C,9G | 0 | 9G | 2C,7G | 0 | 0 | 0 | 0 |
| DOWNY BROME | — | — | — | — | — | — | — | — | — | — | — | — | — | — | — | — | — | — | — | — |

| RATE = KG/HA | CMPD 91 | | CMPD 92 | | CMPD 93 | | CMPD 94 | | CMPD 95 | | CMPD 96 | | CMPD 97 | | CMPD 98 | |
|---|---|---|---|---|---|---|---|---|---|---|---|---|---|---|---|---|
| | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| POSTEMERGENCE | | | | | | | | | | | | | | | | |
| COTTON | 0 | 0 | 5C,9G | 3C,9G | 2C,6G | 0 | 5G | 0 | 9C | 5C,9G | 4C,9G | 3C,9G | 5C,9G | 3C,9G | 4C,9G | 8H |
| MORNINGGLORY | 1C,2H | 1H | 10C | 9C | 5C,9G | 5C,9G | 5C,9G | 2C,6H | 10C | 9C | 4C,9G | 3C,4G | 4C,9G | 4C,8H | 4C,9H | 3C,7H |
| COCKLEBUR | 2G | 0 | 5C,9G | 2C,8H | 4C,9H | 7H | 3C,8H | 3H | 9C | 3C,8G | 4C,9H | 4C,9H | 4C,9G | 4C,9G | 3C,9G | 3C,5G |
| NUTSEDGE | 0 | 0 | 3C,8G | 0 | 0 | 0 | 0 | 0 | 10C | 10C | 9C | 9C | 3G | 3G | 2C,8G | 8G |
| CRABGRASS | 0 | 0 | 2C,4G | 0 | 3G | 0 | 2G | 0 | 10C | 10C | 3G | 3G | 5C,9G | 5C,9G | 3G | 0 |
| BARNYARDGRASS | 0 | 0 | 4C,9H | 2H | 3C,8H | 2H | 6H | 4H | 9C | 9C | 3C,6G | 2C,5G | 5C,9G | 3C,9G | 3C,7H | 2C,4H |
| WILD OATS | 0 | 0 | 3C,9G | 3C,9G | 3C,7G | 2G | 6H | 0 | 5C,9G | 3C,5G | 3C,8G | 3C,7G | 9C | 2C,9G | 9G | 8G |
| WHEAT | 2G | 0 | 9G | 7G | 2C,6G | 0 | 4G | 3G | 4C,9G | 4C,9G | 3C,6H | 2C,7G | 4C,9G | 9G | 8G | 8G |

-continued

| | | | | | | | | | | | | | | | | |
|---|---|---|---|---|---|---|---|---|---|---|---|---|---|---|---|---|
| CORN | 8G | 0 | 9C | 3U,9G | 9G | 9G | 3C,9G | 8G | 3C,9H | 3C,4H | 0 | 0 | 2G | 0 | 0 | 0 |
| SOYBEANS | 2C,5H | 0 | 3C,7H | 3C,7H | 5C,9G | 3C,7H | 3C,9G | 3C,8G | 9C | 5C,9G | 4C,9G | 3C,9G | 3C,8H | 4H | 4C,9G | 3C,7H |
| RICE | 4G | 0 | 9C | 9C | 2C,5G | 0 | 7G | 4G | 9C | 9C | 4C,9H | 3C,9G | 5C,9G | 4C,9G | 5C,9G | 4C,9G |
| SORGHUM | 2C,6H | 3G | 9C | 9C | 9G | 9C | 3C,9G | 8G | 5C,9G | 4C,9G | 9G | 4C,9H | 6C,9G | 4C,9G | 4C,8H | 3C,7H |
| CHEATGRASS | 3G | 0 | 9G | 8G | 7G | 0 | 3C,7G | 3G | 9C | 4C,9G | 3C,7G | 9G | 5C,9G | 9G | 4C,9G | 7G |
| SUGARBEETS | 2G | 2G | 9C | 5C,9H | 9C | 9C | 9C | 7G | 9C | 4C,9G | 5C,9H | 7G | 5C,9G | 3C,7G | 3C,5G | 1C,1H |
| VELVETLEAF | 4G | 0 | 3C,7G | 6G | 3G | 4G | 5G | 3G | 10C | 0 | 3C,6G | 4C,9G | 3C,7G | 3C,8G | 3C,8H | 3C,6G |
| GIANT FOXTAIL | 4G | 0 | 5C,9G | 3C,8G | 7G | 6G | 6G | 3G | 3C,7G | 4C,9G | 3C,6G | 2C,3G | 3C,7G | 2G | 3C,5G | 0 |
| BARLEY | 0 | 0 | 4C,9G | 6G | 2C,4G | 0 | 2C,4G | 0 | 5C,9G | 4C,9G | 9G | 7G | 4C,9G | 7G | 9G | 7G |
| DOWNY BROME | — | — | — | — | — | — | — | — | — | — | — | — | — | — | — | — |
| PREEMERGENCE | | | | | | | | | | | | | | | | |
| COTTON | 0 | 0 | 0 | 0 | 0 | 0 | 0 | 0 | 2C,9G | 6G | 2C,5G | 2G | 2C,7G | 0 | 1C | 0 |
| MORNINGGLORY | 0 | 0 | 2G | 0 | 0 | 0 | 0 | 0 | 3C,8H | 2C,3G | 7H | 0 | 3C,7H | 2G | 2C,5G | 0 |
| COCKLEBUR | 0 | 0 | 0 | 0 | 0 | 0 | 0 | 0 | 9H | — | 2C,7H | 2C | 3C,5H | 1H | 1C,1H | 0 |
| NUTSEDGE | 0 | 0 | 0 | 0 | 5G | 0 | 0 | 0 | 0 | 3G | 8G | 0 | 0 | 0 | 10E | 0 |
| CRABGRASS | 0 | 0 | 3G | 0 | 0 | 0 | 0 | 0 | 8G | 3G | 2C,2G | 0 | 8G | 2G | 6G | 0 |
| BARNYARDGRASS | 0 | 0 | 0 | 0 | 0 | 0 | 3G | 0 | 2G | 0 | 3G | 2G | 6G | 1H | 0 | 0 |
| WILD OATS | 0 | 0 | 3G | 0 | 0 | 0 | 0 | 0 | 2C,5G | 0 | 2C,5G | 2G | 2G | 0 | 2C,6G | 0 |
| WHEAT | 0 | 0 | 0 | 0 | 0 | 0 | 0 | 0 | 8G | 7G | 8G | 6G | 8G | 2G | 2C,8G | 0 |
| CORN | 0 | 0 | 1C | 0 | 0 | 0 | 0 | 0 | 3C,7G | 3G | 0 | 0 | 0 | 0 | 0 | 3H |
| SOYBEANS | 0 | 0 | 0 | 0 | 0 | 0 | 0 | 0 | 4C,9H | 3C,7G | 3C,6H | 2C,3H | 3C,7G | 3G | 3C,6G | 0 |
| RICE | 0 | 0 | 5G | 0 | 2C | 0 | 0 | 0 | 9H | 5G | 3C,7G | 0 | 3C,9H | 2G | 3C,3G | 0 |
| SORGHUM | 0 | 0 | 3C,8H | 0 | 2G | 0 | 0 | 0 | 3C,8H | 3C,3G | 3C,4G | 2G | 3C,9H | 0 | 3C,7G | 0 |
| CHEATGRASS | 0 | 0 | 4G | 0 | 2H | 0 | 0 | 0 | 7G | 3G | 3G | 5G | 8G | 3C,5G | 3C,7G | 0 |
| SUGARBEETS | 0 | 0 | 4H | 0 | 0 | 0 | 0 | 0 | 4G | 5H | 3C,6H | 5G | 5H | 3G | 4H | 2G |
| VELVETLEAF | 0 | 0 | 0 | 0 | 0 | 0 | 0 | 0 | 5H | 3H | 4H | 2C,2G | 3H | 0 | 1C | 0 |
| GIANT FOXTAIL | 0 | 0 | 3G | 0 | 0 | 0 | 2G | 0 | 2G | 2G | 2G | 0 | 0 | 0 | 0 | 0 |
| BARLEY | 0 | 0 | 0 | 0 | 0 | 0 | 0 | 0 | 3C,8G | 7G | 8G | 5G | 3G | 9G | 9G | 8G |
| DOWNY BROME | — | — | — | — | — | — | — | — | — | — | — | — | — | — | — | — |

TEST B

Seeds of barley (*Hordeum vulgare*), barnyardgrass (*Echinochloa crus-galli*), blackgrass (*Alopecurus myosuroides*), cheatgrass (*Bromus secalinus*) or downy brome (*Bromus tectorum*), chickweed (*Stellaria media*), cocklebur (*Xanthium pensylvanicum*), corn (*Zea mays*), cotton (*Gossypium hirsutum*), crabgrass (Digitaria spp.), giant foxtail (Setaria faberi), green foxtail (*Setaria viridis*), jimsonweed (*Datura stramonium*), johnsongrass (*Sorghum halepense*), lambsquarters (*Chenopodium album*), morningglory (Ipomoea spp.), rape (*Brassica napus*), rice (*Oryza sativa*), sicklepod (*Cassia obtusifolia*), soybean (*Glycine max*), sugarbeet (*Beta vulgaris*), teaweed (Sida spinosa), velvetleaf (*Abutilon theophrasti*), wheat (*Triticum aestivum*), wild buckwheat (*Polygonum convolvulus*), and wild oat (*Avena fatua*) and purple nutsedge (*Cyperus rotundus*) tubers were planted and treated preemergence with test chemicals dissolved in a non-phytotoxic solvent. At the same time, these crop and weed species were also treated with postemergence applications of test chemicals. Plants ranged in height from two to eighteen cm for postemergence treatments. Treated plants and controls were maintained in a greenhouse for approximately 24 days, after which all species were compared to controls and visually evaluated. The ratings, summarized in Table B, are based on a scale of 0 to 100 where 0 is no effect and 100 is complete control. A dash (—) response means no test.

TABLE B

POSTEMERGENCE

| RATE = G/HA | CMPD 1 | | | CMPD 2 | | | CMPD 3 | | | CMPD 4 | | | CMPD 5 | | | CMPD 6 | | | CMPD 7 | |
|---|---|---|---|---|---|---|---|---|---|---|---|---|---|---|---|---|---|---|---|---|
|  | 62 | 16 | 4 | 62 | 16 | 4 | 250 | 62 | 16 | 4 | 250 | 62 | 16 | 4 | 250 | 62 | 16 | 4 | 250 | 62 |
| GIANT FOXTAIL | 90 | 60 | 30 | 100 | 90 | 0 | 100 | 100 | 70 | 50 | 30 | 80 | 50 | 0 | 100 | 90 | 60 | 30 | 100 | 40 |
| VELVETLEAF | 90 | 80 | 70 | 100 | 100 | 50 | 100 | 100 | 70 | 50 | 30 | 100 | 80 | 30 | 100 | 100 | 90 | 70 | 100 | 80 |
| SUGARBEET | 100 | 90 | 60 | 100 | 100 | 0 | 100 | 100 | 90 | 90 | 100 | 100 | 100 | 70 | 100 | 100 | 100 | 90 | 100 | 100 |
| CRABGRASS | 70 | 50 | 30 | 100 | 90 | 0 | 90 | 100 | 60 | 30 | 0 | 60 | 0 | 0 | 100 | 90 | 40 | 10 | 90 | 0 |
| TEAWEED | 70 | 50 | 30 | 100 | 100 | 0 | 90 | 100 | 80 | 70 | 0 | 50 | 60 | 0 | 100 | 100 | 70 | 40 | 100 | 80 |
| JIMSONWEED | 100 | 100 | 60 | 100 | 100 | 40 | 100 | 100 | 100 | 90 | 30 | 80 | 90 | 30 | 100 | 100 | 100 | 90 | 100 | 40 |
| RICE | 90 | 60 | 30 | 100 | 90 | 0 | 100 | 100 | 70 | 30 | 30 | 70 | 30 | 0 | 90 | 100 | 100 | 80 | 90 | 40 |
| COCKLEBUR | 100 | 90 | 50 | 100 | 100 | 30 | 70 | 70 | 50 | 60 | 60 | 80 | 60 | 0 | 100 | 100 | 100 | 80 | 100 | 40 |
| COTTON | 60 | 0 | 0 | 90 | 80 40 | 100 | 30 | 50 | 90 | 0 | 30 | 30 | 0 | 30 | 70 | 20 | 0 | 90 | 80 |
| SOYBEAN | 100 | 60 | 40 | 100 | 100 | 20 | 100 | 100 | 100 | 70 | 60 | 60 | 100 | 0 | 100 | 100 | 100 | 80 | 80 | 80 |
| BARNYARDGRASS | 90 | 70 | 50 | 100 | 100 | 30 | 100 | 100 | 70 | 50 | 0 | 50 | 70 | 0 | 100 | 100 | 100 | 80 | 90 | 30 |
| WILD OAT | 50 | 30 | 0 | 100 | 70 | 50 | 30 | 60 | 80 | 30 | 40 | 50 | 90 | 30 | 100 | 90 | 10 | 20 | 20 | 0 |
| MORNINGGLORY | 70 | 50 | 30 | 100 | 100 | 50 | 70 | 90 | 50 | 60 | 30 | 70 | 60 | 0 | 100 | 100 | 90 | 40 | 90 | 0 |
| WHEAT | 30 | 0 | 0 | 80 | 60 | 30 | 80 | 60 | 30 | 50 | 0 | 30 | 30 | 30 | 90 | 40 | 10 | 0 | 20 | 30 |
| SICKLEPOD | 100 | 100 | 60 | 100 | 100 | 80 | 100 | 100 | 60 | 20 | 0 | 30 | 70 | 0 | 100 | 100 | 100 | 30 | 90 | 80 |
| JOHNSONGRASS | 80 | 50 | 30 | 100 | 100 | 60 | 100 | 100 | 70 | 30 | 0 | 70 | 30 | 0 | 100 | 100 | 100 | 20 | 20 | 20 |
| NUTSEDGE | 100 | 100 | 60 | 100 | 100 | 50 | 100 | 100 | 70 | 50 | 30 | 70 | 60 | 0 | 90 | 100 | 100 | 80 | 90 | 50 |
| CORN | 100 | 80 | 100 | 100 | 100 | 100 | 100 | 100 | 100 | 100 | 70 | 100 | 100 | 70 | 100 | 100 | 100 | 100 | 30 | 10 |
| WILD BUCKWHEAT | 0 | 0 | 30 | 100 | 100 | 30 | 100 | 100 | 60 | 60 | 30 | 60 | 50 | 30 | 100 | 100 | 90 | 40 | — | 100 |
| BLACKGRASS | 100 | 90 | 70 | 100 | 100 | 50 | 100 | 100 | 90 | 30 | 70 | 90 | 100 | 70 | 90 | — | 100 | 70 | 100 | 30 |
| RAPE | 30 | 0 | 0 | 100 | 60 | 100 | 70 | 70 | 30 | 50 | 30 | 30 | 30 | 50 | 60 | 30 | 30 | 40 | 10 | 100 |
| BARLEY | 30 | 0 | 50 | 100 | 90 | 50 | 100 | 100 | 50 | 30 | 0 | 30 | 100 | 90 | 100 | 90 | 30 | 0 | — | 30 |
| GREEN FOXTAIL | 70 | 30 | 0 | 100 | 80 | 30 | 100 | 100 | 70 | 70 | 30 | 50 | 60 | 30 | 100 | 100 | 60 | 20 | 10 | 100 |
| CHEATGRASS | 60 | 30 | 0 | 90 | 60 | 30 | — | — | 50 | 50 | 0 | 30 | 30 | 30 | 90 | 30 | 100 | — | 40 | — |
| LAMBSQUARTERS | 100 | 90 | 60 | 100 | 100 | 80 | 100 | 100 | 90 | 70 | 0 | 50 | 90 | 50 | 100 | 100 | 100 | 80 | 80 | 80 |
| CHICKWEED | 90 | 60 | 30 | 100 | 100 | 70 | 100 | 100 | 100 | 70 | 50 | 90 | 100 | 30 | 100 | 100 | 90 | 90 | 100 | 100 |
| DOWNY BROME | — | — | — | — | — | — | 100 | 100 | 100 | — | 50 | — | 80 | — | 100 | 100 | 90 | 70 | 50 | 30 |

PREEMERGENCE

| RATE = G/HA | CMPD 1 | | | CMPD 2 | | | CMPD 3 | | | CMPD 4 | | | CMPD 5 | | | CMPD 6 | | | CMPD 7 | |
|---|---|---|---|---|---|---|---|---|---|---|---|---|---|---|---|---|---|---|---|---|
|  | 250 | 62 | 16 | 4 | 62 | 16 | 4 | 250 | 62 | 16 | 4 | 250 | 62 | 16 | 4 | 62 | 16 | 4 | 1 | 250 | 62 |
| GIANT FOXTAIL | 100 | 40 | 20 | 0 | 100 | 70 | 50 | 100 | 100 | 70 | 40 | 100 | 90 | 70 | 30 | 0 | 90 | 40 | 40 | 0 | 20 | 0 |
| VELVETLEAF | 100 | 70 | 40 | 30 | 90 | 40 | 30 | 100 | 90 | 50 | — | 80 | 50 | 30 | 30 | 30 | 100 | 100 | 90 | 50 | 30 | 70 | 30 |
| SUGARBEET | 100 | 90 | 60 | 30 | 100 | 80 | 70 | 100 | 100 | 80 | 60 | 100 | 100 | 90 | 60 | 30 | 100 | 80 | 80 | 60 | 70 | 80 | 60 |
| CRABGRASS | 80 | 40 | 0 | 0 | 90 | 30 | 30 | 70 | 80 | 30 | 20 | 50 | 20 | 20 | 40 | 30 | 90 | 60 | 40 | 40 | 0 | 0 |
| TEAWEED | 90 | 70 | 40 | 0 | 90 | 50 | 30 | 100 | 80 | 70 | 30 | 100 | 80 | 30 | 30 | 30 | 80 | 40 | 60 | 30 | 20 | 30 |
| JIMSONWEED | 90 | 80 | 30 | 30 | 90 | 30 | 30 | 100 | 90 | 70 | 30 | 100 | 70 | 50 | 50 | 10 | 100 | 80 | 40 | 30 | 20 | 30 |
| RICE | 100 | 100 | 80 | 40 | 100 | 50 | 30 | 100 | 90 | 80 | 60 | 100 | 100 | 100 | 90 | 20 | 100 | 100 | 100 | 90 | 30 | 60 | 20 |
| COCKLEBUR | 80 | 40 | 20 | 0 | 80 | 20 | 30 | 100 | 90 | 20 | 20 | 80 | 60 | 70 | 30 | — | 90 | 40 | 30 | 0 | 0 |
| COTTON | 80 | 50 | 10 | 0 | 30 | 20 | 0 | 90 | 80 | 30 | 0 | 30 | 30 | 0 | 50 | 20 | 80 | 30 | 70 | 30 | 30 | 20 |
| SOYBEAN | 80 | 30 | 0 | 0 | 80 | 90 | 10 | 100 | 60 | 50 | 0 | 80 | 30 | 40 | 30 | 0 | 90 | 80 | 60 | 30 | 20 | 30 | 20 |
| BARNYARDGRASS | 100 | 100 | 50 | 20 | 100 | 80 | 40 | 100 | 100 | 50 | 10 | 90 | 80 | 40 | 20 | 20 | 100 | 80 | 40 | 20 | 30 | 20 |
| WILD OAT | 50 | 30 | 10 | 0 | 70 | 50 | 20 | 100 | 70 | 40 | 30 | 90 | 60 | 20 | 50 | 0 | 80 | 40 | 30 | — | 40 | 30 | 0 |
| MORNINGGLORY | 90 | 80 | 40 | 30 | 90 | 30 | 40 | 100 | 70 | 50 | 10 | 80 | 50 | 50 | 60 | 40 | 90 | 70 | 50 | 40 | 0 | 0 |
| WHEAT | 40 | 10 | 0 | 0 | 40 | 10 | 20 | 100 | 40 | 40 | 30 | 100 | 60 | 30 | 20 | 0 | 90 | 30 | 10 | 10 | 40 | 0 |
| SICKLEPOD | 90 | 40 | — | 80 | 70 | 50 | 0 | 40 | 50 | 20 | 30 | 40 | 100 | 60 | 30 | 30 | 100 | 70 | 40 | 40 | 0 | 40 |
| JOHNSONGRASS | 100 | 90 | 80 | 30 | 100 | 40 | 40 | 100 | 90 | 80 | 20 | 100 | 80 | 30 | 40 | 0 | 100 | 90 | 60 | 40 | 0 | 40 | 30 |
| NUTSEDGE | 80 | 60 | 30 | 0 | 60 | 40 | — | 100 | 60 | 30 | 0 | 90 | 50 | 40 | 30 | 0 | 60 | 30 | 30 | 20 | 20 |
| CORN | 100 | 50 | 30 | 10 | 90 | 90 | 0 | 100 | 100 | 80 | 10 | 90 | 30 | 10 | 0 | 0 | 100 | 100 | 30 | 0 | 10 | 0 |

TABLE B-continued

|  | CMPD 7 | CMPD 8 | | | | CMPD 9 | | | | CMPD 10 | | | | CMPD 11 | | | | CMPD 12 | | | | CMPD 13 |
|---|---|---|---|---|---|---|---|---|---|---|---|---|---|---|---|---|---|---|---|---|---|---|
| RATE = G/HA | 16 | 250 | 62 | 16 | 4 | 250 | 62 | 16 | 4 | 250 | 62 | 16 | 4 | 250 | 62 | 16 | 4 | 250 | 62 | 16 | 4 | 4 |
| WILD BUCKWHEAT | 90 | — | 0 | 100 | 90 | — | 0 | 80 | 100 | — | 50 | 100 | 80 | — | 20 | 100 | 90 | 30 | — | 100 | 100 | 0 |
| BLACKGRASS | 80 | 40 | 10 | 90 | 90 | 50 | 40 | 100 | 80 | 40 | 90 | 90 | 70 | — | 70 | 80 | 70 | — | 0 | 100 | 80 | 30 |
| RAPE | 100 | 60 | 30 | 70 | 100 | 70 | 60 | 100 | 80 | 50 | 60 | 100 | 80 | 80 | 30 | 80 | 80 | 0 | 0 | 100 | 80 | 30 |
| BARLEY | 10 | 0 | 0 | 0 | 40 | 80 | 10 | 30 | 20 | 0 | 10 | 40 | 20 | 10 | 0 | 70 | 10 | 0 | — | 100 | 70 | 0 |
| GREEN FOXTAIL | 90 | 10 | 0 | 100 | 100 | 20 | 40 | 100 | 100 | 70 | 40 | 100 | 100 | 100 | 20 | 100 | 100 | 0 | — | 100 | 100 | 0 |
| CHEATGRASS | 90 | 50 | 30 | 100 | 80 | 100 | 50 | 100 | 70 | 40 | 50 | 90 | 70 | 100 | 20 | 70 | 40 | 0 | 50 | — | 90 | 10 |
| LAMBSQUARTERS | 100 | 50 | 0 | 100 | 100 | 70 | 40 | 100 | 100 | 60 | 90 | 100 | 60 | 100 | 0 | 100 | — | 70 | 50 | — | 90 | — |
| CHICKWEED | 90 | 70 | 20 | 100 | 100 | 80 | 60 | 100 | 90 | 90 | 100 | 100 | 90 | 100 | — | 90 | — | 30 | 40 | 80 | 100 | 40 |
| DOWNY BROME | — | — | — | — | — | — | — | — | — | — | 70 | 50 | — | 100 | 100 | 80 | — | 100 | 100 | 30 | — | 0 |

POSTEMERGENCE

|  | CMPD 8 | CMPD 9 | | | | CMPD 10 | | | | CMPD 11 | | | | CMPD 12 | | | | CMPD 13 |
|---|---|---|---|---|---|---|---|---|---|---|---|---|---|---|---|---|---|---|
| RATE = G/HA | 16 | 250 | 62 | 16 | 4 | 250 | 62 | 16 | 4 | 250 | 62 | 16 | 4 | 250 | 62 | 16 | 4 | 4 |
| GIANT FOXTAIL | 0 | 100 | 100 | 80 | 60 | 100 | 100 | 80 | 50 | 100 | 80 | 50 | 60 | 30 | 100 | 70 | 50 | 70 |
| VELVETLEAF | 70 | 100 | 80 | 90 | 70 | 100 | 100 | 100 | 80 | 70 | 70 | 30 | 60 | 0 | 80 | 70 | 60 | 50 |
| SUGARBEET | 80 | 100 | 90 | 100 | 70 | 100 | 100 | 90 | 70 | 100 | 100 | 80 | 70 | 0 | 100 | 90 | 80 | 70 |
| CRABGRASS | 0 | 60 | 70 | 0 | 0 | 0 | 0 | 40 | 20 | 70 | 50 | 40 | 30 | 0 | 50 | 30 | 70 | 30 |
| TEAWEED | 0 | 100 | 100 | 70 | 50 | 100 | 100 | 90 | 70 | 100 | 70 | 50 | 70 | 0 | 80 | 70 | 60 | 60 |
| JIMSONWEED | 0 | 100 | 70 | 30 | 70 | 100 | 100 | 100 | 90 | 100 | 70 | 30 | 40 | 20 | 90 | 90 | 70 | 50 |
| RICE | 0 | 100 | 100 | 80 | 80 | 100 | 80 | 90 | 30 | 100 | 60 | 50 | 50 | 20 | 90 | 80 | 50 | 70 |
| COCKLEBUR | 40 | 100 | 70 | 100 | 80 | 100 | 50 | 90 | 70 | 100 | 70 | 70 | 80 | 0 | 100 | 70 | 60 | 70 |
| COTTON | 20 | 70 | 50 | 30 | 0 | 100 | 20 | 50 | 0 | 40 | 30 | 20 | 0 | 0 | 50 | 50 | 50 | 0 |
| SOYBEAN | 30 | 100 | 100 | 100 | 90 | 100 | 100 | 100 | 100 | 100 | 60 | 100 | 100 | 0 | 100 | 100 | 0 | 100 |
| BARNYARDGRASS | 70 | 100 | 90 | 30 | 50 | 100 | 70 | 50 | 30 | 100 | 80 | 70 | 70 | 100 | 70 | 70 | 60 | 80 |
| WILD OAT | 10 | 100 | 80 | 60 | 50 | 100 | 100 | 100 | 0 | 60 | 60 | 50 | 60 | 0 | 50 | 30 | 30 | 70 |
| MORNINGGLORY | 0 | 100 | 70 | 80 | 80 | 100 | 100 | 50 | 30 | 70 | 50 | 60 | 70 | 30 | 70 | 70 | 0 | 70 |
| WHEAT | 0 | 100 | 70 | 30 | 30 | 80 | 60 | 30 | 30 | 50 | 30 | 30 | 0 | 0 | 60 | 30 | 30 | 0 |
| SICKLEPOD | 0 | 80 | 50 | 30 | 30 | 90 | 30 | 70 | 60 | 50 | 80 | 50 | 50 | 0 | 30 | 30 | 0 | 50 |
| JOHNSONGRASS | 20 | 100 | 100 | 50 | 60 | 100 | 100 | 80 | 30 | 90 | 30 | 70 | 30 | 70 | 80 | 50 | 70 | 60 |
| NUTSEDGE | 0 | 100 | 50 | 50 | 0 | 100 | 50 | 70 | 30 | 90 | 70 | 30 | 50 | 0 | 60 | 30 | 0 | 30 |
| CORN | 30 | 100 | 100 | 70 | 50 | 100 | 100 | 70 | 60 | 100 | 90 | 60 | 70 | 70 | 100 | 50 | 50 | 80 |
| WILD BUCKWHEAT | 0 | 90 | 50 | 0 | — | 100 | 70 | 30 | 0 | 60 | 50 | 30 | 70 | 0 | 100 | 70 | 0 | 100 |
| BLACKGRASS | 40 | 100 | 100 | 80 | 60 | 90 | 70 | 80 | 30 | 90 | 50 | 50 | 50 | 50 | 100 | 50 | 50 | 80 |
| RAPE | 10 | 90 | 90 | 90 | 60 | 100 | 100 | 60 | 70 | 100 | 90 | 30 | 40 | 30 | 70 | 70 | 30 | 30 |
| BARLEY | 90 | 30 | 70 | 70 | 0 | 90 | 30 | 50 | 0 | 60 | 60 | 50 | 50 | 50 | 50 | 50 | 50 | 90 |
| GREEN FOXTAIL | 0 | 70 | 50 | 0 | 0 | 100 | 100 | 70 | 0 | 100 | 70 | 50 | 70 | 30 | 100 | 70 | 0 | 0 |
| CHEATGRASS | 20 | 100 | 100 | 60 | 60 | 100 | 100 | 70 | 50 | 100 | 70 | 50 | 60 | 30 | 100 | 70 | 50 | 30 |
| LAMBSQUARTERS | 40 | 100 | 80 | 50 | 50 | 100 | 100 | 90 | 70 | 100 | 90 | 80 | 70 | 50 | 30 | 30 | — | 60 |
| CHICKWEED | 80 | 100 | 100 | 90 | 70 | 100 | 100 | 100 | 100 | 100 | 80 | 80 | 80 | 70 | 100 | 90 | 90 | 90 |
| DOWNY BROME | 20 | 100 | 100 | 70 | 50 | 100 | 70 | 90 | 30 | 50 | 70 | 50 | 50 | 50 | 70 | 50 | 60 | 50 |

PREEMERGENCE

|  | CMPD 11 | | | | CMPD 12 | | | | CMPD 13 | | | | CMPD 15 | | | | CMPD 20 |
|---|---|---|---|---|---|---|---|---|---|---|---|---|---|---|---|---|---|
| RATE = G/HA | 250 | 62 | 16 | 4 | 250 | 62 | 16 | 4 | 250 | 62 | 16 | 4 | 250 | 62 | 16 | 4 | 4 |
| GIANT FOXTAIL | 100 | 100 | 80 | 30 | 100 | 70 | 40 | 30 | 100 | 60 | 50 | 30 | 100 | 90 | 40 | 50 | 20 |
| VELVETLEAF | 90 | 60 | 30 | 40 | 90 | 70 | 70 | 40 | 90 | 50 | 70 | 70 | 90 | 80 | 70 | 80 | 30 |
| SUGARBEET | 100 | 90 | 60 | 50 | 100 | 30 | 90 | 50 | 100 | 70 | 70 | 50 | 100 | 90 | 70 | 70 | 50 |
| CRABGRASS | 90 | 60 | 30 | 80 | 100 | 80 | 70 | 30 | 100 | 40 | 50 | 30 | 100 | 70 | 90 | 60 | 30 |
| TEAWEED | 80 | 60 | 0 | 50 | 80 | 30 | 50 | 30 | 70 | 30 | 30 | 60 | 95 | 80 | 85 | 90 | 30 |
| JIMSONWEED | 90 | 50 | 50 | 70 | 70 | 50 | 30 | 50 | 50 | 50 | 70 | 50 | 90 | 70 | 50 | 70 | 50 |
| JIMSONWEED | 70 | 30 | 70 | 30 | 50 | 100 | 80 | 30 | 50 | 50 | 50 | 70 | 90 | 80 | 60 | 50 | 30 |
| RICE | 90 | 80 | 70 | 70 | 100 | 80 | 50 | 30 | 60 | 60 | 50 | 70 | 90 | 80 | 60 | 60 | 30 |
| COCKLEBUR | 70 | 30 | — | — | 100 | — | — | — | 70 | — | — | — | 90 | — | — | — | 20 |

TABLE B-continued

| | CMPD 22 | CMPD 15 | | | CMPD 20 | | | CMPD 22 | | | CMPD 23 | | CMPD 27 | | | CMPD 28 | | | CMPD 29 |
|---|---|---|---|---|---|---|---|---|---|---|---|---|---|---|---|---|---|---|---|
| | 62 | 16 | 4 | 62 | 16 | 4 | 1 | 250 | 62 | 16 | 4 | 16 | 62 | 250 | 16 | 4 | 62 | 16 | 4 | 250 | 62 |
| COTTON | 70 | 30 | 0 | 0 | 0 | 0 | 30 | 0 | 0 | 0 | 0 | 0 | 30 | 50 | 0 | 80 | 30 | 90 | 80 | 50 | 20 |
| SOYBEAN | 70 | 50 | 30 | 40 | 0 | 70 | 70 | 30 | 90 | 60 | 30 | 60 | 0 | 30 | 0 | 80 | 30 | 100 | 70 | 20 | 0 |
| BARNYARDGRASS | 90 | 60 | 30 | 30 | 0 | 100 | 60 | 30 | 90 | 60 | 50 | 50 | 0 | 0 | 30 | 100 | 30 | 80 | 100 | 40 | 20 |
| WILD OAT | 80 | 60 | 30 | 30 | 0 | 80 | 50 | 30 | 80 | 70 | 30 | 50 | 30 | 70 | 30 | 70 | 50 | 100 | 50 | 20 | 0 |
| MORNINGGLORY | 80 | 60 | 30 | 30 | 0 | 60 | 50 | — | 70 | 30 | 50 | 60 | 30 | 60 | 0 | 80 | 50 | 100 | 80 | 60 | 20 |
| WHEAT | 60 | 0 | 0 | 30 | 0 | 60 | 20 | 0 | 70 | 30 | 0 | 30 | 0 | 50 | 50 | 0 | 30 | 100 | 40 | 10 | 0 |
| SICKLEPOD | 90 | 80 | 70 | 30 | 30 | 90 | 90 | 50 | 100 | 60 | 50 | 80 | 30 | 60 | 30 | 80 | 50 | 100 | 60 | 60 | 30 |
| JOHNSONGRASS | 90 | 80 | 30 | 80 | 60 | 100 | 90 | 60 | 90 | 90 | 90 | 30 | 30 | 50 | 0 | 90 | 30 | 100 | 90 | 90 | 0 |
| NUTSEDGE | 60 | 30 | 0 | 30 | 0 | 70 | 50 | 30 | 80 | 50 | 70 | 60 | 0 | 30 | 30 | 100 | 50 | 90 | 60 | 20 | 30 |
| CORN | 90 | 60 | 30 | 80 | 30 | 70 | 70 | 30 | 90 | 70 | 70 | 70 | 30 | 50 | 0 | 90 | 30 | 100 | 40 | 30 | 0 |
| WILD BUCKWHEAT | 90 | 70 | 50 | 70 | 50 | 90 | 90 | 70 | 90 | 80 | 60 | 90 | 0 | 30 | 50 | 100 | 60 | 100 | 80 | 30 | 20 |
| BLACKGRASS | 90 | 70 | 50 | 50 | 0 | 100 | 60 | 60 | 100 | 70 | 50 | 70 | 50 | 70 | 80 | 90 | 70 | 100 | 90 | 70 | 30 |
| RAPE | 0 | 0 | 0 | 0 | 0 | 90 | 60 | 30 | 90 | 60 | 30 | 60 | 30 | 80 | 70 | 100 | 70 | 100 | 90 | 30 | 20 |
| BARLEY | 60 | 0 | 30.0 | 90 | 0 | 90 | 100 | 80 | 100 | 100 | 60 | 30 | 50 | 90 | 0 | 90 | 30 | 90 | 90 | 0 | 0 |
| GREEN FOXTAIL | 100 | 80 | 50 | 100 | 90 | 100 | — | — | — | — | — | — | — | — | — | — | — | — | — | 40 | 30 |
| CHEATGRASS | — | — | — | — | — | — | — | — | — | — | — | — | — | — | — | — | — | — | — | — | — |
| LAMBSQUARTERS | 90 | 70 | 50 | 60 | 50 | 90 | 90 | 90 | 100 | 90 | 80 | 90 | 30 | 60 | 30 | 90 | 50 | 100 | 90 | 90 | 80 |
| CHICKWEED | 90 | 70 | 30 | 70 | 30 | 100 | 100 | 100 | 100 | 100 | 90 | 100 | 80 | 100 | 80 | 100 | 70 | 100 | 100 | 80 | 80 |
| DOWNY BROME | 90 | 60 | 30 | 50 | 0 | 100 | 90 | 60 | 100 | 70 | 50 | 90 | 50 | 100 | 30 | 90 | 30 | 100 | 60 | 20 | 0 |
| RATE = G/HA | 62 | 16 | 4 | 62 | 16 | 4 | 1 | 250 | 62 | 16 | 4 | 16 | 62 | 250 | 16 | 4 | 62 | 16 | 4 | 250 | 62 |

POSTEMERGENCE

| | CMPD 22 | | | CMPD 23 | | CMPD 27 | | | CMPD 28 | | | CMPD 29 | | CMPD 31 | | CMPD 32 | | CMPD 40 | | CMPD 41 |
|---|---|---|---|---|---|---|---|---|---|---|---|---|---|---|---|---|---|---|---|---|---|
| | 62 | 16 | 4 | 16 | 62 | 250 | 62 | 16 | 4 | 62 | 16 | 1 | 250 | 62 | 16 | 250 | 62 | 250 | 62 | 16 | 4 | 250 |
| GIANT FOXTAIL | 100 | 90 | 60 | 100 | 100 | 100 | 100 | 50 | 20 | 80 | 100 | 10 | 100 | 90 | 50 | 100 | 100 | 80 | 70 | 70 | 100 |
| VELVETLEAF | 100 | 100 | 90 | 90 | 100 | 100 | 100 | 70 | 40 | 100 | 100 | 40 | 100 | 90 | 70 | 100 | 100 | 100 | 80 | 80 | 100 | 90 |
| SUGARBEET | 100 | 100 | 100 | 100 | 100 | 100 | 100 | 90 | 60 | 100 | 80 | 30 | 100 | 100 | 90 | 100 | 100 | 80 | 100 | 80 | 100 | 100 |
| CRABGRASS | 100 | 70 | 50 | 80 | 100 | 100 | 100 | 50 | 40 | 100 | 30 | 10 | 100 | 50 | 50 | 100 | 100 | 30 | 70 | 30 | 50 | 50 |
| TEAWEED | 100 | 90 | 70 | 70 | 100 | 100 | 100 | 40 | 30 | 80 | 70 | 20 | 100 | 40 | 40 | 100 | 100 | 70 | 50 | 50 | 80 | 80 |
| JIMSONWEED | 100 | 90 | 60 | 80 | 100 | 100 | 100 | 100 | 90 | 100 | 100 | 80 | 100 | 80 | 60 | 100 | 100 | 100 | 80 | 80 | 90 | 90 |
| RICE | 100 | 80 | 70 | 70 | 100 | 100 | 100 | 40 | 40 | 100 | 40 | 20 | 100 | 70 | 40 | 100 | 100 | 90 | 80 | 80 | 100 | 90 |
| COCKLEBUR | 100 | 100 | 80 | 100 | 100 | 100 | 100 | 80 | 60 | 100 | 60 | 80 | 100 | 90 | 60 | 100 | 100 | 80 | 80 | 40 | 80 | 20 |
| COTTON | 100 | 60 | 30 | 70 | 100 | 80 | 100 | 20 | 0 | 70 | 30 | 10 | 70 | 50 | 0 | 100 | 100 | 50 | 40 | 10 | 30 | 60 |
| SOYBEAN | 100 | 100 | 70 | 100 | 100 | 100 | 100 | 70 | 80 | 100 | 60 | 60 | 100 | 80 | 80 | 100 | 100 | 90 | 70 | 70 | 80 | 100 |
| BARNYARDGRASS | 100 | 80 | 30 | 70 | 100 | 80 | 100 | 50 | 20 | 100 | 20 | 40 | 100 | 50 | 20 | 100 | 100 | 50 | 40 | 10 | 50 | 40 |
| WILD OAT | 80 | 50 | 30 | 50 | 100 | 100 | 100 | 70 | 50 | 100 | 60 | 20 | 100 | 70 | 50 | 100 | 100 | 80 | 70 | 70 | 80 | 70 |
| MORNINGGLORY | 100 | 90 | 30 | 100 | 100 | 100 | 100 | 40 | 40 | 100 | 40 | 40 | 100 | 90 | 70 | 100 | 100 | 90 | 50 | 50 | 90 | 40 |
| WHEAT | 60 | 30 | 0 | 70 | 90 | 80 | 80 | 20 | 0 | 70 | 70 | 0 | 70 | 20 | 0 | 80 | 100 | 100 | 90 | 90 | 90 | 100 |
| SICKLEPOD | 100 | 80 | 30 | 50 | 100 | 100 | — | 60 | 50 | 100 | 50 | 30 | 100 | 50 | 50 | 100 | 100 | 10 | 10 | 10 | 50 | — |
| JOHNSONGRASS | 100 | 80 | 50 | 100 | 100 | 100 | 100 | 70 | 60 | 100 | 70 | 30 | 100 | 70 | 70 | 100 | 100 | 70 | 100 | 70 | 50 | 0 |
| NUTSEDGE | 100 | 100 | 40 | 70 | 100 | 100 | 100 | 60 | 50 | 100 | 50 | 40 | 100 | 50 | 0 | 100 | 100 | 90 | 50 | 50 | 40 | 100 |
| CORN | 100 | 100 | 80 | 100 | 100 | 100 | 100 | 90 | 30 | 100 | 80 | 20 | 100 | 90 | 20 | 100 | 100 | 90 | 90 | 40 | 100 | 90 |
| WILD BUCKWHEAT | 100 | 100 | 60 | 100 | 100 | 100 | 100 | 50 | 10 | 90 | 40 | 10 | 100 | 100 | 50 | 100 | 100 | — | — | 10 | 80 | 100 |
| BLACKGRASS | 80 | 50 | 30 | 100 | 100 | 100 | 100 | 40 | 50 | 100 | 60 | 70 | 100 | 50 | 70 | 100 | 100 | 90 | 90 | 70 | 80 | 40 |
| RAPE | 100 | 90 | 60 | 80 | 100 | 100 | 100 | 40 | 20 | 100 | 40 | 40 | 100 | 80 | 40 | 100 | 100 | 40 | 40 | 40 | 100 | 90 |
| BARLEY | 60 | 30 | 0 | 80 | 60 | 100 | — | 30 | 0 | 60 | 30 | 0 | 70 | 20 | 0 | 80 | 80 | 70 | 70 | 70 | 90 | 90 |
| GREEN FOXTAIL | 100 | 50 | 50 | 50 | 80 | 100 | 60 | 10 | 30 | 80 | 10 | 0 | 70 | 20 | 30 | 100 | 100 | 20 | 20 | 10 | 20 | 70 |
| CHEATGRASS | 70 | 50 | 30 | 0 | 100 | 100 | 100 | 40 | 40 | 60 | 30 | — | 90 | 70 | 40 | 100 | 100 | 100 | 100 | 90 | 90 | — |
| LAMBSQUARTERS | — | — | — | — | — | — | — | — | — | — | — | — | — | — | — | — | — | — | — | — | — | 0 |
| CHICKWEED | 100 | 100 | 70 | 100 | 100 | 100 | 100 | 60 | 80 | 100 | 70 | 90 | 100 | 100 | 60 | 100 | 100 | 90 | 90 | 70 | 100 | 100 |
| DOWNY BROME | 100 | 100 | 50 | 100 | 90 | 100 | 100 | 30 | 30 | 80 | 20 | 20 | 100 | 80 | 80 | 100 | 80 | 100 | 100 | 70 | 100 | 90 |
| RATE = G/HA | 62 | 16 | 4 | 16 | 62 | 250 | 62 | 16 | 4 | 62 | 16 | 1 | 250 | 62 | 16 | 250 | 62 | 250 | 62 | 16 | 4 | 250 |

TABLE B-continued

| | | | | | | | | | | | PREEMERGENCE | | | | | | | | | | | |
|---|---|---|---|---|---|---|---|---|---|---|---|---|---|---|---|---|---|---|---|---|---|---|
| GIANT FOXTAIL | 90 | 80 | 60 | 20 | 50 | 40 | 40 | 0 | 50 | 0 | 0 | 30 | 95 | 90 | 80 | 70 | 80 | 50 | 70 | — | 100 | 100 | 100 |
| VELVETLEAF | 90 | 80 | 60 | 50 | 90 | 70 | 70 | 40 | 80 | 50 | 30 | 30 | 90 | 80 | 20 | 90 | 20 | 30 | 100 | 80 | 100 | 40 | 90 |
| SUGARBEET | 100 | 90 | 80 | 70 | 100 | 80 | 70 | 60 | 100 | 90 | 60 | 70 | 80 | 80 | 0 | 100 | 0 | 30 | 100 | 100 | 100 | 100 | 100 |
| CRABGRASS | 100 | 80 | 80 | 30 | 90 | 80 | 30 | 0 | 70 | 50 | 30 | 30 | 80 | 50 | 20 | 70 | 50 | 30 | 90 | 70 | 90 | 85 | 90 |
| TEAWEED | 90 | 80 | 50 | 30 | 90 | 40 | 20 | 10 | 90 | 60 | 30 | 0 | 90 | 30 | 0 | 80 | 30 | 30 | 80 | 80 | 100 | 90 | 100 |
| JIMSONWEED | 100 | 90 | 40 | 30 | 100 | 80 | 40 | 0 | 90 | 80 | 30 | 30 | 90 | 30 | 0 | 80 | 30 | 0 | 90 | 90 | 100 | 80 | 100 |
| RICE | 100 | 100 | 90 | 30 | 100 | 80 | 90 | 20 | 100 | 80 | 60 | 30 | 90 | 30 | 80 | 95 | 80 | 85 | 100 | 90 | 100 | 30 | 90 |
| COCKLEBUR | 80 | 50 | 30 | 0 | 40 | 20 | 20 | 50 | 90 | 60 | 70 | 80 | 90 | 50 | 40 | 60 | 50 | 30 | 80 | 40 | 80 | 70 | 90 |
| COTTON | 40 | 30 | 20 | 20 | 70 | 50 | 40 | 0 | 60 | 30 | 0 | 0 | 90 | 0 | 30 | 30 | 0 | 0 | 100 | 60 | 100 | 100 | 80 |
| SOYBEAN | 90 | 50 | 40 | 10 | 90 | 60 | 40 | 10 | 70 | 0 | 0 | 0 | 80 | 0 | 80 | 80 | 60 | 0 | 100 | 50 | 100 | 60 | 70 |
| BARNYARDGRASS | 100 | 100 | 50 | 40 | 100 | 80 | 40 | 0 | 50 | 40 | 30 | 30 | 90 | 80 | 30 | 40 | 30 | 30 | 100 | 80 | 100 | 80 | 100 |
| WILD OAT | 100 | 80 | 50 | 40 | 80 | 50 | 40 | 20 | 80 | 50 | 60 | 20 | 80 | 30 | 80 | 30 | 30 | 0 | 80 | 40 | 85 | 80 | 80 |
| MORNINGGLORY | 100 | 70 | 50 | 30 | 100 | 90 | 60 | 30 | 90 | 80 | 60 | 30 | 90 | 90 | 30 | 70 | 60 | 50 | 90 | 70 | 100 | 50 | 80 |
| WHEAT | 80 | 70 | 40 | 0 | 80 | 70 | — | 0 | 70 | 30 | 30 | 0 | 40 | 30 | 0 | 40 | 40 | 0 | 90 | 40 | 100 | 90 | 100 |
| SICKLEPOD | 100 | 100 | 40 | 30 | 100 | 100 | 80 | 30 | 80 | 50 | 50 | 30 | 100 | 40 | 40 | 90 | 70 | 30 | 100 | 90 | 100 | 90 | 90 |
| JOHNSONGRASS | 100 | 100 | 80 | 70 | 100 | 90 | 0 | — | 80 | 40 | 30 | 0 | 90 | 70 | 50 | 100 | 100 | 90 | 100 | 90 | 95 | 90 | 90 |
| NUTSEDGE | 100 | 40 | — | 20 | 30 | 10 | 30 | 0 | 80 | 0 | 0 | 50 | 0 | 0 | 30 | 70 | 50 | 30 | 100 | 30 | 100 | 100 | 100 |
| CORN | 100 | 90 | 30 | 10 | 100 | 90 | 60 | — | 70 | 90 | 70 | 0 | 90 | 60 | 90 | 50 | 40 | 50 | 50 | 40 | 100 | 80 | 100 |
| WILD BUCKWHEAT | 100 | 100 | 80 | 100 | 100 | 90 | 30 | 0 | 100 | 50 | 30 | 0 | 100 | 90 | 90 | 100 | 70 | 0 | 100 | 100 | 100 | 100 | 100 |
| BLACKGRASS | 90 | 90 | 60 | — | 90 | 40 | 60 | — | 70 | 30 | 0 | 50 | 80 | 70 | 60 | 90 | 50 | 50 | 90 | 80 | 100 | 80 | 90 |
| RAPE | 100 | 100 | 80 | 40 | 100 | 50 | 30 | 30 | 50 | 30 | 0 | 30 | 100 | 80 | 40 | 80 | 0 | 0 | 100 | 60 | 100 | 100 | 100 |
| BARLEY | 70 | 70 | 20 | 50 | 90 | 30 | 0 | 0 | 70 | 30 | 0 | 50 | 80 | 40 | 30 | 60 | 30 | 80 | 90 | 90 | 100 | 70 | 50 |
| GREEN FOXTAIL | 100 | 80 | 40 | 0 | 100 | 60 | 30 | — | 100 | 100 | 50 | 0 | 100 | 80 | 90 | 100 | 100 | 0 | 100 | 100 | 100 | 100 | 100 |
| CHEATGRASS | — | — | — | — | — | — | — | — | — | — | — | — | — | — | — | — | — | — | — | — | — | — | — |
| LAMBSQUARTERS | 100 | 90 | 40 | 40 | 100 | 70 | 80 | 60 | 90 | 80 | 50 | 50 | 80 | 60 | 80 | 100 | 90 | 30 | 90 | 100 | 90 | 90 | 90 |
| CHICKWEED | 100 | 100 | 100 | 80 | 100 | 100 | 100 | 80 | 100 | 100 | 100 | 100 | 100 | 100 | 50 | 100 | 100 | 50 | 100 | 100 | 100 | 100 | 100 |
| DOWNY BROME | 100 | 100 | 90 | 30 | 100 | 50 | 0 | 0 | 100 | 80 | 30 | 90 | 60 | 40 | 90 | 90 | 60 | 90 | 90 | 90 | 100 | 90 | 100 |

POSTEMERGENCE

| RATE = G/HA | CMPD 29 | | CMPD 31 | | CMPD 42 | | CMPD 44 | | CMPD 32 | | CMPD 40 | | | CMPD 41 | | | CMPD 42 | | CMPD 44 | |
|---|---|---|---|---|---|---|---|---|---|---|---|---|---|---|---|---|---|---|---|---|
| | 16 | 4 | 62 | 4 | 250 | 62 | 17 | 250 | 62 | 4 | 250 | 62 | 16 | 4 | 62 | 16 | 1 | 250 | 62 | 4 | 16 | 250 | 62 | 16 | 4 |
| GIANT FOXTAIL | 80 | 30 | 100 | 70 | 100 | 100 | 100 | 100 | 100 | 40 | 100 | 100 | 100 | 100 | 100 | 80 | 50 | 100 | 80 | 40 | 50 | 100 | 100 | 90 | 60 |
| VELVETLEAF | 70 | 40 | 100 | 100 | 100 | 80 | 50 | 100 | 70 | 80 | 100 | 100 | 100 | 100 | 100 | 90 | 30 | 100 | 90 | 80 | 20 | 100 | 100 | 100 | 90 |
| SUGARBEET | 100 | 90 | 100 | 100 | 100 | 100 | 100 | 100 | 100 | 70 | 100 | 100 | 100 | 100 | 100 | 100 | 90 | 100 | 80 | 50 | 80 | 100 | 100 | 100 | 100 |
| CRABGRASS | 20 | 0 | 80 | 10 | 80 | 40 | 70 | 100 | 100 | — | 100 | 90 | 50 | 40 | 80 | 60 | 0 | 60 | 40 | 0 | 30 | 100 | 90 | 40 | 30 |
| TEAWEED | 30 | 0 | 100 | 70 | 100 | 90 | 40 | 100 | 100 | 40 | 100 | 100 | 80 | 50 | 60 | 90 | 40 | 90 | 60 | 20 | 30 | 100 | 100 | 80 | 50 |
| JIMSONWEED | 80 | — | 100 | 100 | 100 | 100 | 90 | 100 | 100 | 80 | 100 | 100 | 100 | 80 | 100 | 100 | 60 | 100 | 80 | 30 | 60 | 100 | 100 | 90 | 80 |
| RICE | 40 | 40 | 100 | 70 | 100 | 90 | 60 | 100 | 100 | 70 | 100 | 100 | 100 | 90 | 90 | 90 | 60 | 100 | 90 | 40 | 80 | 100 | 100 | 100 | 80 |
| COCKLEBUR | 90 | 0 | 100 | 90 | 100 | 60 | 60 | 100 | 100 | 30 | 100 | 100 | 180 | 100 | 100 | 100 | 50 | 100 | 100 | 40 | 70 | 100 | 100 | 90 | 80 |
| COTTON | 0 | 40 | 100 | 70 | 90 | 90 | 40 | 100 | 90 | 10 | 90 | 100 | 100 | 90 | 70 | 80 | 0 | 80 | 60 | 0 | 40 | 90 | 80 | 60 | 20 |
| SOYBEAN | 50 | 0 | 90 | 40 | 90 | 60 | 40 | 90 | 90 | 10 | 90 | 90 | 90 | 50 | 60 | 40 | 80 | 80 | 40 | 0 | 0 | 90 | 80 | 80 | 20 |
| BARNYARDGRASS | 50 | 40 | 100 | 90 | 100 | 100 | 90 | 100 | 100 | 80 | 100 | 100 | 100 | 50 | 100 | 40 | 0 | 100 | 90 | 0 | 80 | 100 | 100 | 100 | 40 |
| WILD OAT | 50 | 0 | 100 | 70 | 90 | 80 | 70 | 90 | 80 | 70 | 90 | 100 | 50 | 90 | 90 | 90 | 40 | 70 | 40 | 40 | 60 | 100 | 100 | 70 | 40 |
| MORNINGGLORY | 90 | 60 | 100 | 90 | 100 | 100 | 90 | 100 | 100 | 80 | 100 | 100 | 90 | 100 | 100 | 80 | 90 | 100 | 70 | 30 | 90 | 100 | 100 | 100 | 90 |
| WHEAT | 50 | 0 | 100 | 70 | 90 | 80 | 50 | 100 | 80 | 20 | 90 | 100 | 40 | 20 | 60 | 30 | 10 | 60 | 40 | 10 | 10 | 100 | 100 | 50 | 30 |
| SICKLEPOD | 90 | 60 | 100 | 90 | 100 | 100 | 70 | 100 | 100 | 70 | 100 | 100 | 100 | 100 | 100 | 50 | 50 | 80 | 30 | 30 | 40 | 100 | 100 | 100 | 40 |
| JOHNSONGRASS | 20 | 0 | 100 | 80 | 100 | 100 | 80 | 100 | 100 | 70 | 100 | 100 | 100 | 100 | 100 | 20 | 40 | 100 | 40 | 30 | 0 | 100 | 100 | 70 | 80 |
| NUTSEDGE | 80 | 50 | 100 | 70 | 100 | 100 | 90 | 100 | 100 | 50 | 100 | 100 | 100 | 100 | 100 | 100 | 90 | 100 | 100 | 0 | 80 | 100 | 100 | 90 | 80 |
| CORN | 0 | 0 | 70 | 50 | 70 | 60 | 50 | 100 | 60 | 30 | 60 | 100 | 80 | 60 | 60 | 30 | 90 | 90 | 30 | 0 | 40 | 100 | 100 | 50 | 70 |
| WILD BUCKWHEAT | 90 | 20 | 100 | 100 | 100 | 100 | 100 | 100 | 100 | 90 | 100 | 100 | 100 | 100 | 100 | 90 | 80 | 100 | 90 | 60 | 80 | 100 | 100 | 100 | 80 |
| BLACKGRASS | 100 | 80 | 100 | 100 | 100 | 100 | 100 | 100 | 100 | 60 | 100 | 100 | 100 | 80 | 100 | 80 | 80 | 100 | 80 | 10 | 60 | 100 | 100 | 100 | 90 |
| RAPE | 80 | 40 | 100 | 90 | 90 | 60 | 90 | 100 | 60 | 40 | 100 | 100 | 80 | 50 | 50 | 20 | 20 | 80 | 50 | 30 | 10 | 100 | 100 | 50 | 50 |
| BARLEY | 90 | 90 | 100 | 0 | 70 | 70 | 0 | 100 | 70 | 0 | 100 | 100 | 100 | 40 | 40 | 100 | 100 | 40 | 50 | 90 | 0 | 100 | 100 | 70 | 100 |
| GREEN FOXTAIL | 80 | 50 | 100 | 30 | 100 | 100 | 30 | 100 | 100 | 10 | 100 | 100 | 90 | 50 | 90 | 20 | 10 | 40 | 30 | 90 | 30 | 100 | 100 | 70 | 40 |
| CHEATGRASS | 60 | 40 | 100 | 90 | 100 | 100 | 90 | 100 | 100 | 60 | 100 | 100 | 100 | 100 | 100 | 40 | 60 | 100 | 40 | 10 | 0 | 100 | 100 | 90 | 50 |
| LAMBSQUARTERS | — | — | — | — | — | — | — | — | — | — | — | — | — | — | — | — | — | — | — | — | — | — | — | — | — |
| CHICKWEED | 0 | 0 | 100 | 50 | 100 | 100 | 50 | 100 | 100 | 40 | 100 | 100 | 100 | 100 | 100 | 60 | 60 | 100 | 90 | 60 | 60 | 100 | 100 | 100 | 60 |
| DOWNY BROME | 100 | 100 | 100 | 50 | 100 | 100 | 50 | 100 | 100 | 0 | 100 | 100 | 60 | 100 | 100 | 60 | 60 | 100 | 50 | 30 | 30 | 100 | 100 | 100 | — |
| | 80 | 40 | 100 | 80 | 100 | 100 | 80 | 100 | 100 | 40 | 100 | 100 | 70 | 90 | 80 | 50 | 100 | 80 | 40 | — | 100 | 100 | 80 | 70 |

PREEMERGENCE

| RATE = G/HA | CMPD 41 | CMPLD 46 | | CMPD 45 | | | CMPD 47 | | | CMPD 48 | | | CMPD 49 | | |
|---|---|---|---|---|---|---|---|---|---|---|---|---|---|---|---|
| | 62 | 250 | 62 | 250 | 62 | 16 | 250 | 62 | 16 | 250 | 62 | 16 | 250 | 62 | 16 |
| GIANT FOXTAIL | 90 | 100 | 95 | 90 | 80 | 40 | 90 | 90 | 60 | 90 | 30 | 0 | 90 | 90 | 70 |
| VELVETLEAF | 30 | 60 | 90 | 80 | 40 | 0 | 90 | 60 | 80 | 90 | 70 | 50 | 100 | 85 | 80 |
| SUGARBEET | 90 | 90 | 90 | 100 | 100 | 70 | 90 | 85 | 70 | 90 | 70 | 70 | 80 | 80 | 70 |
| CRABGRASS | 80 | 100 | 85 | 95 | 100 | 90 | 90 | 80 | 70 | 90 | 80 | 50 | 80 | 80 | 70 |
| TEAWEED | 80 | 100 | 80 | 100 | 100 | 0 | 90 | 70 | 30 | 90 | 30 | 0 | 80 | 80 | 60 |
| JIMSONWEED | 80 | 100 | 80 | 100 | 90 | 0 | 90 | 60 | 30 | 90 | 70 | 30 | 80 | 80 | 60 |
| RICE | 90 | 100 | 100 | 90 | 100 | 100 | 90 | 70 | 30 | 80 | 30 | 0 | 70 | 70 | 70 |
| COCKLEBUR | 100 | 80 | 80 | 70 | 30 | 30 | 70 | 80 | 30 | 70 | 50 | 50 | 70 | 50 | 50 |
| COTTON | 60 | 80 | 80 | 100 | 60 | 20 | 70 | 30 | 30 | 70 | 50 | 30 | 50 | 30 | 30 |
| SOYBEAN | 50 | 80 | 60 | 80 | 50 | 0 | 30 | 60 | 30 | 30 | 0 | 0 | 50 | 50 | 30 |
| BARNYARDGRASS | 80 | 100 | 100 | 70 | 60 | 30 | 90 | 50 | 30 | 60 | 60 | 30 | 70 | 70 | 30 |
| WILD OAT | 60 | 70 | 40 | 100 | 40 | 80 | 70 | 80 | 70 | 0 | 0 | 0 | 80 | 50 | 30 |
| MORNINGGLORY | 30 | 70 | 80 | 90 | 40 | 20 | 50 | 60 | 30 | 50 | 60 | 0 | 50 | 70 | 30 |
| WHEAT | 90 | 80 | 30 | 100 | 95 | 70 | 70 | 80 | 70 | 90 | 70 | 30 | 70 | 50 | 50 |
| SICKLEPOD | 40 | 100 | 40 | 95 | 90 | 80 | 60 | 60 | 50 | 40 | 70 | 0 | 0 | 0 | 0 |
| JOHNSONGRASS | 85 | 95 | 80 | 85 | 90 | 20 | 80 | 80 | 60 | 50 | 80 | 30 | 60 | 60 | 60 |
| NUTSEDGE | 50 | 80 | 40 | 70 | 20 | 20 | 40 | 70 | 100 | 100 | 90 | 50 | 70 | 70 | 50 |
| CORN | 80 | 100 | 100 | 90 | 90 | 20 | 0 | 70 | 0 | 90 | 80 | 0 | 80 | 80 | 70 |

-continued

| | CMPD 45 | | | CMPD 46 | | | U,26/37 CMPD 51 | | | CMPD 47 | | | CMPD 48 | | | CMPD 49 | | | CMPD 50 | | | CMPD 51 | |
|---|---|---|---|---|---|---|---|---|---|---|---|---|---|---|---|---|---|---|---|---|---|---|---|
| RATE = G/HA | 250 | 62 | 16 | 4 | 250 | 62 | 16 | 4 | 250 | 62 | 16 | 4 | 250 | 62 | 16 | 4 | 250 | 62 | 16 | 4 | 250 | 62 | 16 | 4 |
| WILD BUCKWHEAT | | 100 | 100 | 100 | | 100 | 100 | 100 | | | | | | 100 | 90 | 100 | | 100 | 90 | 100 | | 100 | 90 | 80 |
| BLACKGRASS | | 80 | 90 | 80 | | 90 | 80 | 80 | | | | | | 100 | 100 | 70 | | 70 | 50 | 50 | | 30 | 70 | 85 30 |
| RAPE | | 90 | 100 | 50 | | 100 | 80 | 50 | | | | | | 70 | 50 | 50 | | 50 | 0 | 0 | | 0 | 60 | 50 50 |
| BARLEY | | 30 | 40 | 80 | | 100 | 100 | 80 | | | | | | 30 | 40 | 0 | | 0 | 0 | 0 | | 0 | 0 | 0 0 |
| GREEN FOXTAIL | | 100 | 90 | 90 | | 100 | 100 | 90 | | | | | | 90 | 70 | 70 | | 30 | 30 | 30 | | 100 | 70 | 100 30 |
| CHEATGRASS | | — | — | — | | — | — | — | | | | | | — | 100 | — | | — | — | — | | — | 100 | 90 — |
| LAMBSQUARTER | | 90 | 90 | 90 | | 90 | 90 | 40 | | | | | | 100 | 80 | 80 | | 100 | 50 | 80 | | 95 | 80 | 90 50 |
| CHICKWEED | | 80 | 100 | 100 | | 100 | 100 | 100 | | | | | | 100 | 100 | 70 | | 90 | 70 | 100 | | 80 | 60 | 100 70 |
| DOWNY BROME | | 90 | 100 | 100 | | 100 | 100 | 100 | | | | | | 100 | 100 | 95 | | 100 | 0 | 60 | | 30 | 0 | 90 30 |

POSTEMERGENCE

| | CMPD 50 | | | U,26/37 CMPD 51 | | | CMPD 52 | | | CMPD 53 | | | CMPD 54 | | | CMPD 55 | | | CMPD 56 | | | CMPD 57 |
|---|---|---|---|---|---|---|---|---|---|---|---|---|---|---|---|---|---|---|---|---|---|---|---|
| RATE = G/HA | 250 | 62 | 16 | 4 | 1 | 250 | 62 | 16 | 4 | 250 | 62 | 16 | 4 | 250 | 62 | 16 | 4 | 250 | 62 | 16 | 4 | 250 |
| GIANT FOXTAIL | 90 | 100 | 70 | 0 | 50 | 100 | 90 | 80 | 30 | 100 | 90 | 80 | 30 | 100 | 90 | 50 | 20 | 100 | 70 | 50 | 30 | 90 |
| VELVETLEAF | 100 | 100 | 100 | 50 | 70 | 90 | 80 | 70 | 80 | 80 | 70 | 90 | 20 | 100 | 90 | 90 | 80 | 100 | 95 | 90 | 80 | 100 |
| SUGARBEET 100 | 100 | 100 | 70 | 70 | 80 | 100 | 100 | 100 | 100 | 100 | 90 | 100 | 90 | 100 | 30 | 100 | 30 | 100 | 80 | 100 | 70 | |
| CRABGRASS | 80 | 80 | 50 | 30 | 30 | 80 | 90 | 40 | 20 | 80 | 50 | 40 | 50 | 60 | 30 | 20 | 20 | 100 | 50 | 50 | 0 | |
| TEAWEED | 90 | 80 | 70 | 0 | 80 | 95 | 90 | 80 | 80 | 60 | 100 | 80 | 20 | 90 | 90 | 60 | 20 | 90 | 80 | 60 | 70 | 100 |
| JIMSONWEED | 70 | 80 | 50 | 30 | 50 | 100 | 80 | 70 | 20 | 100 | 70 | 100 | 80 | 90 | 90 | 90 | 40 | 90 | 100 | 95 | 40 | |
| RICE | 70 | 80 | 60 | 30 | 0 | 100 | 90 | 60 | 40 | 60 | 60 | 40 | 0 | 90 | 90 | 70 | 20 | 90 | 70 | 50 | 20 | 90 |
| COCKLEBUR | 100 | 70 | 80 | 0 | 40 | 100 | 70 | 30 | 30 | 80 | 30 | 20 | 80 | 70 | 20 | 50 | 0 | 90 | 100 | 80 | 0 | 90 |
| COTTON | 90 | 60 | 30 | 0 | 90 | 60 | 60 | 0 | 50 | 0 | 0 | 20 | 60 | 50 | 20 | 0 | 60 | 50 | 50 | 0 | 90 | |
| SOYBEAN | 80 | 60 | 20 | 0 | 0 | 50 | 30 | 0 | 50 | 40 | 30 | 0 | 70 | 50 | 30 | 0 | 90 | 50 | 50 | 0 | 90 | |

-continued

| | CMPD 51 | | | | CMPD 52 | | | | CMPD 53 | | | | CMPD 54 | | CMPD 55 | | CMPD 56 | | CMPD 57 | |
|---|---|---|---|---|---|---|---|---|---|---|---|---|---|---|---|---|---|---|---|---|
| RATE = G/HA | 16 | 4 | 250 | 62 | 16 | 4 | 250 | 62 | 16 | 4 | 250 | 62 | 16 | 4 | 62 | 16 | 4 | 62 | 16 | 4 |
| BARNYARDGRASS | 100 | 100 | 80 | 70 | 100 | 30 | 0 | 50 | 100 | 70 | 0 | 50 | 95 | 30 | 80 | 95 | 30 | 100 | 95 | 90 |
| WILD OAT | 70 | 50 | 100 | 100 | 30 | 75 | 0 | 70 | 80 | 20 | 70 | 70 | 100 | 0 | 50 | 100 | 0 | 80 | 80 | 60 |
| MORNINGGLORY | 90 | 70 | 100 | 60 | 30 | 100 | 30 | 100 | 90 | 70 | 75 | 100 | 100 | 0 | 50 | 100 | 0 | 100 | 100 | 70 |
| WHEAT | 70 | 60 | 0 | 0 | 0 | 0 | 50 | 50 | 60 | 30 | 100 | 100 | 60 | 0 | 20 | 60 | 20 | 80 | 70 | 40 |
| SICKLEPOD | 90 | 80 | 70 | 50 | 50 | 60 | 0 | 80 | 70 | 80 | 60 | 50 | 80 | 0 | 40 | 60 | — | 80 | 80 | 60 |
| JOHNSONGRASS | 90 | 70 | 90 | 30 | 90 | 90 | 70 | 80 | 30 | 70 | 60 | 70 | 100 | 0 | 80 | 90 | 0 | 100 | 90 | 80 |
| NUTSEDGE | 30 | — | 95 | — | 90 | 30 | 30 | 0 | 100 | 30 | 80 | 0 | 100 | — | 20 | 90 | 30 | 100 | 100 | 90 |
| CORN | 90 | 60 | 100 | 0 | 100 | 100 | 100 | 100 | 100 | 100 | 100 | 100 | 100 | 100 | 60 | 100 | 100 | 80 | 100 | 0 |
| WILD BUCKWHEAT | 100 | 70 | 95 | 0 | 70 | 0 | 60 | 50 | 70 | 30 | 60 | 70 | 90 | 0 | 90 | 80 | 0 | 90 | 90 | 80 |
| BLACKGRASS | 80 | 70 | 100 | 30 | 100 | 30 | 0 | 90 | 80 | 30 | 100 | 90 | 80 | 30 | 70 | 80 | 30 | 80 | 70 | 70 |
| RAPE | 100 | 90 | 100 | 60 | 70 | 60 | 50 | 80 | 90 | 70 | 90 | 80 | 100 | 0 | 80 | 100 | 0 | 100 | 100 | 70 |
| BARLEY | 40 | 0 | 70 | 0 | 80 | 0 | 0 | 0 | 30 | 30 | 30 | 0 | 100 | 0 | 40 | 100 | 30 | 40 | 40 | 100 |
| GREEN FOXTAIL | 100 | 80 | 100 | 0 | 100 | 100 | 50 | 30 | 100 | 80 | 100 | 50 | 80 | 70 | 80 | 50 | 70 | 90 | 90 | 60 |
| CHEATGRASS | — | — | — | — | — | — | — | — | — | — | — | — | — | — | — | — | — | — | — | — |
| LAMBSQUARTERS | 100 | 90 | 90 | 50 | 100 | 90 | 50 | 85 | 90 | 90 | 70 | 80 | 100 | 100 | 80 | 90 | 80 | 90 | 90 | 90 |
| CHICKWEED | 100 | 90 | 100 | 50 | 100 | 90 | 30 | 100 | 90 | 90 | 60 | 100 | 100 | 100 | 80 | 100 | 60 | 100 | 100 | 80 |
| DOWNY BROME | 70 | 50 | 90 | 30 | 60 | 30 | 0 | 50 | 30 | 0 | 0 | 50 | 80 | 0 | 40 | 70 | 0 | 80 | 70 | 40 |

POSTEMERGENCE

| | CMPD 51 | | CMPD 52 | | CMPD 53 | | CMPD 54 | | CMPD 55 | | CMPD 56 | | CMPD 57 | |
|---|---|---|---|---|---|---|---|---|---|---|---|---|---|---|
| RATE = G/HA | 62 | 16 | 4 | 62 | 16 | 4 | 62 | 16 | 4 | 62 | 16 | 4 | 62 | 16 | 4 |
| GIANT FOXTAIL | 30 | 0 | | 30 | 0 | 70 | 50 | 30 | 30 | 0 | 50 | 0 | 70 | 20 | 0 |
| VELVETLEAF | 70 | 40 | | 75 | 70 | 75 | 70 | 80 | 60 | 80 | 80 | 80 | 100 | 40 | 30 |
| SUGARBEET | 100 | 60 | | 100 | 100 | 100 | 100 | 100 | 70 | 100 | 100 | 100 | 100 | 100 | 40 |
| CRABGRASS | 30 | 0 | | 0 | 0 | 0 | 50 | 50 | 20 | 30 | 50 | 30 | 100 | 60 | 0 |
| TEAWEED | 70 | 30 | | 80 | 70 | 60 | 50 | 60 | 50 | 70 | 60 | 60 | 80 | 30 | 70 |
| JIMSONWEED | 90 | 40 | | 80 | 80 | 60 | 50 | 50 | 20 | 50 | 70 | 80 | 90 | 30 | 30 |
| RICE | 30 | 0 | | 80 | 80 | 60 | 40 | 50 | 30 | 70 | 50 | 40 | 100 | 70 | 0 |
| COCKLEBUR | 80 | 40 | | 60 | 70 | 70 | 100 | 100 | 30 | 50 | 70 | 30 | 100 | 30 | 0 |
| COTTON | 30 | 0 | | 85 | 0 | 0 | 80 | 50 | 20 | 70 | 70 | 40 | 90 | 0 | 0 |
| SOYBEAN | 50 | 30 | | 100 | 50 | 40 | 30 | 30 | 20 | 70 | 70 | 30 | 100 | 40 | 0 |
| BARNYARDGRASS | 90 | 60 | | 70 | 60 | 100 | 60 | 80 | 30 | 100 | 80 | 60 | 100 | 40 | 0 |
| WILD OAT | 80 | 70 | | 80 | 30 | 90 | 30 | 30 | 20 | 10 | 80 | 40 | 70 | 0 | 60 |
| MORNINGGLORY | 80 | 60 | | 100 | 60 | 60 | 70 | 100 | 50 | 0 | 80 | 70 | 100 | 0 | 0 |
| WHEAT | 80 | 50 | | 100 | 50 | 70 | 30 | 20 | 20 | 90 | 70 | 0 | 100 | 70 | 0 |
| SICKLEPOD | 80 | 50 | | 100 | 60 | 50 | 40 | 60 | 20 | 70 | 30 | 70 | 80 | 30 | 30 |
| JOHNSONGRASS | 70 | 0 | | 100 | 90 | 80 | 60 | 80 | 40 | 90 | 70 | 40 | 100 | 20 | 0 |
| NUTSEDGE | 90 | 60 | | 100 | 40 | 90 | 60 | 70 | 70 | 30 | 30 | 30 | 100 | 40 | 20 |
| CORN | 30 | 0 | | 80 | 50 | 60 | 0 | 0 | 0 | 70 | 0 | 20 | 100 | 30 | 70 |
| WILD BUCKWHEAT | 0 | 0 | | 50 | 80 | 80 | 30 | 30 | 20 | 20 | 50 | 30 | 100 | 70 | 0 |
| BLACKGRASS | 60 | 30 | | 80 | 50 | 100 | 50 | 50 | 20 | 70 | 70 | 70 | 90 | 30 | 40 |
| RAPE | 50 | 0 | | 60 | 60 | 100 | 100 | 100 | 30 | 100 | 70 | 40 | 100 | 80 | 70 |
| BARLEY | 100 | 80 | | 100 | 50 | 100 | 90 | 80 | 50 | 60 | 40 | 80 | 70 | 30 | 30 |
| GREEN FOXTAIL | 60 | 50 | | 70 | 30 | 60 | 60 | 60 | 30 | 30 | 60 | 30 | 100 | 70 | 40 |
| CHEATGRASS | — | — | | — | — | — | — | — | — | — | — | — | — | — | — |
| LAMBSQUARTERS | 70 | 50 | | 60 | 50 | 100 | 80 | 80 | 50 | 100 | 80 | 100 | 100 | 70 | 70 |
| CHICKWEED | 90 | 70 | | 100 | 100 | 100 | 100 | 100 | 70 | 100 | 80 | 60 | 100 | 40 | 40 |
| DOWNY BROME | 30 | 0 | | 90 | 70 | 60 | 50 | 50 | 30 | 50 | 60 | 40 | 90 | 60 | 0 |

| | CMPD 57 | | CMPD 58 | | CMPD 59 | | CMPD 60 | | CMPD 61 | | CMPD 62 | | CMPD 63 | |
|---|---|---|---|---|---|---|---|---|---|---|---|---|---|---|
| RATE = G/HA | 62 | 16 | 4 | 62 | 16 | 4 | 62 | 16 | 4 | 62 | 16 | 4 | 62 | 16 | 4 |
| GIANT FOXTAIL | 90 | 90 | 40 | 20 | 0 | 90 | 40 | 30 | 40 | 40 | 0 | 0 | 70 | 70 | 40 |
| VELVETLEAF | 90 | 50 | 50 | 0 | 0 | 100 | 80 | 90 | 100 | 70 | 80 | 20 | 90 | 90 | 40 |

| | | | | | | | | | | | | | | | | | | | | | | | | | |
|---|---|---|---|---|---|---|---|---|---|---|---|---|---|---|---|---|---|---|---|---|---|---|---|---|---|
| SUGARBEET | 50 | 30 | 0 | 90 | 80 | 30 | 0 | 90 | 0 | 70 | 0 | 30 | 60 | 30 | 0 | 100 | 40 | 20 | 0 | 60 | 30 | 0 | 80 | 80 | 50 |
| CRABGRASS | 80 | 40 | 70 | 80 | 50 | 30 | 30 | 70 | 80 | 100 | 90 | 40 | 80 | 70 | 20 | 90 | 90 | 50 | 20 | 90 | 70 | 60 | 100 | 80 | 40 |
| TEAWEED | 90 | 30 | 0 | 90 | 90 | 90 | 30 | 90 | 90 | 0 | 90 | — | — | — | — | — | — | — | — | — | — | — | — | — | — |
| JIMSONWEED | 50 | 40 | 20 | 90 | 50 | 50 | 20 | 70 | 0 | 100 | 0 | 20 | 80 | 30 | 0 | 100 | 80 | 10 | 0 | 80 | 30 | 10 | 100 | 90 | 40 |
| RICE | 90 | 80 | 60 | 90 | 60 | 80 | 0 | 90 | 100 | 30 | 100 | 30 | 100 | 70 | 10 | 100 | 30 | 10 | 10 | 100 | 70 | 10 | 60 | 100 | 10 |
| COCKLEBUR | 80 | 80 | 60 | 100 | 80 | 30 | 20 | 100 | 80 | 40 | 50 | 10 | 50 | 10 | 10 | 50 | 30 | 10 | 10 | 30 | — | 10 | 100 | 100 | 0 |
| COTTON | 90 | 80 | 30 | 90 | 50 | 50 | 0 | 100 | 90 | 20 | 100 | 20 | 90 | 30 | 30 | 100 | 30 | 10 | 30 | 100 | 60 | 30 | 60 | 100 | 30 |
| SOYBEAN | 60 | 10 | 0 | 90 | 50 | 20 | 20 | 90 | 70 | 0 | 100 | 0 | 90 | 40 | 0 | 90 | 60 | 0 | 0 | 90 | 0 | 0 | 90 | 90 | 0 |
| BARNYARDGRASS | 70 | 20 | 0 | 100 | 80 | 30 | 0 | 95 | 100 | 0 | 90 | 20 | 100 | 50 | 10 | 100 | 80 | 60 | 0 | 100 | 0 | 10 | 100 | 90 | 30 |
| WILD OAT | 70 | 40 | 40 | 60 | 40 | 30 | 0 | 60 | 70 | 30 | 100 | 0 | 50 | 10 | 0 | 50 | 10 | 0 | 10 | 60 | 70 | 40 | 60 | 90 | 0 |
| MORNINGGLORY | 100 | 70 | 20 | 100 | 100 | 100 | 0 | 100 | 100 | 30 | 100 | 20 | 100 | 80 | 30 | 100 | 80 | 60 | 30 | 100 | 20 | 40 | 100 | 90 | 90 |
| WHEAT | 60 | 20 | 0 | 40 | 20 | 30 | 0 | 80 | 50 | 0 | 70 | 0 | 40 | 10 | 0 | 40 | 10 | 0 | 0 | 40 | 20 | 0 | 30 | 10 | 0 |
| SICKLEPOD | 40 | 40 | 0 | 80 | 20 | 50 | 50 | 80 | 80 | 0 | 90 | — | — | — | — | — | — | — | — | — | — | — | — | — | — |
| JOHNSONGRASS | 50 | 50 | 0 | 50 | 20 | 20 | 0 | 80 | 20 | 50 | 100 | 0 | 50 | 40 | 0 | 100 | 90 | 40 | 0 | 80 | 70 | 50 | 80 | 90 | 80 |
| NUTSEDGE | 90 | 50 | 20 | 90 | 80 | 20 | 30 | 90 | 90 | 0 | 100 | 20 | 40 | 40 | 20 | 90 | 70 | 10 | 40 | 20 | 10 | 0 | 100 | 30 | 100 |
| CORN | 90 | 90 | 80 | 50 | 20 | 90 | 40 | 0 | 20 | 80 | 100 | 50 | 90 | 50 | 50 | 100 | 20 | 100 | 50 | 40 | 90 | 40 | 100 | 50 | 20 |
| WILD BUCKWHEAT | 70 | 50 | 40 | 80 | 80 | 50 | 30 | 70 | 90 | 40 | 90 | 40 | 70 | 10 | 40 | 90 | 60 | 40 | 40 | 100 | 60 | 30 | 100 | 40 | 0 |
| BLACKGRASS | 100 | 40 | 30 | 100 | 100 | 30 | 40 | 100 | 70 | 20 | 80 | 100 | — | 10 | — | — | — | — | — | — | — | — | — | — | — |
| RAPE | 50 | 40 | 40 | 50 | 40 | 20 | 30 | 40 | 60 | 80 | 50 | 0 | 100 | 20 | 0 | 10 | 0 | 0 | 0 | 0 | 0 | 0 | 0 | 0 | 0 |
| BARLEY | 90 | 60 | 40 | 100 | 80 | 30 | 0 | 95 | 40 | 20 | 100 | 0 | 90 | 0 | 20 | 100 | 90 | 40 | 40 | 90 | 50 | 30 | 100 | 100 | 40 |
| GREEN FOXTAIL | — | — | 0 | — | — | — | — | — | — | 0 | — | 0 | — | 0 | 0 | — | — | — | — | — | — | — | — | — | — |
| CHEATGRASS | 90 | 90 | 0 | 80 | 80 | 50 | 30 | 90 | 90 | 50 | 50 | — | 90 | 40 | 0 | 10 | 40 | 0 | 0 | 80 | 50 | 0 | 80 | 90 | 0 |
| LAMBSQUARTERS | 90 | 50 | 30 | 100 | 90 | 50 | 50 | 90 | 80 | 30 | 100 | — | 90 | 90 | 20 | 100 | 30 | — | 0 | 90 | — | 0 | 100 | 30 | 40 |
| CHICKWEED | 60 | 40 | 30 | 90 | 40 | 30 | 20 | 50 | 30 | 20 | 100 | — | 30 | — | — | 30 | — | — | — | — | — | — | 90 | — | — |
| DOWNY BROME | — | — | — | — | — | — | — | — | — | — | 100 | — | — | — | — | — | — | — | — | — | — | — | — | — | — |

| RATE = G/HA | CMPD 58 | | | CMPD 59 | | | CMPD 60 | | | CMPD 61 | | | CMPD 62 | | | CMPD 63 | | | CMPD 64 | | |
|---|---|---|---|---|---|---|---|---|---|---|---|---|---|---|---|---|---|---|---|---|---|
| | 62 | 16 | 4 | 62 | 16 | 4 | 62 | 16 | 4 | 62 | 16 | 4 | 62 | 16 | 4 | 62 | 16 | 4 | 62 | 16 | 4 |
| GIANT FOXTAIL | 70 | 40 | 30 | 70 | 50 | 30 | 100 | 70 | 70 | 100 | 70 | — | 100 | 60 | 0 | 100 | 70 | 0 | 100 | 30 | 0 |
| VELVETLEAF | 100 | 90 | 60 | 100 | 90 | 50 | 100 | 100 | 100 | 100 | 100 | 80 | 100 | 100 | 20 | 100 | 100 | 50 | 100 | 70 | 50 |
| SUGARBEET | 100 | 100 | 100 | 100 | 100 | 100 | 100 | 100 | 90 | 100 | 100 | 0 | 100 | 80 | 0 | 100 | 100 | 100 | 100 | 100 | 100 |
| CRABGRASS | 50 | 40 | 0 | 50 | 50 | 20 | 60 | 30 | 0 | 50 | 50 | 50 | 80 | 60 | 0 | 100 | 50 | 30 | 100 | 60 | 30 |
| TEAWEED | 60 | 50 | 20 | 100 | 90 | 30 | 80 | 40 | 40 | 70 | 70 | 90 | 50 | 30 | 0 | 100 | 70 | 0 | 80 | 30 | 0 |
| JIMSONWEED | 100 | 80 | 80 | 100 | 80 | 70 | 100 | 80 | 85 | 100 | 100 | 100 | 100 | 40 | 90 | 100 | 90 | 90 | 100 | 90 | 90 |
| RICE | 90 | 90 | 30 | 90 | 90 | 80 | 90 | 100 | 90 | 80 | 80 | 70 | 100 | 40 | 0 | 100 | 100 | 0 | 90 | 40 | 30 |
| COCKLEBUR | 80 | 50 | 50 | 80 | 90 | 40 | 100 | 100 | 50 | 100 | 80 | 90 | 100 | 20 | 20 | 100 | 100 | 40 | 100 | 90 | 0 |
| COTTON | 90 | 90 | 100 | 90 | 90 | 100 | 100 | 100 | 90 | 80 | 80 | 90 | 100 | 100 | 100 | 100 | 100 | 30 | 100 | 100 | 30 |
| SOYBEAN | 90 | 100 | 80 | 100 | 100 | 30 | 100 | 100 | 100 | 100 | 80 | 90 | 100 | 30 | 20 | 100 | 100 | 60 | 100 | 90 | 60 |
| BARNYARDGRASS | 80 | 80 | 40 | 80 | 90 | 70 | 100 | 90 | 60 | 100 | 90 | 90 | 100 | 100 | 100 | 100 | 100 | 70 | 100 | 90 | 70 |
| WILD OAT | 80 | 80 | 30 | 100 | 80 | 40 | 100 | 40 | 70 | 40 | 20 | 20 | 70 | 30 | 60 | 90 | 60 | 60 | 100 | 100 | 0 |
| MORNINGGLORY | 90 | 40 | 50 | 90 | 80 | 80 | 90 | 60 | 60 | 100 | 100 | 70 | 100 | 70 | 80 | 100 | 90 | 70 | 100 | 90 | 90 |
| WHEAT | 100 | 70 | 20 | 100 | 70 | 40 | 100 | 60 | 60 | 70 | 70 | 100 | 80 | 100 | 70 | 100 | 80 | 90 | 100 | 90 | 90 |
| SICKLEPOD | 50 | 40 | 50 | 50 | 40 | 50 | 90 | 70 | 40 | 90 | 80 | 40 | 80 | 40 | 0 | 100 | 50 | 60 | 70 | 30 | 0 |
| JOHNSONGRASS | 100 | 100 | 100 | 100 | 60 | 30 | 100 | 80 | 80 | 80 | 80 | 40 | 100 | 100 | 30 | 100 | 50 | 0 | 70 | 50 | 0 |
| NUTSEDGE | 30 | 20 | 0 | 30 | 20 | 0 | 100 | 100 | 100 | 100 | 100 | 20 | 100 | 20 | 0 | 100 | 0 | 0 | 90 | 0 | 0 |
| CORN | 100 | 40 | 3 | 100 | 100 | 40 | 100 | 100 | 80 | 100 | 100 | 80 | 100 | 90 | 80 | 100 | 100 | 90 | 100 | 100 | 100 |
| WILD BUCKWHEAT | 100 | 100 | 70 | 100 | 100 | 90 | 100 | 90 | 70 | 100 | 70 | 30 | 100 | 60 | 50 | 100 | 80 | 70 | 100 | 80 | 80 |
| BLACKGRASS | 80 | 50 | 40 | 80 | 50 | 40 | 80 | 70 | 30 | 80 | 70 | 30 | 80 | 50 | 50 | 100 | 90 | 40 | 100 | 80 | 50 |
| RAPE | 100 | 100 | 100 | 100 | 100 | 100 | 100 | 100 | 100 | 100 | 100 | 100 | 100 | 100 | 100 | 100 | 100 | 100 | 100 | 100 | 100 |
| BARLEY | 100 | 70 | 40 | 100 | 60 | 30 | 70 | 40 | 40 | 70 | 50 | 40 | 70 | 50 | 40 | 100 | 40 | 30 | 90 | 40 | 0 |
| GREEN FOXTAIL | 70 | 70 | 70 | 100 | 70 | 30 | 100 | 80 | 80 | 100 | 70 | 20 | 60 | 30 | 0 | 100 | 60 | 10 | 100 | 50 | 0 |
| CHEATGRASS | — | — | — | — | — | — | — | — | — | — | — | — | — | — | — | — | — | — | — | — | — |
| LAMBSQUARTERS | 70 | 70 | 30 | 100 | 80 | 0 | 100 | 80 | 80 | 90 | 90 | 90 | 90 | 50 | 50 | 90 | 50 | 90 | 80 | 40 | 50 |
| CHICKWEED | 100 | 100 | 80 | 100 | 100 | 80 | 100 | 100 | 30 | 100 | 100 | 100 | 100 | 100 | 80 | 100 | 70 | 80 | 100 | 100 | 70 |
| DOWNY BROME | 90 | 70 | 40 | 90 | 40 | 40 | 90 | 70 | 50 | 90 | 70 | 50 | 90 | 40 | 40 | 100 | 100 | 30 | 100 | 100 | 0 |

| RATE = G/HA | CMPD 63 | | CMPD 64 | | CMPD 65 | | | CMPD 66 | | | CMPD 67 | | | CMPD 68 | | | CMPD 70 | | | CMPD 71 | | |
|---|---|---|---|---|---|---|---|---|---|---|---|---|---|---|---|---|---|---|---|---|---|---|---|
| | 250 | 16 | 250 | 16 | 250 | 62 | 16 | 250 | 62 | 16 | 250 | 62 | 16 | 250 | 62 | 16 | 250 | 62 | 16 | 250 | 62 | 16 | 4 |
| | PREEMERGENCE | | | | | | | | | | | | | | | | | | | | | | |
| GIANT FOXTAIL | 90 | 10 | 50 | 90 | 90 | 80 | 50 | 70 | 90 | 70 | 100 | 90 | 70 | 100 | 90 | 70 | 90 | 80 | 30 | 100 | 70 | 20 | 0 |
| VELVETLEAF | 100 | 10 | 50 | 80 | 100 | 100 | 100 | 80 | 100 | 50 | 100 | 100 | 80 | 100 | 70 | 50 | 80 | 30 | 0 | 50 | 20 | 0 | 0 |
| SUGARBEET | 100 | 40 | 70 | 80 | 100 | 100 | 100 | 80 | 90 | 90 | 100 | 100 | 80 | 90 | 90 | 90 | 40 | 30 | 20 | 90 | 80 | 30 | 0 |
| CRABGRASS | 100 | 20 | — | 80 | 100 | 100 | 100 | 80 | 100 | 70 | 100 | 90 | 70 | 90 | 90 | 70 | 90 | 40 | 20 | 90 | 40 | 20 | 0 |
| TEAWEED | 100 | 0 | 60 | 50 | 100 | 100 | 80 | 70 | 80 | 0 | 100 | 90 | 20 | 90 | 30 | 0 | 70 | 30 | 50 | 100 | 0 | 0 | 30 |
| JIMSONWEED | 100 | 0 | 20 | 100 | 100 | 100 | 80 | 80 | 100 | 0 | 90 | 90 | 70 | 100 | 90 | 0 | 100 | 80 | 0 | 30 | 30 | 30 | 0 |
| RICE | 90 | — | 60 | 50 | 100 | 100 | 80 | 70 | 50 | 0 | 80 | 100 | 0 | 90 | 20 | 0 | 0 | 0 | 0 | 20 | 0 | 0 | 0 |
| COCKLEBUR | 100 | 0 | 30 | 100 | 100 | 100 | 90 | 50 | 30 | 50 | 60 | 30 | 60 | 20 | 30 | 0 | 20 | 20 | 0 | 90 | 30 | 0 | 0 |
| COTTON | 90 | 0 | 20 | 30 | 100 | 100 | 80 | 50 | 50 | 0 | 80 | 50 | 80 | 70 | 50 | 0 | 70 | 70 | 20 | 70 | 20 | 30 | 0 |
| SOYBEAN | 100 | 0 | 20 | 100 | 100 | 100 | 80 | 20 | 20 | 0 | 50 | 20 | 0 | 50 | 20 | 0 | 20 | 30 | 0 | 30 | 50 | 0 | 0 |
| BARNYARDGRASS | 100 | 20 | 40 | 80 | 100 | 100 | 90 | 40 | 40 | 20 | 100 | 0 | 60 | 70 | 40 | 50 | 70 | 70 | 0 | 100 | 40 | 20 | 30 |
| WILD OAT | 80 | 0 | 0 | 90 | 70 | 90 | 80 | 30 | 100 | 50 | 80 | 80 | 80 | 80 | 30 | 20 | 80 | 20 | 20 | 70 | 30 | 0 | 0 |
| MORNINGGLORY | 100 | 20 | 50 | 90 | 100 | 100 | 90 | 40 | 20 | 0 | 70 | 30 | 30 | 50 | 30 | 40 | 70 | 70 | 70 | 100 | 50 | 50 | 0 |
| WHEAT | 100 | 70 | 40 | 90 | 100 | 100 | 90 | 20 | 20 | 50 | 60 | 50 | 60 | 70 | 50 | 0 | 30 | 30 | 30 | 30 | 0 | 0 | 0 |
| SICKLEPOD | 100 | 0 | 0 | 10 | 100 | 100 | 90 | 30 | 30 | 0 | 90 | 30 | 30 | 80 | 50 | 50 | 20 | 20 | 20 | 40 | 20 | 0 | 0 |
| JOHNSONGRASS | 100 | — | 50 | 100 | 100 | 100 | 80 | 40 | 30 | 0 | 80 | 50 | 60 | 70 | 20 | 0 | 70 | 70 | 0 | 70 | 70 | 50 | 0 |
| NUTSEDGE | 100 | 40 | 40 | 90 | 100 | 100 | 90 | 90 | 40 | 20 | 90 | 40 | 50 | 80 | 30 | 0 | 40 | 30 | 20 | 30 | 30 | 0 | 0 |
| CORN | 100 | 10 | 100 | 100 | 100 | 100 | 90 | 90 | 100 | 0 | 100 | 70 | 90 | 100 | 70 | 80 | 100 | 40 | 0 | 0 | 80 | 0 | 0 |
| WILD BUCKWHEAT | — | 90 | — | 90 | — | — | — | — | — | — | — | — | — | — | — | — | — | — | — | — | — | — | — |

-continued

| | CMPD 64 | | | CMPD 65 | | | CMPD 66 | | | CMPD 67 | | | CMPD 68 | | | CMPD 70 | | | CMPD 71 | | |
|---|---|---|---|---|---|---|---|---|---|---|---|---|---|---|---|---|---|---|---|---|
| BLACKGRASS | — | — | 100 | 90 | 100 | 100 | 30 | 100 | 80 | 30 | 50 | 90 | 90 | 100 | 80 | 70 | 30 | 30 | 50 | 40 | 30 |
| RAPE | — | — | 60 | 0 | 10 | — | 0 | 100 | 100 | 100 | 100 | 100 | 100 | 100 | 100 | 30 | 0 | 0 | 70 | 0 | 0 |
| BARLEY | 0 | 60 | 100 | — | 100 | — | 20 | 80 | 90 | 20 | 40 | 50 | 80 | 60 | 50 | 50 | 20 | 0 | 20 | 0 | 0 |
| GREEN FOXTAIL | 0 | 100 | 100 | 60 | 60 | — | — | 50 | 90 | 30 | 20 | 90 | 40 | 100 | 95 | 80 | 30 | 0 | 70 | 30 | 0 |
| CHEATGRASS | — | — | — | — | — | — | — | — | — | — | — | — | — | — | — | — | — | — | — | — | — |
| LAMBSQUARTERS | — | — | — | — | — | — | — | 90 | 100 | 70 | 90 | 90 | 90 | 100 | 90 | 80 | 50 | 30 | 0 | 0 | 0 |
| CHICKWEED | — | — | 100 | 100 | — | — | 0 | 80 | 90 | 30 | 90 | 100 | 100 | 100 | 90 | 70 | 50 | 0 | 80 | 50 | 0 |
| DOWNY BROME | 0 | 100 | 100 | 60 | 60 | — | 0 | 70 | 90 | 40 | 80 | 100 | 70 | 80 | 70 | 20 | 0 | 0 | 30 | 30 | 0 |

| RATE = G/HA | 4 | 1 | 250 | 16 | 62 | 250 | 4 | 62 | 16 | 4 | 62 | 1 | 250 | 4 | 62 | 16 | 4 | 62 | 16 | 4 | 62 |

POSTEMERGENCE

| | CMPD 72 | | | CMPD 74 | | | CMPD 76 | | | CMPD 77 | | | CMPD 80 | | | CMPD 81 | | | CMPD 82 | | |
|---|---|---|---|---|---|---|---|---|---|---|---|---|---|---|---|---|---|---|---|---|---|
| GIANT FOXTAIL | 30 | 0 | 100 | 30 | 90 | 60 | 20 | 0 | 100 | 40 | 100 | 40 | 70 | 40 | 30 | 70 | 100 | 60 | 50 | 85 | 60 |
| VELVETLEAF | 80 | 60 | 100 | 90 | 100 | 100 | 90 | 60 | 90 | 70 | 100 | 90 | 90 | 70 | 80 | 80 | 90 | 70 | 30 | 90 | 80 |
| SUGARBEET | 60 | 50 | 100 | 100 | 70 | 60 | 100 | 30 | 100 | 100 | 100 | 100 | 100 | 100 | 60 | 100 | 100 | 60 | 90 | 100 | 100 |
| CRABGRASS | 80 | 70 | 30 | 0 | 90 | 100 | 70 | 50 | 100 | 0 | 90 | 30 | 50 | 0 | 30 | 50 | 100 | 70 | 30 | 90 | 0 |
| TEAWEED | 80 | 50 | 100 | 80 | 80 | 90 | 0 | 60 | 100 | 0 | 70 | 30 | 60 | 30 | 50 | 60 | 80 | 80 | 30 | 30 | 80 |
| JIMSONWEED | 80 | 60 | 100 | 90 | 100 | 100 | 40 | 100 | 100 | 30 | 100 | 50 | 100 | 70 | 40 | 90 | 100 | 80 | 30 | 100 | 80 |
| RICE | 80 | 30 | 100 | 50 | 100 | 100 | 30 | 60 | 100 | 85 | 100 | 70 | 60 | 90 | 70 | 50 | 70 | 50 | 30 | 90 | 85 |
| COCKLEBUR | 90 | 40 | 100 | 20 | 70 | 90 | 40 | 95 | 70 | 30 | 90 | 90 | 100 | 90 | 30 | 30 | 100 | 80 | 70 | 100 | 100 |
| COTTON | 50 | 30 | 100 | 30 | 50 | 70 | 70 | 40 | 100 | 40 | 100 | 80 | 80 | 50 | 20 | 60 | 70 | 60 | 40 | 70 | 50 |
| SOYBEAN | 100 | 70 | 100 | 90 | 100 | 100 | 30 | 90 | 100 | 90 | 100 | 90 | 80 | 90 | 100 | 60 | 100 | 100 | 100 | 100 | |
| BARNYARDGRASS | 80 | 20 | 100 | 50 | 50 | 90 | 70 | 40 | 40 | 100 | 100 | 40 | 100 | 30 | 30 | 70 | 100 | 60 | 20 | 80 | |
| WILD OAT | 30 | 30 | 100 | 50 | 100 | 100 | 30 | 30 | 100 | 50 | 100 | 70 | 70 | 60 | 80 | 80 | 90 | 40 | 40 | 80 | |
| MORNINGGLORY | 80 | 50 | 100 | 20 | 100 | 100 | 80 | 100 | 95 | 70 | 100 | 90 | 95 | 90 | 60 | 30 | 20 | 100 | 95 | 100 | |
| WHEAT | 90 | 90 | 100 | 60 | 100 | 100 | 80 | 100 | 100 | 0 | 90 | 30 | 100 | 30 | 60 | 30 | 90 | 100 | 0 | 100 | |
| SICKLEPOD | 50 | 0 | 100 | 0 | 80 | 90 | 0 | 30 | 90 | 40 | 100 | 80 | 30 | 40 | 30 | 20 | 30 | 90 | 90 | 90 | |
| JOHNSONGRASS | 90 | 20 | 100 | 80 | 90 | 100 | 80 | 70 | 100 | 30 | 80 | 40 | 20 | 70 | 80 | 80 | 100 | 100 | 20 | 100 | |
| NUTSEDGE | 70 | 20 | 80 | 0 | 70 | 90 | 20 | 60 | 80 | 60 | 90 | 80 | 90 | 20 | 30 | 60 | 80 | 80 | 80 | 80 | |
| CORN | 40 | 0 | 100 | 60 | 50 | 100 | 0 | 30 | 100 | 20 | 90 | 30 | 70 | 70 | — | 30 | 90 | 100 | 20 | 90 | |
| WILD BUCKWHEAT | 70 | 40 | 100 | 90 | 100 | 100 | 30 | 70 | 90 | 70 | 100 | 90 | 100 | 40 | 40 | 40 | 100 | 100 | 40 | 100 | |
| BLACKGRASS | 80 | 70 | 100 | 100 | 100 | 100 | 80 | 30 | 100 | 100 | 100 | 80 | 100 | 60 | 60 | 70 | 100 | 90 | 60 | 100 | |
| RAPE | 90 | 80 | 100 | 100 | 100 | 95 | 95 | 80 | 95 | 0 | 90 | 70 | 100 | 100 | 100 | 100 | 100 | 100 | 95 | 100 | |
| BARLEY | 90 | 80 | 100 | 30 | 90 | 50 | 40 | 60 | 40 | 0 | 80 | 30 | 70 | 30 | 30 | 30 | 100 | 50 | 0 | 70 | |
| GREEN FOXTAIL | 40 | 20 | 90 | — | — | — | — | — | — | — | — | — | 70 | 40 | — | 70 | 80 | 0 | 0 | 50 | |
| CHEATGRASS | — | — | — | — | 50 | 100 | — | 100 | 80 | 70 | 100 | 100 | 95 | 30 | 40 | 40 | 100 | 80 | 30 | 100 | |
| LAMBSQUARTERS | 70 | 70 | 100 | 70 | 70 | 100 | — | 100 | 100 | 95 | 100 | 80 | 100 | 70 | 40 | 80 | 100 | 100 | 100 | 100 | |
| CHICKWEED | 90 | 80 | 100 | 80 | 80 | 100 | 30 | 30 | 30 | 70 | 100 | 90 | 100 | 30 | 0 | 60 | 100 | 0 | 0 | 100 | |
| DOWNY BROME | 80 | 0 | 100 | 60 | 100 | 90 | 70 | 0 | 70 | 0 | 90 | 70 | 40 | 40 | 0 | 30 | 100 | 80 | 30 | 80 | |

| RATE = G/HA | 62 | 16 | 4 | 62 | 16 | 250 | 16 | 62 | 1 | 4 | 250 | 1 | 62 | 4 | 16 | 1 | 16 | 62 | 250 | 4 | 62 |

PREEMERGENCE

| | CMPD 80 | | | CMPD 81 | | | CMPD 82 |
|---|---|---|---|---|---|---|---|
| GIANT FOXTAIL | 70 | 50 | 60 | 40 | 100 | 70 | 50 | 60 |
| VELVETLEAF | 90 | 30 | 40 | 20 | 70 | 50 | 30 | 80 |
| SUGARBEET | 70 | 60 | 70 | 50 | 70 | 60 | 50 | 100 |
| CRABGRASS | 90 | 80 | 50 | 0 | 100 | 80 | 30 | 80 |
| TEAWEED | 90 | 80 | 60 | 0 | 80 | 50 | 30 | 80 |
| JIMSONWEED | 90 | 80 | 70 | 20 | 80 | 80 | 30 | 80 |
| RICE | 80 | 30 | 60 | 0 | 100 | 70 | 30 | 85 |
| COCKLEBUR | 100 | 80 | 80 | 30 | 100 | 100 | 30 | 100 |
| COTTON | 0 | 0 | 50 | 0 | 60 | 60 | 30 | 50 |

| RATE = G/HA | 62 | 16 | 4 | 1 | 62 | 16 | 4 | 250 |

-continued

| | CMPD 72 | | | | CMPD 74 | | | | CMPD 76 | | | | CMPD 77 | | | | CMPD 80 | | | | CMPD 81 | | | | CMPD 82 | | |
|---|---|---|---|---|---|---|---|---|---|---|---|---|---|---|---|---|---|---|---|---|---|---|---|---|---|---|
| SOYBEAN | 40 | 20 | 0 | 0 | 70 | 30 | 20 | 0 | 0 | 0 | 0 | 0 | 0 | 70 | 20 | 0 | 0 | 0 | 0 | 0 | 70 | 50 | 20 | 0 | 90 | 60 | 0 |
| BARNYARDGRASS | 90 | 60 | 30 | 30 | 100 | 90 | 60 | 30 | 60 | 60 | 30 | 100 | 100 | 60 | 30 | 40 | 30 | 30 | 0 | 100 | 90 | 60 | 30 | 100 | 80 |
| WILD OAT | 60 | 30 | 0 | 0 | 70 | 50 | 0 | 0 | 30 | 30 | 0 | 60 | 30 | 0 | 0 | 0 | 0 | 0 | 0 | 70 | 50 | 0 | 0 | 80 | 0 |
| MORNINGGLORY | 90 | 70 | 30 | 20 | 90 | 60 | 0 | 0 | 30 | 50 | 30 | 90 | 60 | 30 | 0 | 30 | 0 | 0 | 0 | 90 | 50 | 0 | 0 | 90 | 0 |
| WHEAT | 50 | 30 | 0 | 0 | 70 | 30 | 0 | 0 | 50 | 0 | 0 | 60 | 30 | 30 | 0 | 30 | 0 | 0 | 0 | 60 | 30 | 30 | 0 | 70 | 0 |
| SICKLEPOD | 90 | 60 | 30 | 0 | 90 | 80 | 50 | 30 | 90 | 50 | 30 | 80 | 80 | 60 | 30 | 50 | 30 | 0 | 30 | 80 | 60 | 70 | 30 | 80 | 30 |
| JOHNSONGRASS | 90 | 50 | 0 | 0 | 90 | 70 | 40 | 0 | 50 | 40 | 30 | 100 | 80 | 30 | 0 | 0 | 0 | 0 | 30 | 100 | 80 | 30 | 30 | 90 | 30 |
| NUTSEDGE | 100 | 80 | 30 | 0 | 100 | 50 | 30 | 30 | 100 | 60 | 60 | 90 | 60 | 50 | 30 | 30 | 30 | 30 | 60 | 100 | 70 | 100 | 70 | 100 | 60 |
| CORN | 90 | 20 | 0 | 0 | 90 | 80 | 0 | 0 | 50 | 0 | 0 | 80 | 30 | 0 | 0 | 0 | 0 | 0 | 0 | 80 | 30 | 30 | 0 | 80 | 0 |
| WILD BUCKWHEAT | — | — | — | — | — | — | — | — | — | — | — | — | — | — | — | — | — | — | — | — | — | — | — | — | — |
| BLACKGRASS | 80 | 70 | 50 | 30 | 90 | 80 | 70 | 60 | 80 | 60 | 50 | 90 | 70 | 50 | 30 | 50 | 30 | 0 | 30 | 90 | 70 | 80 | 60 | 100 | 60 |
| RAPE | 90 | 70 | 50 | 40 | 100 | 90 | 70 | 50 | 90 | 70 | 30 | 100 | 100 | 100 | 30 | 100 | 30 | 30 | 60 | 100 | 80 | 80 | 30 | 100 | 30 |
| BARLEY | 40 | 20 | 0 | 0 | 70 | 30 | 0 | 30 | 30 | 0 | 30 | 70 | 30 | 30 | 0 | 40 | 0 | 0 | 0 | 70 | 30 | 60 | 0 | 80 | 0 |
| GREEN FOXTAIL | 100 | 90 | 60 | 30 | 100 | 100 | 90 | 0 | 90 | 80 | 30 | 100 | 100 | 80 | 50 | 90 | 30 | 0 | 90 | 100 | 100 | 90 | 60 | 100 | 70 |
| CHEATGRASS | — | — | — | — | — | — | — | — | — | — | — | — | — | — | — | — | — | — | — | — | — | — | — | — | — |
| LAMBSQUARTERS | 100 | 90 | 80 | 50 | 100 | 100 | 100 | 70 | 90 | 70 | 30 | 100 | 100 | 70 | 50 | 100 | 100 | 100 | 100 | 100 | 100 | 100 | 70 | 100 | 100 |
| CHICKWEED | 100 | 90 | 80 | 70 | 100 | 100 | 90 | 70 | 95 | 90 | 80 | 100 | 100 | 80 | 30 | 80 | 60 | 60 | 0 | 100 | 90 | 100 | 80 | 100 | 80 |
| DOWNY BROME | 30 | 40 | 0 | 0 | 80 | 80 | 50 | 30 | 50 | 30 | 0 | 80 | 30 | 30 | 0 | 0 | 0 | 0 | 30 | 70 | 50 | 30 | 30 | 80 | 30 |

| RATE = G/HA | 62 | 16 | 4 | 1 | 62 | 16 | 4 | 1 | 62 | 16 | 4 | 1 | 62 | 16 | 4 | 1 | 62 | 16 | 4 | 1 | 62 | 16 | 4 | 250 | 62 | 16 | 4 |

POSTEMERGENCE

| | CMPD 82 | | | CMPD 95 | | | CMPD 96 | | | CMPD 97 | | |
|---|---|---|---|---|---|---|---|---|---|---|---|---|
| GIANT FOXTAIL | 80 | 50 | 30 | 0 | 100 | 80 | 50 | 30 | 100 | 30 | 30 | 100 | 70 |
| VELVETLEAF | 100 | 80 | 50 | 0 | 90 | 70 | 50 | 40 | 100 | 30 | 50 | 70 | 50 |
| SUGARBEET | 100 | 100 | 0 | 100 | 100 | 60 | 0 | 100 | 100 | 0 | 100 | 100 | 90 |
| CRABGRASS | 0 | 0 | 0 | 0 | 30 | 30 | 0 | 0 | 50 | 30 | 0 | 100 | 70 |
| TEAWEED | 70 | 50 | 40 | 20 | 70 | 60 | 30 | 30 | 90 | 0 | 50 | 90 | 30 |
| JIMSONWEED | 90 | 70 | 60 | 50 | 100 | 80 | 50 | 30 | 100 | 0 | 90 | 90 | 60 |
| RICE | 80 | 80 | 30 | 30 | 100 | 70 | 50 | 0 | 70 | 0 | 50 | 90 | 30 |
| COCKLEBUR | 30 | 0 | 0 | 0 | 100 | 60 | 90 | 30 | 90 | 30 | 30 | 50 | 30 |
| COTTON | 60 | 0 | 0 | 0 | 90 | 30 | 20 | 0 | 70 | 100 | 0 | 20 | 0 |
| SOYBEAN | 100 | 100 | 70 | 30 | 90 | 80 | 60 | 30 | 90 | 0 | 30 | 90 | 70 |
| BARNYARDGRASS | 90 | 60 | 50 | 0 | 80 | 70 | 60 | 30 | 100 | 70 | 40 | 100 | 80 |
| WILD OAT | 80 | 70 | 30 | 0 | 70 | 60 | 40 | 0 | 90 | 40 | 0 | 90 | 60 |
| MORNINGGLORY | 80 | 70 | 50 | 0 | 70 | 50 | 50 | 0 | 80 | 0 | 30 | 80 | 60 |
| WHEAT | 70 | 40 | 40 | 30 | 30 | 30 | 30 | 0 | 80 | 0 | 30 | 70 | 30 |
| SICKLEPOD | 50 | 50 | 40 | 30 | 100 | 60 | 50 | 30 | 80 | 30 | 30 | 50 | 30 |
| JOHNSONGRASS | 90 | 70 | 60 | 30 | 100 | 90 | 80 | 50 | 80 | 30 | 30 | 90 | 60 |
| NUTSEDGE | 80 | 70 | 70 | 50 | 100 | 90 | 70 | 70 | 60 | 0 | 50 | 50 | 30 |
| CORN | 70 | 60 | 50 | 0 | 90 | 90 | 60 | 50 | 70 | 100 | 30 | 40 | 0 |
| WILD BUCKWHEAT | 100 | 100 | 70 | 80 | 100 | 100 | 100 | 80 | 100 | 30 | 100 | 100 | 100 |
| BLACKGRASS | 100 | 70 | 50 | 30 | 70 | 80 | 60 | 60 | 100 | 0 | 30 | 80 | 50 |
| RAPE | 100 | 100 | 80 | 30 | 100 | 100 | 90 | 100 | 100 | 60 | 100 | 100 | 100 |
| BARLEY | 60 | 40 | 40 | 30 | 70 | 80 | 50 | 30 | 100 | 60 | 30 | 100 | 60 |
| GREEN FOXTAIL | 80 | 40 | 40 | 30 | 100 | 60 | 60 | 0 | 90 | 0 | 50 | 70 | 50 |
| CHEATGRASS | — | — | — | — | — | — | — | — | — | — | — | — | — |
| LAMBSQUARTERS | 100 | 100 | 80 | 50 | 100 | 100 | 80 | 50 | 100 | 50 | 50 | 100 | 70 |
| CHICKWEED | 90 | 80 | 70 | 70 | 100 | 100 | 100 | 30 | 100 | 70 | 80 | 100 | 70 |
| DOWNY BROME | 70 | 40 | 20 | 0 | 40 | 0 | 30 | 0 | 90 | 0 | 0 | 90 | 30 |

| RATE = G/HA | 16 | 4 | 250 | 62 | 16 | 4 | 250 | 62 | 16 | 4 | 250 | 62 | 16 | 4 |

-continued

PREEMERGENCE

| | CMPD 82 | | CMPD 95 | | | | CMPD 96 | | | | CMPD 97 | | | |
|---|---|---|---|---|---|---|---|---|---|---|---|---|---|---|
| RATE = G/HA | 16 | 4 | 62 | 16 | 4 | 1 | 62 | 16 | 4 | 1 | 62 | 16 | 4 | 1 |
| GIANT FOXTAIL | 30 | 0 | 40 | — | 20 | 0 | 40 | 0 | 0 | 0 | 100 | 40 | 0 | 0 |
| VELVETLEAF | 40 | 20 | 90 | 80 | 20 | 30 | 80 | 50 | 30 | 30 | 90 | 70 | 40 | 30 |
| SUGARBEET | 70 | 50 | 100 | 60 | 50 | 40 | — | — | 40 | 30 | 90 | 70 | 40 | 20 |
| CRABGRASS | 80 | 50 | 90 | 80 | 70 | 50 | 80 | 70 | 40 | 0 | 90 | 50 | 80 | — |
| TEAWEED | 50 | 30 | 100 | 90 | 70 | 70 | 90 | 80 | 70 | 20 | 100 | 90 | 80 | — |
| JIMSONWEED | 80 | 30 | 90 | 80 | 40 | — | 90 | 40 | 30 | 50 | 90 | 40 | 40 | 40 |
| RICE | 90 | 70 | 100 | 90 | 90 | 50 | 100 | 80 | 30 | 30 | 100 | 90 | 80 | 10 |
| COCKLEBUR | 70 | 30 | 90 | 70 | 80 | 30 | 90 | 40 | 30 | 0 | 90 | 40 | 30 | — |
| COTTON | 30 | 0 | 80 | 40 | 50 | 0 | 80 | 40 | 30 | 0 | 100 | 70 | 50 | — |
| SOYBEAN | 30 | 0 | 70 | 60 | 30 | 0 | 80 | 40 | 10 | 0 | 80 | 30 | 10 | 0 |
| BARNYARDGRASS | 80 | 60 | 90 | 40 | 30 | 30 | — | 70 | 30 | — | 100 | 70 | 30 | 30 |
| WILD OAT | 30 | 0 | 70 | 60 | 40 | 0 | 40 | 40 | 20 | 30 | 70 | 70 | 40 | 0 |
| MORNINGGLORY | 40 | 0 | 90 | 40 | 20 | 30 | 70 | 50 | 30 | 0 | 70 | 40 | 10 | 0 |
| WHEAT | 60 | 50 | 70 | 50 | — | 0 | 50 | 30 | — | 20 | 60 | 30 | — | 0 |
| SICKLEPOD | 60 | 30 | 100 | 40 | 40 | 0 | 60 | 40 | 40 | 0 | — | — | — | — |
| JOHNSONGRASS | 80 | 60 | 90 | 60 | 40 | 30 | 80 | 30 | — | 20 | 90 | 40 | 30 | 30 |
| NUTSEDGE | 60 | 30 | 90 | 70 | 10 | 40 | 40 | 70 | 30 | — | — | — | — | — |
| CORN | 60 | 30 | 90 | 30 | 40 | 30 | 20 | 0 | 10 | 0 | 80 | 50 | 0 | 0 |
| WILD BUCKWHEAT | 50 | 0 | 80 | 90 | 40 | 30 | 90 | 30 | 30 | 30 | 90 | 50 | 50 | 30 |
| BLACKGRASS | 60 | 50 | 100 | 80 | 40 | 30 | 100 | 70 | 70 | 10 | 100 | 90 | 50 | 40 |
| RAPE | 50 | 40 | 80 | 50 | 50 | 10 | 70 | 60 | 20 | 30 | 70 | 70 | 70 | 50 |
| BARLEY | 0 | 0 | 80 | — | — | 20 | 60 | 20 | — | — | 30 | 30 | 30 | 10 |
| GREEN FOXTAIL | 50 | 40 | 70 | 50 | — | — | 100 | 50 | 10 | 10 | 80 | 40 | 0 | 0 |
| CHEATGRASS | — | — | 100 | 90 | 80 | 80 | — | 80 | — | 40 | — | — | — | — |
| LAMBSQUARTERS | 90 | 80 | 100 | 90 | 90 | 80 | 90 | 80 | 80 | 50 | 90 | 80 | 80 | 40 |
| CHICKWEED | 80 | 70 | 100 | 90 | 80 | 80 | 90 | 60 | 80 | 20 | 90 | 90 | 40 | 30 |
| DOWNY BROME | 30 | 0 | 100 | 80 | 40 | 40 | 100 | 60 | 50 | 0 | 100 | 80 | 30 | 0 |

POSTEMERGENCE

| | CMPD 95 | | | | CMPD 96 | | | | CMPD 97 | | | |
|---|---|---|---|---|---|---|---|---|---|---|---|---|
| RATE = G/HA | 62 | 16 | 4 | 1 | 62 | 16 | 4 | 1 | 62 | 16 | 4 | 1 |
| GIANT FOXTAIL | 30 | 20 | 0 | 0 | 10 | 0 | 0 | 0 | 50 | 30 | 10 | 0 |
| VELVETLEAF | 100 | 100 | 90 | 70 | 100 | 90 | 70 | 70 | 100 | 50 | 40 | 40 |
| SUGARBEET | 100 | 100 | 80 | 20 | 90 | 90 | 30 | 0 | 100 | 70 | 40 | 0 |
| CRABGRASS | 0 | 0 | 0 | 0 | 0 | — | 0 | 0 | 70 | 30 | 0 | — |
| TEAWEED | 80 | 70 | 70 | 50 | 70 | 80 | 60 | 20 | 80 | 70 | 30 | 40 |
| JIMSONWEED | 90 | 90 | 70 | 30 | 70 | 40 | 70 | 50 | 100 | 30 | 50 | 10 |
| RICE | 60 | 40 | 20 | 0 | 30 | 30 | 20 | 30 | 30 | 70 | 30 | 0 |
| COCKLEBUR | 50 | 50 | 10 | 0 | — | — | — | — | 100 | 80 | 10 | — |
| COTTON | 90 | 80 | 80 | 50 | 80 | 80 | 70 | 50 | 70 | 50 | 30 | 30 |
| SOYBEAN | 100 | 90 | 80 | 30 | 80 | 80 | 70 | 40 | 100 | 90 | 40 | 40 |
| BARNYARDGRASS | 100 | 100 | 80 | 40 | 90 | 80 | 50 | 0 | 100 | 100 | 80 | 0 |
| WILD OAT | 100 | 90 | 40 | 0 | 90 | 90 | 70 | 40 | 20 | 30 | 50 | 30 |
| MORNINGGLORY | 100 | 90 | 80 | 80 | 70 | 70 | — | 0 | 100 | 90 | 80 | 70 |
| WHEAT | 0 | 0 | 0 | 0 | 0 | 0 | 40 | 0 | 0 | 0 | 50 | 30 |
| SICKLEPOD | 30 | 10 | 0 | 0 | 10 | 40 | 0 | 0 | 90 | 80 | — | 0 |
| JOHNSONGRASS | 100 | 80 | 60 | 0 | 80 | 100 | 60 | 0 | 80 | 50 | 50 | 20 |
| NUTSEDGE | 60 | 30 | — | 0 | 10 | 0 | 40 | 0 | 40 | — | — | 40 |
| CORN | 20 | 20 | 10 | 0 | 80 | 40 | 0 | 0 | 100 | 0 | 0 | 0 |
| WILD BUCKWHEAT | 100 | 80 | 90 | 40 | 90 | 100 | 60 | 40 | 90 | 90 | 70 | 40 |
| BLACKGRASS | 100 | 90 | 70 | 80 | 100 | 90 | 90 | 80 | 100 | 80 | 80 | 60 |
| RAPE | 100 | 100 | 70 | 80 | 90 | 100 | 80 | 80 | 100 | 100 | 100 | 80 |

-continued

| | | | | | | | | | | | | | | | |
|---|---|---|---|---|---|---|---|---|---|---|---|---|---|---|---|
| BARLEY | 50 | 40 | 100 | 90 | 80 | 40 | 80 | 50 | 40 | 30 | 80 | 60 | 40 | 30 |
| GREEN FOXTAIL | 0 | 0 | 0 | 20 | 0 | 0 | 0 | 0 | 0 | 0 | 20 | 10 | 0 | 0 |
| CHEATGRASS | 50 | 30 | — | — | — | — | — | — | — | — | — | — | — | — |
| LAMBSQUARTERS | 50 | 30 | 100 | 100 | 100 | 80 | 100 | 80 | 20 | 30 | 100 | 100 | 40 | 40 |
| CHICKWEED | 100 | 60 | 100 | 100 | 90 | 60 | 100 | 100 | 20 | 0 | 100 | 90 | 40 | 0 |
| DOWNY BROME | 0 | 0 | 100 | 100 | 70 | 30 | 100 | 90 | 70 | 40 | 100 | 90 | 50 | 30 |

TEST C

Seeds of annual bluegrass (*Poa annua*), spring and winter barley (*Hordeum vulgare*), birdseye speedwell (*Veronica persica*), blackgrass (*Alopecurus myosuroides*), black nightshade (*Solanum nigrum*), catchweed bedstraw (*Galium aparine*), cheatgrass (*Bromus secalinus*), downy brome (*Bromus tectorum*), field pennycress (*Thlaspi arvense*), field violet (*Viola arvensis*), green foxtail (*Setaria viridis*), Italian ryegrass (*Lolium multiflorum*), ivyleaf speedwell (*Veronica hederaefolia*), jointed goatgrass (*Aegilops cylindrica*), kochia (*Kochia scoparia*), lambsquarters (*Chenopodium album*), rape (*Brassica napus*), Russian thistle (*Salsola kali*), scentless chamomile (*Matricaria inodora*), sugarbeet (*Beta vulgaris*), spring and winter wheat (*Triticum aestivum*), wild buckwheat (*Polygonum convolvulus*), and wild oat (*Avena fatua*) were planted and treated preemergence with test chemicals dissolved in a non-phytotoxic solvent. At the same time, these crop and weed species were also treated with postemergence applications of test chemicals. Plants ranged in height from two to twenty-four cm for postemergence treatments. Blackgrass and wild oat were treated postemergence at two growth stages. Treated plants and controls were maintained in a greenhouse for approximately 21 days, after which all species were compared to controls and visually evaluated. The ratings, summarized in Table C, are based on a scale of 0 to 100 where 0 is no effect and 100 is complete control. A dash (—) response means no test.

TABLE C

| RATE G/HA | CMPD 1 | | | | | CMPD 6 | | | | | CMPD 13 | | | | CMPD 20 | | | |
|---|---|---|---|---|---|---|---|---|---|---|---|---|---|---|---|---|---|---|
| | 125 | 64 | 32 | 16 | 8 | 64 | 32 | 16 | 8 | 4 | 32 | 16 | 8 | 4 | 32 | 16 | 8 | 4 | 2 |
| POSTEMERGENCE | | | | | | | | | | | | | | | | | | | |
| SPRING WHEAT | 0 | 0 | 0 | 0 | 0 | 100 | 90 | 80 | 70 | 60 | 20 | 20 | 20 | 0 | 70 | 60 | 50 | 40 | 30 |
| SPRING BARLEY | 10 | 0 | 0 | 0 | 0 | 60 | 40 | 30 | 30 | 20 | 50 | 40 | 30 | 30 | 80 | 60 | 50 | 20 | 20 |
| WILD OAT STAGE 1 | 60 | 60 | 20 | 20 | 20 | 100 | 100 | 100 | 80 | 50 | 80 | 50 | 20 | 0 | 100 | 100 | 90 | 90 | 90 |
| DOWNY BROME | 20 | 10 | 10 | 0 | 0 | 90 | 70 | 70 | 60 | 40 | 60 | 90 | 40 | 20 | 70 | 40 | 40 | 20 | 0 |
| CHEATGRASS | 60 | 40 | 40 | 20 | 20 | 80 | 70 | 70 | 40 | 30 | 60 | 60 | 50 | 30 | 50 | 50 | 50 | 40 | 20 |
| BLACKGRASS STAGE 1 | 10 | 0 | 0 | 0 | 0 | 90 | 80 | 50 | 40 | 30 | 100 | 80 | 50 | 40 | 90 | 90 | 80 | 40 | 30 |
| BLUEGRASS | 20 | 0 | 0 | 50 | 40 | 90 | 70 | 80 | 40 | 30 | 40 | 20 | 10 | 0 | 60 | 60 | 30 | 20 | 0 |
| GREEN FOXTAIL | 80 | 70 | 70 | 50 | 30 | 100 | 100 | 100 | 100 | 80 | 90 | 90 | 90 | 70 | 40 | 40 | 40 | 20 | 30 |
| ITALIAN RYEGRASS | 100 | 100 | 90 | 70 | 70 | 100 | 100 | 100 | 70 | 50 | 80 | 40 | 40 | 20 | 100 | 100 | 90 | 70 | 0 |
| RAPE | 100 | 100 | 100 | 100 | 100 | 100 | 100 | 100 | 100 | 80 | 100 | 100 | 100 | 100 | 100 | 100 | 100 | 100 | 100 |
| WINTER WHEAT | 10 | 0 | 0 | 0 | 0 | 80 | 70 | 70 | 60 | 40 | 40 | 20 | 10 | 30 | 70 | 60 | 60 | 30 | 20 |
| WINTER BARLEY | 10 | 0 | 0 | 0 | 0 | 80 | 80 | 70 | 50 | 40 | 80 | 60 | 40 | 20 | 80 | 80 | 60 | 50 | 40 |
| JOINTED GOATGRASS | 0 | 0 | 0 | 0 | 0 | 90 | 90 | 80 | 80 | 20 | 90 | 90 | 50 | 20 | 100 | 100 | 90 | 90 | 90 |
| WILD OAT STAGE 2 | 70 | 30 | 30 | 0 | 0 | 90 | 60 | 60 | 30 | 20 | 40 | 10 | 10 | 0 | 80 | 70 | 70 | 50 | 30 |
| BLACKGRASS STAGE 2 | 50 | 50 | 50 | — | 10 | 80 | 100 | 100 | 80 | 20 | 60 | 30 | 20 | 10 | 80 | 80 | 50 | 40 | 30 |
| CATCHWEED BEDSTRAW | 100 | 70 | 60 | 40 | 30 | 100 | 100 | 100 | 70 | 20 | 100 | 30 | 0 | 0 | 100 | 100 | 100 | 100 | 10 |
| WILD BUCKWHEAT | 90 | 90 | 70 | 40 | 20 | 100 | 100 | 70 | 70 | 20 | 100 | 100 | 80 | 60 | 90 | 80 | 60 | 40 | 60 |
| KOCHIA | 100 | 90 | 90 | 70 | 70 | 100 | 70 | 70 | 50 | 20 | 100 | 100 | 80 | 70 | 80 | 70 | 70 | 30 | 20 |
| SCENTLESS CHAMOMILE | 100 | 90 | 70 | 20 | 50 | 100 | 100 | 100 | 100 | 20 | 100 | 20 | 20 | 20 | 0 | 0 | 0 | 0 | 10 |
| BLACK NIGHTSHADE | 50 | 50 | 30 | 70 | 30 | 70 | 30 | 30 | 10 | 0 | 70 | 30 | 20 | 0 | — | — | — | — | — |
| RUSSIAN THISTLE | — | — | 90 | 70 | 40 | — | — | — | — | 40 | 0 | 0 | 0 | 0 | 0 | 0 | 0 | 0 | 0 |
| BIRDSEYE SPEEDWELL | 100 | 100 | 100 | 80 | 60 | 100 | 100 | 60 | 60 | 80 | 100 | 100 | 100 | 100 | 100 | 100 | 100 | 90 | 90 |
| SUGARBEET | 100 | 100 | 90 | 90 | 30 | 100 | 100 | 100 | 100 | 10 | 100 | 50 | 50 | 0 | 10 | 10 | 0 | 0 | 0 |
| IVYLEAF SPEEDWELL | 100 | 40 | 20 | 0 | 0 | 60 | 40 | 20 | 20 | 30 | 100 | 50 | 50 | 40 | 40 | 90 | 90 | 80 | 70 |
| LAMBSQUARTERS | 100 | 80 | 70 | 60 | 30 | 100 | 100 | 70 | 60 | 0 | 100 | 80 | 80 | 40 | 90 | 90 | 80 | 90 | 0 |
| FIELD PENNYCRESS | 70 | 40 | 0 | 0 | 0 | 100 | 100 | 100 | 60 | 30 | 100 | 80 | 20 | 40 | 90 | 90 | 90 | 80 | 70 |
| FIELD VIOLET | 0 | 0 | 0 | 0 | 0 | 30 | 0 | 0 | 0 | 40 | 60 | 50 | 20 | 0 | 20 | 0 | 0 | 0 | 0 |

| RATE G/HA | CMPD 22 | | | | | CMPD 23 | | | | | CMPD 27 | | | | CMPD 28 | | | |
|---|---|---|---|---|---|---|---|---|---|---|---|---|---|---|---|---|---|---|
| | 64 | 32 | 16 | 8 | 4 | 32 | 16 | 8 | 4 | 2 | 64 | 32 | 16 | 8 | 125 | 64 | 32 | 16 | 8 |
| POSTEMERGENCE | | | | | | | | | | | | | | | | | | | |
| SPRING WHEAT | 100 | 90 | 40 | 40 | 30 | 50 | 20 | 0 | 0 | 0 | 10 | 0 | 0 | 0 | 50 | 40 | 20 | 10 | 0 |
| SPRING BARLEY | 90 | 70 | 60 | 50 | 30 | 30 | 10 | 10 | 0 | 0 | 0 | 0 | 0 | 0 | 70 | 60 | 30 | 10 | 0 |
| WILD OAT STAGE 1 | 100 | 100 | 100 | 100 | 60 | 100 | 90 | 80 | 60 | 60 | 90 | 80 | 0 | 0 | 100 | 100 | 90 | 90 | 90 |
| DOWNY BROME | 100 | 90 | 90 | 70 | 40 | 50 | 30 | 30 | 10 | 20 | 40 | 0 | 0 | 0 | 90 | 80 | 50 | 20 | 0 |
| CHEATGRASS | 100 | 90 | 70 | 70 | 20 | 80 | 70 | 30 | 30 | 0 | 60 | 30 | 10 | 0 | 100 | 90 | 80 | 40 | 10 |
| BLACKGRASS STAGE 1 | 70 | 70 | 60 | 30 | 30 | 70 | 20 | 20 | 30 | 20 | 40 | 20 | 30 | 0 | 80 | 70 | 30 | 20 | 10 |
| BLUEGRASS | 90 | 80 | 40 | 50 | 20 | 70 | 90 | 70 | 60 | 0 | 60 | 20 | 20 | 0 | 80 | 60 | 40 | 20 | 0 |
| GREEN FOXTAIL | 80 | 70 | 100 | 40 | 30 | 100 | 100 | 100 | 90 | 20 | 80 | 40 | 10 | 0 | 100 | 90 | 80 | 60 | 50 |
| ITALIAN RYEGRASS | 100 | 100 | 100 | 90 | 70 | 40 | 10 | 20 | 0 | 10 | 40 | 20 | 10 | 0 | 100 | 90 | 70 | 50 | 10 |
| RAPE | 100 | 100 | 100 | 100 | 100 | 100 | 100 | 70 | 60 | 10 | 100 | 70 | 70 | 0 | 100 | 100 | 80 | 50 | 0 |
| WINTER WHEAT | 60 | 60 | 50 | 40 | 30 | 30 | 10 | 20 | 10 | 0 | 40 | 10 | 10 | 0 | 80 | 60 | 30 | 10 | 20 |
| WINTER BARLEY | 90 | 90 | 70 | 50 | 40 | 30 | 40 | 10 | 0 | 0 | 10 | 0 | 0 | 0 | 90 | 90 | 80 | 30 | 10 |
| JOINTED GOATGRASS | 100 | 100 | 80 | 60 | 70 | 20 | 10 | 50 | 20 | 0 | 20 | 70 | 70 | 30 | 90 | 80 | 80 | 30 | 30 |
| WILD OAT STAGE 2 | 90 | 90 | 80 | 90 | 20 | 100 | 100 | 50 | 10 | 20 | 80 | 60 | 20 | 0 | 90 | 80 | 80 | 80 | 80 |
| BLACKGRASS STAGE 2 | 100 | 50 | 50 | 40 | 0 | 60 | 60 | 60 | 20 | 0 | 40 | 10 | 10 | 0 | 90 | 60 | 40 | 20 | 0 |
| CATCHWEED BEDSTRAW | 90 | 60 | 50 | 20 | 30 | 70 | 60 | 10 | 0 | 0 | 40 | 0 | 0 | 0 | 80 | 50 | 50 | 20 | 0 |
| WILD BUCKWHEAT | 90 | 40 | 30 | 30 | 0 | 60 | 30 | 50 | 0 | 70 | 10 | 0 | 0 | 0 | 90 | 0 | 20 | 0 | 0 |
| KOCHIA | 40 | 30 | 10 | 0 | 0 | 70 | 60 | 0 | 40 | 0 | 10 | 0 | 0 | 0 | 70 | 60 | 0 | 0 | 0 |

TABLE C-continued

| | CMPD 56 | | CMPD 29 | | | | | CMPD 57 | | | | | CMPD 54 | | | | | CMPD 64 | | | | CMPD 55 | | | | | CMPD 67 | | | |
|---|---|---|---|---|---|---|---|---|---|---|---|---|---|---|---|---|---|---|---|---|---|---|---|---|---|---|---|---|---|---|---|
| RATE G/HA | 125 | 64 | 32 | 16 | 8 | 32 | 16 | 8 | 4 | 2 | 64 | 32 | 16 | 8 | 4 | 2 | 16 | 8 | 4 | 1 | 125 | 64 | 32 | 16 | 8 | 32 | 16 | 8 | 4 | 2 | 1 |
| SCENTLESS CHAMOMILE | 100 | 60 | 50 | 50 | 30 | 100 | 90 | | | | 70 | 70 | 50 | 20 | 10 | 0 | 100 | 80 | 70 | 0 | | 70 | 70 | 60 | 0 | 50 | 40 | 50 | 10 | 0 | 0 |
| BLACK NIGHTSHADE | 40 | 20 | 10 | 0 | 0 | 10 | 0 | 0 | 20 | 0 | 0 | 0 | 0 | 0 | 20 | 20 | 60 | 60 | 10 | 10 | | 50 | 0 | 0 | 0 | 40 | 20 | 40 | 0 | 0 | 0 |
| RUSSIAN THISTLE | — | — | — | — | — | — | — | — | — | — | — | — | — | — | — | — | — | — | — | — | | — | — | — | — | — | — | — | — | — | — |
| BIRDSEYE SPEEDWELL | 0 | 0 | 0 | 0 | 0 | 0 | 20 | 0 | 70 | 20 | 40 | 20 | 0 | 0 | 40 | 20 | 100 | 80 | 70 | 0 | | 100 | 20 | 0 | 0 | 90 | 70 | 100 | 70 | 50 | 30 |
| DOWNY BROME | 100 | 100 | 100 | 80 | 60 | 100 | 100 | 60 | 100 | 40 | 0 | 0 | 30 | 20 | 0 | 0 | 100 | 80 | 60 | 0 | | 30 | 100 | 100 | 0 | 10 | 10 | 0 | 0 | 0 | 0 |
| CHEATGRASS | 0 | 0 | 0 | 0 | 0 | 0 | 0 | 40 | 0 | 0 | 10 | 0 | 0 | 0 | 60 | 0 | 90 | 70 | 50 | 20 | | 100 | 0 | 0 | 0 | 90 | 70 | 90 | 0 | 0 | 0 |
| IVYLEAF SPEEDWELL | 0 | 0 | 0 | 80 | 0 | 20 | 20 | 20 | 0 | 0 | 20 | 20 | 10 | 0 | 0 | 20 | 80 | 80 | 30 | 30 | | 50 | 0 | 10 | 0 | 0 | 0 | 0 | 0 | 0 | 0 |
| LAMBSQUARTERS | 20 | 10 | 0 | 80 | 60 | 70 | 70 | 0 | 0 | 0 | 70 | 80 | 60 | 30 | 10 | 10 | 70 | 80 | 60 | 20 | | 10 | 20 | 20 | 0 | 0 | 10 | 10 | 20 | 10 | 0 |
| FIELD PENNYCRESS | 100 | 90 | 80 | 80 | 40 | 100 | 100 | 50 | 100 | 0 | 80 | 80 | 50 | 40 | 60 | 30 | 100 | 80 | 70 | 30 | | 70 | 30 | 30 | 20 | 60 | 50 | 60 | 60 | 50 | 30 |
| FIELD VIOLET | 0 | 0 | 0 | 0 | 0 | 0 | 0 | 0 | 0 | 0 | 90 | 80 | 90 | 70 | 70 | 100 | 0 | 80 | 0 | 20 | | 10 | 0 | 0 | 0 | 0 | 0 | 20 | 0 | 0 | 30 |

| | CMPD 56 | | CMPD 29 | | | | CMPD 57 | | | | | CMPD 54 | | | | | CMPD 64 | | | | CMPD 55 | | | | | CMPD 67 | | | |
|---|---|---|---|---|---|---|---|---|---|---|---|---|---|---|---|---|---|---|---|---|---|---|---|---|---|---|---|---|---|---|
| RATE G/HA | 4 | 2 | 32 | 16 | 8 | 4 | 32 | 16 | 8 | 4 | 2 | 64 | 32 | 16 | 8 | 4 | 2 | 16 | 8 | 4 | 1 | 125 | 64 | 32 | 16 | 8 | 32 | 16 | 8 | 4 | 2 |
| POSTEMERGENCE | | | | | | | | | | | | | | | | | | | | | | | | | | | | | | | |
| SPRING WHEAT | 0 | 0 | 100 | 100 | 100 | 100 | 0 | 0 | 0 | 0 | 0 | 10 | 0 | 10 | 30 | 10 | 0 | 100 | 90 | 0 | 0 | 0 | 0 | 0 | 0 | 0 | 60 | 10 | 10 | 0 | 0 |
| SPRING BARLEY | 10 | 40 | 100 | 100 | 80 | 50 | 0 | 0 | 40 | 0 | 20 | 40 | 40 | 60 | 50 | 100 | 20 | 100 | 100 | 10 | 0 | 10 | 10 | 50 | 30 | 0 | 60 | 10 | 10 | 0 | 0 |
| WILD OAT STAGE 1 | 0 | 10 | 100 | 100 | 90 | 100 | 0 | 0 | 0 | 0 | 0 | 70 | 80 | 100 | 100 | 80 | 70 | 80 | 80 | 80 | 0 | 40 | 20 | 80 | 80 | 0 | 100 | 60 | 70 | 40 | 30 |
| DOWNY BROME | 70 | 0 | 100 | 100 | 80 | 60 | 0 | 40 | 0 | 0 | 0 | 50 | 60 | 70 | 40 | 60 | 0 | 80 | 70 | 30 | 0 | 40 | 30 | 60 | 40 | 30 | 20 | 10 | 20 | 20 | 10 |
| CHEATGRASS | 0 | 0 | 100 | 80 | 70 | 70 | 0 | 0 | 0 | 0 | 20 | 30 | 30 | 60 | 30 | 50 | 70 | 80 | 80 | 20 | 0 | 30 | 0 | 40 | 30 | 20 | 70 | 20 | 30 | 20 | 20 |
| BLACKGRASS STAGE 1 | 20 | 0 | 100 | 80 | 70 | 70 | 0 | 0 | 40 | 0 | 10 | 10 | 10 | 30 | 10 | 30 | 10 | 60 | 50 | 30 | 10 | 50 | 20 | 80 | 40 | 20 | 80 | 30 | 80 | 60 | 50 |
| BLUEGRASS | 0 | 0 | 100 | 60 | 60 | 80 | 0 | 0 | 20 | 0 | 0 | 50 | 40 | 80 | 60 | 70 | 30 | 80 | 60 | 20 | 30 | 30 | 0 | 30 | 20 | 40 | 100 | 60 | 80 | 60 | 30 |
| GREEN FOXTAIL | 10 | 0 | 100 | 90 | 70 | 20 | 0 | 0 | 0 | 0 | 0 | 80 | 100 | 80 | 70 | 70 | 20 | 80 | 70 | 40 | 20 | 100 | 100 | 100 | 90 | 90 | | | | | |

TABLE C-continued

| | CMPD 1 | | | | | CMPD 22 | | | CMPD 6 | | | | | CMPD 23 | | | CMPD 13 | | | CMPD 27 | | | | CMPD 20 | | | |
|---|---|---|---|---|---|---|---|---|---|---|---|---|---|---|---|---|---|---|---|---|---|---|---|---|---|---|---|
| RATE G/HA | 125 | 64 | 32 | 16 | 8 | 32 | 16 | 8 | 64 | 32 | 16 | 8 | 2 | 16 | 8 | 4 | 8 | 4 | 2 | 32 | 16 | 8 | 4 | 16 | 8 | 4 | 2 |
| ITALIAN RYEGRASS | 0 | 0 | 40 | 10 | 0 | 30 | 10 | 0 | 70 | 90 | 90 | 80 | 90 | 0 | 0 | 20 | 10 | 30 | 0 | 20 | 30 | 0 | 0 | 0 | 30 | 0 | 0 |
| RAPE | 70 | 40 | 100 | 90 | 90 | 0 | 0 | 0 | 100 | 100 | 90 | 100 | 70 | 10 | 20 | 0 | 70 | 0 | 0 | 100 | 10 | 20 | 70 | 90 | 50 | 70 | 20 |
| WINTER WHEAT | 20 | 0 | 60 | 50 | 20 | 0 | 0 | 0 | 100 | 80 | 60 | 30 | 50 | 0 | 70 | 0 | 80 | 0 | 0 | 100 | 20 | 10 | 0 | 0 | 10 | 10 | 0 |
| WINTER BARLEY | 20 | 10 | 40 | 20 | 10 | 0 | 0 | 0 | 100 | 100 | 60 | 30 | 70 | 0 | 60 | 0 | 100 | 0 | 0 | 70 | 0 | 20 | 0 | 20 | 20 | 0 | 0 |
| JOINTED GOATGRASS | 0 | 0 | 0 | 0 | 0 | 0 | 0 | 0 | 100 | 80 | 60 | 50 | 0 | 0 | 50 | 0 | 70 | 0 | 10 | 100 | 40 | 10 | 0 | 30 | 20 | 30 | 0 |
| WILD OAT STAGE 2 | 0 | 0 | 10 | 0 | 0 | 0 | 0 | 0 | 100 | 100 | 90 | 80 | 90 | 0 | 30 | 0 | 80 | 10 | 0 | 70 | 70 | 40 | 30 | 40 | 60 | 60 | 30 |
| BLACKGRASS STAGE 2 | 70 | 30 | 100 | 80 | 50 | 0 | 0 | 0 | 100 | 100 | 90 | 100 | 80 | 0 | 30 | 30 | 70 | 20 | 10 | 100 | 50 | 20 | 0 | 90 | 40 | 40 | 0 |
| CATCHWEED BEDSTRAW | 0 | 0 | 10 | 0 | 0 | 20 | 0 | 10 | 100 | 90 | 70 | 50 | 60 | 0 | 40 | 0 | 60 | 50 | 0 | 100 | 80 | 50 | 40 | 10 | 30 | 0 | 30 |
| WILD BUCKWHEAT | 10 | 0 | 20 | 10 | 0 | 0 | 0 | 20 | 80 | 100 | 80 | 40 | 80 | 0 | 30 | 40 | 30 | 20 | 0 | 50 | 80 | 20 | 30 | 20 | 50 | 20 | 0 |
| KOCHIA | — | — | 70 | 30 | 30 | 20 | 10 | 0 | 70 | 70 | 70 | 50 | 70 | 0 | 40 | 10 | 50 | 30 | 0 | 30 | 60 | 30 | 0 | 50 | 40 | 10 | 0 |
| SCENTLESS CHAMOMILE | 30 | 0 | 30 | 20 | 20 | 0 | 0 | 20 | 50 | 30 | 60 | 30 | 60 | 0 | 30 | 0 | 30 | 30 | 0 | 80 | 50 | 20 | 30 | 30 | 50 | 30 | 10 |
| BLACK NIGHTSHADE | 20 | 0 | 30 | 30 | 20 | 0 | 0 | 10 | 100 | 90 | 80 | 50 | 50 | 0 | 50 | 10 | 60 | 70 | 0 | 50 | 70 | 60 | 50 | 50 | 0 | 0 | 0 |
| RUSSIAN THISTLE | 0 | — | 0 | 0 | 10 | 0 | 0 | — | 20 | 10 | 10 | 0 | 0 | — | 0 | 0 | 0 | 0 | — | 0 | 0 | 0 | — | 50 | 50 | 10 | 0 |
| BIRDSEYE SPEEDWELL | — | — | 0 | 0 | 0 | 0 | 0 | 0 | 50 | 0 | 0 | 0 | 0 | — | 0 | 0 | 0 | 0 | — | — | — | — | — | — | — | — | — |
| SUGARBEET | 0 | 0 | 60 | 30 | 0 | 30 | 0 | 0 | 90 | 80 | 70 | 80 | 50 | 0 | 60 | 30 | 50 | 40 | 0 | 90 | 60 | 20 | 0 | 70 | 70 | 70 | 50 |
| IVYLEAF SPEEDWELL | 40 | 20 | 0 | 30 | 0 | 30 | 0 | 30 | 90 | 90 | 90 | 80 | 70 | 0 | 90 | 40 | 80 | 40 | 10 | 100 | 40 | 50 | 60 | 80 | 60 | 60 | 40 |
| LAMBSQUARTERS | 30 | 10 | 0 | 0 | 30 | 0 | 0 | 0 | 80 | 100 | 90 | 70 | 80 | 0 | 100 | 40 | 50 | 40 | — | 90 | 70 | 50 | 20 | 90 | 50 | 20 | 0 |
| FIELD PENNYCRESS | 70 | 20 | 40 | 40 | 60 | 10 | 0 | 30 | 100 | 90 | 100 | 90 | 90 | 0 | 80 | 40 | 60 | 60 | 0 | 70 | 80 | 70 | 40 | 50 | 50 | 50 | 30 |
| FIELD VIOLET | 0 | 50 | 90 | 0 | 0 | 20 | 0 | 0 | 50 | 60 | 80 | 50 | 60 | — | 80 | 40 | 10 | 30 | 0 | 70 | 70 | 40 | 0 | 30 | 30 | 0 | 0 |

| | CMPD 1 | | | | | CMPD 22 | | | CMPD 6 | | | | | CMPD 23 | | | CMPD 13 | | | CMPD 27 | | | | CMPD 20 | | | |
|---|---|---|---|---|---|---|---|---|---|---|---|---|---|---|---|---|---|---|---|---|---|---|---|---|---|---|---|
| RATE G/HA | 125 | 64 | 32 | 16 | 8 | 32 | 16 | 8 | 64 | 32 | 16 | 8 | 2 | 16 | 8 | 4 | 8 | 4 | 2 | 32 | 16 | 8 | 4 | 16 | 8 | 4 | 2 |

PREEMERGENCE

| | | | | | |
|---|---|---|---|---|---|
| SPRING WHEAT | 40 | 30 | 30 | 10 | 0 |
| SPRING BARLEY | 30 | 20 | 0 | 0 | 0 |
| WILD OAT | 20 | 0 | 0 | 0 | 0 |
| DOWNY BROME | 20 | 10 | 40 | 30 | 20 |
| CHEATGRASS | 70 | 40 | 70 | 0 | 20 |
| BLACKGRASS | 60 | 40 | 40 | 30 | 10 |
| BLUEGRASS | 50 | 40 | 40 | 20 | 20 |
| GREEN FOXTAIL | 90 | 70 | 30 | 30 | 30 |
| ITALIAN RYEGRASS | 80 | 70 | 30 | 10 | 0 |
| RAPE | 100 | 100 | 100 | 70 | 0 |
| WINTER WHEAT | 30 | 20 | 0 | 20 | 0 |
| WINTER BARLEY | 40 | 30 | 20 | 0 | 10 |
| JOINTED GOATGRASS | 30 | 10 | 0 | 0 | 0 |
| CATCHWEED BEDSTRAW | 40 | 50 | 50 | 40 | 0 |
| WILD BUCKWHEAT | 70 | 20 | 10 | 40 | 0 |
| KOCHIA | 50 | 20 | 10 | 0 | 40 |
| SCENTLESS CHAMOMILE | 80 | 80 | 70 | 60 | 0 |
| BLACK NIGHTSHADE | 50 | 20 | 10 | 0 | 0 |
| RUSSIAN THISTLE | — | — | — | — | — |
| BIRDSEYE SPEEDWELL | 70 | 60 | 30 | 20 | 0 |
| SUGARBEET | 80 | 60 | 40 | 20 | 30 |
| IVYLEAF SPEEDWELL | 100 | 100 | 90 | 50 | 50 |
| LAMBSQUARTERS | 90 | 90 | 60 | 40 | 40 |
| FIELD PENNYCRESS | 100 | 90 | 50 | 50 | 30 |
| FIELD VIOLET | 50 | 20 | 0 | 0 | 0 |

| RATE G/HA | 64 | 32 |
|---|---|---|

PREEMERGENCE

TABLE C-continued

| | CMPD 29 | | | | | CMPD 54 | | | | | |
|---|---|---|---|---|---|---|---|---|---|---|---|
| | 125 | 64 | 32 | 16 | 8 | 32 | 16 | 8 | 4 | 2 | 1 |
| SPRING WHEAT | 90 | 80 | 70 | 70 | 50 | 90 | 80 | 60 | 60 | 50 | 40 |
| SPRING BARLEY | 50 | 40 | 40 | 20 | 10 | 70 | 40 | 0 | 20 | 0 | 0 |
| WILD OAT | 30 | 30 | 30 | 20 | 10 | 30 | 10 | 0 | 10 | 0 | 0 |
| DOWNY BROME | 90 | 60 | 40 | 20 | 20 | 80 | 50 | 20 | 40 | 20 | 0 |
| CHEATGRASS | 100 | 80 | 70 | 30 | 20 | 90 | 90 | 20 | 60 | 20 | 0 |
| BLACKGRASS | 80 | 70 | 80 | 60 | 30 | 70 | 40 | 0 | 20 | 10 | 0 |
| BLUEGRASS | 90 | 80 | 80 | 70 | 50 | 80 | 70 | 10 | 50 | 30 | 20 |
| GREEN FOXTAIL | 70 | 60 | 50 | 40 | 20 | 80 | 40 | 20 | 50 | 20 | 10 |
| ITALIAN RYEGRASS | 80 | 60 | 30 | 20 | 0 | 90 | 80 | 20 | 100 | 40 | 0 |
| RAPE | 90 | 90 | 60 | 20 | 30 | 90 | 10 | 10 | 40 | 10 | 30 |
| WINTER WHEAT | 90 | 70 | 80 | 40 | 30 | 70 | 80 | 20 | 30 | 0 | 0 |
| WINTER BARLEY | 60 | 60 | 50 | 50 | 30 | 70 | 60 | 40 | 70 | 0 | 0 |
| JOINTED GOATGRASS | 30 | 30 | 10 | 0 | 0 | 80 | 80 | 0 | 0 | 0 | 0 |
| CATCHWEED BEDSTRAW | 90 | 70 | 60 | 40 | 30 | 30 | 60 | 0 | 20 | 10 | 30 |
| WILD BUCKWHEAT | 90 | 70 | 70 | 60 | 40 | 40 | 20 | 0 | 50 | 0 | 0 |
| KOCHIA | 30 | 20 | 0 | 0 | 0 | 20 | 10 | 10 | 0 | 0 | 0 |
| SCENTLESS CHAMOMILE | 100 | 90 | 80 | 60 | 40 | 90 | 80 | 80 | 40 | 40 | 30 |
| BLACK NIGHTSHADE | 90 | 50 | 40 | 30 | 0 | 30 | 10 | 0 | 0 | 0 | 0 |
| RUSSIAN THISTLE | — | — | — | — | — | — | — | — | — | — | — |
| BIRDSEYE SPEEDWELL | 40 | 0 | 0 | 0 | 0 | 40 | 40 | 0 | 40 | 0 | 70 |
| SUGARBEET | 100 | 90 | 90 | 70 | 60 | 100 | 10 | 60 | 70 | 70 | 0 |
| IVYLEAF SPEEDWELL | 100 | 60 | 40 | 0 | 0 | 10 | 10 | 0 | 10 | 10 | 0 |
| LAMBSQUARTERS | 100 | 80 | 80 | 60 | 20 | 80 | 80 | 0 | 70 | 50 | 0 |
| FIELD PENNYCRESS | 90 | 90 | 60 | 30 | 0 | 50 | 20 | 0 | 0 | 0 | 0 |
| FIELD VIOLET | 40 | 30 | 0 | 0 | 0 | 70 | 80 | 50 | 40 | 30 | 30 |

| | CMPD 55 | | | | | CMPD 56 | | | | | |
|---|---|---|---|---|---|---|---|---|---|---|---|
| RATE G/HA | 125 | 64 | 32 | 16 | 8 | 32 | 16 | 8 | 4 | 2 | 1 |
| PREEMERGENCE | | | | | | | | | | | |
| SPRING WHEAT | 30 | 10 | 0 | 0 | 0 | 0 | 0 | 0 | 0 | 0 | 0 |
| SPRING BARLEY | 20 | 0 | 0 | 0 | 0 | 40 | 10 | 0 | 0 | 0 | 0 |
| WILD OAT | 30 | 0 | 10 | 10 | 0 | 0 | 0 | 0 | 0 | 0 | 0 |
| DOWNY BROME | 10 | 10 | 10 | 0 | 10 | 70 | 50 | 10 | 0 | 0 | 0 |
| CHEATGRASS | 20 | 10 | 10 | 0 | 0 | 20 | 10 | 0 | 0 | 0 | 0 |
| BLACKGRASS | 0 | 0 | 0 | 0 | 0 | 0 | 0 | 0 | 0 | 0 | 0 |
| BLUEGRASS | 80 | 70 | 10 | 30 | 10 | 20 | 0 | 10 | 0 | 0 | 0 |
| GREEN FOXTAIL | 60 | 30 | 10 | 10 | 20 | 40 | 10 | 0 | 0 | 0 | 0 |
| ITALIAN RYEGRASS | 30 | 10 | 10 | 0 | 0 | 10 | 10 | 10 | 0 | 0 | 0 |
| RAPE | 10 | 10 | 10 | 0 | 10 | 20 | 10 | 20 | 0 | 0 | 0 |
| WINTER WHEAT | 70 | 40 | 30 | 30 | 0 | 40 | 10 | 0 | 0 | 0 | 0 |
| WINTER BARLEY | 30 | 20 | 30 | 70 | 10 | 70 | 70 | 30 | 0 | 0 | 0 |
| JOINTED GOATGRASS | 10 | 10 | 10 | 10 | 20 | 10 | 10 | 20 | 20 | 0 | 0 |
| CATCHWEED BEDSTRAW | 70 | 40 | 30 | 30 | 0 | 20 | 10 | 0 | 0 | 0 | 0 |
| WILD BUCKWHEAT | 30 | 20 | 20 | 10 | 0 | 40 | 10 | 0 | 0 | 0 | 0 |
| KOCHIA | 100 | 70 | 70 | 30 | 20 | 70 | 70 | 40 | 20 | 20 | 50 |
| SCENTLESS CHAMOMILE | 60 | — | — | — | — | — | — | — | 80 | 70 | 0 |
| BLACK NIGHTSHADE | 80 | 80 | 60 | 50 | 0 | 90 | 90 | 60 | 30 | 20 | 10 |
| RUSSIAN THISTLE | 20 | 10 | 10 | 0 | 0 | 60 | 60 | 50 | 50 | 40 | 30 |
| BIRDSEYE SPEEDWELL | 0 | — | 0 | 0 | 0 | 60 | 60 | 30 | 20 | 20 | 10 |
| SUGARBEET | 70 | 70 | 50 | 40 | 20 | 90 | 90 | 80 | 70 | 20 | 0 |
| IVYLEAF SPEEDWELL | 20 | — | 20 | 20 | 20 | 100 | 100 | 90 | 50 | 50 | 10 |

TABLE C-continued

| | CMPD 57 | | | | | | CMPD 64 | | | | | | CMPD 67 | | | | | |
|---|---|---|---|---|---|---|---|---|---|---|---|---|---|---|---|---|---|---|
| RATE G/HA | 32 | 16 | 8 | 4 | 2 | 1 | 32 | 16 | 8 | 4 | 2 | 1 | 32 | 16 | 8 | 4 | 2 | 1 |
| PREEMERGENCE | | | | | | | | | | | | | | | | | | |
| SPRING WHEAT | 20 | 10 | 0 | 0 | 0 | 0 | 100 | 90 | 40 | 40 | 10 | 0 | 10 | 10 | 0 | 0 | 0 | 0 |
| SPRING BARLEY | 10 | 0 | 0 | 0 | 0 | 0 | 80 | 70 | 40 | 30 | 10 | 0 | 30 | 30 | 0 | 0 | 0 | 0 |
| WILD OAT | 10 | 0 | 0 | 0 | 0 | 0 | 70 | 50 | 20 | 10 | 0 | 0 | 50 | 30 | 10 | 10 | 0 | 0 |
| DOWNY BROME | 20 | 0 | 0 | 0 | 0 | 0 | 90 | 80 | 70 | 30 | 20 | 10 | 10 | 10 | 10 | 0 | 0 | 0 |
| CHEATGRASS | 0 | 0 | 0 | 0 | 0 | 0 | 90 | 80 | 70 | 50 | 30 | 20 | 40 | 10 | 10 | 0 | 0 | 0 |
| BLACKGRASS | 30 | 10 | 10 | 0 | 0 | 10 | 90 | 90 | 80 | 60 | 40 | 0 | 10 | 10 | 0 | 0 | 0 | 0 |
| BLUEGRASS | 10 | 0 | 0 | 0 | 0 | 20 | 90 | 90 | 80 | 40 | 20 | 0 | 20 | 10 | 0 | 0 | 0 | 0 |
| GREEN FOXTAIL | 30 | 0 | 0 | 0 | 0 | 0 | 100 | 30 | 10 | 10 | 0 | 0 | 40 | 30 | 20 | 0 | 0 | 10 |
| ITALIAN RYEGRASS | 10 | 70 | 30 | 0 | 0 | 0 | 30 | 60 | 50 | 40 | 20 | 0 | 90 | 70 | 50 | 30 | 20 | 10 |
| RAPE | 100 | 20 | 0 | 0 | 0 | 0 | 100 | 70 | 60 | 10 | 10 | 0 | 10 | 10 | 0 | 0 | 0 | 0 |
| WINTER WHEAT | 40 | 10 | 0 | 0 | 0 | 0 | 80 | 70 | 30 | 0 | 0 | 0 | 20 | 10 | 10 | 0 | 0 | 0 |
| WINTER BARLEY | 30 | 0 | 0 | 0 | 0 | 0 | 90 | 50 | 10 | 0 | 0 | 0 | 10 | 0 | 0 | 0 | 0 | 0 |
| JOINTED GOATGRASS | 20 | 40 | 20 | 10 | 0 | 0 | 70 | 70 | 50 | 0 | 0 | 0 | 40 | 30 | 10 | 10 | 0 | 0 |
| CATCHWEED BEDSTRAW | 40 | 40 | 0 | 0 | 0 | 0 | 50 | 50 | 30 | 0 | 0 | 0 | 30 | 30 | 10 | 0 | 0 | 0 |
| WILD BUCKWHEAT | 40 | 10 | 20 | 0 | 0 | 20 | 30 | 30 | 30 | 10 | 0 | 10 | 90 | 70 | 10 | 0 | 0 | 10 |
| KOCHIA | 40 | 30 | 0 | 10 | 0 | 0 | 90 | 80 | 70 | 50 | 50 | 10 | 90 | 80 | 40 | 40 | 30 | 10 |
| SCENTLESS CHAMOMILE | 90 | 80 | 80 | 70 | 30 | 20 | 20 | 20 | 20 | 10 | 10 | 10 | 80 | 30 | 60 | 20 | 0 | 0 |
| BLACK NIGHTSHADE | 70 | 50 | 50 | 40 | 20 | 0 | 10 | 0 | 0 | 0 | 0 | 0 | 30 | 10 | 20 | 0 | 0 | 0 |
| RUSSIAN THISTLE | — | — | — | — | — | — | 50 | 60 | 30 | 0 | 0 | 0 | 10 | 10 | 0 | 0 | 0 | 0 |
| BIRDSEYE SPEEDWELL | 80 | 80 | 50 | 30 | 20 | 0 | 100 | 90 | 70 | 60 | 50 | 40 | 100 | 100 | 90 | 60 | 40 | 30 |
| SUGARBEET | 60 | 60 | 40 | 30 | 20 | 20 | 70 | 70 | 70 | 50 | 10 | 10 | 0 | 0 | 0 | 0 | 0 | 0 |
| IVYLEAF SPEEDWELL | 80 | 80 | 40 | 40 | 30 | 0 | 90 | 60 | 50 | 20 | 20 | 0 | 80 | 50 | 20 | 10 | 0 | 0 |
| LAMBSQUARTERS | 60 | 80 | 40 | 40 | 20 | 20 | 100 | 90 | 80 | 30 | 10 | 0 | 100 | 70 | 60 | 60 | 30 | 20 |
| FIELD PENNYCRESS | 100 | 90 | 90 | 90 | 80 | 70 | 100 | 90 | — | 20 | 10 | 0 | 50 | 20 | 10 | 0 | 0 | 0 |
| FIELD VIOLET | 100 | 70 | 70 | 40 | 40 | 30 | 100 | 30 | 30 | 20 | 10 | 0 | 50 | 20 | 0 | 0 | 0 | 0 |

TEST D

Seeds of annual bluegrass (*Poa annua*), barley (*Hordeum vulgare*), blackgrass (*Alopecurus myosuroides*), chickweed (*Stellaria media*), green foxtail (*Setaria viridis*), ladysthumb smartweed (*Polygonum persicaria*), lambsquarters (*Chenopodium album*), redroot pigweed (*Amaranthus retroflexus*), sugarbeet (*Beta vulgaris*), wild buckwheat (*Polygonum convolvulus*), wild mustard (Brassica spp.), and wild oat (*Avena fatua*) were planted and treated preemergence with test chemicals dissolved in a non-phytotoxic solvent. At the same time, these crop and weed species were also treated with postemergence applications of test chemicals. Plants ranged in height from two or twenty cm for postemergence treatments. Treated plants and controls were maintained in a greenhouse for approximately 24 days, after which all species were compared to controls and visually evaluated. The ratings, summarized in Table D, are based on a scale of 0 to 100 where 0 is no effect and 100 is complete control.

(*Brachiaria platyphylla*), cocklebur (*Xanthium pensylvanicum*), cotton (*Gossypium hirsutum*), fall panicum (*Panicum dichotomiflorm*), goosegrass, (*Eluesine indica*), groundcherry (*Physalis heterophylla*), ivyleaf morningglory (*Ipomoea hederacea*), johnsongrass (*Sorghum halepense*), ladysthumb smartweed (*Polygonum persicaria*), lambsquarters (*Chenopodium album*), large crabgrass (*Digitaria sanguinalis*), prickly sida (*Sida spinosa*), purslane (*Portulaca oleracea*), redroot pigweed (*Amaranthus retroflexus*), sicklepod (*Cassia obtusifolia*), and velvetlead (*Abutilon theophrasti*) and purple nutsedge (*Cyperus rotundus*) tubers were planted and treated preemergence with test chemicals dissolved in a non-phytotoxic solvent. At the same time, these crop and weed species were also treated with postemergence applications of test chemicals. Plants ranged in height from five to twelve cm for postemergence treatments. Treated plants and controls were maintained in a greenhouse for approximately 21 days, after which all species were compared to controls annd visually evaluated. The ratings, summarized in Table E, are based on a scale of 0 to 100 where 0 is no effect and 100 is complete control. A dash (−) response means no test.

TABLE D

| | CMPD 55 | | | | CMPD 59 | | | CMPD 55 | | CMPD 59 | |
|---|---|---|---|---|---|---|---|---|---|---|---|
| RATE GM/HA | 64 | 32 | 16 | 8 | 64 | 32 | 16 | 64 | 32 | 64 | 32 |
| | POSTEMERGENCE | | | | | | | PREEMERGENCE | | | |
| BARLEY | 30 | 0 | 0 | 0 | 70 | 50 | 30 | 30 | 20 | 30 | 30 |
| CHICKWEED | 80 | 40 | 20 | 0 | 100 | 100 | 100 | 80 | 30 | 100 | 0 |
| LAMBSQUARTERS | 100 | 100 | 30 | 30 | 100 | 100 | 75 | 70 | 70 | 100 | 100 |
| REDROOT PIGWEED | 100 | 100 | 100 | 80 | 100 | 100 | 100 | 100 | 70 | 100 | 100 |
| LADYSTHUMB SMARTWEED | 90 | 70 | 70 | 70 | 90 | 80 | 80 | 50 | 50 | 100 | 0 |
| WILD BUCKWHEAT | 100 | 80 | 80 | 30 | 100 | 100 | 90 | 30 | 30 | 100 | 20 |
| MUSTARD | 100 | 100 | 100 | 80 | 100 | 100 | 100 | 100 | 100 | 100 | 100 |
| BLUEGRASS | 100 | 0 | 0 | 0 | 100 | 20 | 20 | 0 | 0 | 30 | 0 |
| BLACKGRASS | 40 | 20 | 0 | 0 | 90 | 70 | 0 | 50 | 50 | 50 | 20 |
| GREEN FOXTAIL | 70 | 70 | 70 | 0 | 100 | 80 | 30 | 70 | 30 | 90 | 90 |
| WILD OAT | 20 | 20 | 20 | 0 | 90 | 70 | 40 | 30 | 20 | 50 | 30 |
| SUGARBEET | 80 | 70 | 40 | 30 | 100 | 90 | 70 | 30 | 30 | 80 | 60 |

TEST E

Seeds of barnyardgrass (*Echinochloa crus-galli*), bermudagrass (*cynodon dactylon*), broadleaf signalgrass

TABLE E

| | CMPD 1 | | | | | CMPD 6 | | | | |
|---|---|---|---|---|---|---|---|---|---|---|
| RATE GM/HA | 64 | 32 | 16 | 8 | 4 | 16 | 8 | 4 | 2 | 1 |
| | POSTEMERGENCE | | | | | | | | | |
| COTTON | 30 | 0 | 0 | 0 | 0 | 90 | 60 | 15 | 10 | 0 |
| REDROOT PIGWEED | 100 | 100 | 100 | 80 | 70 | 100 | 100 | 100 | 100 | 100 |
| LAMBSQUARTERS | 100 | 95 | 100 | 50 | 0 | 100 | 100 | 100 | 90 | 20 |
| VELVETLEAF | 100 | 95 | 90 | 60 | 50 | 95 | 90 | 70 | 60 | 30 |
| PRICKLY SIDA | 80 | 20 | 20 | 0 | 0 | 60 | 50 | 40 | 10 | 0 |
| SICKLEPOD | 50 | 0 | 0 | 0 | 0 | 100 | 95 | 95 | 40 | 30 |
| COCKLEBUR | 98 | 80 | 90 | 60 | 60 | 100 | 100 | 95 | 60 | 60 |
| PURSLANE | 100 | 90 | 60 | 60 | 50 | 100 | 100 | 95 | 95 | 90 |
| IVYLEAF MORNINGGLORY | 95 | 30 | 0 | 0 | 0 | 100 | 100 | 95 | 90 | 80 |
| GOOSEGRASS | 0 | 0 | 0 | 0 | 0 | 20 | 0 | 0 | 0 | 0 |
| BERMUDAGRASS | 0 | 0 | 0 | 0 | 0 | 50 | 50 | 30 | 10 | 0 |
| BARNYARDGRASS | 100 | 50 | 30 | 30 | 30 | 98 | 95 | 90 | 70 | 40 |
| JOHNSONGRASS | 50 | 30 | 20 | 0 | 0 | 100 | 100 | 90 | 90 | 60 |
| FALL PANICUM | 0 | 0 | 0 | 0 | 0 | 70 | 60 | 40 | 30 | 0 |
| LARGE CRABGRASS | 0 | 0 | 0 | 0 | 0 | 60 | 20 | 10 | 0 | 0 |
| SIGNALGRASS | 20 | 0 | 0 | 0 | 0 | 100 | 98 | 90 | 80 | 60 |
| PURPLE NUTSEDGE | 100 | 70 | 20 | 20 | 0 | 0 | 0 | 0 | 0 | 0 |
| LADYSTHUMB SMARTWEED | 100 | 70 | 50 | 0 | 0 | 100 | 100 | 100 | 100 | 50 |
| GROUNDCHERRY | 100 | 20 | 0 | 0 | 0 | 60 | 60 | 30 | 20 | 10 |
| | CMPD 22 | | | | | CMPD 23 | | | | |
| RATE GM/HA | 16 | 8 | 4 | 2 | 1 | 16 | 8 | 4 | 2 | 1 |
| | POSTEMERGENCE | | | | | | | | | |
| COTTON | 20 | 10 | 0 | 0 | 0 | 40 | 40 | 10 | 0 | 0 |
| REDROOT PIGWEED | 100 | 90 | 70 | 60 | 50 | 100 | 100 | 100 | 95 | 90 |
| LAMBSQUARTERS | 60 | 20 | 0 | 0 | 0 | 100 | 95 | 95 | 70 | 0 |
| VELVETLEAF | 95 | 60 | 30 | 10 | 0 | 95 | 90 | 80 | 60 | 40 |

TABLE E-continued

| | | | | | | | | | | |
|---|---|---|---|---|---|---|---|---|---|---|
| PRICKLY SIDA | 10 | 10 | 0 | 0 | 0 | 60 | 50 | 30 | 20 | 0 |
| SICKLEPOD | 60 | 40 | 0 | 0 | 0 | 90 | 90 | 30 | 0 | 0 |
| COCKLEBUR | 100 | 95 | 70 | 0 | 0 | 100 | 100 | 100 | 90 | 40 |
| PURSLANE | 0 | 0 | 0 | 0 | 0 | 100 | 100 | 98 | 95 | — |
| IVYLEAF MORNINGGLORY | 40 | 40 | 20 | 10 | 10 | 98 | 98 | 98 | 95 | 50 |
| GOOSEGRASS | 0 | 0 | 0 | 0 | 0 | 0 | 0 | 0 | 0 | 0 |
| BERMUDAGRASS | 20 | 20 | 0 | 0 | 0 | 20 | 20 | 0 | 0 | 0 |
| BARNYARDGRASS | 70 | 30 | 20 | 0 | 0 | 95 | 95 | 80 | 50 | 40 |
| JOHNSONGRASS | 60 | 30 | 20 | 10 | 0 | 90 | 80 | 60 | 30 | 30 |
| FALL PANICUM | 60 | 0 | 0 | 0 | 0 | 50 | 0 | 0 | 0 | 0 |
| LARGE CRABGRASS | 0 | 0 | 0 | 0 | 0 | 20 | 0 | 0 | 0 | 0 |
| SIGNALGRASS | 60 | 20 | 20 | 0 | 0 | 60 | 40 | 20 | 20 | 10 |
| PURPLE NUTSEDGE | 30 | 0 | 0 | 0 | 0 | 0 | 0 | 0 | 0 | 0 |
| LADYSTHUMB SMARTWEED | 100 | 95 | 80 | 20 | 20 | 100 | 98 | 80 | 50 | 50 |
| GROUNDCHERRY | 30 | 0 | 0 | 0 | 0 | 60 | 30 | 0 | 0 | 0 |

What is claimed is:

1. A compound of the formula $$R_4\text{-phenyl}(R_1)(R_2\text{-}N(R_3))(N(O)_p)(S(O)_2NHC(W)N(R)\text{-}A) \quad I$$

wherein
W is O or S;
R is H or $CH_3$;
$R_1$ is H, F, Cl, Br, I, CN, $C_1$-$C_2$ alkyl, $C_1$-$C_2$ haloalkyl, $OCH_3$, $OCH_2CH_3$, $OCH_2CF_3$, $OCF_2H$, $SCH_3$, $SCF_2H$, $C_1$-$C_3$ alkylsulfonyl or $SO_2CF_2H$;
$R_2$ is H, $C_1$-$C_4$ alkyl, $C_1$-$C_2$ haloalkyl, CN, OH, $C_1$-$C_2$ alkoxy, $NH_2$, $NHCH_3$, $N(CH_3)_2$, $C_1$-$C_2$ alkyl substituted by CN, $C_1$-$C_2$ alkoxy or $C_1$-$C_2$ alkylthio, $C_3$-$C_4$ cycloalkyl, $C_3$-$C_4$ alkenyl, $C_3$-$C_4$ alkynyl or $C(O)R_5$;
$R_3$ is H, $C_1$-$C_4$ alkyl or $C_1$-$C_2$ haloalkyl; or
$R_2$ and $R_3$ may be taken together as $-(CH_2)_n-$ or $-CH_2CH_2OCH_2CH_2-$ or $$=C(R_6)(R_7);$$

$R_4$ is H, F, Cl or $CH_3$;
$R_5$ is H, $C_1$-$C_3$ alkyl, $C_1$-$C_2$ alkoxy, $NH_2$, $NHCH_3$ or $N(CH_3)_2$;
$R_6$ is H, $C_1$-$C_2$ alkyl or phenyl;
$R_7$ is H or $CH_3$;
n is 2, 3, 4 or 5;
p is 0 or 1;

A is A-1 (triazine with X, Y, Z substituents) or A-6 ($-CH_2-$ pyrimidine with $OCH_3$, $X_3$);

X is H, $C_1$-$C_4$ alkyl, $C_1$-$C_4$ alkoxy, $C_2$-$C_4$ haloalkoxy, $C_1$-$C_4$ haloalkyl, $C_1$-$C_4$ haloalkylthio, $C_1$-$C_4$ alkylthio, $C_2$-$C_5$ alkoxyalkyl, $C_2$-$C_5$ alkoxyalkoxy, amino, $C_1$-$C_3$ alkylamino or di($C_1$-$C_3$ alkyl)amino;
Y is H, $C_1$-$C_4$ alkyl, $C_1$-$C_4$ alkoxy, $C_2$-$C_4$ haloalkoxy, $C_1$-$C_4$ haloalkylthio, $C_1$-$C_4$ alkylthio, $C_2$-$C_5$ alkoxyalkyl, $C_2$-$C_5$ alkoxyalkoxy, amino, $C_1$-$C_3$ alkylamino, di($C_1$-$C_3$ alkyl)amino, $C_3$-$C_4$ alkenyloxy, $C_3$-$C_4$ alkynyloxy, $C_2$-$C_5$ alkylthioalkyl, $C_2$-$C_5$ alkylsulfinylalkyl, $C_2$-$C_5$ alkylsulfonylalkyl, $C_1$-$C_4$ haloalkyl, $C_2$-$C_4$ alkynyl, $C_3$-$C_5$ cycloalkyl, azido, cyano, $$CR_a(O)-, -C(Q_1R_b)(R_a)(Q_2R_c), -C(Q_1)(Q_2)(CH_2)_m(R_a), -CR_a(Q_1)(Q_2)CH_3$$

or $N(OCH_3)CH_3$;
m is 2 or 3;
$Q_1$ and $Q_2$ are independently O or S;
$R_a$ is H or $C_1$-$C_3$ alkyl;
$R_b$ and $R_c$ are independently $C_1$-$C_3$ alkyl;
Z is N; and
$X_3$ is $CH_3$ or $OCH_3$;
and their agriculturally suitable salts; provided that
(1) when W is S, then R is H, A is A-1, and Y is $CH_3$, $OCH_3$, $OC_2H_5$, $CH_2OCH_3$, $C_2H_5$, $CF_3$, $SCH_3$, $OCH_2CH=CH_2$, $OCH_2\equiv CH$, $OCH_2CH_2OCH_3$, $CH(OCH_3)_2$ or $$-CH(OCH_2O-) \text{ (methylenedioxy ring)};$$

and
(2) when the total number of carbon atoms of X and Y is greater than four, then the combined number of carbons of $R_2$ and $R_3$ is less than or equal to six.

2. The compounds of claim 1 wherein
$R_2$ is $C_1$-$C_2$ haloalkyl, OH, $C_1$-$C_2$ alkoxy, $NH_2$, $NHCH_3$, $N(CH_3)_2$, $C_1$-$C_2$ alkyl substituted by $C_1$-$C_2$ alkylthio, $C_3$-$C_4$ cycloalkyl or $C(O)R_5$;
$R_3$ is H, $C_1$-$C_4$ alkyl or $C_1$-$C_2$ haloalkyl; or
$R_2$ and $R_3$ are taken together as $-(CH_2)_n-$ or $$=C(R_6)(R_7);$$

and
n is 2 or 3.

3. The compounds of claim 2 wherein
W is O;

X is $C_1$-$C_2$ alkyl, $C_1$-$C_2$ alkoxy, $CH_2F$, $CF_3$, $OCH_2CH_2F$, $OCH_2CHF_2$, $OCH_2CF_3$, $CH_2Cl$ or $CH_2Br$; and Y is H, $C_1$-$C_2$ alkyl, $C_1$-$C_2$ alkoxy, $CH_2OCH_3$, $CH_2OCH_2CH_3$, $NHCH_3$, $N(OCH_3)CH_3$, $N(CH_3)_2$, $CF_3$, $SCH_3$, $OCH_2CH=CH_2$, $OCH_2C\equiv CH$, $OCH_2CH_2OCH_3$, $CH_2SCH_3$, $C(O)R_a$,

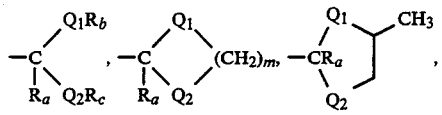

$SCF_2H$, cyclopropyl, $C\equiv CH$ or $C\equiv CCH_3$.

4. The compounds of claim 3 wherein
$R_2$ is $NH_2$, $NHCH_3$, $N(CH_3)_2$, $CF_3$, $CF_2H$, OH, $OCH_3$, $CH_2SCH_3$, cyclopropyl or $C(O)R_5$;
$R_3$ is H, $CH_3$ or $CH_2CH_3$; or
$R_2$ and $R_3$ are taken together as

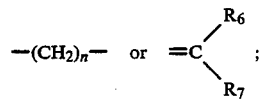

$R_5$ is H, $CH_3$, $OCH_3$, $NH_2$, $NHCH_3$ or $N(CH_3)_2$; and
$R_6$ is H or $C_1$-$C_2$ alkyl.

5. The compounds of claim 4 wherein
A is A-1;
X is $CH_3$, $OCH_3$, $OCH_2CH_3$ or $OCH_2CF_3$; and
Y is $CH_3$, $OCH_3$, $CH_2CH_3$, $CH_2OCH_3$, $NHCH_3$ or $CH(OCH_3)_2$.

6. The compounds of claim 5 wherein
R is H;
$R_1$ is H; and
p is O.

7. The compounds of claim 1 wherein
$R_2$ is H, $C_1$-$C_4$ alkyl, CN, $C_1$-$C_2$ alkyl substituted by CN or $C_1$-$C_2$ alkoxy, $C_3$-$C_4$ alkenyl or $C_3$-$C_4$ alkynyl;
$R_3$ is H, $C_1$-$C_4$ alkyl or $C_1$-$C_2$ haloalkyl; or
$R_2$ and $R_3$ are taken together as —$(CH_2)_n$— or —$CH_2CH_2OCH_2CH_2$—; and n is 4 or 5.

8. The compounds of claim 7 wherein
W is O;
X is $C_1$-$C_2$ alkyl, $C_1$-$C_2$ alkoxy, $CH_2F$, $CF_3$, $OCH_2CH_2F$, $OCH_2CHF_2$, $OCH_2CF_3$, $CH_2Cl$ or $CH_2Br$; and
Y is H, $C_1$-$C_2$ alkyl, $C_1$-$C_2$ alkoxy, $CH_2OCH_3$, $CH_2OCH_2CH_3$, $NHCH_3$, $N(OCH_3)CH_3$, $N(CH_3)_2$, $CF_3$, $SCH_3$, $OCH_2CH=CH_2$, $OCH_2C\equiv CH$, $OCH_2CH_2OCH_3$, $CH_2SCH_3$, $C(O)R_a$,

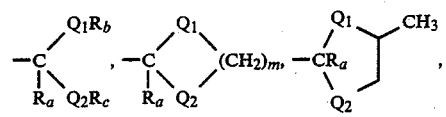

$SCF_2H$, cyclopropyl, $C\equiv CH$ or $C\equiv CCH_3$.

9. The compounds of claim 8 wherein $R_2$ is H, $C_1$-$C_4$ alkyl, CN, $CH_2CN$, $CH_2OCH_3$, allyl or propargyl; and
$R_3$ is H, $CH_3$ or $CH_2CH_3$.

10. The compounds of claim 9 wherein
A is A-1;
X is $CH_3$, $OCH_3$, $OCH_2CH_3$ or $OCH_2CF_3$; and
Y is $CH_3$, $OCH_3$, $CH_2CH_3$, $CH_2OCH_3$, $NHCH_3$ or $CH(OCH_3)_2$.

11. The compounds of claim 10 wherein
R is H;
$R_1$ is H; and
p is O.

12. The compound of claim 1 which is 6-(dimethylamino)-N-[[[4-ethoxy-6-(methylamino)-1,3,5-triazin-2-yl]amino]carbonyl]-2-pyridinesulfonamide.

13. The compound of claim 1 which is N-[[[(4-ethoxy-6-(dimethylamino)-1,3,5-triazin-2-yl]amino]carbonyl]-6-(methylamino)-2-pyridinesulfonamide.

14. An agriculturally suitable composition for controlling the growth of undesired vegetation comprising an effective amount of a compound as in any claims 1–11 and 12–13 and at least one of the following: surfactant, solid diluent or liquid diluent.

15. A method for controlling the growth of undesired vegetation which comprises applying to the locus to be protected an effective amount of a compound as in any of claims 1–11 and 12–13.

* * * * *

UNITED STATES PATENT AND TRADEMARK OFFICE
CERTIFICATE OF CORRECTION

PATENT NO. : 4,946,494
DATED : August 7, 1990
INVENTOR(S) : Eric D. Taylor

It is certified that error appears in the above-identified patent and that said Letters Patent is hereby corrected as shown below:

The name of the Inventor change "Eric D. Taylor" to -- Eric G. Taylor -

In the specification

Column 4, line 16, change "$Y_{4L}$" to -- $Y_4$ --.

Column 4, line 38, change "byy" to -- by --.

Column 7, line 49, remove the parenthesis before " 4-ethoxy- ".

Column 11, line 46, change "f" to -- F --.

Column 11, line 51, change "m-chloroperoxybezoic" to -- m-chloroperoxy benzoic --.

Column 12, line 19, change "snieckus" to -- Snieckus --.

Column 12, line 67, change "a" to -- A --.

Column 43, the ninth compound, change "$Cl_3$" to -- Cl --.

Column 43, the 47th compound change "$Cl_3$" to -- Cl -- and "OCH" to -- $OCH_3$ --.

Column 45, the 41st compound change "$Cl_3$" to -- Cl -- and "OCH" to -- $OCH_3$ --.

UNITED STATES PATENT AND TRADEMARK OFFICE
CERTIFICATE OF CORRECTION

PATENT NO. : 4,946,494
DATED : August 7, 1990
INVENTOR(S) : Eric D. Taylor

It is certified that error appears in the above-identified patent and that said Letters Patent is hereby corrected as shown below:

Column 160, line 42, change "liquids" to -- liquid --.

Column 170, delete lines 33-35.

Column 195 for cotton for Compound 2 change the ratings at 62, 16, 4 and 1 G/HA to 90, 80, 40, 0 respectively.

Column 199-200 for Compound 23 the Rate = G/HA should read 62, 16, 4, 1.

Column 204 the ratings for the rate of 250 are missing. Therefore add the rate "250" and thereunder for the weeds and crops listed add the ratings "100, 90, 100, 90, 100, 90, 100, 90, 80, 70, 100, 90, 80, 100, 90, 90, 90, 90" the first rating being for Giant Foxtail and the last for corn.

Column 206, before the rating for GIANT FOXTAIL for Compounds 50-57 add "PREEMERGENCE".

Column 206 before "Compound 51" delete " U ,26/37".

Column 206 under Compound 57, the data is incomplete. The data should recite under the rate of 250 G/HA the following: 90, 100, 90, 100, 90, 90, 90, 90, 100, 90.

UNITED STATES PATENT AND TRADEMARK OFFICE
CERTIFICATE OF CORRECTION

PATENT NO. : 4,946,494
DATED : August 7, 1990
INVENTOR(S) : Eric D. Taylor

It is certified that error appears in the above-identified patent and that said Letters Patent is hereby corrected as shown below:

Column 208 before the rating for GIANT FOXTAIL for Compound 57-63 add "PREEMERGENCE".

Column 211 before the rating for GIANT FOXTAIL for Compound 58-64 add "POSTEMERGENCE".

In the claims:
Column 238
Claim 13, first line delete "N-[[[(4-" and substitute therefore -- N-[[[4- --.

Signed and Sealed this

Tenth Day of November, 1992

Attest:

DOUGLAS B. COMER

Attesting Officer

Acting Commissioner of Patents and Trademarks